(12) United States Patent
Springer et al.

(10) Patent No.: US 11,608,330 B2
(45) Date of Patent: *Mar. 21, 2023

(54) METHYLAMINE DERIVATIVES AS LYSYSL OXIDASE INHIBITORS FOR THE TREATMENT OF CANCER

(71) Applicant: The Institute of Cancer Research: Royal Cancer Hospital, London (GB)

(72) Inventors: Caroline Springer, Sutton (GB); Richard Marais, Manchester (GB); Dan Niculescu-Duvaz, Sutton (GB); Leo Leung, Sutton (GB); Deborah Smithen, Sutton (GB); Cedric Callens, Singapore (SG); Haoran Tang, Manchester (GB)

(73) Assignee: THE INSTITUTE OF CANCER RESEARCH: ROYAL CANCER HOSPITAL, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/221,549

(22) Filed: Apr. 2, 2021

(65) Prior Publication Data
US 2022/0372028 A1 Nov. 24, 2022

Related U.S. Application Data

(63) Continuation of application No. 16/908,487, filed on Jun. 22, 2020, now Pat. No. 10,995,088, which is a continuation of application No. 15/999,458, filed as application No. PCT/GB2017/050421 on Feb. 17, 2017, now Pat. No. 10,807,974.

(30) Foreign Application Priority Data

Feb. 19, 2016 (GB) ...................... 1602934

(51) Int. Cl.
| | | |
|---|---|---|
| C07D 417/12 | (2006.01) | |
| A61P 35/00 | (2006.01) | |
| C07D 263/46 | (2006.01) | |
| C07D 277/26 | (2006.01) | |
| C07D 277/36 | (2006.01) | |
| C07D 333/18 | (2006.01) | |
| C07D 333/34 | (2006.01) | |
| C07D 409/12 | (2006.01) | |
| C12Q 1/37 | (2006.01) | |

(52) U.S. Cl.
CPC ............ *C07D 417/12* (2013.01); *A61P 35/00* (2018.01); *C07D 263/46* (2013.01); *C07D 277/26* (2013.01); *C07D 277/36* (2013.01); *C07D 333/18* (2013.01); *C07D 333/34* (2013.01); *C07D 409/12* (2013.01); *C12Q 1/37* (2013.01); *C12Y 304/21* (2013.01)

(58) Field of Classification Search
CPC .. C07D 417/12; C07D 263/46; C07D 277/26; C07D 277/36; C07D 333/18; C07D 333/34; C07D 409/12; A61P 35/00; C12Q 1/37; C12Y 304/21
USPC ........................................................ 514/369
See application file for complete search history.

(56) References Cited

U.S. PATENT DOCUMENTS

| | | | |
|---|---|---|---|
| 7,320,977 B2 | 1/2008 | Schohe-Loop et al. | |
| 10,807,974 B2* | 10/2020 | Springer | C07D 333/18 |
| 10,995,088 B2* | 5/2021 | Springer | C07D 333/34 |
| 2021/0152966 A1 | 5/2021 | Mathur | |

FOREIGN PATENT DOCUMENTS

| | | |
|---|---|---|
| DE | 10216144 A1 | 11/2003 |
| DE | 102004056226 A1 | 5/2006 |
| EP | 0295049 A1 | 12/1988 |
| EP | 0330218 A2 | 8/1989 |
| EP | 0786455 A1 | 7/1997 |
| EP | 2005957 A1 | 12/2008 |
| EP | 2196459 A1 | 6/2010 |
| EP | 2233495 A1 | 9/2010 |
| WO | WO 2006/053555 A2 | 5/2006 |
| WO | WO 2006/072833 A1 | 7/2006 |
| WO | WO 2007/005737 A2 | 1/2007 |
| WO | WO 2007/126457 A2 | 11/2007 |

(Continued)

OTHER PUBLICATIONS

Cancer [online], [retrieved on Jul. 6, 2007] Retrieved from the Internet, URL: http://www.nim.nih.gov/medlineplus/cancer.html (Year: 2007).*

(Continued)

*Primary Examiner* — Kristin A Vajda

(57) ABSTRACT

Provided are compounds of the Formula (I), or a pharmaceutically acceptable salt thereof:

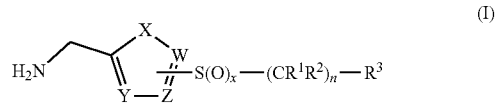

wherein W, X, Y, Z, x, $R^1$, $R^2$, $R^3$, x and n are defined in the specification. The compounds are inhibitors of lysyl oxidase (LOX) and lysyl oxidase-like (LOXL) family members (LOXL1, LOXL2, LOXL3, LOXL4) and are useful in therapy, particularly in the treatment of cancer. Also disclosed are LOX inhibitors for use in the treatment of a cancer associated with EGFR and biomarkers that predict responsiveness to a LOX inhibitor.

34 Claims, 17 Drawing Sheets

Specification includes a Sequence Listing.

(56) References Cited

FOREIGN PATENT DOCUMENTS

| WO | WO 2009/017833 A2 | 2/2009 |
|---|---|---|
| WO | WO 2014/070939 A1 | 5/2014 |
| WO | WO 2016/144702 A1 | 9/2016 |
| WO | WO 2016/144703 A1 | 9/2016 |
| WO | WO 2017/003862 A1 | 1/2017 |
| WO | WO 2017/015221 A1 | 1/2017 |

OTHER PUBLICATIONS

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

Anderson, C. et al., "*Chemical genetics suggests a critical role for lysyl oxidase in zebrafish notochord morphogenesis*", Mol. BioSyst., 2007, 3, 51-59.

Aslam, T., et al. "*Optical molecular imaging of lysyl oxidase activity-detection of active fibrogenesis in human lung tissue*", Chem. Sci., 2015, 6, 4946-4953.

Burke, A. et al., "*Comparing hydrazine-derived reactive groups as inhibitors of quinone-dependent amine oxidases*", J. of Enzyme Inhibition and Medicinal Chemistry, 2017, vol. 32, No. 1, 496-503.

Carrington, M.J., et al., "*The inhibition of lysyl oxidase in vivo by isoniazid and its reversal by pyridoxal Effect on collagen cross-linking in the chick embryo*", Biochem. J. (1984) 221, 837-843.

Chang, J., et al., "*Pre-clinical evaluation of small molecule LOXL2 inhibitors in breast cancer*", Oncotarget, 2017, vol. 8, (No. 16), pp. 26066-26078.

Levene, C.I., et al., "*Inhibition of chick embryo lysyl oxidase by various lathyrogens and the antagonistic effect of pyridoxal*", Int. J. Exp. Path. (1992) 73, 613-624.

Liu, G., et al., "*Irreversible Inhibition of Lysyl Oxidase by Homocysteine Thiolactone and Its Selenium and Oxygen Analogues*", The Journal of Biological Chemistry, vol. 272, No. 51, Issue of Dec. 19, pp. 32370-32377, 1997.

Pinnell, S., et al., "*The Cross-Linking of Collagen and Elastin: Enzymatic Conversion of Lysine in Peptide Linkage to α-Aminoadipic-δ-Semialdehyde (Allysine) by an Extract from Bone*", PNAS, v. 61, p. 708-716 (1968).

Sion, A. et al., "Lysyl oxidase (LOX) and hypoxia induced metastases", Cancer Biology & Therapy, vol. 5, Issue 8, pp. 909-911(2006).

Office Action corresponding to Israel Patent Application No. 261015, dated Jul. 19, 2020.

Tang, S.S., et al., "*β-Substituted Ethylamine Derivatives as Suicide Inhibitors of Lysyl Oxidase*" The Journal of Biological Chemistry, vol. 259, No. 2, Issue of Jan. 25, pp. 975-979, 1984.

Williamson, P.R., et al., "*Electronegativity of Aromatic Amines as a Basis for the Development of Ground State Inhibitors of Lysyl Oxidase*", The Journal of Biological Chemistry, vol. 262, No. 30, Issue of Oct. 25, pp. 14520-14524, 1987.

Retrieved from STN Database, Accession No. 439672-75-0, 2019.

\* cited by examiner

| | | 1 | 2 | 3 | 4 | 5 | 6 | 7 | 8 | 9 | 10 | 11 | 12 | |
|---|---|---|---|---|---|---|---|---|---|---|---|---|---|---|
| | | 100μM | 30μM | 10μM | 3μM | 1μM | 0.3μM | 0.1μM | 0.03μM | 0.01μM | 0.003μM | 7355 | CONTROLS | |
| Cpdxx1 | A | 40μl LOX + Assay Buffer + 0.5μl Test Compound 1 + 10μl Start Mix ||||||||||| 40μl LOX + Assay Buffer + 0.5μl BAPN + 10μl Start Mix | No HRP 40μl LOX + Assay Buffer + 10μl Start Mix Minus HRP (<100 cpm) | 100μM |
| Cpdxx1 | B | 40μl LOX + Assay Buffer + 0.5μl Test Compound 1 + 10μl Start Mix ||||||||||| | 30μM |
| Cpdxx2 | C | 40μl LOX + Assay Buffer + 0.5μl Test Compound 2 + 10μl Start Mix ||||||||||| | DMSO 40μl LOX + Assay Buffer + 0.5μl DMSO + 10μl Start Mix (1800-3000) | 10μM |
| Cpdxx2 | D | 40μl LOX + Assay Buffer + 0.5μl Test Compound 2 + 10μl Start Mix ||||||||||| | | 3μM |
| Cpdxx3 | E | 40μl LOX + Assay Buffer + 0.5μl Test Compound 3 + 10μl Start Mix ||||||||||| | | 1μM |
| Cpdxx3 | F | 40μl LOX + Assay Buffer + 0.5μl Test Compound 3 + 10μl Start Mix ||||||||||| | | 0.3μM |
| Cpdxx4 | G | 40μl LOX + Assay Buffer + 0.5μl Test Compound 4 + 10μl Start Mix ||||||||||| | No LOX 40μl Assay Buffer only + 10μl Start Mix (100-200cpm) | 0.1μM |
| Cpdxx4 | H | 40μl LOX + Assay Buffer + 0.5μl Test Compound 4 + 10μl Start Mix ||||||||||| | | 0.03μM |

FIGURE 24

| | | 1 (100μM) | 2 (30μM) | 3 (10μM) | 4 (3μM) | 5 (1μM) | 6 (0.3μM) | 7 (0.1μM) | 8 (0.03μM) | 9 (0.011μM) | 10 (0.00.3μM) | 11 (Na₃VO₄) | 12 (CONTROLS) | |
|---|---|---|---|---|---|---|---|---|---|---|---|---|---|---|
| Cpdxx1 | A | 40μl H$_2$O$_2$ + Assay Buffer + 0.5μl Test Compound 1 + 10μl Start Mix | | | | | | | | | | 40μl H$_2$O$_2$ + Assay Buffer + 0.5μl Na$_3$VO$_4$ + 10μl Start Mix | No HRP 40μl H$_2$O$_2$ + 10μl Start Mix Minus HRP | 100μM |
| Cpdxx1 | B | 40μl H$_2$O$_2$ + Assay Buffer + 0.5μl Test Compound 1 + 10μl Start Mix | | | | | | | | | | | | 30μM |
| Cpdxx2 | C | 40μl H$_2$O$_2$ + Assay Buffer + 0.5μl Test Compound 2 + 10μl Start Mix | | | | | | | | | | | DMSO 40μl H$_2$O$_2$ + 0.5μl DMSO + 10μl Start Mix | 10μM |
| Cpdxx2 | D | 40μl H$_2$O$_2$ + Assay Buffer + 0.5μl Test Compound 2 + 10μl Start Mix | | | | | | | | | | | | 3μM |
| Cpdxx3 | E | 40μl H$_2$O$_2$ + Assay Buffer + 0.5μl Test Compound 3 + 10μl Start Mix | | | | | | | | | | | | 1μM |
| Cpdxx3 | F | 40μl H$_2$O$_2$ + Assay Buffer + 0.5μl Test Compound 3 + 10μl Start Mix | | | | | | | | | | | | 0.3μM |
| Cpdxx4 | G | 40μl H$_2$O$_2$ + Assay Buffer + 0.5μl Test Compound 4 + 10μl Start Mix | | | | | | | | | | | No H$_2$O$_2$ 40μl Assay 10μl Start Mix *(100-200cpm)* | 0.1μM |
| Cpdxx4 | H | 40μl H$_2$O$_2$ + Assay Buffer + 0.5μl Test Compound 4 + 10μl Start Mix | | | | | | | | | | | | 0.03μM |

FIGURE 25

| | | 1 | 2 | 3 | 4 | 5 | 6 | 7 | 8 | 9 | 10 | 11 | 12 | |
|---|---|---|---|---|---|---|---|---|---|---|---|---|---|---|
| | | 100µM | 30µM | 10µM | 3µM | 1µM | 0.3µM | 0.1µM | 0.03µM | 0.01µM | 0.003µM | BAPN | CONTROLS | |
| Cpdxx1 | A | 40µl LOXL2 + Assay Buffer + 0.5µl Test Compound 1 + 10µl Start Mix + 50µl Detection Reagent ||||||||||| 40µl LOXL2 + Assay Buffer + 0.5µl BAPN + 10µl Start Mix + 50µl Detection Reagent | No Luciferin 40µl LOXL2 + 10µl Start Mix + | 100µM |
| Cpdxx1 | B | 40µl LOXL2 + Assay Buffer + 0.5µl Test Compound 1 + 10µl Start Mix + 50µl Detection Reagent ||||||||||| ^ | 50µl Assay Buffer not luciferin (<100 cpm) | 30µM |
| Cpdxx2 | C | 40µl LOXL2 + Assay Buffer + 0.5µl Test Compound 2 + 10µl Start Mix + 50µl Detection Reagent ||||||||||| ^ | DMSO 40µl LOXL2 + 0.5µl DMSO + | 10µM |
| Cpdxx2 | D | 40µl LOXL2 + Assay Buffer + 0.5µl Test Compound 2 + 10µl Start Mix + 50µl Detection Reagent ||||||||||| ^ | 10µl Start Mix + 50µl Luciferin (18-25 000 cpm) | 3µM |
| Cpdxx3 | E | 40µl LOXL2 + Assay Buffer + 0.5µl Test Compound 3 + 10µl Start Mix + 50µl Detection Reagent ||||||||||| ^ | BAPN 0.01µM | 1µM |
| Cpdxx3 | F | 40µl LOXL2 + Assay Buffer + 0.5µl Test Compound 3 + 10µl Start Mix + 50µl Detection Reagent ||||||||||| ^ | BAPN 0.003µM | 0.3µM |
| Cpdxx4 | G | 40µl LOXL2 + Assay Buffer + 0.5µl Test Compound 4 + 10µl Start Mix + 50µl Detection Reagent ||||||||||| ^ | No LOXL2 40µl Assay Buffer only + | 0.1µM |
| Cpdxx4 | H | 40µl LOXL2 + Assay Buffer + 0.5µl Test Compound 4 + 10µl Start Mix + 50µl Detection Reagent ||||||||||| ^ | 10µl Start Mix + 50µl Luciferin (1800-2500cpm) | 0.03µM |

FIGURE 26

| | | 1 | 2 | 3 | 4 | 5 | 6 | 7 | 8 | 9 | 10 | 11 | 12 | | |
|---|---|---|---|---|---|---|---|---|---|---|---|---|---|---|---|
| | | 100μM | 30μM | 10μM | 3μM | 1μM | 0.3μM | 0.1μM | 0.03μM | 0.01μM | 0.00.3μM | Clorgyline | CONTROLS | | |
| Cpdxx 1 | A | 25μl MAO Substrate + 0.5μl Test Compound + 25 μl MAO-A enzyme + 50 μl Luciferin | | | | | | | | | | 25μl MAO-A/B enzyme + 25μl Clorgyline + 25μl MAO Substrate + 0.5μl Clorgyline + 50μl Luciferin | No Luciferin 25μl MAO Substrate + 25μl MAO | 1μM | 100μM |
| Cpdxx 1 | B | 25μl MAO Substrate + 0.5μl Test Compound + 25 μl MAO-A enzyme + 50 μl Luciferin | | | | | | | | | | | enzyme + 50μl Reaction Buffer | 0.3μM | 30μM |
| Cpdxx 2 | C | 25μl MAO Substrate + 0.5μl Test Compound + 25 μl MAO-A enzyme + 50 μl Luciferin | | | | | | | | | | | DMSO 25μl MAO Substrate + 0.5μl DMSO + | 0.1μM | 10μM |
| Cpdxx 2 | D | 25μl MAO Substrate + 0.5μl Test Compound + 25 μl MAO-A enzyme + 50 μl Luciferin | | | | | | | | | | | 25μl MAO enzyme + 50μl Luciferin | 0.03μM | 3μM |
| Cpdxx 3 | E | 25μl MAO Substrate + 0.5μl Test Compound + 25 μl MAO-A enzyme + 50 μl Luciferin | | | | | | | | | | | Blow Out 25μl MAO Substrate + 1μl undiluted | 0.01μM | 1μM |
| Cpdxx 3 | F | 25μl MAO Substrate + 0.5μl Test Compound + 25 μl MAO-A enzyme + 50 μl Luciferin | | | | | | | | | | | MAO enzyme (+ 24μl buffer) + 50μl Luciferin | 0.003μM | 0.3μM |
| Cpdxx 4 | G | 25μl MAO Substrate + 0.5μl Test Compound + 25 μl MAO-A enzyme + 50 μl Luciferin | | | | | | | | | | | No MAO enzyme 25μl MAO Substrate + 25 μl Reaction | 0.001μM | 0.1μM |
| Cpdxx 4 | H | 25μl MAO Substrate + 0.5μl Test Compound + 25 μl MAO-A enzyme + 50 μl Luciferin | | | | | | | | | | | Buffer + 50μl Luciferin | 0.0003μM | 0.03μM |

FIGURE 27

| | | 1 | 2 | 3 | 4 | 5 | 6 | 7 | 8 | 9 | 10 | 11 | 12 | |
|---|---|---|---|---|---|---|---|---|---|---|---|---|---|---|
| | | 100µM | 30µM | 10µM | 3µM | 1µM | 0.3µM | 0.1µM | 0.03µM | 0.01µM | 0.003µM | Deprenyl | CONTROLS | |
| Cpdxx1 | A | 25µl MAO Substrate + 0.5µl Test Compound + 25 µl MAO-B enzyme + 50 µl Luciferin | | | | | | | | | | 25µl MAO Substrate + 0.5µl Deprenyl + 25µl MAO-A/B enzyme + 50µl Luciferin | No Luciferin 25µl MAO Substrate + 25µl MAO enzyme + 50µl Reaction Buffer | 1µM |
| Cpdxx1 | B | 25µl MAO Substrate + 0.5µl Test Compound + 25 µl MAO-B enzyme + 50 µl Luciferin | | | | | | | | | | | | 100µM |
| | | | | | | | | | | | | | | 0.3µM |
| | | | | | | | | | | | | | | 30µM |
| Cpdxx2 | C | 25µl MAO Substrate + 0.5µl Test Compound + 25 µl MAO-B enzyme + 50 µl Luciferin | | | | | | | | | | | DMSO 25µl MAO Substrate + 0.5µl DMSO + 25µl MAO enzyme + 50µl Luciferin | 0.1µM |
| | | | | | | | | | | | | | | 10µM |
| Cpdxx2 | D | 25µl MAO Substrate + 0.5µl Test Compound + 25 µl MAO-B enzyme + 50 µl Luciferin | | | | | | | | | | | | 0.03µM |
| | | | | | | | | | | | | | | 3µM |
| Cpdxx3 | E | 25µl MAO Substrate + 0.5µl Test Compound + 25 µl MAO-B enzyme + 50 µl Luciferin | | | | | | | | | | | Blow Out 25µl MAO Substrate + 1µl undiluted MAO enzyme (+ 24µl buffer) + 50µl Luciferin | 0.01µM |
| | | | | | | | | | | | | | | 1µM |
| Cpdxx3 | F | 25µl MAO Substrate + 0.5µl Test Compound + 25 µl MAO-B enzyme + 50 µl Luciferin | | | | | | | | | | | | 0.003µM |
| | | | | | | | | | | | | | | 0.3µM |
| Cpdxx4 | G | 25µl MAO Substrate + 0.5µl Test Compound + 25 µl MAO-B enzyme + 50 µl Luciferin | | | | | | | | | | | No MAO enzyme 25µl MAO Substrate + 25 µl Reaction Buffer + 50µl Luciferin | 0.001µM |
| | | | | | | | | | | | | | | 0.1µM |
| Cpdxx4 | H | 25µl MAO Substrate + 0.5µl Test Compound + 25 µl MAO-B enzyme + 50 µl Luciferin | | | | | | | | | | | | 0.0003µM |
| | | | | | | | | | | | | | | 0.03µM |

FIGURE 28

DAO Assay Plate Layout

| | | 100μM | 30μM | 10μM | 3μM | 1μM | 0.3μM | 0.1μM | 0.03μM | 0.01μM | 0.00.3μM | Aminoguanidine | CONTROLS |
|---|---|---|---|---|---|---|---|---|---|---|---|---|---|
| | | 1 | 2 | 3 | 4 | 5 | 6 | 7 | 8 | 9 | 10 | 11 | 12 |
| x1 | A | 40μl DAO in Assay Buffer + 0.5μl Test Compound 1 + 10μl Start Mix + 50μl Detection Reagen | | | | | | | | | | 40μl DAO in Assay Buffer + 0.5ul aminoguanidine +10μl Start Mix + 50μl Detection Reagent | No Luciferin 40μl DAO + 10μl Start Mix + 50μl Assay Buffer not luciferin (<100 cpm) |
| x1 | B | 40μl DAO in Assay Buffer + 0.5μl Test Compound 1 + 10μl Start Mix + 50μl Detection Reagent | | | | | | | | | | | |
| x2 | C | 40μl DAO in Assay Buffer + 0.5μl Test Compound 2 + 10μl Start Mix + 50μl Detection Reagent | | | | | | | | | | | DMSO 40μl DAO + 0.5μl DMSO + 10μl Start Mix + 50μl Luciferin (18-25 000 cpm) |
| x2 | D | 40μl DAO in Assay Buffer + 0.5μl Test Compound 2 + 10μl Start Mix + 50μl Detection Reagent | | | | | | | | | | | |
| x3 | E | 40μl DAO in Assay Buffer + 0.5μl Test Compound 3 + 10μl Start Mix + 50μl Detection Reagent | | | | | | | | | | | Aminoguanidine 0.001uM |
| x3 | F | 40μl DAO in Assay Buffer + 0.5μl Test Compound 3 + 10μl Start Mix + 50μl Detection Reagent | | | | | | | | | | | Aminoguanidine 0.0003uM |
| x4 | G | 40μl DAO in Assay Buffer + 0.5μl Test Compound 4 + 10μl Start Mix + 50μl Detection Reagent | | | | | | | | | | | No DAO 40μl Assay Buffer only + 10μl Start Mix + 50μl Luciferin (1800-2500cpm) |
| x4 | H | 40μl DAO in Assay Buffer + 0.5μl Test Compound 4 + 10μl Start Mix + 50μl Detection Reagent | | | | | | | | | | | |

METHYLAMINE DERIVATIVES AS LYSYSL OXIDASE INHIBITORS FOR THE TREATMENT OF CANCER

CROSS-REFERENCE TO RELATED APPLICATIONS

This application is a continuation of U.S. application Ser. No. 16/908,487 filed on Jun. 22, 2020, now U.S. Pat. No. 10,995,088 B2 issued on May 4, 2021, which is a continuation of U.S. application Ser. No. 15/999,458 filed on Aug. 17, 2018, now U.S. Pat. No. 10,807,974 B2 issued on Oct. 20, 2020, which is a US National Phase of International Patent Application No. PCT/GB2017/050421 filed on Feb. 17, 2017, which claims priority to United Kingdom Patent Application No. 1602934.0, filed on Feb. 19, 2016, the disclosure of which is incorporated herein in its entirety for all purposes.

REFERENCE TO SEQUENCE LISTING

The Sequence Listing text copy submitted herewith via EFS-Web was created on Jun. 10, 2021, is entitled 0639995040US02_ST25.txt, is 1 kilobyte in size and is herein incorporated by reference in its entirety.

COMPOUNDS

This invention relates to compounds. More specifically, the invention relates to compounds useful as lysyl oxidase (LOX) and lysyl oxidase-like (LOXL) family members (LOXL1, LOXL2, LOXL3, LOXL4) inhibitors, to pharmaceutical compositions comprising the compounds, to the compounds for use in the treatment of conditions mediated by LOX and LOXL, for example cancer; to a LOX inhibitor for use in the treatment of a cancer associated with EGFR and to biomarkers that predict responsiveness to a LOX inhibitor.

BACKGROUND

LOX (protein-6-lysine-oxidase; EC 1.4.3.13) is an extracellular enzyme that catalyses oxidative deamination of the primary amines of lysine and hydroxylysine in proteins such as collagen and tropoelastin to generate peptidyl-[α]-aminoadipic-[δ]-semialdehyde, an aldehyde that spontaneously condenses to form inter- and intra-chain cross-links (Lucero and Kagan 2006). LOX regulates maturation of proteins in the extracellular matrix (ECM), thereby contributing to ECM tensile strength and function and so playing an important role in connective tissue remodelling. Other proteins have been reported as substrates for oxidation by LOX, such as basic fibroblast growth factor, PDGFR-β and other cationic proteins (Kagan and Li 2003, Li, Nugent et al. 2003, Lucero and Kagan 2006, Lucero, Ravid et al. 2008).

LOX is secreted as a precursor protein that is proteolytically processed by procollagen C-proteinases (bone morphogenetic protein 1—BMP-1) and mammalian tolloid-like protein (mTLL-1)(Uzel, Scott et al. 2001) to generate an 18 kDa pro-peptide and the 32 kDa active LOX enzyme (Lucero and Kagan 2006). The catalytic domain contains copper and a lysine-tyrosylquinone (LTQ) cofactor. LTQ is formed by post-translational oxidation of a catalytic site tyrosine (Tyr349), which then condenses onto a lysine, also within the catalytic site (Lys314), to form a stable covalent modification that is an essential part of the catalytic mechanism (Lucero and Kagan 2006) (Kagan and Li 2003).

LOX is part of a protein family consisting of five paralogues, LOX, LOX-like 1 [LOXL1], LOX-like 2 [LOXL2], LOX-like 3 [LOXL3] and LOX-like 4 [LOXL4]), all containing a conserved catalytic region. LOX enzymes play a crucial role in maintaining ECM stability, by initiating and regulating the crosslinking of collagens and elastin within the extracellular matrix (ECM). The activity of these enzymes is key to maintaining the normal tensile and elastic features of connective tissue of many organ systems within the body. LOX expression decreases during ageing indicating that its activity is especially important during development.

In addition to its role in tissue remodelling, LOX also plays a critical role in primary cancer and metastasis. Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013).

Expression of LOX is elevated in more than 70% of breast cancer patients with Estrogen Receptor negative disease, in 80% of head & neck cancer patients, in 33% of primary colorectal carcinomas (CRC) and 48% of metastatic tissues from patients with CRC (Baker, Cox et al. 2011), and in cirrhotic hepatocellular carcinoma (HCC) patients with a history of alcoholism (Huang, Ho et al. 2013). As discussed in more detail in the description, LOX is also overexpressed in numerous other cancers including lung, prostate and pancreatic cancers.

Elevated LOX expression is also associated with metastasis and decreased patient survival (Baker, Cox et al. 2011, Wilgus, Borczuk et al. 2011)

Other members of the LOX family have been implicated in proliferative diseases such as cancer. LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015).

Studies have suggested that LOX and LOXL2 do not compensate one another, as manipulation of LOX expression did not affect LOXL2 levels in a colorectal cancer model (Baker, Cox et al. 2011). Thus while LOX and LOXL2 are involved in similar extra-cellular processes, it appears that they have distinct roles.

LOXL1 was found to be overexpressed in metastatic non-small cells lung cancer (NSCLC), and the metastatic phenotype can be reduced by inhibition with LOXL1 siRNA (Lee, Kim et al. 2011).

LOXL3 mRNA was expressed in Hs578T highly invasive breast cancer cells, but not in poorly invasive and non-metastatic breast cancer cells MCF7 and T47D (Kirschmann, Seftor et al. 2002). Overexpression of LOXL3 in MDCK epithelial cells induces an epithelial-mesenchymal transition (EMT) process, which is a key step in the progression of metastasis (Peinado, Del Carmen Iglesias-de la Cruz et al. 2005).

In a study on the mRNA levels of LOXL4 in head and neck squamous cell carcinomas, high expression of LOXL4 gene was detected in 71% of all carcinomas and only in 9% of the healthy mucosa samples, indicating that LOXL4 may serve as a selective molecular marker in primary and metastatic head and neck carcinoma (Scola and Gorogh 2010). Up-regulation of LOXL4 was demonstrated in invasive HNC and revealed a significant correlation between LOXL4 expression and local lymph node metastases and higher tumour stages (Goeroegh, Weise et al. 2007). LOXL4 promotes metastasis in gastric cancer (Li, Zhao et al. 2015). LOXL4 together with LOXL2 has been found to be required for metastatic niche formation in a breast orthotopic mouse model (Wong, Gilkes et al. 2011).

LOX and LOXL are implicated in fibrotic diseases, such as liver fibrosis, lung fibrosis, kidney fibrosis, cardiac fibrosis, myelofibrosis and scleroderma. Both LOX and LOXL are highly expressed in fibrotic areas, in surrounding myofibroblasts and in serum of patients with fibrotic conditions (Kagan 1994) (Kim, Peyrol et al. 1999) (Siegel, Chen et al. 1978) (Jourdan-Le Saux, Gleyzal et al. 1994) (Murawaki, Kusakabe et al. 1991).

LOX is also implicated in cardiovascular disease. As discussed in the detailed description of the invention, LOX inhibition may prove beneficial in the treatment or prevention of cardiovascular conditions, including hypertensive heart disease, heart failure, cardiac hypertrophy and atherosclerosis.

LOX is associated with the amyloid-beta (As) related pathological hallmarks (such as cerebral amyloid angiopathy and senile plaques) of both Alzheimer's disease (AD) and hereditary cerebral hemorrhage with amyloidosis of the Dutch type (HCHWA-D) pathogenesis (Wilhelmus, Bol et al. 2013). LOX activity is increased in the hippocampal samples of Alzheimer's disease and also in non-Alzheimer's dementia (Gilad, Kagan et al. 2005). LOX is increased at the site of brain injury (Gilad, Kagan et al. 2001) and spinal cord injury and its inhibition lead to accelerated functional recovery in an unilateral spinal cord dissection model (Gilad and Gilad 2001).

LOXLs are implicated in pulmonary diseases. LOXL2 and LOXL3 are likely to have a role in Primary Alveolar Proteinosis (PAP) since both are expressed in PAP tissue, but not normal lung tissue (Neufeld and Brekhman 2009).

LOX inhibition may be beneficial in the treatment of various ocular conditions. Inhibition of LOX or LOXL2 prevents neovascularization and fibrosis following laser-induced choroidal neovascularization (CNV). Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010).

LOX is implicated in inflammatory conditions and may be useful in the treatment of conditions including, but not limited to acute respiratory distress syndrome (ARDS) (Mambetsariev, Tian et al. 2014).

LOX is the main isoenzyme expressed in human adipose tissue and that its expression is strongly upregulated in samples from obese patients. s-aminopropionitrile reduces body weight gain and improves the metabolic profile in diet-induced obesity in rats (Miana, Galan et al. 2015) and reduces local adipose tissue inflammation (Halberg, Khan et al. 2009).

LOX is upregulated in endometriosis and may be implicated in the establishment and progression of endometriotic lesions (Ruiz, Dutil et al. 2011) (Dentillo, Meola et al. 2010).

Certain LOX inhibitors are known. These include β-aminopropionitrile (BAPN), haloamines, 1,2-diamines, allyl and propargyl amines, hydrazines, semicarbazide and thiolactones, benzylamines, mercaptopyridine and pyridazinone compounds (Pinnell and Martin 1968) (Tang, Simpson et al. 1984) (Palfreyman, McDonald et al. 1989) (Sayre 2007) (Carrington, Bird et al. 1984) (Levene, Sharman et al. 1992) (Liu, Nellaiappan et al. 1997) (Williamson and Kagan 1987) (Anderson, Bartlett et al. 2007) (Schohe-Loop, Burchardt et al. 2003) (Burchardt 2006, Aslam, Miele et al. 2015). However, in general these compounds are either non-selective, lack potency or are unsuitable for use in patients. It is believed that the only LOX inhibitor which has progressed to clinical trials in humans is BAPN. However, it is believed that this compound has not been used clinically since 1978. More recent LOX and LOXL2 inhibitors have been described: LOX inhibitors containing hydrazine and hydrazide groups (Burke et al, 2017); LOXL2 inhibitors: derivatives of haloallylamine (Chang et al, 2017), pyridines (Rowbottom et al, 2016a; Rowbottom et al, 2016b), pyrimidines (Rowbottom & Hutchinson, 2017a) and chromenones (Rowbottom & Hutchinson, 2017b).

There is therefore a need for new LOX inhibitors.

BRIEF SUMMARY OF THE DISCLOSURE

In accordance with the present invention there is provided a compound of Formula (I):

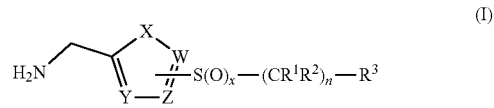

wherein:

X is selected from the group consisting of: S, $NR^N$ and O; wherein $R^N$ is selected from the group consisting of: H, $C_{1-4}$ alkyl, $C_{1-4}$ haloalkyl and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, =O, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl; Y is selected from the group consisting of: N and CR; wherein R is selected from the group consisting of: H, halo, $C_{1-4}$ alkyl, $C_{1-4}$ haloalkyl, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, =O, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl; one of W and Z is carbon and is bonded to the

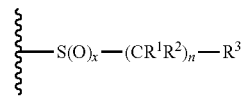

residue and the other of W and Z is selected from the group consisting of: N and CR; wherein R is selected from the group consisting of: H, halo, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{3-6}$ cycloalkyl groups are themselves optionally substituted with a substituent selected from the group consisting of: $R^{A1}$, halo, $-OR^{A1}$, $=O$, $-NR^{A1}R^{B1}$, $-SR^{A1}$, CN, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

x is 1 or 2;

n is 0, 1, 2, 3, 4, 5 or 6;

$R^1$ and $R^2$ are independently selected at each occurrence from: H, halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, or together $R^1$ and $R^2$ are $=O$, wherein the $C_{1-4}$ alkyl, $C_{1-4}$ haloalkyl and $C_{3-6}$ cycloalkyl groups are themselves optionally substituted with $R^{A1}$, halo, $-OR^{A1}$, $=O$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

when n is 0, $R^3$ is optionally substituted 3- to 15-membered ring system, including 0, 1, 2 or 3 heteroatoms selected from N, O or S, wherein the ring system is connected to the remainder of the compound of Formula (I) via a carbon atom, and when n is 1, 2, 3, 4, 5 or 6 $R^3$ is selected from the group consisting of optionally substituted 3- to 15-membered ring system, including 0, 1, 2 or 3 heteroatoms selected from N, O or S, halo, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$ and $-C(O)OR^{A1}$; and $R^{A1}$ and $R^{B1}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A1}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group $-NR^{A1}R^{B1}$, $R^{A1}$ and $R^{B1}$, together with the nitrogen atom to which they are bonded can form a 4- to 7-membered ring system; and wherein in the specific group $-NR^{A5}R^{B5}$, $R^{A5}$ and $R^{B5}$, together with the nitrogen atom to which they are bonded can form a 4- to 7-membered ring system;

with the proviso that the following compounds are excluded:

(i)

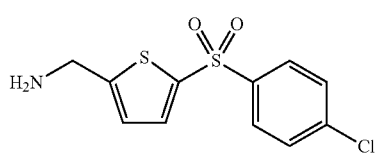

(ii)

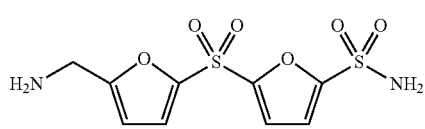

-continued (iii)

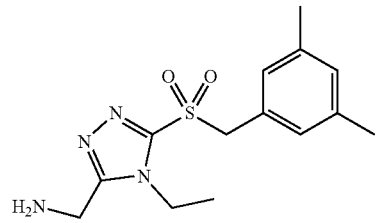

(iv)

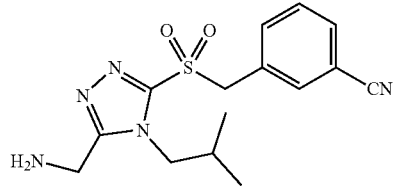

(v)

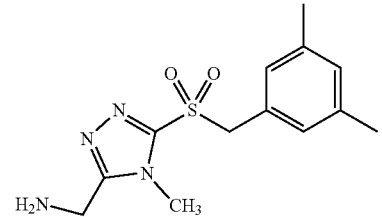

(vi)

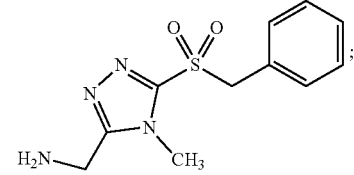

or a pharmaceutically acceptable salt thereof.

In accordance with the present invention there is also provided a compound of Formula (I):

(I)

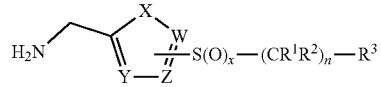

wherein:

X is selected from the group consisting of: S, $NR^N$ and O; wherein $R^N$ is selected from the group consisting of: H, $C_{1-4}$ alkyl, $C_{1-4}$ haloalkyl and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, $=O$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

Y is selected from the group consisting of: N and CR;

one of W and Z is carbon and is bonded to the

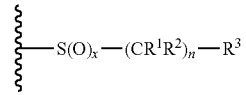

residue and the other of W and Z is selected from the group consisting of: N and CR; wherein:

each R is independently selected from the group consisting of: H, halo, $C_{1-4}$ alkyl, $C_{1-4}$ haloalkyl, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, $=O$, $-NR^{A1}R^{B1}$, $-SR^{A1}$, CN, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

x is 1 or 2;

n is 0, 1, 2, 3, 4, 5 or 6;

$R^1$ and $R^2$ are independently selected at each occurrence from: H, halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, or together $R^1$ and $R^2$ are $=O$, wherein the $C_{1-4}$ alkyl, $C_{1-4}$ haloalkyl and $C_{3-6}$ cycloalkyl groups are themselves optionally substituted with $R^{A1}$, halo, $-OR^{A1}$, $=O$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

when n is 0, $R^3$ is optionally substituted 3- to 15-membered ring system, including 0, 1, 2 or 3 heteroatoms selected from N, O or S, wherein the ring system is connected to the remainder of the compound of Formula (I) via a carbon atom, and when n is 1, 2, 3, 4, 5 or 6 $R^3$ is selected from the group consisting of optionally substituted 3- to 15-membered ring system, including 0, 1, 2 or 3 heteroatoms selected from N, O or S, halo, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$ and $-C(O)OR^{A1}$; and $R^{A1}$ and $R^{B1}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group $-NR^{A1}R^{B1}$, $R^{A1}$ and $R^{B1}$, together with the nitrogen atom to which they are bonded can form a 4- to 7-membered ring system; and wherein in the specific group $-NR^{A5}R^{B5}$, $R^{A5}$ and $R^{B5}$, together with the nitrogen atom to which they are bonded can form a 4- to 7-membered ring system;

with the proviso that the following compounds are excluded:

(i)

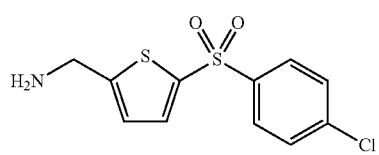

(ii)

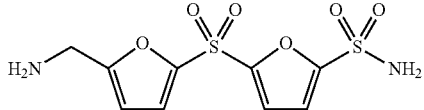

(iii)

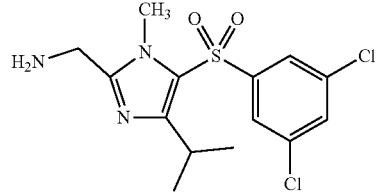

(iv)

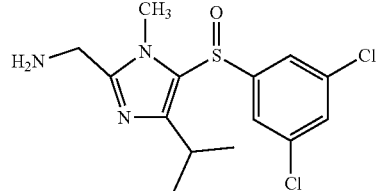

(v)

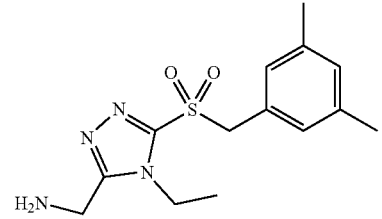

(vi)

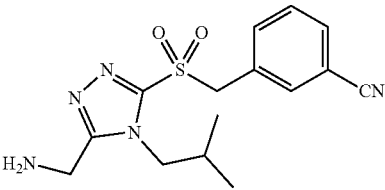

(vii)

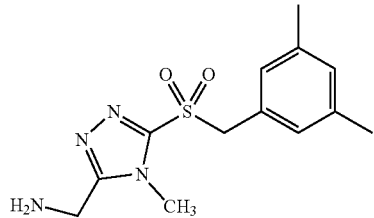

(viii)

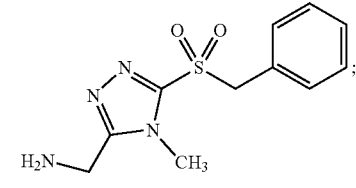

or a pharmaceutically acceptable salt thereof.

Generally Applicable Embodiments

In an embodiment, X is selected from the group consisting of: S, $NR^N$ and O; wherein $R^N$ is selected from the group consisting of: H, $C_{1-4}$ alkyl and $C_{1-4}$ haloalkyl, wherein the $C_{1-4}$ alkyl and $C_{1-4}$ haloalkyl groups are themselves optionally substituted with a substituent selected from the group consisting of: $R^{A1}$, halo, —$OR^{A1}$, =O, —$NR^{A1}R^{B1}$, —$SR^{A1}$, —CN, —$NO_2$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$, —C(O)$OR^{A1}$ and $C_{3-6}$ cycloalkyl.

In an embodiment, X is selected from the group consisting of: S, NH and O.

In an embodiment, one of W and Z is carbon and is bonded to the

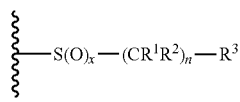

residue and the other of W and Z is selected from the group consisting of: N and CR; wherein R is selected from the group consisting of: H, halo, —$OR^{A1}$, —$NR^{A1}R^{B1}$, —$SR^{A1}$, —CN, —$NO_2$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$ and —C(O)$OR^{A1}$.

In an embodiment, one of W and Z is carbon and is bonded to the

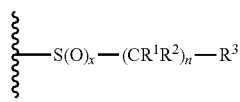

residue and the other of W and Z is selected from the group consisting of: N and CH.

In an embodiment, Y is selected from the group consisting of: N and CR; wherein R is selected from the group consisting of: H, halo, —$OR^{A1}$, —$NR^{A1}R^{B1}$, —$SR^{A1}$, —CN, —$NO_2$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$, —C(O)$OR^{A1}$ and $C_{3-6}$ cycloalkyl, wherein the $C_{3-6}$ cycloalkyl groups are themselves optionally substituted with a substituent selected from the group consisting of: $R^{A1}$, halo, —$OR^{A1}$, =O, —$NR^{A1}R^{B1}$, —$SR^{A1}$, CN, —$NO_2$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$, —C(O)$OR^{A1}$ and $C_{3-6}$ cycloalkyl.

In an embodiment, Y is selected from the group consisting of: N and CR; wherein R is selected from the group consisting of: H, halo, —$OR^{A1}$, —$NR^{A1}R^{B1}$, —$SR^{A1}$, —CN, —$NO_2$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$ and —C(O)$OR^{A1}$.

In an embodiment, Y is selected from the group consisting of: N and CH.

In an embodiment, the substituents on the 3- to 15-membered ring system are selected from the group consisting of: halo, $C_{1-4}$ alkyl, $C_{2-4}$ alkenyl, $C_{2-4}$ alkynyl, $C_{1-4}$ haloalkyl, 6-membered aryl, 5- or 6-membered heteroaryl including 1, 2 or 3 heteroatoms selected from the group consisting of O, N or S, —$OR^{A1}$, =O, —$NR^{A1}R^{B1}$, —$SR^{A1}$, —CN, —$NO_2$, —$N_3$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$, —C(O)$OR^{A1}$ and $C_{3-6}$ cycloalkyl, wherein the $C_{1-4}$ alkyl, $C_{2-4}$ alkenyl, $C_{2-4}$ alkynyl, $C_{1-4}$ haloalkyl, 6-membered aryl, 5- or 6-membered heteroaryl and $C_{3-6}$ cycloalkyl groups are optionally substituted with $R^{A1}$, halo, —$OR^{A1}$, =O, —$NR^{A1}R^{B1}$, —$SR^{A1}$, —CN, —$NO_2$, —$N_3$, —$NR^{A1}C(O)R^{B1}$, —C(O)$NR^{A1}R^{B1}$, —$NR^{A1}C(O)OR^{B1}$, —OC(O)$NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —C(O)$R^{A1}$, —C(O)$OR^{A1}$ and $C_{3-6}$ cycloalkyl, wherein in the specific group —$NR^{A1}R^{B1}$, $R^{A1}$ and $R^{B1}$, together with the nitrogen atom to which they are bonded can form a 4- to 7-membered ring system. Further substituents for the 3- to 15-membered ring system are provided in the following embodiments.

The following embodiments are generally applicable throughout the remaining disclosure. Thus, the below listed combinations of W, X, Y and Z are generally applicable to all other recited embodiments.

In an embodiment, W, X, Y and Z are selected per the following table:

| W | X | Y | Z |
|---|---|---|---|
| ⸺S(O)$_x$⸺(CR$^1$R$^2$)$_n$⸺R$^3$ | S | CR | CR |
| ⸺S(O)$_x$⸺(CR$^1$R$^2$)$_n$⸺R$^3$ | S | N | CR |
| ⸺S(O)$_x$⸺(CR$^1$R$^2$)$_n$⸺R$^3$ | S | CR | N |
| ⸺S(O)$_x$⸺(CR$^1$R$^2$)$_n$⸺R$^3$ | S | N | N |
| ⸺S(O)$_x$⸺(CR$^1$R$^2$)$_n$⸺R$^3$ | O | CR | CR |
| ⸺S(O)$_x$⸺(CR$^1$R$^2$)$_n$⸺R$^3$ | O | N | CR |
| ⸺S(O)$_x$⸺(CR$^1$R$^2$)$_n$⸺R$^3$ | O | CR | N |
| ⸺S(O)$_x$⸺(CR$^1$R$^2$)$_n$⸺R$^3$ | O | N | N |
| ⸺S(O)$_x$⸺(CR$^1$R$^2$)$_n$⸺R$^3$ | NR$^N$ | CR | CR |
| ⸺S(O)$_x$⸺(CR$^1$R$^2$)$_n$⸺R$^3$ | NR$^N$ | N | CR |

-continued

| W | X | Y | Z | |
|---|---|---|---|---|
| $-S(O)_x-(CR^1R^2)_n-R^3$ | $NR^N$ | CR | N | |
| $-S(O)_x-(CR^1R^2)_n-R^3$ | $NR^N$ | N | N | |
| | CR | S | CR | $-S(O)_x-(CR^1R^2)_n-R^3$ |
| | CR | S | N | $-S(O)_x-(CR^1R^2)_n-R^3$ |
| | N | S | CR | $-S(O)_x-(CR^1R^2)_n-R^3$ |
| | N | S | N | $-S(O)_x-(CR^1R^2)_n-R^3$ |
| | CR | O | CR | $-S(O)_x-(CR^1R^2)_n-R^3$ |
| | CR | O | N | $-S(O)_x-(CR^1R^2)_n-R^3$ |
| | N | O | CR | $-S(O)_x-(CR^1R^2)_n-R^3$ |
| | N | O | N | $-S(O)_x-(CR^1R^2)_n-R^3$ |
| | CR | $NR^N$ | CR | $-S(O)_x-(CR^1R^2)_n-R^3$ |
| | CR | $NR^N$ | N | $-S(O)_x-(CR^1R^2)_n-R^3$ |
| | N | $NR^N$ | CR | $-S(O)_x-(CR^1R^2)_n-R^3$ |
| | N | $NR^N$ | N | $-S(O)_x-(CR^1R^2)_n-R^3$ |

In the above table, the

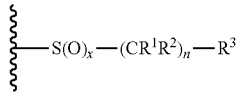

residue of the compound of Formula (I) can be substituted by the analogous portion of the Formulae of the other compounds of the invention, e.g. the compounds of Formulae (II), (Ill), (IV), (Va), (Vb) and (Vc).

The following embodiments are also generally applicable throughout the remaining disclosure. Thus, the following embodiments relating to x are generally applicable to all other recited embodiments. In an embodiment, x is 1. In an embodiment, x is 2. Preferably, x is 2.

In an embodiment, n is 1, 2, 3, 4, 5 or 6. Preferably, n is 1, 2, 3 or 4.

In an embodiment, n is 1, 2, 3, 4, 5 or 6 and $R^3$ is as defined as per the following embodiments:

In an embodiment, $R^3$ is selected from the group consisting of: halo, 6-membered aryl, 5- or 6-membered heteroaryl including 1, 2 or 3 heteroatoms selected from N, O or S, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl. In an embodiment, the 6-membered aryl and 5- or 6-membered heteroaryl groups can be substituted with 1, 2 or 3 substituents selected from the group consisting of: halo, $C_{1-4}$ alkyl, $C_{1-4}$ haloalkyl, $-OR^{A1}$, $-NR^{A1}R^{B1}$, $-CN$, $-NO_2$, $-N_3$, $-NR^{A1}C(O)R^{B1}$, $-C(O)NR^{A1}R^{B1}$, $-NR^{A1}C(O)OR^{B1}$, $-O(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl. The $R^{A1}$ and $R^{B1}$ groups are at each occurrence independently selected from the group consisting of: H, $C_{1-4}$ alkyl and $C_{1-4}$ haloalkyl. In the specific group $-NR^{A1}R^{B1}$, $R^{A1}$ and $R^{B1}$, together with the nitrogen atom to which they are bonded can form a 4- to 7-membered ring system.

In an embodiment, n is 1 and $R^3$ is selected from the group consisting of: halo, 6-membered aryl, 5- or 6-membered heteroaryl including 1, 2 or 3 heteroatoms selected from N, O or S, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl.

In an embodiment, n is 2 and $R^3$ is selected from the group consisting of: halo, 6-membered aryl, 5- or 6-membered heteroaryl including 1, 2 or 3 heteroatoms selected from N, O or S, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl.

In an embodiment, n is 3 and $R^3$ is selected from the group consisting of: halo, 6-membered aryl, 5- or 6-membered heteroaryl including 1, 2 or 3 heteroatoms selected from N, O or S, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl.

In an embodiment, n is 4 and $R^3$ is selected from the group consisting of: halo, 6-membered aryl, 5- or 6-membered heteroaryl including 1, 2 or 3 heteroatoms selected from N, O or S, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl.

In an embodiment, $R^3$ is selected from the group consisting of: halo, 6-membered aryl, 5- or 6-membered heteroaryl including 1, 2 or 3 heteroatoms selected from N, O or S, —OR$^{A1}$, —NR$^{A1}$R$^{B1}$, —CN, —NO$_2$, —SO$_2$R$^{A1}$, —C(O) R$^{A1}$, —C(O)OR$^{A1}$ and C$_{3-6}$ cycloalkyl.

In an embodiment, R$^3$ is 6-membered aryl. In an embodiment, R$^3$ is phenyl.

In an embodiment, R$^3$ is —SO$_2$R$^{A1}$. Preferably, R$^{A1}$ is C$_{1-4}$ alkyl, more preferably methyl.

In an embodiment, R$^3$ is —NR$^{A1}$R$^{B1}$.

In an embodiment, n is 1 and R$^3$ is 6-membered aryl. In an embodiment, n is 1 and R$^3$ is phenyl.

In an embodiment, n is 4 and R$^3$ is —SO$_2$RA. Preferably, R$^{A1}$ is C$_{1-4}$ alkyl, more preferably methyl.

In an embodiment, R$^1$ and R$^2$ are each H.

In an embodiment, n is 0.

In an embodiment, n is 0 and R$^3$ is as defined as per the following embodiments:

In an embodiment, R$^3$ is an unsubstituted or substituted 3- to 15-membered ring system, including 0, 1, 2 or 3 heteroatoms selected from N, O or S, wherein the ring system is connected to the remainder of the compound of Formula (I) via a carbon atom.

In an embodiment, the compound of the present invention has a structure according to Formula (II):

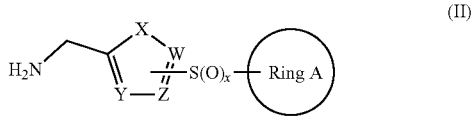

(II)

wherein W, X, Y, Z and x are as defined for the compound of Formula (I) and wherein "Ring A" an unsubstituted or substituted 3- to 15-membered ring system, including 0, 1, 2 or 3 heteroatoms selected from N, O or S, wherein the ring system is connected to the remainder of the compound of Formula (I) via a carbon atom. In an embodiment, "Ring A" an unsubstituted or substituted 3- to 12-membered ring system, including 0, 1, 2 or 3 heteroatoms selected from N, O or S, wherein the ring system is connected to the remainder of the compound of Formula (I) via a carbon atom.

In an embodiment, the 3- to 15-membered ring system, including 0, 1, 2 or 3 heteroatoms selected from N, O or S is substituted with a substituent selected from the group consisting of: halo, C$_{1-4}$ alkyl, C$_{1-4}$ haloalkyl, C$_{1-4}$ alkyl substituted with a substituent selected from the group consisting of: halo, C$_{1-4}$ alkyl, C$_{1-4}$ haloalkyl, —OR$^{A1}$, =O, —NR$^{A1}$R$^{B1}$, —SR$^{A1}$, —CN, —NO$_2$, —N$_3$, —NR$^{A1}$C(O)R$^{B1}$, —C(O)NR$^{A1}$R$^{B1}$, —NR$^{A1}$C(O)OR$^{B1}$, —OC(O)NR$^{A1}$R$^{B1}$, —NR$^{A1}$C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl, 6-membered aryl, 5- or 6-membered heteroaryl including 1, 2 or 3 heteroatoms selected from the group consisting of O, N or S, —OR$^{A1}$, =O, —NR$^{A1}$R$^{B1}$, —SR$^{A1}$, —CN, —NO$_2$, —N$_3$, —NR$^{A1}$C(O)R$^{B1}$, —C(O)NR$^{A1}$R$^{B1}$, —NR$^{A1}$C(O)OR$^{B1}$, —OC(O)NR$^{A1}$R$^{B1}$, —NR$^{A1}$C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl.

In an embodiment, Ring A is an unsubstituted or substituted C$_{3-8}$ cycloalkyl or an unsubstituted or substituted C$_{3-8}$ cycloalkenyl. In an embodiment, Ring A is an unsubstituted or substituted group selected from the group consisting of: cyclopropyl, cyclobutyl, cyclopentyl, cyclohexyl, cycloheptyl, cyclooctyl, cyclopropenyl, cyclobutenyl, cyclopentenyl, cyclopentadienyl, cyclohexenyl, cyclohexadienyl, cycloheptenyl, cycloheptadienyl, cyclooctenyl and cyclooctadienyl.

In a preferred embodiment, Ring A is an unsubstituted or substituted C$_5$ or C$_6$ cycloalkyl. In an embodiment, Ring A is an unsubstituted or substituted cyclohexyl, preferably unsubstituted cyclohexyl.

When Ring A is substituted, the substituents of Ring A are selected from the group consisting of: halo, C$_{1-4}$ alkyl, C$_{1-4}$ haloalkyl, 6-membered aryl, 5- or 6-membered heteroaryl including 1, 2 or 3 heteroatoms selected from N, O or S, —OR$^{A1}$, =O, —NR$^{A1}$R$^{B1}$, —SR$^{A1}$, —CN, —NO$_2$, —NR$^{A1}$C(O)R$^{B1}$, —C(O)NR$^{A1}$R$^{B1}$, —NR$^{A1}$C(O)OR$^{B1}$, —OC(O)NR$^{A1}$R$^{B1}$, —NR$^{A1}$C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl, wherein the C$_{1-4}$ alkyl, C$_{1-4}$ haloalkyl, 6-membered aryl, 5- or 6-membered heteroaryl and C$_{3-6}$ cycloalkyl groups are (where chemically possible) optionally substituted with a substituent selected from the group consisting of: R$^{A1}$, halo, —OR$^{A1}$, =O, —NR$^{A1}$R$^{B1}$, —SR$^{A1}$, —CN, —NO$_2$, —N$_3$, —NR$^{A1}$C(O)R$^{B1}$, —C(O)NR$^{A1}$R$^{B1}$, —NR$^{A1}$C(O)OR$^{B1}$, —OC(O)NR$^{A1}$R$^{B1}$, —NR$^{A1}$C(O)NR$^{A1}$R$^{B1}$, —NR$^{A1}$SO$_2$R$^{B1}$, —SO$_2$NR$^{A1}$R$^{B1}$, —SO$_2$R$^{A1}$, —C(O)R$^{A1}$, —C(O)OR$^{A1}$ and C$_{3-6}$ cycloalkyl, R$^{A1}$ and R$^{B1}$ are at each occurrence independently selected from the group consisting of: H, C$_{1-4}$ alkyl, C$_{1-4}$ haloalkyl, C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl. In the specific group —NR$^{A1}$R$^{B1}$, R$^{A1}$ and R$^{B1}$, together with the nitrogen atom to which they are bonded can form a 4- to 7-membered ring system. In the specific group —NR$^{A5}$R$^{B5}$, R$^{A5}$ and R$^{B5}$, together with the nitrogen atom to which they are bonded can form a 4- to 7-membered ring system.

When Ring A is substituted, the substituents of Ring A are preferably selected from the group consisting of: halo, 6-membered aryl, —OR$^{A1}$ and —NR$^{A1}$SO$_2$R$^{B1}$, wherein R$^{A1}$ and R$^{B1}$ are at each occurrence independently selected from the group consisting of: H, C$_{1-4}$ alkyl, C$_{1-4}$ haloalkyl, C$_{1-4}$ alkyl substituted with OH. Preferably R$^{A1}$ and R$^{B1}$ are at each occurrence independently selected from the group consisting of: H and C$_{1-4}$ alkyl.

In an embodiment, Ring A is an unsubstituted or substituted 5- to 10-membered ring system, including 0, 1, 2 or 3 heteroatoms selected from N, O or S, wherein the ring system is connected to the remainder of the compound of Formula (I) via a carbon atom.

In an embodiment Ring A is an unsubstituted or substituted group selected from the group consisting of: indanyl, indenyl, tetralinyl, oxiranyl, aziridinyl, azetidinyl, oxetanyl, tetrahydrofuranyl, pyrrolidinyl, pyrrolinyl, imidazolidinyl, imidazolinyl, succinimidyl, pyrazolidinyl, pyrazolinyl, oxazolidinyl, oxazolinyl, dioxolanyl, isoxazolidinyl, isoxazolinyl, thiazolidinyl, thiazolinyl, isothiazolidinyl, isothiazolinyl, piperidinyl, morpholinyl, thiomorpholinyl, thiomorpholinyl dioxide, piperazinyl, dioxanyl, dihydropyranyl, tetrahydropyranyl, indolinyl, isoindolinyl, chromenyl, chromanyl, isochromanyl, dihydroquinolinyl, tetrahydroquinolinyl, dihydroisoquinolinyl, tetrahydroisoquinolinyl, phenyl, naphthyl, pyridyl, pyridazinyl, pyrimidinyl, pyrazinyl, thiophenyl, furanyl, pyrrolyl, pyrazolyl, imidazolyl, triazolyl, tetrazolyl, oxazolyl, isoxazolyl, thiazolyl, isothiazolyl, thiadiazolyl, oxadiazolyl, quinolinyl, isoquinolinyl, indolyl, isoindolyl, benzimidazolyl, benzothiophenyl, benzofuranyl, benzothiazolyl and benzoxazolyl.

In an embodiment Ring A is an unsubstituted or substituted 6- to 10-membered aryl or an unsubstituted or substituted 5- to 10-membered heteroaryl including 1, 2 or 3 heteroatoms selected from N, O or S, wherein the ring system is connected to the remainder of the compound of Formula (I) via a carbon atom.

In an embodiment, Ring A is an unsubstituted or substituted 6- to 10-membered aryl. Preferably, Ring A is an unsubstituted or substituted phenyl or unsubstituted or substituted naphthyl.

In an embodiment, Ring A is an unsubstituted or substituted 10- to 14-membered aryl. Preferably, Ring A is an unsubstituted or substituted anthracene.

In an embodiment, Ring A is an unsubstituted or substituted 5- to 10-membered heteroaryl including 1, 2 or 3 heteroatoms selected from N, O or S. In an embodiment, Ring A is an unsubstituted or substituted heteroaryl group selected from the group consisting of: pyridyl, pyridazinyl, pyrimidinyl, pyrazinyl, thiophenyl, furanyl, pyrrolyl, pyrazolyl, imidazolyl, triazolyl, oxazolyl, isoxazolyl, thiazolyl, isothiazolyl, thiadiazolyl, oxadiazolyl, quinolinyl, isoquinolinyl, indolyl, isoindolyl, benzimidazolyl, benzothiophenyl, benzofuranyl, benzothiazolyl and benzoxazolyl. Preferably, Ring A is unsubstituted or substituted thiophenyl or pyridyl. Preferably, Ring A is an unsubstituted or substituted tetralinyl, quinolinyl, pyrazolyl or pyrimidinyl.

When Ring A is substituted, the substituents of Ring A are selected from the group consisting of: halo, $C_{1-4}$ alkyl, $C_{2-4}$ alkenyl, $C_{2-4}$ alkynyl, $C_{1-4}$ haloalkyl, 6-membered aryl, 5- or 6-membered heteroaryl including 1, 2 or 3 heteroatoms selected from N, O or S, $-OR^{A1}$, $-NR^{A1}R^{B1}$, $-SR^{A1}$, $-CN$, $-NO_2$, $-N_3$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{1-4}$ alkyl, $C_{2-4}$ alkenyl, $C_{2-4}$ alkynyl, $C_{1-4}$ haloalkyl, 6-membered aryl, 5- or 6-membered heteroaryl and $C_{3-6}$ cycloalkyl groups are optionally substituted with a substituent selected from the group consisting of: $R^{A1}$, halo, $-OR^{A1}$, $=O$, $-NR^{A1}R^{B1}$, $-SR^{A1}$, $-CN$, $-NO_2$, $-N_3$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein $R^{A1}$ and $R^{B1}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In the specific group $-NR^{A1}R^{B1}$, $R^{A1}$ and $R^{B1}$, together with the nitrogen atom to which they are bonded can form a 4- to 7-membered ring system. In the specific group $-NR^{A1}R^{B5}$, $R^{A5}$ and $R^{B5}$, together with the nitrogen atom to which they are bonded can form a 4- to 7-membered ring system. The 4- to 7-membered ring system that is formed by $R^{A1}$, $R^{B1}$ and the nitrogen atom to which they are bonded or formed by $R^{A5}$, $R^{B5}$ and the nitrogen atom to which they are bonded can optionally be substituted by a 6-membered aryl or a 5- or 6-membered heteroaryl including 1, 2 or 3 heteroatoms selected from N, O or S.

When Ring A is substituted, the substituents of Ring A are preferably selected from the group consisting of: halo (e.g. F, Cl, Br or I), 6-membered aryl, $-OR^{A1}$, $-SO_2R^{A1}$ and $-NR^{A1}SO_2R^{B1}$, wherein $R^{A1}$ and $R^{B1}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A1}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-14}$ alkyl, preferably H. In the specific group $-NR^{A5}R^{B5}$, $R^{A5}$ and $R^{B5}$, together with the nitrogen atom to which they are bonded can form a 4- to 7-membered ring system. Preferably $R^{A1}$ and $R^{B1}$ are at each occurrence independently selected from the group consisting of: H and $C_{1-4}$ alkyl. More preferably $R^{A1}$ and $R^{B1}$ are at each occurrence independently selected from the group consisting of: H and $C_1$ alkyl.

When Ring A is substituted, the substituents of Ring A are preferably selected from the group consisting of: halo (e.g. F, Cl, Br or I), $C_{1-4}$ alkyl, $C_{1-4}$ haloalkyl, 6-membered aryl, 5- or 6-membered heteroaryl including 1, 2 or 3 heteroatoms selected from N, O or S, $-OR^{A1}$, $-NR^{A1}R^{B1}$, $-C(O)NR^{A1}R^{B1}$, $-SO_2NR^{A1}R^{B1}$, $-SO_2R^{A1}$ and $-C(O)OR^{A1}$, wherein the $C_{1-4}$ alkyl, $C_{1-4}$ haloalkyl, 6-membered aryl and 5- or 6-membered heteroaryl are optionally substituted with a substituent selected from the group consisting of: $R^{A1}$, halo and $C_{3-6}$ cycloalkyl, wherein $R^{A1}$ and $R^{B1}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In the specific group $-NR^{A1}R^{B1}$, $R^{A1}$ and $R^{B1}$, together with the nitrogen atom to which they are bonded can form a 4- to 7-membered ring system. In the specific group $-NR^{A5}R^{B5}$, $R^{A5}$ and $R^{B5}$, together with the nitrogen atom to which they are bonded can form a 4- to 7-membered ring system. The 4- to 7-membered ring system that is formed by $R^{A1}$, $R^{B1}$ and the nitrogen atom to which they are bonded or formed by $R^{A5}$, $R^{B5}$ and the nitrogen atom to which they are bonded can optionally be substituted by a 6-membered aryl or a 5- or 6-membered heteroaryl including 1, 2 or 3 heteroatoms selected from N, O or S.

In an embodiment, Ring A is an unsubstituted or substituted 6- to 10-membered aryl. Preferably, Ring A is an unsubstituted or substituted phenyl.

In an embodiment, the compound of the present invention has a structure according to Formula (III):

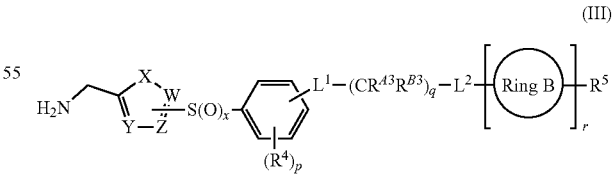

(III)

wherein W, X, Y, Z and x are as defined for the compound of Formula (I);

$R^4$ is independently at each occurrence selected from the group consisting of: halo, $C_{1-4}$ alkyl, $C_{2-4}$ alkenyl, $C_{2-4}$ alkynyl (optionally substituted with trimethylsilyl—TMS), $C_{1-4}$ haloalkyl, 6-membered aryl, 5- or 6-membered heteroaryl including 1, 2 or 3 heteroatoms selected from N, O or S, —OR$^{A2}$, —NR$^{A2}$R$^{B2}$, —SR$^{A2}$, —CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A1}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein the C$_{1-4}$ alkyl, C$_{2-4}$ alkenyl, C$_{2-4}$ alkynyl, C$_{1-4}$ haloalkyl, 6-membered aryl, 5- or 6-membered heteroaryl and C$_{3-6}$ cycloalkyl groups are optionally substituted with R$^{A2}$, halo, —OR$^{A2}$, =O, —NR$^{A2}$R$^{B2}$, —SR$^{A1}$, —CN, —NO$_2$, —N$_3$, —NR$^{A1}$C(O)R$^{B2}$, —C(O)NR$^{A1}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein R$^{A2}$ and R$^{B2}$ are at each occurrence independently selected from the group consisting of: H, C$_{1-4}$ alkyl, C$_{1-4}$ haloalkyl, 6-membered aryl, 5- or 6-membered heteroaryl including 1, 2 or 3 heteroatoms selected from the group consisting of O, N or S and C$_{3-6}$ cycloalkyl, wherein the C$_{1-4}$ alkyl, C$_{1-4}$ haloalkyl, 6-membered aryl, 5- or 6-membered heteroaryl and C$_{3-6}$ cycloalkyl groups are themselves optionally substituted with a substituent selected from the group consisting of —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl; wherein in the specific group —NR$^{A1}$R$^{B2}$, R$^{A1}$ and R$^{B2}$, together with the nitrogen atom to which they are bonded can form a 4- to 7-membered ring system; and wherein in the specific group —NR$^{A5}$R$^{B5}$, R$^{A5}$ and R$^{B5}$, together with the nitrogen atom to which they are bonded can form a 4- to 7-membered ring system;

p is 0, 1 or 2;

L$^1$ is a linker moiety selected from the group consisting of: a bond, —O—, —NR$^{A2}$—, —S—, —NR$^{A2}$C(O)—, —NR$^{A2}$C(O)O—, NR$^{A2}$C(O)NR$^{B2}$—, —C(O)NR$^{A2}$—, —OC(O)NR$^{A2}$—, —NR$^{A2}$SO$_2$—, —SO$_2$NR$^{A2}$—, —SO$_2$—, —C(O)—, —C(O)O—, —OC(O)—;

R$^{A3}$ and R$^{B3}$ are each independently selected at each occurrence from the group consisting of: H, halo, C$_{1-4}$ alkyl, C$_{1-4}$ haloalkyl, —OR$^{A2}$, —NR$^{A2}$R$^{B2}$, —CN, —NO$_2$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, or together R$^{A3}$ and R$^{B3}$ are =O, wherein the C$_{1-4}$ alkyl, C$_{1-4}$ haloalkyl and C$_{3-6}$ cycloalkyl groups are themselves optionally substituted with R$^{A2}$, halo, —OR$^{A2}$, =O, —NR$^{A2}$R$^{B2}$, —SR$^{A2}$, —CN, —NO$_2$, —NR$^{A2}$C(O)R$^{B2}$, —C(O)NR$^{A2}$R$^{B2}$, —NR$^2$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A1}$R$^{B2}$, —SO$_2$R$^{A2}$, —C(O)R$^{A2}$, —C(O)OR$^{A2}$ and C$_{3-6}$ cycloalkyl;

q is 0, 1, 2, 3 or 4;

L$^2$ is a linker moiety selected from the group consisting of: a bond, —O—, —NR$^{A2}$—, —S—, —NR$^{A2}$C(O)—, —NR$^{A2}$C(O)O—, NR$^{A2}$C(O)NR$^{B2}$—, —C(O)NR$^{A2}$—, —OC(O)NR$^{A2}$—, —NR$^{A2}$SO$_2$—, —SO$_2$NR$^{A2}$—, —SO$_2$—, —C(O)—, —C(O)O—, —OC(O)—;

r is 0 or 1;

"Ring B" is an unsubstituted 3- to 12-membered ring system, including 0, 1, 2 or 3 heteroatoms selected from N, O or S, or substituted 3- to 12-membered ring system, including 0, 1, 2 or 3 heteroatoms selected from N, O or S which is substituted with a substituent selected from the group consisting of: halo, C$_{1-4}$ alkyl, C$_{1-4}$ haloalkyl, 6-membered aryl, 5- or 6-membered heteroaryl including 1, 2 or 3 heteroatoms selected from the group consisting of O, N or S, —OR$^{A2}$, =O, —NR$^{A2}$R$^{B2}$, —SR$^{A2}$, —CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A1}$R$^{B2}$, —SO$_2$R$^{A2}$, —C(O)R$^{A2}$, —C(O)OR$^{A2}$ and C$_{3-6}$ cycloalkyl, wherein the C$_{1-4}$ alkyl, C$_{1-4}$ haloalkyl, 6-membered aryl, 5- or 6-membered heteroaryl and C$_{3-6}$ cycloalkyl groups are themselves optionally substituted with R$^{A2}$, halo, —OR$^{A2}$, =O, —NR$^{A2}$R$^{B2}$, —SR$^{A2}$, —CN, —NO$_2$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A1}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl;

R$^5$ is selected from the group consisting of: H, halo, C$_{1-4}$ alkyl, C$_{1-4}$ haloalkyl, —OR$^{A2}$, —NR$^{A2}$R$^{B2}$, —SR$^{A2}$ CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A1}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$, C$_{3-6}$ cycloalkyl, wherein the C$_{1-4}$ alkyl, C$_{1-4}$ haloalkyl and C$_{3-6}$ cycloalkyl groups are themselves optionally substituted with a substituent selected from the group consisting of: R$^{A2}$, halo, —OR$^{A2}$, =O, —NR$^{A2}$R$^{B2}$, —SR$^{A2}$, —CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl.

For the absence of doubt, when L$^1$ is a bond, L$^2$ is a bond and q is 0, the moiety -L$^1$-(CR$^{A3}$R$^{B3}$)$_q$-L$^2$- is a single bond.

In an embodiment, p is 0.

In an embodiment, p is 1 and R$^4$ is selected from the group consisting of halo, C$_{1-4}$ alkyl, C$_{1-4}$ haloalkyl, —OR$^{A2}$, —NR$^{A2}$R$^{B2}$, —CN, —NO$_2$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein R$^{A2}$ and R$^{B2}$ are at each occurrence independently selected from the group consisting of: H, C$_{1-4}$ alkyl, C$_{1-4}$ haloalkyl and C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A1}$ and C$_{3-6}$ cycloalkyl, wherein R$^{A5}$ and R$^{B5}$ are each independently selected from the group consisting of H and C$_{1-4}$ alkyl.

In an embodiment, p is 1 and R$^4$ is selected from the group consisting of halo, C$_{1-4}$ alkyl, C$_{1-4}$ haloalkyl, —OR$^{A2}$, —NR$^{A2}$R$^{B2}$, —C(O)NR$^{A2}$R$^{B2}$, —SO$_2$R$^{A2}$ and —C(O)OR$^{A2}$, wherein the C$_{1-4}$ alkyl and C$_{1-4}$ haloalkyl are optionally substituted with R$^{A2}$, halo, —OR$^{A2}$, =O, —NR$^{A2}$R$^{B2}$, —SR$^{A2}$, —CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein R$^{A2}$ and R$^{B2}$ are at each occurrence independently selected from the group consisting of: H, C$_{1-4}$ alkyl, C$_{1-4}$ haloalkyl, 6-membered aryl, 5- or 6-membered heteroaryl including 1, 2 or 3 heteroatoms selected from the group consisting of O, N or S and C$_{3-6}$ cycloalkyl, wherein the C$_{1-4}$ alkyl, C$_{1-4}$ haloalkyl, 6-membered aryl, 5- or 6-membered heteroaryl and C$_{3-6}$ cycloalkyl groups are themselves optionally substituted with a substituent selected from the group consisting of —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl; wherein in the specific group —NR$^{A2}$R$^{B2}$, R$^{A2}$ and R$^{B2}$, together with the nitrogen atom to which they are bonded can form a 4- to 7-membered ring system; and wherein in the specific group —NR$^{A5}$R$^{B5}$, R$^{A5}$ and R$^{B5}$, together with the nitrogen atom to which they are bonded can form a 4- to 7-membered ring system.

In an embodiment, $L^1$ is a linker moiety selected from the group consisting of: $-NR^{A2}C(O)-$, $-C(O)NR^{A2}-$, $-NR^{A2}C(O)NR^{B2}-$, $-NR^{A2}SO_2-$, $-SO_2NR^{A2}-$, $-C(O)-$, $-C(O)O-$ and $-OC(O)-$, wherein $R^{A2}$ and $R^{B2}$ are each independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $L^1$ is a linker moiety selected from the group consisting of: $-C(O)NR^{A2}-$, $-C(O)-$ and $-C(O)O-$, wherein $R^{A2}$ is selected from the group consisting of: H, $C_{1-4}$ alkyl, $C_{1-4}$ haloalkyl and $C_{1-4}$ alkyl substituted with a substituent selected from the group consisting of: $-OR^{A1}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^{A2}$ is H.

In an embodiment, $L^1$ is a bond.

In an embodiment, q is 0.

In an embodiment, q is 1, 2, 3 or 4. Preferably, q is 1 or 2. More preferably, q is 2.

In an embodiment, $R^{A3}$ and $R^{B3}$ are each independently selected from the group consisting of: H, halo, $C_{1-4}$ alkyl and $C_{1-4}$ haloalkyl. Preferably, $R^{A3}$ and $R^{B3}$ are each H.

In an embodiment, $L^2$ is a bond.

In an embodiment, $L^2$ is a linker moiety selected from the group consisting of: $-NR^{A2}C(O)-$, $-C(O)NR^{A2}-$, $-NR^{A1}SO_2-$, $-SO_2NR^{A1}-$ and $-SO_2-$. Preferably, $L^2$ is $-SO_2-$.

In an embodiment, r is 0.

In an embodiment, r is 1. In an embodiment, Ring B is an unsubstituted or substituted 6- to 10-membered aryl or an unsubstituted or substituted 5- to 10-membered heteroaryl including 1, 2 or 3 heteroatoms selected from N, O or S. In an embodiment, Ring B is an unsubstituted or substituted 6- to 10-membered aryl. Preferably, Ring B is an unsubstituted or substituted phenyl. In an embodiment, Ring B is an unsubstituted or substituted 5- to 10-membered heteroaryl including 1, 2 or 3 heteroatoms selected from N, O or S. Preferably, Ring B is an unsubstituted or substituted pyrazolyl, an unsubstituted or substituted isoxazolyl, an unsubstituted or substituted pyridinyl, an unsubstituted or substituted thiophenyl, an unsubstituted or substituted imidazole. In an embodiment, Ring B is an unsubstituted or substituted 4- to 10-membered heterocycloalkyl including 1, 2 or 3 heteroatoms selected from N, O or S. Preferably, Ring B is an unsubstituted or substituted 5-membered heterocycloalkyl including 1, 2 or 3 heteroatoms selected from N, O or S. More preferably Ring B is pyrrolidinyl.

When Ring B is substituted, the substituents of Ring B are selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

When Ring B is substituted, the substituents of Ring B are preferably selected from the group consisting of: halo, 6-membered aryl, $-OR^{A2}$, $-SO_2R^{A2}$, $-C(O)OR^{A2}$ and $-NR^{A2}SO_2R^{B2}$, wherein $R^{A1}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. Preferably $R^{A2}$ and $R^{B2}$ are at each occurrence independently selected from the group consisting of: H and $C_{1-4}$ alkyl.

When Ring B is substituted, the substituents of Ring B are selected from the group consisting of: halo, oxide, $C_{1-4}$ alkyl, $C_{1-4}$ haloalkyl, $C_{3-6}$ cycloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, Ring B is an unsubstituted phenyl.

In an embodiment, $R^5$ is selected from the group consisting of: H, $C_{1-4}$ alkyl, $C_{1-4}$ haloalkyl, $-O-C_{1-4}$ alkyl, $-O-C_{1-4}$ haloalkyl, $-OR^{A2}$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$ and $-C(O)OR^{A2}$, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^5$ is selected from the group consisting of: H, $C_{1-4}$ alkyl, $-OR^{A2}$, and $-C(O)OR^{A2}$, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, p is 0 and $L^1$, q, $R^{A3}$, $R^{B3}$ $L^2$, r, Ring B and $R^5$ are as defined as per the following embodiments.

In an embodiment, $L^1$ is a linker moiety selected from the group consisting of: $-NR^{A2}C(O)-$, $-C(O)NR^{A2}-$, $-NR^{A2}C(O)NR^{B2}-$, $-NR^{A2}SO_2-$, $-SO_2NR^{A2}-$, $-SO_2-$, $-C(O)-$, $-C(O)O-$ and $-OC(O)-$. In an embodiment, $L^1$ is a linker moiety selected from the group consisting of: $-C(O)NR^{A2}-$, $-C(O)-$ and $-C(O)O-$. In an embodiment, $R^{A2}$ and $R^{B2}$ are each independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{85}$ are each independently selected from the group consisting of H and C$_{1-4}$ alkyl. In an embodiment, R$^{A2}$ is H.

In an embodiment, L$^1$ is a linker moiety selected from the group consisting of: —C(O)NR$^{A2}$—, —C(O)— and —C(O)O— and q, R$^{A3}$, R$^{B3}$, L$^2$, r, Ring B and R$^5$ are as defined as per the following embodiments.

In an embodiment, q is 0.

In an embodiment, q is 1 or 2. More preferably, q is 2.

In an embodiment, q is 0 and L$^2$, r, Ring B and R$^5$ are as defined as per the following embodiments. In an alternative embodiment, q is 1 or 2 and R$^{A3}$, R$^{B3}$, L$^2$, r, Ring B and R$^5$ are as defined as per the following embodiments.

In an embodiment, R$^{A3}$ and R$^{B3}$ are each independently selected from the group consisting of: H, halo, C$_{1-4}$ alkyl and C$_{1-4}$ haloalkyl. Preferably, R$^{A3}$ and R$^{B3}$ are each H.

In an embodiment, R$^{A3}$ and R$^{B3}$ are each independently selected from the group consisting of: H, halo, C$_{1-4}$ alkyl and C$_{1-4}$ haloalkyl and L$^2$, r, Ring B and R$^5$ are as defined as per the following embodiments. In an embodiment, R$^{A3}$ and R$^{B3}$ are each H and L$^2$, r, Ring B and R$^5$ are as defined as per the following embodiments.

In an embodiment, L$^2$ is a linker moiety selected from the group consisting of: a bond, NR$^{A2}$C(O)—, —C(O)NR$^{A2}$—, —NR$^{A2}$SO$_2$—, —SO$_2$NR$^{A2}$— and —SO$_2$—. In an embodiment, L$^2$ is a bond. In an embodiment, L$^2$ is —SO$_2$—.

In an embodiment, L$^2$ is a bond and r, Ring B and R$^5$ are as defined as per the following embodiments. In an alternative embodiment, L$^2$ is —SO$_2$— and r, Ring B and R$^5$ are as defined as per the following embodiments.

In an embodiment, r is 0 and R$^5$ is as defined as per the following embodiments. In an alternative embodiment, r is 1 and Ring B and R$^5$ are as defined as per the following embodiments.

In an embodiment, Ring B is an unsubstituted or substituted 6- to 10-membered aryl or an unsubstituted or substituted 5- to 10-membered heteroaryl including 1, 2 or 3 heteroatoms selected from N, O or S. In an embodiment, Ring B is an unsubstituted or substituted 6- to 10-membered aryl. Preferably, Ring B is an unsubstituted or substituted phenyl. More preferably, Ring B is an unsubstituted phenyl.

In an embodiment, Ring B is an unsubstituted or substituted 4- to 10-membered heterocycloalkyl including 1, 2 or 3 heteroatoms selected from N, O or S. Preferably, Ring B is an unsubstituted or substituted 5-membered heterocycloalkyl including 1, 2 or 3 heteroatoms selected from N, O or S, more preferably Ring B is pyrrolidinyl.

In an embodiment, Ring B is an unsubstituted or substituted phenyl (preferably unsubstituted phenyl) and R$^5$ is as defined as per the following embodiments. In an alternative embodiment, Ring B is an unsubstituted or substituted pyrrolidinyl and R$^5$ is as defined as per the following embodiments.

In an embodiment, R$^5$ is selected from the group consisting of: H, C$_{1-4}$ alkyl, —OR$^{A2}$, and —C(O)OR$^{A2}$, wherein R$^{A2}$ and R$^{B2}$ are at each occurrence independently selected from the group consisting of: H, C$_{1-4}$ alkyl, C$_{1-4}$ haloalkyl and C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A1}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl. Preferably, R$^{A2}$ and R$^{B2}$ are at each occurrence independently H or C$_1$ alkyl.

In an embodiment, the compound of the present invention has a structure according to Formula (III) above; wherein W, X, Y, Z and x are as defined for the compound of Formula (I); and wherein R$^4$, p, L$^1$, R$^{A3}$, R$^{B3}$, q, L$^2$, Ring B, r and R$^5$ are as defined for the compound of Formula (III).

In an embodiment, p is 0 and L$^1$, q, R$^{A3}$, R$^{B3}$ L$^2$, r, Ring B and R$^5$ are as defined as per the following embodiments.

In an embodiment, p is 1 and R$^4$ is selected from the group consisting of: halo, C$_{1-4}$ alkyl, C$_{1-4}$ haloalkyl, —OR$^{A2}$, —NR$^{A2}$R$^{B2}$, —C(O)NR$^{A2}$R$^{B2}$, —SO$_2$R$^{A2}$ and —C(O)OR$^{A2}$, wherein the C$_{1-4}$ alkyl and C$_{1-4}$ haloalkyl are optionally substituted with —OR$^{A2}$, wherein R$^{A2}$ and R$^{B2}$ are at each occurrence independently selected from the group consisting of: H, C$_{1-4}$ alkyl and C$_{1-4}$ alkyl substituted with —OR$^{A5}$ wherein R$^{A5}$ is selected from the group consisting of H and C$_{1-4}$ alkyl; wherein in the specific group —NR$^{A2}$R$^{B2}$, R$^{A2}$ and R$^{B2}$, together with the nitrogen atom to which they are bonded can form a 4- to 7-membered ring system; L$^1$, q, R$^{A3}$, R$^{B3}$, L$^2$, r, Ring B and R$^5$ are as defined as per the following embodiments.

In an embodiment, L$^1$ is a bond, q is 0, L$^2$ is a bond (such that Ring B is directly bonded to the phenyl ring):

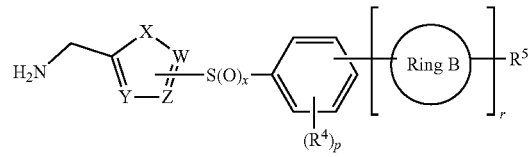

and r, Ring B and R$^5$ are as defined as per the following embodiments.

In an embodiment, r is 1 and Ring B and R$^5$ are as defined as per the following embodiments.

In an embodiment, Ring B is an unsubstituted or substituted phenyl (preferably unsubstituted phenyl) and R$^5$ is as defined as per the following embodiments. In an alternative embodiment, Ring B is an unsubstituted or substituted pyrrolidinyl and R$^5$ is as defined as per the following embodiments. In an alternative embodiment, Ring B is an unsubstituted or substituted or substituted pyrazolyl, an unsubstituted or substituted isoxazolyl, an unsubstituted or substituted pyridinyl, an unsubstituted or substituted thiophenyl, an unsubstituted or substituted imidazole and R$^5$ is as defined as per the following embodiments.

In an embodiment, R$^5$ is selected from the group consisting of: H, halo, C$_{1-4}$ alkyl, C$_{1-4}$ haloalkyl, C$_{3-6}$ cycloalkyl and C$_{1-4}$ alkyl substituted with a substituent selected from the group consisting of: —OR$^{A2}$, —NR$^{A2}$R$^{B2}$, —CN, —NO$_2$, —N$_3$, —NR$^{A2}$C(O)R$^{B2}$, —C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein R$^{A2}$ and R$^{B2}$ are each independently selected from the group consisting of H and C$_{1-4}$ alkyl.

In an embodiment, the compound of the present invention has a structure according to Formula (III) above; wherein W, X, Y, Z and x are as defined for the compound of Formula (I); and wherein R$^4$, p, L$^1$, R$^{A3}$, R$^{B3}$ q L$^2$, Ring B, r and R$^5$ are as defined for the compound of Formula (III).

In an embodiment, p is 0.

In an embodiment, p is 1 and R$^4$ is selected from the group consisting of halo, C$_{1-4}$ alkyl, C$_{1-4}$ haloalkyl, —OR$^{A2}$, —NR$^{A2}$R$^{B2}$, —CN, —NO$_2$, —NR$^{A2}$C(O)R$^{B2}$, —C(O)

$-NR^{A2}R^{B2}$, $-NR^{A2}SO_2R^{B2}$, $-SO_2NR^{A1}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{85}$ are each independently selected from the group consisting of H and $C_{1-4}$ alkyl.

In an embodiment, $L^1$ is a linker moiety selected from the group consisting of: $-NR^{A2}SO_2-$, $-SO_2NR^{A2}-$ and $-SO_2-$; wherein $R^{A2}$ is selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}SR^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^{A2}$ is H. In a preferred embodiment, $L^1$ is $-SO_2-$.

In an embodiment, q is 0.

In an embodiment, q is 1, 2, 3 or 4. Preferably, q is 1, 2 or 3. More preferably, q is 2 or 3.

In an embodiment, $R^{A3}$ and $R^{B3}$ are each independently selected from the group consisting of: H, halo, $C_{1-4}$ alkyl and $C_{1-4}$ haloalkyl. Preferably, $R^{A3}$ and $R^{B3}$ are each H.

In an embodiment, $L^2$ is a bond.

In an embodiment, $L^2$ is a linker moiety selected from the group consisting of: $-NR^{A2}-$, $-NR^{A2}C(O)-$, $-C(O)NR^{A2}-$, $-NR^{A2}SO_2-$, $-SO_2NR^{A2}-$ and $-SO_2-$. In an embodiment, $L^2$ is a linker moiety selected from the group consisting of: $-NR^{A2}-$, $-NR^{A2}C(O)-$ and $-NR^{A1}SO_2-$. In an embodiment, $R^{A2}$ is H.

In an embodiment, r is 0.

In an embodiment, r is 1. In an embodiment, Ring B is an unsubstituted or substituted 6- to 10-membered aryl, unsubstituted or substituted 5- to 10-membered heteroaryl including 1, 2 or 3 heteroatoms selected from N, O or S, an unsubstituted or substituted 3- to 10-membered cycloalkyl (preferably an unsubstituted or substituted 3- to 6-membered cycloalkyl) or an unsubstituted or substituted 4- to 10-membered heterocycloalkyl (preferably an unsubstituted or substituted 4- to 7-membered heterocycloalkyl) including 1, 2 or 3 heteroatoms selected from N, O or S.

In an embodiment, Ring B is an unsubstituted or substituted 6- to 10-membered aryl. Preferably, Ring B is an unsubstituted or substituted phenyl.

In an embodiment, Ring B is an unsubstituted or substituted 4- to 10-membered heterocycloalkyl including 1, 2 or 3 heteroatoms selected from N, O or S. In an embodiment, Ring B is an unsubstituted or substituted 4-, 5-, 6- or 7-membered heterocycloalkyl including 1, 2 or 3 heteroatoms selected from N, O or S. Preferably, the unsubstituted or substituted 4-, 5-, 6- or 7-membered heterocycloalkyl includes 1 or 2 nitrogen atoms.

When Ring B is substituted, the substituents of Ring B are selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

When Ring B is substituted, the substituents of Ring B are preferably selected from the group consisting of: halo, 6-membered aryl, $-OR^{A2}$, $-SO_2R^{A2}$ and $-NR^{A2}SO_2R^{B2}$, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. Preferably $R^{A2}$ and $R^{B2}$ are at each occurrence independently selected from the group consisting of: H and $C_{1-4}$ alkyl.

In an embodiment, Ring B is an unsubstituted phenyl. In an embodiment, Ring B is unsubstituted pyrrolidinyl. In an embodiment, Ring B is unsubstituted piperazinyl. In an embodiment, Ring B is unsubstituted 1,3-diazepanyl.

In an embodiment, $R^5$ is selected from the group consisting of: H, $C_{1-4}$ alkyl, $C_{1-4}$ haloalkyl, $-OR^{A2}$, $-NR^{A2}R^{B2}$, $-N_3$, $-C(O)R^{A2}$, $-C(O)NR^{A2}R^{B2}$ and $-SO_2R^{A2}$, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OH$, $-O-C_{1-4}$ alkyl, $NH_2$, $-NH(C_{1-4}$ alkyl), $-N(C_{1-4}$ alkyl)$_2$, $-SH$, $-S-C_{1-4}$ alkyl, $-CN$, $-NO_2$, 6-membered aryl, 5- or 6-membered heteroaryl including 1, 2 or 3 heteroatoms selected from the group consisting of O, N or S and $C_{3-6}$ cycloalkyl.

In an embodiment, $R^5$ is selected from the group consisting of: H, $C_{1-4}$ alkyl, $-OR^{A2}$, $-NR^{A2}R^{B2}$, $-N_3$, $-C(O)R^{A2}$, $-C(O)NR^{A2}R^{B2}$ and $-SO_2R^{A2}$, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OH$, $-O-C_{1-4}$ alkyl, $NH_2$, $-NH(C_{1-4}$ alkyl), $-N(C_{1-4}$ alkyl)$_2$, $-SH$, $-S-C_{1-4}$ alkyl, $-CN$, $-NO_2$, 6-membered aryl, 5- or 6-membered heteroaryl including 1, 2 or 3 heteroatoms selected from the group consisting of O, N or S and $C_{3-6}$ cycloalkyl. In an embodiment, $R^{A2}$ and $R^{B2}$ are at each occurrence independently selected from the group consisting of: H, $C_1$ alkyl and $C_2$ alkyl.

In an embodiment, p is 0 and $L^1$, q, $R^{A3}$, $R^{B3}$, $L^2$, r, Ring B and $R^5$ are as defined as per the following embodiments.

In an embodiment, $L^1$ is a linker moiety selected from the group consisting of: $-NR^{A2}SO_2-$, $-SO_2NR^{A2}-$ and $-SO_2-$, wherein $R^{A2}$ is selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^{A2}$ is H. In a preferred embodiment, $L^1$ is $-SO_2-$.

In an embodiment, $L^1$ is $-SO_2-$ and q, $R^{A3}$, $R^{B3}$, $L^2$, r, Ring B and $R^5$ are as defined as per the following embodiments.

In an embodiment, q is 0.

In an embodiment, q is 1, 2, 3 or 4. Preferably, q is 1, 2 or 3. More preferably, q is 2 or 3.

In an embodiment, q is 0 and $L^2$, r, Ring B and $R^5$ are as defined as per the following embodiments. In an alternative embodiment, q is 2 or 3 and $R^{A3}$, $R^{B3}$, $L^2$, r, Ring B and $R^5$ are as defined as per the following embodiments.

In an embodiment, $R^{A3}$ and $R^{B3}$ are each independently selected from the group consisting of: H, halo, $C_{1-4}$ alkyl and $C_{1-4}$ haloalkyl. Preferably, $R^{A3}$ and $R^{B3}$ are each H.

In an embodiment, $R^{A3}$ and $R^{B3}$ are each independently selected from the group consisting of: H, halo, $C_{1-4}$ alkyl and $C_{1-4}$ haloalkyl and $L^2$, r, Ring B and $R^5$ are as defined as per the following embodiments. In an embodiment, $R^{A3}$ and $R^{B3}$ are each H and $L^2$, r, Ring B and $R^5$ are as defined as per the following embodiments.

In an embodiment, $L^2$ is a bond and r, Ring B and $R^5$ are as defined as per the following embodiments. In an alternative embodiment, $L^2$ is a linker moiety selected from the group consisting of: $-NR^{A2}-$, $-NR^{A2}C(O)-$ and $-NR^{A2}SO_2-$ and r, Ring B and $R^5$ are as defined as per the following embodiments. In an embodiment, $R^{A2}$ is H.

In an embodiment, r is 0.

In an embodiment, r is 1. In an embodiment, Ring B is an unsubstituted or substituted 6- to 10-membered aryl or an unsubstituted or substituted 4- to 10-membered heterocycloalkyl including 1, 2 or 3 heteroatoms selected from N, O or S. In an embodiment, Ring B is an unsubstituted or substituted 6- to 10-membered aryl. Preferably, Ring B is an unsubstituted or substituted phenyl. In an embodiment, Ring B is an unsubstituted or substituted 4- to 10-membered heterocycloalkyl including 1, 2 or 3 heteroatoms selected from N, O or S. In an embodiment, Ring B is an unsubstituted or substituted 4-, 5-, 6- or 7-membered heterocycloalkyl including 1, 2 or 3 heteroatoms selected from N, O or S. Preferably, the unsubstituted or substituted 4-, 5-, 6- or 7-membered heterocycloalkyl includes 1 or 2 nitrogen atoms. In an embodiment, Ring B is an unsubstituted phenyl. In an embodiment, Ring B is unsubstituted pyrrolidinyl. In an embodiment, Ring B is unsubstituted piperazinyl. In an embodiment, Ring B is unsubstituted 1,3-diazepanyl.

In an embodiment, r is 0 and $R^5$ is as defined as per the following embodiments. In an embodiment, r is 1 and Ring B is unsubstituted phenyl, unsubstituted pyrrolidinyl, unsubstituted piperazinyl or unsubstituted 1,3-diazepanyl and $R^5$ is as defined as per the following embodiments.

In an embodiment, $R^5$ is selected from the group consisting of: H, $C_{1-4}$ alkyl, $C_{1-4}$ haloalkyl, $-OR^{A2}$, $-NR^{A2}R^{B2}$, $-N_3$, $-C(O)NR^{A2}R^{B2}$ and $-SO_2R^{A2}$, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OH$, $-O-C_{1-4}$ alkyl, $NH_2$, $-NH(C_{1-4}$ alkyl), $-N(C_{1-4}$ alkyl$)_2$, $-CN$, $-NO_2$, 6-membered aryl, 5- or 6-membered heteroaryl including 1, 2 or 3 heteroatoms selected from the group consisting of O, N or S and $C_{3-6}$ cycloalkyl. In an embodiment, $R^5$ is selected from the group consisting of: H, $C_{1-4}$ alkyl, $-OR^{A2}$, $-NR^{A2}R^{B2}$, $-N_3$, $-C(O)NR^{A2}R^{B2}$ and $-SO_2R^{A2}$, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OH$, $-O-C_{1-4}$ alkyl, $NH_2$, $-NH(C_{1-4}$ alkyl), $-N(C_{1-4}$ alkyl$)_2$, $-CN$, $-NO_2$, 6-membered aryl, 5- or 6-membered heteroaryl including 1, 2 or 3 heteroatoms selected from the group consisting of O, N or S and $C_{3-6}$ cycloalkyl. In an embodiment, $R^{A2}$ and $R^{B2}$ are at each occurrence independently selected from the group consisting of: H, $C_1$ alkyl and $C_2$ alkyl.

In an embodiment, the compound of the present invention has a structure according to Formula (III) above;
wherein W, X, Y, Z and x are as defined for the compound of Formula (I);
wherein $R^4$, p, $L^1$, $R^{A3}$, $R^{B3}$ $L^2$, Ring B, r and $R^5$ are as defined for the compound of Formula (III); and
wherein p is 1 or 2 and q is 1, 2, 3 or 4;
provided that one $R^4$ substituent, together with the atom to which it is bonded, forms a 5- or 6-membered ring with one of $R^{A3}$ or $R^{B3}$, wherein at least one $R^4$ substituent is selected from the group consisting of $C_{1-4}$ alkylene and $C_{2-4}$ alkenylene and at least one $R^{A3}$ or $R^{B3}$ substituent is selected from the group consisting of: $C_{1-4}$ alkylene and $C_{2-4}$ alkenylene.

In an embodiment, p is 1.

In an embodiment, $R^4$ is a $C_{1-4}$ alkylene residue and one of $R^{A3}$ and $R^{B3}$ is a $C_{1-4}$ alkylene residue, such that $R^4$, together with the atom to which it is bonded, forms a 5- or 6-membered ring with one of $R^{A3}$ or $R^{B3}$ and the other of $R^{A3}$ and $R^{B3}$ is H.

In an embodiment, q is 1.

In an embodiment $L^1$ is selected from the group consisting of: $-O-$, $-NR^{A2}-$, $-S-$ and $-SO_2-$. In an embodiment $L^1$ is $-SO_2-$.

In an embodiment $L^2$ is a bond.

In an embodiment r is 0.

In an embodiment $R^5$ is H.

In an embodiment $L^2$ is a bond, r is 0 and $R^5$ is H.

In an embodiment, the compound of the present invention has a structure according to Formula (III) above;
wherein W, X, Y, Z and x are as defined for the compound of Formula (I); and
wherein $R^4$, p, $L^1$, $R^{A3}$, $R^{B3}$, q, $L^2$, Ring B, r and $R^5$ are as defined for the compound of Formula (III).

In an embodiment, p is 0.

In an embodiment, p is 1 and $R^4$ is selected from the group consisting of halo, $C_{1-4}$ alkyl, $C_{1-4}$ haloalkyl, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, $L^1$ is a linker moiety selected from the group consisting of: $-NR^{A2}SO_2-$, $-SO_2NR^{A2}-$ and $-SO_2-$; wherein $R^{A2}$ is selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In a preferred embodiment, $L^1$ is $-SO_2-$. In a preferred embodiment, $L^1$ is $-SO_2NR^{A2}-$. In an embodiment, $R^{A2}$ is H or $C_{1-4}$ alkyl, preferably $C_1$ alkyl.

In an embodiment, q is 0.

In an embodiment, q is 1, 2, 3 or 4. Preferably, q is 1, 2 or 3. More preferably, q is 2 or 3.

In an embodiment, $R^{A3}$ and $R^{B3}$ are each independently selected from the group consisting of: H, halo, $C_{1-4}$ alkyl and $C_{1-4}$ haloalkyl. Preferably, $R^{A3}$ and $R^{B3}$ are each H.

In an embodiment, $L^2$ is a bond.

In an embodiment, $L^2$ is a linker moiety selected from the group consisting of: $-NR^{A2}-$, $-NR^{A2}C(O)-$, $-C(O)NR^{A2}-$, $-NR^{A2}SO_2-$, $-SO_2NR^{A2}-$ and $-SO_2-$. In an embodiment, $L^2$ is a linker moiety selected from the group consisting of: $-NR^{A2}-$, $-NR^{A2}C(O)-$ and $-NR^{A2}SO_2-$. In an embodiment, $R^{A2}$ is H.

In an embodiment, r is 0.

In an embodiment, r is 1. In an embodiment, Ring B is an unsubstituted or substituted 6- to 10-membered aryl, unsubstituted or substituted 5- to 10-membered heteroaryl including 1, 2 or 3 heteroatoms selected from N, O or S, an unsubstituted or substituted 3- to 10-membered cycloalkyl or an unsubstituted or substituted 4- to 10-membered heterocycloalkyl including 1, 2 or 3 heteroatoms selected from N, O or S.

In an embodiment, Ring B is an unsubstituted or substituted 4- to 10-membered heterocycloalkyl including 1, 2 or 3 heteroatoms selected from N, O or S. In an embodiment, Ring B is an unsubstituted or substituted 4-, 5-, 6- or 7-membered heterocycloalkyl including 1, 2 or 3 heteroatoms selected from N, O or S. In an embodiment, Ring B is an unsubstituted or substituted heterocycloalkyl ring selected from the group consisting of: azetidinyl, oxetanyl, tetrahydrofuranyl, pyrrolidinyl, imidazolidinyl, succinimidyl, pyrazolidinyl, oxazolidinyl, dioxolanyl, isoxazolidinyl, thiazolidinyl, isothiazolidinyl, piperidinyl, morpholinyl, thiomorpholinyl, thiomorpholinyl dioxide, piperazinyl, dioxanyl, tetrahydropyranyl, azepanyl and diazepanyl. Preferably, the unsubstituted or substituted 5-, 6- or 7-membered heterocycloalkyl includes 1 or 2 nitrogen atoms. More preferably, Ring B is an unsubstituted or substituted 5-membered heterocycloalkyl including 1, 2 or 3 heteroatoms selected from N, O or S.

When Ring B is substituted, the substituents of Ring B are selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A1}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

When Ring B is substituted, the substituents of Ring B are preferably selected from the group consisting of: halo, $C_{1-4}$ alkyl and $C_{1-4}$ haloalkyl.

In an embodiment, Ring B is unsubstituted pyrrolidinyl.

In an embodiment, $R^5$ is selected from the group consisting of: H; $C_{1-4}$ alkyl; $C_{1-4}$ haloalkyl; $C_1$-4 alkyl or $C_{1-4}$ haloalkyl substituted with a substituent selected from the group consisting of: $-OR^{A2}$, $-NR^{A2}R^{B2}$, $-CN$, $-NO_2$, $-N_3$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A1}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. Preferably $R^5$ is selected from the group consisting of H, $C_1$ alkyl and $C_1$ alkyl substituted with OH.

In an embodiment, p is 0 and $L^1$, q, $R^{A3}$, $R^{B3}$, $L^2$, r, Ring B and $R^5$ are as defined as per the following embodiments:

In an embodiment, $L^1$ is a linker moiety selected from the group consisting of: $-NR^{A2}SO_2-$, $-SO_2NR^{A2}-$ and $-SO_2-$, wherein $R^{A2}$ is selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}SR^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In a preferred embodiment, $L^1$ is $-SO_2-$. In a preferred embodiment, $L^1$ is $-SO_2NR^{A2}-$. In an embodiment, $R^{A2}$ is H or $C_{1-4}$ alkyl, preferably $C_1$ alkyl.

In an embodiment, $L^1$ is $-SO_2-$ and q, $R^{A3}$, $R^{B3}$, $L^2$, r, Ring B and $R^5$ are as defined as per the following embodiments. In an alternative embodiment, $L^1$ is $-SO_2NR^{A2}-$, preferably $SO_2NMe$, and q, $R^{A3}$, $R^{B3}$, $L^2$, r, Ring B and $R^5$ are as defined as per the following embodiments.

In an embodiment, q is 0.

In an embodiment, q is 0 and $L^2$, r, Ring B and $R^5$ are as defined as per the following embodiments.

In an embodiment, $L^2$ is a bond.

In an embodiment, $L^2$ is a bond and r, Ring B and $R^5$ are as defined as per the following embodiments.

In an embodiment, r is 0.

In an embodiment, r is 1. In an embodiment, Ring B is an unsubstituted or substituted 4- to 10-membered heterocycloalkyl including 1, 2 or 3 heteroatoms selected from N, O or S. In an embodiment, Ring B is an unsubstituted or substituted 4-, 5-, 6- or 7-membered heterocycloalkyl including 1, 2 or 3 heteroatoms selected from N, O or S. Preferably, the unsubstituted or substituted 5-, 6- or 7-membered heterocycloalkyl includes 1 or 2 nitrogen atoms. In an embodiment, Ring B is unsubstituted pyrrolidinyl.

In an embodiment, r is 0 and $R^5$ is as defined as per the following embodiments. In an embodiment, r is 1 and Ring B is unsubstituted pyrrolidinyl and $R^5$ is as defined as per the following embodiments.

In an embodiment, $R^5$ is selected from the group consisting of: H; $C_{1-4}$ alkyl; $C_{1-4}$ haloalkyl; $C_{1-4}$ alkyl or $C_{1-4}$ haloalkyl substituted with a substituent selected from the group consisting of: $-OR^{A2}$, $-NR^{A2}R^{B2}$, $-CN$, $-NO_2$, $-N_3$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-8}$ cycloalkyl; wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. Preferably $R^5$ is selected from the group consisting of H, $C_1$ alkyl and $C_1$ alkyl substituted with OH.

In an embodiment, the compound of the present invention has a structure according to Formula (IV):

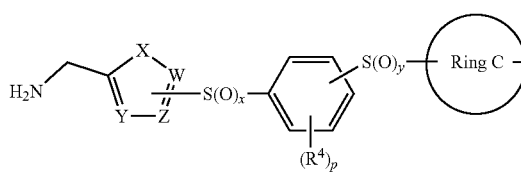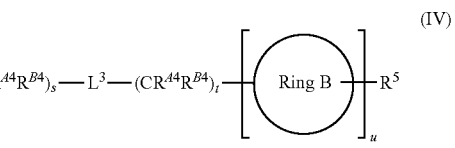

wherein W, X, Y, Z and x are as defined for the compound of Formula (I);
wherein $R^4$ and p are as defined for the compound of Formula (III);
y is 1 or 2;
"Ring C" is an unsubstituted 4- to 12-membered ring system, including 0, 1, 2 or 3 heteroatoms selected from N, O or S; or substituted 4- to 12-membered ring system, including 0, 1, 2 or 3 heteroatoms selected from N, O or S which is substituted with a substituent selected from the group consisting of: halo, $C_{1-4}$ alkyl, $C_{1-4}$ haloalkyl, 6-membered aryl, 5- or 6-membered heteroaryl including 1, 2 or 3 heteroatoms selected from the group consisting of O, N or S, $-OR^{A2}$, $=O$, $-NR^{A2}R^{B2}$, $-SR^{A2}$, $-CN$, $-NO_2$, $-N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl;
$L^3$ is a linker moiety selected from the group consisting of: a bond, $-O-$, $-NR^{A2}-$, $-S-$, $-NR^{A2}C(O)-$, $-NR^{A2}C(O)O-$, $-C(O)NR^{A2}-$, $-OC(O)NR^{A2}-$, $-NR^{A2}C(O)NR^{B2}-$, $-NR^{A1}SO_2-$, $-SO_2NR^{A2}-$, $-SO_2-$, $-C(O)-$, $-C(O)O-$, $-OC(O)-$;
$R^{A4}$ and $R^{B4}$ are each independently selected at each occurrence from the group consisting of: H, halo, $C_{1-4}$ alkyl, $C_{1-4}$ haloalkyl, $-OR^{A2}$, $-NR^{A2}R^{B2}$, $-CN$, $-NO_2$, $-NR^{A1}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl; or together $R^{A4}$ and $R^{B4}$ are $=O$, wherein the $C_{1-4}$ alkyl, $C_{1-4}$ haloalkyl and $C_{3-6}$ cycloalkyl groups are themselves optionally substituted with $R^{A2}$, halo, $-OR^{A1}$, $=O$, $-NR^{A2}R^{B2}$, $-SR^{A2}$, $-CN$, $-NO_2$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A1}R^{B2}$, $-SO_2R^{A2}$, $-C(O)R^{A2}$, $-C(O)OR^{A1}$ and $C_{3-6}$ cycloalkyl;
wherein $R^{A2}$ and $R^{B2}$ are at each occurrence independently selected from the group consisting of: H, $C_{1-4}$ alkyl, $C_{1-4}$ haloalkyl, 6-membered aryl, 5- or 6-membered heteroaryl including 1, 2 or 3 heteroatoms selected from the group consisting of O, N or S and $C_{3-6}$ cycloalkyl, wherein the $C_{1-4}$ alkyl, $C_{1-4}$ haloalkyl, 6-membered aryl, 5- or 6-membered heteroaryl and $C_{3-6}$ cycloalkyl groups are themselves optionally substituted with a substituent selected from the group consisting of $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group $-NR^{A2}R^{B2}$, $R^{A2}$ and $R^{B2}$, together with the nitrogen atom to which they are bonded can form a 4- to 7-membered ring system; and wherein in the specific group $-NR^{A5}R^{B5}$, $R^{A5}$ and $R^{B5}$, together with the nitrogen atom to which they are bonded can form a 4- to 7-membered ring system;

s is 0, 1, 2, 3 or 4;
t is 0, 1, 2, 3 or 4;
u is 0 or 1;
"Ring D" is an unsubstituted 4- to 12-membered ring system, including 0, 1, 2 or 3 heteroatoms selected from N, O or S; or substituted 4- to 12-membered ring system, including 0, 1, 2 or 3 heteroatoms selected from N, O or S which is substituted with a substituent selected from the group consisting of: halo, $C_{1-4}$ alkyl, $C_{1-4}$ haloalkyl, 6-membered aryl, 5- or 6-membered heteroaryl including 1, 2 or 3 heteroatoms selected from the group consisting of O, N or S, $-OR^{A2}$, $-NR^{A2}R^{B2}$, $-SR^{A2}$, $-CN$, $-NO_2$, $N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl;
$R^5$ is selected from the group consisting of: H, halo, $C_{1-4}$ alkyl, $C_{1-4}$ haloalkyl, $-O-C_{1-4}$ alkyl, $-O-C_{1-4}$ haloalkyl), $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group $-NR^{A2}R^{B2}$, $R^{A2}$ and $R^{B2}$, together with the nitrogen atom to which they are bonded can form a 4- to 7-membered ring system; and wherein in the specific group $-NR^{A5}R^{B5}$, $R^{A5}$ and $R^{B5}$, together with the nitrogen atom to which they are bonded can form a 4- to 7-membered ring system.

In an embodiment, p is 0.
In an embodiment, p is 1 and $R^4$ is selected from the group consisting of halo, $C_{1-4}$ alkyl, $C_{1-4}$ haloalkyl, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A1}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, y is 1.
In an embodiment, y is 2.
In an embodiment, Ring C is an unsubstituted or substituted 4- to 10-membered heterocycloalkyl including 1, 2 or 3 heteroatoms selected from N, O or S. In an embodiment, Ring C is an unsubstituted or substituted 4-, 5-, 6- or 7-membered heterocycloalkyl including 1, 2 or 3 heteroatoms selected from N, O or S. In an embodiment, Ring C is an unsubstituted or substituted heterocycloalkyl ring selected from the group consisting of: azetidinyl, oxetanyl, tetrahydrofuranyl, pyrrolidinyl, imidazolidinyl, succinimidyl, pyrazolidinyl, oxazolidinyl, dioxolanyl, isoxazolidinyl, thiazolidinyl, isothiazolidinyl, piperidinyl, morpholinyl, thiomorpholinyl, piperazinyl, dioxanyl, tetrahydropyranyl, azepanyl and diazepanyl. Preferably, the unsubstituted or substituted 5-, 6- or 7-membered heterocycloalkyl includes 1 or 2 nitrogen atoms. More preferably, Ring C is an unsubstituted or substituted 5-membered heterocycloalkyl including 1, 2 or 3 heteroatoms selected from N, O or S.

When Ring C is substituted, the substituents of Ring C are selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-CN$, $-NO_2$, $-NR^{A2}C(O)R^{B2}$, $-C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-14}$ haloalkyl, $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, Ring C is unsubstituted pyrrolidinyl.

In an embodiment, s is 1.

In an embodiment, t is 1. In an embodiment, t is 0.

In an embodiment, $R^{A4}$ and $R^{B4}$ are each independently selected from the group consisting of: H, halo, $C_{1-4}$ alkyl and $C_{1-4}$ haloalkyl. Preferably, $R^{A4}$ and $R^{B4}$ are each H.

In an embodiment, $L^3$ is a linker moiety selected from the group consisting of: $-O-$, $-NR^{A2}$, $-S-$, $-NR^{A2}C(O)-$, $-NR^{A2}C(O)O-$, $-C(O)NR^{A2}-$, $-NR^{A2}C(O)NR^{B2}-$, $-OC(O)NR^{A2}-$, $-NR^{A1}SO_2-$ and $-SO_2NR^{A2}-$. In an embodiment, $L^3$ is a linker moiety selected from the group consisting of: $-O-$, $-NR^{A2}C(O)O-$, $-OC(O)NR^{A2}-$, $-NR^{A2}SO_2-$ and $-SO_2NR^{A2}-$. In an embodiment, $L^3$ is a linker moiety selected from the group consisting of: $-O-$, $-OC(O)NR^{A2}-$ and $-NR^{A2}SO_2-$.

In an embodiment, u is 0. In an embodiment, u is 1.

In an embodiment, Ring D is an unsubstituted or substituted 6- to 10-membered aryl. Preferably, Ring D is an unsubstituted or substituted phenyl.

When Ring D is substituted, the substituents of Ring B are selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-CN$, $-NO_2$, $-NR^{A1}C(O)R^{B2}$, $-C(O)NR^{A2}R^{B2}$, $-NR^{A1}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl, Cia alkyl substituted with a substituent selected from the group consisting of: $-OR^{A5}$, $-NR^{A5}R^{B2}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, Ring D is an unsubstituted phenyl.

In an embodiment, $R^5$ is selected from the group consisting of: H, halo, $C_{1-4}$ alkyl, $C_{1-4}$ haloalkyl, $-OR^{A2}$, $-NR^{A2}R^{B2}$, wherein $R^{A2}$ and $R^{B2}$ are at each occurrence independently selected from the group consisting of: H, $C_{1-4}$ alkyl, $C_{1-4}$ haloalkyl and Cia alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^5$ is selected from the group consisting of: H and halo, preferably $R^5$ is selected from the group consisting of: H and F. In an embodiment, $R^5$ is $C_{1-4}$ alkyl, preferably $C_1$, $C_2$, $C_3$ or $C_4$ alkyl.

In an embodiment, p is 0 and y, Ring C, s, $R^{A4}$, $R^{B4}$, $L^3$, t, u, Ring D and $R^5$ are as defined as per the following embodiments.

In an embodiment, y is 1. In an embodiment, y is 2.

In an embodiment, y is 1 and Ring C, s, $R^{A4}$, $R^{B4}$, $L^3$, t, u, Ring D and $R^5$ are as defined as per the following embodiments. In an embodiment, y is 2 and Ring C, s, $R^{A4}$, $R^{B4}$, $L^3$, t, u, Ring D and $R^5$ are as defined as per the following embodiments.

In an embodiment, Ring C is an unsubstituted or substituted 4- to 10-membered heterocycloalkyl including 1, 2 or 3 heteroatoms selected from N, O or S. In an embodiment, Ring C is an unsubstituted or substituted 5-, 6- or 7-membered heterocycloalkyl including 1, 2 or 3 heteroatoms selected from N, O or S. Preferably, the unsubstituted or substituted 5-, 6- or 7-membered heterocycloalkyl includes 1 or 2 nitrogen atoms. In an embodiment, Ring C is unsubstituted pyrrolidinyl.

In an embodiment, Ring C is unsubstituted pyrrolidinyl and s, $R^{A4}$, $R^{B4}$, $L^3$, t, u, Ring D and $R^5$ are as defined as per the following embodiments.

In an embodiment, s is 1 and $R^{A4}$, $R^{B4}$, $L^3$, t, u, Ring D and $R^5$ are as defined as per the following embodiments.

In an embodiment, s is 1 and $R^{A4}$ and $R^{B4}$ are each H and $L^3$, t, u, Ring D and $R^5$ are as defined as per the following embodiments.

In an embodiment, t is 1 and $R^{A4}$ and $R^{B4}$ are each H and $L^3$, u, Ring D and $R^5$ are as defined as per the following embodiments.

In an embodiment, t is 0 and $L^3$, u, Ring D and $R^5$ are as defined as per the following embodiments.

In an embodiment, $L^3$ is a linker moiety selected from the group consisting of: $-O-$, $-OC(O)NR^{A2}-$ and $-NR^{A2}SO_2-$ and u, Ring D and $R^5$ are as defined as per the following embodiments.

In an embodiment, u is 0 and $R^5$ is as defined as per the following embodiments. In an embodiment, u is 1 and Ring D and $R^5$ are as defined as per the following embodiments.

In an embodiment, Ring D is an unsubstituted or substituted 6- to 10-membered aryl, preferably an unsubstituted or substituted phenyl, and $R^5$ is as defined as per the following embodiments.

In an embodiment, $R^5$ is selected from the group consisting of: H, halo (e.g. F, Cl, Br or I), $C_{1-4}$ alkyl, $C_{1-4}$ haloalkyl, $-OR^{A2}$, $-NR^{A2}R^{B2}$, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl. In an embodiment, $R^5$ is selected from the group consisting of: H and halo, preferably $R^5$ is selected from the group consisting of: H and F. In an embodiment, $R^5$ is $C_{1-4}$ alkyl, preferably $C_1$, $C_2$, $C_3$ or $C_4$ alkyl.

In an embodiment, the compound of the present invention has a structure according to Formula (Va), (Vb) or (Vc):

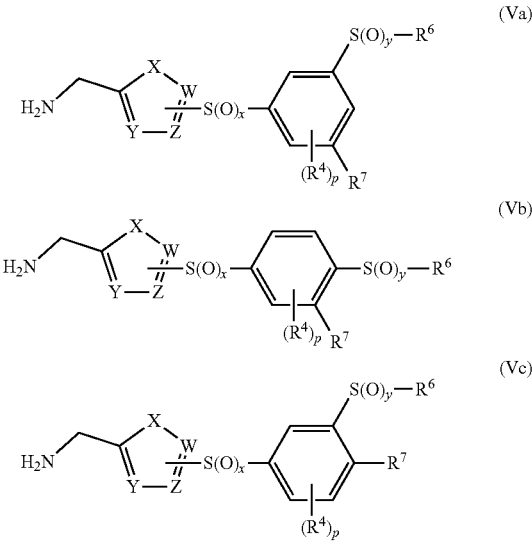

wherein W, X, Y, Z and x are as defined for the compound of Formula (I);
wherein $R^4$ and p are as defined for the compound of Formula (III);
y is 1 or 2;
$R^6$ is selected from the group consisting of: unsubstituted $C_{1-4}$ alkyl; $C_{1-4}$ alkyl substituted with one or more substituents selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $=O$, $-NR^{A2}R^{B2}$, $-SR^{A2}$, $-CN$, $-NO_2$, $-N_3$, $-NR^{A2}C(O)R^{B2}$, $-C(O)NR^{A1}R^{B2}$, $-NR^{A2}C(O)OR^{B2}$, $-OC(O)NR^{A1}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl; an unsubstituted 3- to 12-membered ring system, including 0, 1, 2 or 3 heteroatoms selected from N, O or S; and a 3- to 12-membered ring system, including 0, 1, 2 or 3 heteroatoms selected from N, O or S, substituted with one or more substituents selected from the group consisting of: halo, $C_{1-4}$ alkyl, $C_{1-4}$ haloalkyl, 6-membered aryl, 5- or 6-membered heteroaryl including 1, 2 or 3 heteroatoms selected from N, O or S, $-OR^{A2}$, $=O$, $-NR^{A2}R^{B2}$, $-SR^{A2}$, $-CN$, $-NO_2$, $-N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl;
$R^7$ is selected from the group consisting of: halo, $C_{1-4}$ alkyl, $C_{2-4}$ alkenyl, $C_{2-4}$ alkynyl (optionally substituted with TMS), $C_{1-4}$ haloalkyl, unsubstituted or substituted 6- to 10-membered aryl, unsubstituted or substituted 5- to 10-membered heteroaryl including 1, 2 or 3 heteroatoms selected from N, O or S, an unsubstituted or substituted 3- to 10-membered cycloalkyl (preferably an unsubstituted or substituted 3- to 6-membered cycloalkyl) or an unsubstituted or substituted 4- to 10-membered heterocycloalkyl (preferably an unsubstituted or substituted 4- to 7-membered heterocycloalkyl) including 1, 2 or 3 heteroatoms selected from N, O or S, $-OR^{A2}$, $-NR^{A2}R^{B2}$, $-SR^{A2}$, $-CN$, $-NO_2$, $-N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$ and $-C(O)OR^{A2}$, wherein the $C_{1-4}$ alkyl, $C_{2-4}$ alkenyl, $C_{2-4}$ alkynyl, $C_{1-4}$ haloalkyl, 6- to 10-membered aryl, 5- to 10-membered heteroaryl, 3- to 10-membered cycloalkyl and 4- to 10-membered heterocycloalkyl groups are optionally substituted with $R^{A2}$, halo, $-OR^{A2}$, $=O$, $-NR^{A2}R^{B2}$, $-SR^{A2}$, $-CN$, $-NO_2$, $-N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl;
wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A5}R^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group $-NR^{A2}R^{B2}$, $R^{A2}$ and $R^{B2}$, together with the nitrogen atom to which they are bonded can form a 4- to 7-membered ring system; and wherein in the specific group $-NR^{A5}R^{B5}$, $R^{A5}$ and $R^{B5}$, together with the nitrogen atom to which they are bonded can form a 4- to 7-membered ring system.

In an embodiment, y is 2.
In an embodiment, p is 0.
In an embodiment, $R^6$ is selected from the group consisting of: unsubstituted $C_{1-4}$ alkyl and an unsubstituted 3- to 12-membered ring system, including 0, 1, 2 or 3 heteroatoms selected from N, O or S.
In an embodiment, $R^6$ is selected from the group consisting of: unsubstituted $C_1$, $C_2$ or $C_3$ alkyl, for example methyl, ethyl, n-propyl or iso-propyl.
In an embodiment, $R^6$ is a 5-, 6- or 7-membered ring system including 0, 1, 2 or 3 heteroatoms selected from N, O or S. In an embodiment, $R^6$ is a 5- membered ring system including 0 or 1 heteroatoms selected from N, O or S. In an embodiment, $R^6$ is pyrrolidine.
In an embodiment, $R^7$ is selected from the group consisting of: $C_{1-4}$ alkyl, $C_{2-4}$ alkenyl, $C_{2-4}$ alkynyl (optionally substituted with TMS), $C_{1-4}$ haloalkyl, 6-membered aryl, 5- or 6-membered heteroaryl including 1, 2 or 3 heteroatoms selected from N, O or S, $-OR^{A2}$, $-NR^{A2}R^{B2}$, $-SR^{A2}$, $-CN$ and $-NO_2$, wherein the $C_{1-4}$ alkyl, $C_{2-4}$ alkenyl, $C_{2-4}$ alkynyl, $C_{1-4}$ haloalkyl, 6-membered aryl, 5- or 6-membered heteroaryl and $C_{3-6}$ cycloalkyl groups are optionally substituted with $R^{A2}$, halo, $-OR^{A2}$, $=O$, $-NR^{A2}R^{B2}$, $-SR^{A2}$, $-CN$, $-NO_2$, $-N_3$, $-NR^{A2}C(O)R^{B2}$, $-C(O)NR^{A2}R^{B2}$, $-NR^{A2}C(O)OR^{B2}$, $-OC(O)NR^{A2}R^{B2}$, $-NR^{A2}C(O)NR^{A2}R^{B2}$, $-NR^{A2}SO_2R^{B2}$, $-SO_2NR^{A2}R^{B2}$, $-SO_2R^{A2}$, $-C(O)R^{A2}$, $-C(O)OR^{A2}$ and $C_{3-6}$ cycloalkyl, wherein $R^{A2}$ and $R^{B2}$ are at each occurrence independently selected from the group consisting of: H, $C_{1-4}$ alkyl, $C_{1-4}$ haloalkyl and $C_{1-4}$ alkyl substituted with a substituent selected from the group consisting of: $-OR^{A5}$, $-NR^{A1}SR^{B5}$, $-CN$, $-NO_2$, $-N_3$, $-NR^{A5}C(O)R^{B5}$, $-C(O)NR^{A5}R^{B5}$, $-NR^{A5}SO_2R^{B5}$, $-SO_2NR^{A5}R^{B5}$, $-SO_2R^{A5}$, $-C(O)R^{A5}$, $-C(O)OR^{A5}$ and $C_{3-6}$ cycloalkyl, wherein $R^{A5}$ and $R^{B5}$ are each independently selected from the group consisting of H and $C_{1-4}$ alkyl.

In an embodiment, $R^7$ is selected from the group consisting of: $C_{1-4}$ alkyl, $C_{2-4}$ alkynyl (optionally substituted with TMS), $C_{1-4}$ haloalkyl, 6-membered aryl, 5- or 6-membered heteroaryl including 1, 2 or 3 heteroatoms selected from N, O or S, and —OR$^{A2}$, wherein the C$_{1-4}$ alkyl, C$_{2-4}$ alkynyl, C$_{1-4}$ haloalkyl, 6-membered aryl and 5- or 6-membered heteroaryl groups are optionally substituted with R$^{A2}$, halo, —OR$^{A2}$, ═O, —NR$^{A2}$R$^{B2}$, —SR$^{A2}$, —CN, —NO$_2$, —N$_3$, —NR$^{A2}$C(O)R$^{B2}$, —C(O)NR$^{A2}$R$^{B2}$, —NR$^{A2}$C(O)OR$^{B2}$, —OC(O)NR$^{A2}$R$^{B2}$, —NR$^{A2}$C(O)NR$^{A2}$R$^{B2}$, —NR$^{A2}$SO$_2$R$^{B2}$, —SO$_2$NR$^{A2}$R$^{B2}$, —SO$_2$R$^{A2}$, —C(O)R$^{A2}$, —C(O)OR$^{A2}$ and C$_{3-6}$ cycloalkyl, wherein R$^{A2}$ and R$^{B2}$ are selected from the group consisting of: H, C$_{1-4}$ alkyl, C$_{1-4}$ haloalkyl and C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl.

In an embodiment, R$^7$ is C$_{1-4}$ alkyl, optionally R$^7$ is C$_1$, C$_2$, C$_3$ or C$_4$ alkyl. Preferably, R$^7$ is C$_4$ alkyl. More preferably R$^7$ is tert-butyl.

In an embodiment, R$^7$ is C$_{1-4}$ haloalkyl, optionally R$^7$ is C$_1$, C$_2$, C$_3$ or C$_4$ haloalkyl. Preferably, R$^7$ is C$_1$ haloalkyl. More preferably R$^7$ is CF$_3$.

In an embodiment, R$^7$ is —OR$^{A2}$, wherein R$^{A2}$ is selected from the group consisting of: H, C$_{1-4}$ alkyl, C$_{1-4}$ haloalkyl and C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl. Preferably, R$^7$ is —OR$^{A2}$, wherein R$^{A2}$ is C$_1$, C$_2$, C$_3$ or C$_4$ alkyl. More preferably, R$^{A2}$ is ethyl, iso-propyl or tert-butyl.

In an embodiment, R$^7$ is 6-membered aryl which is optionally substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl. In an embodiment, R$^7$ is unsubstituted phenyl. In an embodiment, R$^7$ is phenyl substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl. In an embodiment, R$^7$ is phenyl substituted with 1, 2 or 3 substituents independently selected from the group consisting of: halo, C$_{1-4}$ alkyl and —O—C$_{1-4}$ alkyl. Preferably, R$^7$ is substituted with 1 or 2 substituents selected from the group consisting of: C$_1$ alkyl, C$_2$ alkyl, C$_3$ alkyl, C$_4$ alkyl, —O—C$_1$ alkyl, —O—C$_2$ alkyl, —O—C$_3$ alkyl, —O—C$_4$ alkyl, chloro and fluoro. Preferably, R$^7$ is substituted with 1 or 2 substituents selected from the group consisting of: C$_1$ alkyl, C$_2$ alkyl, —O—C$_1$ alkyl, —O—C$_2$ alkyl, chloro and fluoro.

In an embodiment, R$^7$ is 5- or 6-membered heteroaryl including 1, 2 or 3 heteroatoms selected from N, O or S which is optionally substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl.

In an embodiment, R$^7$ is selected from the group consisting of: azetidinyl, oxetanyl, tetrahydrofuranyl, pyrrolidinyl, pyrrolinyl, imidazolidinyl, imidazolinyl, succinimidyl, pyrazolidinyl, pyrazolinyl, oxazolidinyl, oxazolinyl, dioxolanyl, isoxazolidinyl, isoxazolinyl, thiazolidinyl, thiazolinyl, isothiazolidinyl, isothiazolinyl, piperidinyl, morpholinyl, thiomorpholinyl, piperazinyl, dioxanyl, dihydropyranyl, tetrahydropyranyl, pyridyl, pyridazinyl, pyrimidinyl, pyrazinyl, thiophenyl, furanyl, pyrrolyl, pyrazolyl, imidazolyl, triazolyl, oxazolyl, isoxazolyl, thiazolyl, isothiazolyl, oxadiazolyl, azepanyl and diazepanyl which is optionally substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl.

In an embodiment, R$^7$ is selected from the group consisting of: pyridyl, thiophenyl and pyrazolyl which is optionally substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl. Preferably, R$^7$ is substituted with 1 or 2 substituents selected from the group consisting of: C$_1$ alkyl, C$_2$ alkyl, —O—C$_1$ alkyl, —O—C$_2$ alkyl, chloro and fluoro. More preferably, R$^7$ is substituted a C$_1$ alkyl.

In an embodiment, R$^7$ is C$_{2-4}$ alkynyl, which is optionally substituted with TMS.

In an embodiment, p is 0 and y, R$^6$ and R$^7$ are as defined as per the following embodiments.

In an embodiment, y is 1 and R$^6$ and R$^7$ are as defined as per the following embodiments. In an embodiment, y is 2 and R$^6$ and R$^7$ are as defined as per the following embodiments.

In an embodiment, R$^6$ is selected from the group consisting of: unsubstituted C$_1$, C$_2$ or C$_3$ alkyl, for example methyl, ethyl, n-propyl or iso-propyl and R$^7$ is as defined as per the following embodiments.

In an embodiment, R$^7$ is C$_{1-4}$ alkyl, optionally R$^7$ is C$_1$, C$_2$, C$_3$ or C$_4$ alkyl. Preferably, R$^7$ is C$_4$ alkyl. More preferably R$^7$ is tert-butyl.

In an embodiment, R$^7$ is C$_{1-4}$ haloalkyl, optionally R$^7$ is C$_1$, C$_2$, C$_3$ or C$_4$ haloalkyl. Preferably, R$^7$ is C$_1$ haloalkyl. More preferably R$^7$ is CF$_3$.

In an embodiment, R$^7$ is —OR$^{A2}$, wherein R$^{A2}$ is selected from the group consisting of: H, C$_{1-4}$ alkyl, C$_{1-4}$ haloalkyl and C$_{1-4}$ alkyl substituted with a substituent selected from the group consisting of: —OR$^{A5}$, —NR$^{A5}$R$^{B5}$, —CN, —NO$_2$, —N$_3$, —NR$^{A5}$C(O)R$^{B5}$, —C(O)NR$^{A5}$R$^{B5}$, —NR$^{A5}$SO$_2$R$^{B5}$, —SO$_2$NR$^{A5}$R$^{B5}$, —SO$_2$R$^{A5}$, —C(O)R$^{A5}$, —C(O)OR$^{A5}$ and C$_{3-6}$ cycloalkyl, wherein R$^{A5}$ and R$^{B5}$ are each independently selected from the group consisting of H and C$_{1-4}$ alkyl. Preferably, R$^7$ is —OR$^{A2}$, wherein R$^{A2}$ is C$_1$, C$_2$, C$_3$ or C$_4$ alkyl. More preferably, R$^{A2}$ is ethyl, iso-propyl or tert-butyl.

In an embodiment, R$^7$ is 6-membered aryl which is optionally substituted with 1, 2 or 3 substituents independently selected from the group consisting of: halo, C$_{1-4}$ alkyl, C$_{1-4}$ haloalkyl, —O—C$_1$-4 alkyl, —O—C$_{1-4}$ haloalkyl. In an embodiment, R$^7$ is unsubstituted phenyl. In an embodiment, R$^7$ is phenyl substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl. In an embodiment, R$^7$ is phenyl substituted with 1, 2 or 3 substituents independently selected from the group consisting of: halo, C$_{1-4}$ alkyl and —O—C$_{1-4}$ alkyl. Preferably, R$^7$ is substituted with 1 or 2 substituents selected from the group consisting of: C$_1$ alkyl, C$_2$ alkyl, —O—C$_1$ alkyl, —O—C$_2$ alkyl, chloro and fluoro.

In an embodiment, R$^7$ is 5- or 6-membered heteroaryl including 1, 2 or 3 heteroatoms selected from N, O or S which is optionally substituted with 1, 2 or 3 substituents independently selected from the group consisting of: halo, C$_{1-4}$ alkyl, C$_{1-4}$ haloalkyl, —O—C$_{1-4}$ alkyl, —O—C$_{1-4}$ haloalkyl.

In an embodiment, R$^7$ is selected from the group consisting of: azetidinyl, oxetanyl, tetrahydrofuranyl, pyrrolidinyl, pyrrolinyl, imidazolidinyl, imidazolinyl, succinimidyl, pyrazolidinyl, pyrazolinyl, oxazolidinyl, oxazolinyl, dioxolanyl, isoxazolidinyl, isoxazolinyl, thiazolidinyl, thiazolinyl, isothiazolidinyl, isothiazolinyl, piperidinyl, morpholinyl, thiomorpholinyl, piperazinyl, dioxanyl, dihydropyranyl, tetrahydropyranyl, pyridyl, pyridazinyl, pyrimidinyl, pyrazinyl, thiophenyl, furanyl, pyrrolyl, pyrazolyl, imidazolyl, triazolyl, oxazolyl, isoxazolyl, thiazolyl, isothiazolyl, oxadiazolyl, azepanyl and diazepanyl which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl.

In an embodiment, $R^7$ is selected from the group consisting of: pyridyl, thiophenyl and pyrazolyl which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl. Preferably, $R^7$ is substituted with 1 or 2 substituents selected from the group consisting of: $C_1$ alkyl, $C_2$ alkyl, —O—$C_1$ alkyl, —O—$C_2$ alkyl, chloro and fluoro. More preferably, $R^7$ is substituted a $C_1$ alkyl.

In an embodiment, $R^7$ is $C_{2-4}$ alkynyl, which is optionally substituted with TMS.

In an embodiment, $R^6$ is pyrrolidine and $R^7$ is as defined as per the following embodiments:

In an embodiment, $R^7$ is $C_{1-4}$ alkyl, optionally $R^7$ is $C_1$, $C_2$, $C_3$ or $C_4$ alkyl. Preferably, $R^7$ is $C_4$ alkyl. More preferably $R^7$ is tert-butyl.

In an embodiment, $R^7$ is $C_{1-4}$ haloalkyl, optionally $R^7$ is $C_1$, $C_2$, $C_3$ or $C_4$ haloalkyl. Preferably, $R^7$ is $C_1$ haloalkyl. More preferably $R^7$ is $CF_3$.

In an embodiment, $R^7$ is —$OR^{A2}$, wherein $R^{A2}$ is selected from the group consisting of: H, $C_{1-4}$ alkyl, $C_{1-4}$ haloalkyl and $C_{1-4}$ alkyl substituted with a substituent selected from the group consisting of: —$OR^{A5}$, —$NR^{A5}R^{B5}$, —CN, —$NO_2$, —$N_3$, —$NR^{A5}C(O)R^{B5}$, —$C(O)NR^{A5}R^{B5}$, —$NR^{A5}SO_2R^{B5}$, —$SO_2NR^{A5}R^{B5}$, —$SO_2R^{A5}$, —$C(O)R^{A5}$, —$C(O)OR^{A5}$ and $C_{3-6}$ cycloalkyl, wherein $R^{A5}$ and $R^{B5}$ are each independently selected from the group consisting of H and $C_{1-4}$ alkyl. Preferably, $R^7$ is —$OR^{A2}$, wherein $R^{A2}$ is $C_1$, $C_2$, $C_3$ or $C_4$ alkyl. More preferably, $R^{A2}$ is ethyl, iso-propyl or tert-butyl.

In an embodiment, $R^7$ is 6-membered aryl which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl. In an embodiment, $R^7$ is unsubstituted phenyl. In an embodiment, $R^7$ is phenyl substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl. In an embodiment, $R^7$ is phenyl substituted with 1, 2 or 3 substituents independently selected from the group consisting of: halo, $C_{1-4}$ alkyl and —O—$C_{1-4}$ alkyl. Preferably, $R^7$ is substituted with 1 or 2 substituents selected from the group consisting of: $C_1$ alkyl, $C_2$ alkyl, —O—$C_1$ alkyl, —O—$C_2$ alkyl, chloro and fluoro.

In an embodiment, $R^7$ is 5- or 6-membered heteroaryl including 1, 2 or 3 heteroatoms selected from N, O or S which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl.

In an embodiment, $R^7$ is selected from the group consisting of: azetidinyl, oxetanyl, tetrahydrofuranyl, pyrrolidinyl, pyrrolinyl, imidazolidinyl, imidazolinyl, succinimidyl, pyrazolidinyl, pyrazolinyl, oxazolidinyl, oxazolinyl, dioxolanyl, isoxazolidinyl, isoxazolinyl, thiazolidinyl, thiazolinyl, isothiazolidinyl, isothiazolinyl, piperidinyl, morpholinyl, thiomorpholinyl, piperazinyl, dioxanyl, dihydropyranyl, tetrahydropyranyl, pyridyl, pyridazinyl, pyrimidinyl, pyrazinyl, thiophenyl, furanyl, pyrrolyl, pyrazolyl, imidazolyl, triazolyl, oxazolyl, isoxazolyl, thiazolyl, isothiazolyl, oxadiazolyl, azepanyl and diazepanyl which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl.

In an embodiment, $R^7$ is selected from the group consisting of: pyridyl, thiophenyl and pyrazolyl which is optionally substituted with 1, 2 or 3 substituents independently selected from the group consisting of: halo, $C_{1-4}$ alkyl, $C_{1-4}$ haloalkyl, —O—$C_{1-4}$ alkyl, —O—$C_{1-4}$ haloalkyl. Preferably, $R^7$ is substituted with 1 or 2 substituents selected from the group consisting of: $C_1$ alkyl, $C_2$ alkyl, —O—$C_1$ alkyl, —O—$C_2$ alkyl, chloro and fluoro. More preferably, $R^7$ is substituted a $C_1$ alkyl.

In an embodiment, $R^7$ is $C_{2-4}$ alkynyl, which is optionally substituted with TMS.

In a preferred embodiment, the compound of the present invention has a structure according to Formula (VI):

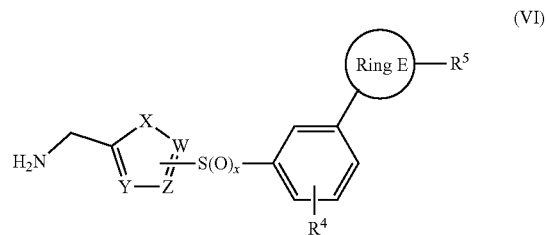

(VI)

wherein W, X, Y, Z and x are as defined for the compound of Formula (I);

$R^4$ is selected from the group consisting of $C_{1-4}$ alkyl, $C_{1-4}$ haloalkyl, halo, —$OR^{A2}$, —$C(O)NR^{A2}R^{B2}$, —$SO_2R^{A2}$ and —$C(O)OR^{A2}$;

wherein $R^{A2}$ and $R^{B2}$ are at each occurrence independently selected from the group consisting of: H and $C_{1-4}$ alkyl, wherein the $C_{1-4}$ alkyl is optionally substituted with —OH; wherein in the specific group —$NR^{A2}R^{B2}$, $R^{A2}$ and $R^{B2}$, together with the nitrogen atom to which they are bonded can form a 4- to 7-membered ring system;

"Ring E" is selected from the group consisting of: phenyl, pyrrolidinyl, pyrazolyl and pyridinyl;

$R^5$ is selected from the group consisting of: H, $C_{1-4}$ alkyl and $C_{1-4}$ alkyl substituted with —O—$C_{1-4}$ alkyl.

In an embodiment, X is S.

In an embodiment, Y is CR. In an embodiment, R is H or F.

In an embodiment, Y is N.

In an embodiment, W is carbon and is bonded to

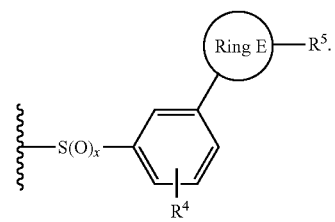

In an embodiment, Z is CR. In an embodiment, R is H.
In an embodiment, W is CR. In an embodiment, R is H.

In an embodiment, Z is carbon and is bonded to

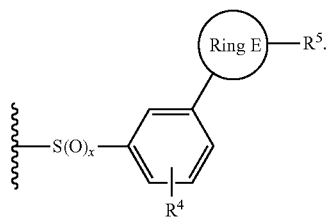

In an embodiment, the compound of formula (VI) has the structure:

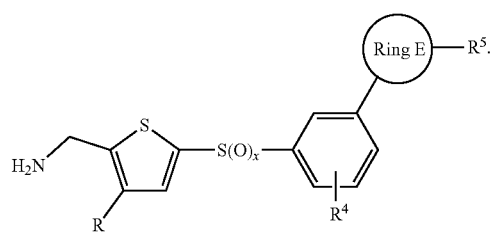

In an embodiment, the compound of formula (VI) has the structure:

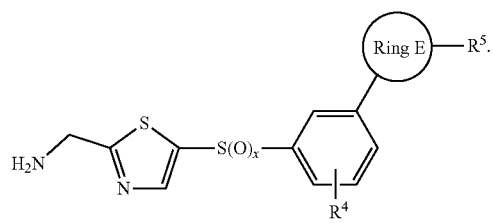

In an embodiment, the compound of formula (VI) has the structure:

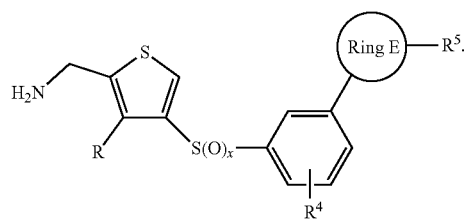

In an embodiment, the compound of formula (VI) has the structure:

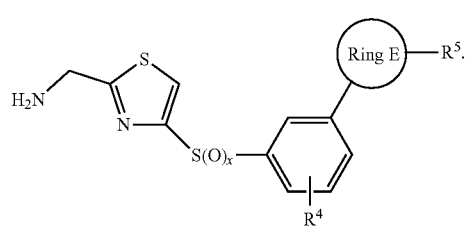

In an embodiment x is 2.

In an embodiment, $R^4$ is meta- to the —S(O)$_x$— group:

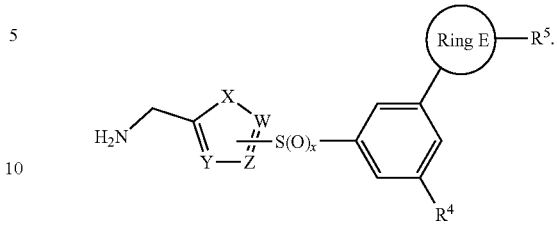

In an embodiment, $R^4$ is para- to the —S(O)$_x$— group:

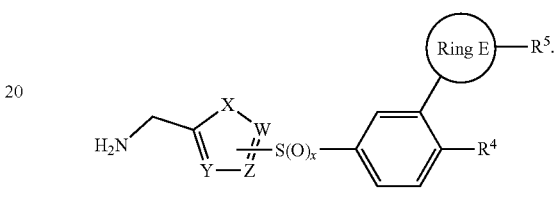

In an embodiment, $R^4$ is selected from the group consisting of —CH$_2$CH$_3$, —OCH$_3$,

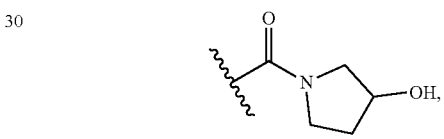

—SO$_2$Me, —C(O)NMe$_2$ and —C(O)OH.

In an embodiment, Ring E is phenyl, optionally

In an embodiment, Ring E is

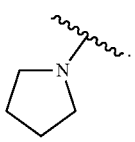 [SMILES: *N1CCCC1]

In an embodiment, Ring E is

In an embodiment, Ring E is
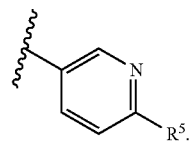
In an embodiment, R⁵ is selected from the group consisting of: H, —CH₃ and —CH₂OCH₃.
In an embodiment, the compound is selected from the group consisting of:
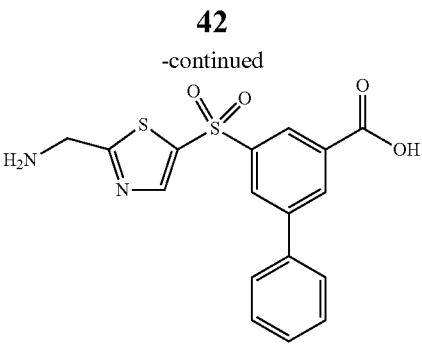
In an embodiment, the compound is:
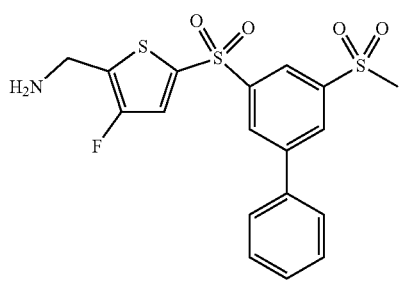 [SMILES: CS(=O)(=O)c1cc(-c2ccccc2)cc(S(=O)(=O)c2cc(F)c(CN)s2)c1]
In an embodiment, the compound is:
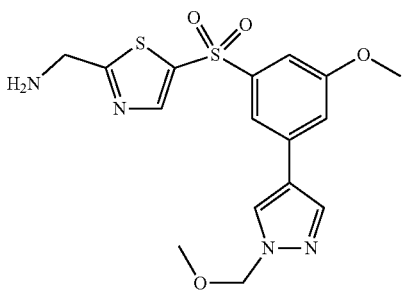 [SMILES: COCn1cc(-c2cc(OC)cc(S(=O)(=O)c3cnc(CN)s3)c2)cn1]

in an embodiment, the compound is:

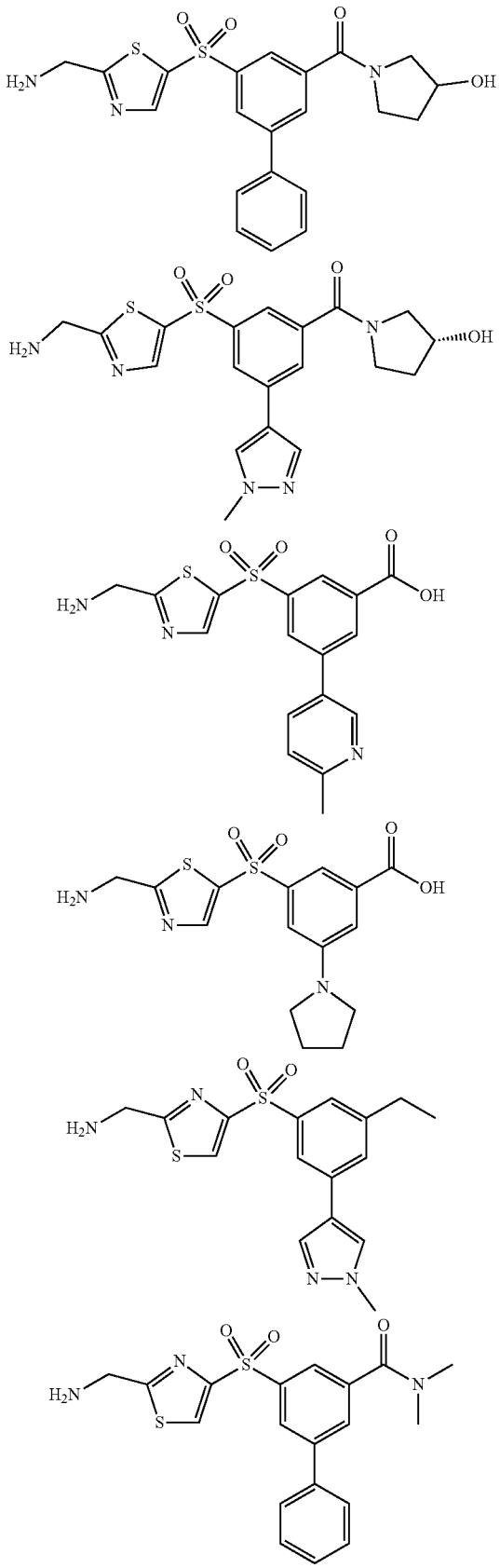

Also provided is a compound selected from the compounds recited in table 1 below or a pharmaceutically acceptable salt thereof.

Also provided is a pharmaceutical formulation comprising a compound of the invention, or a pharmaceutically acceptable salt thereof, and a pharmaceutically acceptable excipient.

A further aspect provides a compound of the invention, or a pharmaceutically acceptable salt thereof, for use as a medicament.

Further provided is a compound of the invention, or a pharmaceutically acceptable salt or N-oxide thereof, for use in the treatment of a condition which is modulated by LOX, for example a condition which is modulated by LOX, LOXL1, LOXL2, LOXL3 or LOLXL4 or a combination thereof.

Also provided is a compound of the invention, or a pharmaceutically acceptable, for use in the treatment of a proliferative disease for example a cancer. The compound of the invention may be used alone or in combination with one or more additional anti-tumour agent and/or radiotherapy for the treatment of a cancer. The compound of the invention may be for use in the treatment of a non-metastatic cancer. The compound of the invention may be for use in the treatment of metastatic cancer. The compound of the invention may be for use in the prevention or treatment of tumour metastasis.

A further aspect provides a compound of the invention, or a pharmaceutically acceptable salt thereof, for use in the treatment of a condition selected from a fibrotic condition, an inflammatory condition, cardiovascular disease, pulmonary diseases, neurodegenerative diseases, ocular conditions particularly those characterized by neovascularization, viral infection, endometriosis, psoriasis and adiposity Also provided is a method of inhibiting LOX activity (for example LOX, LOXL1, LOXL2, LOXL3 or LOLXL4) in a human or animal subject in need of such inhibition, the method comprising administering to said subject an effective amount of a compound of the invention, or a pharmaceutically acceptable salt thereof.

The present invention further provides a method of synthesising a compound of the invention, or a pharmaceutically acceptable salt thereof.

In another aspect, the present invention provides novel intermediates as defined herein which are suitable for use in any one of the synthetic methods as set out herein.

Preferred, suitable, and optional features of any one particular aspect of the present invention are also preferred, suitable, and optional features of any other aspect.

BRIEF DESCRIPTION OF THE DRAWINGS

FIG. 23 shows a LOX Assay Plate Layout.
FIG. 24 shows a HRP Counter Assay Plate Layout.
FIG. 25 shows a ROS-Glo LOX Assay Plate Layout.
FIG. 26 shows a MAO-A Assay Plate Layout.
FIG. 27 shows a MAO-B Assay Plate Layout.
FIG. 28 shows a DAO Assay Plate Layout.

DETAILED DESCRIPTION

Definitions

Figure 1:
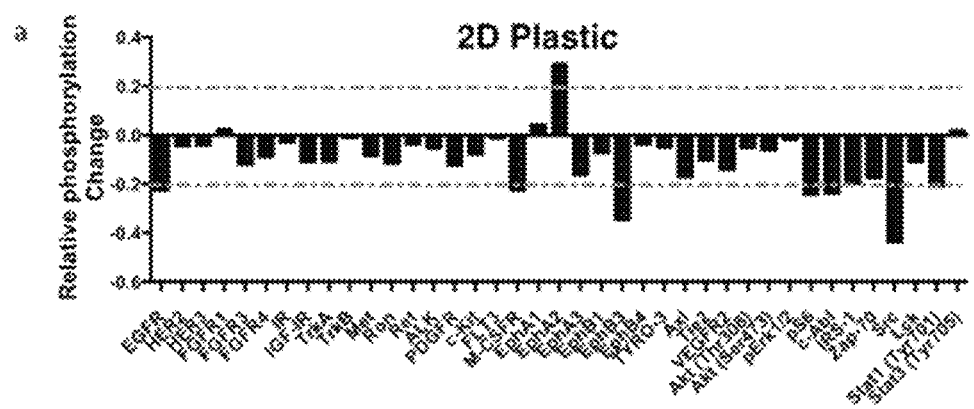
FIG. 1 shows a receptor tyrosine kinase (RTK) antibody array, illustrating the relative phosphorylation change in LOX depleted in MDA-MB-231 breast cancer cells grown in a) standard plastic (2D) culture conditions and b) in collagen gels (3D).
Figure 1:
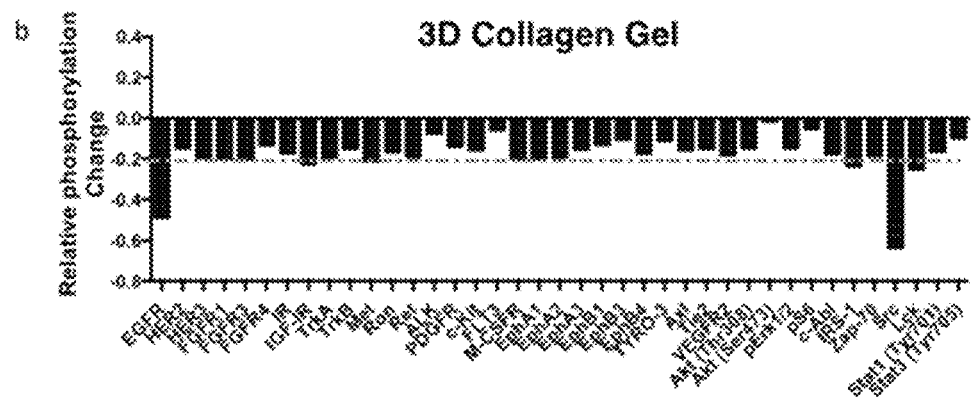

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

The term "halo" or "halogen" refers to one of the halogens, group 17 of the periodic table. In particular the term refers to fluorine, chlorine, bromine and iodine. Preferably, the term refers to fluorine or chlorine.

The term $C_{m*n}$ refers to a group with m to n carbon atoms.

The term "$C_{1-6}$ alkyl" refers to a linear or branched hydrocarbon chain containing 1, 2, 3, 4, 5 or 6 carbon atoms, for example methyl, ethyl, n-propyl, iso-propyl, n-butyl, sec-butyl, tert-butyl, n-pentyl and n-hexyl. "$C_{1-4}$ alkyl" similarly refers to such groups containing up to 4 carbon atoms. Alkylene groups are divalent alkyl groups and may likewise be linear or branched and have two points of attachment to the remainder of the molecule. Furthermore, an alkylene group may, for example, correspond to one of those alkyl groups listed in this paragraph. The alkyl and alkylene groups may be unsubstituted or substituted by one or more substituents. Possible substituents are described below. Substituents for the alkyl group may be halogen, e.g. fluorine, chlorine, bromine and iodine, OH, $C_1$-$C_4$ alkoxy. Other substituents for the alkyl group may alternatively be used.

The term "$C_{1-6}$ haloalkyl", e.g. "$C_{1-4}$ haloalkyl", refers to a hydrocarbon chain substituted with at least one halogen atom independently chosen at each occurrence, for example fluorine, chlorine, bromine and iodine. The halogen atom may be present at any position on the hydrocarbon chain. For example, $C_{1-6}$ haloalkyl may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoromethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl.

The term "$C_{2-6}$ alkenyl" includes a branched or linear hydrocarbon chain containing at least one double bond and having 2, 3, 4, 5 or 6 carbon atoms. The double bond(s) may be present as the E or Z isomer. The double bond may be at any possible position of the hydrocarbon chain. For example, the "$C_{2-6}$ alkenyl" may be ethenyl, propenyl, butenyl, butadienyl, pentenyl, pentadienyl, hexenyl and hexadienyl.

The term "$C_{2-6}$ alkynyl" includes a branched or linear hydrocarbon chain containing at least one triple bond and having 2, 3, 4, 5 or 6 carbon atoms. The triple bond may be at any possible position of the hydrocarbon chain. For example, the "$C_{2-6}$ alkynyl" may be ethynyl, propynyl, butynyl, pentynyl and hexynyl.

The term "$C_{3-6}$ cycloalkyl" includes a saturated hydrocarbon ring system containing 3, 4, 5 or 6 carbon atoms. For example, the "$C_3$-$C_6$ cycloalkyl" may be cyclopropyl, cyclobutyl, cyclopentyl, cyclohexyl, bicycle[2.1.1]hexane or bicycle[1.1.1]pentane.

The term "heterocyclyl", "heterocyclic" or "heterocycle" includes a non-aromatic saturated or partially saturated monocyclic or fused, bridged, or spiro bicyclic heterocyclic ring system(s). Monocyclic heterocyclic rings may contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles may contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles comprising at least one nitrogen in a ring position include, for example, azetidinyl, pyrrolidinyl, piperidinyl, piperazinyl, morpholinyl, thiomorpholinyl, tetrahydrotriazinyl, tetrahydropyrazolyl, tetrahydropyridinyl, homopiperidinyl, homopiperazinyl, 3,8-diaza-bicyclo[3.2.1]octanyl, 8-aza-bicyclo[3.2.1]octanyl, 2,5-Diaza-bicyclo[2.2.1]heptanyl and the like. Typical sulfur containing heterocycles include tetrahydrothienyl, dihydro-1,3-dithiol, tetrahydro-2H-thiopyran, and hexahydrothiepine. Other heterocycles include dihydro oxathiolyl, tetrahydro oxazolyl, tetrahydro-oxadiazolyl, tetrahydrodioxazolyl, tetrahydrooxathiazolyl, hexahydrotriazinyl, tetrahydro oxazinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O), for example, 2 oxopyrrolidinyl, 2-oxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. For example, the term "piperidino" or "morpholino" refers to a piperidin-1-yl or morpholin-4-yl ring that is linked via the ring nitrogen.

The term "bridged ring systems" includes ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane, and quinuclidine.

The term "spiro bi-cyclic ring systems" includes ring systems in which two ring systems share one common spiro carbon atom, i.e. the heterocyclic ring is linked to a further carbocyclic or heterocyclic ring through a single common spiro carbon atom. Examples of spiro ring systems include 3,8-diaza-bicyclo[3.2.1]octane, 2,5-Diaza-bicyclo[2.2.1]heptane, 6-azaspiro[3.4]octane, 2-oxa-6-azaspiro[3.4]octane, 2-azaspiro[3.3]heptane, 2-oxa-6-azaspiro[3.3]heptane, 6-oxa-2-azaspiro[3.4]octane, 2,7-diaza-spiro[4.4]nonane, 2-azaspiro[3.5]nonane, 2-oxa-7-azaspiro[3.5]nonane and 2-oxa-6-azaspiro[3.5]nonane.

"Heterocyclyl-$C_{m-n}$ alkyl" includes a heterocyclyl group covalently attached to a $C_{m-n}$ alkylene group, both of which are defined herein.

The term "aromatic" when applied to a substituent as a whole includes a single ring or polycyclic ring system with 4n+2 electrons in a conjugated π system within the ring or ring system where all atoms contributing to the conjugated π system are in the same plane.

The term "aryl" includes an aromatic hydrocarbon ring system. The ring system has 4n+2 electrons in a conjugated π system within a ring where all atoms contributing to the conjugated π system are in the same plane. For example, the "aryl" may be phenyl and naphthyl. The aryl system itself may be substituted with other groups.

The term "heteroaryl" includes an aromatic mono- or bicyclic ring incorporating one or more (for example 1-4, particularly 1, 2 or 3) heteroatoms selected from nitrogen, oxygen or sulfur. The ring or ring system has 4n+2 electrons in a conjugated π system where all atoms contributing to the conjugated π system are in the same plane.

Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl and imidazo[1,2-b][1,2,4]triazinyl. Examples of heteroaryl groups comprising at least one nitrogen in a ring position include pyrrolyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, indolyl, isoindolyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl and pteridinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl-$C_{m\text{-}n}$ alkyl-" includes a heteroaryl group covalently attached to a $C_{m\text{-}n}$ alkylene group, both of which are defined herein. Examples of heteroaralkyl groups include pyridin-3-ylmethyl and the like.

The term "optionally substituted" includes either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

A bond terminating in a represents that the bond is connected to another atom that is not shown in the structure. A bond terminating inside a cyclic structure and not terminating at an atom of the ring structure represents that the bond may be connected to any of the atoms in the ring structure where allowed by valency.

Where a moiety is substituted, it may be substituted at any point on the moiety where chemically possible and consistent with atomic valency requirements. The moiety may be substituted by one or more substituents, e.g. 1, 2, 3 or 4 substituents; optionally there are 1 or 2 substituents on a group. Where there are two or more substituents, the substituents may be the same or different.

Substituents are only present at positions where they are chemically possible, the person skilled in the art being able to decide (either experimentally or theoretically) without undue effort which substitutions are chemically possible and which are not.

Ortho, meta and para substitution are well understood terms in the art. For the absence of doubt, "ortho" substitution is a substitution pattern where adjacent carbons possess a substituent, whether a simple group, for example the fluoro group in the example below, or other portions of the molecule, as indicated by the bond ending in

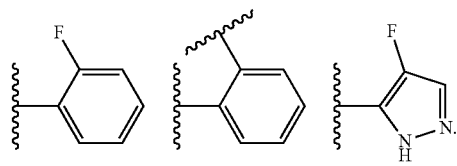

"Meta" substitution is a substitution pattern where two substituents are on carbons one carbon removed from each other, i.e. with a single carbon atom between the substituted carbons. In other words there is a substituent on the second atom away from the atom with another substituent. For example the groups below are meta substituted.

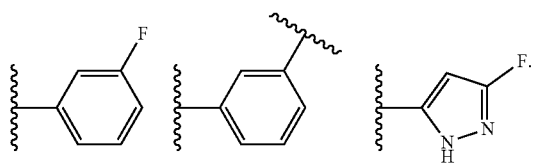

"Para" substitution is a substitution pattern where two substituents are on carbons two carbons removed from each other, i.e. with two carbon atoms between the substituted carbons. In other words there is a substituent on the third atom away from the atom with another substituent. For example the groups below are para substituted.

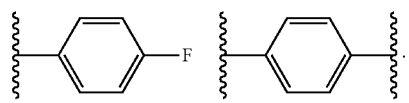

The term "acyl" includes an organic radical derived from, for example, an organic acid by the removal of the hydroxyl group, e.g. a radical having the formula R—C(O)—, where R may be selected from H, $C_{1-6}$ alkyl, $C_{3-6}$ cycloalkyl, phenyl, benzyl or phenethyl group, e.g. R is H or $C_{1-3}$ alkyl. In one embodiment acyl is alkyl-carbonyl. Examples of acyl groups include, but are not limited to, formyl, acetyl, propionyl and butyryl. A particular acyl group is acetyl (also represented as Ac).

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

The invention contemplates pharmaceutically acceptable salts of the compounds of the invention. These may include the acid addition and base salts of the compounds. These may be acid addition and base salts of the compounds.

Suitable acid addition salts are formed from acids which form non-toxic salts. Examples include the acetate, aspartate, benzoate, besylate, bicarbonate/carbonate, bisulfate/sulfate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 1,5-naphthalenedisulfonate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate and hemicalcium salts. For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of the invention may be prepared by for example, one or more of the following methods:

(i) by reacting the compound of the invention with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound of the invention to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Where a compound of the invention has two or more stereo centres any combination of (R) and (S) stereoisomers is contemplated. The combination of (R) and (S) stereoisomers may result in a diastereomeric mixture or a single diastereoisomer. The compounds of the invention may be present as a single stereoisomer or may be mixtures of stereoisomers, for example racemic mixtures and other enantiomeric mixtures, and diasteroemeric mixtures. Where the mixture is a mixture of enantiomers the enantiomeric excess may be any of those disclosed above. Where the compound is a single stereoisomer the compounds may still contain other diasteroisomers or enantiomers as impurities. Hence a single stereoisomer does not necessarily have an enantiomeric excess (e.e.) or diastereomeric excess (d.e.) of 100% but could have an e.e. or d.e. of about at least 85%

The compounds of this invention may possess one or more asymmetric centres; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess LOX inhibitory activity.

Compounds and salts described in this specification may be isotopically-labelled (or "radio-labelled"). Accordingly, one or more atoms are replaced by an atom having an atomic mass or mass number different from the atomic mass or mass number typically found in nature. Examples of radionuclides that may be incorporated include $^2$H (also written as "D" for deuterium), $^3$H (also written as "T" for tritium), $^{11}$C, $^{13}$C, $^{14}$C, $^{15}$O, $^{18}$O, $^{18}$F and the like. The radionuclide that is used will depend on the specific application of that radio-labelled derivative. For example, for in vitro competition assays, $^3$H or $^{14}$C are often useful. For radio-imaging applications, $^{11}$C or $^{18}$F are often useful. In some embodiments, the radionuclide is $^3$H. In some embodiments, the radionuclide is $^{14}$C. In some embodiments, the radionuclide is $^{11}$C. And in some embodiments, the radionuclide is $^8$F.

It is also to be understood that certain compounds of the invention may exist in solvated as well as unsolvated forms such as, for example, hydrated forms. It is to be understood that the invention encompasses all such solvated forms that possess LOX inhibitory activity.

It is also to be understood that certain compounds of the invention may exhibit polymorphism, and that the invention encompasses all such forms that possess LOX inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

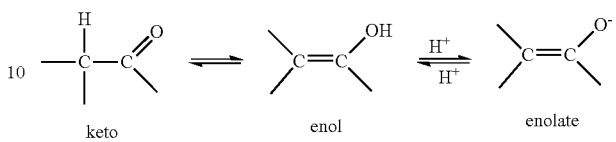

keto          enol          enolate

The in vivo effects of a compound of the invention may be exerted in part by one or more metabolites that are formed within the human or animal body after administration of a compound of the invention.

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl or trifluoroacetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.
General Synthetic Routes
Synthetic Routes to Compounds of Formula (I)

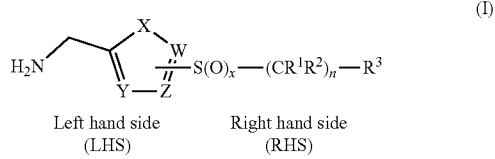

A. Methods for Attaching the RHS Sulfonyl/Sulfinyl Side Chain to the LHS Aminomethyl-Heteroarylsulfonyl (or Aminomethyl-Heteroarylsulfinyl) Core Synthetic routes to compounds of Formula (I) are exemplified for thiophene or thiazole examples. It should be understood that the same synthetic routes can be applied for other instances of X, W, Y and Z described in this application. For clarification, when used below, left hand side fragment (LHS) is referring to the aminomethylheteroaryl fragment as drawn above and right hand side fragment (RHS) to the side chain such as $—S(O)_x—(CR^1R^2)_n—R^3$ in Formula (I).

A1) Nucleophilic substitution—RHS side chain $(S(O)_x (CR^1R^2)_n R^3)$ as nucleophile

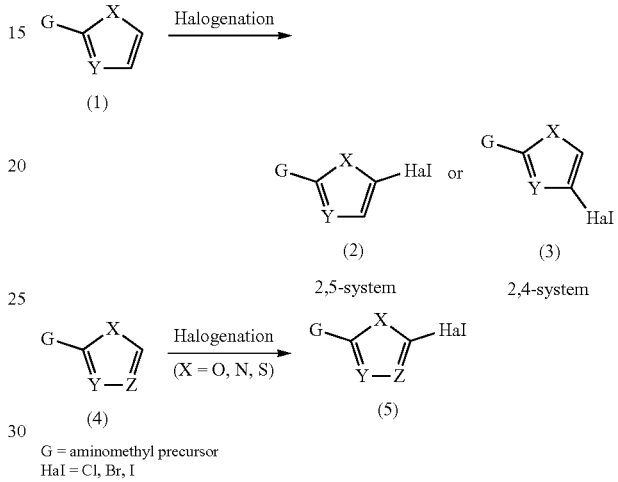

G = aminomethyl precursor
Hal = Cl, Br, I

Haloheteroaryls (2) and (3) are essential building blocks for the synthesis of compounds of Formula (I) where W or $Z=-S(O)_x—C(R^1R^2)_n—R^3$. These building blocks are either commercially available, for example 5-bromothiophene-2-carbonitrile, or can be synthesised by halogenation of the heteroaryl rings (1) as shown in Scheme 1. Group G can be any suitable precursors of the aminomethyl moiety, for example a hydrogen, a nitrile, a carbonyl, a methyl, a protected hydroxymethyl or a protected aminomethyl group. Depending on the conditions employed, the alpha halogenation product (2) or the beta product (3) can be obtained, which will serve as the building blocks for the 2-aminomethyl-5-sulfonyl and 2-aminomethyl-4-sufonyl analogues respectively. For clarification, alpha halogenation refers to conversion of W from CH to C-Halogen. Beta halogenation refers to conversion of Z from CH to C-Halogen. For heteroaryl ring containing 3 heteroatoms (4, X=O, N or S), only one possible position can be halogenated, leading to haloheteroaryl (5).

Scheme 2

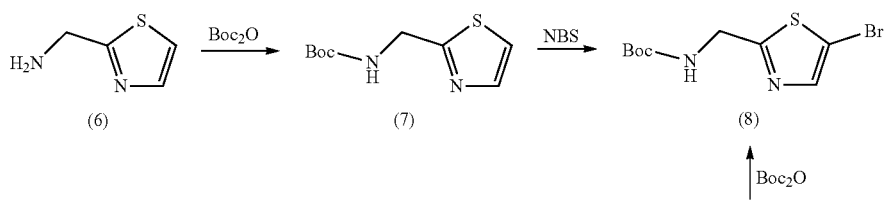

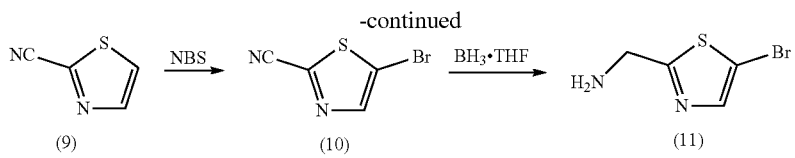

For example, the bromothiazole building block (8) can be synthesised from the alpha bromination of protected aminomethylthiazole (AMTz) (7) using N-bromosuccinimide (NBS) (Hynes, 2009) as illustrated in Scheme 2. Alternatively, bromination of cyanothiazole (9) can afford cyanobromothiazole (10), which can be an important building block itself. Reduction of the nitrile of cyanobromothiazole (10) and subsequent Boc protection affords bromothiazole (8).

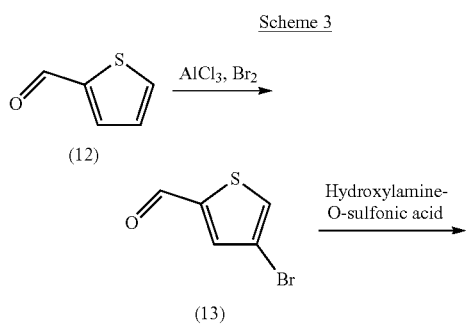

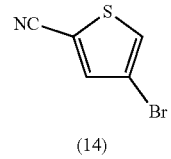

A beta halogenation example is illustrated in Scheme 3, using the methods of Renault et al (Renault, 1997). Hence, treatment of thiophene-2-carbaldehyde (12) with bromine ($Br_2$) in the presence of aluminium trichloride ($AlCl_3$) leads to beta brominated intermediate (13). This can be employed directly as a building block for subsequent RHS side chain attachment (see subsequent sections). Alternatively, it can be converted to a more convenient building block, for example 4-bromothiophene-2-carbonitrile (14) using hydroxylamine-O-sulfonic acid {Zhi, 2000 #374}.

A1a—Substitution of 5- or 4-Halo-2-Carbonitrile Analogues:

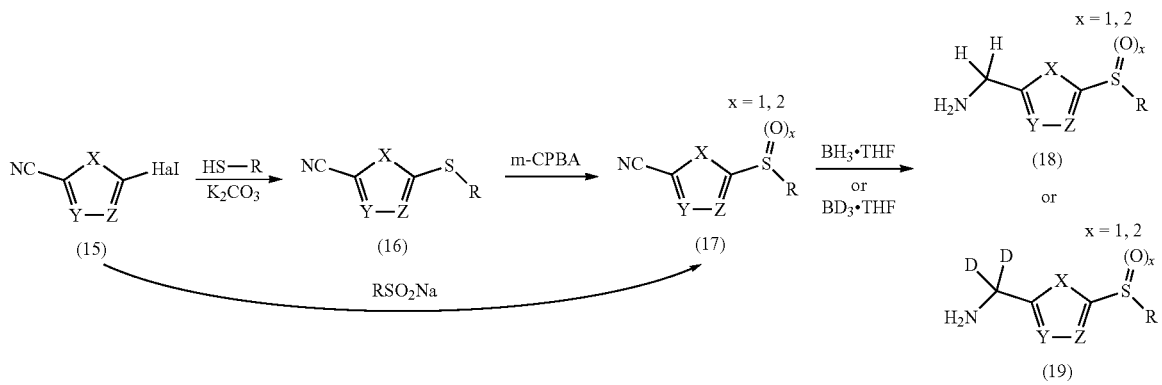

$R = -(CR^1R^2)_n-R^3$ or a convenient precursor thereof
Hal = F, Cl, Br or I
$W = -S(O)_x-C(R^1R^2)_n-R^3$ in Formula (I)

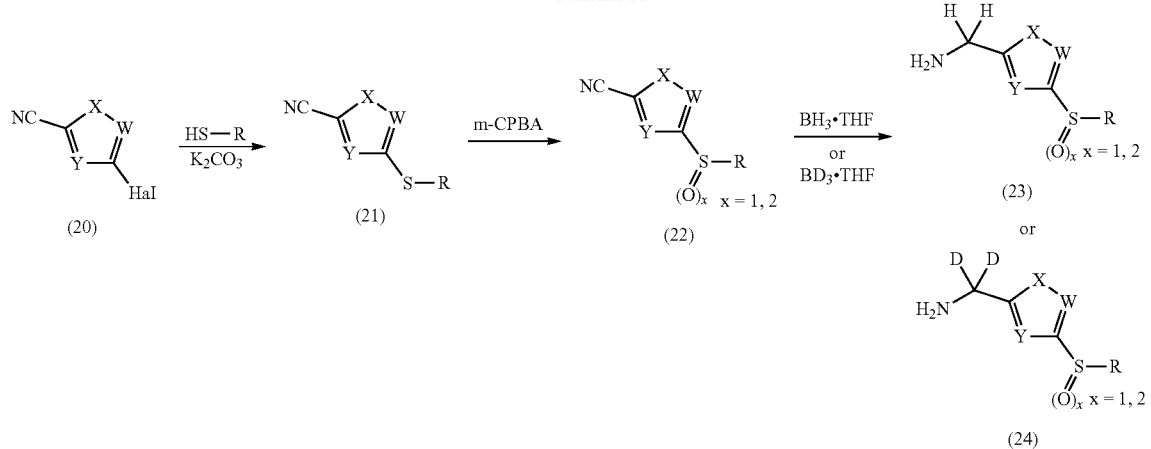

Z = -S(O)$_x$-C(R$^1$R$^2$)$_n$-R$^3$ in Formula (I)

Sulfonyl and sulfinyl compounds of Formula (I) where W=—S(O)$_x$—C(R$^1$R$^2$)$_n$—R$^3$ can be conveniently synthesised from 5-halo-2-carbonitriles (15) which are commercially available or can be synthesised for the different examples of X, Y, Z, W. 5-halo-2-carbonitriles (15) can undergo nucleophilic substitution with a range of conveniently substituted alkyl, cycloalkyl, heterocycloalkyl, aryl or heteroaryl thiols to generate the corresponding thioethers (16), as shown in Scheme 4. Subsequent oxidation of the thioether group using one equivalent of m-CPBA leads to the corresponding sulfoxides (17, x=1), whilst >2 equivalents of m-CPBA affords the sulfones (17, x=2). Alternatively, sulfones (17, x=2) can be obtained directly from the reaction of 5-halo-2-carbonitriles (15) with alkyl or aryl sulfinates. The nitrile group of intermediates (17) can be subsequently reduced, for example with borane-THF complex (BH$_3$.THF) or lithium aluminium hydride (LiAlH$_4$), to afford 2-aminomethyl-5-sulfonyl or -sulfinyl analogues (18). The BH$_3$.THF reagent can be replaced by BD$_3$.THF to give the dideuterated analogues (19).

A similar method can be used to synthesise 2-aminomethyl-4-sulfonyl analogues (23) of formula (I) where Z=—S(O)$_x$—C(R$^1$R$^2$)$_n$—R$^3$. Thioethers (21) can be obtained from 4-halo-2-carbonitriles (20) by nucleophilic substitution as described above. Subsequent S-oxidation using m-CPBA leads to sulfoxides/sulfones (22), which can be reduced by BH$_3$.THF to afford 2-aminomethyl-5-sulfinyl-(x=1) or 2-aminomethyl-5-sulfonyl-heteroaryl (x=2) analogues (23). Similarly, the dideuterated analogues (24) can be obtained when the reduction is performed using BD$_3$.THF instead of BH$_3$.THF.

Scheme 5

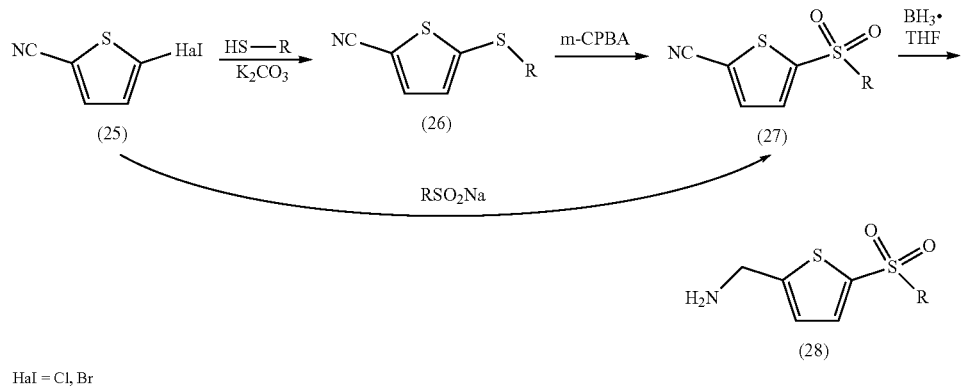

HaI = Cl, Br

Aminomethylthiophene (AMT)-sulfone analogues (28; X=S, Y=Z=CH, x=2 in formula I), for example, can be obtained from the commercially available 5-bromo- or 5-chlorothiophene-2-carbonitrile (25) by this method, as exemplified in Scheme 5.

Scheme 6

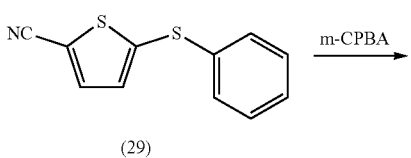

-continued

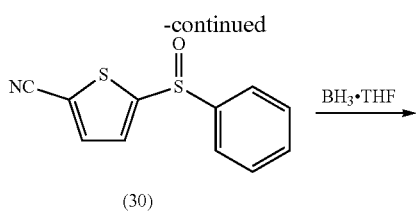

(30)

(31)

In another example, mono S-oxidation of intermediate (29) using one equivalent of m-CPBA gives sulfoxide (30), which can undergo subsequent borane-mediated reduction to afford (5-(phenylsulfinyl)thiophen-2-yl)methanamine (31) as illustrated in Scheme 6.

Scheme 7

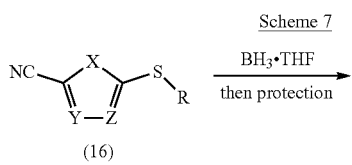

(16)

(32)

(18)

R = -(CR$^1$R$^2$)$_n$-R$^3$ or a convenient precursor thereof
PG = protecting group
W = -S(O)$_x$-C(R$^1$R$^2$)$_n$-R$^3$ in Formula (I)

(21)

(33)

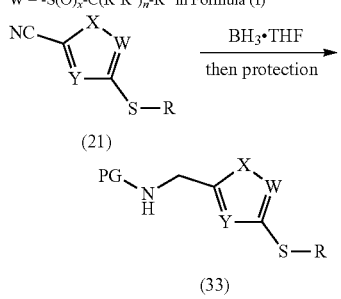

(23)

Z = -S(O)$_x$-C(R$^1$R$^2$)$_n$-R$^3$ in Formula (I)

Another highly versatile synthetic route based on intermediate thioethers (16) or (21) begins with the reduction of the nitrile moiety using, for example, BH$_3$.THF as shown in Scheme 7. In-situ protection of the resulting primary amino group affords the corresponding protected thioethers (32) or (33). Subsequent oxidation using m-CPBA affords the corresponding protected sulfone/sulfoxides, which can undergo protecting group (PG) removal to furnish the desired 2-aminomethyl-5-sulfonyl or -sulfinyl analogues (18) or 2-aminomethyl-4-sulfonyl or -sulfinyl analogues (23).

Scheme 8

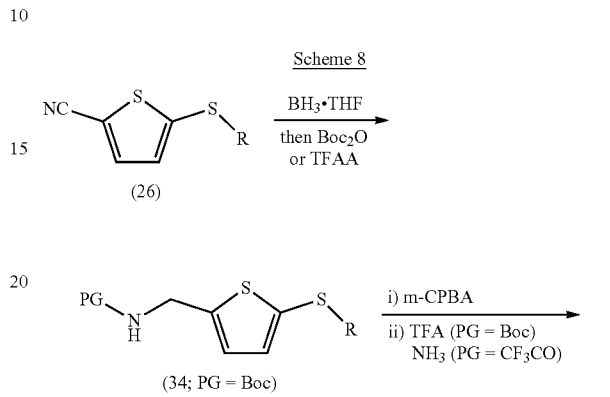

(26)

(34; PG = Boc)
(35; PG = CF$_3$CO)

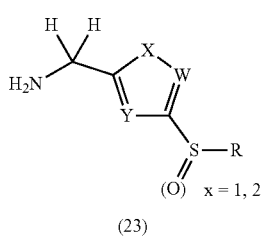

(28)

(36)

(37)

(38)

For thiophene examples, the reduction of nitrile intermediate (26) using BH$_3$.THF followed by in-situ protection of the resulting primary amino group, with for example, BoC$_2$O or trifluoroacetic anhydride (TFAA), affords protected thioethers (34) and (35) respectively as exemplified in Scheme 8. Oxidation of the thioether moiety using m-CPBA followed by removal of the protecting group (PG) with acid or ammonia respectively furnishes the desired AMT analogues (28). Similarly, in another example, 2-aminomethyl-5-sulfonyl-1,4-thiazole analogues (38) can be derived from the commercially available 2-chlorothiazole-5-carbonitrile (36).

A1b—Substitution of 5-Halo-2-Carbonyl Analogues:

Scheme 9

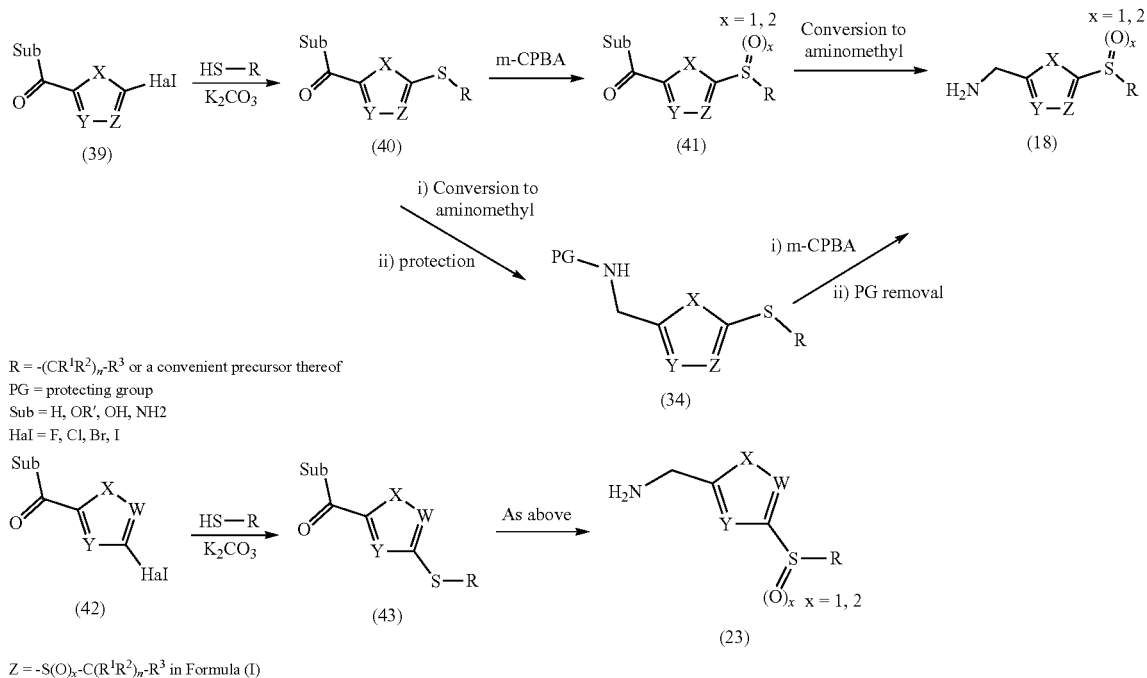

Sulfone compounds of formula (I) where W or Z=—S(O)$_x$—C(R$^1$R$^2$)$_n$—R$^3$ can be synthesised from 5-halo-2-carbonyl (39) or 4-halo-2-carbonyl heteroaryls (42) respectively, which might be commercially available instead of nitriles or can be synthesised more conveniently. Carbonyl compounds in this context refer to carboxylic acids, esters, aldehydes and amides. In Scheme 9 (exemplified for 5-halo-2-carbonyl starting material (39)), the starting haloheteroaryl carbonyl compounds can be substituted with thiols to afford thioethers (40). The thioethers can be oxidised to sulfones or sulfoxides (41) as previously described. The carbonyl group can then be converted to the aminomethyl moiety to furnish the desired 2-aminomethyl-heteroaryl analogues (18). Alternatively, the carbonyl moiety of thioethers (40) can be converted to aminomethyl and protected with for example (but not limited to) a Boc group. This intermediates (34) can subsequently be oxidised to the corresponding sulfone/sulfoxides and then deprotected to afford the desired 2-aminomethyl-5-sulfinyl- and -sulfonyl analogues (18). 2-Aminomethyl-4-sulfinyl and -sulfonyl analogues (23) can be obtained from 4-halo-2-carbonyl heteroaryls (42) via thioether (43) in a similar manner.

Scheme 10

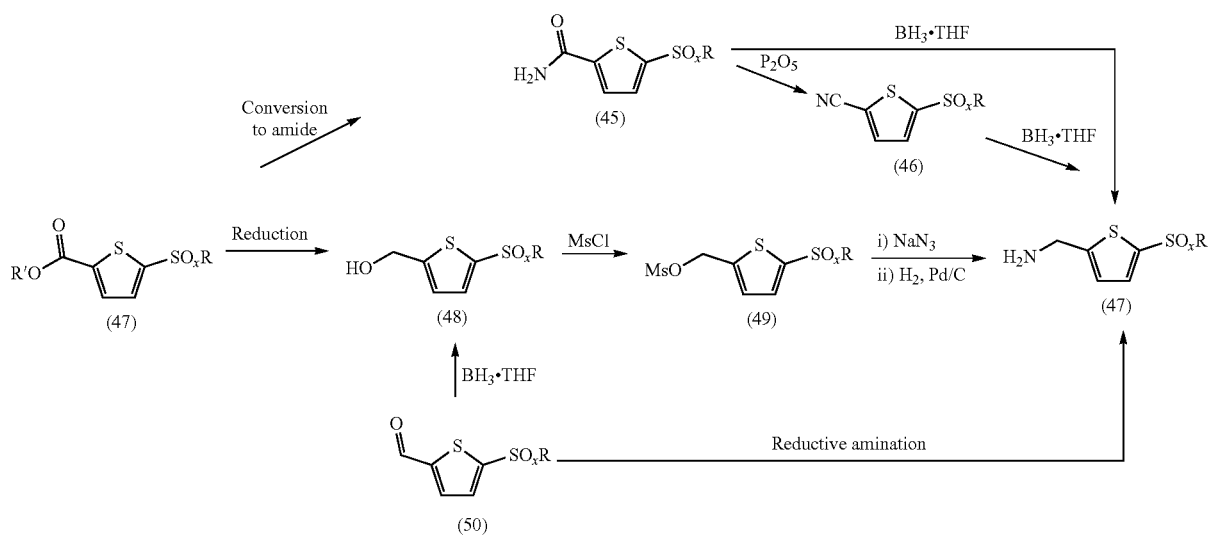

Examples of functional group interconversion from the carbonyl to the desired aminomethyl moieties are shown in Scheme 10 for thiophene examples with a sulfone in 5-position already in place (x=2), but can be applied for thioethers (x=0) or sulfoxides (x=1) in other instances of X, W, Y and Z described in this application. For example, esters (44, R'=alkyl, aryl, heteroaryl, preferably alkyl), carboxylic acids (44, R' =H) and aldehydes (50) can be reduced to the corresponding alcohols (48) using suitable reduction agents, for example diisobutylaluminium hydride (DIBAL-H) for esters, BH$_3$.THF for carboxylic acids and aldehydes. Alcohols (48) can be sulfonylated with, for example, methanesulfonyl chloride to give intermediate mesylate (49). Displacement of the mesylate with, for example, sodium azide and subsequent hydrogenolysis furnishes the desired AMT analogues (47). Carboxylic esters (44.) can be directly converted to amides (45) by treatment with NH$_3$ at elevated temperature or via the corresponding carboxylic acids (44, R' =H). Carboxylic acids (44, R' =H) can be converted to amides (45) using a suitable coupling reagent, for example dicyclohexylcarbodiimide (DCC), or via the corresponding acyl chloride. The resultant amides (45) can be reduced to amine (47) directly using, for example, BH$_3$.THF. Alternatively, it can be dehydrated to nitriles (46) with, for example, trifluoroacetic anhydride or with P2O5, and subsequently reduced to amines (47) using BH$_3$.THF. Aldehydes (50) can be converted directly to amines (47) by reductive amination using, for example, ammonium formate and sodium triacetoxyborohydride. Alternative, it can be converted to the amine (47) via the corresponding oxime using hydroxylamine, followed by oxime reduction using, for example, zinc and acetic acid.

A2) Nucleophilic Substitution—Aminomethyl-Heteroaryl Moiety as Nucleophile:

A2a—Heteroaryl-Thiol Nucleophile

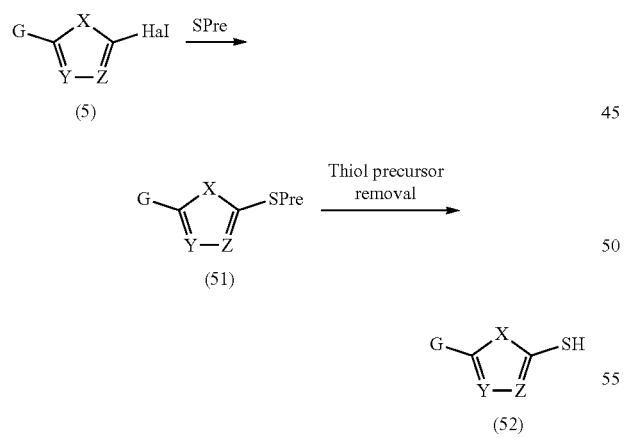

SPre = thiol precursor
G = aminomethyl precursor
Hal = F, Cl, Br or I
W = -S(O)$_x$-C(R$^1$R$^2$)$_n$-R$^3$ in Formula (I)

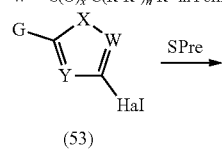

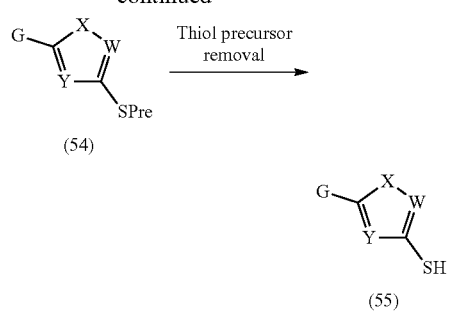

Z = -S(O)$_x$-C(R$^1$R$^2$)$_n$-R$^3$ in Formula (I)

Heteroarylthiols (52) and (55) are essential building blocks for this method. These building blocks are either commercially available, or can be synthesised from haloheteroaryls (5) or (53) as shown in Scheme 11. Group G can be any suitable precursors of the aminomethyl moiety, for example a hydrogen, a nitrile, a carbonyl, a methyl, a protected hydroxymethyl or a protected aminomethyl group. The halide group of haloheteroaryls (5) or (53) can be substituted with a suitable thiol precursor (SPre), for example by nucleophilic substitution or metal catalysed cross coupling, to afford heteroarylthiol precursors (51) or (54). The precursor groups can be subsequently removed to reveal the desired thiols (52) or (55) respectively.

Scheme 12

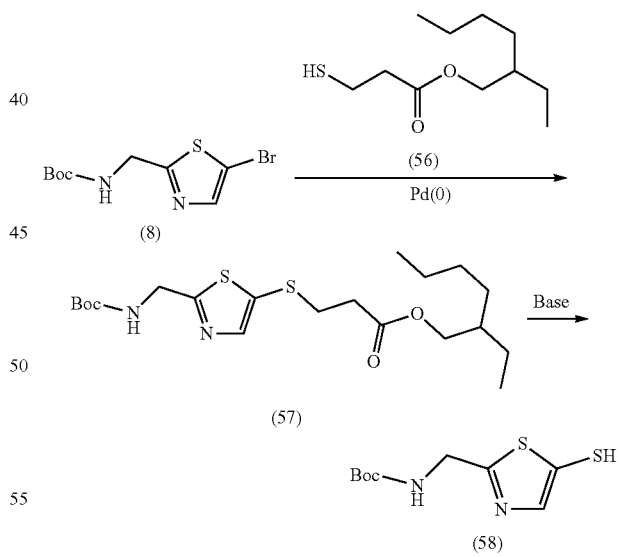

For example, in Scheme 12, the thiol precursor is 2-ethylhexyl 3-mercaptopropanoate (57). Thiazolethiol building block (58) can be synthesised from the sulfide intermediate (57), as exemplified in Scheme 12. Hence, Pd-catalysed cross coupling of bromothiazole (8) and 2-ethylhexyl 3-mercaptopropanoate affords sulfide (57), which can be converted to thiazolethiol (58) under basic conditions in a retro-Michael reaction.

Scheme 13

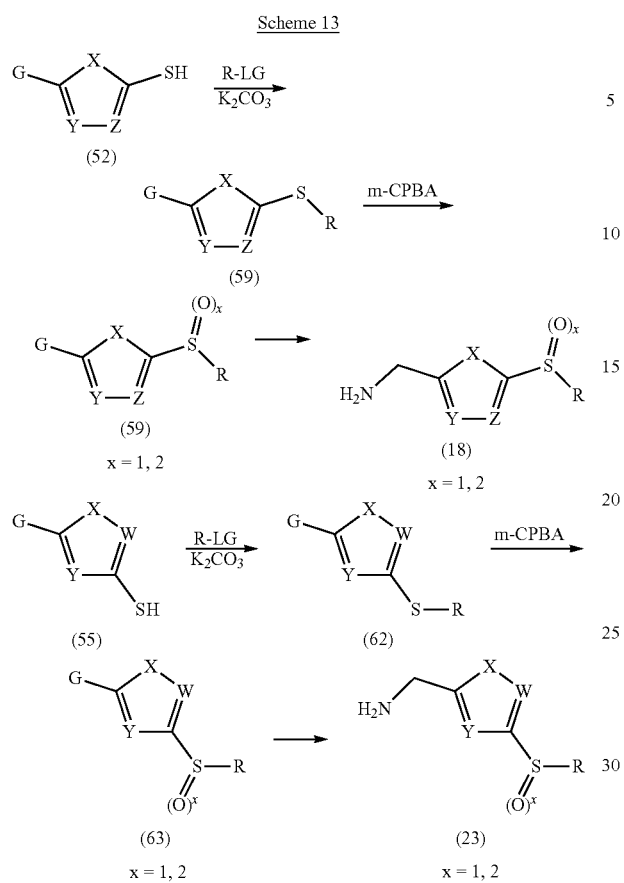

R = -(CR¹R²)ₙ-R³ or a convenient precursor thereof
LG = leaving group: F, Cl, Br, I, Sulfonates
G = aminomethyl precursor
W = -S(O)ₓ-C(R¹R²)ₙ-R³ in Formula (I)
Z = -S(O)ₓ-C(R¹R²)ₙ-R³ in Formula (I)

The heteroayl-5-thiol building blocks (52) can be used to synthesise sulfonyl and sulfinyl compounds of formula (I) where W=—S(O)ₓ—C(R¹R²)ₙ—R³ as illustrated in Scheme 13. Group G can be any suitable precursors of the aminomethyl moiety, for example, a hydrogen, a methyl, a nitrile, a carbonyl, a protected hydroxymethyl or a protected aminomethyl group. Condensation of heteroarylthiol (52) with a range of conveniently substituted alkyl, cycloalkyl, heterocycloalkyl, aryl or heteroaryl halides (R-LG; LG=F, Cl, Br, I, sulfonates) in the presence of a base, for example K₂CO₃, can generate the corresponding thioethers (59). The thioethers can be oxidised to the corresponding sulfones/sulfoxides (60) with m-CPBA. These can be subsequently converted to the desired aminomethyl heteroaryl targets (18) using conditions specific to particular G groups. Similarly, compounds of formula (I) where Z=—S(O)ₓ—C(R¹R²)ₙ—R³ (23) can be obtained from heteroaryl-4-thiol (55).

Scheme 14

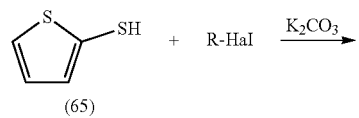

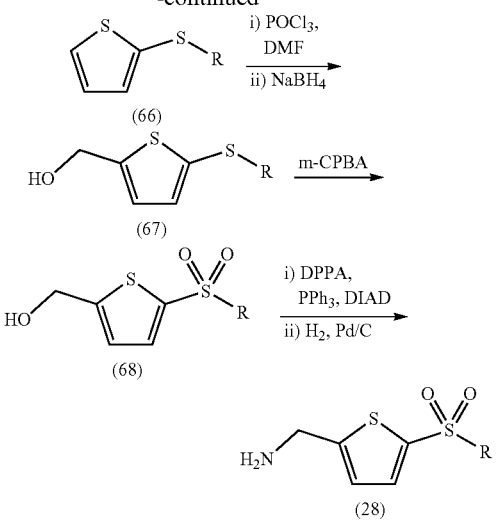

An example using the method described above for the construction of AMT analogues is exemplified in Scheme 14. The commercially available thiophen-2-thiol (65) undergoes a condensation reaction with, for example, a conveniently substituted alkyl-, aryl- or heteroaryl halide in the presence of a base, for example, K₂CO₃, to afford the corresponding thioethers (66). Formylation of the thiophene ring employing phosphorus oxychloride and dimethyformamide gives the corresponding aldehydes, which can be reduced to alcohols (67) using sodium borohydride. S-oxidation with m-CPBA affords sulfonyl-alcohols (68). The hydroxyl group of intermediate (68) can be converted to the corresponding amino group by different methods. For example, the method illustrated in Scheme 14 involves conversion to the corresponding azide under Mitsunobu conditions using diphenylphosphoryl azide (DPPA), PPh₃ and diisopropyl azodicarboxylate (DIAD). The azide product can undergo subsequent hydrogenolysis over Pd/C catalyst to afford the AMT analogues with the desired substitutions (28).

Scheme 15

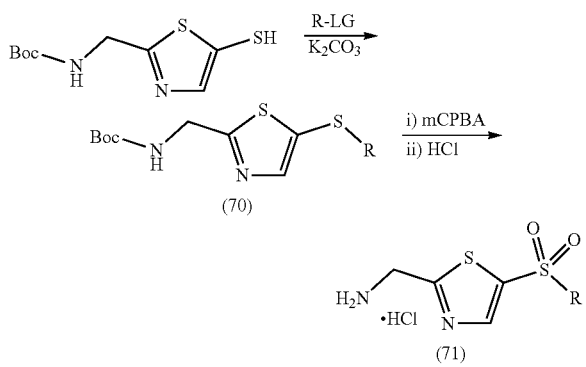

LG = leaving group: halo, mesyl, tosyl, trifyl

In another example, thiazolethiol (58) can be condensed with, for example, a conveniently substituted alkyl, aryl or heteroaryl halide in the presence of a base, for example, K₂CO₃, to afford thioethers (70), as illustrated in Scheme 15.

After S-oxidation, the protecting group can be subsequently removed to afford the desired aminomethylthiazole (AMTz) analogues (71) as the hydrochloride salt.

A2b—Metallated Heterocycle as Nucleophile

Scheme 16

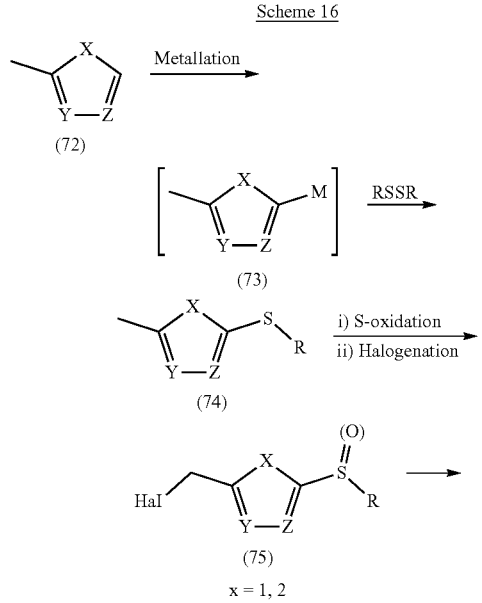

R = -(CR$^1$R$^2$)$_n$-R$^3$ or a convenient precursor thereof
Hal = Cl, Br, I

Some heterocycles can be deprotonated in the 5-position using strong organometallic bases, for example alkyl lithium, Grignard reagents and organocuprates, to afford 5-metallated-2-methyl-heterocycles (73) as exemplified in Scheme 16. This metallated species can undergo substitution with conveniently substituted alkyl, cycloalkyl, heterocycloalkyl, aryl or heteroaryl disulfides (RSSR) to afford thioethers (74). Subsequent S-oxidation followed by benzylic halogenation affords heteroarylmethyl halide (75). The halide can then be substituted with the amino group using various methods, for example, displacement with sodium azide followed by reduction of the azido moiety to afford the desired aminomethylheteroaryl analogues (18).

Scheme 17

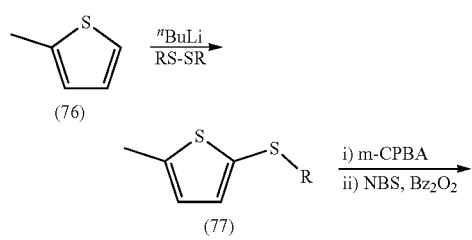

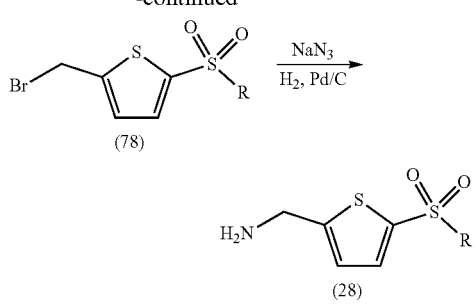

Scheme 17 exemplifies the synthesis of thiophene analogues (28) using this method, starting from the commercially available 2-methylthiophene (76). Lithiated 2-methylthiophene, generated in situ from treatment with "BuLi, can react with a range of disulfides (RS-SR) to afford thiophene thioethers (77). The thioethers can be oxidised to the corresponding sulfones with m-CPBA, and subsequent benzylic bromination using for example NBS and benzoyl peroxide (Bz$_2$O$_2$) affords alkyl bromides (78). These can be converted to the desired AMT-analogues (28) by various methods, for example, condensation with sodium azide followed by hydrogenolysis over Pd/C catalyst as exemplified in Scheme 17.

A3) Metal-Catalysed Cross Coupling

A3a—Coupling of Heteroaryl Halide with Substituted Thiols

Scheme 18

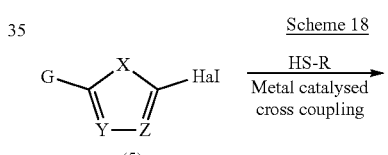

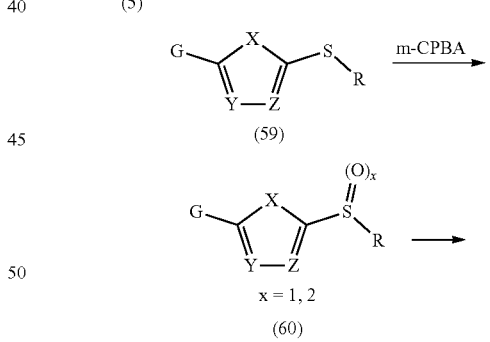

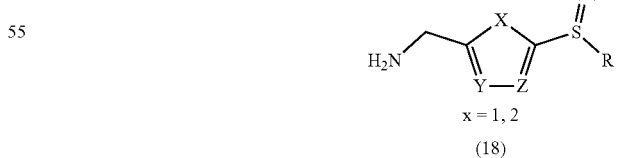

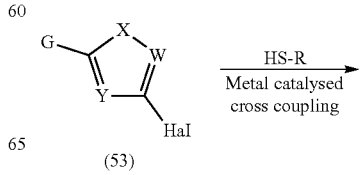

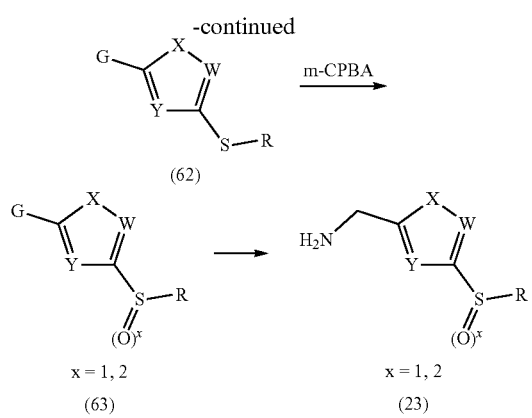

R = -(CR¹R²)ₙ-R³ or a convenient precursor thereof
Hal = Br, I
G = aminomethyl precursor
W = -S(O)ₓ-C(R¹R²)ₙ-R³ in Formula (I)
Z = -S(O)ₓ-C(R¹R²)ₙ-R³ in Formula (I)

Sulfonyl and sulfinyl compounds of formula (I) where W=—S(O)$_x$—C(R$^1$R$^2$)$_n$—R$^3$ can be conveniently synthesised from heteroaryl halides (5; Hal=preferably Br or I), which are commercially available or can be easily synthesised for most examples of X, Y, Z as exemplified in Scheme 18. Group G can be any suitable precursors of the aminomethyl moiety, for example, a nitrile, a carbonyl, a methyl, a protected hydroxymethyl or a protected aminomethyl group. Transition metal-catalysed cross coupling of compound (5) with a range of conveniently substituted alkyl, cycloalkyl, heterocycloalkyl, aryl or heteroaryl thiols using, for example, Pd(O) or Cu(I) can generate the corresponding thioethers (59). The thioethers can be oxidised to the corresponding sulfones/sulfoxides (60) with m-CPBA. These can be subsequently converted to the desired aminomethyl heteroaryl targets (18) using conditions specific to particular G groups. 2-Aminomethyl-4-sulfonyl or -sulfinyl analogues (23) where Z=—S(O)$_x$—C(R$^1$R$^2$)$_n$—R$^3$ can also be obtained by this method from halide (53).

The commercially available 4-bromothiophene-2-carbonitrile (14), for example, can undergo a palladium(0) catalysed cross coupling with alkyl, cycloalkyl, heterocycloalkyl, aryl or heteroaryl thiols to afford thioether intermediates (79), as exemplified in Scheme 19. The intermediates can be oxidised to the corresponding sulfone (80) using m-CPBA. Subsequent borane-mediated nitrile reduction gives the desired product (81).

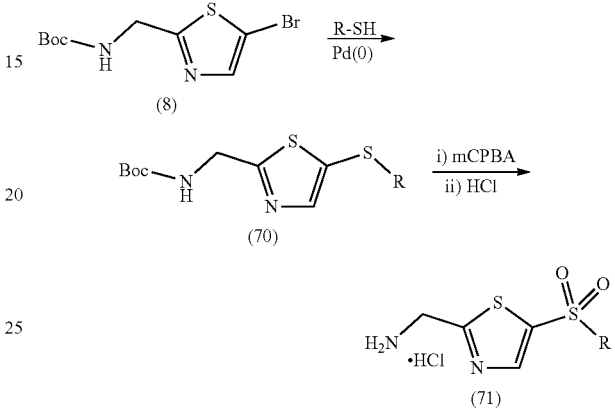

The example in Scheme 20 illustrates the synthesis of aminomethylthiazole (AMTz) analogues by this method. Bromothiazole (8) can undergo Pd catalysed coupling with conveniently substituted alkyl, cycloalkyl, heterocycloalkyl, aryl or heteroaryl thiols to afford the corresponding thioethers (70). After S-oxidation, the Boc protecting group can be removed with HCl to afford the desired AMTz analogues (71).

A3b—Coupling of Heteroarylthiol with Substituted Aryl or Heteroaryl Halides/Sulfonates

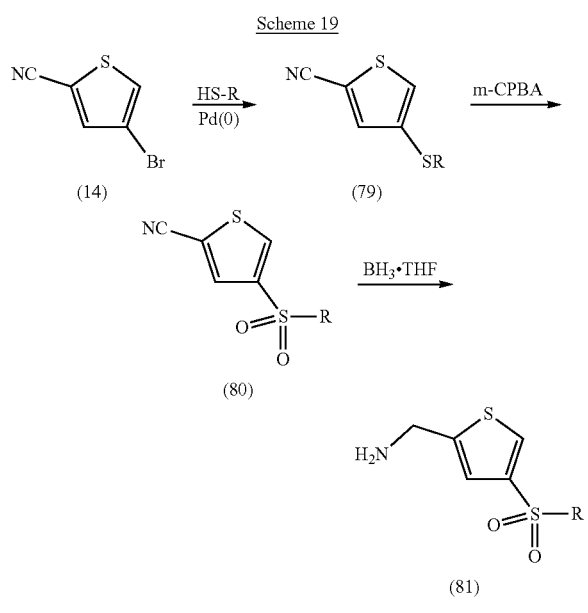

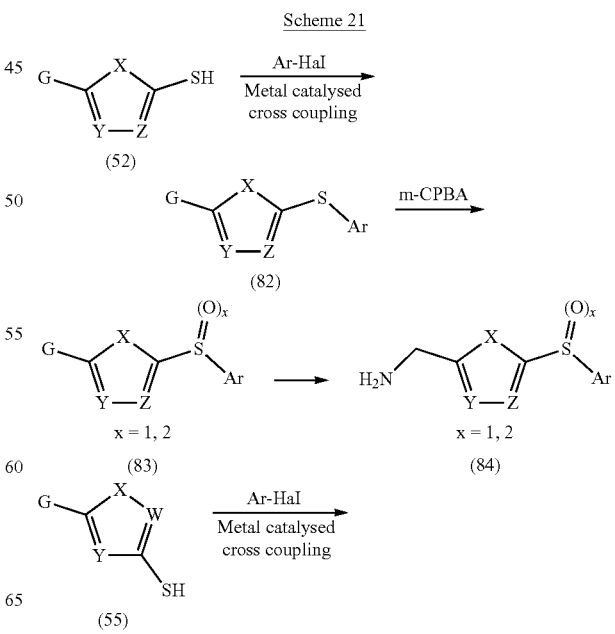

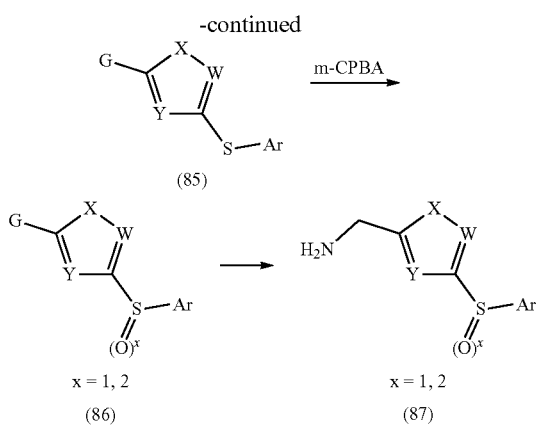

Ar = aryl, heteroaryl
Hal = Br, I
G = aminomethyl precursor

Sulfonyl and sulfinyl compounds of formula (I) where W=—S(O)$_x$—C(R$^1$R$^2$)$_n$—R$^3$ (n=0, R$^3$=Ar) can be conveniently synthesised from heteroarylthiols (52), which are commercially available or can be synthesised for the different examples of X, Y, Z as exemplified in Scheme 21. Group G can be any suitable precursors of the aminomethyl moiety, for example, a nitrile or a protected aminomethyl group. Transition metal-catalysed cross coupling of compound (52) with a range of conveniently substituted aryl or heteroaryl thiols using, for example, Pd(0) or Cu(I) can generate the corresponding thioethers (82). The thioethers can be oxidised to the corresponding sulfones/sulfoxides (83) with m-CPBA. These can be subsequently converted to the desired aminomethyl heteroaryl targets (84) using conditions specific to particular G groups. 2-Aminomethyl-4-sulfonyl or -sulfinyl analogues (87) can also be obtained from thiol (55) by this method.

Examples of commercially available or easily accessible conveniently substituted heteroaryls useful as starting materials for compounds of Formulas I-V are listed in the table below.

| W | X | Y | Z | Example of starting material |
|---|---|---|---|---|
| —S(O)$_x$—(CR$^1$R$^2$)$_n$—R$^3$ | S | CR | CR | NC—[thiophene]—Br<br>Commercial |
| —S(O)$_x$—(CR$^1$R$^2$)$_n$—R$^3$ | S | N | CR | H$_2$N—[thiazole]—Br · HCl<br>Commercial |
| —S(O)$_x$—(CR$^1$R$^2$)$_n$—R$^3$ | S | CR | N | H$_2$N—[thiazole]—Br<br>Commercial |
| —S(O)$_x$—(CR$^1$R$^2$)$_n$—R$^3$ | S | N | N | Boc-NH—[thiadiazole]—Br<br>Commercial |
| —S(O)$_x$—(CR$^1$R$^2$)$_n$—R$^3$ | O | CR | CR | H$_2$N—[furan]—Br<br>Commercial |
| —S(O)$_x$—(CR$^1$R$^2$)$_n$—R$^3$ | O | N | CR | Boc-NH—[oxazole]—Br<br>Commercial |
| —S(O)$_x$—(CR$^1$R$^2$)$_n$—R$^3$ | O | CR | N | EtO$_2$C—[oxazole]—Br<br>Commercial |

-continued

| W | X | Y | Z | Example of starting material |
|---|---|---|---|---|
| ⸺S(O)$_x$⸺(CR$^1$R$^2$)$_n$⸺R$^3$ | O | N | N | (ethyl 5-bromo-1,3,4-oxadiazole-2-carboxylate) Commercial and WO2007/143824 A1 Commercial |
| ⸺S(O)$_x$⸺(CR$^1$R$^2$)$_n$⸺R$^3$ | NR$^N$ | CR | CR | (5-bromo-1H-pyrrole-2-carbaldehyde) Commercial; (ethyl 5-bromo-1H-pyrrole-2-carboxylate) Commercial |
| ⸺S(O)$_x$⸺(CR$^1$R$^2$)$_n$⸺R$^3$ | NR$^N$ | N | CR | (2-(aminomethyl)-1H-imidazole) Commercial; (5-bromo-2-(hydroxymethyl)-1H-imidazole) Commercial |
| ⸺S(O)$_x$⸺(CR$^1$R$^2$)$_n$⸺R$^3$ | NR$^N$ | CR | N | (1-benzyl-1H-imidazole-5-carbaldehyde) Commercial; (methyl 2-bromo-1H-imidazole-5-carboxylate) Commercial |
| ⸺S(O)$_x$⸺(CR$^1$R$^2$)$_n$⸺R$^3$ | NR$^N$ | N | N | (4H-1,2,4-triazole-3-carbonitrile) Commercial; (4-(aminomethyl)-4H-1,2,4-triazole) Commercial |
| CR | S | CR | ⸺S(O)$_x$⸺(CR$^1$R$^2$)$_n$⸺R$^3$ | (4-bromo-2-cyanothiophene) Commercial |

-continued

| W | X | Y | Z | Example of starting material |
|---|---|---|---|---|
| CR | S | N | $-S(O)_x-(CR^1R^2)_n-R^3$ | 2-formyl-4-bromothiazole, Commercial |
| N | S | CR | $-S(O)_x-(CR^1R^2)_n-R^3$ | 3-chloroisothiazole-5-carboxylic acid, Commercial |
| N | S | N | $-S(O)_x-(CR^1R^2)_n-R^3$ | methyl 3-chloro-1,2-thiazole-5-carboxylate, Commercial |
| CR | O | CR | $-S(O)_x-(CR^1R^2)_n-R^3$ | 4-bromo-2-furaldehyde, Commercial |
| CR | O | N | $-S(O)_x-(CR^1R^2)_n-R^3$ | 4-bromo-2-formyloxazole, Commercial |
| N | O | CR | $-S(O)_x-(CR^1R^2)_n-R^3$ | 5-(aminomethyl)-3-bromoisoxazole, Commercial |
| N | O | N | $-S(O)_x-(CR^1R^2)_n-R^3$ | 3-bromo-5-(bromomethyl)-1,2,4-oxadiazole, Commercial |
| CR | NR$^N$ | CR | $-S(O)_x-(CR^1R^2)_n-R^3$ | 4-bromo-1H-pyrrole-2-carbonitrile, Commercial; 4-bromo-1-methyl-1H-pyrrole-2-carbonitrile, Commercial |

-continued

| W | X | Y | Z | Example of starting material |
|---|---|---|---|---|
| CR | NR$^N$ | N | —S(O)$_x$—(CR$^1$R$^2$)$_n$—R$^3$ | Commercial; Commercial |
| N |  | NR$^N$ CR | —S(O)$_x$—(CR$^1$R$^2$)$_n$—R$^3$ | Commercial; Commercial |
| N | NR$^N$ | N | —S(O)$_x$—(CR$^1$R$^2$)$_n$—R$^3$ | Commercial; Commercial |

B. Synthesis and derivatisation of group —C(R$^1$R$^2$)$_n$—R$^3$

The —C(R$^1$R$^2$)$_n$—R$^3$ group can be introduced as a thiol (HS—C(R$^1$R$^2$)$_n$—R$^3$), disulfide (R$^3$—C(R$^1$R$^2$)$_n$—S—S—C(R$^1$R$^2$)$_n$—R$^3$) or as halides/sulfonates (LG-C(R$^1$R$^2$)$_n$—R$^3$ where LG=F, Cl, Br, I, OSO$_2$Me, OSO$_2$PhMe, OSO$_2$CF$_3$, etc) as described in the routes above. These thiol, disulfide and halide/sulfonates intermediates can be fully derivatised prior to coupling and conversion to the final product of formula I-V and used as building blocks in any of the general methods described above, without the need of any further modification.

Alternatively, any of the intermediates in the routes above that are formed after the coupling step of the LHS heteroaryl and the RHS groups can be further modified to afford the desired product.

Examples of both approaches are described below. It should be clear to anyone skilled in the art that these examples are not limiting and other desired combinations of substituents can be accessed by similar methods.

B1—Synthetic Routes to Analogues with RHS Side Chain of Formula (I) (when n>0):

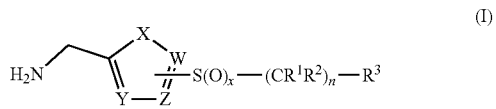

(I)

Scheme 22

Example of further modification of RHS group post-synthesis.

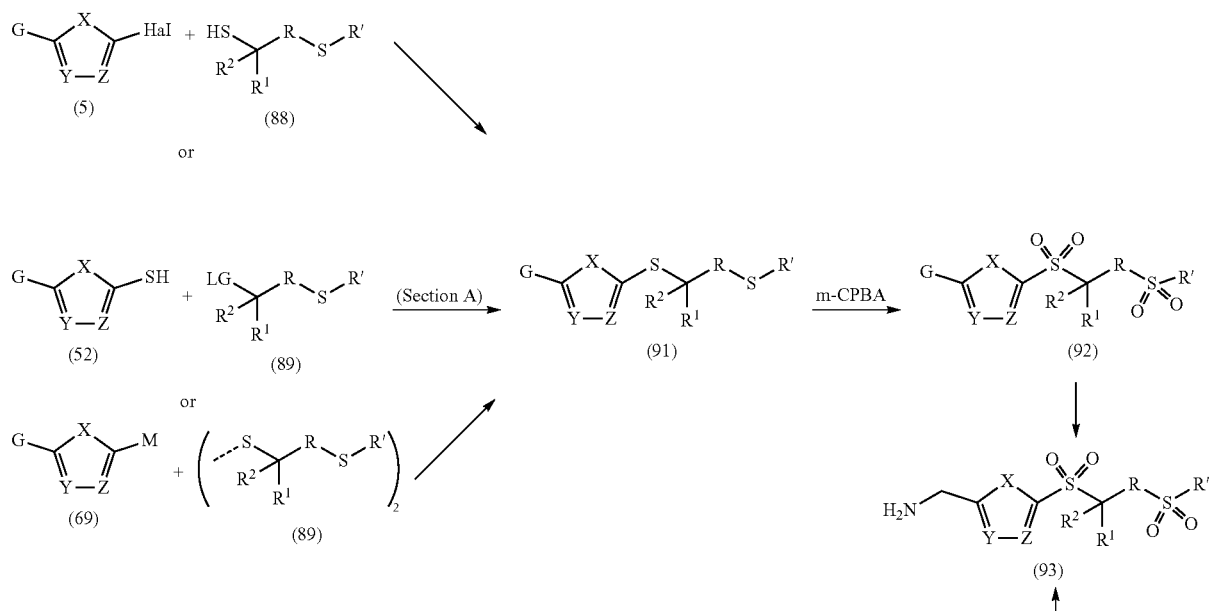

Example of coupling with pre-formed final RHS fragment.

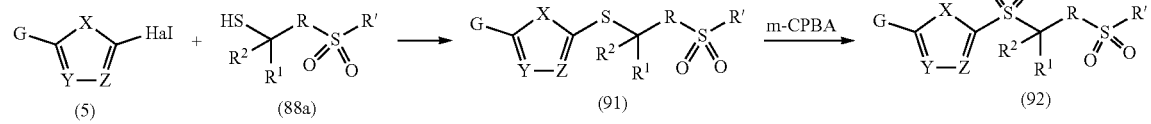

W = -S(O)$_x$-C(R$^1$R$^2$)$_n$-R$^3$ in Formula (I),
R$^2$ = H
HaI = F, Cl, Br, I
G = Aminomethyl precursor
LG = F, Cl, Br, I, OSO$_2$R″, OH (Mitsunobu)
R = substituted alkyl, (hetero)cycloalkyl, (hetero)aryl
Section A: any of the methods described in section A The two approaches mentioned above (preformed RHS fragment or further modification of RHS fragment after coupling with LHS heteroaryl) are exemplified in Scheme 22 for a RHS chain containing a sulfone (SO$_2$R) group. This is for illustration purposes and other desired groups on RHS fragment can be introduced pre- or post-coupling.

The synthesis of compounds of formula (I) [W=—S(O)$_r$—C(R$^1$R$^2$)$_n$—R$^3$ (n>0)] where the RHS side chain precursors are readily commercially available and requires no further modifications is described in Section A. In the example shown here, a fragment bearing the sulfone group (88a) is coupled with LHS fragment precursor (5) to form intermediate (91a) already bearing the sulfone substituent. For the synthesis of analogues with a (substituted) alkyl-, cycloalkyl-, heterocycloalkyl-, benzyl- or heteroarylmethyl-sulfonyl (CHR$^1$ASO$_2$R'; Scheme 22) side chain, it may be more convenient to start from the corresponding sulfido precursors such as sulfido-thiols (88), sulfido-halides, —sulfonates or alcohol (89) and sulfido-disulfide (90) as exemplified in Scheme 22. These sulfido precursors (88), (89) and (90) can be converted to bis-sulfide (91) by any one of the methods previous described in Section A. Group G can be any suitable precursors of the aminomethyl moiety, for example a hydrogen, a nitrile, a carbonyl, a methyl, a protected hydroxymethyl or a protected aminomethyl group. In this case, both the sulfide groups can be oxidised to bis-sulfones (92) using, for example, m-CPBA. Bis-sulfones (92) can be subsequently converted to the desired aminomethyl heteroaryl analogues (93) using methods specific for the G group, previously described. The example in Scheme 22 is illustrated for 2-aminomethyl-5-sulfonyl heteroaryl compounds. This method is also suitable for the synthesis of the regioisomeric 2-aminomethyl-4-heteroaryl sulfonyl compounds (Z=—S(O)$_x$—C(R$^1$R$^2$)$_n$—R$^3$).

Scheme 23

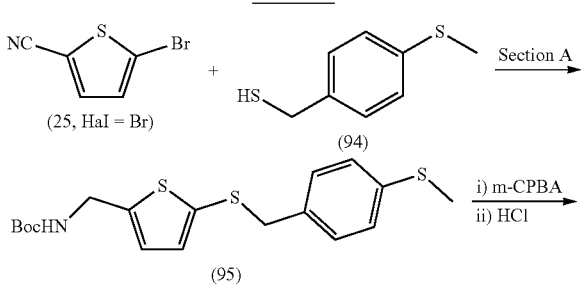

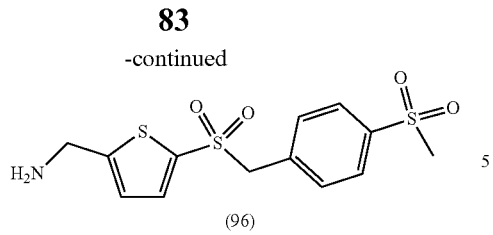

(96)

For example, AMT analogue with a sulfonylbenzyl side chain (96) can be obtained from bis-sulfide (95) as illustrated in Scheme 23. (4-(methylthio)phenyl)methanethiol (94) and 2-cyano-5-bromothiophene (25, Hal=Br) can be converted to bis-sulfide (95) by methods described in Section A. Oxidation of both the sulfide groups using m-CPBA oxidation affords the corresponding bis-sulfone, which provides the desired AMT compound (96) after Boc deprotection using HCl.

Scheme 24

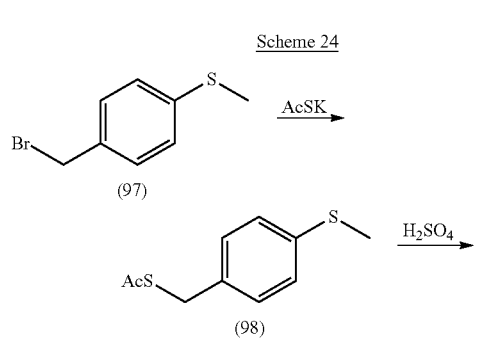

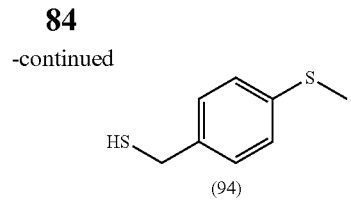

(94)

Desirable thiol building blocks such as (4-(methylthio)phenyl)methanethiol (94) can be synthesised by a number of methods, for example, from the corresponding alkyl bromide as illustrated in Scheme 24. The bromide group on benzyl bromide (97) can be substituted for a suitable thio precursor, for example (but not limiting to) thioacetate. The thioacetate formed (98) can be hydrolysed to the corresponding thiol (94) in acidic conditions.

B2—Synthetic Routes to Analogues with RHS Side Chain of Formula (II):

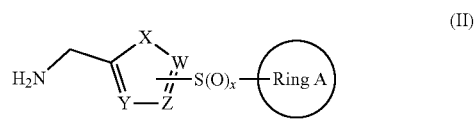

(II)

For compounds of formula (II) where W=S(O)$_x$-(Ring A), Ring A can be attached to the aminomethylheteroaryl core by the methods described in section A if the Ring A precursors are readily available commercially. The methods described in the subsequent sections allow the synthesis of analogues where Ring A is further functionalised, and are valid for certain substituents selected from the set described in embodiment [0050].

B2a—Substituents Linked to Ring a Via a Heteroatom

Scheme 25

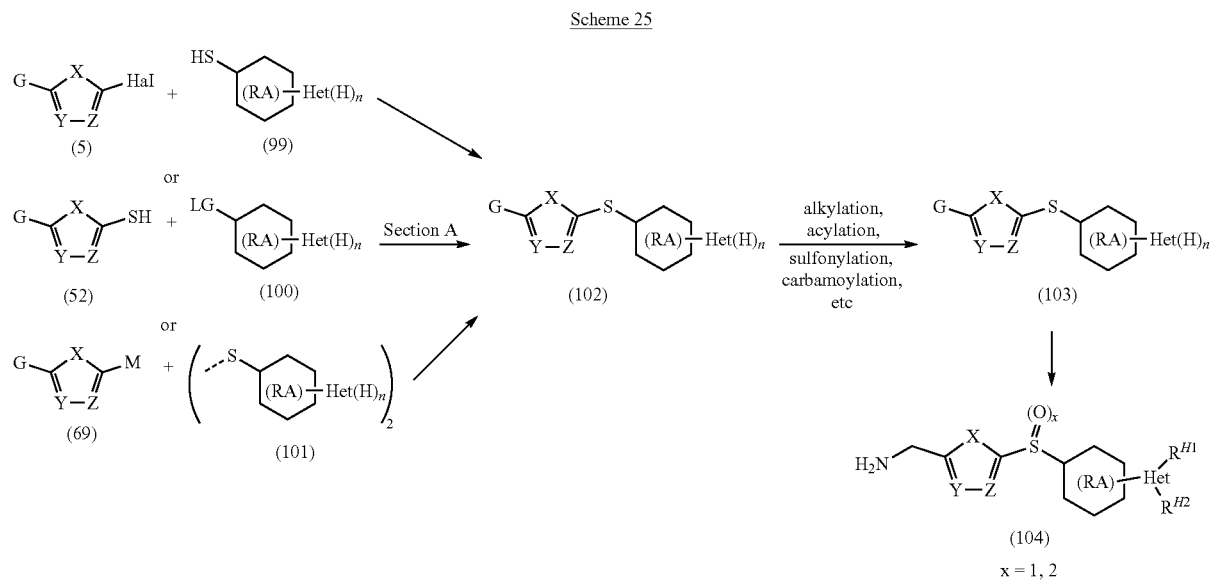

x = 1, 2

W = -S(O)$_x$-C(R$^1$R$^2$)$_n$-R$^3$ in Formula (I)
(RA) = Ring A = (hetero)aryl (3 to 15 membered), (hetero)cycloalkyl
Hal = F, Cl, Br, I
G = Aminomethyl precursor
LG = F, Cl, Br, I, OSO$_2$R″
Het = O, N The method described in Scheme 25 allows additional substitutions on Ring A to be attached via a heteroatom (Het), where Het can be N, O and hence Het(H)$_n$ is OH or NH$_2$. A suitably protected form of OH or NH$_2$ can be used instead and deprotected to free hydroxyl or amine when required. For analogues with Het=S, synthetic methods are described in Section B2c. Group G can be any suitable precursors of the aminomethyl moiety, for example a hydrogen, a nitrile, a carbonyl, a methyl, a protected hydroxymethyl or a protected aminomethyl group. Het-substituted phenyl sulfide (102) can be obtained by any one of the methods described in Section A, for example by the condensation of heteroaryl halide (5) and Het-substituted thiophenol (99). Sulfide (102) can undergo a wide range of reactions at the -Het(H)$_n$ group, for example alkylation, acylation, sulfonylation, carbamoylation etc. with conveniently substituted (cyclo)alkyl halides/sulfonates, acid chlorides/anhydrides, sulfonyl chlorides/anhydrides, chloroformates, isocyanates to afford the corresponding anilines, amides, sulfonamides, carbamates, ureas for N-linked analogues (103, Het=N) respectively, and (cyclo)alkyl ethers, esters, sulfonates, carbonates, carbamates are obtained for O-linked analogues (103, Het=O). These substituted phenyl thioethers (103) can be converted to the desired aminomethylheteroaryl analogues (104) by methods described in Section A. The example in Scheme 25 is illustrated for 2-aminomethyl-5-sulfonyl heteroaryl compounds. This method is also suitable for the synthesis of the regioisomeric 2-aminomethyl-4-heteroaryl sulfonyl compounds (Z= S(O)$_x$-(Ring A)).

Scheme 26

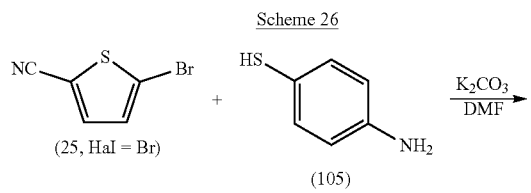

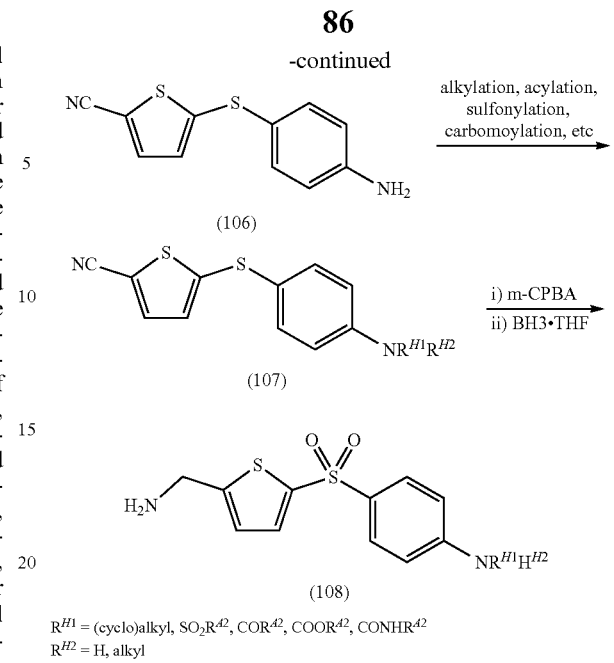

For example, the thiol group of 4-aminobenzenethiol (105) can react selectively with bromothiophene-2-carbonitrile (25, Hal=Br) to form 4-aminophenylsulfide (106) as illustrated in Scheme 26 This can be condensed with, for example, acyl chlorides/anhydrides, sulfonyl chlorides/anhydrides, chloroformates, isocyanates etc. to give the corresponding amides, sulfonamides, carbamates, urea (107), which can be converted to the desired AMT analogues (108) by the aforementioned m-CPBA oxidation/BH$_3$.THF reduction sequence.

B2b—Substituents Linked to Ring a Via a Carbonyl Group

Scheme 27

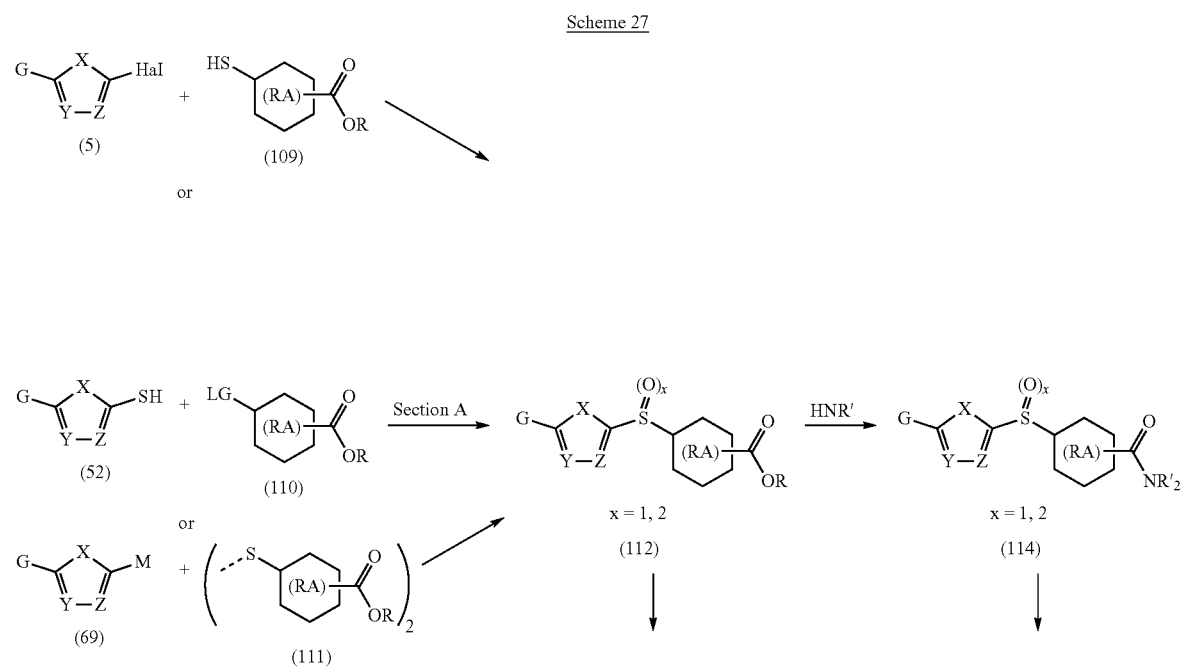

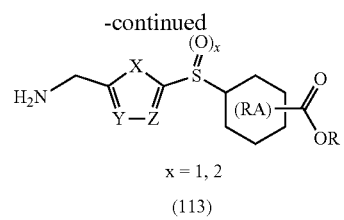
(113) x = 1, 2

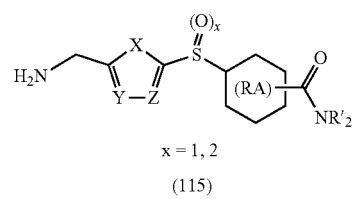
(115) x = 1, 2

W = -S(O)$_x$-C(R$_1$R$_2$)$^n$-R$_3$ in Formula (I)
(RA) - Ring A = (hetero)aryl (3 or 15 membered), (hetero)cycloalkyl
HaI = F, Cl, Br, I
G = Aminomethyl precursor
LG = F, Cl, Br, I, OSO$_2$R″
R = H, alkyl, (hetero)aryl
R′ = H, alkyl, (hetero)cycloalkyl, (hetero)aryl Analogues with Ring A substituted with a carboxlic ester or a carboxamide can be obtained by the synthetic route exemplified in Scheme 27. Group G can be any suitable precursors of the aminomethyl moiety, for example a hydrogen, a nitrile, a carbonyl, a methyl, a protected hydroxymethyl or a protected aminomethyl group. Sulfonyl/sulfinyl-phenyl ester (112) can be obtained by any one of the methods described in Section A, for example from the nucleophilic substitution of heteroaryl halide (5) and thiophenols conveniently substituted with a wide range of alkyl, cycloalkyl and heterocycloalkyl carboxylates (109). Esters (112) can be converted to the desired aminoheteroaryl analogues (113) by methods specific to the G group as previous described. Alternatively, the ester moiety of intermediate (112) can be converted, either directly or via the carboxylic acid, to the corresponding substituted amide (R′=H, substituted alkyl, cycloalkyl, heterocycloalkyl, aryl, heteroaryl) to afford intermediate (114). This can subsequently be converted to the desired aminomethylheteroaryl analogues (115) using the methods described in Section A. The example in Scheme 27 is illustrated for 2-aminomethyl-5-sulfonyl heteroaryl compounds. This method is also suitable for the synthesis of the regioisomeric 2-aminomethyl-4-heteroaryl sulfonyl compounds (Z=S(O)$_x$-(Ring A)).

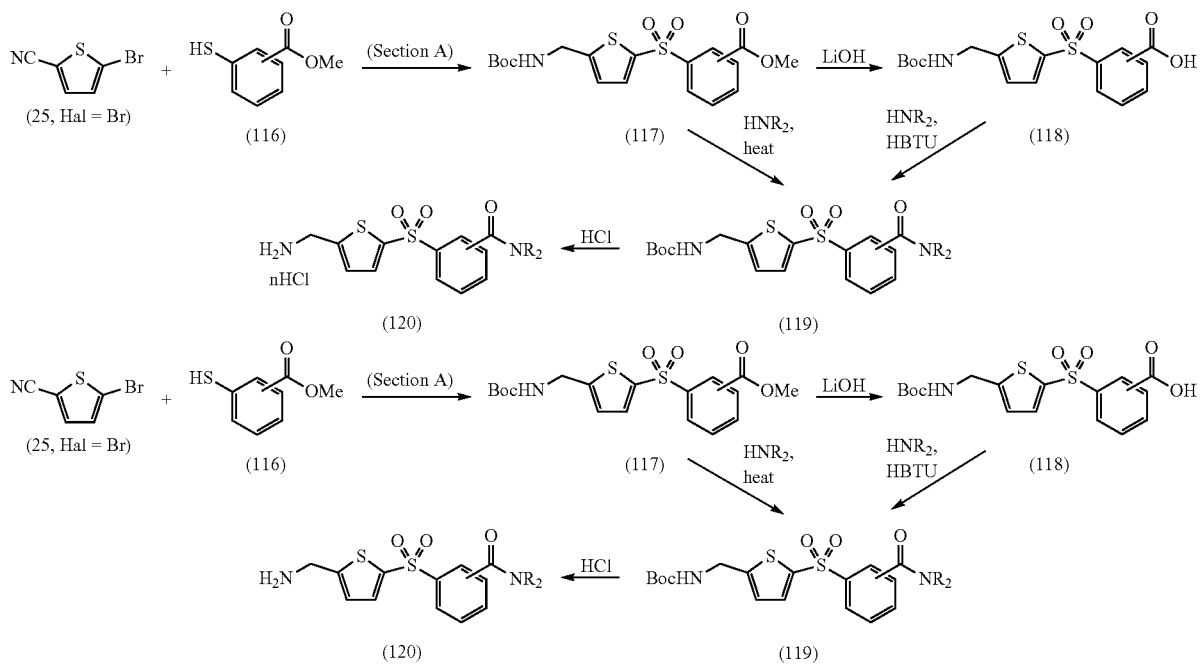

Scheme 28

For example, the ester intermediates (117) can be obtained from methyl mercaptobenzoate (116) and 5-bromothiophene-2-carbonitrile (25, Hal=Br) in 4 steps (See Section A, Schemes 5 and 8), as illustrated in Scheme 28. Direct conversion of esters (117) to amides (119) can be accomplished by treatment with selected primary and secondary amines at elevated temperature. Alternatively, saponification of esters (117) furnishes the corresponding carboxylic acids (118). The carboxyl group can be conveniently substituted with a range of primary and secondary amines by the use of suitable coupling reagent, for example HBTU or EDCI, to afford the corresponding amides (119).

Subsequent amine deprotection furnishes AMT analogues (120) with the desired carboxamide substitutions.

B2c—Substituents Linked to Ring a Via a Sulfonyl Group suitable for the synthesis of the regioisomeric 2-aminomethyl-4-heteroaryl sulfonyl compounds (Z=S(O)$_x$-(Ring A)).

Scheme 29

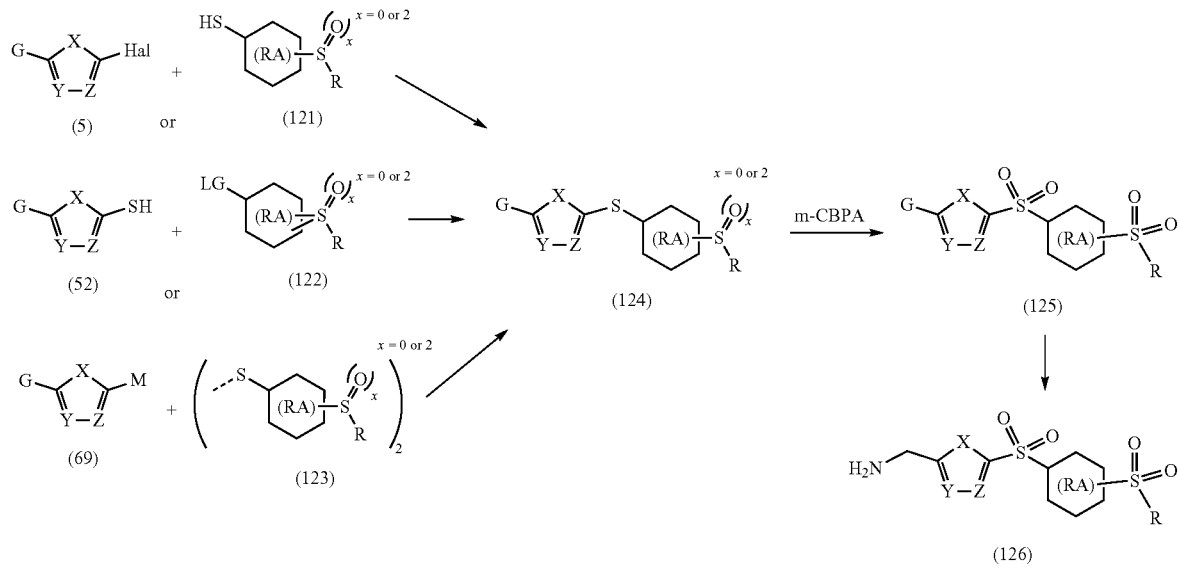

W = -S(O)$_x$-C(R$^1$R$^2$)$_n$-R$^3$ in Formula (I)
(RA) - Ring A = aryl, heteroaryl (5 or 6 membered), cycloalkyl, heterocycloalkyl
Hal = F, Cl, Br, I
G = Aminomethyl precursor
LG = F, Cl, Br, I, OSO$_2$R″

Compounds of formula (II) with sulfonyl substituents (SO$_2$R) attached to Ring A can be obtained by the synthetic routes exemplified in Scheme 29.

In one approach, ring A can be attached to the aminomethylheteroaryl core with the sulfonyl substituents (SO$_2$R) already installed. Conveniently substituted alkyl, cycloalkyl, heterocycloalkyl, aryl heteroaryl sulfonyl-thiophenols (121, x=2) can be condensed with heteroaryl halides (5) to give the corresponding sulfonyl-sulfides (124, x=2) (Scheme 29). After sulfide-to-sulfonyl oxidation, the resultant bis-sulfonyl (125) can be converted to the desired aminomethylheteroaryl analogues (126) by methods specific to the G group as previously described.

Alternatively the sulfur substituent is initially installed as the sulfide (SR) before the sulfide is eventually oxidised to the sulfonyl level (SO$_2$R). In the former approach, bis-sulfides (124, x=0) can be obtained from any one of the methods described in Section A, for example from the nucleophilic substitution of heteroaryl halides (5) and conveniently substituted aryl or heteroaryl sulfido-thiophenols (121, x=0). Group G can be any suitable precursors of the aminomethyl moiety, for example a hydrogen, a nitrile, a carbonyl, a methyl, a protected hydroxymethyl or a protected aminomethyl group. Both sulfide groups of bis-sulfides (124, x=0) can be oxidised to the corresponding bis-sulfonyl intermediate (125) using, for example, m-CPBA. The bis sulfonyl intermediate (125) can be subsequently converted to the desired aminomethylheteroaryl analogues (126) by methods specific to the G group previous described.

The example in Scheme 29 is illustrated for 2-aminomethyl-5-sulfonyl heteroaryl compounds. This method is also Scheme 30

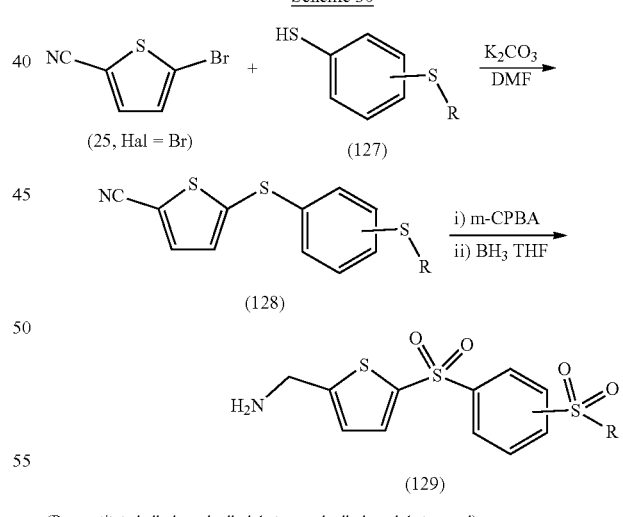

(R = sustituted alkyl, cycloalkyl, heterocycloalkyl, aryl, heteroaryl)

For example, the condensation of conveniently substituted sulfido-thiophenols (127) with 5-bromothiophene-2-carbonitrile (25, Hal=Br) leads to bis-sulfides (128) as illustrated in Scheme 30. Subsequent treatment with m-CBPA converts both sulfide groups into the corresponding sulfones. The resulting bis-sulfone can be reduced with BH$_3$.THF to afford the desired AMT analogues (129).

Scheme 31

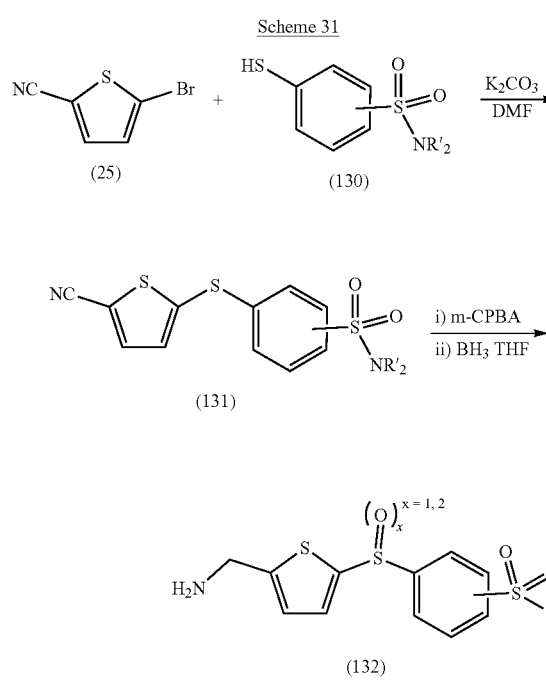

(R' = H, substituted alkyl, cycloalkyl, heterocycloalkyl, aryl, heteroaryl)

In another example, sulfonamide substituents can be introduced to Ring A using this method, starting from conveniently substituted sulfonamido-thiols (130) and 5-bromothiophene-2-carbonitrile (25) as illustrated in Scheme 31. The resulting sulfide intermediates (131) can be converted to the desired AMT-analogues (132) as previously described.

Scheme 32

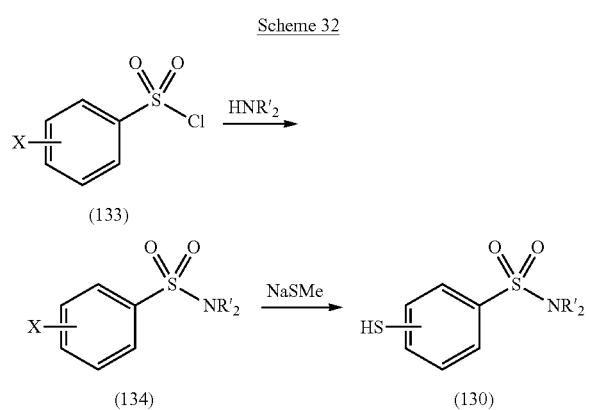

X = F or Cl; para or meta

Scheme 32 exemplifies the synthesis of some sulfonamido-thiophenol building blocks (130), starting from the commercially available para/meta fluoro- or chlorobenzenesulfonyl chlorides (133). Hence, condensation of sulfonyl chloride (133) with conveniently substituted primary or secondary amines affords the corresponding sulfonamides (134). Subsequent treatment with NaSMe (>2 equiv.) furnishes the desired thiophenols (130).

Scheme 33

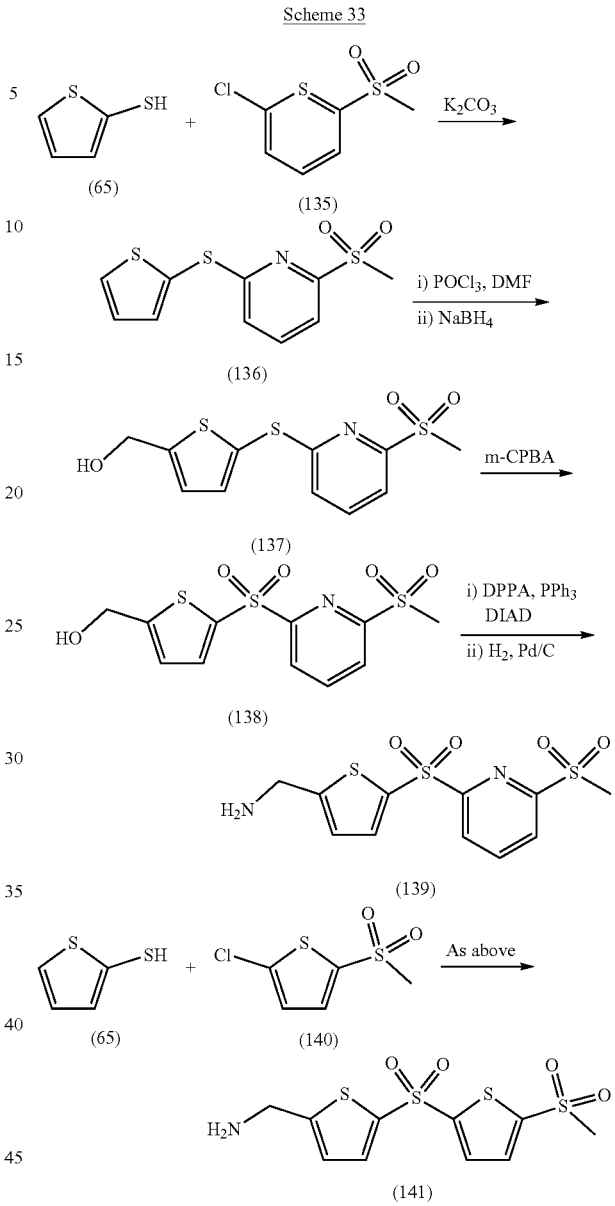

In another example, condensation of the commercially available thiophene-2-thiol (65) with haloaryl or haloheteroaryl (exemplified in Scheme 33 with chloropyridines (135)) leads to thioethers (136). Formylation of the thiophene ring employing phosphorus oxychloride and dimethylformamide gives the corresponding aldehydes, which can be reduced to alcohols (137) using sodium borohydride. S-oxidation with m-CPBA affords sulfonyl-alcohol (138). The hydroxyl group of intermediate (138) can be converted to the corresponding amino group by different methods. For example, the method illustrated in Scheme 33 involves conversion to the corresponding azide under Mitsunobu conditions using DPPA, PPh$_3$ and DIAD. The azide product can undergo subsequent hydrogenolysis over Pd/C catalyst to afford the AMT analogues with the desired substitutions (141). The method described in Scheme 33 can also be applied to the synthesis of other examples with heterocyclic ring A, for example, bis-thiophene analogues (141).

Scheme 34

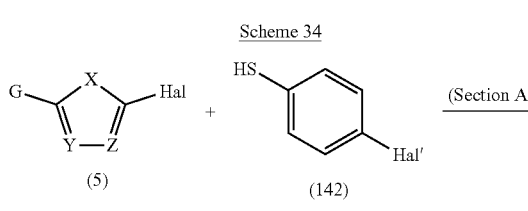

(143)

(144)

(145)

Hal = F, Cl, Br, I
G = Aminomethyl precursor
Hal' = F, Cl, Br, I

In an alternative method, sulfonyl substituents can be obtained, for example, by halogen displacement or cross coupling from halogen substituted Ring A, as exemplified in Scheme 34. The 4-halobenzene intermediate (143) can be obtained by any one of the methods described in Section A, with the nucleophilic substitution between 4-halothiophenol (142) and heteroaryl halide (5) and subsequent sulfide-to-sulfone oxidation illustrated here. Group G can be any suitable precursors of the aminomethyl moiety, for example a hydrogen, a nitrile, a carbonyl, a methyl, a protected hydroxymethyl or a protected aminomethyl group. Intermediate (143) can be conveniently substituted with any suitable nucleophiles (by nucleophilic substitution) or coupling partners (by cross coupling) to afford intermediate (144). This versatile intermediate can be used to attach various substituents on ring A, for example it can be substituted with amines and alcohols to produce anilines and ethers, and with carbon-based nucleophiles or coupling partners to introduce alkyl, alkenyl, alkynyl, aryl or heteroaryl substituents. When alkyl, cycloalkyl, heterocycloalkyl, aryl, heteroaryl thiols are employed as the nucleophiles, for example, the corresponding sulfides (R=SR'') are obtained which can be subsequently oxidised to the bis-sulfone intermediates (144, R=SO$_2$R') with m-CPBA. This intermediate can be converted to the desired aminomethylheteroaryl analogues (145) using conditions specific to the G group previously described. The example in Scheme 34 is illustrated for 2-aminomethyl-5-sulfonyl heteroaryl compounds. This method is also suitable for the synthesis of the regioisomeric 2-aminomethyl-4-heteroaryl sulfonyl compounds (Z=S(O)$_x$-(Ring A)).

Scheme 35

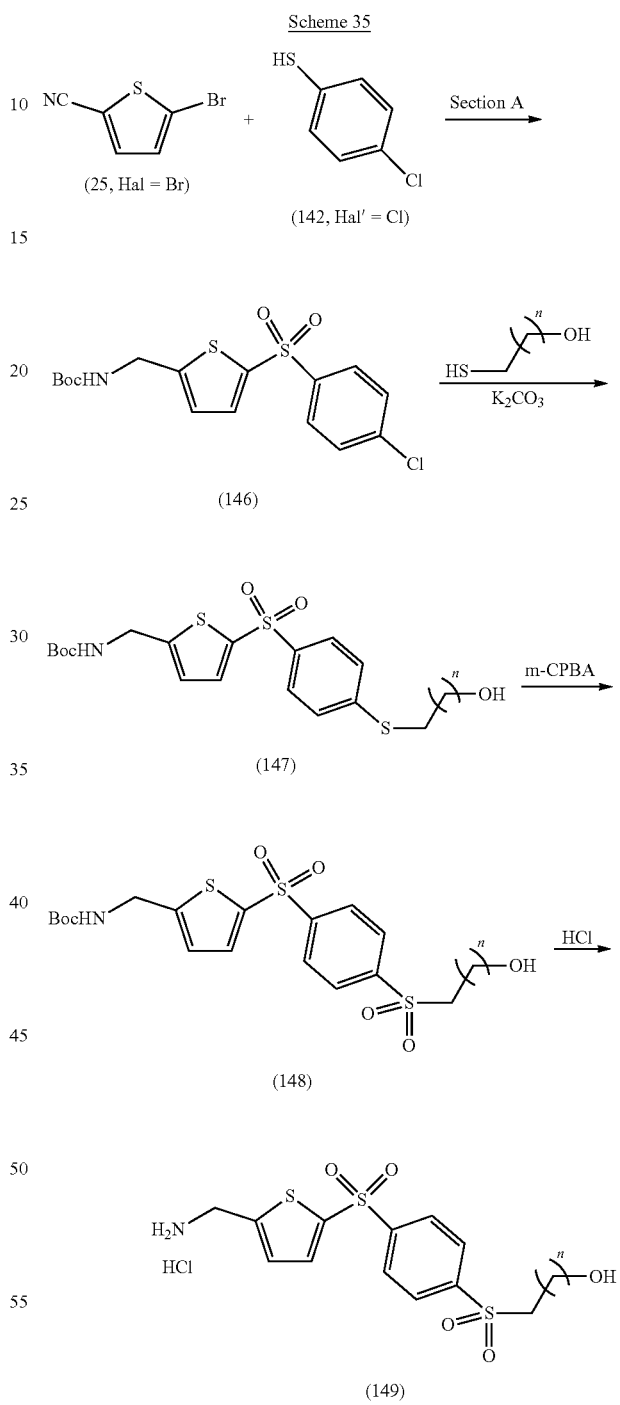

For example, chlorophenyl sulfone (146) can be obtained from 5-bromothiophene-2-carbonitrile (25, Hal=Br) and 4-chloro-thiophenol (142, Hal'=Cl) by methods previous described, as show in Scheme 35. The chlorine atom of sulfone (146) can be conveniently substituted with other functional groups, for example mercaptoethanol or other mercaptoalkanols to afford sulfides (147), which can be subsequently oxidised to the bis-sulfone intermediates (148) with m-CPBA. This intermediate can be treated with HCl for the removal of the Boc protecting group, affording the 5-sulfonylphenyl-sulfonyl AMT analogues (149).

B3—Synthetic Routes to Compounds of Formula (III):

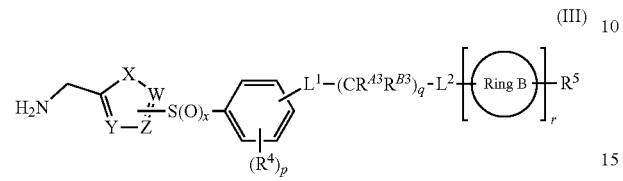

The synthesis of compounds of formula (III) [W=S(O)$_x$Ar(R$^4$)$_p$-L$_1$-(CR$^{43}$R$^{B3}$)$_q$-L$^2$-[Ring B]$_r$—R$^5$] where the RHS side chain precursors are readily commercially available and requires no further modifications is described in Section A. The methods below illustrated some of (but not limited to) the modifications to introduce particular substitutions on the RHS side chain. The RHS fragment with the desired substitutions can be directly attached to the LHS heteroaryl fragment as a thiol (or disulfide, halide, etc).

Alternatively, a convenient RHS intermediate can be attached to the LHS heteroaryl fragment and then conveniently modified to introduce the desired R$^4$, L$^1$, —(CR$^{43}$R$^{B3}$)$_q$—, L$^2$, Ring B or/and R$^5$ groups. All the examples described in this section are illustrated for 2-aminomethyl-5-sulfonyl heteroaryl compounds. All the methods employed are also suitable for the synthesis of the regioisomeric 2-aminomethyl-4-heteroaryl sulfonyl compounds (W=S(O)$_x$Ar(R$^4$)$_p$-L$_1$-(CR$^{43}$R$^{B3}$)$_q$-L$^2$-[Ring B]$_r$—R$^5$).

Scheme 36

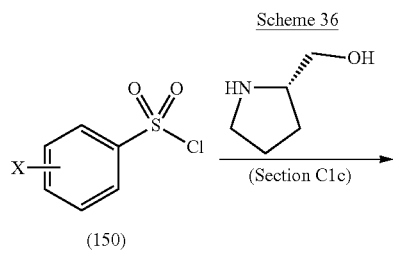

(150)

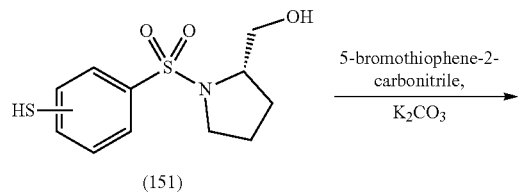

(151)

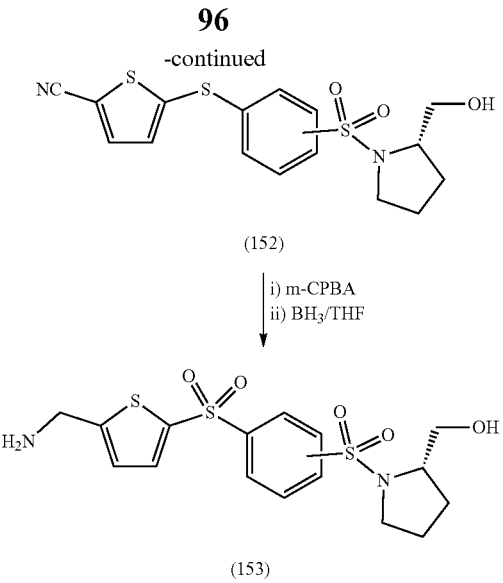

X = F or Cl; para or meta

For example, substituted heterocycloalkyl rings can be introduced to the RHS fragment at the initial stages of the synthetic route, as exemplified in Scheme 36 (p=0, q=0, L$_1$=SO$_2$, L$_2$=bond). para/meta Fluoro- or chlorobenzenesulfonyl chlorides (150) can be condensed with conveniently substituted cyclic amines, cyclic diamines, other cyclic heterocycloalkyls containing a secondary amine or other amines containing a cyclic substituent (S-prolinol exemplified here), to afford the corresponding sulfonamides. These can be converted to the desired thiophenols (151) by methods similar to those described in Scheme 32. These thiols can be condensed with 5-bromothiophene-2-carbonitrile (25, Hal=Br), and then subsequently converted to the desired AMT analogues (153) by methods described in Section A Scheme 37

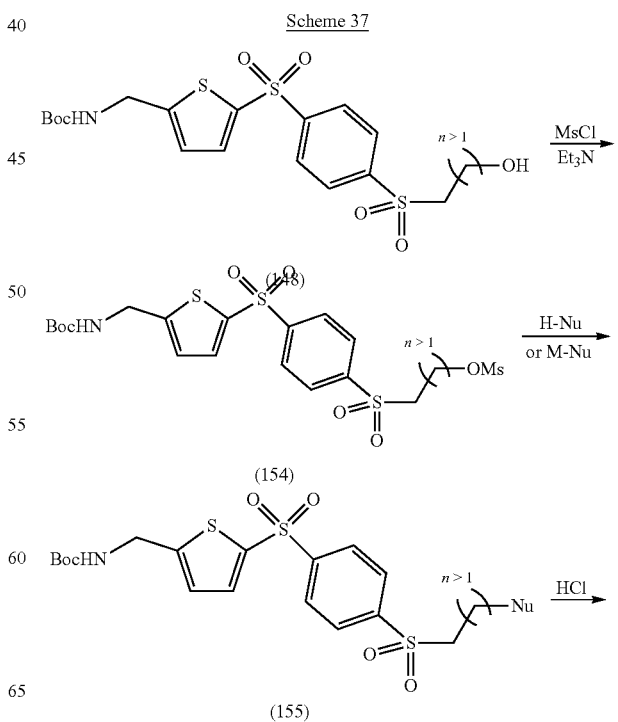

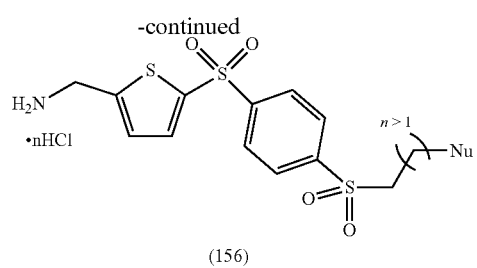

(156)

For n = 1

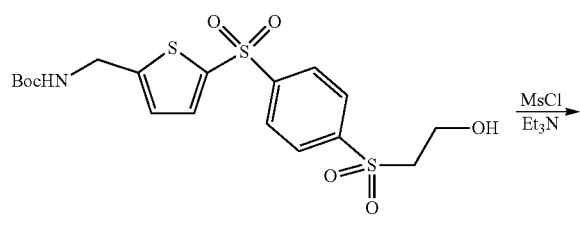

(148, n = 1)

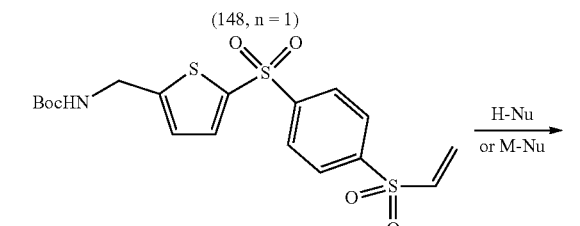

(157)

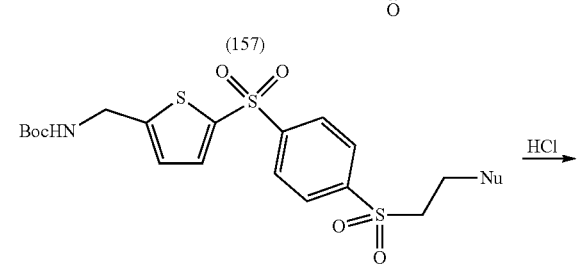

(158)

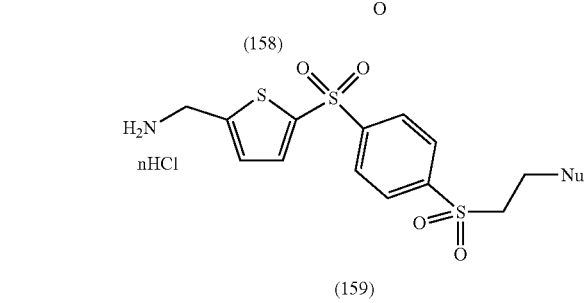

(159)

Nu = ring B-containing nucleophile

Scheme 37 exemplifies a synthetic route for compounds of formula (III), where Ring B can be substituted cycloalkyl, cycloheteroalkyl, aryl, heteroaryl, and is attached via a sulfonylalkyl side chain (p=0, q=n+1, L1=SO₂, L2=bond, R³=H). For example, hydroxyalkyl sulfone intermediates (148) can be obtained by methods described in Scheme 35. The hydroxyl group can be converted to a leaving group, for example the mesylate, by treatment with methanesulfonyl chloride as shown in Scheme 37. The resultant mesylate (154) can be conveniently substituted with a range of nucleophiles (H-Nu and M-Nu, M=Cu, Zn etc.) containing a ring system, for example cycloalkyl- or heterocycloalkyl-substituted primary and secondary amines, cycloalkyl- or heterocycloalkyl-substituted alcohols, phenols, anilines etc., aryl, and heteroaryl cuprates to afford the corresponding sulfones (155). Hydroxyethyl sulfone (148, n=1) furnishes vinyl sulfone (157) upon treatment with mesyl chloride. Nucleophiles (H-Nu and M-Nu) similar to above can be introduced to vinyl sulfone (157) by Michael-type addition, leading to the corresponding sulfones (158). Sulfones (155) and (158) can be converted to the desired AMT analogues (156) and (159) by treatment with HCl.

Scheme 38

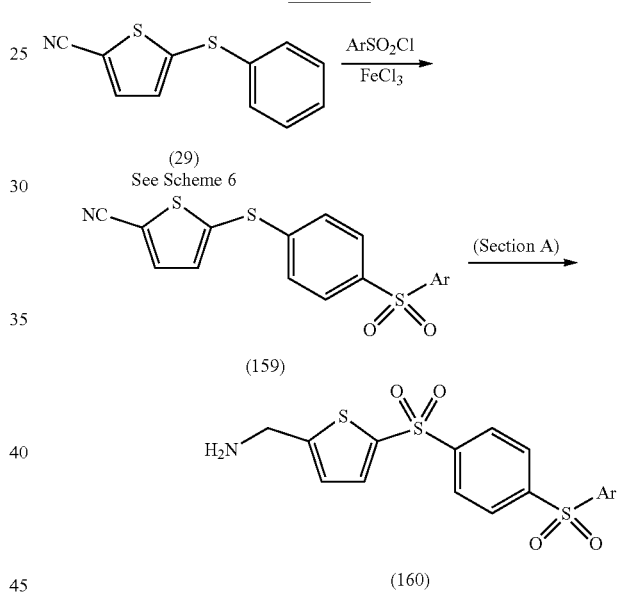

Another example of route to compounds of Formula (III), where Ring B=aryl or heteroaryl (p=0, q=0, L1=SO₂, L2=bond), uses the Friedel Craft reaction as described in Scheme 38. Hence, treatment of thioether (29; see Scheme 6 for synthetic methods) with conveniently substituted aryl- or heteroaryl-sulfonyl chlorides in the presence of a Lewis acid catalyst such as FeCl₃ leads selectively to the corresponding para-sulfonylated intermediate (159). This can then be converted to the desired AMT analogues (160) by methods previously described.

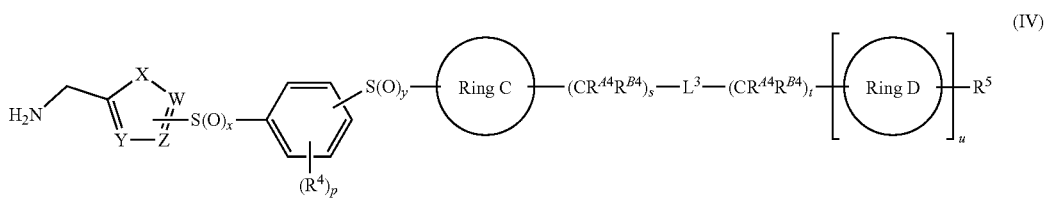

(IV)

Compounds of formula (IV) can be synthesised by any of the methods described above. In a non-limiting example shown in Scheme 39, Ring D can be introduced via a carbamate or a urea linker to a pyrrolidinemethyl intermediate (152, p=0, Ring C=pyrrolidine, —(CR$^{A4}$R$^{B4}$)$_s$— =CH$_2$, L$^3$=OCONH or NCONH, t=0) obtained by methods previously described in Scheme 36. Hence, addition of conveniently substituted aryl- or heteroaryl isocyanates to hydroxypyrrolidinemethyl- or aminopyrrolidinemethyl intermediates (152) affords the corresponding carbamates or ureas (161). These can be converted to the desired AMT analogues (162) by methods previously described. Derivatisation of alcohols to form numerous types of linkages to a cycloalkyl, heterocycloalkyl, aryl, heteroaryl or a chain bearing one of these groups is well known in the art, thus not limiting to only carbamates and ureas. All the examples described in this section are illustrated for 2-aminomethyl-5-sulfonyl heteroaryl compounds. All the methods employed are also suitable for the synthesis of the regioisomeric 2-aminomethyl-4-heteroaryl sulfonyl compounds.

Scheme 39

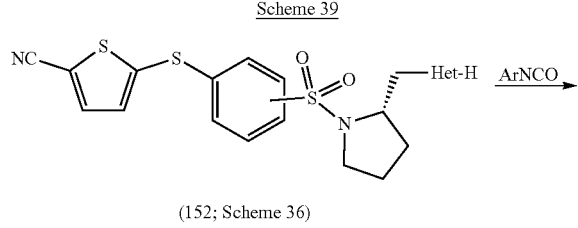

(152; Scheme 36)

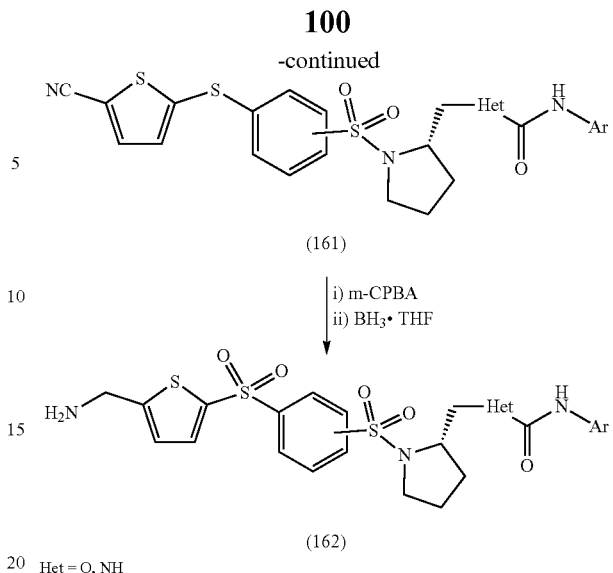

Het = O, NH

Synthetic Routes to Compounds of Formula (Va)

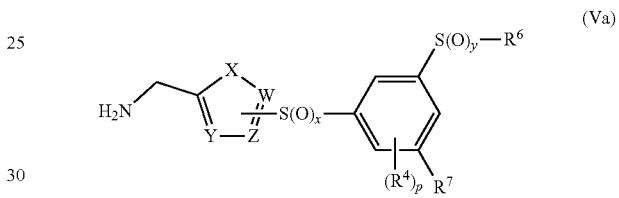

In general, compounds of formula (Va) can be synthesised by any of the methods described previously in Section A and B2c. In addition, compounds of this class can be synthesised via the bis-sulfonyl intermediate (164, Scheme 40) bearing a leaving group (LG), which can be obtained by any one of the methods previous described. Group G can be any suitable precursors of the aminomethyl moiety, for example a hydrogen, a nitrile, a carbonyl, a methyl, a protected hydroxymethyl or a protected aminomethyl group. As illustrated in Scheme 40, the leaving group (LG) on intermediate (164) can be conveniently substituted for a range of aryl, heteroaryl, alkynyl, alkenyl and amino substituents using metal catalysed cross couplings, for example Suzuki coupling employing boronic acids/boronates, Stille coupling employing stannates, Sonogashira coupling employing alkynyl cuprates, Heck coupling employing alkenes and Buchwald coupling employing amines. The coupled product (165) can be converted to the desired aminomethylheteroaryl analogues (166) by methods previously described.

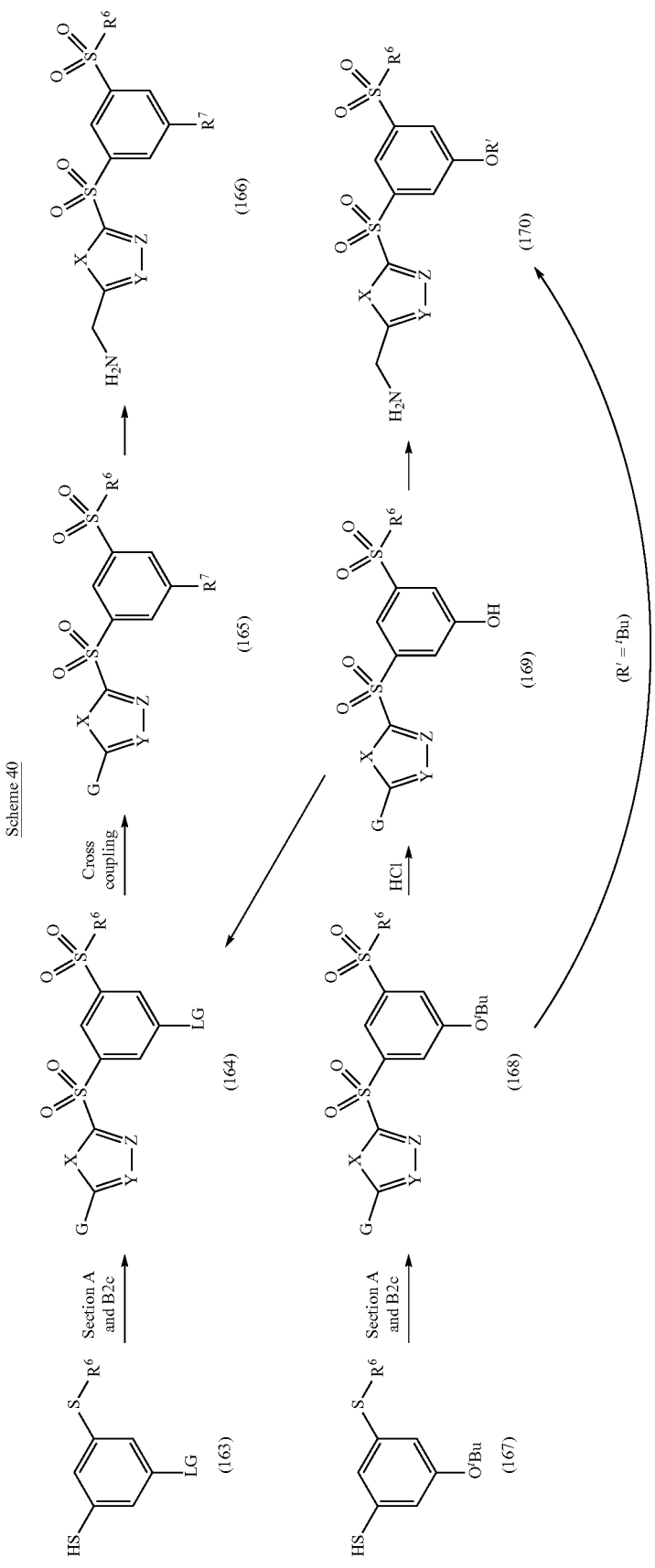

Compounds of formula (Va) with alkoxy R⁷ substituent can be synthesised from tert-butyl ethers (168, Scheme 40), which can be obtained by any of methods previous described in Section A and B2c, for example by the condensation of heteroaryl halides (5) and conveniently substituted thiophenols (163). tert-Butyl ethers (168) can be converted to the final aminoheteroaryl analogues (170, R'=$^t$Bu) directly by methods specific to group G previously described. Alternative they can undergo alcohol deprotection using, for example, HCl to afford phenols (169). Phenols (169) can be converted to intermediate (164) by sulfonation with, for example, triflic anhydride, to afford the corresponding triflate (164, LG=OTf). This can undergo metal catalysed cross couplings with the same set of substrate as aforementioned to afford intermediates (165), which can be subsequently converted to the aminomethyl heteroaryl targets (166) using methods specific to Group G previously described. Alkoxy substituted analogues (170) can be obtained by the condensation of phenols (169) with conveniently substituted alkyl-, cycloalkyl-, heterocycloalkyl halides/sulfonates/trichloro-acetimidates to give the corresponding alkoxides. These can subsequently be converted to the desired aminomethylheteroaryl analogues (170) by methods specific to Group G previous described in Section A. All the examples described in this section are illustrated for 2-aminomethyl-5-sulfonyl heteroaryl compounds. All the methods employed are also suitable for the synthesis of the regioisomeric 2-aminomethyl-4-heteroaryl sulfonyl compounds.

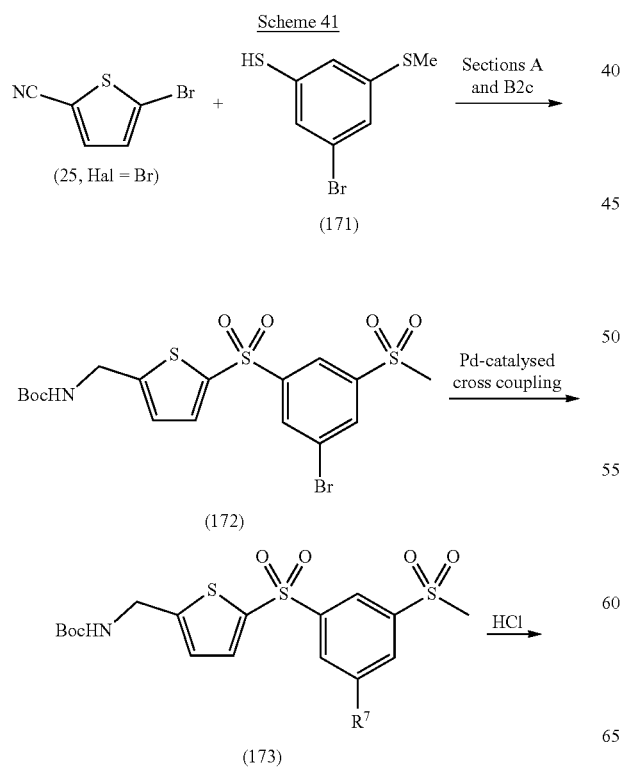

For example, analogues of formula Va with R⁷ substituents alkenyl, alkynyl, alkyl, cycloalkyl, heterocycloalkyl, aryl, heteroaryl can be obtained via bromide intermediate (172, Scheme 41), which can be synthesised from 5-bromo-thiophene-2-carbonitrile (25, Hal=Br) and conveniently substituted thiophenols, for example 3-bromo-5-(methylthio) benzenethiol (171) as illustrated in Scheme 41. The bromine atom of intermediate (172) can be conveniently substituted using a range of Pd(0) catalysed coupling processes. The Boc protecting group of the cross-coupled product (172) can be subsequently removed by treatment with HCl to afford 5-(1,3-bis-sulfonylaryl) AMT analogues with the desired substitutents (174).

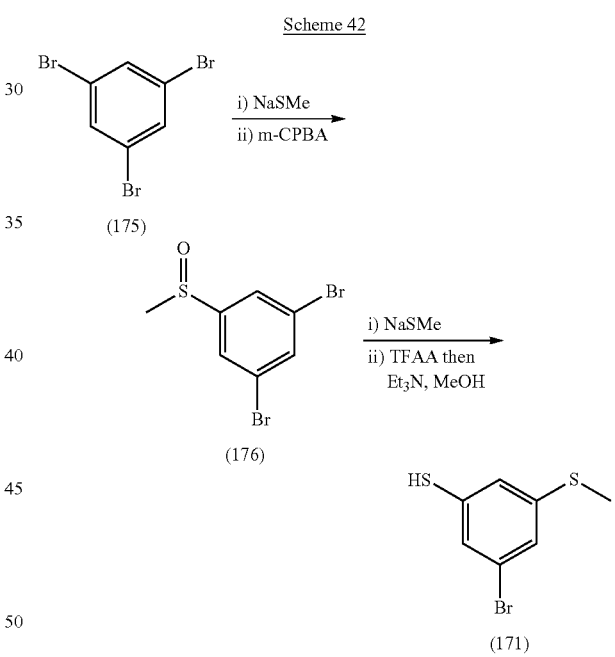

The synthesis of one of the thiophenol starting materials (163), for example 3-bromo-5-(methylthio)benzenethiol (171), from the commercially available 1,3,5-tribromobenzene (175) is described in Scheme 42. One of the three bromide groups can be substituted with sodium thiomethoxide to afford the corresponding monosulfide, which can be selectively oxidised to sulfoxide (176) using one equivalent of m-CPBA. At this point, one of the two remaining bromides can be conveniently substituted with thiolates, for example sodium thiomethoxide, as shown in Scheme 42. The corresponding sulfoxido-sulfide product can then undergo a Pummerer-type reaction employing trifluoroacetic anhydride, triethylamine and methanol to afford 3-bromo-5-(methylthio)benzenethiol (171).

Scheme 43

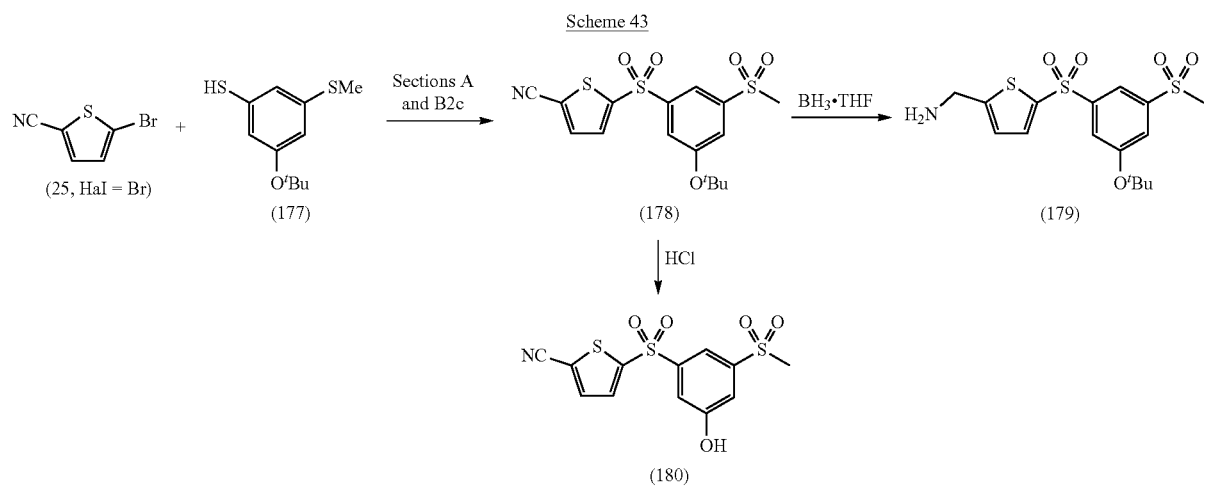

In another example, synthesis of analogues of formula Va with alkoxy substituents ($R^7$) is illustrated in Scheme 43. tert-Butyl ether (178) can be obtained from 5-bromothiophene-2-carbonitrile (25, Hal=Br) and thiophenol (177) by methods previously described. It can be converted directly to the tert-butoxy AMT analogue (179) using $BH_3$.THF. To allow further substitutions on the oxygen atom, the tert-butyl moiety of (178) can be removed by treatment with HCl, affording phenol (180).

using $BH_3$.THF affords the desired AMT analogues (182) as illustrated in Scheme 44. Furthermore, the free hydroxyl group of phenol (180) can be converted to a leaving group, for example a triflate (183), which can be conveniently substituted using a range of Pd-catalysed coupling processes, for example with alkyl, cycloalkyl, aryl, heteroaryl or alkenyl boronic acids/boronates (Suzuki) or the equivalent stannates (Stille), alkynyl cuprate (Sonogashira), ami- Scheme 44

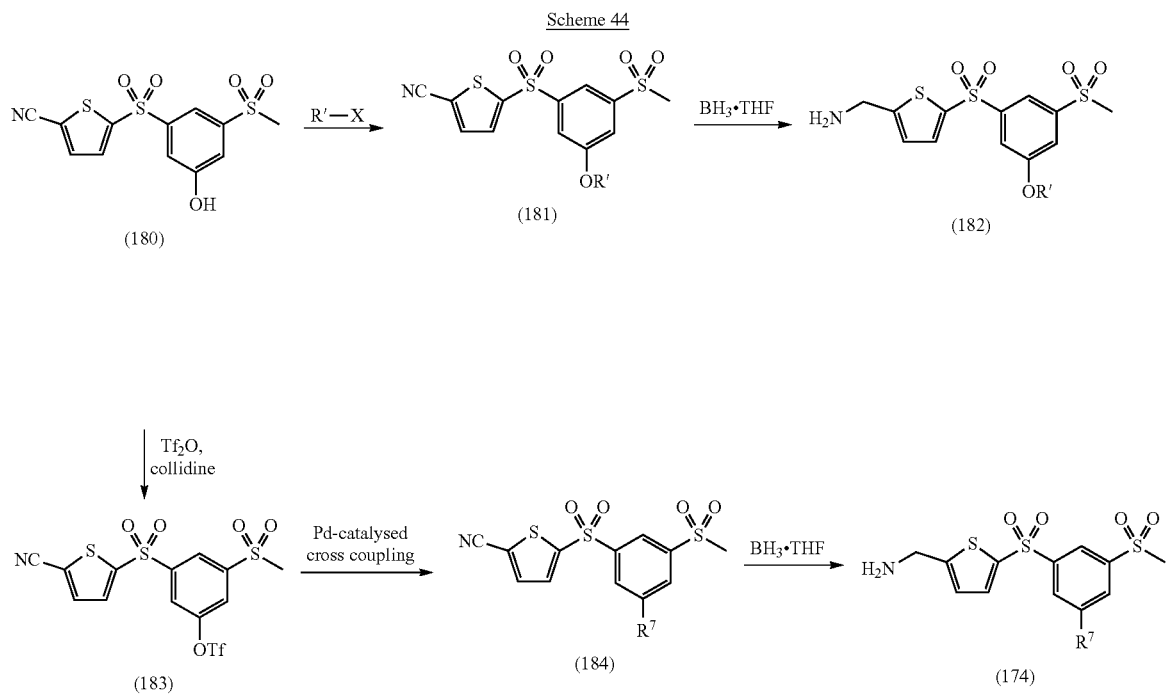

$R^7$ = alkyl, cycloalkyl, heterocycloalkyl, alkenyl, alkynyl, aryl, heteroaryl, $NR'_2$ The phenol intermediate (180) can be alkylated with conveniently substituted primary and secondary alkyl halides/sulfonates or tertiary alkyl trichloroacetimidate to afford the corresponding ethers (181), which upon reduction nes (Buchwald) e.t.c. The cross-coupled products (184) can be subsequently reduced by $BH_3$.THF to afford analogues of formula Va (174) where $R^7$ is a carbon- or nitrogen-based substituent.

Scheme 45

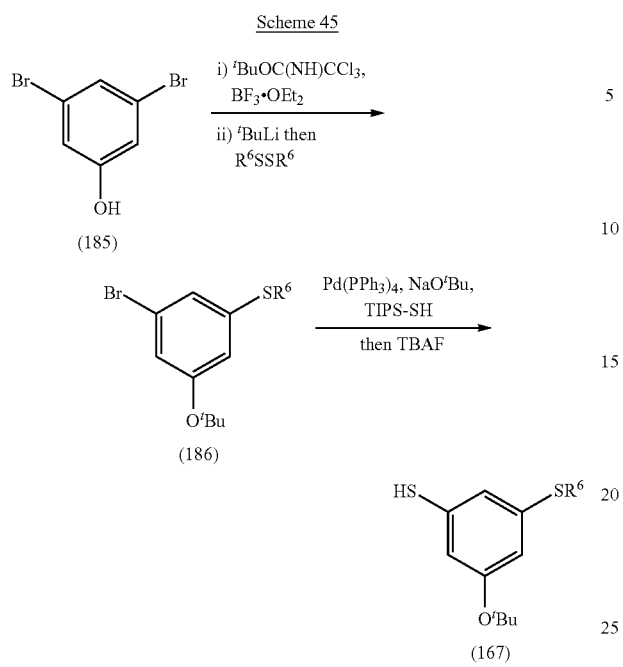

The synthesis of the thiophenol building blocks (167) is illustrated in Scheme 45. The commercially available 3,5-dibromophenol (184) is first converted to the corresponding tert-butyl ether by treatment with tert-butyl trichloroacetimidate ($^t$BuOC(NH)CCl$_3$) in the presence of BF$_3$·OEt$_2$. Lithium-bromine exchange and subsequent quenching with a conveniently substituted disulfide (R$^6$SSR$^6$), for example dimethyl disulfide (R$^6$=Me), furnishes sulfides (186). This can then undergo a Pd(0) catalysed cross coupling with a thiol precursor, for example triisopropylsilylthiol (TIPS-SH), to afford the expected silyl sulfides, which is treated with TBAF to reveal the desired thiophenols (187).

Synthetic Routes to Compounds of Formula (Vb)

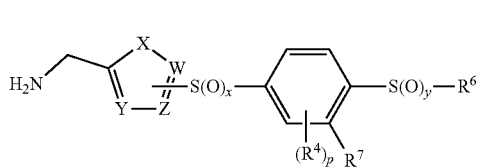

(Vb)

In general, compounds of formula (Vb) can be synthesised by any of the methods described previously. In addition, compounds of this class can be synthesised via the halide intermediates (188, Scheme 46), which can be obtained by any one of the methods previous described, for example from the condensation of heteroaryl halides (5) and conveniently substituted thiols (187). Group G can be any suitable precursors of the aminomethyl moiety, for example a hydrogen, a nitrile, a carbonyl, a methyl, a protected hydroxymethyl or a protected aminomethyl group.

Scheme 46

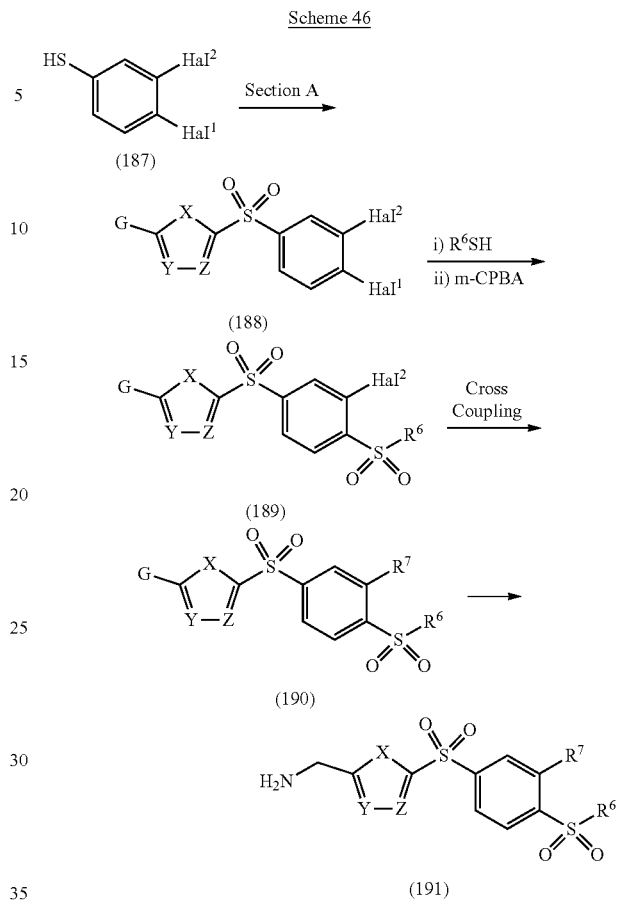

G = Aminomethyl precursor
R$^6$ = substituted alkyl, cycloalkyl, heterocycloalkyl, aryl, heteroaryl
R$^7$ = susbstituted alkyl, cycloalkyl, heterocycloalkyl, aryl, heteroaryl, alkenyl, NR'$_2$
Hal$^1$ = F, Cl, Br
Hal$^2$ = Cl, Br, I, As exemplified in Scheme 46, the halide group (Hal$^1$, preferably F and Cl) para to the sulfonyl moiety on sulfonylphenyl intermediate (188) can undergo selective nucleophilic substitution with a conveniently substituted alkyl, cycloalkyl, heterocycloalkyl, aryl and heteroaryl thiols (R$^6$SH) to afford the corresponding sulfides, which can be subsequently oxidised to sulfone (189) using m-CPBA. The halide group (Hal$^2$, preferably I, Br and Cl) of sulfone (189) can be conveniently substituted with a range of aryl, heteroaryl, alkynyl, alkenyl and amino substituents using metal catalysed cross couplings, for example Suzuki coupling employing boronic acids/boronates, Stille coupling employing stannates, Sonogashira coupling employing alkynyl cuprates, Heck coupling employing alkenes and Buchwald coupling employing amines. The coupled products (190) can be converted to the desired aminomethylheteroaryl analogues (191) by methods previously described. All the examples described in this section are illustrated for 2-aminomethyl-5-sulfonyl heteroaryl compounds. All the methods employed are also suitable for the synthesis of the regioisomeric 2-aminomethyl-4-heteroaryl sulfonyl compounds.

Scheme 47

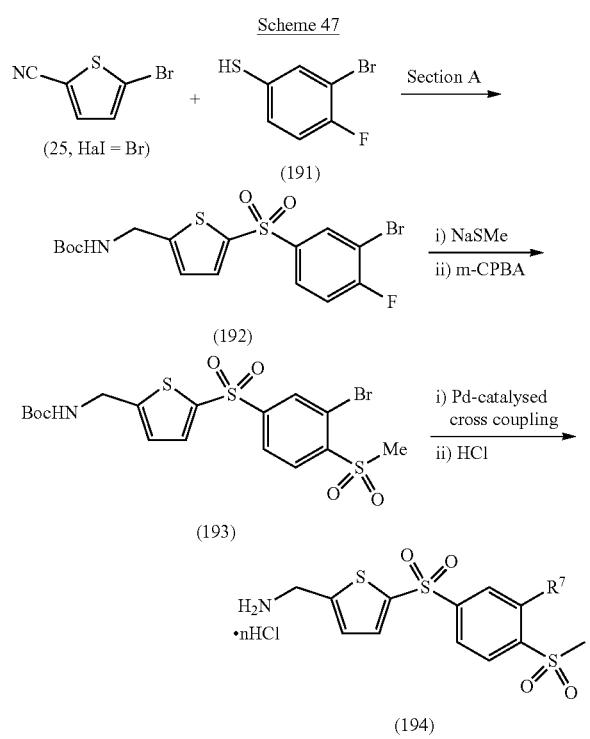

R[7] = alkyl, cycloalkyl, alkenyl, alkynyl, aryl, heteroaryl, NR'$_2$ equivalent stannates (Stille), alkynyl cuprate (Sonogashira) e.t.c. as well as amines (Buchwald). The Boc protecting group of the cross-coupled product can be subsequently removed by treatment with HCl to afford 5-(1,4-bis-sulfonylaryl) AMT analogues (194) with the desired R[7] substitutents.

Synthetic Routes to Compounds of Formula (Vc)

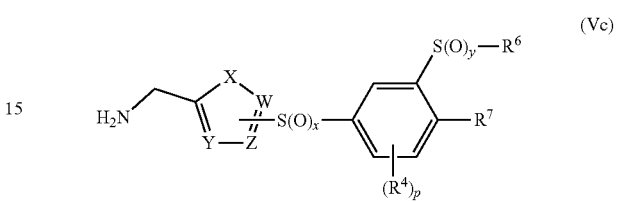

In general, compounds of formula (Vc) can be synthesised by methods described in Section A. In addition, compounds of this class can be synthesised via the halide intermediate (196, Scheme 48), which can be obtained by methods previous described in Section A and B2c, for example by the condensation of heteroaryl halides (5) and conveniently substituted thiols (195). Group G can be any suitable precursors of the aminomethyl moiety, for example a hydrogen, a nitrile, a carbonyl, a methyl, a protected hydroxymethyl or a protected aminomethyl group.

Scheme 48

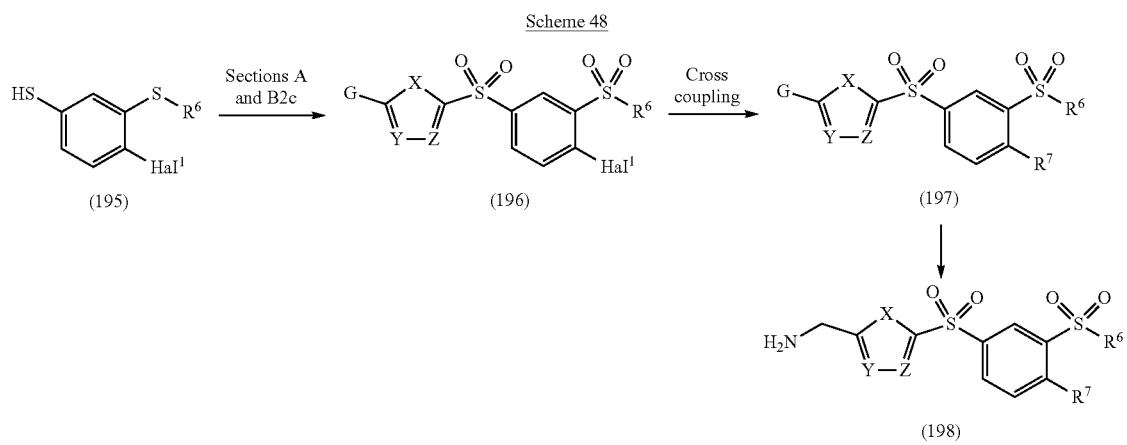

G = Aminomethyl precursor
R[6] = substituted alkyl, cycloalkyl, hetercycloalkyl, aryl, heteroaryl
R[7] = substituted alkyl, cycloalkyl, heterocycloalkyl, aryl, heteroaryl, alkynyl, alkenyl, NR'$_2$
Hal[1] = Cl, Br, I An AMT example is illustrated in Scheme 47. Fluorobenzene intermediate (192) can be obtained from 5-bromothiophene-2-carbonitrile (25, Hal=Br) and 3-bromo-4-fluorobenzenethiol (191), both commercially available, by methods previous described. Condensation with a thiolate (sodium thiomethoxide in this example), and subsequent sulfide oxidation furnishes bis-sulfonyl bromobenzene (193). The bromine atom of intermediate (193) can be conveniently substituted using a range of Pd(0) catalysed coupling processes, for example with alkyl, cycloalkyl, aryl, heteroaryl or alkenyl boronic acids/boronates (Suzuki) or the equivalent stannates (Stille), alkynyl cuprate (Sonogashira) e.t.c.

As exemplified in Scheme 48, the halide group (Hal[1]) on bis-sulfonylphenyl intermediate (196) can be conveniently substituted for a range of aryl, heteroaryl, alkynyl, alkenyl and amino substituents using metal catalysed cross couplings, for example Suzuki coupling employing boronic acids/boronates, Stille coupling employing stannates, Sonogashira coupling employing alkynyl cuprates, Heck coupling employing alkenes and Buchwald coupling or direct aromatic nucleophilic substitution employing amines. The coupled products (197) can be converted to the desired aminomethylheteroaryl analogues (198) by methods specific to Group G previously described. The methods described above are illustrated for 2-aminomethyl-5-sulfonyl heteroaryl compounds, but are also suitable for the synthesis of the regioisomeric 2-aminomethyl-4-heteroaryl sulfonyl compounds.

Scheme 49

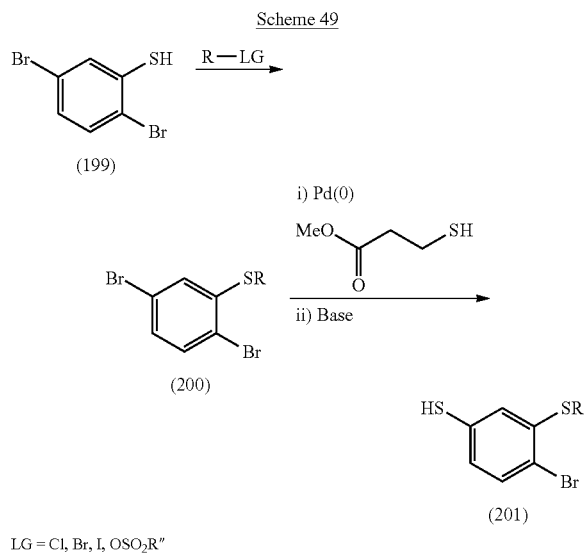

LG = Cl, Br, I, OSO₂R″

An example of the synthesis of thiophenol building blocks (201) is illustrated in Scheme 49. The commercially available 2,5-dibromophenol (199) can undergo nucleophilic substitution with a range of conveniently substituted alkyl, cycloalkyl or heterocycloalkyl halides or sulfonates to afford thioethers (200). The meta bromide group can undergo selectively Pd(0) catalysed cross coupling with methyl 3-mercaptopropanoate as described in Section A2a, which after treatment with base affords the desired thiophenol building block (201).

Synthetic Routes to Compounds of Formula (VI)

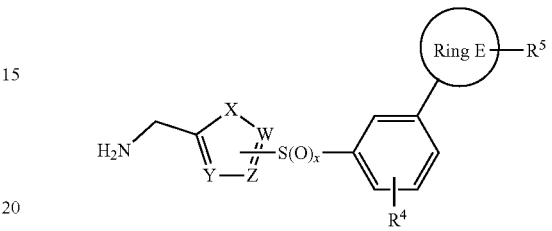

In general, compounds of formula (VI) can be synthesised by methods described in Sections A and B of the General Synthetic Methods. In addition, compounds with carboxylic acid (205) or carboxamide (207) can be synthesised via the tert-butyl carboxylate intermediate (203, Scheme 50), which can be obtained by methods previously described. Group G can be any suitable precursors of the aminomethyl moiety, for example a hydrogen, a nitrile, a carbonyl, a methyl, a protected hydroxymethyl or a protected aminomethyl group.

Scheme 50

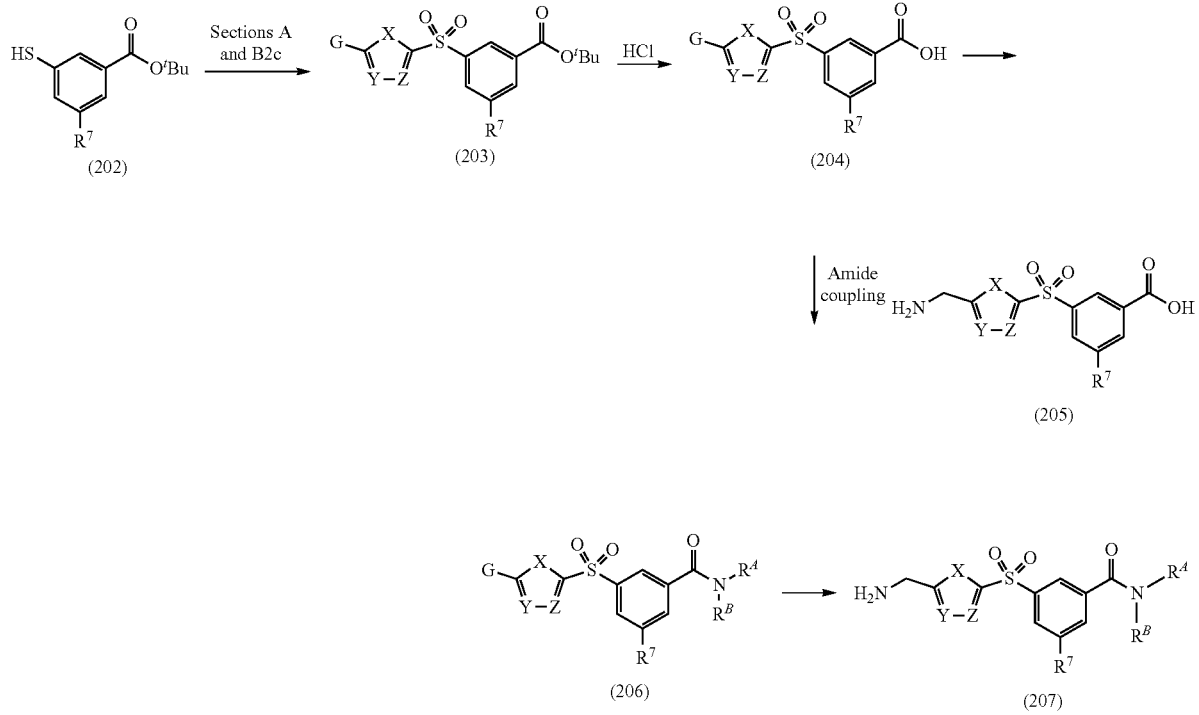

G = Aminomethyl precursor
$R^A$ and/or $R^B$ =H, (subsituted) alkyl, cycloalkyl, heterocycloalkyl, aryl, heteroaryl; or $NR^AR^B$ = (substituted) heterocycloalkyl
$R^7$ = (substituted) alkyl, cycloalkyl, heterocycloalkyl, aryl, heteroaryl, alkynyl, alkenyl, $NR'_2$ As illustrated in Scheme 50, the tert-butyl group of intermediate (203) can be removed by treatment with an acid, for example HCl, to afford the corresponding carboxylic acid (204). The carboxylic acid (204) can be converted to the desired aminomethylheteroaryl analogues (205) by methods previously described. Alternatively, the carboxyl group can be condensed with a range of conveniently substituted primary and acyclic secondary amines to afford the corresponding acyclic amides (206; NR$^A$R$^B$=acyclic), or with optionally substituted cyclic amines to afford the corresponding cyclic amides (206; NR$^A$R$^B$=cyclic). The amide intermediates (206) can be converted to the desired aminomethylheteroaryl analogues (207) by methods previously described.

Scheme 51

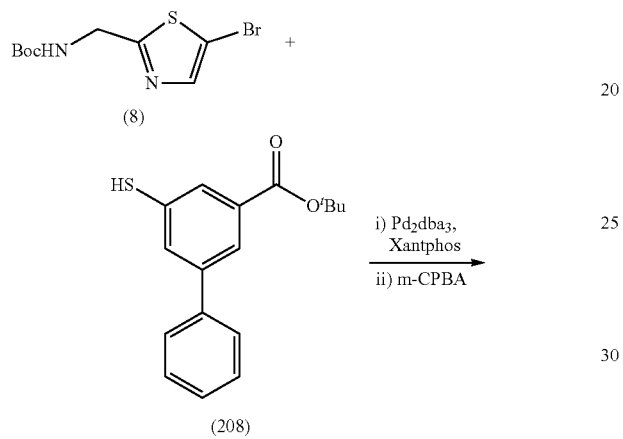

(208)

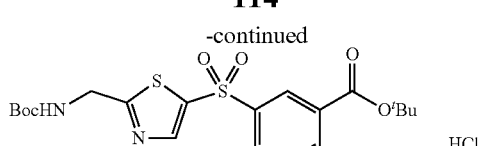

(209)

For example, the tert-butyl ester intermediate (209) can be synthesised from tert-butyl ((5-bromothiazol-2-yl)methyl) carbamate (8) and tert-butyl 5-mercapto-[1,1'-biphenyl]-3-carboxylate (209) by a Pd-catalysed cross coupling followed by m-CPBA oxidation of the resultant sulfide (Scheme 51) as previously described. In this example, both the Boc protecting group for the amino functionality and the tert-butyl ester are cleaved concomitantly by treatment with HCl to afford carboxyl-aminomethylthiazole analogue (210).

Scheme 52

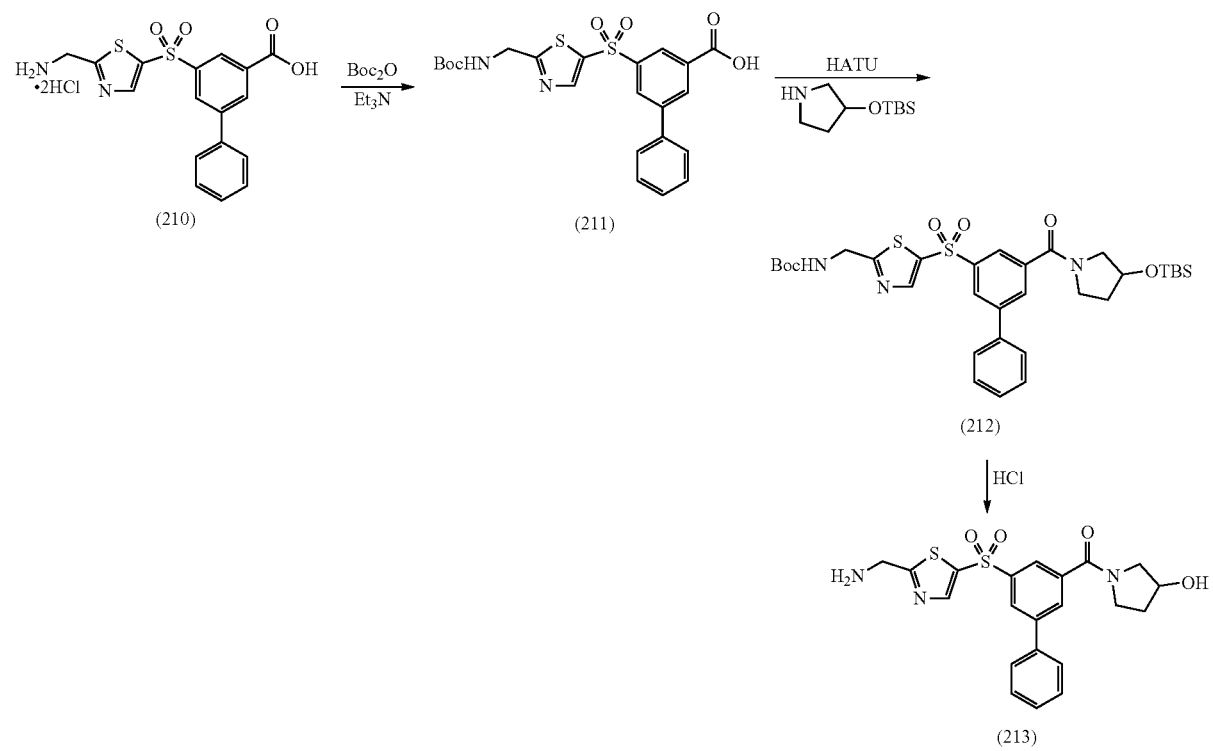

The amino group of analogue (210) can be selectively protected with 1 equivalent of Boc$_2$O to afford carboxylic acid intermediate (211), as illustrated in Scheme 52. The carboxyl group can undergo amide coupling mediated by common coupling agents, for example HATU, with a range of conveniently substituted amines, in this example 3-((tert-butyldimethylsilyl)oxy)pyrrolidine, to afford amide (212). Both the Boc and the TBS protecting group can be removed by treatment with HCl to afford the desired amido-aminomethylthiazole analogue (213).

Synthesis of 2-Halothiophenes

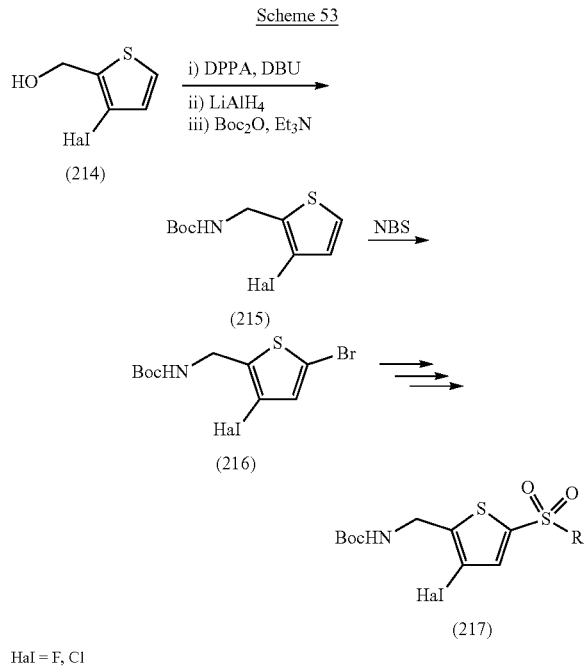

Scheme 53

Hal = F, Cl

An example of AMT analogues of Formula (I) (Y=C-Hal) is demonstrated in Scheme 53. (3-Fluorothiophen-2-yl)methanol (214, Y=CF) can be converted to bromothiophene intermediate (216) in straightforward steps. Treatment of alcohol (214) with diphenylphosphoryl azide (DPPA) leads to 2-(azidomethyl)-3-fluorothiophene, which can undergo subsequent azide reduction using LiAlH$_4$ and Boc protection to afford carbamate (215). Selective bromination using NBS leads to bromothiophene (216), which can be converted to the desired AMT analogues by methods described above.

Further information on the preparation of the compounds of the invention is provided in the Examples section. The general reaction schemes and specific methods described in the Examples form a further aspect of the invention.

The resultant compound of the invention from the processes defined above can be isolated and purified using techniques well known in the art.

Compounds of the invention may exist in a single crystal form or in a mixture of crystal forms or they may be amorphous. Thus, compounds of the invention intended for pharmaceutical use may be administered as crystalline or amorphous products. They may be obtained, for example, as solid plugs, powders, or films by methods such as precipitation, crystallization, freeze drying, or spray drying, or evaporative drying. Microwave or radio frequency drying may be used for this purpose.

The processes defined herein may further comprise the step of subjecting the compound of the invention to a salt exchange, particularly in situations where the compound of the invention is formed as a mixture of different salt forms. The salt exchange suitably comprises immobilising the compound of the invention on a suitable solid support or resin, and eluting the compounds with an appropriate acid to yield a single salt of the compound of the invention.

In a further aspect of the invention, there is provided a compound of the invention obtainable by any one of the processes defined herein.

Certain of the intermediates described in the reaction schemes above and in the Examples herein are novel. Such novel intermediates, or a salt thereof, particularly a pharmaceutically acceptable salt thereof, form a further aspect of the invention.

Pharmaceutical Compositions

In accordance with another aspect, the present invention provides a pharmaceutical formulation comprising a compound of the invention, or a pharmaceutically acceptable salt thereof, and a pharmaceutically acceptable excipient.

Conventional procedures for the selection and preparation of suitable pharmaceutical formulations are described in, for example, "Pharmaceuticals—The Science of Dosage Form Designs", M. E. Aulton, Churchill Livingstone, 1988.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of a condition is an amount sufficient to symptomatically relieve in a warm-blooded animal, particularly a human the symptoms of the condition or to slow the progression of the condition.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the invention will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, a daily dose selected from 0.1 mg/kg to 100 mg/kg, 1 mg/kg to 75 mg/kg, 1 mg/kg to 50 mg/kg, 1 mg/kg to 20 mg/kg or 5 mg/kg to 10 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Suitably the compound of the invention is adminstered orally, for example in the form of a tablet, or capsule doasage form. The daily dose administered orally may be, for example a total daily dose selected from 1 mg to 1000 mg, 5 mg to 1000 mg, 10 mg to 750 mg or 25 mg to 500 mg. Typically, unit dosage forms will contain about 0.5 mg to 0.5 g of a compound of this invention.

Therapeutic Uses and Applications

In accordance with another aspect, the present invention provides a compound of the invention, or a pharmaceutically acceptable salt thereof, for use as a medicament.

A further aspect of the invention provides a compound of the invention, or a pharmaceutically acceptable salt thereof, for use in the treatment of a disease or medical condition mediated by LOX.

Also provided is the use of a compound of the invention, or a pharmaceutically acceptable salt therefor in the manufacture of a medicament for the treatment of a disease or medical condition mediated by LOX.

Also provided is a method of treating a disease or medical condition mediated by LOX in a subject in need thereof, the method comprising administering to the subject an effective amount of a compound of the invention, or a pharmaceutically acceptable salt thereof.

Unless stated otherwise reference to the treatment of a disease or medical condition mediated by LOX is intended to encompass diseases or medical conditions mediated by any one of LOX, LOXL1, LOXL2, LOXL3 or LOXL4.

In the following sections of the application reference is made to a compound of the invention, or a pharmaceutically acceptable salt for use in the treatment of certain diseases or conditions. It is to be understood that any reference herein to a compound for a particular use is also intended to be a reference to (i) the use of the compound of the invention, or pharmaceutically acceptable salt thereof, in the manufacture of a medicament for the treatment of that disease or condition; and (ii) a method of treating the disease or condition in a subject, the method comprising administering to the subject a therapeutically effective amount of the compound of the invention, or pharmaceutically acceptable salt thereof.

The disease of medical condition mediated by LOX may be any of the diseases or medical conditions listed in this application.

As discussed in the background to the invention the role of the LOX family of may have distinct roles in diseases such as cancer. Accordingly the selective inhibition of a LOX may be advantageous. In one embodiment there is provided a compound of the invention, or pharmaceutically acceptable salt thereof, for use in the selective inhibition of LOX, LOXL1, LOXL2, LOXL3 or LOXL4. In other embodiments it may be advantageous to inhibit two or more members of the LOX family. Accordingly in another embodiment there is provided a compound of the invention, or pharmaceutically acceptable salt thereof, for use in the inhibition of two or more members of the LOX family selected from LOX, LOXL1, LOXL2, LOXL3 or LOXL4.

Proliferative Diseases

A further aspect of the invention provides a compound of the invention, or a pharmaceutically acceptable salt thereof, for use in the treatment of a proliferative disease. The proliferative disease may be malignant or non-malignant.

As mentioned in the Background to the invention, LOX plays a critical role in primary cancer and metastasis. Evidence supporting this role of LOX in primary tumour growth and metastasis is described below.

Studies have shown that LOX plays a fundamental role in the growth of primary tumours in colorectal and lung cancer (Gao, Xiao et al. 2010, Baker, Cox et al. 2011) and glioblastoma (Mammoto, Jiang et al. 2013). PDAC KRAS$^{mut}$/p53$^{wt}$ cells (which endogenously express low levels of LOX) were engineered to express high levels of human LOX. In murine allograft models using these cells primary tumour growth is increased significantly (Miller, Morton et al. 2015). Lysyl oxidase activity participates in primary tumor growth in a transgenic mouse model of aggressive pancreatic ductal adenocarcinoma (PDAC) by directly impacting the senescence stability (Wiel, Augert et al. 2013).

Expression of LOX is elevated in more than 70% of breast cancer patients with Estrogen Receptor negative disease, in 80% of head & neck cancer patients, in 33% of primary colorectal carcinomas (CRC) and 48% of metastatic tissues from patients with CRC (Baker, Cox et al. 2011), and in cirrhotic HCC patients with a history of alcoholism (Huang, Ho et al. 2013). LOX is also overexpressed in lung adenocarcinoma (Wilgus, Borczuk et al. 2011), LKB1-mutant lung cancer (Gao, Xiao et al. 2010), aggressive prostate adenocarcinoma (Stewart, Gray et al. 2008), uveal melanoma (Abourbih, Di Cesare et al. 2010), oral and oropharyngeal squamous carcinoma (Albinger-Hegyi, Stoeckli et al. 2010), thyroid cancer (Boufraqech, Nilubol et al. 2015), myeloproliferative neoplasms, especially myelofibrosis (Papadantonakis, Matsuura et al. 2012, Tadmor, Bejar et al. 2013) and pancreatic cancer (Sansom 2012, Miller, Morton et al. 2015).

Lysyl-Oxidase-Like 2 (LOXL2) and Cancer

LOXL2 is another member of the LOX family that is involved in the cross-linking of extracellular collagens and elastin (Vadasz, Kessler et al. 2005) (Kim, Kim et al. 2010). In addition to conserved C-terminal region, the LOXL2 protein has scavenger receptor cysteine-rich regions that are commonly found in cell surface receptors and adhesion molecules, as well as a cytokine receptor-like domain.

LOXL2 expression has been found upregulated in breast, gastric, colon, esophageal, head and neck, lung and laryngeal carcinomas, as reviewed in Barker et al (Barker, Cox et al. 2012) and in renal cells carcinoma (Hase, Jingushi et al. 2014) (Nishikawa, Chiyomaru et al. 2015). High LOXL2 expression has been associated with poor prognosis in patients with squamous cell carcinoma, laryngeal, oesophagus and breast cancer, increased metastases in colon and breast cancer, as well as drug resistance in pancreatic cancer cells—reviewed in Barker et al (Barker, Cox et al. 2012). Additionally, it has been shown that LOXL2 up-regulation increases the invasiveness of otherwise non-invasive breast cancer cells (Akiri, Sabo et al. 2003). Furthermore, LOXL2 and LOXL4 are required for metastatic niche formation in a breast orthotopic mouse model (Wong et al, 2011). LOXL2 expression is associated with lymph node metastasis, histological grades and poor prognosis in cholangiocarcinoma, and knockdown of LOXL2 reduces invasion and metastasis (Xu, Li et al. 2014). HCC metastasis relies on LOXL2, which is overexpressed in tumor tissues and sera of HCC patients (Wong, Tse et al. 2014).

LOXL2 transcription is regulated by HIF-1 and upregulation of LOXL2 in hypoxia has been shown to downregulate E-cadherin leading to epithelial to mesenchymal transition (EMT) (Schietke, Warnecke et al. 2010) which is a key step in tumour progression, invasion and metastasis. This is in agreement with other reports where LOXL2 was shown to be involved in both EMT and tumour progression in murine squamous and spindle cell carcinomas (Fong, Dietzsch et al. 2007) (Moreno-Bueno, Salvador et al. 2011). LOXL2 expression is positively associated in CRC (Offenberg, Brunner et al. 2008). LOXL2 has also been linked to Src kinase/focal adhesion kinase (Src/FAK) pathway activation, and this appears to be the major pathway where secreted LOXL2 induces gastric tumour cell invasion and metastasis (Peng, Ran et al. 2009).

Several reports describe an intracellular epigenetic role for LOXL2 in transcriptional regulation, either indirectly via the stabilisation of the EMT-essential transcription factor Snail1 (Peinado, Del Carmen Iglesias-de la Cruz et al. 2005), or directly via oxidation of trimethylated histone H3 (Herranz, Dave et al. 2012) (Millanes-Romero, Herranz et al. 2013). In certain cancers such as basal-like breast carcinoma and larynx squamous cell carcinoma perinuclear expression of LOXL2 is a marker of tumour aggressiveness and poor prognostic (Moreno-Bueno, Salvador et al. 2011) (Peinado, Moreno-Bueno et al. 2008).

Barry-Hamilton et al. reported that LOXL2 antibody treatment significantly reduces bone metastases from intracardiac injection of breast carcinoma cells (Barry-Hamilton, Spangler et al. 2010). In addition, Barker et al have provided preclinical evidence that LOXL2 inhibition is highly effective against spontaneous lung, liver and bone metastases of mammary carcinoma cells (Barker, Chang et al. 2011). Therefore, LOXL2 also represents a promising therapeutic target for the treatment of primary and metastatic cancer.

As mentioned in the Background to the Invention it is thought that although LOX and LOXL2 are involved in similar extra-cellular processes, it appears that they have distinct roles.

Other members of the LOX family, LOXL1, LOXL3 and LOXL3 are also implicated in proliferative conditions including cancer (see Background to the Invention).

Accordingly in one embodiment there is provided a compound of the invention, or pharmaceutically acceptable salt thereof for use in the treatment of a cancer. In one embodiment the cancer is non-metastatic. Accordingly the compound of the invention, or a pharmaceutically acceptable salt thereof may be for use in the treatment of a primary tumour in a subject.

The Role of LOX in Cancer Metastasis

Elevated LOX expression is associated with metastasis and decreased patient survival (Baker, Cox et al. 2011, Wilgus, Borczuk et al. 2011) Increased LOX expression is associated with disease grade, increased distant metastasis and lower overall survival in breast cancer patients with oestrogen receptor (ER)-negative tumours (Erler, Bennewith et al. 2006), in head & neck cancer patients (Albinger-Hegyi, Stoeckli et al. 2010, Toustrup, Sorensen et al. 2011), gastric cancer (Kasashima, Yashiro et al. 2015), hepatocellular carcinoma (Zhu, Huang et al. 2015), non-small cells lung cancer (Liu, Ping et al. 2014) and astrocytomas (da Silva, Uno et al. 2015). LOX expression is a determinant of poor survival in pancreatic cancer (Miller, Morton et al. 2015). Inhibition of LOX eliminates metastasis in mice with orthotopically grown human breast cancer (Erler, Bennewith et al. 2006) and inhibits tumour angiogenesis in a human colorectal cancer model (Baker, Bird et al. 2013).

A polyclonal antibody that was raised against LOX and shown to inhibit its enzymatic activity, was able to block the metastatic spread of tumour cells to the lungs and livers of recipient mice in an orthotopic model of metastatic human breast cancer (Erler et al, 2006). Suppression of LOX expression using shRNA blocks metastatic spread of the breast cancer cells and that BAPN, the non-selective small molecule inhibitor of LOX can block metastatic tumour growth of these cells in mice (Erler et al, 2006). Furthermore, inhibition of tumour-secreted LOX by genetic (shRNA), antibody (Ab) or the irreversible non-selective small molecule inhibitor BAPN, significantly reduced invasion and metastasis of orthotopic human breast tumours or circulating human breast cancer cells (Bondareva, Downey et al. 2009, Erler, Bennewith et al. 2009, Levental, Yu et al. 2009), CRC (Baker, Cox et al. 2011), HCC (Huang, Ho et al. 2013), LKB1-mutant lung adenocarcinoma (Gao, Xiao et al. 2010), anaplastic thyroid cancer (Boufraqech, Nilubol et al. 2015) and PDAC in mice (Sansom 2012). High expression of LOX in primary breast tumours leads to osteolytic lesion formation; silencing or inhibition of LOX activity abrogates tumour-driven bone metastases (Cox, Rumney et al. 2015).

LOX family members (especially LOX and LOXL2) play a critical role in the metastatic spread of cancer cells (Erler, Bennewith et al. 2006, Bondareva, Downey et al. 2009, Erler, Bennewith et al. 2009, Levental, Yu et al. 2009, Gao, Xiao et al. 2010). In response to hypoxia (a condition that occurs due to inadequate blood supply when solid tumours exceed about 1 $cm^3$ in size), cancer cells produce and secrete LOX into the circulation (Erler, Bennewith et al. 2009).

LOX regulates invasion of cancer cells in vitro. Thus, cancer cells expressing high levels of LOX show increased ability to invade 3D collagen I and Matrigel matrices (Kirschmann, Seftor et al. 2002) (Erler, Bennewith et al. 2006). Furthermore, experimental over-expression of LOX enhances invasion of cancer cells, whereas genetic knockdown of LOX using RNA interference (RNAi; with both short hairpin RNA [shRNA] or small interfering RNA [siRNA]) or antisense technology) inhibits the in vitro invasion activity of cancer cells (Kirschmann, Seftor et al. 2002) (Erler, Bennewith et al. 2006). Similarly, a non-selective small molecule inhibitor of LOX, beta-aminopropionitrile (BAPN) also blocks the in vitro invasion activity of several human cancer cell lines (Kirschmann, Seftor et al. 2002) (Erler, Bennewith et al. 2006). LOX enhances hypoxia-induced invasion and migration in cervical cancer cells mediated by the EMT which can be inhibited by BAPN (Yang, Li et al. 2013). These studies implicate LOX in the invasive behaviour of cancer cells.

One of the critical functions of LOX appears to be to act remotely to pre-condition the niche at future sites of metastasis. Tumour cell metastasis is facilitated by these "premetastatic niches" formed in destination organs using invading bone marrow-derived dendritic cells (BMDCs). This "nest-building" activity is initiated when LOX becomes deposited at discreet sites in the target organ (Erler, Bennewith et al. 2009). Studies have shown that bone marrow derived cell recruitment is an essential step in niche conditioning and metastatic spread of cancer (Kaplan et al, 2005). This mechanism underlines the importance of LOX for the invasive activity of cancer cells and for the earliest stages of metastasis, when the cancer cells first migrate out of the primary tumour. It has been shown that BMDCs and LOX co-localise in human metastatic tissue, and inhibition of LOX can prevent BMDC recruitment and metastasis in models of breast cancer metastasis (Erler, Bennewith et al. 2009).

In addition to its roles in the early phases of metastasis, there is evidence that LOX is necessary to maintain the growth of the cancer cells once they arrive at the new metastatic sites because inhibition of LOX causes regression of these lesions, even after the development of metastatic disease (Erler, Bennewith et al. 2006) (Erler, Bennewith et al. 2009) (Bondareva, Downey et al. 2009). It was shown that although depletion of LOX does not affect tumour cell proliferation on plastic, it suppresses their growth in recombinant basement membrane (Matrigel) matrices (Erler, Bennewith et al. 2006). Furthermore, cancer cells do not colonise the lungs efficiently when LOX is inhibited by shRNA (Erler et al, 2006) and it was found that metastatic lung tumours regress when mice are treated with LOX neutralising antibodies (Erler, Bennewith et al. 2006). Notably, the colonisation of the lung by human breast cancer cells was enhanced when the cells were co-injected with conditioned medium from cells expressing LOX, but this was blocked if the mice were treated with conditioned medium in the presence of BAPN or a LOX antibody (Erler, Bennewith et al. 2009). These findings demonstrate a requirement for tumour-secreted LOX to maintain metastatic growth.

LOX is essential for phosphorylation of the focal adhesion kinase (FAK) downstream of integrin signalling (Erler, Bennewith et al. 2006). FAK is a tyrosine kinase that interacts with several signalling molecules and is critical for cell survival (van Nimwegen and van de Water 2007). LOX-mediated collagen cross-linking results in increased tissue stiffness and activation of the FAK/SRC signalling in in vitro and in vivo models of CRC. Cells expressing high levels of enzymatically active LOX have an increased capacity to proliferate, invade and metastasise. Thus LOX have both cell-dependent and cell-autonomous roles in metastatic tumour growth at several levels: enhances the ability of cancer cells to invade locally, possibly by enhancing migration away from the primary site; conditions the future metastatic sites in preparation for the arrival of the BMDCs and then tumour cells; supports the survival/proliferation of the cancer cells once they colonise the niche.

Accordingly the compound of the invention, or a pharmaceutically acceptable salt thereof may be for use in the treatment of metastatic cancer in a subject.

In another embodiment of the invention there is provided a compound of the invention, or a pharmaceutically acceptable salt thereof may be for use as an inhibitor of the motility of tumour cells. In another embodiment the compound of the invention, or a pharmaceutically acceptable salt thereof may be for use as an inhibitor of the dissemination and invasiveness of mammalian cancer cells leading to inhibition of metastatic tumour growth. In particular a compound of the invention, or a pharmaceutically acceptable salt thereof may be for use as an anti-invasive agent for use in the containment and/or treatment of solid tumour disease. In another embodiment a compound of the invention, or a pharmaceutically acceptable salt thereof may be for use in the prevention or inhibition of cancer metastasis.

LOX Family, Fibroblasts and Stroma

Cancer associated fibroblasts are recruited by cancer cells recruit fibroblasts through various growth factors and cytokines and form a myofibroblastic microenvironment that promotes cancer growth, survival, local invasion and metastasis (Karagiannis, Poutahidis et al. 2012). Persistent presence of myofibroblasts in cancer contributes to desmoplasia, a cancer-specific type of fibrosis. Desmoplasia and increased fibrosis have been associated with progression of several cancers such as breast, pancreatic, colorectal, gastric and hepatocellular (Barker, Cox et al. 2012). Lysyl oxidase family members expression, either secreted by cancer cells or by activated fibroblasts, has been found associated with tumour ECM, tumour stroma or tumour-associated vasculature of several cancers, such as colorectal, pancreatic, breast, laryngeal, endometrial, testicular, hepatocellular, renal (reviewed in Barker et al (Barker, Cox et al. 2012)), gastric cancer (Kasashima, Yashiro et al. 2014), and to be involved in their progression and metastasis (Akiri, Sabo et al. 2003, Barry-Hamilton, Spangler et al. 2010, Barker, Bird et al. 2013) (Pickup, Laklai et al. 2013). Expression of LOXL4 is enhanced in keratocystic odontogenic tumors (KCOT) stromal tissues and primary KCOT stromal fibroblasts (Jiang, Sima et al. 2014)

In one embodiment there is provided a compound of the invention, or a pharmaceutically acceptable salt thereof for use in the treatment of desmoplasia.

As discussed herein, the compound of the invention, or a pharmaceutically acceptable salt thereof may be for use in the treatment of a cancer, which may be non-metastatic or metastatic and which may be a solid tumour or a haematological ("liquid") cancer selected from, for example:

(1) Carcinoma, including for example tumours derived from stratified squamous epithelia (squamous cell carcinomas) and tumours arising within organs or glands (adenocarcinomas). Examples include breast, colon, lung, prostate, ovary, esophageal carcinoma (including, but not limited to, esophageal adenocarcinoma and squamous cell carcinoma), basal-like breast carcinoma, basal cell carcinoma (a form of skin cancer), squamous cell carcinoma (various tissues), head and neck carcinoma (including, but not limited to, squamous cell carcinomas), stomach carcinoma (including, but not limited to, stomach adenocarcinoma, gastrointestinal stromal tumor), signet ring cell carcinoma, bladder carcinoma (including transitional cell carcinoma (a malignant neoplasm of the bladder)), bronchogenic carcinoma, colorectal carcinoma (including, but not limited to, colon carcinoma and rectal carcinoma), anal carcinoma, gastric carcinoma, lung carcinoma (including but not limited to small cell carcinoma and non-small cell carcinoma of the lung, lung adenocarcinoma, squamous cell carcinoma, large cell carcinoma, bronchioloalveolar carcinoma, and mesothelioma), neuroendocrine tumors (including but not limited to carcinoids of the gastrointestinal tract, breast, and other organs), adrenocortical carcinoma, thyroid carcinoma, pancreatic carcinoma (including, but not limited to, pancreatic ductal adenocarcinoma, pancreatic adenocarcinoma, acinar cell carcinoma, intraductal papillary mucinous neoplasm with invasive carcinoma, mucinous cystic neoplasm with invasive carcinoma, islet cell carcinoma and neuroendocrine tumors), breast carcinoma (including, but not limited to, ductal carcinoma, lobular carcinoma, inflammatory breast cancer, clear cell carcinoma, mucinous carcinoma), ovarian carcinoma (including, but not limited to, ovarian epithelial carcinoma or surface epithelial-stromal tumor including serous tumor, endometrioid tumor and mucinous cystadenocarcinoma, sex-cord-stromal tumor), liver and bile duct carcinoma (including, but not limited to, hepatocellular carcinoma, cholangiocarcinoma and hemangioma), prostate carcinoma, adenocarcinoma, brain tumours (including, but not limited to glioma, glioblastoma and medulloblastoma), germ cell tumors, sweat gland carcinoma, sebaceous gland carcinoma, papillary carcinoma, papillary adenocarcinoma, cystadenocarcinoma, kidney carcinoma (including, but not limited to, renal cell carcinoma, clear cell carcinoma and Wilm's tumor), medullary carcinoma, ductal carcinoma in situ or bile duct carcinoma, choriocarcinoma, seminoma, embryonal carcinoma, cervical carcinoma, uterine carcinoma (including, but not limited to, endometrial adenocarcinoma, uterine papillary serous carcinoma, uterine clear-cell carcinoma, uterine sarcomas and leiomyosarcomas, mixed mullerian tumors), testicular carcinoma, osteogenic carcinoma, epithelial carcinoma, sarcomatoid carcinoma, nasopharyngeal carcinoma, laryngeal carcinoma; oral and oropharyngeal squamous carcinoma;

(2) Sarcomas, including: osteosarcoma and osteogenic sarcoma (bone); chondrosarcoma (cartilage); leiomyosarcoma (smooth muscle); rhabdomyosarcoma (skeletal muscle); mesothelial sarcoma and mesothelioma (membranous lining of body cavities); fibrosarcoma (fibrous tissue); angiosarcoma and hemangioendothelioma (blood vessels); liposarcoma (adipose tissue); glioma and astrocytoma (neurogenic connective tissue found in the brain); myxosarcoma (primitive embryonic connective tissue); chordoma, endotheliosarcoma, lymphangiosarcoma, lymphangioendotheliosarcoma, synovioma, Ewing's sarcoma, mesenchymous and mixed mesodermal tumor (mixed connective tissue types) and other soft tissue sarcomas;

(3) Myeloma and multiple myeloma;

(4) Hematopoietic tumours, including: myelogenous and granulocytic leukemia (malignancy of the myeloid and granulocytic white blood cell series); lymphatic, lymphocytic, and lymphoblastic leukemia (malignancy of the lymphoid and lymphocytic blood cell series); polycythemia vera and erythremia (malignancy of various blood cell products, but with red cells predominating); myelofibrosis.

(5) Lymphomas, including: Hodgkin and Non-Hodgkin lymphomas;

(6) Solid tumors of the nervous system including medulloblastoma, craniopharyngioma, ependymoma, pinealoma, hemangioblastoma, acoustic neuroma, oligodendroglioma, meningioma, neuroblastoma and schwannoma;

(7) Melanoma, uveal melanoma and retinoblastoma; and (8) Mixed Types, including, e.g., adenosquamous carcinoma, mixed mesodermal tumor, carcinosarcoma or teratocarcinoma.

In a particular embodiment a compound of the invention, or a pharmaceutically acceptable salt thereof may be for use in the treatment of a cancer selected from pancreatic, colorectal, breast and lung cancer.

A compound of the invention, or a pharmaceutically acceptable salt thereof the invention may be for use in the treatment of a benign proliferative disease. The benign disease may be a benign tumour, for example hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas, pyogenic granulomas, moles, uterine fibroids, thyroid adenomas, adrenocortical adenomas or pituitary adenomas. The benign condition may be endometriosis or a keratocystic odontogenic tumor.

Fibrotic Diseases

As discussed in the Background to the invention, LOX and LOXL are implicated in fibrotic diseases. Accordingly a compound of the invention or a pharmaceutically acceptable salt thereof may be for use in the treatment of a fibrotic disorder. The fibrotic disorder may be a disorder characterised by excess fibrosis, e.g., an excess of fibrous connective tissue in a tissue or organ, e.g., triggered by a reparative or reactive process, e.g., in response to injury (e.g., scarring, healing) or excess fibrotic tissue arising from a single cell line (e.g., fibroma).

LOX has been implicated in the pathogenesis of renal fibrosis and its inhibition with the alleviation of the symptoms (Di Donato, Ghiggeri et al. 1997, Haase 2009, Chen, Lin et al. 2015). Hyperuricemia results in hypertension, intrarenal vascular disease, and renal injury and is associated with increased expression of lysyl oxidase (LOX) and fibronectin in kidneys (Yang, Wang et al. 2010).

Similar involvement of LOX or LOXL2 in the pathology of disease and reduction in symptoms has been demonstrated for lung fibrosis (Barry-Hamilton, Spangler et al. 2010) (Haase 2009, Cox, Bird et al. 2013, Chien, Richards et al. 2014).

LOX and LOXL2 are involved in liver fibrosis (Kagan 1994, Marshall and Smith 2011) (Ricard-Blum, Bresson-Hadni et al. 1996) (Smith and Van Vlasselaer 2011) (Georges, Hui et al. 2007), liver cirrhosis (the last stage of liver fibrosis) (Kagan 1994) and related diseases such as Wilson's disease and primary biliary cirrhosis (Vadasz, Kessler et al. 2005). Simtuzumab (GS-6624; AB-0024), an allosteric humanised monoclonal antibody which inhibits LOXL2, is in clinical trials for the treatment of a number of fibrotic conditons: myelofibrosis (Primary myelofibrosis, Post Polycythemia Vera or Post Essential Thrombocythemia Myelofibrosis), idiopathic pulmonary fibrosis (IPF), liver fibrosis due to non-alcoholic steatohepatitis (NASH), HIV and/or Hepatitis C-infection or primary sclerosing cholangitis (PSC) and compensated liver cirrhosis due to NASH. Levels of lysyl oxidase are increased in patients with scleroderma and systemic sclerosis (Chanoki, Ishii et al. 1995) (Rimar, Rosner et al. 2014).

The fibrotic disorder may be any of those discussed in the above three paragraphs. In one embodiment the compound of the invention or a pharmaceutically acceptable salt thereof may be for use in the treatment of a fibrotic disorder selected from:

(i) a fibrotic condition affecting the lungs, for example pulmonary fibrosis secondary to cystic fibrosis; idiopathic pulmonary fibrosis; coal worker's progressive massive fibrosis; cryptogenic fibrosing alveolitis, chronic fibrosing interstitial pneumonia, interstitial lung disease (ILD), diffuse parenchymal lung disease (DPLD), emphysema and chronic obstructive pulmonary disease (COPD), or chronic asthma; or (ii) a fibrotic condition affecting the liver, for example cirrhosis, and associated conditions such as chronic viral hepatitis B or C, Wilson's disease, non-alcoholic fatty liver disease (NAFLD), alcoholic steatohepatitis (ASH), non-alcoholic steatohepatitis (NASH), primary biliary cirrhosis (PBC), biliary cirrhosis or autoimmune hepatitis; or (iii) a fibrotic condition affecting the kidneys, for example diabetic nephropathy, vesicoureteral reflux, tubulointerstitial renal fibrosis; glomerulonephritis or glomerular nephritis, including focal segmental glomerulosclerosis and membranous glomerulonephritis or mesangiocapillary glomerular nephritis;

(iv) a fibrotic condition affecting the heart or vascular system, for example endomyocardial fibrosis; old myocardial infarction; atrial fibrosis; congestive heart failure, cardiomyopathy, hypertensive heart disease (HHD), hypertension (for example pulmonary hypertension) and fibrosis associated with hypertension, atherosclerosis, restenosis (e.g. coronary, carotid, and cerebral lesions), and heart disease associated with cardiac ischemic events; or (v) a fibrotic condition affecting the mediastinum, for example mediastinal fibrosis; or (vi) a fibrotic condition affecting bone, for example myelofibrosis, including primary myelofibrosis, post polycythemia vera or post essential thrombocythemia myelofibrosis; or (vii) a fibrotic condition affecting the retroperitoneum, for example retroperitoneal fibrosis skin; or (viii) a fibrotic condition affecting the skin, for example nephrogenic systemic fibrosis, keloid formation and scarring, systemic sclerosis or scleroderma; or (ix) a fibrotic condition affecting the GI tract, for example a fibrotic intestinal disorder, inflammatory bowel disease, ulcertative colitis or Crohn's disease; or (x) a fibrotic condition affecting connective tissue, for example arthrofibrosis; or capsulitis; or (xi) a fibrotic condition affecting the eye, for example ocular fibrosis following surgery or pseudoexfoliation syndrome glaucoma.

LOX Family, Angiogenesis and Vasculature Permeability

Angiogenesis, the formation of new blood vessels, is essential for tumor growth and progression.

LOX and LOXL2 are key players in promoting angiogenesis in a number of tumour models, such as colorectal (Baker, Bird et al. 2013), ovarian, lung cancer (Zaffryar-Eilot, Marshall et al. 2013), melanoma (Osawa, Ohga et al. 2013), glioblastoma (Mammoto, Jiang et al. 2013). LOX is overexpressed in tumour endothelial cells (Osawa, Ohga et al. 2013). Increased LOX tumour expression is associated with increased VEGF expression (Mammoto, Jiang et al. 2013), (Baker, Bird et al. 2013).

Additionally, LOXL2 inhibition led to the normalisation of vasculature and increased tumour perfusion in ovarian xenograft and lung allograft mice models (Zaffryar-Eilot, Marshall et al. 2013).

Excessive angiogenesis is involved in a number of diseases in addition to cancer discussed above. LOX mediates vascular permeability by modulating the stiffness of the endothelial barrier. Abnormal vascular permeability, such as present in diseases such as pulmonary edema and acute respiratory distress syndrome (ARDS) or endotoxin-induced lung injury can be normalised by LOX inhibition (Mammoto, Mammoto et al. 2013) (Ingber and Mammoto 2014).

Accordingly a compound of the invention or a pharmaceutically acceptable salt thereof may be for use as an anti-angiogenic agent. A compound of the invention or a pharmaceutically acceptable salt thereof may be for use in vascular normalisation.

In one embodiment a compound of the invention or a pharmaceutically acceptable salt thereof may be for use in the treatment is treatment of pulmonary embolism, emphysema, pleural effusion, pulmonary oedema, brain swelling, plural effusion, pericardial effusion and ascites.

In one embodiment a compound of the invention or a pharmaceutically acceptable salt thereof may be for use in the treatment is treatment of ischemia; ischemic stroke, ischemic heart disease, cerebral infarct, peripheral vascular disease, elephantiasis, lymphatic obstruction.

In one embodiment, the treatment is treatment of age-related macular degeneration (AMD), diabetic retinopathy and retinopathy of prematurity.

Inflammatory Disorders

Exacerbated inflammation and lung barrier dysfunction are hallmarks of acute respiratory distress syndrome (ARDS), a condition with dangerously high rates of morbidity and mortality. Increased LOX activity has been associated with bacterial lipopolysaccharide (LPS) induced inflammation. Inhibition of LPS-induced ECM crosslinking and stiffening by LOX suppression reduced EC inflammatory activation and lung dysfunction. Thus LOX inhibitors can be useful for the treatment of ARDS (Mambetsariev, Tian et al. 2014). LOX and LOXL1 reduction and collagen crosslinking reduction have been associated with decreased inflammation in an Angiotensin II induced model of hypertension (Gonzalez, Rhaleb et al. 2014).

In an embodiment there is provided a compound of the invention, or a pharmaceutically acceptable salt thereof may be useful in the treatment of an inflammatory condition. The inflammatory condition may be any of those described herein. For example the compound of the invention, or a pharmaceutically acceptable salt thereof may be for use in the treatment of acute inflammation (e.g., mediated by an acute infection).

In an embodiment the compound of the invention, or a pharmaceutically acceptable salt thereof may be for use in the treatment of chronic inflammatory disease, for example a disease selected from inflammatory bowel diseases (e.g. Crohn's disease and ulcerative colitis), psoriasis, sarcoidosis, rheumatoid arthritis, osteoarthritis, psoriatic arthritis, Reiter's syndrome, traumatic arthritis, rubella arthritis, acute synovitis, gouty arthritis and spondylitis.

In an embodiment the compound of the invention, or a pharmaceutically acceptable salt thereof may be for use in the treatment of rheumatoid arthritis; osteoarthritis; psoriatic arthritis; Reiter's syndrome; traumatic arthritis; rubella arthritis; acute synovitis; gouty arthritis; or spondylitis; diabetes or gout.

In an embodiment the compound of the invention, or a pharmaceutically acceptable salt thereof may be for use in the treatment of psoriasis; eczema; sarcoidosis, allergic rhinitis; allergic conjunctivitis; asthma, acute respiratory distress syndrome, acute lung injury (ALI), acute respiratory distress syndrome (ARDS), endotoxin-induced lung injury, pulmonary inflammation, chronic obstructive pulmonary disease and systemic cachexia.

In an embodiment the compound of the invention, or a pharmaceutically acceptable salt thereof may be for use in the treatment of rheumatoid arthritis, osteoarthritis, psoriatic arthritis, Reiter's syndrome, traumatic arthritis, rubella arthritis, acute synovitis, gouty arthritis or spondylitis, diabetes or gout.

In an embodiment the compound of the invention, or a pharmaceutically acceptable salt thereof may be for use in the treatment of endotoxemia; toxic shock syndrome, inflammatory bowel disease, atherosclerosis, irritable bowel syndrome, Crohn's disease, ulcerative colitis, a bone resorption disease, osteoporosis, diabetes, reperfusion injury, graft versus host reaction, allograft rejection, sepsis, septic shock, endotoxic shock, Gram negative sepsis, glomerulonephritis, restenosis, vasculitis, or thrombosis.

In another embodiment the compound of the invention, or a pharmaceutically acceptable salt thereof may be for use in the treatment of polymyositis, systemic lupus or interstitial nephritis.

Cardiovascular Disease

Interrupting collagen crosslinking by LOX with BAPN treatment reduces myocardial fibrosis in a mouse model, which is useful as potential therapeutic targeting of collagen regulation and thereby age-related myocardial fibrosis (Rosin, Sopel et al. 2015). Increased expression of LOX is associated with myocardial fibrosis and cardiac dysfunction (Zibadi, Vazquez et al. 2010) (Gao, Xiao et al. 2010) (Lopez, Gonzalez et al. 2010). Left atrial myocardium of patients with atrial fibrillation express higher levels of lysyl oxidase and fibronectin expression as well as collagen crosslinking. Fibronectin upregulation is mediated by LOX in cardiac fibroblasts (Adam, Theobald et al. 2011). LOX inhibitors can be useful for the prevention of fibrotic atrial remodelling.

Lysyl oxidases play a causal role in experimental pulmonary hypertension and inhibition with BAPN reduces the symptoms (Nave, Mizikova et al. 2014). LOX facilitate the formation of crosslinked and therefore insoluble collagen and the subsequent left ventricle stiffness and systolic dysfunction in patients with hypertensive heart disease (HHD) and heart failure (HF) of hypertensive origin (Lopez, Gonzalez et al. 2013) (Lopez, Querejeta et al. 2012). A role for LOXL1 has been suggested in cardiac hypertrophy and BAPN administration inhibits angiotensin II-induced cardiac hypertrophy in vivo (Ohmura, Yasukawa et al. 2012).

Lysyl oxidase inhibition has been proposed as a therapeutic method for decreasing or preventing recurrent restenosis (Nuthakki, Fleser et al. 2004) (Brasselet, Durand et al. 2005). Increased LOX activity has been observed in atherosclerosis (Kagan, Raghavan et al. 1981).

Accordingly in an embodiment compound of the invention, or a pharmaceutically acceptable salt thereof may be for use in the treatment of a cardiovascular disease, for example any one of the diseases mentioned in this section, e.g. the treatment of atherosclerosis, myocardial fibrosis, prevention of fibrotic atrial remodelling, old myocardial infarction; congestive heart failure, cardiomyopathy, hypertensive heart disease (HHD), hypertension (for example pulmonary hypertension) and fibrosis associated with hypertension, restenosis (e.g. coronary, carotid, and cerebral lesions), and heart disease associated with cardiac ischemic events.

Neurological Conditions

As discussed in the Background to the Invention, LOX is associated with neurological conditions including Alzheimer's disease and other neurological conditions. Accordingly, in one embodiment there is provided a compound of the invention, or a pharmaceutically acceptable salt thereof may be for use in the treatment of a neurological condition mediated by LOX or LOXL. The neurological condition may be Alzheimer's disease (AD) and hereditary cerebral hemorrhage with amyloidosis of the Dutch type (HCHWA-D) or non-Alzheimer's dementia.

LOX is increased at the site of brain injury (Gilad, Kagan et al. 2001) and spinal cord injury and its inhibition lead to accelerated functional recovery in a unilateral spinal cord dissection model (Gilad and Gilad 2001). Accordingly a compound of the invention, or a pharmaceutically acceptable salt thereof may be for use in the treatment nerve damage, for example the promotion of nerve regrowth and/or recovery after spinal cord injury.

Pulmonary Diseases

LOXL2 and LOXL3 are likely to have a role in Primary Alveolar Proteinosis (PAP) since both are expressed in PAP tissue, but not normal lung tissue (Neufeld and Brekhman 2009). Excessive lysyl oxidase activity was linked to the pathologic pulmonary features of bronchopulmonary dysplasia (Kumarasamy, Schmitt et al. 2009). A compound of the invention, or a pharmaceutically acceptable salt thereof may be for use in the treatment of primary alveolar proteinosis (PAP) or bronchopulmonary dysplasia.

Eye Diseases

Increased LOXL2 levels have been associated with failure following glaucoma surgery and treatment with a LOXL2 antibody reduced pathological angiogenesis, inflammation, and ocular fibrosis (Park, Kim et al. 2014) (Van Bergen, Marshall et al. 2013) (Stalmans, Van Bergen et al. 2011). Expression of lysyl oxidase-type enzymes increases following laser-induced choroidal neovascularization (CNV) in a model of age-related macular degeneration (AMD), in parallel with fibrotic damage. Inhibition of LOX or LOXL2 prevents neovascularization and fibrosis following laser-induced CNV. Therefore LOX and LOXL inhibitors can be useful in the treatment of conditions characterized by neovascularization, such as age-related macular degeneration (AMD), diabetic retinopathy and retinopathy of prematurity (Stalmans, Marshall et al. 2010). LOXL1 expression is increased in the initial stages of abnormal fibrogenesis in pseudoexfoliation syndrome/glaucoma tissues (Zenkel, Krysta et al. 2011) (Schlotzer-Schrehardt, Pasutto et al. 2008).

A compound of the invention, or a pharmaceutically acceptable salt thereof may be for use in the treatment of an ocular condition mediated by LOX or a LOXL, for example any of the ocular conditions listed in the paragraph above.

Other Diseases

LOX is the main isoenzyme expressed in human adipose tissue and that its expression is strongly upregulated in samples from obese patients. β-aminopropionitrile reduces body weight gain and improves the metabolic profile in diet-induced obesity in rats (Miana, Galan et al. 2015) and reduces local adipose tissue inflammation (Halberg, Khan et al. 2009). In an embodiment a compound of the invention, or a pharmaceutically acceptable salt thereof may be for use in the treatment of obesity.

LOX has been suggested as a new therapeutic target in bacterial infections and subsequent fibrotic complications. LOX is upregulated in infections with *Staphylococcus Aureus* and inhibition with BAPN influences resulting abscesses morphology and collagenisation (Beerlage, Greb et al. 2013). LOX is implicated also in some parasitic diseases: LOX and LOXLs are upregulated in the early stages of liver granuloma development in schistosomiasis (Decitre, Gleyzal et al. 1998), and BAPN inhibition reduces the size of the granulomas and reduces the egg load in combination with antiparasitic drug PZQ compared to PZQ alone (Giboda, Zenka et al. 1992), In one embodiment, the compound is for use in the treatment of a bacterial infection, for example infection with *Staphylococcus Aureus*. The compound of the invention may be for use in the treatment or prevention of infection associated fibrosis, for example to prevent or inhibit abcess formation associated with the infection. The formation of abcesses can provide a favourable microenvironment for the bacteria to multiply. Inhibition of abcess formation may be beneficial in that it may provide enhanced exposure of the bacertia to antibiotics at the site of infection, because the shielding effect provided by the abcess would be reduced or eliminated. Thus combination treatments comprising a compound of the invention together with an antibiotic agent may provide an enhanced antibacterial effect. The compound of the invention may also be for use in the prevention or inhibition of tissue fibrosis following eradication of the infection and healing of the infection sites.

In one embodiment, the compound is for use in the treatment of a parasitic infection, for example schistosomiasis.

EGFR Mediated Conditions

Elevated levels of the epidermal growth factor receptor (EGFR), a growth-factor-receptor tyrosine kinase, and/or its ligands is observed in many cancer types and is involved in the promotion of tumour growth. EGFR inhibitors have been directed to a number of cancer types, including NSCLC, pancreatic cancer, squamous cells carcinoma, skin cancer, thyroid, colorectal, prostate, gastric, renal, breast, head & neck cancers, glioma, meningiomas, mesothelioma, cervical carcinomas epidermal carcinomas (reviewed in Bianco et al (Bianco, Gelardi et al. 2007)). Elevated EGFR was found to act as a strong indicator of poor prognosis in head and neck, ovarian, cervical, bladder and oesophageal cancers (Nicholson, Gee et al. 2001). EGFR inhibitors have also been proposed for the treatment of metastatic prostate cancer (Ree, Bratland et al. 2008), biliary cancer such as cholangiocarcinoma with a mutation in ERRF11 (Borad, Carpten et al. 2014).

Blockade of the kinase activity of EGFR does not reach maximum therapeutic efficacy. The inventors have demonstrated that LOX inhibitors reduce the level of surface EGFR suggesting the possibility that these compounds will have an effect on reducing EGFR activation.

EGFR inhibition has been targeted as treatment for a number of other diseases, such as prevention and treatment of obesity (Threadgill and Barrick 2007), treatment of Alzheimer's disease (Ma 2013), treatment of Chlamydia infection and related diseases (Tsang and Furdui 2015), treatment of viral diseases (Jung 2010), promotion of axon regeneration (He and Koprivica 2007), treatment of genetic skin disorders characterized by hyperkeratosis, keratinocyte hyperplasia, and/or ichthyosis (Alexandrescu 2009).

Given the role of LOX inhibition in modulating the surface EGFR levels and EGFR signalling, LOX inhibitors could be useful in the treatment of diseases which can be targeted by EGFR inhibition.

In an embodiment there is provided a compound of the invention, or a pharmaceutically acceptable salt thereof may be for use in the treatment of a disorder (e.g., a disease) that is ameliorated by the inhibition of EGFR. The EGFR mediated condition may be, for example, any of those listed in this section or elsewhere in the description. The compound of the invention, or a pharmaceutically acceptable salt thereof may be for use in the treatment of a cancer which over-expresses EGFR. The cancer over-expressing EGFR may be, for example NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers or a biliary cancer such as cholangiocarcinoma.

In one embodiment, the compound is for use in the treatment of a viral infection, for example Rhinovirus, influenza virus, parainfluenza virus, coronavirus, adenovirus, respiratory syncytial virus, picornavirus, metapneumovirus, hantavirus, measles virus, Epstein-Barr virus, herpes simplex virus or cytomegalovirus.

In one embodiment, the compound is for use in the treatment of *Chlamydia* infection.

In one embodiment, the compound is for use in the treatment of a genetic skin disorder, for example a keratinization disorder is selected from among Darier's disease, Hailey-Hailey disease, erythrodermic autosomal recessive lamellar ichthyosis, nonerythrodermic autosomal recessive lamellar ichthyosis, autosomal dominant lamellar ichthyosis, bullous congenital ichthyosiform erythroderma, palmoplantar keratoderma, erythrokeratodermia variabilis, verrucous epidermal nevi, pityriasis rubra pilaris, Netherton syndrome, idiopathic vulgaris, ichthyosis vulgaris, monilethrix, keratosis piliaris, bullous ichthyosiform erythroderma, nonbullous congenital ichthyosis, Sjogren-Larsson syndrome, erythrokeratodermica variabilis, hyperkeratosis lenticularis perstans, eythrokeratodermia figurate variabilis, mutilating keratoderma of Vohwinkel, Harlequin ichthyosis and Tay's syndrome.

LOX and EGFR

In one aspect, the present invention relates to a lysyl oxidase inhibitor for use in the treatment or prevention of a cancer associated with overexpression of EGFR.

In another aspect, the present invention relates to the use of a lysyl oxidase inhibitor in the manufacture of a medicament for the treatment or prevention of a cancer associated with overexpression of EGFR.

Suitably, in all aspects, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects, the lysyl oxidase inhibitor may be a compound of the present invention or a pharmaceutical composition of the present invention.

Suitably, in all aspects of the invention, the lysyl oxidase inhibitor may downregulate expression of MATN2 and/or activate SMAD2. Suitably, the lysyl oxidase inhibitor may downregulate expression of HTRA1. Optionally, in all aspects of the invention, the lysyl inhibitor may inhibit maturation of lysyl oxidase and/or inhibit the catalytic activity of lysyl oxidase. Suitably, the lysyl oxidase inhibitor may not inhibit MAO-A and/or MAO-B.

In a further aspect, the present invention relates to a method of treating or preventing cancer in a subject, said method comprising administering a therapeutically effective amount of a lysyl oxidase inhibitor to said subject, wherein said subject has a cancer associated with overexpression of EGFR.

Optionally, the method may comprise determining the level EGFR in a biological sample of said subject, and administering a lysyl oxidase inhibitor to said subject when the presence of EGFR is determined to be overexpressed in the biological sample.

Optionally, the method may further comprise the steps of determining the level of MATN2, pSMAD2 or HTRA1 or combinations thereof in a biological sample of said subject, and administering a lysyl oxidase inhibitor to said subject when:

a) the level of MATN2 is greater than a reference sample; and/or b) the level of pSMAD2 is lower than a reference sample; and/or c) the level of HTRA1 is greater than a reference sample.

Optionally, said subject may have a cancer selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, in all aspects of the invention, the lysyl oxidase inhibitor may downregulate expression of MATN2 or HTRA1 and/or activate SMAD2. Optionally, in all aspects of the invention, the lysyl inhibitor may inhibit maturation of lysyl oxidase and/or inhibit the catalytic activity of lysyl oxidase. Suitably, the lysyl oxidase inhibitor may not inhibit MAO-A and/or MAO-B.

In a further aspect, the present invention relates to the use of EGFR and/or MATN2 as a biomarker to predict responsiveness or sensitivity of a patient suffering from cancer to treatment with a lysyl oxidase inhibitor. Optionally, one or more further biomarkers may be used such as pSMAD2 and/or HTRA1.

In another aspect, the present invention relates to a method of increasing the sensitivity rate (efficacy rate) of a lysyl oxidase inhibitor to treat cancer in a patient population said method comprising selecting a sub population which overexpresses an EGFR and/or MATN2 and/or HTRA1 biomarker. Optionally, said subgroup may underexpress pSMAD2.

In a further aspect, the present invention relates to a method of identifying a subject having increased likelihood of responsiveness or sensitivity to a lysyl oxidase inhibitor comprising:
  a) determining the level of one or more of EGFR, MATN2, and HTRA1 in a biological sample of the subject;
wherein increased levels EGFR, MATN2, HTRA1 or a combination thereof compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor comprising:
  a) determining the level of one or more of EGFR, MATN2, and HTRA1 in a biological sample of the subject;
wherein increased levels one or more of EGFR, MATN2, and HTRA1 compared to a reference sample identifies the subject as having responsiveness or sensitivity to a lysyl oxidase inhibitor.

Optionally, in all methods of the invention, the methods may comprise a further step of administering a therapeutically effective amount of a lysyl oxidase inhibitor when the subject is identified as having increased likelihood of responsiveness of sensitivity to a lysyl oxidase inhibitor.

In a further aspect, the present invention relates to a method of determining a treatment regimen for a subject with cancer, comprising:
  a) determining the level one or more of EGFR, MATN2, and HTRA1 in a biological sample; and
  b) administering a treatment regimen comprising a therapeutically effective amount of a lysyl oxidase inhibitor, when levels one or more of EGFR, MATN2, and HTRA1 are elevated compared to a reference sample.

Biomarkers

The present invention therefore provides the possibility of a clinical test to predict response to LOX inhibition therapy, preferably prior to a subject commencing LOX inhibition therapy. Such a test will inform the clinician whether the patient is likely to respond to LOX inhibition therapy or not, and enable the clinician to commence alternative therapy if the patient is predicted to be unlikely to respond. This will benefit the patient by targeting their treatment with an appropriate therapy early, rather than relying on the current "trial and error" approach. Such a test will therefore enable better of targeting of LOX inhibition therapy to patients early in their disease, when maximum effect can be achieved, and may result in greater access to these drugs as they are used in a more cost-efficient manner.

The present invention is advantageous in enabling likely responders and non-responders to be identified, so that non-responders may be provided alternative treatment, and those who are not non-responders (and therefore may be a moderate or good responder) may be provided LOX inhibition therapy. As a result of the present invention, LOX inhibition therapies may therefore be used in a more targeted and cost-efficient manner.

For the purposes of the biomarker and stratification aspects disclosed herein a "LOX inhibitor" is an agent which is able to reduce the expression, reduce the catalytic activity or prevent maturation of LOX.

Any suitable source of lysyl oxidase may be employed for the determination of LOX inhibition. The enzyme can be derived, isolated, or recombinantly produced from any source known in the art, including yeast, microbial, and mammalian, that will permit the generation of a suitable product that can generate a detectable reagent or will be biologically active in a suitable assay. In one embodiment, the lysyl oxidase is of human, bovine, or other mammalian origin. See, e.g., Williams, et al., Anal. Biochem. 113:336 (1985); Kirschmann et al., supra; Cancer Res. 62:4478-83 (2002); LOX may be obtained from Accession No. NP00238 (preprotein sequence); Accession No. NM02317 (DNA sequence). A functional fragment or a derivative of lysyl oxidase that still substantially retains its enzymatic activity catalyzing the oxidation of lysyl oxidase can also be used. The lysyl oxidase enzyme can sometimes be the pre-pro-protein, proprotein, the protein, or a biologically active fragment thereof.

The enzymatic activity of lysyl oxidase can be assessed by any suitable method. Exemplary methods of assessing lysyl oxidase activity include that of Trackman et al., Anal. Biochem. 113:336-342 (1981); Kagan, et al., Methods Enzymol. 82A:637-49 (1982); Palamakumbura et al., Anal. Biochem. 300:245-51 (2002); Albini et al., Cancer Res. 47: 3239-45 (1987); Kamath et al, Cancer Res. 61:5933-40 (2001); for example.

The enzymatic activity of the lysyl oxidase may be assessed by detecting and/or quantitating "lysyl oxidase byproducts," such as $H_2O_2$ production; collagen pyridinium residues ammonium production; aldehyde product production; lysyl oxidation, or deoxypyridinoline (Dpd). One may also detect and quantitate cellular invasive capacity in vitro; cellular adhesion and growth in vitro; and metastatic growth in vivo. In vivo models include, but are not limited to suitable syngeneic models, human tumor xenograft models, orthotopic models, metastatic models, transgenic models, and gene knockout models. See, e.g., Teicher, Tumors Models in Cancer Research (Humana Press 2001). uration of LOX.

A compound is an inhibitor of lysyl oxidase expression or biological activity when the compound reduces the expression or activity or lysyl oxidase relative to that observed in the absence of the compound. In one embodiment, a compound is an inhibitor of lysyl oxidase when the compound reduces the incidence of metastasis relative to the observed in the absence of the compound and, in further testing, inhibits metastatic tumor growth.

The tumor inhibition can be quantified using any convenient method of measurement. For example, the incidence of metastasis can be assessed by examining relative dissemination (e.g., number of organ systems involved) and relative tumor burden in these sites. Metastatic growth can be ascertained by microscopic or macroscopic analysis, as appropriate. Tumor metastasis can be reduced by about 10%, 20%, 30%, 40%, 50%, 60%, 70%, 80%, 90%, 95% or greater.

In one embodiment, lysyl oxidase expression is assessed using promoter analysis. Any convenient system for promoter activity analysis can be employed. Typically, the reporter gene system allows promoter activity to be detected using the lysyl oxidase promoter attached to a reporter molecule such that promoter activity results in the expression of the reporter molecule. See, e.g., Ausubel et al., Current Protocols in Molecular Biology (John Wiley & Sons, current edition) at chapter 9.6.

Also, LOX may be inhibited by degradation of its mRNA. An approach to this form of gene regulation is described in Wilson et al. "Modulation of LDL receptor mRNA stability by phorbol esters in human liver cell culture models," Lipid Res. 38, 437-446 (1997).

Exemplary compounds useful in the present invention include, but are not limited to the compounds such as β-aminoproprionitrile (BAPN), as well as the lysyl oxidase inhibitor compounds of the present invention.

Such LOX inhibitors may be used in the LOX inhibition therapy described herein.

The present invention provides an improved method for prediction of response to anti-LOX inhibition therapy, using biomarkers which could not have been predicted from the prior art as being indicative of a favourable response.

Throughout this section, the terms patient and subject are used interchangeably herein to refer to an individual for whom it is desirable to determine likely response to LOX inhibition therapy. Such an individual may have, or be predisposed to having, or expected to develop, cancer.

A biomarker as used herein is a biologically derived indicator of a process, event, or condition. Biomarkers can be used in methods of diagnosis, e.g. clinical screening, and prognosis assessment and in monitoring the results of therapy, identifying patients most likely to respond to a particular therapeutic treatment, drug screening and development. A biomarker may be a gene, exhibiting differential expression between responders and non-responders to LOX inhibition therapy. Expression of a biomarker gene (transcription and optionally translation) may be determined by measuring an expression product of the gene, referred to herein as a target molecule. A combination of two or more biomarkers may be referred to herein as a panel or a genetic signature which correlates with likely response to LOX inhibition therapy.

Predicting response means making a determination of the likely effect of treatment in a subject. Prediction typically means an assessment made prior to commencing the relevant treatment, although it is understood that a prediction of the likely response to a particular treatment may be made whilst a subject is receiving an alternative treatment. Predicting response to therapy, within the scope of the present invention may also include making an assessment of likely continued response to LOX inhibition therapy. Therefore, prediction of response may include a determination of likely response during a course of LOX inhibition therapy.

A sample may be selected from the group comprising tissue sample, such as a biopsy sample; and a body fluid sample. A body fluid sample may be a blood sample. A blood sample may be a peripheral blood sample. It may be a whole blood sample, or cellular extract thereof. In one embodiment, preferably the sample is a tissue sample.

The level of a target molecule herein refers to a measure of the amount of a target molecule in a sample. The level may be based upon a measure of one type of target molecule indicative of expression specific for a particular biomarker (i.e. DNA, RNA or protein). The level may alternatively be based upon a measure of a combination of two or more types of target molecule indicative of expression specific for a particular biomarker (i.e. two or more of DNA, RNA and protein). The level of a target molecule may be expressed as a direct measure of the amount of target molecule (for example concentration (mg/vol sample) or RPKM).

Elevated level means an increase in level (i.e. amount) of a target molecule compared to the level of the same target molecule in a subject who does not have cancer. An elevated level includes any statistically significant increase compared to the control. The level of a target molecule indicative of expression of a biomarker in a subject which does not have cancer or a disease associated with overexpression of EGFR may be referred to as a reference value or baseline value.

The elevated level of the target molecule representative of gene expression may be assessed by comparing the amount of the target molecule present in the patient sample under investigation with a reference value indicative of the amount of the target molecule in a control sample.

References herein to the "same" level of target molecule or biomarker expression indicate that the biomarker expression of the sample is identical to the reference or baseline value. References herein to a "similar" level of target molecule or biomarker expression indicate that the biomarker expression of the sample is not identical to the reference or baseline value but the difference between them is not statistically significant i.e. the levels have comparable quantities.

Suitable control samples for determination of a reference value or baseline value may be derived from individuals without a disease associated with overexpression of EGFR and without cancer. A control sample may be age matched with the patient undergoing investigation. Reference values or baseline value may be obtained from suitable individuals and used as a general reference value for multiple analysis.

Favourable response to LOX inhibition therapy may include, without limitation, treatment or prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms. Thus, favourable response to LOX inhibition therapy includes delay or reduction of proliferation of tumour growth and/or delay of metastasis.

Target molecules as used herein may be selected from the group consisting of: a biomarker protein; and nucleic acid encoding the biomarker protein. The nucleic acid may be DNA or RNA. In an embodiment the nucleic acid is mRNA. Reference herein to a target molecule may include one type of biological molecule (i.e. DNA or RNA or protein) or a combination of two or more types of such biological molecules, all indicative of the expression of the same biomarker.

A binding partner may be selected from the group comprising: complementary nucleic acids; aptamers; receptors, antibodies or antibody fragments. By a specific binding partner is meant a binding partner capable of binding to at least one such target molecule in a manner that can be distinguished from non-specific binding to molecules that are not target molecules. A suitable distinction may, for example, be based on distinguishable differences in the magnitude of such binding.

The first aspect of the present invention may make use of one or more target molecules, each target molecule being indicative of the expression of a different biomarker selected from the group consisting of: EGFR, MATN2, HTRA1 and pSMAD2. The first aspect of the invention may make use of two or more or three or more, target molecules, each being indicative of the expression of a different biomarker selected from the group consisting of: EGFR, MATN2, HTRA1 and pSMAD2.

In an embodiment, the present invention may make use of a target molecule indicative of the expression of EGFR.

In an embodiment, the present invention may make use of a target molecule indicative of the expression of MATN2.

In an embodiment, the present invention may make use of two or more target molecules or three or more biomarkers, each being indicative of the expression of a different biomarker. For example, wherein the biomarkers are EGFR and MATN2; MATN2 and pSMAD2 or EGFR and pSMAD2.

Therefore, the present invention identifies an expression signature which identifies subjects who are unlikely to respond or are likely to respond to LOX inhibition therapy. In an embodiment, the signature is characterized by an up regulation of MATN2, an upregulation of EGFR, an upregulation of homotrimeric HTRA1, a down regulation of pSMAD2 or a combination thereof.

A method of increasing the sensitivity (efficacy) rate, or identifying increased likelihood of response to LOX inhibitors in accordance with the present invention will preferably be carried out in vitro, but it will be appreciated that a method of the invention may also be carried out in vivo.

A level of a target molecule may be investigated using a binding partner for the target molecule. A binding partner may be specific for a target molecule. In the context of the present invention, a binding partner specific to a target molecule will be capable of binding to at least one such target molecule in a manner that can be distinguished from non-specific binding to molecules that are not target molecules. A suitable distinction may, for example, be based on distinguishable differences in the magnitude of such binding.

Reference to a protein target may include precursors or variants produced on translation of the transcripts produced when the gene is expressed. Therefore, where a protein undergoes modification between first translation and its mature form, the precursor and/or the mature protein may be used as suitable target molecules. As above, techniques by which protein target molecules may be preserved within a patient sample, thus facilitating its detection, will be well known to those skilled in the art. A protein target may be found within a cell of a patient sample, or may be secreted or released from the cell.

In embodiments of the present invention where the target molecule is a protein, a binding partner may be used to determine the level of the protein in a sample obtained from the subject. A suitable binding partner may be is selected from the group consisting of: aptamers; receptors, and antibodies or antibody fragments. Suitable methods for determining the level of a protein in a sample are available in the art. For example, in certain embodiments of the methods or devices of the invention the binding partner is an antibody, or antibody fragment, and the detection of the target molecules utilises an immunological method. In certain embodiments of the methods or devices, the immunological method may be an enzyme-linked immunosorbent assay (ELISA) including variants such as sandwich ELISAs; radioimmuno assays (RIA). In other embodiments an immunological method may utilise a lateral flow device. Other suitable techniques may include multiplex assays such as Luminex or proteomic MRM or fluorescence activated cell sorting (FACS); chemiluminescence.

In certain embodiments, a binding partner may be labelled, for example using a reporter moiety such as a fluorophore, chromogenic substrate or chromogenic enzyme. Where it is desired that the invention will make use of reporter moieties, the reporter moieties may be directly attached to the binding partners. Examples of such embodiments include those utilising labelled antibodies. Alternatively, the reporter moieties may be attached to reporter molecules that interact with the binding partners. Examples of such embodiments include those utilising antibodies indirectly attached to a reporter moiety by means of biotin/avidin complex.

In embodiments where the target molecule is a nucleic acid, binding partners may be complementary nucleic acids and aptamers, for example provided in a microarray or chip. Methods for determining the level of a nucleic acid target molecule in a sample are available in the art. In an embodiment, a suitable target molecule representative of gene expression may comprise an RNA transcript translatable to yield a protein. mRNA of this sort will typically be found within a patient sample. In particular, the transcriptome of white blood cells, for example neutrophils, of a patient sample have been found to provide a biomarker signature with improved sensitivity and specificity for determining non-responders and/or good responders to anti-TNF therapy, and the use of mRNA and in particular the transcriptome may represent a preferred embodiment. Use of mRNA as the target molecule has advantages in that the assays for detecting mRNA (such as quantitative rtPCR or the like) tend to be cheaper than methods for detecting protein (such as ELISAs). mRNA assays can be more readily multiplexed, allowing for high throughput analysis; nucleic acids generally show greater stability than their protein counterparts; and processing of the sample to obtain and amplify nucleic acid is generally simpler than for protein.

Techniques by which mRNA may be collected, purified and amplified as necessary, are well known to those skilled in the art. In an embodiment, the present invention may make use of transcriptome analysis for determining biomarker expression. Suitable techniques for determining the level of RNA in a sample, for example by transcriptome analysis, may include hybridization techniques, for example by detecting binding to a nucleic acid library, quantitative PCR, and high throughput sequencing including tag based sequencing such as SAGE (serial analysis of gene expression) and RNA-seq.

The above examples are non-limiting, and the methods of the invention may make use of any appropriate assay by which the presence or elevated levels of a requisite target molecule may be detected. It will be appreciated that suitable assays may be determined with reference to the nature of the target molecule to be detected and/or the nature of the patient sample to be used.

Multiple samples may be processed simultaneously, sequentially or separately. Multiple samples may be processed simultaneously, for example in a high throughput method.

Suitably, the present invention may also provide kits for carrying out the stratification or biomarker methods disclosed herein. Such kits may contain compounds by which the presence or elevated levels of a requisite target molecule may be detected, such as antibodies to one or more biomarkers of the present invention. Optionally, the kit may further comprise one or more of a set of instructions for use, a chart providing reference or baseline values for at least the biomarker to de detected using the kits; and reagents.

Once the amounts or concentrations of the target molecules in the patient sample have been determined, this information may be used as the basis of an assessment of the predicted response to LOX inhibition therapy, which may, in turn, be used to suggest a suitable course of treatment for the patient. The assessment may be qualitative or quantitative.

An elevated level of a biomarker may include at least 10%, 15, 20, 30, 40 50, 60, 70, 80, 90 or 100% or more increase compared to the baseline or reference value level. In one embodiment, an elevated level may be 1 fold or more difference relative to the baseline or reference value, such as a fold difference of 1.5, 2.0, 2.5, 3.0, 3.5, 4.0, 4.5, 5.0, 5.5, 6.0, 6.5, 7.0, 7.5, 8.0, 8.5, 9.0, 9.5, 10, 10.5, 11, 11.5, 12, 12.5, 15 or 20 or any ranges there between. In one embodiment, the higher level is between a 1 and 15 fold difference relative to the baseline level, such as between a 1.5 and 12 fold difference relative to the baseline level. In a further embodiment, the higher level is between a 1 and 7 fold difference relative to the baseline level. It is appreciated that elevation levels may differ from the same biomarker depending on the target molecule being used. Where nucleic acid and protein target molecules are used for any particular biomarker, an elevated level may be expressed individually for a target molecule, or may be expressed as a sum or average of the target molecules.

The invention may produce a quantitative output, based upon elevation values for a biomarker or a sum or biomarkers. Alternatively, the invention may provide a qualitative output, based on likely response, for example yes/no; elevated; non-elevated; responder/non-responder; good, moderate or low based on EULAR criteria, etc. Where the levels of two or more target molecules are determined, a composite score may be determined, which may be compared to a composite score of reference values for the same target molecules.

In certain embodiments the methods or devices of the invention may further involve investigating physiological measurements of the patient.

In a further embodiment, there is provided a method for treating a subject having cancer, wherein it was previously determined (or previously estimated) that the cancer is associated with overexpression of EGFR compared to a reference value, the method comprising administering an therapeutically effective amount of a LOX Inhibitor to the subject.

In a further embodiment, there is provided a method for treating a subject having cancer, wherein it was previously determined (or previously estimated) that a target molecule indicative of expression of MATN2 is increased in a sample from the subject compared to a reference value, the method comprising administering an therapeutically effective amount of a LOX Inhibitor to the subject.

In a further embodiment, there is provided a method for treating a subject having cancer, wherein it was previously determined (or previously estimated) that a target molecule indicative of expression of homotrimeric HTRA1 is increased in a sample from the subject compared to a reference value, the method comprising administering an therapeutically effective amount of a LOX Inhibitor to the subject.

In a further embodiment, there is provided a method for treating a subject having cancer, wherein it was previously determined (or previously estimated) that a target molecule indicative of expression of pSMAD2 is decreased in a sample from the subject compared to a reference value, the method comprising administering an therapeutically effective amount of a LOX Inhibitor to the subject.

The present invention may further provide a method of selecting a treatment regimen for a subject, comprising assaying a sample obtained from the subject, wherein the method comprises predicting whether the subject will be a responder or non-responder to LOX inhibition therapy according to any one of the first, second or third aspects of the present invention, wherein an elevated level of a target molecule according to the first aspect indicates that the subject will benefit from an alternative treatment to LOX inhibition therapy; wherein an elevated level of a target molecule according to the second aspect indicates that the subject will benefit from LOX inhibition therapy.

In a further aspect, the present invention provides kits for use in the methods described herein. Such kits may comprise binding partners capable of specifically binding to a target molecule (e.g. to EGFR, pSMAD2, MATN2, HTRA1 or combinations thereof). In the case of a protein target molecule, such binding partners may comprise antibodies that bind specifically to the protein. Thus, the kits of the present invention may comprise anti-pSMAD2, anti-EGFR, anti-MATN2, anti-HTRA1 or combinations thereof. In the case of a nucleic acid target molecule the binding partner may comprise a nucleic acid complementary to the target molecule. In the case of a protein target molecule the kit may comprise antibody or antibody fragments specific for the target molecule. The kit may also comprise a set of instruction for use of the kit, and reference values for a control sample, in order to determine any elevation in target molecule in the sample.

It is envisaged that the embodiments of the aspects of the present invention apply to the other aspects of the invention, mutatis mutandis.

EGFR

Epidermal Growth Factor Receptor (EGFR, HER1 in humans) is a member of the ErbB family of receptors. EGFR is a cell-surface receptor which is activated by binding of specific ligands such as epidermal growth factor (EGF) and transforming growth factor α (TGFα).

The present inventors have surprisingly shown that lysyl oxidase (LOX) increases EGFR signalling to drive tumour cell growth and metastasis. Without wishing to be bound by theory, LOX inhibitors can disrupt EGFR membrane localisation, block EGFR signalling and, thereby, suppress tumour growth in cancers associated with overexpression of EGFR. As such, LOX inhibitors will have particular utility in the treatment of cancers associated with overexpression of EGFR.

Thus, EGFR may be used as a stratification marker to determine subpopulations which are more likely to respond to treatment with a LOX inhibitor.

In one aspect, the present invention relates to a lysyl oxidase inhibitor for use in the treatment or prevention of a cancer associated with overexpression of EGFR.

In another aspect, the present invention relates to the use of a lysyl oxidase inhibitor in the manufacture of a medicament for the treatment or prevention of a cancer associated with overexpression of EGFR.

In a further aspect, the present invention relates to a method of treating or preventing cancer in a subject, said method comprising administering a therapeutically effective amount of a lysyl oxidase inhibitor to said subject, wherein said subject has a cancer or has a predisposition for a cancer associated with overexpression of EGFR.

Optionally, the method may comprise determining the level EGFR in a biological sample of said subject, and administering a lysyl oxidase inhibitor to said subject when the presence of EGFR is determined to be overexpressed in the biological sample.

By "EGFR overexpression" it is meant the presence of increased copies of the EGFR gene or increased EPGR protein (preferably at the surface) in or on a cancer cell compared to a non-cancerous cell of the same tissue type. Thus, in one embodiment overexpression may be defined as at least a two-fold amplification of the EGFR gene, as determined by fluorescent in-situ hybridization (FISH), or as a positive staining using anti-EGFR antibodies in an immunohistochemistry (IHC) assay. In addition or in the alternative, overexpression may be measured by the fraction of cell membrane labelled with a specific antibody; thus overexpression of EGFR may be defined as at least 1% or at least 2% or at least 3% membranous staining and 1+(or 2+ or 3+) intensity, or at least 10% membranous staining. Furthermore, cells may be classified as cells that do not express, or have undetectable levels of EGFR, cells expressing low levels of EGFR (about 1000 to about 100,00 receptors/cell), medium levels of EGFR (about 10,000 to about 100,000 receptors/cell) and cells expressing high levels of EGFR (about $1 \times 10^6$ or more receptors/cell). Therefore, the cancer susceptible to treatment using a LOX inhibitor of the present invention are cancers characterized by two-fold or greater amplification of the EGFR gene, positive (1+, 2+, or 3+) IHC assay, at least 1%, or at least 10% membranous staining, medium or high levels of EGFR and preferably cancer cells characterized by high levels of EGFR. Suitably, overexpression may be determined using anti-EGFR antibodies (preferably anti-HER1) in an immunohistochemistry (IHC) assay.

Optionally, the method may further comprise the steps of determining the level of MATN2, pSMAD2 or both MATN2 and pSMAD2 in a biological sample of said subject, and administering a lysyl oxidase inhibitor to said subject when:
a) the level of MATN2 is greater than a reference sample;
b) the level of pSMAD2 is lower than a reference sample; or
c) the level of MATN2 is greater than a reference sample and the level of pSMAD2 is lower than a reference sample.

Suitably, the cancer may be selected from the group consisting of: NSCLC, pancreatic cancer, squamous cells carcinoma, skin cancer, thyroid, colorectal, prostate, renal, breast, head & neck cancers, glioma, mesothelioma, epidermal carcinomas ovarian, cervical, bladder and oesophageal cancers and a biliary cancer such as cholangiocarcinoma.

Suitably, the LOX inhibitor may be a LOX inhibitor of the present invention.

Optionally, in all aspects of the invention, the lysyl oxidase inhibitor may inhibit maturation of lysyl oxidase and/or inhibit the catalytic activity of lysyl oxidase. Suitably, the lysyl oxidase inhibitor may not inhibit MAO-A and/or MAO-B. Suitably, inhibition of MAO-A and/or MAO-B may be determined using the in vitro oxidase -A/-B activity assay as described in the Examples. Suitably, the lysyl oxidase inhibitor may not inhibit DAO and/or hERG.

In a further aspect, the present invention relates to the use of EGFR as a biomarker to predict responsiveness or sensitivity of a patient suffering from cancer to treatment with a lysyl oxidase inhibitor. Optionally, one or more further biomarkers may be used such as MATN2, HTRA1 and/or pSMAD2.

In another aspect, the present invention relates to a method of increasing the sensitivity rate (efficacy rate) of a lysyl oxidase inhibitor to treat cancer in a patient population said method comprising selecting a sub population which overexpresses an EGFR and, optionally overexpresses MATN2 and/or HTRA1. Optionally, said subgroup may also exhibit reduced expression of pSMAD2.

In a further aspect, the present invention relates to a method of identifying a subject having increased likelihood of responsiveness or sensitivity to a lysyl oxidase inhibitor comprising:
a) determining the level of EGFR, and optionally MATN2 or HTRA1, in a biological sample of the subject;
wherein increased levels EGFR (and optionally increased MATN2 and/or HTRA1) compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor comprising:
a) determining the level of EGFR and optionally MATN2 or HTRA1, in a biological sample of the subject;
wherein increased levels EGFR (and optionally increased MATN2 and/or HTRA1) compared to a reference sample identifies the subject as having responsiveness or sensitivity to a lysyl oxidase inhibitor.

Optionally, in all methods of the invention, the methods may comprise a further step of administering a therapeutically effective amount of a lysyl oxidase inhibitor when the subject is identified has have increased likelihood of responsiveness or sensitivity to a lysyl oxidase inhibitor.

By "increased likelihood of responsiveness or sensitivity to a LOX inhibitor" it is meant a higher prediction of a favourable effects associated with LOX inhibition therapy.

In a further aspect, the present invention relates to a method of determining a treatment regimen for a subject with cancer, comprising:
a) determining the level of EGFR (and optionally MATN2 or HTRA1) in a biological sample; and
b) administering a treatment regimen comprising a therapeutically effective amount of a lysyl oxidase inhibitor, when levels of EGFR (and optionally increased MATN2 and/or HTRA1) are elevated compared to a reference sample.

MATN2

Matrilin2 (MATN2) is a secreted protein with 10 EGF-like repeats (Wagener, R. et al. The matrilins—adaptor proteins in the extracellular matrix. FEBS Lett 579, 3323-3329, doi:10.1016/j.febslet.2005.03.018 (2005)). A protein sequence of human MATN2 may be obtained from uniprot (Universal protein resource) reference 000339-1.

Advantageously, the present invention has surprisingly shown that recombinant human MATN2 increase the levels of EGFR at the surface of the cell and thus MATN2 strongly enhances EGF-induced EGFR activation. Without wishing to be bound by theory, it is believed that MATN2 binding traps EGFR at the cell surface to present it to EGF for activation.

It has been surprisingly found that LOX inhibitors can downregulate expression of MATN2 which leads to increased internalisation of EGFR. Accordingly, the LOX inhibitors may have particular utility in the treatment of cancers having elevated levels of MATN2 compared to a reference sample.

Suitably, levels of MATN2 may be determined using immunofluorescence using a commercially available anti-human MATN2 antibody (e.g. from R&D). For example, the sample may be subjected to incubation with primary anti-MATN2 antibodies followed by fluorescence secondary antibodies (such as those available from Life Technologies) and then the levels determined using confocal imaging. An identical procedure is carried out on a reference sample so that it can be determined if MATN2 levels are increased.

Thus, the present invention relates to the use MATN2 (optionally in combination with EGFR) as a biomarker to predict responsiveness or sensitivity of a patient suffering from cancer to treatment with a lysyl oxidase inhibitor. Optionally, one or more further biomarkers may be used such as pSMAD2.

In another aspect, the present invention relates to a method of increasing the sensitivity rate (efficacy rate) of a lysyl oxidase inhibitor to treat cancer in a patient population said method comprising selecting a sub population which has enhanced expression of MATN2. Optionally, said subgroup may also exhibit reduced expression of pSMAD2.

In a further aspect, the present invention relates to a method of identifying a subject having increased likelihood of responsiveness or sensitivity to a lysyl oxidase inhibitor comprising:
  a) determining the level of MATN2 in a biological sample of the subject;
wherein increased levels MATN2 compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor comprising:
  a) determining the level of MATN2 in a biological sample of the subject;
wherein increased levels MATN2 compared to a reference sample identifies the subject as having responsiveness or sensitivity to a lysyl oxidase inhibitor.

Optionally, in all methods of the invention, the methods may comprise a further step of administering a therapeutically effective amount of a lysyl oxidase inhibitor when the subject is identified has have increased likelihood of responsiveness of sensitivity to a lysyl oxidase inhibitor.

In a further aspect, the present invention relates to a method of determining a treatment regimen for a subject with cancer, comprising:
  a) determining the level of MATN2 in a biological sample; and
  b) administering a treatment regimen comprising a therapeutically effective amount of a lysyl oxidase inhibitor, when levels MATN2 are elevated compared to a reference sample.

SMAD2

Smad proteins are signal transducers and transcriptional modulators that mediate multiple signaling pathways. SMAD2 mediates the signal of the transforming growth factor (TGF)-beta, and thus regulates multiple cellular processes, such as cell proliferation, apoptosis, and differentiation. This protein is recruited to the TGF-beta receptors through its interaction with the Smad anchor for receptor activation (SARA) protein. In response to TGF-beta signal, this protein is phosphorylated by the TGF-beta receptors. A human protein sequence may be obtained from uniprot (Universal protein resource) reference Q15796.

The present invention has surprisingly found strong activation of SMAD2 in LOX deficient cells and that TGFβ1 downregulates MATN2 mRNA. Without wishing to be bound by theory, it is believed that LOX inhibitors may activate SMAD2 which will lead to the downregulation of MATN2. Accordingly, activation of SMAD2 (which may be measured by upregulation of phospho-SMAD2 (pSMAD2)) will lead to a reduction of EGFR at the cell surface. Thus, SMAD2 may be used as a biomarker to determine response to treatment with a LOX inhibitor.

Suitably, levels of pSMAD2 may be determined using an anti-pSMAD2 antibody (such as those commercially available from Millipore).

HTRA1

HTRA1 is a secreted serine protease known to block TGFβ1 signalling by cleaving mature TGFβ1. A protein sequence for HTRA1 may be obtained from uniprot (Universal protein resource) reference Q92743 version 1.

Advantageously, the present invention has surprisingly shown that LOX depletion reduces the levels of extracellular homotrimeric HTRA1, the active form of this enzyme and HTRA1 suppresses SMAD2 activation and resources MATN2 expression in LOX depleted cells. Without wishing to be bound by theory, it is believed that reducing HTRA1 will activate SMAD2 causing a reduction in the expression of MATN2 mRNA. As the present invention has shown MATN2 binding traps EGFR at the cell surface to present it to EGF for activation, it is believed that elevated protein stability of HTRA1 will indicate an increased likelihood of response to treatment with a LOX inhibitor. Hence, HTRA1 may be used as a biomarker.

Accordingly, the LOX inhibitors may have particular utility in the treatment of cancers having elevated levels of HTRA1 compared to a reference sample.

Suitably, levels of HTRA1 may be determined using immunofluorescence using a commercially available anti-human HTRA1 antibody (anti-human HTRA1 antibody, R&D). For example, the sample may be subjected to incubation with primary anti-HTRA1 antibodies followed by fluorescence secondary antibodies (such as those available from Life Technologies) and then the levels determined using confocal imaging. An identical procedure is carried out on a reference sample so that it can be determined if HTRA1 levels are increased.

Thus, the present invention relates to the use of HTRA1 (optionally in combination with one or more of EGFR, MATN2 and pSMAD2) as a biomarker to predict responsiveness or sensitivity of a patient suffering from cancer to treatment with a lysyl oxidase inhibitor. Optionally, one or more further biomarkers may be used.

In another aspect, the present invention relates to a method of increasing the sensitivity rate (efficacy rate) of a lysyl oxidase inhibitor to treat cancer in a patient population said method comprising selecting a sub population which has enhanced expression of HTRA1 (and optionally EGFR and/or MATN2). Optionally, said subgroup may also under-express pSMAD2.

In a further aspect, the present invention relates to a method of identifying a subject having increased likelihood of responsiveness or sensitivity to a lysyl oxidase inhibitor comprising:
  a) determining the level of HTRA1 in a biological sample of the subject;
wherein increased levels HTRA1 compared to a reference sample indicates an increased likelihood of responsiveness or sensitivity to a lysyl oxidase inhibitor in the subject.

In another aspect, the present invention relates to a method of identifying a subject having responsiveness or sensitivity to a lysyl oxidase inhibitor comprising:
  a) determining the level of HTRA1 in a biological sample of the subject;
wherein increased levels HTRA1 compared to a reference sample identifies the subject as having responsiveness or sensitivity to a lysyl oxidase inhibitor.

Optionally, in all methods of the invention, the methods may comprise a further step of administering a therapeutically effective amount of a lysyl oxidase inhibitor when the subject is identified has have increased likelihood of responsiveness of sensitivity to a lysyl oxidase inhibitor.

In a further aspect, the present invention relates to a method of determining a treatment regimen for a subject with cancer, comprising:
   a) determining the level of HTRA1 in a biological sample; and
   b) administering a treatment regimen comprising a therapeutically effective amount of a lysyl oxidase inhibitor, when levels HTRA1 are elevated compared to a reference sample.

In Vitro Methods

The present invention also provides in vitro methods of internalising EGFR or reducing EGFR expression in a cell, said method comprising the step of contacting the cell with a LOX inhibitor.

In another aspect, the present invention further comprises an in vitro method of downregulating MATN2 expression in a cell, comprising the step of contacting the cell with a LOX inhibitor.

In a further aspect, the present invention also provides upregulating pSMAD2 in a cell comprising contacting a cell with a LOX inhibitor.

Suitably, in all aspects, the cell may be a cell-line, preferably a mammalian cell line.

Suitably, the cell may be a cancer cell, preferably a cancer cell associated with overexpression of EGFR.

Combination Therapies e.g. for the Treatment of Cancer

LOX inhibition can be a useful method for improving the efficacy of other drugs or addressing resistance to drug treatment through a number of mechanisms. Specific inhibition of LOX with siRNA can induce apoptosis of laryngeal cancer Hep-2 cells and enhance the sensitivity of Hep-2 cells to chemotherapeutic drugs such as cisplatin (Dong, Lu et al. 2014) and to radiation (Dong, Xin et al. 2014). LOX-expression and secretion is increased in response to ionizing radiation (IR) and hypoxia, suggesting that LOX may contribute towards an IR-induced migratory phenotype in sublethally-irradiated tumor cells and tumor progression; therefore LOX inhibitors can be used in combination with radiotherapy to reduce side effects in surrounding tissues receiving a reduced radiation dose (Shen, Sharma et al. 2014). LOX and LOXL2 inhibition can alter vascular permeability or normalise vasculature in a tumour environment, which can enhance the delivery or effectiveness of drugs (Ingber and Mammoto 2014) (Marshall, Spangler et al. 2012), for example improved efficacy of treatment in ovarian xenograft and lung allograft mice models with chemotherapeutic agents such as taxol (Zaffryar-Eilot, Marshall et al. 2013). The extracellular matrix has been proposed to have an important role in the resistance to chemotherapeutics. It has been shown that inhibition of LOX for cells grown in collagen (as a surrogate of ECM) reverses their collagen-dependent increased resistance to chemotherapeutics such as erlotinib, cisplatin or methotrexate (Smith and Holzer 2010). Drug diffusion and efficacy is reduced by the enzymatic action of LOX and LOXLs on the ECM in a 3D cell culture (not in 2D) and sensitivity to doxorubicin and paclitaxel can be restored by inhibition with BAPN (Schuetze, Roehrig et al. 2015). LOX inhibition synergized with gemcitabine to kill tumors and significantly prolonged tumor-free survival in a pancreatic mouse model. This was associated with stromal alterations and increased infiltration of macrophages and neutrophils into tumors. Therefore, targeting LOX could improve outcome in surgically resectable disease (Miller, Morton et al. 2015).

The compounds of the invention may be used alone to provide a therapeutic effect. The compounds of the invention may also be used in combination with one or more additional anti-tumour agent and/or radiotherapy.

Such chemotherapy may include one or more of the following categories of anti-cancer agents:

(i) antiproliferative/antineoplastic drugs and combinations thereof, such as alkylating agents (for example cis-platin, oxaliplatin, carboplatin, cyclophosphamide, nitrogen mustard, uracil mustard, bendamustin, melphalan, chlorambucil, chlormethine, busulphan, temozolamide, nitrosoureas, ifosamide, melphalan, pipobroman, triethylene-melamine, triethylenethiophoporamine, carmustine, lomustine, stroptozocin and dacarbazine); antimetabolites (for example gemcitabine and antifolates such as fluoropyrimidines like 5-fluorouracil and tegafur, raltitrexed, methotrexate, pemetrexed, leucovorin, cytosine arabinoside, floxuridine, cytarabine, 6-mercaptopurine, 6-thioguanine, fludarabine phosphate, pentostatine, and gemcitabine and hydroxyurea, and trifluridine with trifluracil); antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors; eribulin); proteasome inhibitors, for example carfilzomib and bortezomib; interferon therapy; and topoisomerase inhibitors (for example epipodophyllotoxins like etoposide and teniposide, amsacrine, topotecan, irinotecan, mitoxantrone and camptothecin); bleomcin, dactinomycin, daunorubicin, doxorubicin, epirubicin, idarubicin, ara-C, paclitaxel (Taxol™), nabpaclitaxel, docetaxel, mithramycin, deoxyco-formycin, mitomycin-C, L-asparaginase, interferons (especially IFN-alpha), etoposide, teniposide, DNA-demethylating agents, (for example, azacitidine or decitabine); and histone de-acetylase (HDAC) inhibitors (for example vorinostat, MS-275, panobinostat, romidepsin, valproic acid, mocetinostat (MGCD0103) and pracinostat SB939; and belinostat, panobinostat); trabectedin;

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride; and navelbene, CPT-II, anastrazole, letrazole, capecitabine, reloxafme, cyclophosphamide, ifosamide, and droloxafine; and abiraterone, Enzalutamide; analogues of somatostatin such as lanreotide;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-HER2 antibody pertuzumab; the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib, 6-acrylamido-N-(3-chloro-4-fluorophenyl)-7-(3-morpholinopropoxy)-quinazolin-4-amine (CI 1033), afatinib, vandetanib, osimertinib and rociletinib) erbB2 tyrosine kinase inhibitors such as lapatinib and antibodies to costimulatory molecules such as CTLA-4, 4-IBB and PD-I, or antibodies to cytokines (IL-10, TGF-beta); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, sorafenib, tipifarnib and lonafarnib, vemurafenib, dabrafenib), inhibitors of cell signalling through MEK (such as trametinib, cobimetinib) and/or AKT kinases, c-kit inhibitors, abl kinase inhibitors such as ponatinib, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors or CDK4/CDK6 inhibitors such as palbociclib; CCR2, CCR4 or CCR6 antagonists; mTOR kinase inhibitors such as Everolimus; Janus kinase family inhibitors such as ruxolitinib; Brunton's tyrosine kinase inhibitors such as Ibrutinib; anaplastic lymphoma kinase—ALK—such as ceritinib, crizotinib, alectinib; c-Met kinase. inhibitors such as cabozantinib; hedgehog signalling pathway inhibitors such as vismodegib, sonidegib; and RAF kinase inhibitors such as those described in WO2006043090, WO2009077766, WO2011092469 or WO2015075483;

(v) antiangiogenic agents such as those which inhibit the effects of vascular endothelial growth factor, [for example the anti-vascular endothelial cell growth factor antibody bevacizumab (Avastin™), anti-VEGF2 antibody ramucirumab; recombinant fusion protein ziv-aflibercept]; thalidomide; pomalidomide; lenalidomide; and for example, a VEGF receptor tyrosine kinase inhibitor such as regorafenib, vandetanib, vatalanib, sunitinib, axitinib and pazopanib and lenvatinib;

(vi) gene therapy approaches, including for example approaches to replace aberrant genes such as aberrant p53 or aberrant BRCA1 or BRCA2; oncolytic viruses such as talimogene laherparepvec;

(vii) immunotherapy approaches, including for example antibody therapy such as denosumab, obinutuzumab, blinatomumab, dinutuximab, idarucizumab, daratumumab, necitumumab, elotuzumab, olaratumab, alemtuzumab, rituximab, ibritumomab tiuxetan (Zevalin®) and ofatumumab; interferons such as interferon α, peginterferon alpha-2b; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); gp100; dendritic cell-based vaccines (such as Ad.p53 DC); toll-like receptor modulators for example TLR-7 or TLR-9 agonists; PD-1, PD-L1, PD-L2 and CTL4-A modulators (for example Nivolumab, pembrolizumab, atezolizumab), antibodies and vaccines; other IDO inhibitors (such as indoximod); anti-PD-1 monoclonal antibodies (such as MK-3475 and nivolumab); anti-PDL1 monoclonal antibodies (such as MEDI-4736 and RG-7446); anti-PDL2 monoclonal antibodies; and anti-CTLA-4 antibodies (such as ipilumumab); antibody-drug conjugates such as Brentuximab vedotin, trastuzumab emtansine.

(viii) cytotoxic agents for example fludaribine (fludara), cladribine, pentostatin (Nipent™);

(ix) targeted therapies, for example PI3K inhibitors, for example idelalisib and perifosine; SMAC (second mitochondriaderived activator of caspases) mimetics, also known as Inhibitor of Apoptosis Proteins (IAPs) antagonists (IAP antagonists). These agents act to supress IAPs, for example XIAP, cIAP1 and cIAP2, and thereby re-establish cellular apoptotic pathways. Particular SMAC mimetics include Birinapant (TL32711, TetraLogic Pharmaceuticals), LCL161 (Novartis), AEG40730 (Aegera Therapeutics), SM-164 (University of Michigan), LBW242 (Novartis), ML101 (Sanford-Burnham Medical Research Institute), AT-406 (Ascenta Therapeutics/University of Michigan), GDC-0917 (Genentech), AEG35156 (Aegera Therapeutic), and HGS1029 (Human Genome Sciences); and agents which target ubiquitin proteasome system (UPS), for example, bortezomib, ixazomib, carfilzomib, marizomib (NPI-0052), and MLN9708; and DNA repair inhibitors such as Olaparib, rucaparib; antiapoptotic BCL proteins family inhibitors such as venetoclax.

(xii) chimeric antigen receptors, anticancer vaccines and arginase inhibitors.

The additional anti-tumour agent may be a single agent or one or more of the additional agents listed herein.

Particular anti-cancer agents which may be used together with a compound of the invention include for example: Such combination treatment may be achieved by way of the simultaneous, sequential or separate dosing of the individual components of the treatment. Such combination products employ the compounds of this invention within a therapeutically effective dosage range described hereinbefore and the other pharmaceutically-active agent within its approved dosage range.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

In some embodiments in which a combination treatment is used, the amount of the compound of the invention and the amount of the other pharmaceutically active agent(s) are, when combined, therapeutically effective to treat a targeted disorder in the patient. In this context, the combined amounts are "therapeutically effective amount" if they are, when combined, sufficient to reduce or completely alleviate symptoms or other detrimental effects of the disorder; cure the disorder; reverse, completely stop, or slow the progress of the disorder; or reduce the risk of the disorder getting worse. Typically, such amounts may be determined by one skilled in the art by, for example, starting with the dosage range described in this specification for the compound of the invention and an approved or otherwise published dosage range(s) of the other pharmaceutically active compound(s).

According to a further aspect of the invention there is provided a compound of the invention as defined hereinbefore and an additional anti-cancer agent as defined hereinbefore, for use in the conjoint treatment of cancer.

According to a further aspect of the invention there is provided a pharmaceutical product comprising a compound of the invention as defined hereinbefore and an additional anti-cancer agent as defined hereinbefore for the conjoint treatment of cancer.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with an additional anti-cancer agent as defined hereinbefore.

According to a further aspect of the invention there is provided a compound of the invention, or a pharmaceutically acceptable salt thereof for use simultaneously, sequentially or separately with an additional anti-cancer agent as defined hereinbefore, in the treatment of a cancer.

The compound of the invention may also be used be used in combination with radiotherapy. Suitable radiotherapy treatments include, for example X-ray therapy, proton beam therapy or electron beam therapies. Radiotherapy may also encompase the use of radionuclide agents, for example $^{131}$I, $^{32}$P, $^{90}$Y, $^{89}$Sr, $^{153}$Sm or $^{223}$Ra. Such radionuclide therapies are well known and commercially available.

According to a further aspect of the invention there is provided a compound of the invention, or a pharmaceutically acceptable salt thereof as defined hereinbefore for use in the treatment of cancer conjointly with radiotherapy.

According to a further aspect of the invention there is provided a method of treatment of a human or animal subject suffering from a cancer comprising administering to the subject a therapeutically effective amount of a compound of the invention, or a pharmaceutically acceptable salt thereof simultaneously, sequentially or separately with radiotherapy.

EXAMPLES

Synthetic Chemistry

General Experimental

Starting materials were purchased from commercial sources or synthesised according to the methods described herein or using literature procedures. Commercial building blocks, reagents and solvents for reactions were reagent grade and used as purchased. Chromatography solvents were HPLC grade and were used without further purification. Thin layer chromatography (TLC) analysis was performed using silica gel 60 F-254 thin layer plates. Flash column chromatography was performed using columns pre-packed with 40-63 µm silica. LCMS and HRMS analyses were performed on a HPLC system with diode array detector operating at 254 nm, fitted with a reverse-phase 50×4.6 mm column at a temperature of 22° C., connected to a Time of Flight (ToF) mass spectrometer (ESI). $^1$H and $^{13}$C NMR spectra were recorded on a Bruker Avance 500 MHz spectrometer using an internal deuterium lock. NMR data is given as follows: chemical shift (δ) in ppm, integration, multiplicity and coupling constants (J) given in Hz.

General Procedures GP1

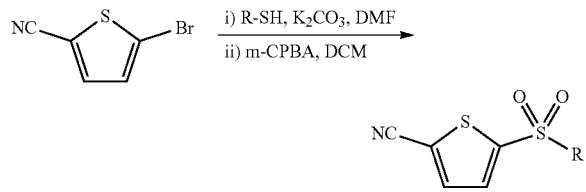

A mixture of 5-bromothiophene-2-carbonitrile (or 5-chlorothiophene-2-carbonitrile), thiol (R-SH), K$_2$CO$_3$ (or NaH) and DMF was stirred at 50° C.-140° C. After cooling to rt, the mixture was diluted with EtOAc. The organic phase was washed with 1:1 H$_2$O/brine (3×), dried over MgSO$_4$ and filtered. The solvent was removed under reduced pressure. The crude was dissolved in DCM. m-CPBA was added in small portions and the mixture was stirred at rt for 3-16 h. When complete conversion was achieved, EtOAc was added. The organic phase was washed with sat. NaHCO$_3$ (3×) [Note: it is recommended to wash with additional sat. Na$_2$S$_2$O$_3$ for large scale preparations], dried over MgSO$_4$ and filtered. The solvent was removed under reduced pressure. The crude was purified by column chromatography to afford the desired sulfone.

General Procedures GP2

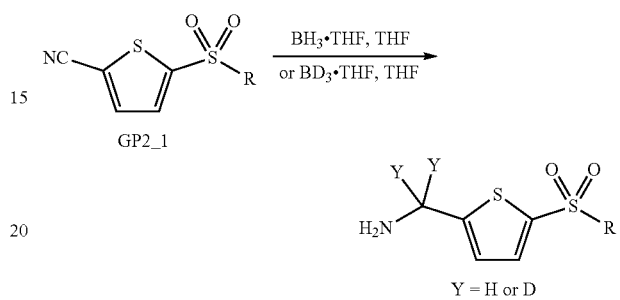

2a—BH$_3$.THF was added to a solution of cyanothiophene GP2_1 in THF, and the mixture was stirred at rt for 1-5 h. EtOH (equal volume to reaction mixture) was then added to quench the reaction. Subsequently, the solution was heated at 70° C. for 1 h to aid borane decomplexation. The solvent was removed under reduced pressure and the crude was purified by column chromatography to afford the desired amine.

2b—BH$_3$.THF was added to a solution of cyanothiophene GP2_1 in THF, and the mixture was stirred at rt for 1-5 h. EtOH (equal volume to reaction mixture) was then added to quench the reaction. Subsequently, the solution was heated at 70° C. for 1 h to aid borane decomplexation. The solvent was removed under reduced pressure and the crude was dissolved in EtOAc. The organic phase was extracted with 0.5 M HCl (3×). The combined aqueous phase was basified with 2 M NaOH to pH>10, then extracted with DCM. The combined organic phase was dried over MgSO$_4$, filtered and the crude was purified by column chromatography to afford the desired amine.

2c—Deuterated borane (BD$_3$.THF) was added to a solution of cyanothiophene GP2_1 in THF, and the mixture was stirred at rt for 1-5 h. EtOH (equal volume to reaction mixture) was then added to quench the reaction. Subsequently, the solution was heated at 70° C. for 1 h to aid deuterated borane decomplexation. The solvent was removed under reduced pressure and the crude was purified by column chromatography to afford the desired amine.

General Procedures GP3

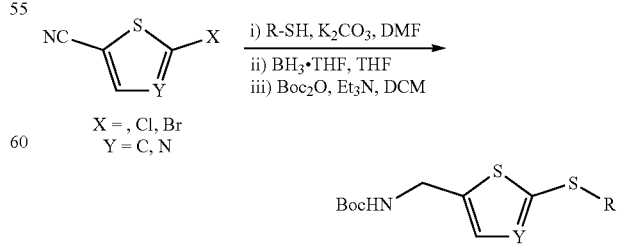

A mixture of 5-bromo or 5-chlorothiophene-2-carbonitrile (or the corresponding 5-bromothiazole-3-carbonitrile), thiol (R-SH), K$_2$CO$_3$ and DMF was stirred at 50° C.-140° C. After cooling to rt, the mixture was diluted with EtOAc. The organic phase was washed with 1:1 H$_2$O/brine (3×), dried over MgSO$_4$ and filtered. The solvent was removed under reduced pressure. The crude could be purified by chromatography if necessary, otherwise THF was added, followed by BH$_3$.THF and the mixture was stirred at rt for 1-5 h. EtOH (equal volume to reaction mixture) was then added to quench the reaction. Subsequently, the solution was heated at 70° C. for 1 h to aid borane decomplexation. The solvent was removed under reduced pressure. The crude was dissolved in DCM. Et$_3$N, followed by Boc$_2$O were added and the mixture was stirred at rt for 16 h. When complete conversion was achieved, more DCM was added. The organic phase was washed with H$_2$O and brine, dried over MgSO$_4$ and filtered. The solvent was removed under reduced pressure. The crude was purified by column chromatography to afford the desired tert-butyl-carbamate.

General Procedures GP4

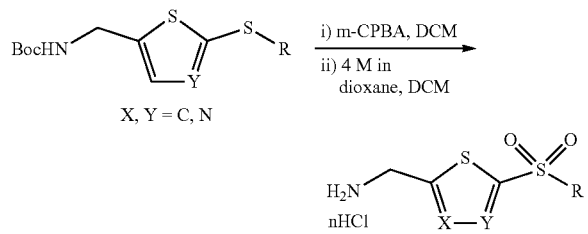

m-CPBA was added in small portions to a solution of the starting sulfide in DCM and the mixture was stirred at rt for 3-16 h. When complete conversion was achieved, EtOAc was added. The organic phase was washed with sat. NaHCO$_3$ (3×), dried over MgSO$_4$ and filtered. The solvent was removed under reduced pressure and the crude sulfone can be purified by chromatography if necessary. 4 M HCl in dioxane was added to the sulfone intermediate (neat or as a solution in DCM) and the mixture was stirred at rt for 1-16 h. The solid was collected, washed with EtOAc and dissolved in MeOH. The solvent was removed under reduced pressure to afford the desired amine hydrochloride. If necessary, this can be further purified by chromatography in its free amine form, which can be obtained by treatment with 7 N NH$_3$ in MeOH.

General Procedures GP5

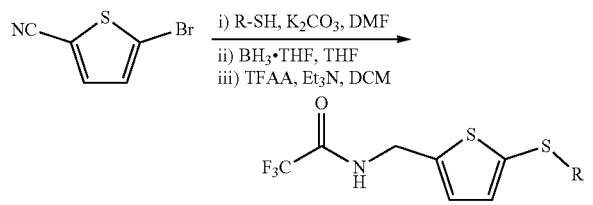

A mixture of 5-bromothiophene-2-carbonitrile (or 5-chlorothiophene-2-carbonitrile), thiol (R-SH), K$_2$CO$_3$ and DMF was stirred at 50° C.-140° C. After cooling to rt, the mixture was diluted with EtOAc. The organic phase was washed with 1:1 H$_2$O/brine (3×), dried over MgSO$_4$ and filtered. The solvent was removed under reduced pressure. The crude could be purified by chromatography if necessary, otherwise THF was added, followed by BH$_3$.THF and the mixture was stirred at rt for 1-5 h. EtOH (equal volume to reaction mixture) was then added to quench the reaction. Subsequently, the solution was heated at 70° C. for 1 h to aid borane decomplexation. The solvent was removed under reduced pressure. The crude was dissolved in DCM. Et$_3$N, followed by TFAA were added and the mixture was stirred at rt for 16 h. When complete conversion was achieved, more DCM was added. The organic phase was washed with H$_2$O and brine, dried over MgSO$_4$ and filtered. The solvent was removed under reduced pressure. The crude was purified by column chromatography to afford the desired trifluoroacetamide.

General Procedures GP6

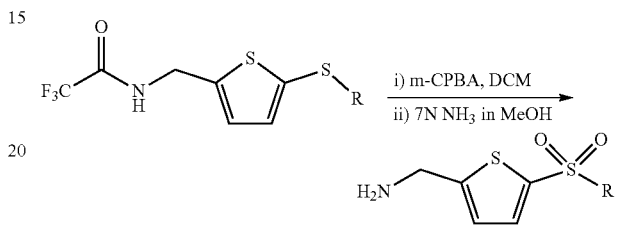

m-CPBA was added in small portions to a solution of the starting sulfide in DCM and the mixture was stirred at rt for 3-16 h. When complete conversion was achieved, EtOAc was added. The organic phase was washed with sat. NaHCO$_3$ (3×), dried over MgSO$_4$ and filtered. The solvent was removed under reduced pressure. 7 N NH$_3$ in MeOH was added to the sulfone intermediate (neat or a solution in DCM) and the mixture was stirred at rt for 1-16 h. The solvent was removed under reduced pressure to afford the desired amine which can be further purified if necessary General procedures GP7

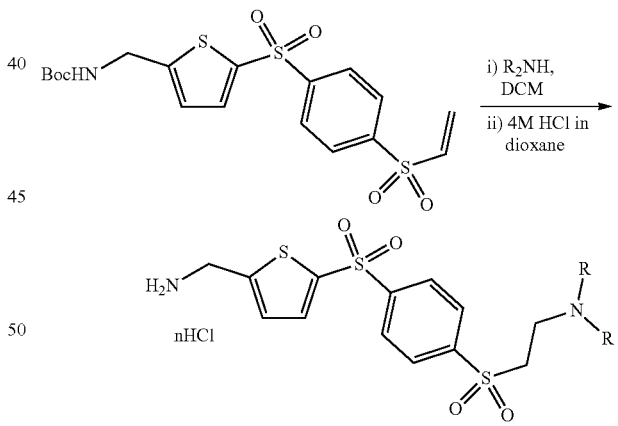

Amine (R$_2$NH) was added to a solution of tert-butyl ((5-((4-(vinylsulfonyl)phenyl)-sulfonyl)thiophen-2-yl)methyl)carbamate in DCM and the mixture was stirred at rt for 1-16 h. The solvent was removed under reduced pressure and the crude could be purified by chromatography if necessary. 4 M HCl in dioxane was added to the intermediate (either neat or in DCM) and the mixture was stirred at rt for 1-16 h. The precipitated solid was collected on a pad of celite and washed with EtOAc. MeOH was added to dissolve the solid and the suspension was filtered. The filtrate was removed under reduced pressure to afford the desired amine hydrochloride. If necessary, this can be fur-

General Procedures GP8

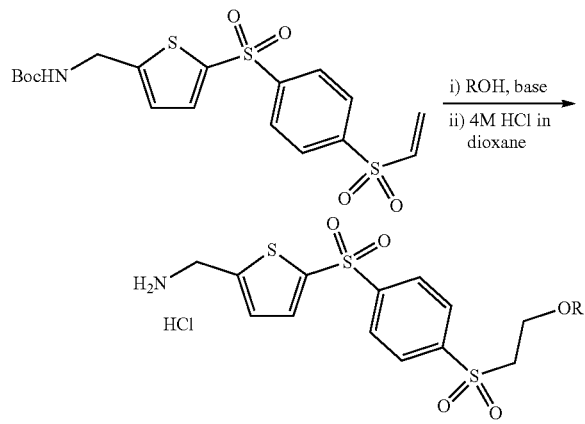

Base (either K₂CO₃ or NaOEt) was added to a solution of tert-butyl ((5-((4-(vinylsulfonyl)phenyl)-sulfonyl)thiophen-2-yl)methyl)carbamate in alcohol (ROH) and the mixture was stirred at rt for 1-16 h. The solvent was removed under reduced pressure and the crude could be purified by chromatography if necessary. 4 M HCl in dioxane was added to the intermediate (either neat or in DCM) and the mixture was stirred at rt for 1-16 h. The precipitated solid was collected on a pad of celite and washed with EtOAc. MeOH was added to dissolve the solid and the suspension was filtered. The solvent was removed under reduced pressure to afford the desired amine hydrochloride. If necessary, this can be further purified by chromatography in its free amine form, which can be obtained by treatment with 7 N NH₃ in MeOH.

General Procedures GP9

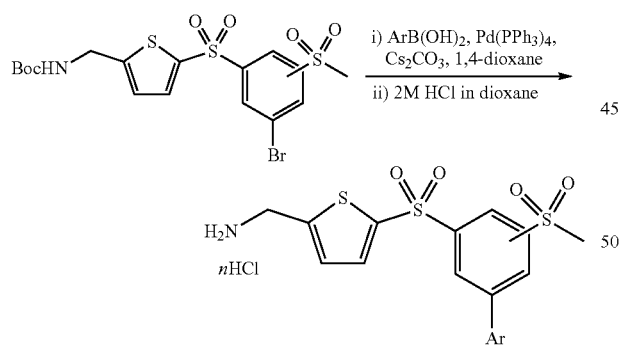

A mixture of tert-butyl ((5-((3-bromo-5-(methylsulfonyl)phenyl)sulfonyl)thiophen-2-yl)methyl)carbamate, Pd(PPh₃)₄, ArB(OH)₂, Cs₂CO₃ and 1,4-dioxane was degassed with argon and then stirred at 100° C. for 16 h. After cooling to rt, the suspension was filtered through celite, washed with DCM and the filtrate was removed under reduced pressure. The crude was purified by column chromatography to afford the desired biaryl intermediate. DCM and 4 M HCl in dioxane were added and the mixture was stirred at rt for 1-16 h. Cyclohexane was added to precipitate the solid product. The mixture was filtered, the solid was washed with EtOAC and dried under vacuum to afford the desired amine hydrochloride. If necessary, this can be further purified by chromatography in its free amine form, which can be obtained by treatment with 7 N NH₃ in MeOH.

General Procedures GP10

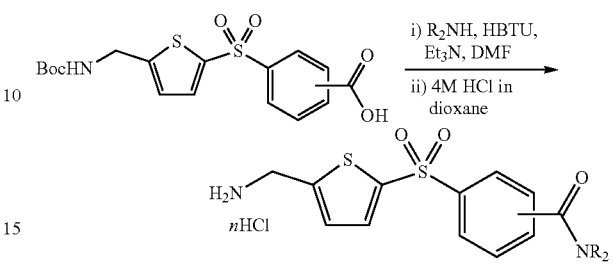

To a solution of the 3- or 4-((5-(((tert-butoxycarbonyl)amino)methyl)thiophen-2-yl)sulfonyl)benzoic acid in DMF was added N,N,N',N'-tetramethyl-O-(1H-benzotriazol-1-yl)uronium hexafluorophosphate (HBTU), Et₃N and then amine (R₂NH). The mixture was stirred at rt for 12 h. EtOAc was added. The organic phase was washed with 1:1 H₂O/brine (3×), dried over MgSO₄, filtered and the solvent was removed under reduced pressure. The crude was treated with 4 M HCl in dioxane and the mixture was stirred at rt for 12 h. The solvent was removed under reduced pressure to afford the desired amine hydrochloride. If necessary, this can be further purified by chromatography in its free amine form, which can be obtained by treatment with 7 N NH₃ in MeOH.

General Procedures GP11

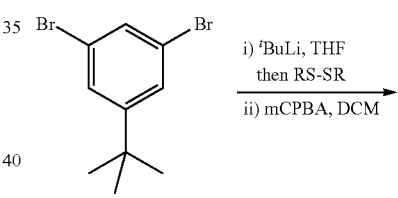

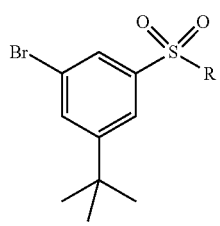

ᵗBuLi was added dropwise over 20 min to a solution of 1,3-dibromo-5-(tert-butyl)benzene in THF at −78° C. and stirring was maintained at −78° C. for 10 min. A solution of disulfide (RSSR) in THF was added dropwise over 20 min at the same temperature and the reaction was warmed slowly to rt. Sat. NH₄Cl was added. The aqueous phase was extracted with EtOAc (3×). The combined organic phase was dried over MgSO₄, filtered and the solvent was removed under reduced pressured. The crude was purified by chromatography m-CPBA was added in small portions to a solution of the intermediate sulfide in DCM. The mixture was stirred at rt for 12 h and diluted with EtOAc. The solution was washed with sat. NaHCO₃ (3×), dried over MgSO₄, filtered and the solvent was subsequently removed under reduced pressure. The crude was purified by chromatography

General Procedures GP12

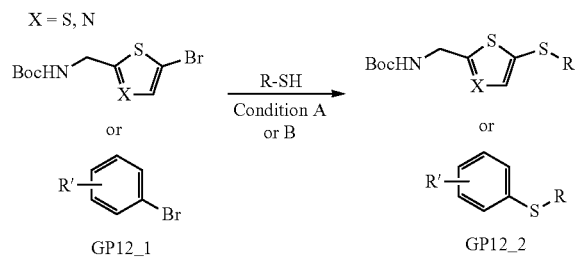

Condition A = Pd₂(dba)₃, Xantphos, NaO'Bu, 'BuOH/toluene (1:5)
Condition B = Pd₂(dba)₃, Xantphos, DIPEA, toluene Condition A—a mixture of bromide GP12_1, Pd$_2$(dba)$_3$ (5 mol %), Xantphos (10 mol %), RSH (1.0-1.2 equiv.), NaO$^t$Bu (1.0-1.2 equiv.) and $^t$BuOH/toluene (1:5) was degassed with argon and then stirred at 100° C. for 16 h. After cooling to rt, the suspension was filtered through celite, washed with DCM and the solvent was removed under reduced pressure. Alternatively, the mixture was centrifuged at 2500 RPM for 5 minutes. The solution was decanted and concentrated under reduced pressure. The crude was purified by chromatography to afford sulfide GP12_2.

Condition B—same as condition A, with DIPEA used instead of NaO$^t$Bu and toluene used instead of $^t$BuOH/toluene.

General Procedures GP13

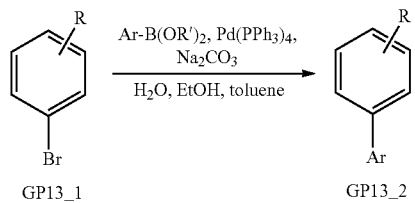

A mixture of bromide GP13_1, Pd(PPh$_3$)$_4$, ArB(OR')$_2$, Na$_2$CO$_3$, H$_2$O, EtOH and toluene was degassed with argon and then stirred at 100° C. for 16 h. After cooling to rt, the mixture was diluted with Et$_2$O and filtered through celite. The organic solution was washed with H$_2$O, dried over Na$_2$SO$_4$, filtered and the solvent was removed under reduced pressure. The crude was purified by chromatography to afford biaryl GP13_2.

General Procedures GP14

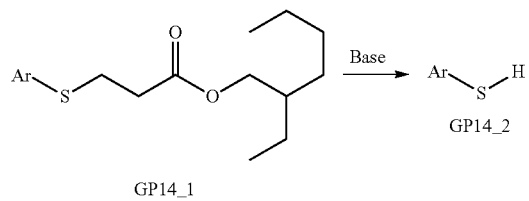

Alkoxide base (NaO$^t$Bu, NaOEt or KO$^t$Bu) was added to a mixture of propionate GP14_1 and $^t$BuOH/toluene (1:5) or THF. The mixture was degassed with argon and stirred at rt for 2-4 h. After diluting with EtOAc, the organic phase was washed with 0.5M HCl and H$_2$O, dried over MgSO$_4$ and filtered. The solvent was removed under reduced pressure and the crude was purified by chromatography if necessary to afford sulfide GP14_2.

General Procedures GP15

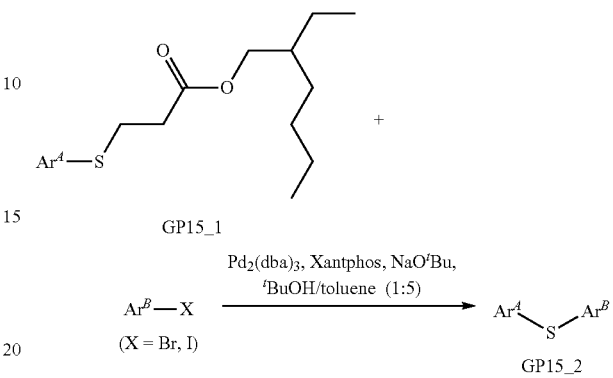

A mixture of sulfido-propionate GP15_1 (1.0 equiv.), aryl halide (Ar$^B$X; 1.0 equiv.), Pd$_2$(dba)$_3$ (5 mol %), Xantphos (10 mol %), NaO$^t$Bu (2.0 equiv.) and $^t$BuOH/toluene (1:5) was degassed with argon and then stirred at 100° C. for 16 h. After cooling to rt, the suspension was either filtered through celite, washed with DCM and the solvent was removed under reduced pressure [Alternatively, the mixture was centrifuged at 2500 RPM for 5 minutes. The solution was decanted and concentrated under reduced pressure]. The crude was purified by chromatography to afford diarylsulfide GP15_2.

General Procedures GP16

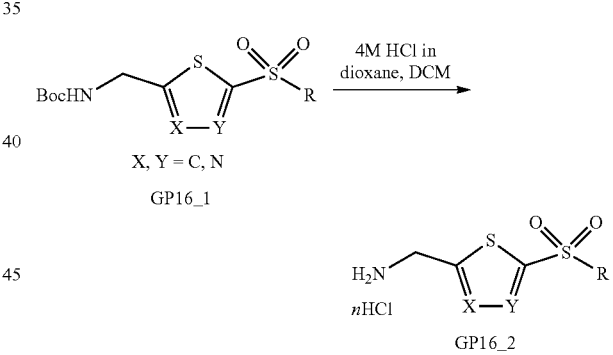

4 M HCl in dioxane was added to tert-butyl carbamate GP16_1 (neat or as a solution in DCM) and the mixture was stirred at rt for 1-16 h. EtOAc was added to precipitate the solid. The suspension was filtered and the solids were filtered, washed with EtOAc to afford the desired amine hydrochloride GP16_2. If necessary, this can be further purified by chromatography in its free amine form, which can be obtained by treatment with 7 N NH$_3$ in MeOH.

General Procedures GP17

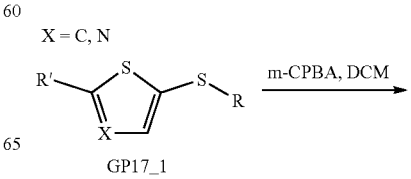

-continued

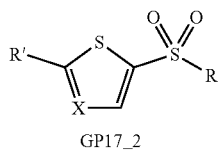

GP17_2 m-CPBA was added in small portions to a solution of sulfide GP17_1 in DCM and the mixture was stirred at rt for 3-16 h. When complete conversion was achieved, EtOAc was added. The organic phase was washed with sat. NaHCO$_3$ (3×) and sat. Na$_2$S$_2$O$_4$, dried over MgSO$_4$ and filtered. The solvent was removed under reduced pressure. The crude was purified by column chromatography to afford sulfone GP17_2.

General Procedures GP18

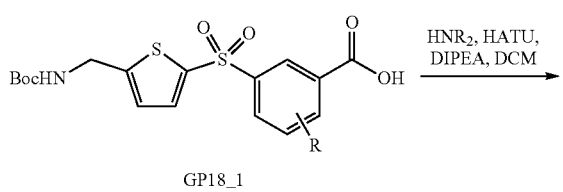

GP18_1

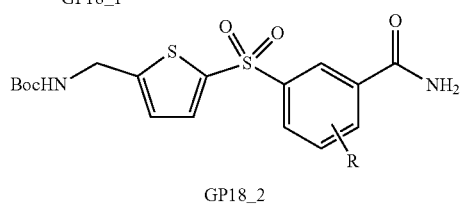

GP18_2

Amine or amine hydrochloride (HNR$_2$) was added to a mixture of carboxylic acid GP18_1, HATU and DIPEA in DMF and the mixture was stirred at rt for 16 h. Water was added and the aqueous phase was extracted by EtOAc (3×). The combined organic layer was washed with brine, dried over Na$_2$SO$_4$ and filtered. The solvent was removed under reduced pressure. The crude was purified by chromatography to afford the desired amide GP18_2.

Example 1: (5-(Benzylsulfonyl)thiophen-2-yl)methanamine

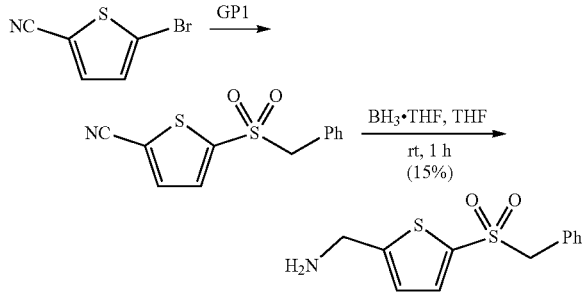

5-(Benzylsulfonyl)thiophene-2-carbonitrile was synthesised according to general procedures GP1—from i) 5-bromothiophene-2-carbonitrile (150 µL, 1.35 mmol), benzylmercaptan (174 µL, 1.49 mmol), NaH (60% in mineral oil; 59.5 mg, 1.49 mmol) and DMF (4.5 mL); 140° C., 16 h. ii) m-CPBA (77%; 757 mg, 3.38 mmol) and DCM (4.5 mL); rt, 4 h. The crude was purified by chromatography (EtOAc/cyclohexane 0→20%) to afford 5-(benzylsulfonyl)thiophene-2-carbonitrile as a white solid (318 mg, 89%). $^1$H NMR (500 MHz, DMSO) δ 8.07 (d, J=4.0 Hz, 1H), 7.72 (d, J=4.0 Hz, 1H), 7.40-7.32 (m, 3H), 7.25-7.18 (m, 2H), 4.93 (s, 2H).

The title compound was synthesised according to general procedures GP2a—from BH$_3$ (1.0 M in THF; 1.10 mL, 1.10 mmol), 5-(benzylsulfonyl)thiophene-2-carbonitrile (151 mg, 0.570 mmol) and THF (2.8 mL); rt, 1 h. The crude was purified by chromatography (MeOH/DCM 0→20%) to afford the title compound as a white crystalline solid (23 mg, 15%). $^1$H NMR (500 MHz, CDCl$_3$) δ 7.38-7.26 (m, 3H), 7.21-7.15 (m, 3H), 6.84 (dt, J=3.8, 1.0 Hz, 1H), 4.39 (s, 2H), 4.07 (d, J=0.9 Hz, 2H), 1.59 (s, 2H). $^{13}$C NMR (126 MHz, CDCl$_3$) δ 158.50, 136.25, 135.25, 130.88, 129.00, 128.74, 128.52, 123.68, 64.15, 41.68. HRMS (ESI) for C$_{12}$H$_{14}$NO$_2$S$_2$ ([M+H]$^+$): Calculated 268.0461; Observed 268.0462.

Example 2: (5-(Naphthalen-2-ylsulfonyl)thiophen-2-yl)methanamine

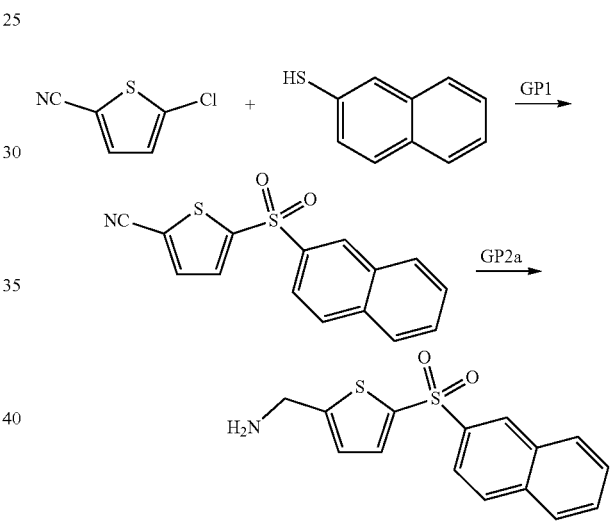

5-(Naphthalen-2-ylsulfonyl)thiophene-2-carbonitrile was synthesised according to general procedures GP1—from i) 5-chlorothiophene-2-carbonitrile (598 mg, 4.18 mmol), naphthalene-2-thiol (670 mg, 4.18 mmol), K$_2$CO$_3$ (721 mg, 5.22 mmol) and DMF (11.6 mL); 130° C., 16 h. ii) m-CPBA (77%; 1.95 g, 8.70 mmol) and DCM (17.4 mL); rt, 5 h. The crude (white solid; 517 mg, 41%) was used in the subsequent transformation without further purification. H NMR (500 MHz, CDCl$_3$) δ 8.62 (d, J=1.4 Hz, 1H), 8.05-8.00 (m, 2H), 7.95-7.90 (m, 2H), 7.73-7.64 (m, 3H), 7.55 (d, J=4.1 Hz, 1H).

The title compound was synthesised according to general procedures GP2a—from BH$_3$ (1.0 M in THF; 5.10 mL, 5.10 mmol), 5-(naphthalen-2-ylsulfonyl)thiophene-2-carbonitrile (510 mg, 1.71 mmol) and THF (10 mL); rt, 3 h. The crude was purified by chromatography (EtOH/cyclohexane 30→100%) to afford the title compound as a white solid (273 mg, 54%). $^1$H NMR (500 MHz, CDCl$_3$) δ 8.58 (s, 1H), 8.01-7.87 (m, 4H), 7.68-7.57 (m, 3H), 6.88 (m, 1H), 4.05 (s, 2H), 1.56 (s, 2H). $^{13}$C NMR (126 MHz, CDCl$_3$) δ 158.24, 140.73, 139.30, 135.17, 133.73, 132.40, 129.75, 129.59, 129.25, 128.71, 128.06, 127.75, 123.82, 122.58, 41.68.

HRMS (ESI) for $C_{15}H_{11}O_2S_2$ ([M-NH$_2$]$^+$): Calculated 287.0195; Observed 287.0207.

Example 3: (5-(Cyclohexylsulfonyl)thiophen-2-yl)methanamine

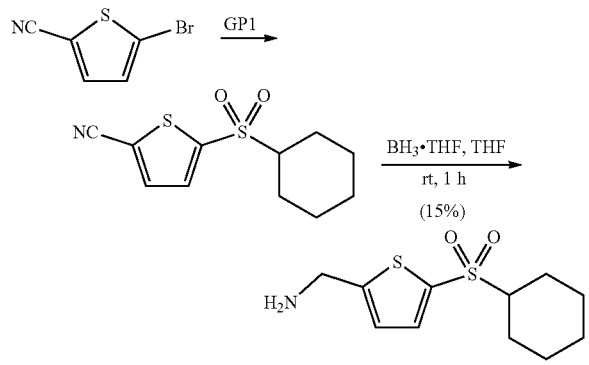

5-(Cyclohexylsulfonyl)thiophene-2-carbonitrile was synthesised according to general procedures GP1—from i) 5-bromothiophene-2-carbonitrile (100 μL, 0.901 mmol), cyclohexylmercaptan (121 μL, 0.991 mmol), NaH (60% in mineral oil; 39.6 mg, 0.985 mmol) and DMF (3.0 mL); 130° C., 16 h. ii) m-CPBA (77%; 489 mg, 2.18 mmol) and DCM (15 mL); rt, 3 h. The crude was purified by chromatography (EtOAc/cyclohexane 0→20%) to afford (cyclohexylsulfonyl)thiophene-2-carbonitrile as a white crystalline solid (50 mg, 22%). $^1$H NMR (500 MHz, CDCl$_3$) δ 7.65 (d, J=4.0 Hz, 1H), 7.61 (d, J=4.0 Hz, 1H), 3.03 (tt, J=12.1, 3.4 Hz, 1H), 2.19-2.11 (m, 2H), 1.97-1.88 (m, 2H), 1.72 (m, 1H), 1.65-1.10 (m, 5H).

BH$_3$.THF (1.0M in THF; 0.58 mL, 0.58 mmol) was added to a solution of 5-(cyclohexylsulfonyl)thiophene-2-carbonitrile (49 mg, 0.192 mmol) in THF (1.9 mL) and the mixture was stirred at rt for 1 h. MeOH was carefully added to quench the reaction. The solvent was removed under reduced pressure and the crude was purified by chromatography (MeOH/DCM 0→15%) to afford the title compound as a white solid (12 mg, 24%). $^1$H NMR (500 MHz, CDCl$_3$) δ 7.50 (d, J=3.8 Hz, 1H), 6.96 (m, 1H), 4.12 (s, 2H), 2.95 (tt, J=12.1, 3.4 Hz, 1H), 2.20-2.12 (m, 2H), 1.92-1.84 (m, 2H), 1.68 (d, J=21.7 Hz, 3H), 1.51-1.38 (m, 2H), 1.33-1.08 (m, 3H). $^{13}$C NMR (126 MHz, CDCl$_3$) δ 158.07, 135.80, 135.11, 123.83, 64.77, 41.72, 25.97, 25.27, 25.19. HRMS (ESI) for $C_{11}H_{17}NO_2S_2$ ([M+H]$^+$): Calculated 260.0773; Observed 260.0785.

Example 4: (5-(2-Bromophenylsulfonyl)thiophen-2-yl)methanamine

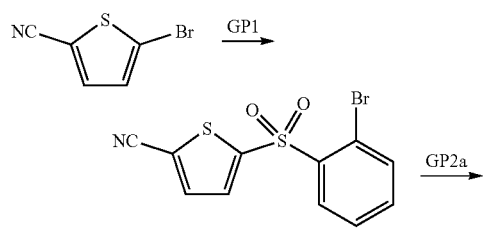

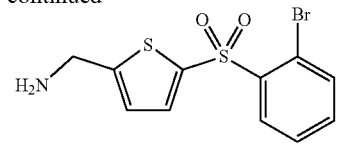

5-((2-Bromophenyl)sulfonyl)thiophene-2-carbonitrile was synthesised according to general procedures GP1—from i) 5-bromothiophene-2-carbonitrile (100 μL, 0.901 mmol), 2-bromobenzenethiol (119 μL, 0.991 mmol), NaH (60% in mineral oil; 39.6 mg, 0.985 mmol) and DMF (3.0 mL); 130° C., 220 h. The crude was purified by chromatography (EtOAc/cyclohexane 0→12%) to afford 5-((2-bromophenyl)thio)thiophene-2-carbonitrile as a white solid (257 mg, 96%). $^1$H NMR (500 MHz, CDCl$_3$) δ 8.62 (d, J=1.4 Hz, 1H), 8.05-8.00 (m, 2H), 7.95-7.90 (m, 2H), 7.73-7.64 (m, 3H), 7.55 (d, J=4.1 Hz, 1H); ii) 5-((2-bromophenyl)thio)thiophene-2-carbonitrile (108 mg, 0.364 mmol), m-CPBA (77%; 204 mg, 0.910 mmol) and DCM (1.8 mL); rt, 5 h. The crude (white solid; 517 mg, 41%) was used in the subsequent transformation without further purification.

The title compound was synthesised according to general procedures GP2a—from BH$_3$ (1.0 M in THF; 1.10 mL, 1.10 mmol), 5-((2-bromophenyl)sulfonyl)thiophene-2-carbonitrile (108 mg, 0.364 mmol) and THF (1.8 mL); rt, 2 h. The crude was purified by chromatography (MeOH/DCM 0→20%) to afford a colourless oil (19 mg, 17%). $^1$H NMR (500 MHz, CDCl$_3$) δ 8.17 (m, 1H), 7.61 (m, 1H), 7.58-7.51 (m, 2H), 7.40 (m, 1H), 6.86 (m, 1H), 4.02 (s, 2H), 1.67 (br, 2H). $^{13}$C NMR (126 MHz, CDCl$_3$) δ 155.99, 144.77, 143.82, 133.31, 133.24, 132.58, 128.58, 126.13, 123.52, 119.99, 41.87.

Example 5: (5-(4-(Methylsulfonyl)phenylsulfonyl)thiophen-2-yl)methanamine

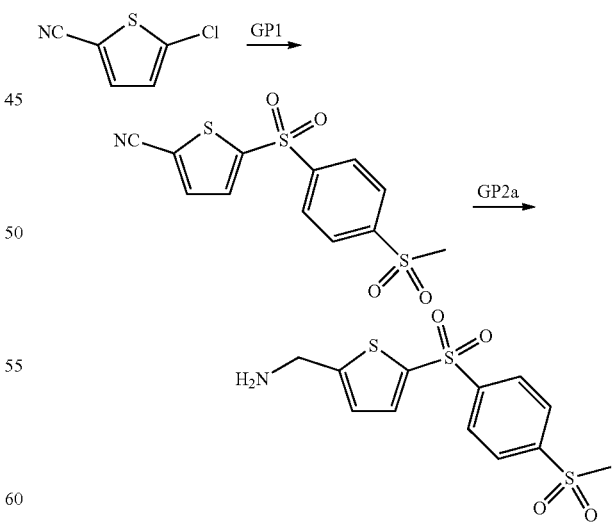

5-((4-(Methylsulfonyl)phenyl)sulfonyl)thiophene-2-carbonitrile was synthesised according to general procedures GP1—from i) 5-chlorothiophene-2-carbonitrile (500 mg, 3.48 mmol), 4-(methylthio)benzenethiol (599 mg, 3.83 mmol), K$_2$CO$_3$ (960 mg, 7.00 mmol) and DMF (11.6 mL);

120° C., 16 h. ii) m-CPBA (77%; 3.90 g, 17.4 mmol) and DCM (23 mL); rt, 2 h. The product was obtained as a white solid which did not require further purification (770 mg, 68%). $^1$H NMR (500 MHz, DMSO) δ 8.35-8.29 (m, 2H), 8.24-8.18 (m, 2H), 8.13-8.08 (m, 2H), 3.31 (s, 3H).

The title compound was synthesised according to general procedures GP2a—from BH$_3$ (1.0 M in THF; 8.40 mL, 8.40 mmol), 5-((4-(methylsulfonyl)phenyl)sulfonyl)thiophene-2-carbonitrile (921 mg, 2.81 mmol) and THF (18 mL); 50° C., 3 h. The crude was purified by chromatography (MeOH/DCM 0→20%) to afford the title compound as a white solid (310 mg, 34%). $^1$H NMR (500 MHz, CDCl$_3$) δ 8.19-8.15 (m, 2H), 8.11-8.06 (m, 2H), 7.63 (d, J=3.9 Hz, 1H), 6.93 (dt, J=3.8, 1.0 Hz, 1H), 4.09 (d, J=0.8 Hz, 2H), 3.08 (s, 3H), 1.61 (s, 2H). $^{13}$C NMR (126 MHz, CDCl$_3$) δ 160.12, 147.61, 144.80, 138.67, 134.95, 128.64, 128.46, 124.12, 44.41, 41.70. HRMS (ESI) for $C_{12}H_{14}NO_4S_3$ ([M+H]$^+$): Calculated 332.0080; Observed 332.0070.

Example 6: (5-(Pyridin-2-ylsulfonyl)thiophen-2-yl)methanamine

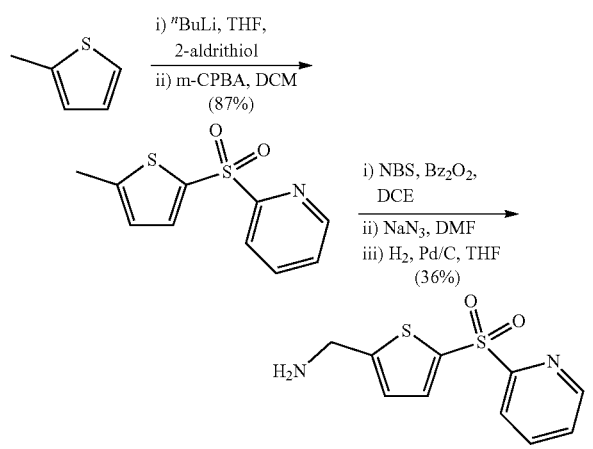

$^n$BuLi (2.5M in hexane; 2.18 mL, 5.45 mmol) was added to a solution of 2-methylthiophene (530 μL, 5.45 mmol) in THF (23 mL) at −78° C. and the mixture was warmed to −40° C. over 30 min. 1,2-Di(pyridin-2-yl)disulfane (2-aldrithiol) (1.0 g, 4.54 mmol) was added and the mixture was warmed to rt over 30 min. H$_2$O (50 mL) was added. The aqueous phase was extracted with DCM (3×50 mL), dried over MgSO$_4$ and filtered. The solvent was removed under reduced pressure and the crude was purified by chromatography (EtOAc/cyclohexane 0→12%) to afford 2-((5-methylthiophen-2-yl)thio)pyridine as a colourless oil (913 mg, 97%). m-CPBA (77%; 750 mg, 3.36 mmol) was added in small portions to a solution of 2-((5-methylthiophen-2-yl)thio)pyridine (303 mg, 1.46 mmol) in DCM (7.3 mL) and the mixture was stirred at rt for 5 h. DCM (30 mL) was added. The organic phase was washed with 1 M NaOH (3×20 mL), dried over MgSO$_4$ and filtered. The solvent was removed under reduced pressure and the crude was purified by chromatography (EtOAc/cyclohexane 10→40%) to afford 2-((5-methylthiophen-2-yl)sulfonyl)pyridine as a white solid (310 mg, 88%). $^1$H NMR (500 MHz, CDCl$_3$) δ 8.89-8.78 (m, 2H), 7.83-7.74 (m, 2H), 7.59 (d, J=3.8 Hz, 1H), 6.82 (dd, J=3.8, 0.9 Hz, 1H), 2.54 (s, 3H).

A mixture of 2-((5-methylthiophen-2-yl)sulfonyl)pyridine (310 mg, 1.30 mmol), Benzoyl peroxide (75%; 20.9 mg, 0.0648 mmol), N-Bromosuccinimide (253 mg, 1.42 mmol) and 1,2-dichloroethane (6.5 mL) was stirred at 80° C. for 16 h. The solvent was removed under reduced pressure and the crude was purified by chromatography (EtOAc/cyclohexane 20→40%) to afford 2-((5-(bromomethyl)thiophen-2-yl)sulfonyl)pyridine as a white solid (294 mg, 71%). A mixture of 2-((5-(bromomethyl)thiophen-2-yl)sulfonyl)pyridine (133 mg, 0.418 mmol), NaN$_3$ (32.6 mg, 0.502 mmol) and DMF (2.1 mL) was stirred at 70° C. for 16 h. After cooling to rt, EtOAc (20 mL) was added. The organic phase was washed with 1:1 H$_2$O/brine (2×20 mL), dried over MgSO$_4$ and filtered. The solvent was removed under reduced pressure and the crude was purified by chromatography (EtOAc/cyclohexane 35→60%). The intermediate was dissolved in THF (2.1 mL) and Pd/C (10%; 44 mg, 0.0418 mmol) was then added. The mixture was stirred at rt under H$_2$ atmosphere (balloon) for 16 h, and subsequently filtered through celite. The solvent was removed under reduced pressure and the crude was purified by chromatography (MeOH/DCM 0→20%) to afford the title compound as a white solid (53 mg, 50%). $^1$H NMR (500 MHz, CDCl$_3$) δ 8.69 (ddd, J=4.7, 1.7, 0.9 Hz, 1H), 8.15 (dt, J=7.9, 1.0 Hz, 1H), 7.92 (td, J=7.8, 1.7 Hz, 1H), 7.70 (d, J=3.8 Hz, 1H), 7.46 (ddd, J=7.6, 4.7, 1.1 Hz, 1H), 6.92 (dt, J=3.9, 1.0 Hz, 1H), 4.07 (d, J=0.9 Hz, 2H), 1.62 (s, 2H). $^{13}$C NMR (126 MHz, CDCl$_3$) δ 159.60, 159.12, 150.48, 138.27, 136.95, 135.65, 127.01, 123.94, 121.78, 41.71. HRMS (ESI) for $C_{10}H_{11}N_2O_2S_2$ ([M+H]$^+$): Calculated 255.0257; Observed 255.0276.

Example 7: (5-(Naphthalen-1-ylsulfonyl)thiophen-2-yl)methanamine

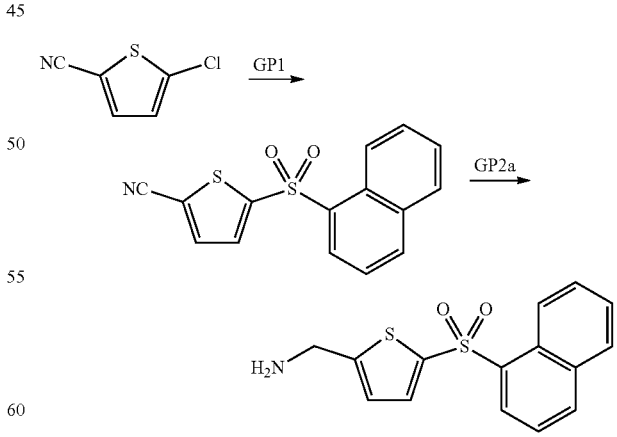

5-(Naphthalen-1-ylsulfonyl)thiophene-2-carbonitrile was synthesised according to general procedures GP1—from i) 5-chlorothiophene-2-carbonitrile (95 μL, 0.901 mmol), naphthalene-1-thiol (137 μL, 0.991 mmol), K$_2$CO$_3$ (250 mg, 1.80 mmol) and DMF (3.0 mL); 120° C., 16 h. ii) m-CPBA (77%; 504 mg, 2.25 mmol) and DCM (15 mL); rt, 16 h. The crude was purified by chromatography (EtOAc/cyclohexane 0→15%) to afford a colourless oil (170 mg, 63%). $^1$H NMR (500 MHz, CDCl$_3$) δ 8.78 (m, 1H), 8.51 (dd, J=7.4, 1.2 Hz, 1H), 8.17 (d, J=8.2 Hz, 1H), 7.96 (d, J=8.2 Hz, 1H), 7.75-7.67 (m, 2H), 7.67-7.59 (m, 2H), 7.49 (d, J=4.1 Hz, 1H).

The title compound was synthesised according to general procedures GP2a—from BH$_3$ (1.0 M in THF; 1.10 mL, 1.10 mmol), 5-(naphthalen-1-ylsulfonyl)thiophene-2-carbonitrile (110 mg, 0.367 mmol) and THF (1.8 mL); rt, 2 h. The crude was purified by chromatography (MeOH/DCM 0→20%) to afford a white crystalline solid (25 mg, 23%). $^1$H NMR (500 MHz, CDCl$_3$) δ 8.86 (dd, J=8.7, 0.8 Hz, 1H), 8.47 (dd, J=7.4, 1.2 Hz, 1H), 8.09 (d, J=8.2 Hz, 1H), 7.95-7.87 (m, 1H), 7.70-7.64 (m, 2H), 7.63-7.54 (m, 2H), 6.84 (dt, J=3.9, 1.0 Hz, 1H), 4.01 (d, J=0.9 Hz, 2H), 1.58 (s, 3H). $^{13}$C NMR (126 MHz, CDCl$_3$) δ 157.61, 141.08, 137.18, 135.25, 134.40, 133.68, 129.61, 129.23, 128.54, 127.07, 124.65, 124.63, 123.50, 41.67. HRMS (ESI) for C$_{15}$H$_{11}$O$_2$S$_2$ ([M-NH$_2$]$^+$): Calculated 287.0195; Observed 287.0226.

Example 8: (5-(4-(Methylsulfonyl)butylsulfonyl)thiophen-2-yl)methanamine

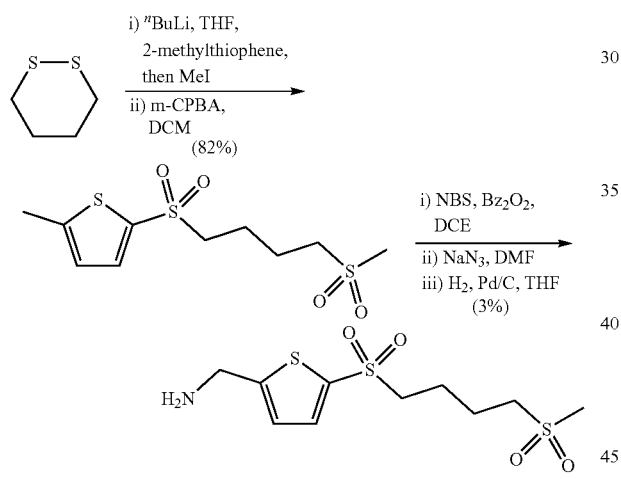

$^n$BuLi (2.5M in hexane; 1.53 mL, 3.82 mmol) was added to a solution of 2-methylthiophene (372 μL, 3.82 mmol) in THF (11.6 mL) at −78° C. and the mixture was warmed to −40° C. over 20 min. A solution of 1,2-dithiane (417 mg, 3.48 mmol) in THF (5.8 mL) was added and the mixture was warmed to rt over 30 min. MeI (216 μL, 3.82 mmol) was subsequently added and the mixture was stirred at rt for a further 2 h. H$_2$O (40 mL) was added and the aqueous phase was extracted with EtOAc (3×50 mL). The combined organic phase was washed with brine (40 mL), dried over MgSO$_4$ and filtered. The solvent was removed under reduced pressure and the crude was purified by chromatography (EtOAc/cyclohexane 0→5%) to afford 2-methyl-5-((4-(methylthio)butyl)thio)thiophene as a pink oil (692 mg, 83%). m-CPBA (77%; 3.03 g, 13.5 mmol) was added in small portions to a solution of 2-methyl-5-((4-(methylthio)butyl)thio)thiophene (686 mg, 2.62 mmol) in DCM (10.5 mL) and the mixture was stirred at rt for 16 h. DCM (20 mL) was added. The organic phase was washed with 2 M NaOH (30 mL), dried over MgSO$_4$ and filtered. The solvent was removed under reduced pressure to afford 2-methyl-5-((4-(methylsulfonyl)butyl)sulfonyl)thiophene as a white solid (863 mg, 99%). $^1$H NMR (500 MHz, CDCl$_3$) δ 7.46 (m, 1H), 6.80 (m, 1H), 3.19 (t, J=7.0 Hz, 2H), 3.01 (t, J=6.8 Hz, 2H), 2.87 (s, 3H), 2.53 (s, 3H), 1.93 (br, 4H).

A mixture of 2-methyl-5-((4-(methylsulfonyl)butyl)sulfonyl)thiophene (860 mg, 2.90 mmol), Bz$_2$O$_2$ (75%; 46.8 mg, 0.145 mmol), NBS (568 mg, 3.19 mmol) and DCE (14.5 mL) was stirred at 70° C. for 16 h. The solvent was removed under reduced pressure and the crude was dissolved in DMF (14.5 mL). NaN$_3$ (226 mg, 3.40 mmol) was added and the mixture was stirred at 70° C. for 5 h. After cooling to rt, EtOAc (30 mL) was added. The organic phase was washed with 1:1 H$_2$O/brine (3×30 mL), dried over MgSO$_4$ and filtered. The solvent was removed under reduced pressure and the crude was purified by chromatography (EtOAc/DCM 5→30%) to afford 2-(azidomethyl)-5-((4-(methylsulfonyl)butyl)sulfonyl)thiophene as a colourless oil (414 mg, 42%). A mixture of (azidomethyl)-5-((4-(methylsulfonyl)butyl)sulfonyl)-thiophene (410 mg, 1.22 mmol) and Pd/C (10%; 129 mg, 0.122 mmol) in THF (6.1 mL) was stirred at rt under H$_2$ atmosphere (balloon) for 16 h, and subsequently filtered through celite. The solvent was removed under reduced pressure and the crude was purified by chromatography (MeOH/DCM 0→20%) to afford the title compound as a white solid (27 mg, 6%). $^1$H NMR (500 MHz, CDCl$_3$) δ 7.54 (d, J=3.8 Hz, 1H), 6.95 (mm, 1H), 4.11 (s, 2H), 3.25-3.19 (m, 2H), 3.05-3.00 (m, 2H), 2.89 (s, 3H), 2.03-1.91 (m, 4H), 1.71 (s, 2H). $^{13}$C NMR (126 MHz, CDCl$_3$) δ 158.73, 137.14, 134.65, 123.97, 56.81, 53.92, 41.63, 40.85, 22.16, 21.11. HRMS (ESI) for C$_{10}$H$_{18}$NO$_4$S$_3$ ([M+H]$^+$): Calculated 312.0393; Observed 312.0417.

Example 9: (5-(3-(Methylsulfonyl)phenylsulfonyl)thiophen-2-yl)methanamine

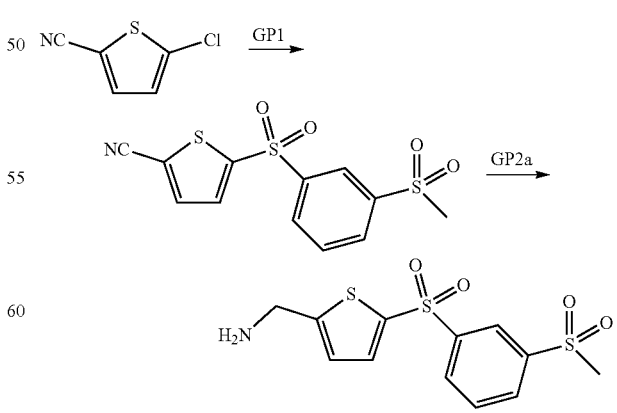

5-((3-(Methylsulfonyl)phenyl)sulfonyl)thiophene-2-carbonitrile was synthesised according to general procedures GP1—from i) 5-chlorothiophene-2-carbonitrile (120 µL, 1.14 mmol), 3-(methylthio)benzenethiol (178 mg, 1.14 mmol), K$_2$CO$_3$ (157 mg, 1.14 mmol) and DMF (5.7 mL); 120° C., 16 h. ii) m-CPBA (77%; 1.15 g, 5.13 mmol) and DCM (5.7 mL); rt, 16 h. The crude was purified by chromatography (EtOAc/DCM 5→30%) to afford a white solid (207 mg, 56%). $^1$H NMR (500 MHz, CDCl$_3$) δ 8.57 (t, J=1.7 Hz, 1H), 8.28 (ddd, J=7.9, 1.8, 1.1 Hz, 1H), 8.23 (ddd, J=7.9, 1.6, 1.1 Hz, 1H), 7.83 (t, J=7.9 Hz, 1H), 7.72 (d, J=4.1 Hz, 1H), 7.60 (d, J=4.1 Hz, 1H), 3.13 (s, 3H). 3.09 (s, 3H), 1.65 (s, 2H). $^{13}$C NMR (126 MHz, CDCl$_3$) δ 160.00, 144.45, 142.31, 138.59, 134.88, 132.21, 131.73, 130.82, 126.38, 124.12, 44.45, 41.64. HRMS (ESI) for C$_{12}$H$_{11}$O$_4$S$_3$ ([M-NH$_2$]$^+$): Calculated 314.9814; Observed 314.9820.

Example 10: (5-(2-(Methylsulfonyl)phenylsulfonyl)thiophen-2-yl)methanamine

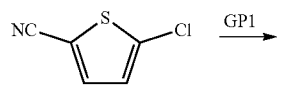

120° C., 16 h. ii) m-CPBA (77%; 839 mg, 3.74 mmol) and DCM (2.8 mL); rt, 6 h. The crude was purified by chromatography (EtOAc/DCM 5→30%) to afford a white solid (46 mg, 17%). $^1$H NMR (500 MHz, CDCl$_3$) δ 8.47 (m, 1H), 8.37 (m, 1H), 7.96-7.87 (m, 3H), 7.54 (d, J=4.1 Hz, 1H), 3.49 (s, 3H).

The title compound was synthesised according to general procedures GP2a—from BH$_3$ (1.0 M in THF; 0.41 mL, 0.41 mmol), 5-((2-(methylsulfonyl)phenyl)sulfonyl)thiophene-2-carbonitrile (45 mg, 0.137 mmol) and THF (0.8 mL); rt, 1 h. The crude was purified by chromatography (MeOH/DCM 0→20%) to afford the title compound as a white solid (17 mg, 39%). $^1$H NMR (500 MHz, CDCl$_3$) δ 8.43 (dd, J=7.5, 1.7 Hz, 1H), 8.33 (dd, J=7.6, 1.6 Hz, 1H), 7.88 (d, J=3.9 Hz, 1H), 7.85-7.76 (m, 2H), 6.88 (dt, J=3.9, 0.9 Hz, 1H), 4.06 (d, J=0.8 Hz, 2H), 3.51 (s, 3H), 1.59 (s, 2H). $^{13}$C NMR (126 MHz, CDCl$_3$) δ 159.33, 142.15, 139.62, 138.92, 136.80, 134.50, 134.07, 132.79, 132.44, 123.74, 45.73, 41.73. HRMS (ESI) for C$_{12}$H$_{14}$NO$_4$S$_3$ ([M+H]$^+$): Calculated 332.0080; Observed 332.0108.

Example 11: N-(4-(5-(Aminomethyl)thiophen-2-ylsulfonyl)phenyl)methanesulfonamide

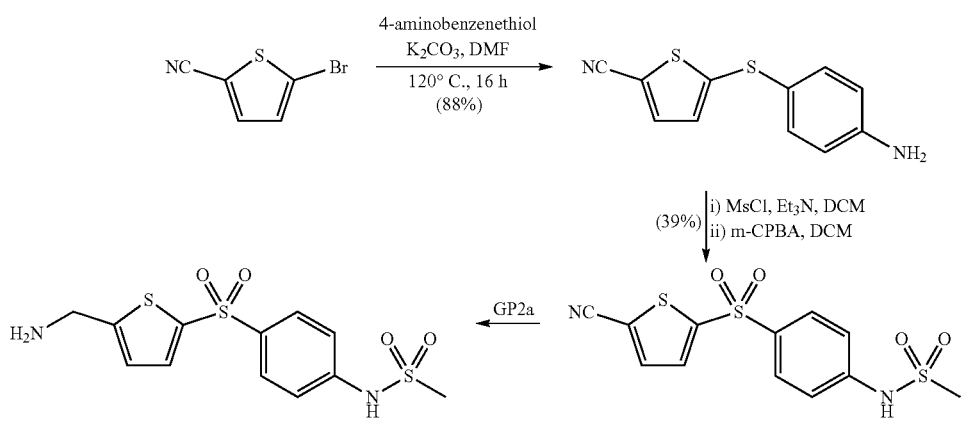

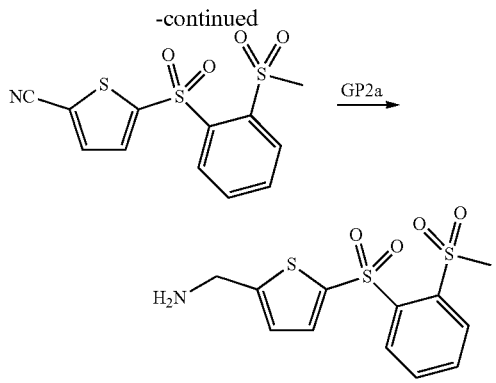

5-((2-(Methylsulfonyl)phenyl)sulfonyl)thiophene-2-carbonitrile was synthesised according to general procedures GP1—from i) 5-chlorothiophene-2-carbonitrile (87.8 µL, 0.832 mmol), 2-(methylthio)benzenethiol (130 mg, 0.832 mmol), K$_2$CO$_3$ (172 mg, 1.25 mmol) and DMF (2.8 mL);

A mixture of 5-bromothiophene-2-carbonitrile (324 mg, 1.72 mmol), K$_2$CO$_3$ (476 mg, 3.44 mmol) and 4-aminobenzenethiol (237 mg, 1.89 mmol) in DMF (5.8 mL) was stirred at 120° C. for 16 h. After cooling to rt, EtOAc (20 mL) was added. The organic phase was washed with 1:1 H$_2$O/brine (3×20 mL), dried over MgSO$_4$ and filtered. The solvent was removed under reduced pressure and the crude was purified by chromatography (EtOAc/cyclohexane 5→40%) to afford 5-((4-aminophenyl)thio)thiophene-2-carbonitrile as an orange solid (353 mg, 88%). $^1$H NMR (500 MHz, CDCl$_3$) δ 7.40 (d, J=3.9 Hz, 1H), 7.34 (d, J=8.3 Hz, 2H), 6.86 (d, J=3.9 Hz, 1H), 6.67 (d, J=8.4 Hz, 2H), 3.92 (br, 2H).

A mixture of 5-((4-aminophenyl)thio)thiophene-2-carbonitrile (120 mg, 0.517 mmol), MsCl (44.0 µL, 0.568 mmol) and pyridine (1.7 mL) was stirred at rt for 16 h. 2 M HCl (30 mL) was added. The aqueous phase was extracted with DCM (3×20 mL). The combined organic phase was dried over MgSO$_4$ and filtered. The solvent was removed under reduced pressure and the crude was dissolved in DCM (2.6 mL). m-CPBA (77%; 254 mg, 1.14 mmol) was added and the mixture was stirred at rt for 5 h. sat. NaHCO$_3$ (40 mL) was added and the aqueous phase was extracted with EtOAc (3×40 mL). The combined organic phase was dried over MgSO$_4$ and filtered. The solvent was removed under reduced pressure and the crude was purified by chromatography (MeOH/DCM 0→15%) to afford N-(4-((5-cyanothiophen-2-yl)sulfonyl)phenyl)methanesulfonamide as a white solid (69 mg, 39%). $^1$H NMR (500 MHz, CDCl$_3$) δ 7.50 (d, J=3.9 Hz, 1H), 7.41-7.37 (m, 2H), 7.26-7.19 (m, 3H), 7.09 (d, J=3.9 Hz, 1H), 3.05 (s, 3H).

The title compound was synthesised according to general procedures GP2a—from BH$_3$ (1.0 M in THF; 0.61 mL, 0.61 mmol), N-(4-((5-cyanothiophen-2-yl)sulfonyl)phenyl)methanesulfonamide (69 mg, 0.202 mmol) and THF (0.6 mL); rt, 1 h. The crude was purified by chromatography (MeOH/DCM 5→25%) to afford the title compound as a yellow solid (2 mg, 3%). $^1$H NMR (500 MHz, MeOD) δ 7.90-7.84 (m, 2H), 7.58 (d, J=3.8 Hz, 1H), 7.38-7.32 (m, 2H), 7.04 (d, J=3.8 Hz, 1H), 4.02 (s, 2H), 3.03 (s, 3H). $^{13}$C NMR (126 MHz, MeOD) δ 156.79, 146.06, 142.74, 136.92, 134.52, 130.00, 126.62, 119.69, 41.34, 40.06. HRMS (ESI) for C$_{12}$H$_{15}$N$_2$O$_4$S$_3$ ([M+H]$^+$): Calculated 347.0188; Observed 347.0190.

Example 12: 4-((5-(Aminomethyl)thiophen-2-yl)sulfonyl)-N,N-dimethylbenzenesulfonamide

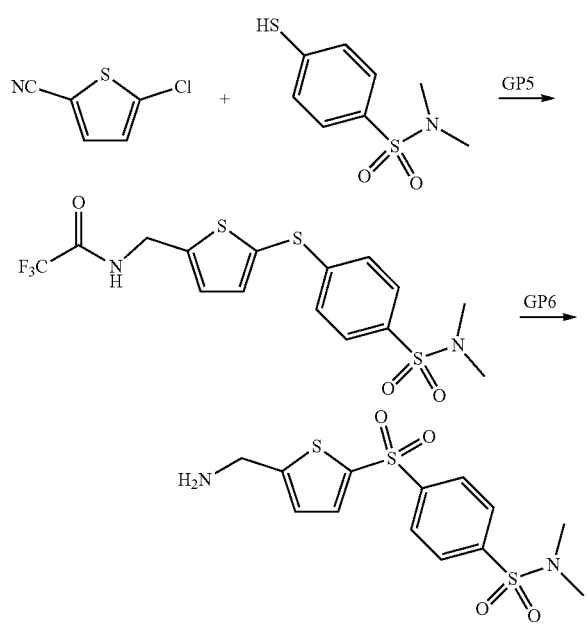

N-((5-((4-(N,N-Dimethylsulfamoyl)phenyl)thio)thiophen-2-yl)methyl)-2,2,2-trifluoroacetamide was synthesised according to general procedures GP5—from i) 5-chlorothiophene-2-carbonitrile (171 mg, 1.19 mmol), 4-mercapto-N,N-dimethylbenzenesulfonamide (235 mg, 1.08 mmol), K$_2$CO$_3$ (224 mg, 1.62 mmol) and DMF (3.6 mL); 130° C., 16 h. Chromatography (EtOAc/cyclohexane 0→35%), 166 mg, 47%. ii) 4-((5-cyanothiophen-2-yl)thio)-N,N-dimethylbenzenesulfonamide (160 mg, 0.494 mmol), BH$_3$ (1.0 M in THF; 1.48 mL, 1.48 mmol), THF (3.0 mL); rt, 1 h. iii) TFAA (82.4 μL, 0.593 mmol), Et$_3$N (89.5 μL, 0.642 mmol), DCM (3.0 mL); rt, 1 h. The crude was purified by chromatography (EtOAc/cyclohexane 5→45%) to afford N-((5-((4-(N,N-dimethylsulfamoyl)phenyl)thio)thiophen-2-yl)methyl)-2,2,2-trifluoroacetamide as a white solid (146 mg, 70% over 2 steps). $^1$H NMR (500 MHz, CDCl$_3$) δ 7.62-7.58 (m, 2H), 7.32 (br, 1H), 7.24-7.18 (m, 3H), 7.04 (d, J=3.6 Hz, 1H), 4.68 (d, J=6.0 Hz, 2H), 2.68 (s, 6H).

The title compound was synthesised according to general procedures GP6—from i) N-((5-((4-(N,N-dimethylsulfamoyl)phenyl)thio)thiophen-2-yl)methyl)-2,2,2-trifluoroacetamide (146 mg, 0.344 mmol), m-CPBA (77%; 170 mg, 0.758 mmol), DCM (2.5 mL); rt, 16 h; chromatography (EtOAc/cyclohexane 10→60%). ii) 7 N NH$_3$ in MeOH (3.0 mL); rt, 16 h. The crude was purified by chromatography (MeOH/DCM 0→10%) to afford a white solid (63 mg, 68% over 2 steps). $^1$H NMR (500 MHz, CDCl$_3$) δ 8.16-8.12 (m, 2H), 7.93-7.89 (m, 2H), 7.64 (d, J=3.9 Hz, 1H), 6.93 (m, 1H), 4.10 (d, J=0.8 Hz, 2H), 2.76 (s, 6H), 1.57 (s, 2H). $^{13}$C NMR (126 MHz, CDCl$_3$) δ 159.82, 146.47, 140.71, 138.96, 134.80, 128.64, 128.17, 124.09, 41.74, 37.93. HRMS (ESI) for C$_{13}$H$_{14}$NO$_4$S$_3$ ([M-NH$_2$]$^+$): Calculated 344.0080; Observed 344.0123.

4-Mercapto-N,N-dimethylbenzenesulfonamide

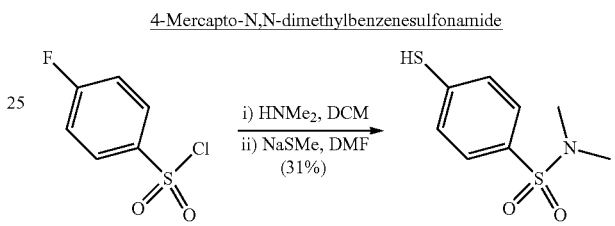

A mixture of 4-fluorobenzene-1-sulfonyl chloride (2.0 g, 10.3 mmol), HNMe$_2$ (2.0M in MeOH; 11.0 mL, 22.0 mmol) and DCM (11.0 mL) was stirred at rt for 5 min. DCM (30 mL) was added. The organic phase was washed with 1 M HCl (30 mL) and brine (30 mL), dried over MgSO$_4$ and filtered. The solvent was removed under reduced pressure to afford 4-fluoro-N,N-dimethylbenzenesulfonamide as a white solid (2.12 g, quant.). A mixture of 4-fluoro-N,N-dimethylbenzenesulfonamide (1.50 g, 7.39 mmol), NaSMe (2.08 g, 29.7 mmol) and DMF (9.0 mL) was stirred at 170° C. in a sealed tube for 16 h. After cooling to rt, 1 M NaOH (40 mL) was added. The aqueous phase was washed with Et$_2$O (2×40 mL), acidified to pH<2 with 2 M HCl and then extracted with Et$_2$O (3×40 mL). The combined organic phase was dried over MgSO$_4$ and filtered. The solvent was removed under reduced pressure to afford 4-mercapto-N,N-dimethylbenzenesulfonamide as an orange oil (503 mg, 31%). $^1$H NMR (500 MHz, CDCl$_3$) δ 7.67-7.58 (m, 2H), 7.43-7.35 (m, 2H), 3.67 (s, 1H), 2.71 (s, 6H).

Example 13: 3-((5-(Aminomethyl)thiophen-2-yl)sulfonyl)-N,N-dimethylbenzenesulfonamide

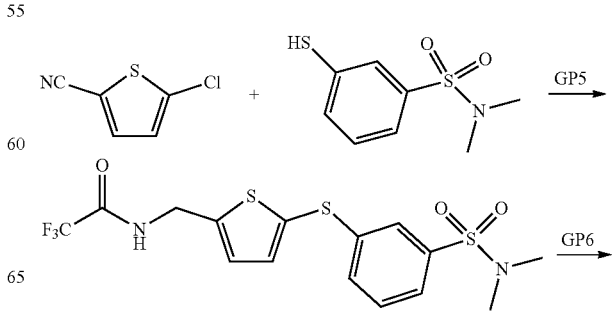

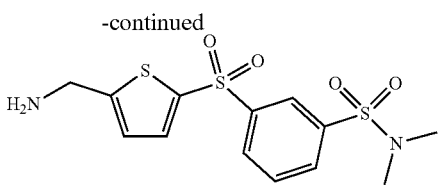

N-((5-((3-(N,N-dimethylsulfamoyl)phenyl)thio)thiophen-2-yl)methyl)-2,2,2-trifluoroacetamide was synthesised according to general procedures GP5—from i) 5-chlorothiophene-2-carbonitrile (326 mg, 2.27 mmol), 3-mercapto-N,N-dimethylbenzenesulfonamide (492 mg, 2.27 mmol), $K_2CO_3$ (469 mg, 3.40 mmol) and DMF (7.6 mL); 130° C., 16 h. Yield—316 mg, 43%. ii) 3-((5-cyanothiophen-2-yl)thio)-N,N-dimethylbenzenesulfonamide (310 mg, 0.957 mmol), $BH_3$ (1.0 M in THF; 2.90 mL, 2.90 mmol), THF (5.8 mL); rt, 1 h. iii) TFAA (200 µL, 1.44 mmol), $Et_3N$ (267 µL, 1.91 mmol), DCM (3.2 mL); rt, 16 h. The crude was purified by chromatography (EtOAc/cyclohexane 5→60%) to afford a light orange gum (191 mg, 44%).

The title compound was synthesised according to general procedures GP6—from i) N-((5-((3-(N,N-dimethylsulfamoyl)phenyl)thio)thiophen-2-yl)methyl)-2,2,2-trifluoroacetamide (187 mg, 0.410 mmol), m-CPBA (77%; 202 mg, 0.901 mmol), DCM (2.7 mL); rt, 6 h; chromatography (EtOAc/cyclohexane 0→60%). ii) 7 N $NH_3$ in MeOH (4.0 mL); rt, 16 h. The crude was purified by chromatography (EtOH/cyclohexane 5→60%) to afford an orange oil (40 mg, 40%). $^1$H NMR (500 MHz, $CDCl_3$) δ 8.35 (t, J=1.7 Hz, 1H), 8.20 (ddd, J=7.9, 1.7, 1.1 Hz, 1H), 7.97 (ddd, J=7.8, 1.6, 1.2 Hz, 1H), 7.73 (t, J=7.9 Hz, 1H), 7.63 (d, J=3.9 Hz, 1H), 6.94 (dt, J=3.8, 1.0 Hz, 1H), 4.10 (d, J=0.6 Hz, 2H), 2.76 (s, 6H), 1.79 (s, 2H). $^{13}$C NMR (126 MHz, $CDCl_3$) δ 159.48, 144.13, 139.00, 137.85, 134.70, 131.86, 131.20, 130.46, 126.36, 124.20, 41.62, 37.95. HRMS (ESI) for $C_{13}H_{17}N_2O_4S_3$ ([M+H]$^+$): Calculated 361.0345; Observed 361.0350.

3-Mercapto-N,N-dimethylbenzenesulfonamide

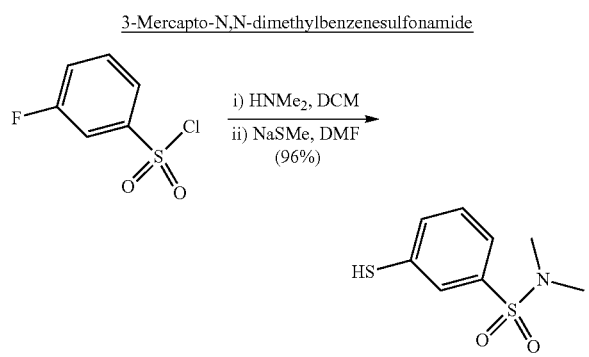

A mixture of 3-fluorobenzene-1-sulfonyl chloride (1.0 g, 5.14 mmol), $HNMe_2$ (2.0 M in MeOH; 5.4 mL, 10.8 mmol) and DCM (17.0 mL) was stirred at rt for 5 min. DCM (30 mL) was added. The organic phase was washed with 1 M HCl (50 mL) and brine (30 mL), dried over $MgSO_4$ and filtered. The solvent was removed under reduced pressure to afford 3-fluoro-N,N-dimethylbenzenesulfonamide as a white solid (1.03 g, 99%). A mixture of 3-fluoro-N,N-dimethylbenzenesulfonamide (0.90 g, 4.43 mmol), NaSMe (1.24 g, 17.7 mmol) and DMF (5.5 mL) was stirred at 165° C. in a sealed tube for 16 h. After cooling to rt, $Et_2O$ (50 mL) was added. The organic phase was extracted with 1 M NaOH (2×30 mL). The combined aqueous phase was acidified to pH<4 with 2 M HCl and then extracted with $Et_2O$ (3×40 mL). The combined organic phase was dried over $MgSO_4$ and filtered. The solvent was removed under reduced pressure to afford 3-mercapto-N,N-dimethylbenzenesulfonamide as a light yellow crystalline solid (903 mg, 97%). $^1$H NMR (500 MHz, $CDCl_3$) δ 7.69 (t, J=1.7 Hz, 1H), 7.55 (dt, J=7.7, 1.4 Hz, 1H), 7.49 (ddd, J=7.9, 1.7, 1.2 Hz, 1H), 7.41 (t, J=7.8 Hz, 1H), 3.64 (s, 1H), 2.74 (s, 6H).

Example 14: (5-((3-(Pyrrolidin-1-ylsulfonyl)phenyl)sulfonyl)thiophen-2-yl)methanamine

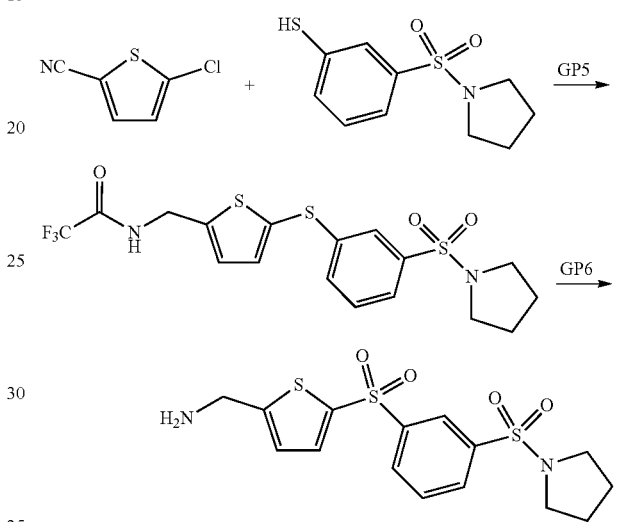

2,2,2-Trifluoro-N-((5-((3-(pyrrolidin-1-ylsulfonyl)phenyl)thio)thiophen-2-yl)methyl)acetamide was synthesised according to general procedures GP5—from i) 5-bromothiophene-2-carbonitrile (211 mg, 1.12 mmol), 3-(pyrrolidin-1-ylsulfonyl)benzenethiol (300 mg, 1.23 mmol), $K_2CO_3$ (255 mg, 1.85 mmol) and DMF (4.1 mL); 125° C., 16 h. Chromatography (EtOAc/cyclohexane 0→50%), 107 mg, 27%. ii) 5-((3-(pyrrolidin-1-ylsulfonyl)phenyl)thio)thiophene-2-carbonitrile (107 mg, 0.305 mmol), $BH_3$ (1.0 M in THF; 0.86 mL, 0.86 mmol), THF (1.5 mL); rt, 1 h. iii) TFAA (85 µL, 0.61 mmol), $Et_3N$ (106 µL, 0.760 mmol), DCM (1.5 mL); rt, 2 h. The crude was purified by chromatography (EtOAc/cyclohexane 5→50%) to afford a yellow oil (107 mg, 78% over 2 steps).

The title compound was synthesised according to general procedures GP6—from i) 2,2,2-trifluoro-N-((5-((3-(pyrrolidin-1-ylsulfonyl)phenyl)thio)thiophen-2-yl)methyl)acetamide (107 mg, 0.238 mmol), m-CPBA (77%; 117 mg, 0.523 mmol), DCM (1.6 mL); rt, 4 h. ii) 7 N $NH_3$ in MeOH (3.0 mL); rt, 16 h. The crude was purified by chromatography (EtOH/cyclohexane 5→40%) to afford a white solid (49 mg, 51%). $^1$H NMR (500 MHz, $CDCl_3$) δ 8.37 (br, 1H), 8.16 (m, J=7.0 Hz, 1H), 8.00 (m, J=7.2 Hz, 1H), 7.69 (t, J=7.8 Hz, 1H), 7.60 (m, 1H), 6.90 (br, 1H), 4.07 (br, 2H), 3.25 (br, 4H), 1.78 (br, 4H), 1.64 (br, 2H). $^{13}$C NMR (126 MHz, $CDCl_3$) δ 159.69, 144.01, 139.17, 138.94, 134.64, 131.61, 131.00, 130.42, 126.07, 124.06, 48.17, 41.64, 25.40. HRMS (ESI) for $C_{15}H_{19}N_2O_4S_3$ ([M+H]$^+$): Calculated 387.0502; Observed 387.0493.

3-(Pyrrolidin-1-ylsulfonyl)benzenethiol

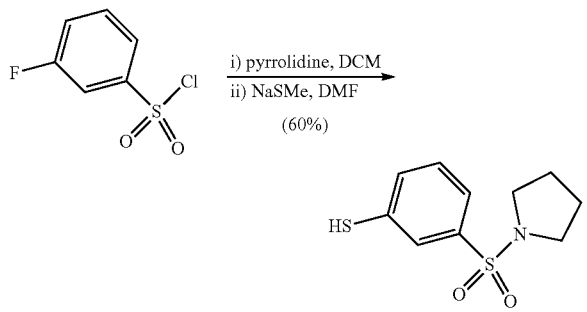

A mixture of 3-fluorobenzene-1-sulfonyl chloride (1.0 g, 5.14 mmol), pyrrolidine (0.99 mL, 11.8 mmol) and DCM (10.3 mL) was stirred at rt for 15 min. EtOAc (40 mL) was added. The organic phase was washed with 1 M HCl (3×30 mL) and brine (30 mL), dried over MgSO$_4$ and filtered. The solvent was removed under reduced pressure to afford 1-((3-fluorophenyl)sulfonyl)pyrrolidine (quant.). 566 mg (2.47 mmol) of the crude was dissolved in DMF (4.9 mL). NaSMe (692 mg, 9.89 mmol) was added and the mixture was stirred at 165° C. in a sealed tube for 16 h. After cooling to rt, Et$_2$O (60 mL) was added. The organic phase was washed with 1:1 1 M HCl/brine (3×30 mL), dried over MgSO$_4$ and filtered. The solvent was removed under reduced pressure to afford 3-(pyrrolidin-1-ylsulfonyl)benzenethiol as a light brown solid (751 mg, 60%). $^1$H NMR (500 MHz, CDCl$_3$) δ 7.89-7.82 (m, 2H), 7.24-7.18 (m, 2H), 3.29-3.20 (m, 4H), 1.85-1.73 (m, 4H), 1.56 (s, 1H).

Example 15: (5-((4-(Pyrrolidin-1-ylsulfonyl)phenyl)sulfonyl)thiophen-2-yl)methanamine

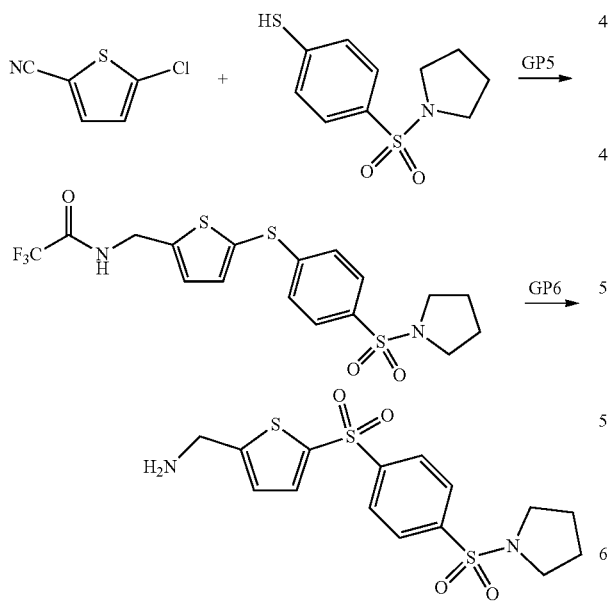

2,2,2-Trifluoro-N-((5-((3-(pyrrolidin-1-ylsulfonyl)phenyl)thio)thiophen-2-yl)methyl)acetamide was synthesised according to general procedures GP5—from i) 5-chlorothiophene-2-carbonitrile (161 mg, 1.12 mmol), 4-(pyrrolidin-1-ylsulfonyl)benzenethiol (300 mg, 1.23 mmol), K$_2$CO$_3$ (255 mg, 1.85 mmol) and DMF (4.1 mL); 125° C., 16 h. Chromatography (EtOAc/cyclohexane 0→50%), 98 mg, 25%. ii) 5-((4-(pyrrolidin-1-ylsulfonyl)phenyl)thio)thiophene-2-carbonitrile (98 mg, 0.279 mmol), BH$_3$ (1.0 M in THF; 0.86 mL, 0.86 mmol), THF (1.5 mL); rt, 1 h. iii) TFAA (78 μL, 0.559 mmol), Et$_3$N (97 μL, 0.699 mmol), DCM (1.3 mL); rt, 2 h. The crude was purified by chromatography (EtOAc/cyclohexane 5→50%) to afford a white solid (91 mg, 72%).

The title compound was synthesised according to general procedures GP6—from i) 2,2,2-trifluoro-N-((5-((4-(pyrrolidin-1-ylsulfonyl)phenyl)thio)thiophen-2-yl)methyl)acetamide (91 mg, 0.202 mmol), m-CPBA (77%; 100 mg, 0.444 mmol), DCM (1.4 mL); rt, 4 h. ii) 7 N NH$_3$ in MeOH (3.0 mL); rt, 16 h. The crude was purified by chromatography (EtOH/cyclohexane 5→40%, then 100%) to afford a white solid (38 mg, 49%). $^1$H NMR (500 MHz, MeOD) δ 8.20-8.15 (m, 2H), 8.04-8.00 (m, 2H), 7.70 (d, J=3.9 Hz, 1H), 7.07 (m, 1H), 4.01 (s, 2H), 3.27-3.22 (m, 4H), 1.79-1.73 (m, 4H). $^{13}$C NMR (126 MHz, MeOD) δ 159.72, 147.61, 143.08, 140.37, 136.09, 129.69, 129.18, 126.59, 49.15, 41.66, 26.28. HRMS (ESI) for C$_{15}$H$_{19}$N$_2$O$_4$S$_3$ ([M+H]$^+$): Calculated 387.0502; Observed 387.0489.

4-(Pyrrolidin-1-ylsulfonyl)benzenethiol

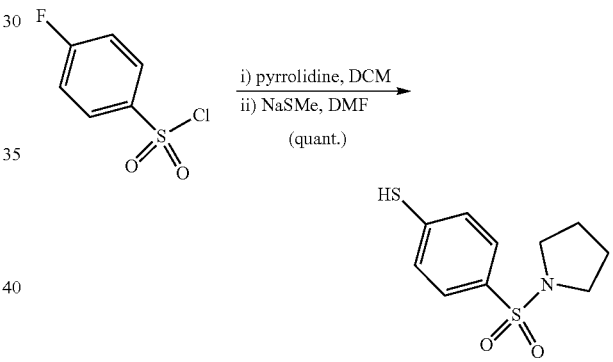

A mixture of 3-fluorobenzene-1-sulfonyl chloride (1.0 g, 5.14 mmol), pyrrolidine (0.99 mL, 11.8 mmol) and DCM (10.3 mL) was stirred at rt for 15 min. EtOAc (50 mL) was added. The organic phase was washed with 1 M HCl (3×30 mL) and brine (30 mL), dried over MgSO$_4$ and filtered. The solvent was removed under reduced pressure to afford 1-((4-fluorophenyl)sulfonyl)pyrrolidine (quant.). 504 mg (2.21 mmol) of this intermediate was dissolved in DMF (4.4 mL). NaSMe (616 mg, 8.79 mmol) was added and the mixture was stirred at 165° C. in a sealed tube for 16 h. After cooling to rt, Et$_2$O (40 mL) was added. The aqueous layer was extracted with 1 M NaOH (3×30 mL). The combined aqueous layer was acidified to pH<4 and extracted with EtOAc (3×30 mL). The combined organic phase was washed with 1:1 H$_2$O/brine (60 mL), dried over MgSO$_4$ and filtered. The solvent was removed under reduced pressure to afford 4-(pyrrolidin-1-ylsulfonyl)benzenethiol as a brown oil (552 mg, quant.). $^1$H NMR (500 MHz, CDCl$_3$) δ 7.70-7.65 (m, 2H), 7.40-7.34 (m, 2H), 3.65 (s, 1H), 3.29-3.18 (m, 4H), 1.83-1.71 (m, 4H).

Example 16: 2-((4-((5-(Aminomethyl)thiophen-2-yl)sulfonyl)phenyl)sulfonyl)ethanol hydrochloride

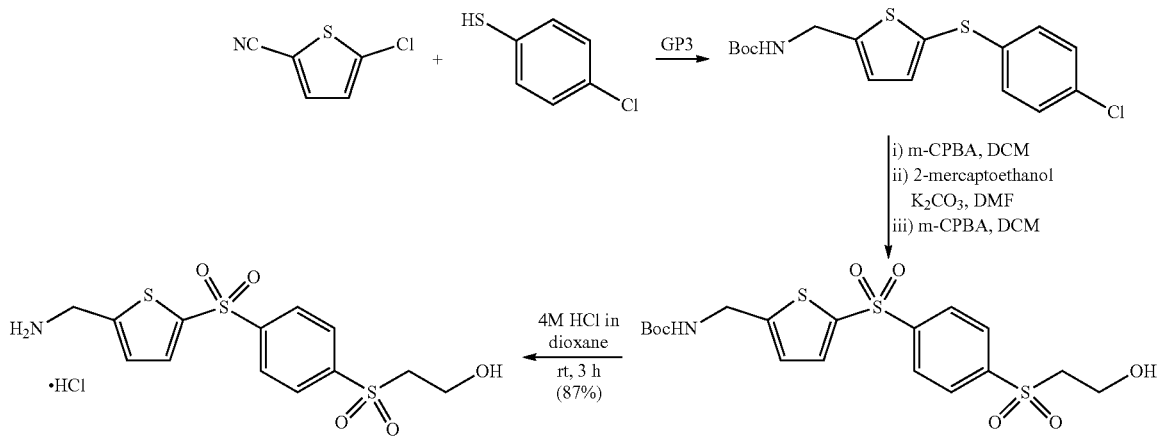

tert-Butyl ((5-((4-chlorophenyl)thio)thiophen-2-yl)methyl)carbamate was synthesised according to general procedures GP3—from i) 5-chlorothiophene-2-carbonitrile (1.0 g, 6.96 mmol), 4-chlorothiophenol (1.21 mg, 8.36 mmol), K₂CO₃ (1.73 g, 12.5 mmol) and DMF (17.5 mL); 130° C., 16 h. Chromatography (EtOAc/cyclohexane 0→5%), 882 mg, 52%. ii) 5-((4-chlorophenyl)thio)thiophene-2-carbonitrile (878 mg, 3.49 mmol), BH₃ (1.0 M in THF; 10.5 mL, 10.5 mmol), THF (21 mL); rt, 1 h. iii) Boc₂O (1.14 g, 5.22 mmol), Et₃N (0.97 mL, 6.97 mmol), DCM (11.6 mL); rt, 16 h. The crude was purified by chromatography (EtOAc/cyclohexane 0→30%) to afford a yellow oil, which was used immediately in the subsequent transformation.

tert-Butyl ((5-((4-chlorophenyl)thio)thiophen-2-yl)methyl)carbamate (from previous step) was dissolved in DCM (17.0 mL). m-CPBA (77%; 1.95 g, 8.71 mmol) was added in small portions and the mixture was stirred at rt for 5 h. EtOAc (60 mL) was added. The organic phase was washed with sat. NaHCO₃ (3×50 mL), dried over MgSO₄ and filtered. The solvent was removed under reduced pressure and the crude was purified by chromatography (EtOAc/cyclohexane 0→50%) to afford tert-butyl ((5-((4-chlorophenyl)sulfonyl)thiophen-2-yl)methyl)carbamate as a light yellow solid (980 mg, 73%). ¹H NMR (500 MHz, CDCl₃) δ 7.93-7.87 (m, 2H), 7.54 (d, J=3.8 Hz, 1H), 7.51-7.47 (m, 2H), 6.92 (d, J=3.8 Hz, 1H), 5.04 (br, 1H), 4.46 (d, J=5.4 Hz, 2H), 1.45 (s, 9H). A mixture of tert-butyl ((5-((4-chlorophenyl)sulfonyl)thiophen-2-yl)methyl)carbamate (2.0 g, 5.15 mmol), K₂CO₃ (2.13 g, 15.5 mmol) and 2-mercaptoethanol (0.90 mL, 12.9 mmol) in DMF (34 mL) was stirred at 50° C. for 3 h. After cooling to rt, EtOAc (100 mL) was added. The organic phase was washed with 1:1 H₂O/brine (5×80 mL), dried over MgSO₄ and filtered. The solvent was removed under reduced pressure and the crude was dissolved in DCM (26 mL). m-CPBA (77%; 2.66 g, 18.6 mmol) was added in small portions and the mixture was stirred at rt for 2 h. EtOAc (90 mL) was added. The organic phase was washed with sat. NaHCO₃ (4×90 mL), dried over MgSO₄ and filtered. The solvent was removed under reduced pressure and the crude was purified by chromatography (EtOAc/cyclohexane 10→60%) to afford tert-butyl ((5-((4-((2-hydroxyethyl)sulfonyl)phenyl)sulfonyl)thiophen-2-yl)methyl)carbamate as a white foam (1.46 g, 61%). ¹H NMR (500 MHz, CDCl₃) δ 8.20-8.14 (m, 2H), 8.11-8.04 (m, 2H), 7.62 (d, J=3.8 Hz, 1H), 6.96 (d, J=3.9 Hz, 1H), 5.07 (br, 1H), 4.47 (d, J=5.9 Hz, 2H), 4.08-4.00 (m, 2H), 3.44-3.30 (m, 2H), 2.51 (t, J=6.2 Hz, 1H), 1.46 (s, 9H).

A mixture of tert-butyl ((5-((4-((2-hydroxyethyl)sulfonyl)phenyl)sulfonyl)thiophen-2-yl)methyl)carbamate (52 mg, 0.113 mmol) and 4 M HCl in dioxane (3.0 mL) was stirred at rt for 3 h. The solids were filtered, washed with EtOAc and then redissolved with hot methanol. The solvent was removed under reduced pressure to afford the title compound as a white solid (39 mg, 87%). ¹H NMR (500 MHz, D₂O) δ 8.37-8.29 (m, 2H), 8.27-8.19 (m, 2H), 7.91 (m, 1H), 7.38 (m, 1H), 4.48 (s, 2H), 4.03-3.95 (m, 2H), 3.72-3.65 (m, 2H). ¹³C NMR (126 MHz, D₂O) δ 146.18, 144.20, 140.94, 136.69, 131.43, 130.19, 129.18, 58.15, 55.77, 38.19. HRMS (ESI) for C₁₃H₁₃O₅S₃ ([M-NH₂]⁺): Calculated 344.9920; Observed 344.9917.

Example 17: 2-((4-((5-(Aminomethyl)thiophen-2-yl)sulfonyl)phenyl)sulfonyl)-N,N-dimethylethanamine dihydrochloride

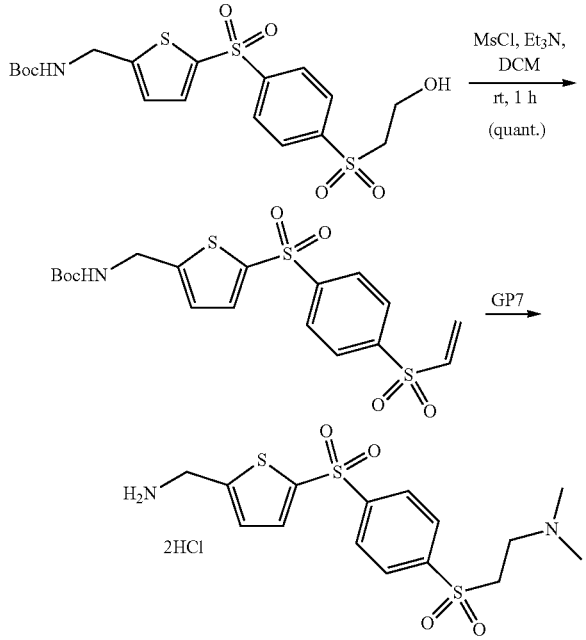

MsCl (109 μL, 1.41 mmol) was added to a solution of tert-butyl ((5-((4-((2-hydroxyethyl)sulfonyl)phenyl)sulfonyl)thiophen-2-yl)methyl)carbamate (500 mg, 1.08 mmol) and Et₃N (453 μL, 3.25 mmol) in DCM (5.4 mL) and the mixture was stirred at rt for 1 h. EtOAc (30 mL) was added. The organic solution was washed with 1:1 H₂O/bine (3×30 mL), dried over MgSO₄, filtered and the solvent was removed under reduced pressure. tert-Butyl ((5-((4-(vinylsulfonyl)phenyl)sulfonyl)thiophen-2-yl)methyl)carbamate was obtained as a light yellow foam (485 mg, quant.) and was used in the subsequent transformation without further purification. ¹H NMR (500 MHz, CDCl₃) δ 8.10 (d, J=7.3 Hz, 2H), 8.00 (d, J=7.6 Hz, 2H), 7.56 (H, 1H), 6.92 (d, J=3.2 Hz, 1H), 6.64 (dd, J=16.5, 9.7 Hz, 1H), 6.52 (d, J=16.5 Hz, 1H), 6.14 (d, J=9.7 Hz, 1H), 5.27 (br, 1H), 4.53-4.31 (m, 2H), 1.41 (s, 9H).

The title compound was synthesised according to general procedures GP7—from i) tert-butyl ((5-((4-(vinylsulfonyl)phenyl)sulfonyl)thiophen-2-yl)methyl)carbamate (72 mg, 0.162 mmol), Me₂NH (2.0 M in MeOH; 89 μL, 0.179 mmol) and DCM (0.8 mL); rt, 16 h. Chromatography (EtOH/cyclohexane 5→80%). ii) 4.0 M HCl in dioxane (4 mL); rt, 16 h. The title compound was obtained as a white solid (62 mg, 94%), which didn't require further purification. ¹H NMR (500 MHz, D₂O) δ 8.39 (d, J=8.1 Hz, 2H), 8.28 (d, J=8.3 Hz, 2H), 7.93 (d, J=3.8 Hz, 1H), 7.41 (m, 1H), 4.51 (s, 2H), 3.99 (d, J=6.8 Hz, 2H), 3.60 (s, 2H), 2.95 (br s, 6H). HRMS (ESI) for C₁₅H₂₁N₂O₄S₃ ([M+H]⁺): Calculated 389.0658; Observed 389.1300.

Example 18: (5-(Phenylsulfonyl)thiophen-2-yl)methanamine

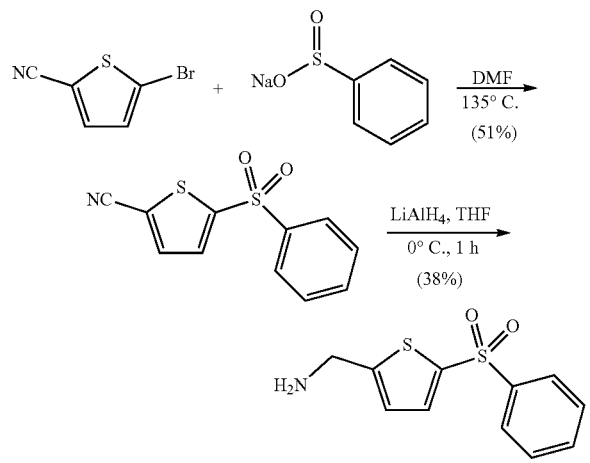

A mixture of 5-bromothiophene-2-carbonitrile (100 mg, 0.532 mmol), sodium benzenesulfinate (138 mg, 0.691 mmol) and DMF (1.0 mL) was stirred at 135° C. for 16 h. After cooling to rt, EtOAc (10 mL) was added. The organic phase was washed with H₂O (2×10 mL) and brine (10 mL), dried over MgSO₄, filtered. The solvent was removed under reduced pressure and the crude was purified by chromatography (EtOAc/cyclohexane 0→20%) to afford 5-(phenylsulfonyl)thiophene-2-carbonitrile as a white crystalline solid (67 mg, 51%). ¹H NMR (500 MHz, CDCl₃) δ 8.03-7.98 (m, 2H), 7.70-7.53 (m, 5H).

A mixture of 5-(phenylsulfonyl)thiophene-2-carbonitrile (39 mg, 0.156 mmol), LiAlH₄ (1.0 M in THF; 160 μL, 0.160 mmol) and THF (1.6 mL) was stirred at 0° C. for 1 h. H₂O (5 mL) was slowly added and the aqueous phase was extracted with DCM (3×8 mL). The combined organic phase was washed with brine (10 mL), dried over MgSO₄, filtered. The solvent was removed under reduced pressure and the crude was purified by chromatography (7 N NH₃ in MeOH/DCM 0→60%) to afford the title compound as a light brown crystalline solid (15 mg, 38%). ¹H NMR (500 MHz, CDCl₃) δ 8.01-7.95 (m, 2H), 7.63-7.48 (m, 4H), 6.88 (dt, J=3.8, 1.0 Hz, 1H), 4.07 (s, 2H), 1.58 (s, 2H). ¹³C NMR (126 MHz, CDCl₃) δ 158.19, 142.50, 140.63, 133.70, 133.26, 129.39, 127.41, 123.80, 41.71. HRMS (ESI) for C₁₁H₁₂NO₂S₂ ([M+H]⁺): Calculated 254.0304; Observed 254.0309.

Example 19: (5-(4-Methoxyphenylsulfonyl)thiophen-2-yl)methanamine

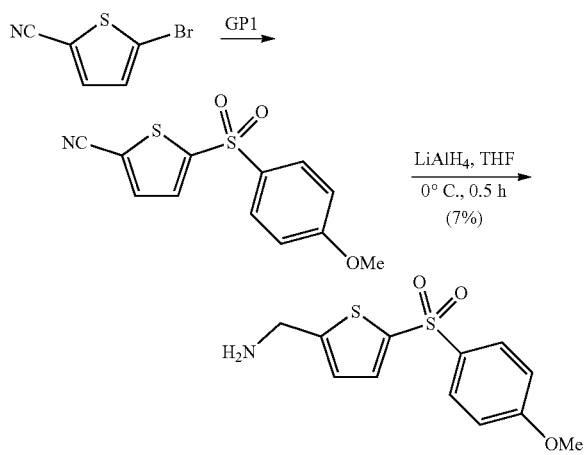

5-((4-methoxyphenyl)sulfonyl)thiophene-2-carbonitrile was synthesised according to general procedures GP1—from i) 5-bromothiophene-2-carbonitrile (89 μL, 0.796 mmol), 4-methoxythiophenol (117 μL, 0.955 mmol), K₂CO₃ (220 mg, 1.59 mmol) and DMF (2.7 mL); 140° C., 20 h. ii) m-CPBA (77%; 249 mg, 1.11 mmol) and DCM (1.7 mL); rt, 16 h. The crude was purified by chromatography (EtOAc/cyclohexane 10→20%) to afford a white solid (113 mg, 51%). ¹H NMR (500 MHz, CDCl₃) δ 7.92 (d, J=8.9 Hz, 2H), 7.58 (d, J=4.0 Hz, 1H), 7.53 (d, J=4.0 Hz, 1H), 7.02 (d, J=9.0 Hz, 2H), 3.87 (s, 3H).

A mixture of 5-((4-methoxyphenyl)sulfonyl)thiophene-2-carbonitrile (113 mg, 0.405 mmol), LiAlH₄ (2.0 M in THF; 200 μL, 0.400 mmol) and THF (1.6 mL) was stirred at 0° C. for 1 h. H₂O (5 mL) was slowly added and the aqueous phase was extracted with DCM (3×8 mL). The combined organic phase was washed with brine (10 mL), dried over MgSO₄, filtered. The solvent was removed under reduced pressure and the crude was purified by chromatography (MeOH/DCM 0→20%) to afford the title compound as an orange oil (8 mg, 7%). ¹H NMR (500 MHz, CDCl₃) δ 7.95-7.83 (m, 2H), 7.51 (d, J=3.8 Hz, 1H), 7.06-6.95 (m, 2H), 6.86-6.83 (m, 1H), 4.04 (s, 2H), 3.85 (s, 4H), 2.13-1.33 (br, 2H). ¹³C NMR (126 MHz, CDCl₃) δ 163.53, 157.36, 141.70, 134.09, 132.95, 129.68, 123.70, 114.63, 55.80, 41.71. HRMS (ESI) for C₁₂H₁₃NO₃S₂ ([M+H]⁺): Calculated 284.0410; Observed 284.0414.

Example 20: 5-(Biphenyl-3-ylsulfonyl)thiophen-2-yl)methanamine hydrochloride

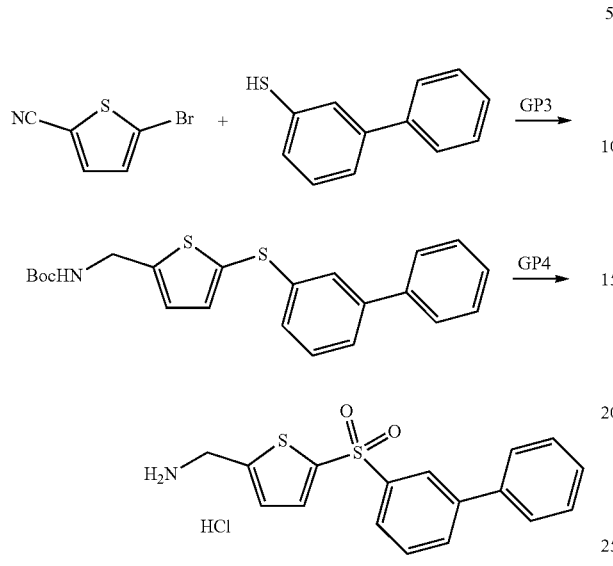

Example 21: (5-(Biphenyl-4-ylsulfonyl)thiophen-2-yl)methanamine hydrochloride

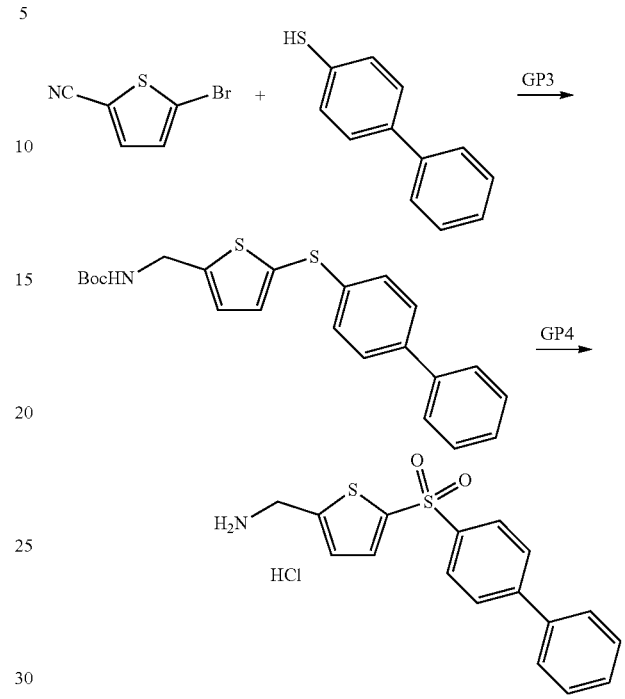

tert-Butyl ((5-([1,1'-biphenyl]-3-ylthio)thiophen-2-yl)methyl)carbamate was synthesised according to general procedures GP3—from i) 5-bromothiophene-2-carbonitrile (160 mg, 1.11 mmol), [1,1'-biphenyl]-3-thiol (223 mg, 1.22 mmol), K$_2$CO$_3$ (308 mg, 2.23 mmol) and DMF (4.6 mL); 120° C., 16 h; 327 mg, 92%. ii) 2-(5-([1,1'-biphenyl]-3-ylthio)thiophen-2-yl)acetonitrile (264 mg, 0.910 mmol), BH$_3$ (1.0 M in THF; 2.7 mL, 2.70 mmol), THF (2.7 mL); rt, 1 h. iii) Boc$_2$O (590 mg, 2.70 mmol), Et$_3$N (250 µL, 1.80 mmol), DCM (3.5 mL); rt, 16 h. The crude was purified by chromatography (EtOAc/cyclohexane 0→30%) to afford tert-butyl ((5-([1,1'-biphenyl]-3-ylthio)thiophen-2-yl)methyl)carbamate as a yellow oil (64 mg, 18%). $^1$H NMR (500 MHz, CDCl$_3$) δ 7.56 (m, 1H), 7.55 (m, 1H), 7.49 (m, 1H), 7.46 (m, 2H), 7.43-7.33 (m, 3H), 7.20 (m, 2H), 6.93 (d, J=3.3 Hz, 1H), 5.04 (s, 1H), 4.49 (s, 2H), 1.50 (s, 9H).

The title compound was synthesised according to general procedures GP4—from i) tert-butyl ((5-([1,1'-biphenyl]-3-ylthio)thiophen-2-yl)methyl)carbamate (64 mg, 0.161 mmol), m-CPBA (77%; 69 mg, 0.402 mmol), DCM (2.0 mL); 45° C., 1.5 h; chromatography (EtOAc/cyclohexane 0→30%). ii) 4 M HCl in dioxane (8.0 mL); rt, 16 h. The white precipitate was filtered, washed with excess EtOAc. It was then dissolved in MeOH and evaporated under reduced pressure to afford a white solid (25 mg, 42% over two steps). $^1$H NMR (500 MHz, MeOD) δ 8.19 (m, 1H), 7.99 (ddd, J=7.8, 1.8, 1.0 Hz, 1H), 7.96 (ddd, J=7.8, 1.8, 1.0 Hz, 1H), 7.81 (d, J=3.9 Hz, 1H), 7.70 (t, J=7.7 Hz, 1H), 7.65 (m, 2H), 7.52 (m, 2H), 7.44 (m, 1H), 7.32 (d, J=3.8 Hz, 1H), 4.38 (s, 2H). $^{13}$C NMR (126 MHz, CDCl$_3$) δ 144.2, 143.8, 142.8, 142.4, 138.8, 133.8, 131.9, 130.3, 130.1, 128.9, 128.2, 126.7, 125.7, 125.1, 37.1. LC-MS (m/z): 313 (100).

tert-Butyl ((5-([1,1'-biphenyl]-4-ylthio)thiophen-2-yl)methyl)carbamate was synthesised according to general procedures GP3—from i) 5-chlorothiophene-2-carbonitrile (168 mg, 1.17 mmol), [1,1'-biphenyl]-4-thiol (235 mg, 1.29 mmol), K$_2$CO$_3$ (356 mg, 2.58 mmol) and DMF (4.6 mL); 120° C., 16 h. Chromatography (EtOAc/cyclohexane 0→20%), 348 mg, 92%. ii) 2-(5-([1,1'-biphenyl]-4-ylthio)thiophen-2-yl)acetonitrile (387 mg, 1.32 mmol), BH$_3$ (1.0 M in THF; 4.0 mL, 4.00 mmol), THF (4.0 mL); rt, 4 h. iii) Boc$_2$O (865 mg, 3.97 mmol), Et$_3$N (370 µL, 2.65 mmol), DCM (5.1 mL); rt, 16 h. The crude was purified by chromatography (EtOAc/cyclohexane 0→30%) to afford tert-butyl ((5-([1,1'-biphenyl]-4-ylthio)thiophen-2-yl)methyl)carbamate as a yellow oil (264 mg, 50% over 2 steps). $^1$H NMR (500 MHz, CDCl$_3$) δ 7.57 (m, 2H), 7.51 (m, 2H), 7.41 (m, 2H), 7.32 (m, 1H), 7.26 (m, 2H), 7.18 (m, 1H), 6.96 (m, 1H), 4.39 (s, 2H), 1.46 (s, 9H).

The title compound was synthesised according to general procedures GP4—from i) tert-butyl ((5-([1,1'-biphenyl]-4-ylthio)thiophen-2-yl)methyl)carbamate (246 mg, 0.690 mmol), m-CPBA (300 mg, 1.74 mmol), DCM (8.0 mL); 45° C., 1 h; chromatography (MeOH/DCM 0→5%). ii) 4 M HCl in dioxane (20 mL); rt, 16 h. The white precipitate was filtered, washed with excess EtOAc. It was then dissolved in MeOH and evaporated under reduced pressure to afford a white solid (60 mg, 26% over two steps). $^1$H NMR (500 MHz, MeOD) δ 8.06 (m, 2H), 7.86 (m, 2H), 7.76 (d, J=3.7 Hz, 1H), 7.67 (m, 2H), 7.49 (m, 2H), 7.44 (m, 1H), 7.29 (d, J=3.6 Hz, 1H), 4.38 (s, 2H). $^{13}$C NMR (126 MHz, MeOD) δ 146.6, 144.7, 143.6, 140.1, 138.8, 133.4, 130.1, 128.8, 128.5, 127.7, 127.6, 126.9, 37.2. LC-MS (m/z): 313 (100).

Example 22: 3-((5-(Aminomethyl)thiophen-2-ylsulfonyl)-N-methylbenzamide hydrochloride

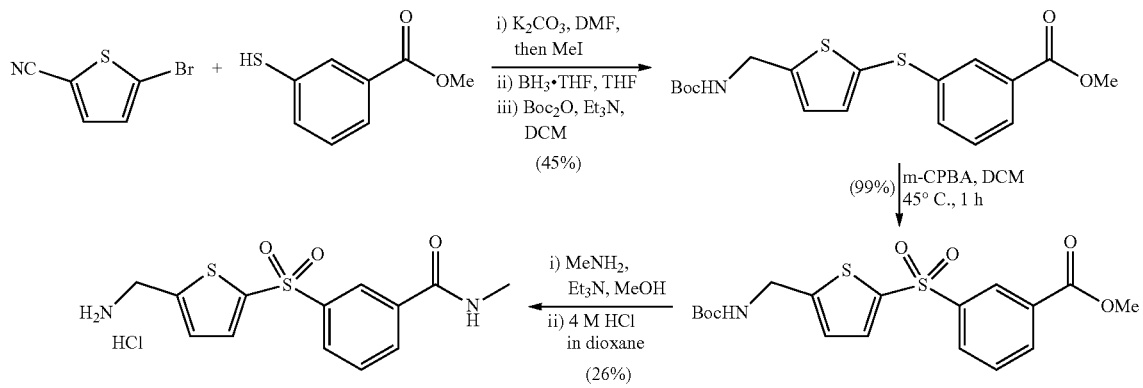

A mixture of 5-bromothiophene-2-carbonitrile (406 mg, 2.83 mmol), 3-mercaptobenzoic acid (479 mg, 3.11 mmol), and $K_2CO_3$ (781 mg, 5.65 mmol) in DMF (11 mL) was stirred at 120° C. for 16 h. After cooling to rt, MeI (406 µL, 6.52 mmol) and $K_2CO_3$ (273 mg, 1.98 mmol) were added and the mixture was stirred at 50° C. for 1 h. More MeI (406 µL) was added and the mixture was stirred at 50° C. for a further 1.5 h. EtOAc was added and the organic phase was washed with $H_2O$/brine 1:1 (3×), dried over $Na_2SO_4$ and filtered. The solvent was removed under reduced pressure and the crude was purified on by chromatography (DCM) to afford methyl 3-((5-(cyanomethyl)thiophen-2-yl)thio)benzoate as a brown oil (611 mg, 78%). To a solution of methyl 3-((5-(cyanomethyl)thiophen-2-yl)thio)benzoate (611 mg, 2.22 mmol) in THF (20 mL) was added $BF_3$.THF complex (1.0 M in THF; 6.6 mL, 6.60 mmol). The mixture was stirred for at rt for 1 h, and then quenched with EtOH. The mixture was heated at reflux for 1 h before the solvent was removed under reduced pressure. DCM (40 mL) was added, followed by $Et_3N$ (620 µL, 4.45 mmol) and $Boc_2O$ (1.45 g, 6.65 mmol). The mixture was stirred at rt for 16 h and then diluted with DCM. The organic phase was washed with $H_2O$, dried over $Na_2SO_4$, filtered and the solvent was removed under reduced pressure. The crude was purified by chromatography (EtOAc/cyclohexane 0→30%) to afford methyl 3-((5-(((tert-butoxycarbonyl)amino)methyl)thiophen-2-yl)thio)benzoate as a sticky yellow oil (482 mg, 57%). $^1$H NMR (500 MHz, MeOD) δ 7.75 (d, J=7.3 Hz, 1H), 7.80 (m, 1H), 7.30 (m, 2H), 7.15 (d, J=3.6 Hz, 1H), 6.94 (d, J=3.7 Hz, 1H), 4.81 (s, 1H), 4.39 (s, 2H), 3.84 (s, 3H), 1.43 (s, 9H).

m-CPBA (77%; 548 mg, 2.44 mmol) was added in portions to a solution of methyl 3-((5-(((tert-butoxycarbonyl)amino)methyl)thiophen-2-yl)thio)benzoate (482 mg, 1.27 mmol) in DCM (16 mL) and the mixture was stirred at 45° C. for 1 h. After cooling down to rt, EtOAc was added. The organic layer was washed with $H_2O$/$NaHCO_3$ 1:1 (3×), dried over $Na_2SO_4$, filtered and the solvent was removed under reduced pressure. The crude was purified by chromatography (MeOH/DCM 0→5%) to afford methyl 3-((5-(((tert-butoxycarbonyl)amino)methyl)thiophen-2-yl)sulfonyl)benzoate as a sticky orange oil. (520 mg, 99%). $^1$H NMR (500 MHz, MeOD) δ 8.52 (m, 1H), 8.25 (m, 1H), 8.18 (m, 1H), 7.71 (m, 1H), 7.65 (d, J=3.6 Hz, 1H), 7.01 (d, J=3.7 Hz, 1H), 4.39 (s, 2H), 3.95 (s, 3H), 1.44 (s, 9H).

A solution of methyl 3-((5-(((tert-butoxycarbonyl)amino)methyl)thiophen-2-yl)sulfonyl)benzoate (100 mg, 0.263 mmol), methylamine in methanol (10 mL) and $Et_3N$ (200 µL, 1.43 mmol) was stirred at reflux for 16 h. After cooling to rt, the solvent was evaporated and DCM was subsequently added. The organic phase was washed with $H_2O$, dried over $Na_2SO_4$, filtered and the solvent was removed under reduced pressure. The crude was purified by chromatography (MeOH/DCM 0→5%) to afford tert-butyl (5-(3-(methylcarbamoyl)phenylsulfonyl)thiophen-2-yl)methylcarbamate, which was treated with 4 M HCl in dioxane (2.0 mL). The mixture was stirred at rt for 16 h. The white precipitate was isolated, washed with excess of EtOAc and then dissolved in MeOH. The solvent was removed under reduced pressure to afford the title hydrochloride as a white solid (27 mg, 26% over two steps). $^1$H NMR (500 MHz, MeOD) δ 8.43 (t, J=1.7 Hz, 1H), 8.16 (ddd, J=7.8, 1.9, 1.2 Hz, 1H), 8.09 (ddd, J=7.8, 1.9, 1.2 Hz, 1H), 7.79 (d, J=3.7 Hz, 1H), 7.71 (t, J=7.7 Hz, 1H), 7.30 (d, J=3.7 Hz, 1H), 4.38 (s, 2H), 2.94 (s, 3H). HRMS calcd for $C_{13}H_{15}N_2O_3S_2$ [M+H]$^+$ 311.0519; found 311.0497.

Example 23: Methyl 3-((5-(aminomethyl)thiophen-2-yl)sulfonyl)benzoate hydrochloride

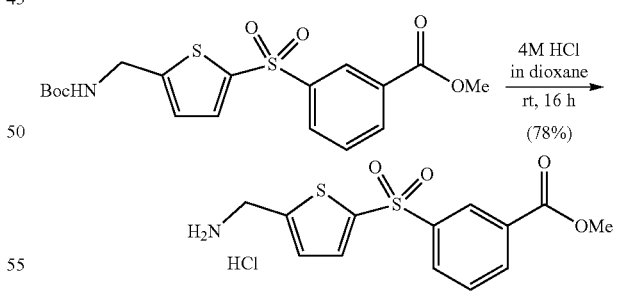

A mixture of methyl 3-((5-(((tert-butoxycarbonyl)amino)methyl)thiophen-2-yl)sulfonyl)benzoate (80 mg, 0.195 mmol) in 4 M HCl in dioxane (2.0 mL) was stirred at rt for 16 h. The white precipitate was isolated, washed with excess EtOAc and then dissolved in MeOH. The solvent was removed under reduced pressure to afford title hydrochloride as a white solid (52 mg, 78%). $^1$H NMR (500 MHz, MeOD) δ 8.55 (t, J=1.6 Hz, 1H), 8.29 (ddd, J=7.9, 1.9, 1.0 Hz, 1H), 8.24 (ddd, J=7.9, 1.9, 1.0 Hz, 1H), 7.79 (d, J=3.9 Hz, 1H), 7.75 (t, J=7.8 Hz, 1H), 7.33 (d, J=3.9 Hz, 1H), 4.39 (s, 2H), 3.96 (s, 3H). LC-MS (m/z): 295 (M-$NH_2$, 100).

Example 24: (5-(Naphthalen-2-ylsulfonyl)thiophen-2-yl)(1,1-²H₂)methanamine

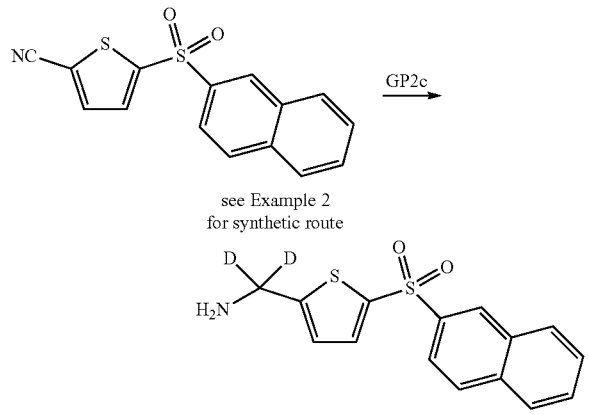

The title compound was synthesised according to general procedures GP2c—from BD₃ (1.0 M in THF; 1.5 mL, 1.5 mmol), 5-(naphthalen-2-ylsulfonyl)thiophene-2-carbonitrile (150 mg, 0.5 mmol) and dry THF (10 mL); rt, 1 h. The crude was purified by chromatography (cyclohexane/ethanol 70:30 to 0:100) to afford the title compound as a white solid (22 mg, 14%). $^1$H NMR (500 MHz, CDCl₃) δ 8.59 (s, 1H), 8.00 (d, J=8.0 Hz, 1H), 7.97-7.92 (m, 2H), 7.90 (d, J=8.3 Hz, 1H), 7.70-7.58 (m, 3H), 6.88 (d, J=3.8 Hz, 1H), 1.65-1.44 (m, 2H). LC-MS for $C_{15}H_9D_2O_2S_2$ (289 [M-NH₂]⁺, 100).

Example 25: (5-((4-(Phenylsulfonyl)phenyl)sulfonyl)thiophen-2-yl)methanamine

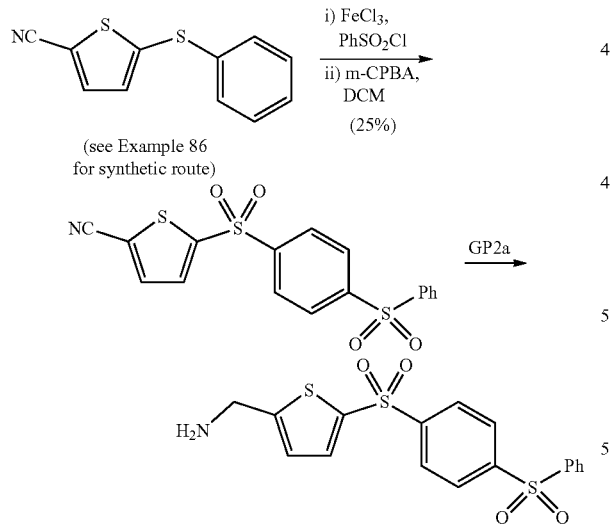

To 5-(phenylthio)thiophene-2-carbonitrile (370 mg, 1.5 mmol) was added FeCl₃ (324 mg, 2 mmol) and then phenylsulfonyl chloride (160 μL, 1.25 mmol). The mixture was heated without solvent at 100° C. for 2 h and stirred at room temperature for a further 12 h. The reaction was quenched with aqueous Na₂CO₃ followed by addition of dichloromethane. The organic phase was separated, dried over MgSO₄, filtered and the solvent was removed under reduced pressure. The crude was purified by column chromatography (DCM/cyclohexane 30→100%) to afford 5-((4-(phenylsulfonyl)phenyl)thio)thiophene-2-carbonitrile as a solid (160 mg, 36%). $^1$H NMR (500 MHz, DMSO) δ 8.07 (d, J=3.9 Hz, 1H), 7.96-7.88 (m, 4H), 7.72-7.67 (m, 1H), 7.65-7.60 (m, 3H), 7.42 (d, J=8.6 Hz, 2H).

5-((4-(Phenylsulfonyl)phenyl)thio)thiophene-2-carbonitrile (160 mg, 0.4 mmol) was dissolved in dichloromethane (3 mL), the solution was cooled at 0° C. and m-CPBA (77%; 330 mg, 1.5 mmol) was added. The reaction mixture was stirred at rt for 3 h, then diluted with EtOAc (10 mL) and extracted with sat. NaHCO₃ (10 mL). The organic layer was dried over MgSO₄, filtered and the solvent was removed under reduced pressure. The residue was purified by chromatography (EtOAc/DCM 0→80%) to afford 5-((4-(phenylsulfonyl)phenyl)sulfonyl)thiophene-2-carbonitrile (110 mg, 70%). $^1$H NMR (500 MHz, DMSO) δ 8.25 (q, J=8.7 Hz, 4H), 8.07 (s, 2H), 8.00 (d, J=8.3 Hz, 2H), 7.78-7.70 (m, 1H), 7.65 (t, J=7.8 Hz, 2H). LC-MS for $C_{17}H_{11}NO_4S_3$ (412 [M+Na]⁺, 100).

The title compound was obtained according to general procedures GP2a—from 5-((4-(phenylsulfonyl)phenyl)sulfonyl)thiophene-2-carbonitrile (40 mg, 0.1 mmol), BH₃ (1.0 M in THF; 0.5 mL, 0.5 mmol) and THF (4 mL); rt, 3 h. The crude was purified by chromatography (EtOH/cyclohexane 0→100%) to afford the product (8 mg, 20%) as a glassy solid. $^1$H NMR (500 MHz, DMSO) δ 8.21-8.13 (m, 4H), 7.99 (dt, J=7.1, 1.3 Hz, 2H), 7.75 (d, J=3.9 Hz, 1H), 7.73-7.70 (m, 1H), 7.64 (t, J=7.8 Hz, 2H), 7.02 (dt, J=3.5, 1.2 Hz, 1H), 3.89 (d, J=1.3 Hz, 2H). HRMS calcd for $C_{17}H_{15}NO_4S_3[M+H]^+$ 394.0236; found 394.0233.

Example 26: (5-((4-((2-(Pyrrolidin-1-yl)ethyl)sulfonyl)phenyl)sulfonyl)thiophen-2-yl)methanamine dihydrochloride

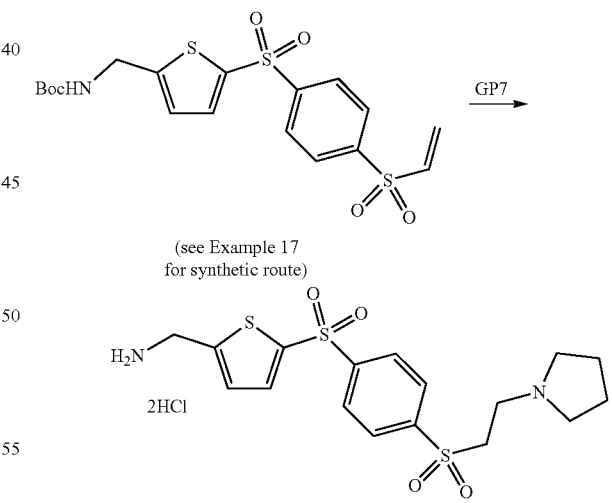

The title compound was synthesised according to general procedures GP7—from i) tert-butyl ((5-((4-(vinylsulfonyl)phenyl)sulfonyl)thiophen-2-yl)methyl)carbamate (61 mg, 0.138 mmol), Pyrrolidine (12.6 μL, 0.151 mmol) and DCM (0.8 mL); rt, 16 h. Chromatography (EtOH/cyclohexane 10→60%). ii) 4.0 M HCl in dioxane (4 mL); rt, 16 h. The title compound was obtained as a white solid (58 mg, quant.), which didn't require further purification. $^1$H NMR (500 MHz, D₂O) δ 8.37 (d, J=7.9 Hz, 2H), 8.27 (d, J=7.9 Hz, 2H), 7.92 (m, 1H), 7.41 (m, 1H), 4.51 (s, 2H), 3.99 (t, J=7.2 Hz, 2H), 3.92-2.98 (m, 6H), 2.13 (br, 4H). $^{13}$C NMR (126 MHz, D$_2$O) δ 146.87, 145.89, 142.50, 140.91, 136.88, 131.77, 130.49, 129.53, 55.66, 51.65, 48.16, 38.08, 23.47. HRMS (ESI) for C$_{17}$H$_{23}$N$_2$O$_4$S$_3$ ([M+H]$^+$): Calculated 415.0815; Observed 415.0828.

Example 27: 2-((4-((5-(Aminomethyl)thiophen-2-yl)sulfonyl)phenyl)sulfonyl)-N-ethylethanamine hydrochloride

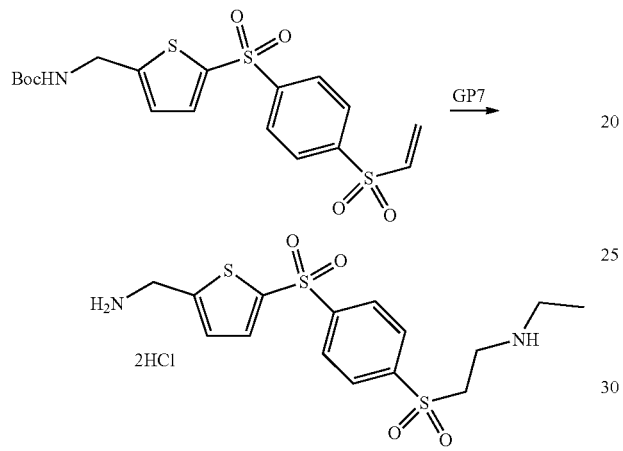

The title compound was synthesised according to general procedures GP7—from i) tert-butyl ((5-((4-(vinylsulfonyl)phenyl)sulfonyl)thiophen-2-yl)methyl)carbamate (84 mg, 0.189 mmol), ethylamine (2.0 M in MeOH; 104 μL, 0.208 mmol) and DCM (1.0 mL); rt, 16 h. Chromatography (EtOH/cyclohexane 10→80%). ii) 4.0 M HCl in dioxane (4 mL); rt, 16 h. The title compound was obtained as a white solid (72 mg, 96%), which didn't require further purification. $^1$H NMR (500 MHz, D$_2$O) δ 8.37 (d, J=7.8 Hz, 2H), 8.27 (d, J=7.8 Hz, 2H), 7.92 (m, 1H), 7.40 (m, 1H), 4.51 (s, 2H), 3.90 (t, J=6.9 Hz, 2H), 3.52 (t, J=6.9 Hz, 2H), 3.19 (q, J=7.2 Hz, 2H), 1.33 (t, J=7.2 Hz, 3H). $^{13}$C NMR (126 MHz, D$_2$O) δ 146.83, 145.88, 142.46, 140.92, 136.86, 131.75, 130.48, 129.51, 51.86, 44.39, 40.71, 38.08, 11.11. HRMS (ESI) for C$_{15}$H$_{21}$N$_2$O$_4$S$_3$ ([M+H]$^+$): Calculated 389.0658; Observed 389.0651.

Example 28: (5-((4-((2-Methoxyethyl)sulfonyl)phenyl)sulfonyl)thiophen-2-yl)methanamine hydrochloride

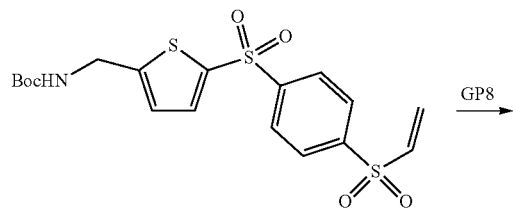

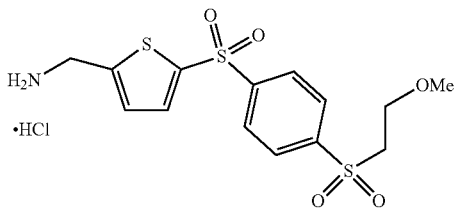

The title compound was synthesised according to general procedures GP8—from i) tert-butyl ((5-((4-(vinylsulfonyl)phenyl)sulfonyl)thiophen-2-yl)methyl)carbamate (65.9 mg, 0.149 mmol), K$_2$CO$_3$ (24.6 mg, 0.178 mmol) and MeOH (1 mL); 2 h, rt. ii) 4 M HCl in dioxane (5 mL); rt, 3 h. The title compound was obtained as a white solid (30 mg, 54% yield) and didn't require further purification. $^1$H NMR (500 MHz, MeOD) δ 8.22 (d, J=8.6 Hz, 2H), 8.13 (d, J=8.6 Hz, 2H), 7.83 (d, J=3.9 Hz, 1H), 7.33 (d, J=3.9 Hz, 1H), 4.39 (s, 2H), 3.72 (t, J=5.6 Hz, 2H), 3.55 (t, J=5.6 Hz, 2H), 3.11 (s, 3H). $^{13}$C NMR (126 MHz, MeOD) δ 147.77, 146.76, 146.08, 144.50, 136.04, 131.78, 130.69, 129.24, 66.83, 58.69, 56.78, 38.43. HRMS (ESI) for C$_{14}$H$_{18}$NO$_5$S$_3$ ([M+H]$^+$): Calculated 376.0342; Observed 376.0333.

Example 29: (5-((4-((2-Ethoxyethyl)sulfonyl)phenyl)sulfonyl)thiophen-2-yl)methanamine hydrochloride

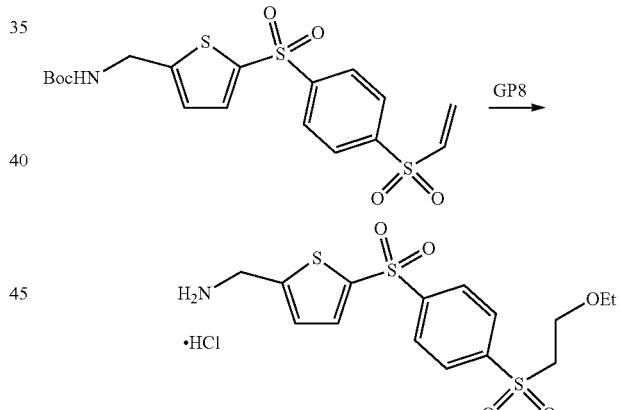

The title compound was synthesised according to general procedures GP8—from i) tert-butyl ((5-((4-(vinylsulfonyl)phenyl)sulfonyl)thiophen-2-yl)methyl)carbamate (59.6 mg, 0.134 mmol), NaOEt (21% in EtOH; 65.3 μL, 0.175 mmol) and EtOH (1 mL); 2 h, rt. ii) 4 M HCl in dioxane (5 mL); rt, 3 h. The title compound was obtained as a white solid (22 mg, 42% yield) and didn't require further purification. $^1$H NMR (500 MHz, MeOD) δ 8.26-8.21 (m, 2H), 8.17-8.12 (m, 2H), 7.83 (d, J=3.9 Hz, 1H), 7.34 (d, J=3.9 Hz, 1H), 4.40 (s, 2H), 3.76 (t, J=5.5 Hz, 2H), 3.56 (t, J=5.4 Hz, 2H), 3.25 (q, J=7.0 Hz, 2H), 0.78 (t, J=7.0 Hz, 3H). $^{13}$C NMR (126 MHz, MeOD) δ 147.71, 146.92, 146.05, 144.51, 136.04, 131.80, 130.75, 129.17, 67.14, 64.95, 56.97, 38.41, 14.95. HRMS (ESI) for C$_{15}$H$_{19}$NO$_5$S$_3$ ([M+H]$^+$): Calculated 390.0498; Observed 390.0499.

Example 30: N-(2-((4-((5-(Aminomethyl)thiophen-2-yl)sulfonyl)phenyl)sulfonyl)ethyl)-methanesulfonamide hydrochloride

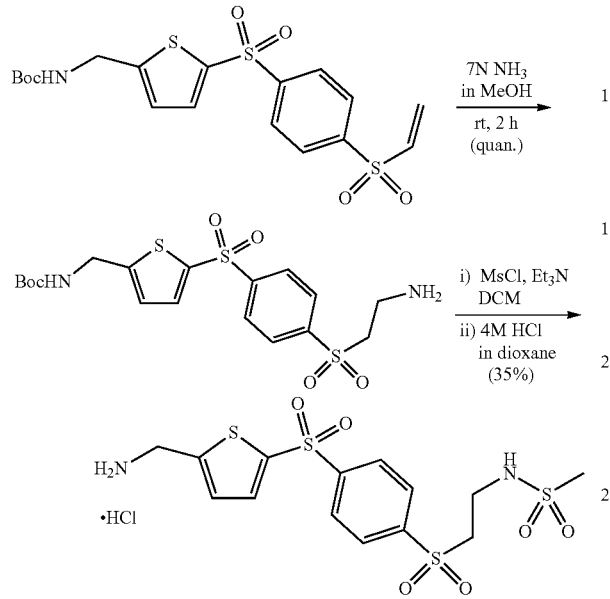

A mixture of tert-butyl ((5-((4-(vinylsulfonyl)phenyl)sulfonyl)thiophen-2-yl)methyl)carbamate (448 mg, 1.01 mmol) and 7 N NH₃ in MeOH (10 mL) was stirred at rt for 2 h. The solvent was removed under reduced pressure to afford tert-butyl ((5-((4-((2-aminoethyl)sulfonyl)phenyl)thio)thiophen-2-yl)methyl)carbamate as a white solid (472 mg, quan.) which didn't required further purification. ¹H NMR (500 MHz, MeOD) δ 7.70 (d, J=3.8 Hz, 1H), 7.03 (d, J=3.9 Hz, 1H), 4.39 (s, 2H), 8.16-8.12 (m, 2H), 3.39 (t, J=6.7 Hz, 2H), 2.96 (t, J=6.7 Hz, 2H), 1.44 (s, 9H), 8.27-8.21 (m, 2H).

MsCl (14.8 µL, 0.191 mmol) was added to a solution of tert-butyl ((5-((4-((2-aminoethyl)sulfonyl)phenyl)sulfonyl)thiophen-2-yl)methyl)carbamate (80 mg, 0.174 mmol) and Et₃N (29.1 µL, 0.209 mmol) in DCM (1.2 mL) and the mixture was stirred at rt for 1 h. DCM (20 mL) was added. The organic solution was washed with H₂O (20 mL) and brine (20 mL), dried over MgSO₄, filtered and the solvent was removed under reduced pressure. The crude was purified by chromatography (EtOAc/DCM 5→50%, then EtOH/EtOAc 5→30%) to afford tert-butyl ((5-((4-((2-(methylsulfonamido)ethyl)sulfonyl)phenyl)sulfonyl)thiophen-2-yl)methyl)carbamate as a white solid (60 mg, 64%). 4 M HCl in dioxane (5 mL) was added to the intermediate and the mixture was stirred at rt for 16 h. The precipitated solid was collected on a pad of celite and washed with EtOAc. MeOH was added to dissolve the solid and the suspension was filtered. The solvent was removed under reduced pressure to afford the title compound as a white solid (36 mg, 54%), which did not require further purification. ¹H NMR (500 MHz, MeOD) δ 8.27-8.23 (m, 2H), 8.20-8.15 (m, 2H), 7.82 (d, J=3.9 Hz, 1H), 7.32 (d, J=3.9 Hz, 1H), 4.38 (s, 2H), 3.53 (t, J=6.7 Hz, 2H), 3.44 (t, J=6.5 Hz, 2H), 2.87 (s, 3H). ¹³C NMR (126 MHz, MeOD) δ 148.07, 146.09, 145.75, 144.43, 136.09, 131.75, 130.80, 129.59, 56.70, 39.87, 38.42, 38.01. HRMS (ESI) for C₁₄H₁₉N₂O₆S₄ ([M+H]⁺): 439.0120; Observed 439.0106.

Example 31: N-(2-((4-((5-(Aminomethyl)thiophen-2-yl)sulfonyl)phenyl)sulfonyl)ethyl)-acetamide hydrochloride

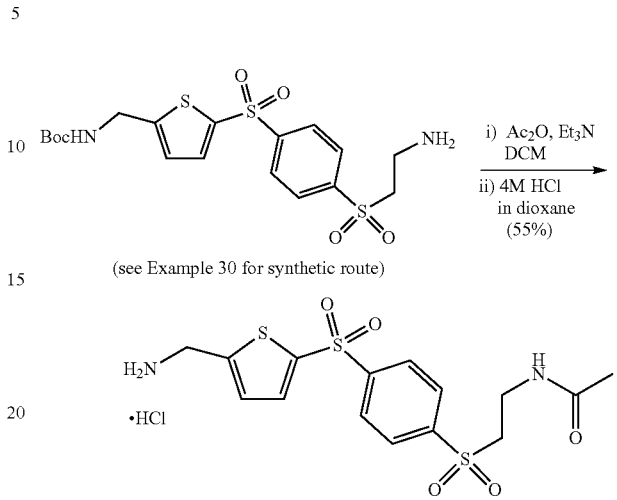

(see Example 30 for synthetic route)

Ac₂O (18.1 µL, 0.191 mmol) was added to a solution of tert-butyl ((5-((4-((2-aminoethyl)sulfonyl)phenyl)sulfonyl)thiophen-2-yl)methyl)carbamate (80 mg, 0.174 mmol) and Et₃N (29.1 µL, 0.209 mmol) in DCM (1.2 mL) and the mixture was stirred at rt for 1 h. DCM (20 mL) was added. The organic solution was washed with H₂O (20 mL) and brine (20 mL), dried over MgSO₄, filtered and the solvent was removed under reduced pressure. The crude was purified by chromatography (EtOAc/DCM 15→100%) to afford tert-butyl ((5-((4-((2-acetamidoethyl)sulfonyl)phenyl)sulfonyl)thiophen-2-yl)methyl)carbamate as a white foam (48 mg, 55%). 4 M HCl in dioxane (5 mL) was added to the intermediate and the mixture was stirred at rt for 16 h. The precipitated solid was collected on a pad of celite and washed with EtOAc. MeOH was added to dissolve the solid and the suspension was filtered. The solvent was removed under reduced pressure to afford the title compound as a white solid (42 mg, quant.), which didn't require further purification. ¹H NMR (500 MHz, MeOD) δ 8.26 (d, J=8.5 Hz, 2H), 8.15 (d, J=8.6 Hz, 2H), 7.83 (d, J=3.9 Hz, 1H), 7.34 (d, J=3.8 Hz, 1H), 4.39 (s, 2H), 3.57-3.44 (m, 4H), 1.69 (s, 3H). ¹³C NMR (126 MHz, MeOD) δ 173.41, 148.05, 146.22, 145.69, 144.29, 136.17, 131.85, 130.69, 129.58, 54.98, 38.43, 34.81, 22.23. HRMS (ESI) for C₁₅H₁₉N₂O₅S₃ ([M+H]⁺): Calculated 403.0451; Observed 403.0453.

Example 32: N-(2-((4-((5-(Aminomethyl)thiophen-2-yl)sulfonyl)phenyl)sulfonyl)ethyl)-benzamide hydrochloride

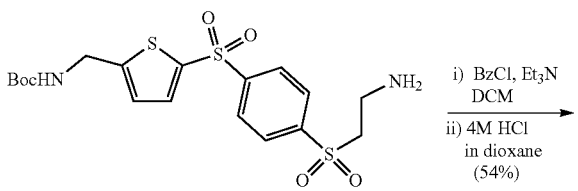

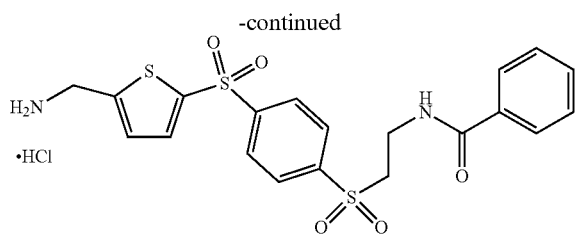

Benzoyl chloride (BzCl, 22.2 µL, 0.191 mmol) was added to a solution of tert-butyl ((5-((4-((2-aminoethyl)sulfonyl)phenyl)sulfonyl)thiophen-2-yl)methyl)carbamate (80 mg, 0.174 mmol) and Et$_3$N (29.1 µL, 0.209 mmol) in DCM (1.2 mL) and the mixture was stirred at rt for 1 h. DCM (20 mL) was added. The organic solution was washed with H$_2$O (20 mL) and brine (20 mL), dried over MgSO$_4$, filtered and the solvent was removed under reduced pressure. The crude was purified by chromatography (EtOAc/DCM 35→90%) to afford tert-butyl ((5-((4-((2-benzamidoethyl)sulfonyl)phenyl)sulfonyl)thiophen-2-yl)methyl)carbamate as a white foam (79 mg, 81%). 4 M HCl in dioxane (5 mL) was added to the intermediate and the mixture was stirred at rt for 16 h. The precipitated solid was collected on a pad of celite and washed with EtOAc. MeOH was added to dissolve the solid and the suspension was filtered. The solvent was removed under reduced pressure to afford the title compound as a white solid (42 mg, 67%), which didn't require further purification. $^1$H NMR (500 MHz, MeOD) δ 8.21-8.13 (m, 4H), 7.78 (d, J=3.9 Hz, 1H), 7.65-7.60 (m, 2H), 7.52 (mm, 1H), 7.41 (dd, J=10.5, 4.8 Hz, 2H), 7.31 (d, J=3.9 Hz, 1H), 4.38 (s, 2H), 3.73 (t, J=6.1 Hz, 2H), 3.65 (t, J=6.0 Hz, 2H). $^{13}$C NMR (126 MHz, MeOD) δ 170.17, 148.00, 146.15, 145.75, 144.39, 136.07, 134.84, 132.99, 131.76, 130.63, 129.59, 128.14, 54.98, 38.42, 35.34. HRMS (ESI) for C$_{20}$H$_{21}$N$_2$O$_5$S$_3$ ([M+H]$^+$): Calculated 465.0607; Observed 465.0607.

Example 33: (5-((4-((2-(Piperazin-1-yl)ethyl)sulfonyl)phenyl)sulfonyl)thiophen-2-yl)methanamine trihydrochloride

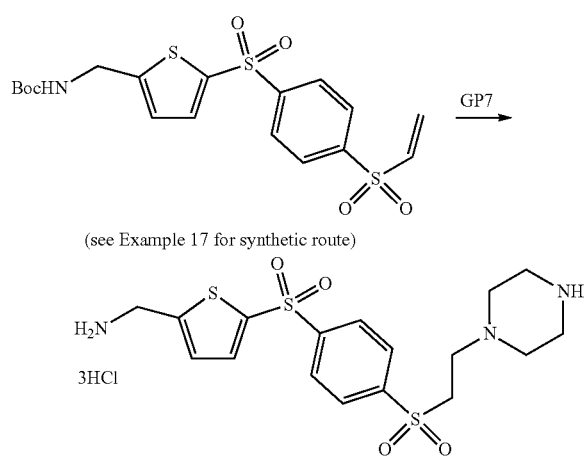

(see Example 17 for synthetic route)

The title compound was synthesised according to general procedures GP7—from i) tert-butyl ((5-((4-(vinylsulfonyl)phenyl)sulfonyl)thiophen-2-yl)methyl)carbamate (256 mg, 0.577 mmol), piperazine (249 mg, 2.89 mmol) and DCM (3.0 mL); rt, 2 h. Chromatography (MeOH/DCM 0→30%), 181 mg, 60%, white solid. ii) tert-butyl ((5-((4-((2-(piperazin-1-yl)ethyl)sulfonyl)phenyl)sulfonyl)thiophen-2-yl)methyl)carbamate (51 mg, 96.3 µmol) 4.0 M HCl in dioxane (4 mL); rt, 16 h. The title compound was obtained as a white solid (51 mg, quant.), which didn't require further purification. $^1$H NMR (500 MHz, D$_2$O) δ 8.32 (d, J=8.3 Hz, 2H), 8.21 (d, J=8.3 Hz, 2H), 7.87 (d, J=3.8 Hz, 1H), 7.35 (d, J=3.7 Hz, 1H), 4.46 (s, 2H), 3.87 (t, J=7.1 Hz, 2H), 3.43-3.31 (m, 6H), 3.29-3.14 (m, 4H). $^{13}$C NMR (126 MHz, D$_2$O) δ 145.79, 145.02, 142.34, 140.07, 136.00, 130.91, 129.60, 128.55, 50.37, 49.77, 48.71, 41.63, 37.21. HRMS (ESI) for C$_{17}$H$_{24}$N$_3$O$_4$S$_3$ ([M+H]$^+$): Calculated 430.0924; Observed 430.0887.

Example 34: (5-((4-((2-(4-(Methylsulfonyl)piperazin-1-yl)ethyl)sulfonyl)phenyl)sulfonyl)-thiophen-2-yl)methanamine dihydrochloride

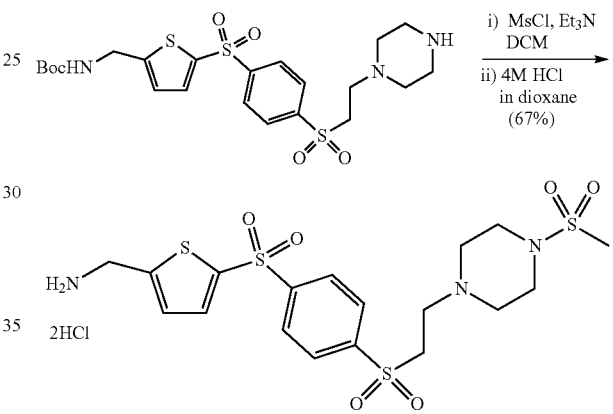

MsCl (11.4 µL, 0.147 mmol) was added to a solution of tert-butyl ((5-((4-((2-(piperazin-1-yl)ethyl)sulfonyl)phenyl)sulfonyl)thiophen-2-yl)methyl)carbamate (65 mg, 0.123 mmol) and Et$_3$N (25.7 µL, 0.184 mmol) in DCM (1.2 mL) and the mixture was stirred at rt for 1 h. DCM (20 mL) was added. The organic solution was washed with H$_2$O (20 mL), dried over MgSO$_4$, filtered and the solvent was removed under reduced pressure. 4 M HCl in dioxane (5 mL) was added and the mixture was stirred at rt for 16 h. The precipitated solid was collected on a pad of celite and washed with EtOAc. MeOH was added to dissolve the solid and the suspension was filtered. The solvent was removed under reduced pressure to afford the title compound as a white solid (48 mg, 67%), which didn't require further purification. $^1$H NMR (500 MHz, D$_2$O) δ 8.32 (d, J=8.3 Hz, 2H), 8.22 (d, J=8.3 Hz, 2H), 7.87 (d, J=3.5 Hz, 1H), 7.36 (d, J=2.5 Hz, 1H), 4.46 (s, 2H), 3.98 (t, J=7.4 Hz, 2H), 3.65-3.58 (m, 2H), 3.54 (br s, 4H), 3.41 (br s, 4H), 3.06 (s, 3H). $^{13}$C NMR (126 MHz, D$_2$O) δ 146.00, 145.05, 141.74, 140.08, 136.02, 130.93, 129.68, 128.69, 51.77, 49.47, 49.24, 42.78, 37.22, 35.32. HRMS (ESI) for C$_{18}$H$_{26}$N$_3$O$_6$S$_4$ ([M+H]$^+$): Calculated 508.0704; Observed 508.0648.

Example 35: (5-((4-((2-(1,4-Diazepan-1-yl)ethyl)sulfonyl)phenyl)sulfonyl)thiophen-2-yl)methanamine trihydrochloride

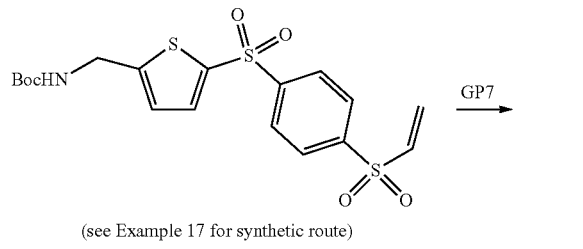

(see Example 17 for synthetic route)

The title compound was synthesised according to general procedures GP7—from i) tert-butyl ((5-((4-(vinylsulfonyl)phenyl)sulfonyl)thiophen-2-yl)methyl)carbamate (185 mg, 0.417 mmol), homopiperazine (418 mg, 4.17 mmol) and DCM (6.0 mL); rt, 1 h. 200 mg, 88%, white solid. ii) tert-butyl ((5-((4-((2-(1,4-diazepan-1-yl)ethyl)sulfonyl)phenyl)sulfonyl)thiophen-2-yl)methyl)carbamate (40 mg, 73.7 µmol) 4.0 M HCl in dioxane (2.0 mL); rt, 16 h. The title compound was obtained as a white solid (36 mg, 89%), which didn't require further purification. $^1$H NMR (500 MHz, MeOD) δ 8.30 (d, J=8.1 Hz, 2H), 8.24 (d, J=8.1 Hz, 2H), 7.85 (d, J=3.6 Hz, 1H), 7.35 (d, J=3.5 Hz, 1H), 4.40 (s, 2H), 4.05-3.93 (m, 2H), 3.84-3.41 (m, 10H), 2.30 (br, 2H). $^{13}$C NMR (126 MHz, MeOD) δ 148.63, 146.32, 144.53, 144.09, 136.30, 131.90, 130.98, 129.88, 55.45, 51.70, 51.53, 51.29, 45.70, 42.35, 38.49, 22.59. HRMS (ESI) for $C_{16}H_{26}N_3O_4S_3$ ([M+H]$^+$): Calculated 444.1080; Observed 444.1075.

Example 36: (5-((4-(Phenethylsulfonyl)phenyl)sulfonyl)thiophen-2-yl)methanamine

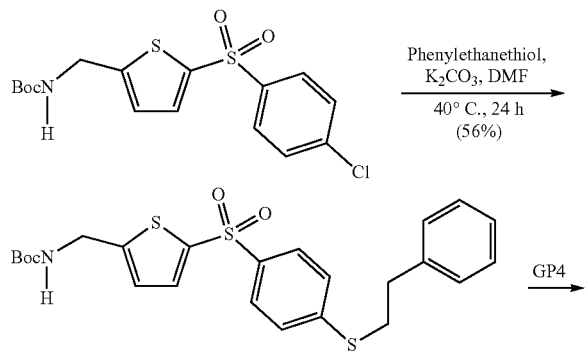

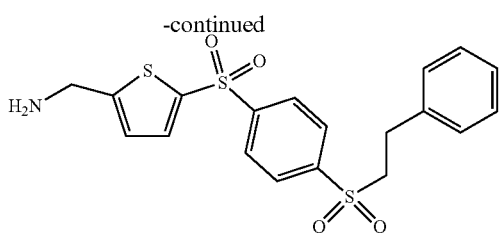

A mixture of tert-butyl ((5-((4-chlorophenyl)sulfonyl)thiophen-2-yl)methyl)carbamate (100 mg, 0.258 mmol), 2-phenylethanethiol (207 µL, 1.55 mmol), $K_2CO_3$ (107 mg, 0.773 mmol) and DMF (1.7 mL) was stirred at 50° C. for 24 h. After cooling to rt, the mixture was diluted with $Et_2O$. The organic phase was washed with sat. $NaHCO_3$ (3×40 mL) and brine (40 mL), dried over $MgSO_4$ and filtered. The solvent was removed under reduced pressure. The crude was purified by column chromatography (EtOAc/cyclohexane 0→30%) to afford tert-butyl ((5-((4-(phenethylthio)phenyl)sulfonyl)thiophen-2-yl)methyl)carbamate as a colourless oil (71 mg, 56%). $^1$H NMR (500 MHz, CDCl$_3$) δ 7.83 (d, J=8.6 Hz, 2H), 7.52 (d, J=3.8 Hz, 1H), 7.37-7.29 (m, 4H), 7.28-7.19 (m, 3H), 6.90 (d, J=3.6 Hz, 1H), 5.07 (br, 1H), 4.45 (br, 2H), 3.24 (dd, J=8.5, 7.0 Hz, 2H), 3.01-2.95 (m, 2H), 1.45 (s, 9H).

The title compound was synthesised according to general procedures GP4—from i) tert-butyl ((5-((4-(phenethylthio)phenyl)sulfonyl)thiophen-2-yl)methyl)carbamate (69.2 mg, 0.141 mmol), m-CPBA (69.2 mg, 0.310 mmol), DCM (1.4 mL); rt, 2 h. ii) 4 M HCl in dioxane (3.0 mL); rt, 3 h. The crude was treated with 1N $NH_3$ in MeOH and purified by column chromatography (EtOH/cyclohexane 50, then 100%) to afford a white solid (61 mg, quant.). $^1$H NMR (500 MHz, DMSO) δ 8.17-8.08 (m, 4H), 7.79 (d, J=3.9 Hz, 1H), 7.18-7.13 (m, 4H), 7.13-7.06 (m, 2H), 3.93 (s, 2H), 3.82-3.72 (m, 2H), 2.97-2.84 (m, 2H), 2.39 (s, 2H). $^{13}$C NMR (126 MHz, DMSO) δ 146.32, 143.38, 137.34, 136.84, 135.54, 129.33, 128.46, 128.27, 127.73, 126.51, 124.06, 54.80, 40.81, 27.85. HRMS (ESI) for $C_{19}H_{20}NO_4S_3$ ([M+H]$^+$): Calculated 422.0549; Observed 422.0548.

tert-Butyl ((5-((4-chlorophenyl)sulfonyl)thiophen-2-yl)methyl)carbamate

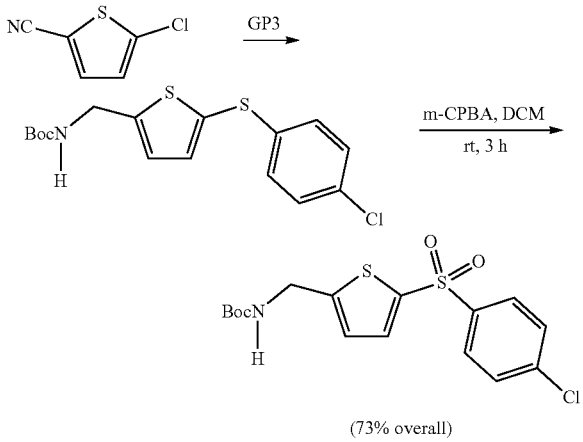

(73% overall)

tert-Butyl ((5-((4-chlorophenyl)thio)thiophen-2-yl)methyl)carbamate was synthesised according to general procedures GP3—from i) 5-chlorothiophene-2-carbonitrile (1.0 g, 6.96 mmol), 4-chlorothiophenol (1.21 mg, 8.36 mmol), K₂CO₃ (1.73 g, 12.5 mmol) and DMF (17.5 mL); 130° C., 16 h. Chromatography (EtOAc/cyclohexane 0→5%), 882 mg, 52%. ii) 5-((4-chlorophenyl)thio)thiophene-2-carbonitrile (878 mg, 3.49 mmol), BH₃ (1.0 M in THF; 10.5 mL, 10.5 mmol), THF (21 mL); rt, 1 h. iii) Boc₂O (1.14 g, 5.22 mmol), Et₃N (0.97 mL, 6.97 mmol), DCM (11.6 mL); rt, 16 h. The crude was purified by chromatography (EtOAc/cyclohexane 0→30%) to afford a yellow oil, which was used immediately in the subsequent transformation.

Crude tert-butyl ((5-((4-chlorophenyl)thio)thiophen-2-yl)methyl)carbamate was dissolved in DCM (17.0 mL). m-CPBA (77%; 1.95 g, 8.71 mmol) was added in small portions and the mixture was stirred at rt for 5 h. EtOAc (60 mL) was added. The organic phase was washed with sat. NaHCO₃ (3×50 mL), dried over MgSO₄ and filtered. The solvent was removed under reduced pressure and the crude was purified by chromatography (EtOAc/cyclohexane 0→50%) to afford tert-butyl ((5-((4-chlorophenyl)sulfonyl)thiophen-2-yl)methyl)carbamate as a light yellow solid (980 mg, 73%). ¹H NMR (500 MHz, CDCl₃) δ 7.93-7.87 (m, 2H), 7.54 (d, J=3.8 Hz, 1H), 7.51-7.47 (m, 2H), 6.92 (d, J=3.8 Hz, 1H), 5.04 (br, 1H), 4.46 (d, J=5.4 Hz, 2H), 1.45 (s, 9H).

Example 37: 4-(2-((4-((5-(Aminomethyl)thiophen-2-yl)sulfonyl)phenyl)sulfonyl)ethyl)-N-ethyl-1,4-diazepane-1-carboxamide dihydrochloride

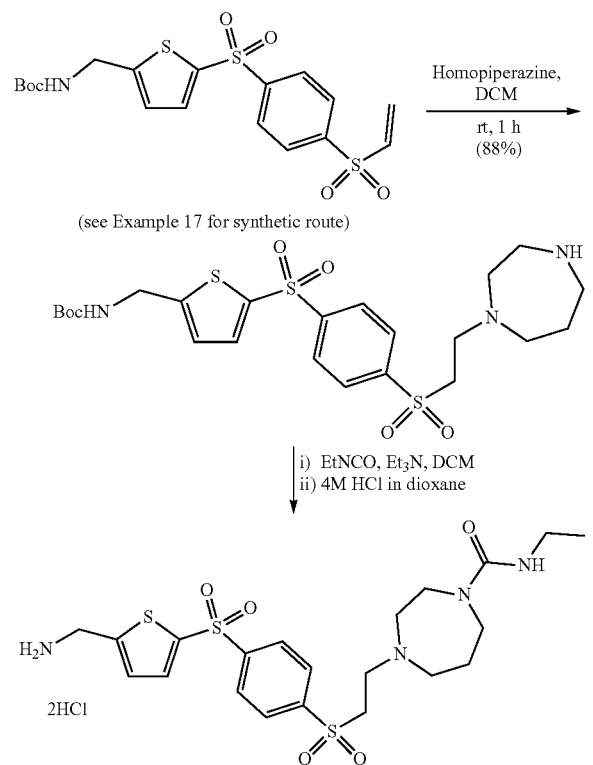

Homopiperazine (418 mg, 4.17 mmol) was added to a solution of tert-butyl ((5-((4-(vinylsulfonyl)phenyl)sulfonyl)thiophen-2-yl)methyl)carbamate (185 mg, 0.417 mmol) in DCM (6.0 mL) and the mixture was stirred at rt for 1 h. EtOAc (40 mL) was added. The organic solution was washed with 1:1 H₂O/brine (4×40 mL), dried over MgSO₄, filtered and the solvent was removed under reduced pressure. tert-Butyl ((5-((4-((2-(1,4-diazepan-1-yl)ethyl)sulfonyl)phenyl)sulfonyl)thiophen-2-yl)methyl)carbamate was obtained as a white solid (200 mg, 88%) and was used in the subsequent transformation without further purification.

EtNCO (12.1 μL, 0.153 mmol) was added to a solution of tert-butyl ((5-((4-((2-(1,4-diazepan-1-yl)ethyl)sulfonyl)phenyl)sulfonyl)thiophen-2-yl)methyl)carbamate (64 mg, 0.118 mmol) and Et₃N (25 μL, 0.177 mmol) in DCM (1.0 mL) and the mixture was stirred at rt for 1 h. EtOAc (30 mL) was added. The organic solution was washed with 1:1 H₂O/brine (3×30 mL), dried over MgSO₄, filtered and the solvent was removed under reduced pressure. 4 M HCl in dioxane (2.5 mL) was then added and the mixture was stirred at rt for 3 h. The precipitated solid was collected on a pad of celite and washed with EtOAc. MeOH was then added to dissolve the solid and the mixture was filtered. The solvent was removed under reduced pressure to afford the title compound as a white solid, which did not require further purification (57 mg, 83%). ¹H NMR (500 MHz, MeOD) δ 8.34-8.27 (m, 2H), 8.26-8.19 (m, 2H), 7.84 (d, J=3.8 Hz, 1H), 7.35 (d, J=3.8 Hz, 1H), 4.40 (s, 2H), 4.14-3.90 (m, 3H), 3.70-3.23 (m, 9H), 3.19 (q, J=7.2 Hz, 2H), 2.21 (br, 2H), 1.11 (t, J=7.2 Hz, 3H). ¹³C NMR (126 MHz, MeOD) δ 159.86, 148.67, 146.32, 144.51, 144.11, 136.29, 131.88, 130.93, 129.87, 57.63, 55.79, 51.25, 51.06, 45.41, 41.55, 38.45, 36.69, 25.57, 15.77. HRMS (ESI) for C₂₁H₃₁N₄O₅S₃ ([M+H]⁺): Calculated 515.1451; Observed 515.1447.

Example 38: 1-(4-(2-((4-((5-(Aminomethyl)thiophen-2-yl)sulfonyl)phenyl)sulfonyl)ethyl)-1,4-diazepan-1-yl)ethanone dihydrochloride

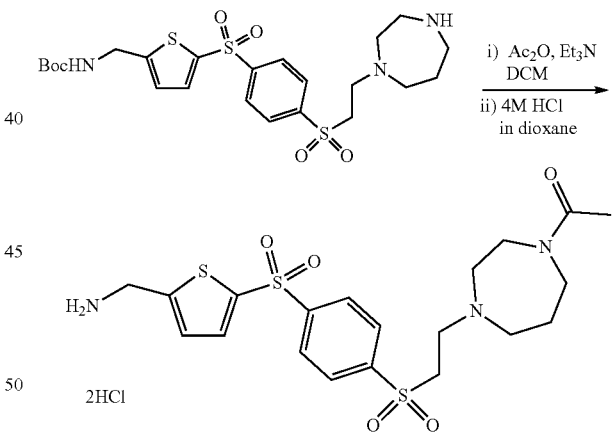

Ac₂O (11.5 μL, 0.122 mmol) was added to a solution of tert-butyl ((5-((4-((2-(1,4-diazepan-1-yl)ethyl)sulfonyl)phenyl)sulfonyl)thiophen-2-yl)methyl)carbamate (51 mg, 0.0938 mmol) and Et₃N (19.6 μL, 0.141 mmol) in DCM (1.0 mL) and the mixture was stirred at rt for 1 h. EtOAc (30 mL) was added. The organic solution was washed with 1:1 H₂O/brine (3×30 mL), dried over MgSO₄, filtered and the solvent was removed under reduced pressure. 4 M HCl in dioxane (2.5 mL) was then added and the mixture was stirred at rt for 3 h. The precipitated solid was collected on a pad of celite and washed with EtOAc. MeOH was then added to dissolve the solid and the mixture was filtered. The solvent was removed under reduced pressure to afford the title compound as a white solid, which did not require further purification (48 mg, 92%). $^1$H NMR (500 MHz, MeOD) δ 8.34-8.27 (m, 2H), 8.27-8.20 (m, 2H), 7.84 (d, J=3.2 Hz, 1H), 7.36 (d, J=3.2 Hz, 1H), 4.40 (s, 2H), 4.24-3.37 (m, 12H), 2.45-2.17 (m, 2H), 2.14 (s, 3H). $^{13}$C NMR (126 MHz, MeOD) δ 172.21, 147.24, 144.95, 143.07, 142.66, 134.91, 130.53, 129.58, 128.49, 54.79, 53.75, 49.99, 49.68, 46.31, 42.89, 37.10, 24.30, 20.27. HRMS (ESI) for $C_{20}H_{28}N_3O_5S_3$ ([M+H]$^+$): Calculated 486.1186; Observed 486.1184.

Example 39: 3-((4-((5-(Aminomethyl)thiophen-2-yl)sulfonyl)phenyl)sulfonyl)propan-1-ol hydrochloride

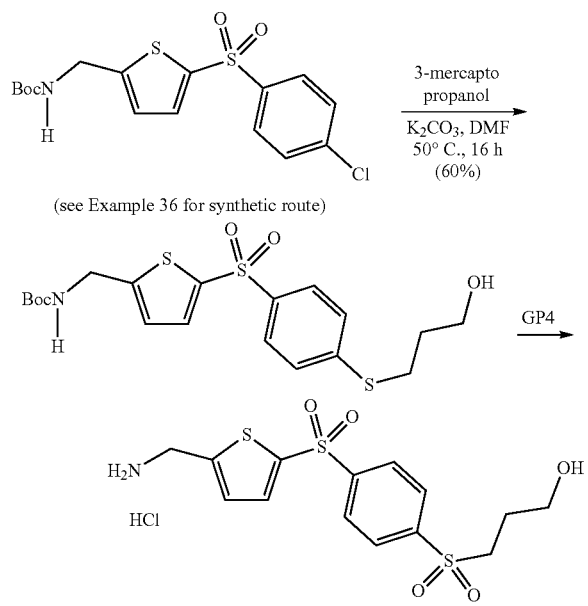

(see Example 36 for synthetic route)

A mixture of tert-butyl ((5-((4-chlorophenyl)sulfonyl)thiophen-2-yl)methyl)carbamate (1.68 g, 4.34 mmol), 3-mercaptopropanol (0.94 mL, 10.8 mmol), $K_2CO_3$ (1.80 g, 13.1 mmol) and DMF (22 mL) was stirred at 50° C. for 16 h. After cooling to rt, EtOAc (60 mL) was added. The organic solution was washed with 1:1 $H_2O$/brine (3×60 mL), dried over $MgSO_4$, filtered and the solvent was removed under reduced pressure. The crude was purified by chromatography (EtOAc/cyclohexane 15→70%) to afford tert-butyl ((5-((4-((3-hydroxypropyl)thio)phenyl)sulfonyl)-thiophen-2-yl)methyl)carbamate as a colourless oil (1.16 g, 60%). $^1$H NMR (500 MHz, CDCl$_3$) δ 7.82 (d, J=8.3 Hz, 2H), 7.51 (d, J=3.7 Hz, 1H), 7.35 (d, J=8.3 Hz, 2H), 6.89 (d, J=3.4 Hz, 1H), 5.07 (s, 1H), 4.44 (d, J=5.1 Hz, 2H), 3.84-3.65 (m, 2H), 3.11 (t, J=7.2 Hz, 2H), 2.00-1.87 (m, 2H), 1.57 (s, 1H), 1.45 (s, 9H).

The title compound was synthesised according to general procedures GP4—from i) tert-butyl ((5-((4-((3-hydroxypropyl)thio)phenyl)sulfonyl)thiophen-2-yl)methyl)carbamate (452 mg, 1.02 mmol), m-CPBA (77%; 502 mg, 2.24 mmol), DCM (5.0 mL); rt, 0.5 h; Chromatography (EtOAc/cyclohexane 40→100%), 379 mg, 78%, white crystalline solid. ii) 4 M HCl in dioxane (1.5 mL); rt, 3 h. The title compound was obtained as a white solid, which did not require further purification (23 mg, quant.). $^1$H NMR (500 MHz, MeOD) δ 8.26 (d, J=8.5 Hz, 2H), 8.15 (d, J=8.5 Hz, 2H), 7.83 (d, J=3.9 Hz, 1H), 7.34 (d, J=3.9 Hz, 1H), 4.39 (s, 2H), 3.58 (t, J=6.1 Hz, 2H), 3.37-3.32 (m, 2H), 1.89-1.80 (m, 2H). $^{13}$C NMR (126 MHz, MeOD) δ 148.02, 146.19, 145.44, 144.33, 136.14, 131.84, 130.66, 129.60, 60.56, 53.60, 38.46, 26.85. HRMS (ESI) for $C_{14}H_{18}NO_5S_3$ ([M+H]$^+$): Calculated 376.0342; Observed 376.0334.

Example 40: (5-((4-((3-Azidopropyl)sulfonyl)phenyl)sulfonyl)thiophen-2-yl)methanamine hydrochloride

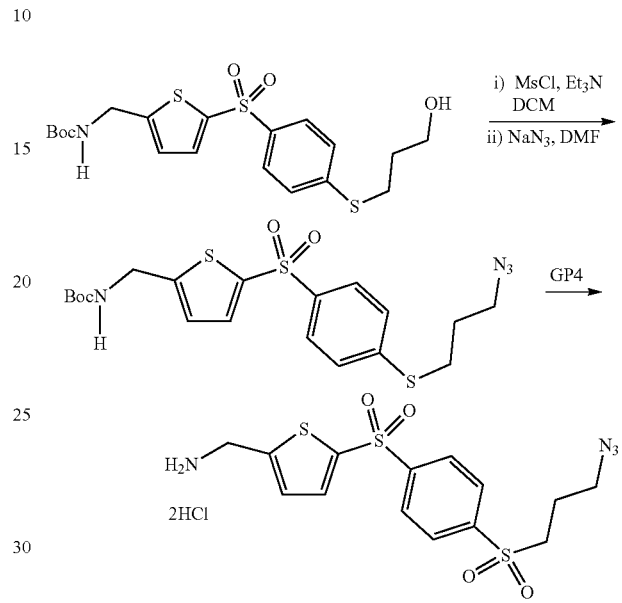

Methanesulfonyl chloride (206 μL, 2.67 mmol) was added to a solution of tert-butyl ((5-((4-((3-hydroxypropyl)thio)phenyl)sulfonyl)thiophen-2-yl)methyl)carbamate (910 mg, 2.05 mmol) and Et$_3$N (429 μL, 3.08 mmol) in DCM (10 mL). The mixture was stirred at rt for 2 h. DCM (30 mL) was added. The organic solution was washed with 1 M HCl, sat NaHCO$_3$, brine, dried over MgSO$_4$ and filtered. The solvent was removed under reduced pressure. The crude was dissolved in DMF (3.4 mL). NaN$_3$ (79.5 mg, 1.22 mmol) was added and the mixture was stirred at 50° C. for 1 h. After cooling to rt, EtOAc (30 mL) was added. The organic solution was washed with 1:1 H$_2$O/brine (3×30 mL), dried over MgSO$_4$, filtered and the solvent was removed under reduced pressure to afford crude tert-butyl ((5-((4-((3-azidopropyl)thio)phenyl)sulfonyl)thiophen-2-yl)methyl)carbamate, which was used in the subsequent transformation without further purification.

The title compound was synthesised according to general procedures GP4—from i) tert-butyl ((5-((4-((3-azidopropyl)thio)phenyl)sulfonyl)thiophen-2-yl)methyl)carbamate (crude), m-CPBA (77%; 456 mg, 2.04 mmol), DCM (5.0 mL); rt, 1.0 h; Chromatography (EtOAc/cyclohexane 20→60%), 232 mg, 46%, white solid. ii) 4 M HCl in dioxane (2.0 mL); rt, 3 h. The title compound was obtained as a white solid, which did not require further purification (16 mg, quant.). $^1$H NMR (500 MHz, MeOD) δ 8.26 (d, J=8.0 Hz, 2H), 8.16 (d, J=8.1 Hz, 2H), 7.83 (d, J=3.0 Hz, 1H), 7.34 (d, J=2.7 Hz, 1H), 4.39 (s, 2H), 3.43 (t, J=6.2 Hz, 2H), 3.39-3.33 (m, 2H), 2.02-1.83 (m, 2H). $^{13}$C NMR (126 MHz, MeOD) δ 146.72, 144.76, 143.89, 142.92, 134.78, 130.45, 129.30, 128.26, 52.28, 49.11, 37.11, 22.19. HRMS (ESI) for $C_{14}H_{17}N_4O_4S_3$ ([M+H]$^+$): Calculated 401.0406; Observed 401.0393.

Example 41: (5-((4-((3-(Pyrrolidin-1-yl)propyl)sulfonyl)phenyl)sulfonyl)thiophen-2-yl)methanamine dihydrochloride

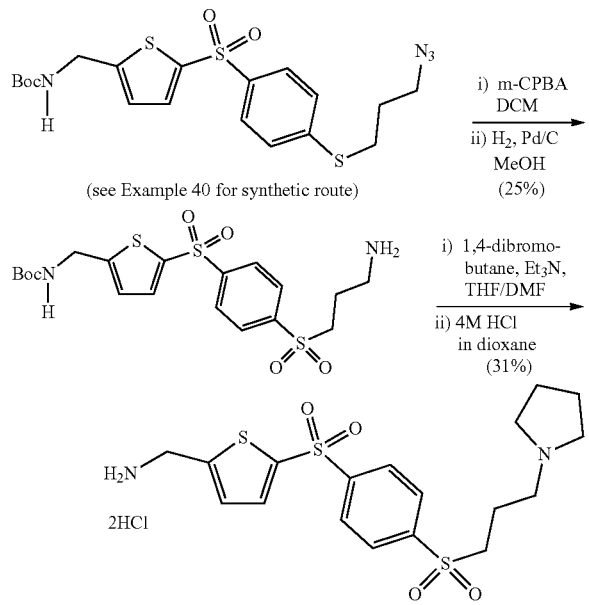

(see Example 40 for synthetic route)

m-CPBA (456 mg, 2.04 mmol) was added to a solution of tert-butyl ((5-((4-((3-azidopropyl)thio)phenyl)sulfonyl)thiophen-2-yl)methyl)carbamate (~1.02 mmol) in DCM (5.0 mL). The mixture was stirred at rt for 1 h and then diluted with EtOAc (30 mL). The organic phase was washed with sat. NaHCO$_3$ (3×30 mL). The combined organic phase was dried over MgSO$_4$, filtered and the solvent was removed under reduced pressure. The crude was purified by chromatography (EtOAc/cyclohexane 20→60%) to afford tert-butyl ((5-((4-((3-azidopropyl)sulfonyl)phenyl)sulfonyl)thiophen-2-yl)methyl)carbamate as a white solid (232 mg, 48%). $^1$H NMR (500 MHz, Chloroform-d) δ 8.19-8.14 (m, 2H), 8.09-8.01 (m, 2H), 7.61 (d, J=3.9 Hz, 1H), 6.96 (d, J=3.9 Hz, 1H), 5.10 (br, 1H), 4.47 (d, J=5.9 Hz, 2H), 3.47 (t, J=6.4 Hz, 2H), 3.26-3.10 (m, 2H), 2.06-1.97 (m, 2H), 1.45 (s, 9H).

A mixture of tert-butyl ((5-((4-((3-azidopropyl)sulfonyl)phenyl)sulfonyl)thiophen-2-yl)methyl)carbamate (215 mg, 0.43 mmol), 10% Pd/C (46 mg, 10%) and THF (2.5 mL) was stirred at rt under H$_2$ atmosphere (balloon) for 16 h. The mixture was filtered through celite, washed with MeOH and the filtrate was evaporated under reduced pressure. The crude was purified by chromatography (MeOH/DCM 5→30%) to afford tert-butyl ((5-((4-((3-aminopropyl)sulfonyl)phenyl)sulfonyl)thiophen-2-yl)methyl)carbamate as a white solid (112 mg, 52%). $^1$H NMR (500 MHz, Chloroform-d) δ 8.17-8.11 (m, 2H), 8.07-8.01 (m, 2H), 7.59 (d, J=3.9 Hz, 1H), 6.94 (d, J=3.9 Hz, 1H), 5.28 (br, 1H), 4.45 (d, J=6.3 Hz, 2H), 3.25-3.17 (m, 2H), 2.78 (t, J=6.7 Hz, 2H), 1.87-1.77 (m, 2H), 1.43 (s, 9H), 1.38-1.15 (br, 2H)

A mixture of tert-butyl ((5-((4-((3-aminopropyl)sulfonyl)phenyl)sulfonyl)thiophen-2-yl)methyl)carbamate (111 mg, 0.234 mmol), 1,4-dibromobutane (31 µL, 0.257 mmol), Et$_3$N (42.4 µL, 0.304 mmol) and DMF/THF (1:1; 2.0 mL) was stirred at 70° C. for 3 h. After cooling to rt, EtOAc (30 mL) was added. The organic solution was washed with 1:1 sat Na$_2$CO$_3$/H$_2$O (30 mL) and brine (30 mL), dried over MgSO$_4$ and filtered. The solvent was removed under reduced pressure. The crude was purified by column chromatography (MeOH/DCM 5→30%) to afford tert-butyl ((5-((4-((3-(pyrrolidin-1-yl)propyl)sulfonyl)phenyl)sulfonyl)thiophen-2-yl)methyl)carbamate as a colourless oil (38 mg, 31%). This was treated with 4 M HCl in dioxane (2.0 mL) and stirred at rt for 16 h. The mixture was filtered. The solid was washed with EtOAc and dissolved in MeOH. The solvent was removed under reduced pressure to afford the title compound as a light brown solid, which did not require further purification (40 mg, quant.). $^1$H NMR (500 MHz, MeOD) δ 8.28 (d, J=8.5 Hz, 2H), 8.19 (d, J=8.5 Hz, 2H), 7.84 (d, J=3.9 Hz, 1H), 7.34 (d, J=3.9 Hz, 1H), 4.39 (s, 2H), 3.51-3.31 (m, 8H), 2.12-2.01 (m, 4H). $^{13}$C NMR (126 MHz, MeOD) δ 146.91, 145.09, 143.55, 142.73, 134.78, 130.31, 129.37, 128.30, 53.86, 52.75, 51.74, 37.07, 22.56. HRMS (ESI) for C$_{18}$H$_{25}$N$_2$O$_4$S$_3$ ([M+H]$^+$): Calculated 429.0971; Observed 429.0958.

Example 42: (5-((3-(Pyrrolidin-1-ylsulfonyl)phenyl)sulfonyl)thiophen-2-yl)(1,1-$^2$H$_2$)methanamine

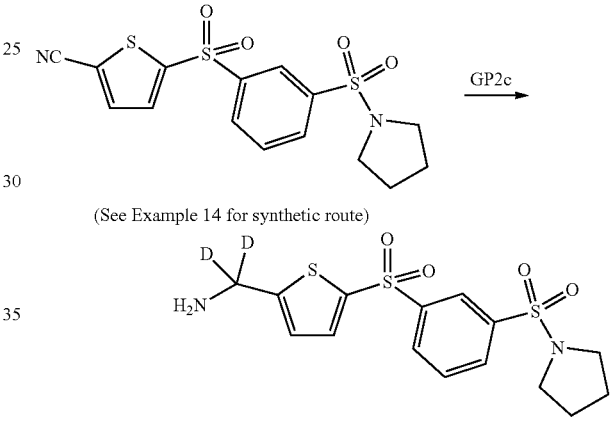

(See Example 14 for synthetic route)

The title compound was synthesised according to general procedures GP2c—from BD$_3$ (1.0 M in THF; 1.50 mL, 1.50 mmol), 5-((3-(pyrrolidin-1-ylsulfonyl)phenyl)sulfonyl)thiophene-2-carbonitrile (192 mg, 0.501 mmol) and THF (1.5 mL); 65° C., 16 h. The crude was purified by chromatography (EtOH/DCM 0→35%) to afford a white solid (37 mg, 19%). $^1$H NMR (500 MHz, CDCl$_3$) δ 8.39 (t, J=1.6 Hz, 1H), 8.18 (ddd, J=7.9, 1.8, 1.1 Hz, 1H), 8.01 (ddd, J=7.8, 1.7, 1.1 Hz, 1H), 7.69 (t, J=7.9 Hz, 1H), 7.62 (d, J=3.9 Hz, 1H), 6.91 (m, 1H), 3.27 (ddd, J=6.8, 4.4, 2.7 Hz, 4H), 1.84-1.75 (m, 4H), 1.56 (br s, 2H). $^{13}$C NMR (126 MHz, CDCl$_3$) δ 159.54 (t, J=9.2 Hz), 144.01, 139.14, 139.03-138.93 (m), 134.69, 131.65, 131.04, 130.41, 126.15, 124.23-124.04 (m), 48.20, 41.46 (dd, J=40.8, 19.7 Hz), 25.44. HRMS (ESI) for C$_{15}$H$_{17}$D$_2$N$_2$O$_4$S$_3$ ([M+H]$^+$): Calculated 389.0627; Observed 389.0608.

Example 43: (S)-(1-((3-((5-(Aminomethyl)thiophen-2-yl)sulfonyl)phenyl)sulfonyl)pyrrolidin-2-yl)methanol

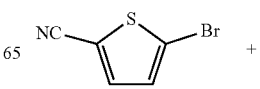 +

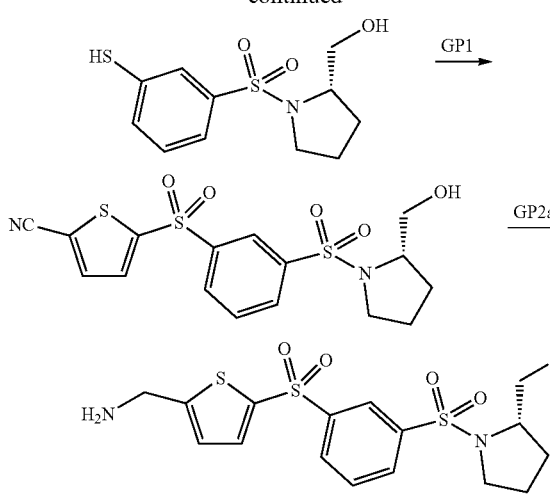

(S)-5-((3-((2-(Hydroxymethyl)pyrrolidin-1-yl)sulfonyl)phenyl)sulfonyl)thiophene-2-carbonitrile was synthesised according to general procedures GP1—from i) 5-bromothiophene-2-carbonitrile (2.75 g, 14.6 mmol), (S)-(1-((3-mercaptophenyl)sulfonyl)pyrrolidin-2-yl)methanol (5.2 g, 19.0 mmol), K$_2$CO$_3$ (3.0 g, 21.9 mmol) and DMF (49 mL); 50° C., 3 h; Chromatography (EtOAc/cyclohexane 20→100%), 2.38 g, 43%, colourless syrup. ii) (S)-5-((3-((2-(hydroxymethyl)pyrrolidin-1-yl)sulfonyl)phenyl)thio)thiophene-2-carbonitrile (180 mg, 0.474 mmol), m-CPBA (77%; 234 mg, 1.04 mmol) and DCM (3.2 mL); rt, 3 h. The crude was used in the subsequent transformation without further purification.

The title compound was synthesised according to general procedures GP2a—from BH$_3$ (1.0 M in THF; 1.42 mL, 1.42 mmol) and THF (1.42 mL); rt, 1 h. The crude was purified by chromatography (EtOH/cyclohexane 20→100%) to afford a white foam (141 mg, 72%). $^1$H NMR (500 MHz, CDCl$_3$) δ 8.37 (t, J=1.8 Hz, 1H), 8.18 (dt, J=7.9, 1.5 Hz, 1H), 8.02 (dt, J=7.8, 1.4 Hz, 1H), 7.70 (t, J=7.9 Hz, 1H), 7.60 (d, J=3.8 Hz, 1H), 6.91 (m, 1H), 4.07 (d, J=1.0 Hz, 2H), 3.69-3.58 (m, 3H), 3.45 (ddd, J=10.4, 6.9, 5.2 Hz, 1H), 3.18 (dt, J=10.4, 7.1 Hz, 1H), 2.13 (br s, 3H), 1.88-1.75 (m, 2H), 1.70-1.58 (m, 1H), 1.55-1.43 (m, 1H). $^{13}$C NMR (126 MHz, CDCl$_3$) δ 159.51, 144.04, 139.01, 138.72, 134.73, 131.69, 131.20, 130.61, 126.10, 124.24, 65.27, 62.06, 50.01, 41.54, 28.72, 24.26. HRMS (ESI) for C$_{16}$H$_{20}$N$_2$O$_5$S$_3$Na ([M+Na]$^+$): Calculated 439.0427; Observed 439.0413.

(S)-(1-((3-Mercaptophenyl)sulfonyl)pyrrolidin-2-yl)methanol

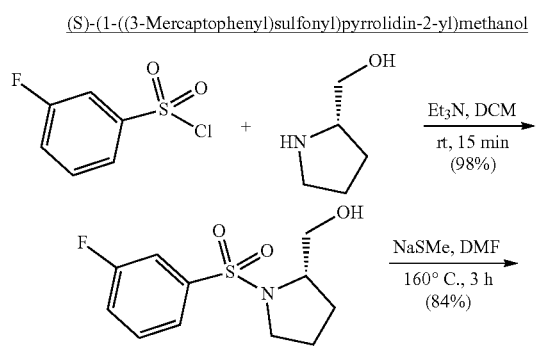

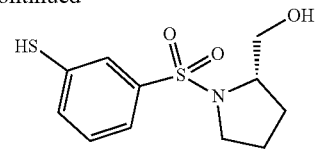

A mixture of 3-fluorobenzenesulfonyl chloride (300 mg, 1.54 mmol), (S)-pyrrolidin-2-ylmethanol (152 μL, 1.54 mmol), Et$_3$N (322 μL, 2.31 mmol) and DCM (7.7 mL) was stirred at rt for 15 min. The solution was diluted with DCM (30 mL), washed with 1M HCl (40 mL) and sat. NaHCO$_3$ (40 mL), dried over MgSO$_4$ and filtered. The solvent was removed under reduced pressure to afford (S)-(1-((3-fluorophenyl)sulfonyl)pyrrolidin-2-yl)methanol as a colourless oil (390 mg, 98%). $^1$H NMR (500 MHz, Chloroform-d) δ 7.67-7.60 (m, 1H), 7.57-7.49 (m, 2H), 7.31 (td, J=8.4, 2.7 Hz, 1H), 3.73-3.61 (m, 3H), 3.45 (m, 1H), 3.20 (m, 1H), 2.93-2.77 (br, 1H), 1.88-1.73 (m, 2H), 1.67 (m, 1H), 1.48 (m, 1H).

A mixture of (S)-(1-((3-fluorophenyl)sulfonyl)pyrrolidin-2-yl)methanol (5.88 g, 22.7 mmol), NaSMe (5.60 g, 79.4 mmol) and DMF (60 mL) was stirred at 160° C. in a sealed tube for 3 h. After cooling to rt, the aqueous phase was washed with DCM (120 mL), acidified to pH<3 and extracted with EtOAc (3×80 mL). The combined organic phase was washed with 1:1 H$_2$O/brine (3×150 mL), dried over MgSO$_4$ and filtered. The solvent was removed under reduced pressure to afford (S)-(1-((3-mercaptophenyl)sulfonyl)pyrrolidin-2-yl)methanol as a yellow oil (5.20 g, 84%). $^1$H NMR (500 MHz, CDCl$_3$) δ 7.75 (t, J=1.7 Hz, 1H), 7.61 (dt, J=7.8, 1.3 Hz, 1H), 7.48 (m, 1H), 7.40 (t, J=7.8 Hz, 1H), 3.73-3.60 (m, 4H), 3.47 (m, 1H), 3.25 (dt, J=10.4, 7.1 Hz, 1H), 2.74 (br, 1H), 1.86-1.68 (m, 3H), 1.51 (m, 1H).

Example 44: (S)-(5-((3-((2-((4-Fluorophenoxy)methyl)pyrrolidin-1-yl)sulfonyl)phenyl)sulfonyl)thiophen-2-yl)methanamine

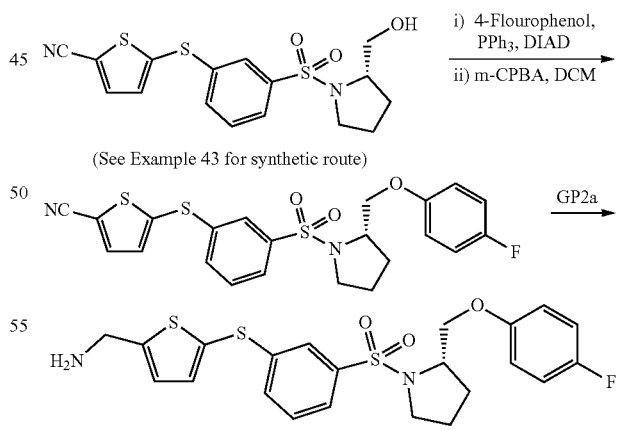

(See Example 43 for synthetic route)

PPh$_3$ (186 mg, 0.711 mmol) was added to a solution of diisopropyl azodicarboxylate (DIAD) (140 μL, 0.711 mmol) and (S)-5-((3-((2-(hydroxymethyl)pyrrolidin-1-yl)sulfonyl)phenyl)thio)thiophene-2-carbonitrile (180 mg, 0.474 mmol) in THF (2.4 mL) and the mixture was stirred at rt for 5 min. 4-Fluorophenol (106 mg, 0.947 mmol) in THF (1 mL) was added and the reaction mixture was stirred at rt for a further 24 h. EtOAc (20 mL) was added and the organic phase was washed with sat. NaHCO₃ (3×20 mL), dried over MgSO₄, filtered and the solvent was removed under reduced pressure. The crude was purified by chromatography (EtOAC/cyclohexane 0→80%) to afford (S)-5-((3-((2-((4-fluorophenoxy)methyl)pyrrolidin-1-yl)sulfonyl)phenyl)thio)thiophene-2-carbonitrile (173 mg, 77%) as a colourless oil.

m-CPBA (77%; 93.3 mg, 0.416 mmol) was added to a solution of (S)-5-((3-((2-((4-fluorophenoxy)methyl)pyrrolidin-1-yl)sulfonyl)phenyl)thio)thiophene-2-carbonitrile (79 mg, 0.166 mmol) in DCM (1.0 mL) and the mixture was stirred at rt for 1 h. When complete conversion was achieved, EtOAc was added (10 mL). The organic phase was washed with sat. NaHCO₃ (3×10 mL), dried over MgSO₄ and filtered. The solvent was removed under reduced pressure. The crude was purified by chromatography (EtOAc/cyclohexane 30→80%) to afford (S)-5-((3-((2-((4-fluorophenoxy)methyl)pyrrolidin-1-yl)sulfonyl)phenyl)sulfonyl)thiophene-2-carbonitrile as a colourless oil (65 mg, 77%). ¹H NMR (500 MHz, CDCl₃) δ 8.44 (s, 1H), 8.17 (d, J=7.9 Hz, 1H), 8.09 (d, J=7.9 Hz, 1H), 7.73 (t, J=7.9 Hz, 1H), 7.67 (d, J=4.0 Hz, 1H), 7.57 (d, J=4.0 Hz, 1H), 6.97 (t, J=8.6 Hz, 2H), 6.85-6.77 (m, 2H), 4.17 (dd, J=9.1, 3.0 Hz, 1H), 4.01-3.88 (m, 2H), 3.54 (m, 1H), 3.18 (m, 1H), 2.08-1.95 (m, 2H), 1.78-1.66 (m, 2H).

The title compound was synthesised according to general procedures GP2a—from BH₃ (1.0 M in THF; 0.5 mL, 0.5 mmol), (S)-5-((3-((2-((4-fluorophenoxy)methyl)pyrrolidin-1-yl)sulfonyl)phenyl)sulfonyl)thiophene-2-carbonitrile (65 mg, 0.128 mmol) and THF (0.5 mL); rt, 1 h. The crude was purified by chromatography (EtOH/cyclohexane 30→100%) to afford a colourless oil (29 mg, 44%). ¹H NMR (500 MHz, CDCl₃) δ 8.41 (s, 1H), 8.17 (d, J=7.9 Hz, 1H), 8.01 (d, J=7.8 Hz, 1H), 7.66 (t, J=7.9 Hz, 1H), 7.60 (d, J=3.8 Hz, 1H), 6.98 (t, J=8.5 Hz, 2H), 6.90 (d, J=3.8 Hz, 1H), 6.87-6.78 (m, 2H), 4.19 (dd, J=9.0, 2.9 Hz, 1H), 4.07 (s, 2H), 4.01-3.87 (m, 2H), 3.54 (m, 1H), 3.16 (m, 1H), 2.07-1.92 (m, 2H), 1.85-1.49 (m, 4H). ¹³C NMR (126 MHz, CDCl₃) δ 159.76, 157.51 (d, J=238.4 Hz), 154.51 (d, J=1.7 Hz), 144.13, 139.29, 138.85, 134.71, 131.58, 131.21, 130.53, 126.15, 124.05, 116.02 (d, J=23.0 Hz), 115.54 (d, J=8.1 Hz), 70.30, 58.85, 49.63, 41.67, 28.95, 24.13. ¹⁹F NMR (471 MHz, CDCl₃). HRMS (ESI) for C₂₂H₂₃FN₂O₅S₃Na ([M+Na]⁺): Calculated 533.0645; Observed 533.0636.

Example 45: (S)-(1-((3-((5-(Aminomethyl)thiophen-2-yl)sulfonyl)phenyl)sulfonyl)pyrrolidin-2-yl)methyl (4-fluorophenyl)carbamate

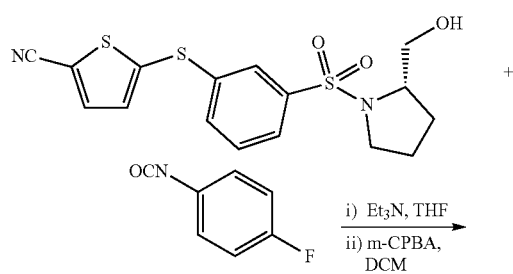

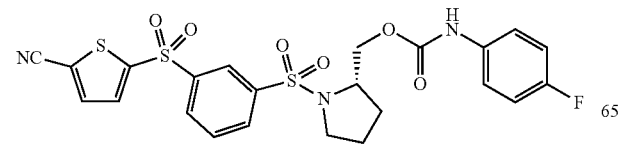

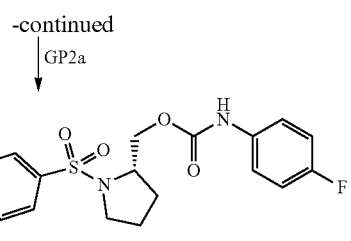

1-Fluoro-4-isocyanatobenzene (48.6 μL, 0.429 mmol) was added to a mixture of (S)-5-((3-((2-(hydroxymethyl)pyrrolidin-1-yl)sulfonyl)phenyl)thio)thiophene-2-carbonitrile (136 mg, 0.357 mmol) and Et₃N (60.0 μL, 0.429 mmol) in THF (1.8 mL) and the reaction was stirred at rt for 3 h. EtOAc (20 mL) was added. The organic phase was washed with H₂O (20 mL) and brine (20 mL), dried over MgSO₄, filtered and the solvent was removed under reduced pressure. The crude was purified by chromatography (EtOAc/cyclohexane 10→30%) to afford (S)-(1-((3-((5-cyanothiophen-2-yl)sulfonyl)phenyl)thio)pyrrolidin-2-yl)methyl (4-fluorophenyl)carbamate as a white foam (182 mg, 98%). DCM (1.8 mL) was added followed by m-CPBA (77%; 173 mg, 0.774 mmol) and the mixture was stirred at rt for 1 h. When complete conversion was achieved, EtOAc was added (10 mL). The organic phase was washed with sat. NaHCO₃ (3×10 mL), dried over MgSO₄ and filtered. The solvent was removed under reduced pressure. The crude was purified by chromatography (EtOAc/cyclohexane 15→60%) to afford (S)-(1-((3-((5-cyanothiophen-2-yl)sulfonyl)phenyl)sulfonyl)pyrrolidin-2-yl)methyl (4-fluorophenyl)carbamatea as a white solid (165 mg, 85%).

The title compound was synthesised according to general procedures GP2a—from BH₃ (1.0 M in THF; 0.9 mL, 0.9 mmol), (S)-(1-((3-((5-cyanothiophen-2-yl)sulfonyl)phenyl)sulfonyl)pyrrolidin-2-yl)methyl (4-fluorophenyl)carbamate (165 mg, 0.30 mmol) and THF (0.9 mL); rt, 0.5 h. The crude was purified by chromatography (EtOH/cyclohexane 30→100%) to afford a white foam (50 mg, 30%). ¹H NMR (500 MHz, CDCl₃) δ 8.52 (s, 1H), 8.16 (m, 1H), 8.06 (m, 1H), 7.69 (t, J=7.9 Hz, 1H), 7.61 (d, J=3.9 Hz, 1H), 7.46-7.28 (m, 3H), 7.03-6.95 (m, 2H), 6.90 (d, J=3.8 Hz, 1H), 4.34 (dd, J=11.4, 4.6 Hz, 1H), 4.23 (dd, J=11.4, 5.5 Hz, 1H), 4.11-4.02 (m, 3H), 3.42-3.25 (m, 2H), 1.97-1.66 (m, 4H), 1.59 (br s, 2H). ¹³C NMR (126 MHz, CDCl₃) δ 159.89, 159.08 (d, J=242.0 Hz), 153.49, 143.86, 140.57, 138.62, 134.77, 134.03 (br), 130.84 (d, J=62.1 Hz), 126.10, 124.16, 120.60 (br), 115.72 (d, J=22.3 Hz), 66.04, 59.15, 49.27, 41.65, 28.77, 24.49. ¹⁹F NMR (471 MHz, CDCl₃) δ−119.59. HRMS (ESI) for C₂₃H₂₅FN₃O₆S₃Na ([M+Na]⁺): Calculated 554.0884; Observed 554.0870.

Example 46: (S)-(5-((3-((2-((Benzyloxy)methyl)pyrrolidin-1-yl)sulfonyl)phenyl)sulfonyl) thiophen-2-yl)methanamine

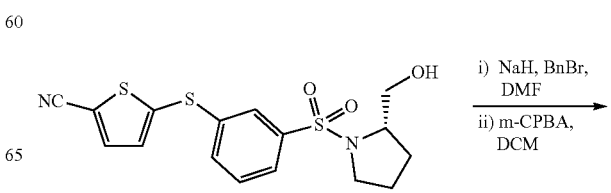

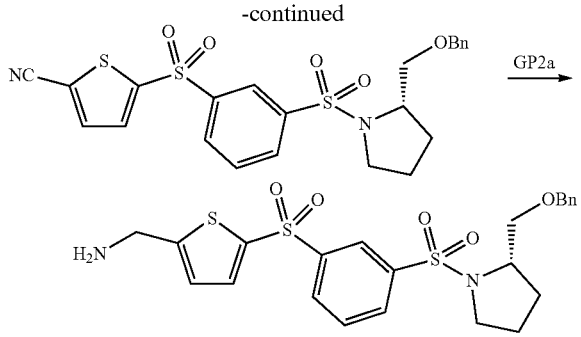

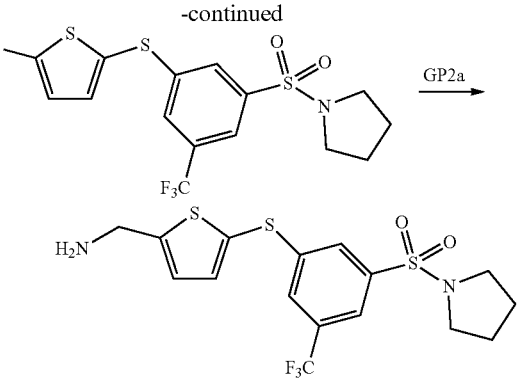

NaH (60% in mineral oil; 18.2 mg, 0.454 mmol) was added to a solution of (S)-5-((3-((2-(hydroxymethyl)pyrrolidin-1-yl)sulfonyl)phenyl)thio)thiophene-2-carbonitrile (144 mg, 0.378 mmol) and BnBr (54.0 µL, 0.454 mmol) in DMF (1.9 mL). The mixture was stirred at rt for 3 h and then diluted with EtOAc (20 mL). The organic phase was washed with 1:1 H$_2$O/brine (3×20 mL), dried over MgSO$_4$, filtered and the solvent was removed under reduced pressure. The crude was purified by chromatography (EtOAc/cyclohexane 0→30%) to afford (S)-5-((3-((2-((benzyloxy)methyl)pyrrolidin-1-yl)sulfonyl)phenyl)thio)thiophene-2-carbonitrile (52 mg, 29%) as a white foam. DCM (1.0 mL) was added followed by m-CPBA (77%; 62 mg, 0.276 mmol) and the mixture was stirred at rt for 3 h. When complete conversion was achieved, EtOAc was added (10 mL). The organic phase was washed with sat. NaHCO$_3$ (3×10 mL), dried over MgSO$_4$ and filtered. The solvent was removed under reduced pressure to afford (S)-5-((3-((2-((benzyloxy)methyl)pyrrolidin-1-yl)sulfonyl)phenyl)sulfonyl)thiophene-2-carbonitrile, which was used in the subsequent transformation without further purification.

The title compound was synthesised according to general procedures GP2a—from (S)-5-((3-((2-((benzyloxy)methyl)pyrrolidin-1-yl)sulfonyl)phenyl)sulfonyl)thiophene-2-carbonitrile (crude), BH$_3$ (1.0 M in THF; 0.33 mL, 0.33 mmol) and THF (0.6 mL); rt, 0.5 h. The crude was purified by chromatography (EtOH/cyclohexane 20→100%) to afford a white foam (34 mg, 61%). $^1$H NMR (500 MHz, CDCl$_3$) δ 8.40 (t, J=1.6 Hz, 1H), 8.17 (dt, J=7.9, 1.3 Hz, 1H), 8.00 (dt, J=7.8, 1.3 Hz, 1H), 7.68-7.59 (m, 2H), 7.39-7.28 (m, 5H), 6.90 (d, J=3.8 Hz, 1H), 4.53 (AB system; d, J=11.9 Hz, 1H), 4.50 (AB system; d, J=11.9 Hz, 1H), 4.06 (s, 2H), 3.80 (m, 1H), 3.69 (dd, J=9.5, 3.7 Hz, 1H), 3.53-3.42 (m, 2H), 3.14 (m, 1H), 1.97-1.83 (m, 2H), 1.73-1.56 (m, 4H). $^{13}$C NMR (126 MHz, CDCl$_3$) δ 159.63, 144.01, 139.68, 139.00, 138.20, 134.68, 131.67, 131.05, 130.40, 128.55, 127.83, 127.79, 126.20, 124.07, 73.53, 72.60, 59.60, 49.50, 41.68, 28.96, 24.19. HRMS (ESI) for C$_{23}$H$_{27}$N$_2$O$_5$S$_3$ ([M+H]$^+$): Calculated 507.1077; Observed 507.1060.

Example 47: (5-((3-(Pyrrolidin-1-ylsulfonyl)-5-(trifluoromethyl)phenyl)sulfonyl)thiophen-2-yl)methanamine

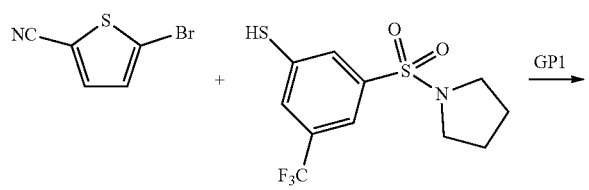

5-((3-(Pyrrolidin-1-ylsulfonyl)-5-(trifluoromethyl)phenyl)sulfonyl)thiophene-2-carbonitrile was synthesised according to general procedures GP1—from i) 5-bromothiophene-2-carbonitrile (210 mg, 1.13 mmol), 3-(pyrrolidin-1-ylsulfonyl)-5-(trifluoromethyl)benzenethiol (386 mg, 1.24 mmol), K$_2$CO$_3$ (257 mg, 1.86 mmol) and DMF (4.1 mL); 60° C., 6 h. ii) m-CPBA (77%; 523 mg, 2.33 mmol) and DCM (3.8 mL); rt, 16 h. The crude was purified by chromatography (EtOAc/cyclohexane 10→50%) to afford a white solid (205 mg, 40%). $^1$H NMR (500 MHz, CDCl$_3$) δ 8.57 (br, 1H), 8.41 (br, 1H), 8.29 (br, 1H), 7.77 (d, J=4.0 Hz, 1H), 7.64 (d, J=4.0 Hz, 1H), 3.33-3.23 (m, 4H), 1.93-1.82 (m, 4H).

The title compound was synthesised according to general procedures GP2a—from BH$_3$ (1.0 M in THF; 1.0 mL, 1.0 mmol), 5-((3-(pyrrolidin-1-ylsulfonyl)-5-(trifluoromethyl)phenyl)sulfonyl)thiophene-2-carbonitrile (150 mg, 0.333 mmol) and THF (1.0 mL); rt, 1 h. The crude was purified by chromatography (EtOH/cyclohexane 20→100%) to afford a white solid (58 mg, 39%). $^1$H NMR (500 MHz, CDCl$_3$) δ 8.53 (m, 1H), 8.39 (m, 1H), 8.25-8.19 (m, 1H), 7.67 (d, J=3.9 Hz, 1H), 6.95 (dt, J=3.9, 1.0 Hz, 1H), 4.10 (s, 2H), 3.35-3.23 (m, 4H), 1.90-1.80 (m, 4H), 1.61 (br s, 2H). $^{13}$C NMR (126 MHz, CDCl$_3$) δ 160.93, 145.48, 140.88, 137.68, 135.46, 133.30 (q, J=34.5 Hz), 129.04, 128.24 (q, J=3.3 Hz), 127.72 (q, J=3.5 Hz), 124.28, 122.46 (q, J=273.6 Hz), 48.28, 41.70, 25.49. $^{19}$F NMR (471 MHz, CDCl$_3$) δ −62.73. HRMS (ESI) for C$_{16}$H$_{18}$F$_3$N$_2$O$_4$S$_3$ ([M+H]$^+$): Calculated 455.0375; Observed 455.0386.

3-(Pyrrolidin-1-ylsulfonyl)-5-(trifluoromethyl)benzenethiol

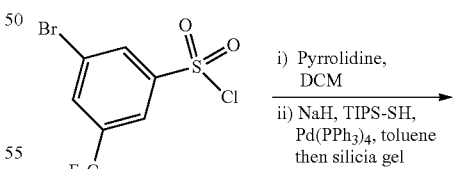

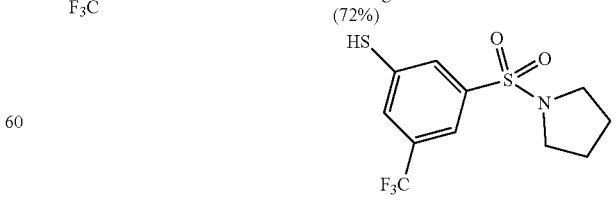

Pyrroline (1.30 mL, 15.5 mmol) was added to a solution of 3-Bromo-5-(trifluoromethyl)benzenesulfonyl chloride (1.09 mL, 6.20 mmol) in DCM (21 mL). The mixture was stirred at rt for 15 min, and then diluted with DCM (20 mL). The organic layer was washed with H₂O (40 mL), dried over MgSO₄, filtered and the solvent was removed under reduced pressure to afford 1-((3-bromo-5-(trifluoromethyl)phenyl)sulfonyl)pyrrolidine (2.43 g, quant.) as a white crystalline solid that is used in the subsequent transformation without further purification.

NaH (60% in mineral oil; 61.4 mg, 1.53 mmol) was added to a solution of triisopropylsilylmercaptan (TIPS-SH) (330 µL, 1.53 mmol) and 5-(trifluoromethyl)phenyl)sulfonyl)pyrrolidine (386 mg, 1.24 mmol) in toluene (6.2 mL) and the mixture was stirred at rt for 10 min. Pd(PPh₃)₄ (161 mg, 10%) was added and the mixture was degassed before it was stirred at 100° C. for 16 h. After cooling to rt, silica gel (~5 g) was added and the suspension was stirred vigorously for 0.5 h. The solvent was removed under reduced pressure and the crude-silica mixture was purified by chromatography (EtOAc/cyclohexane 20% then 100% to give 3-(Pyrrolidin-1-ylsulfonyl)-5-(trifluoromethyl)benzenethiol as a white solid (257 mg, 72%). ¹H NMR (500 MHz, Chloroform-d) δ 7.87 (br, 1H), 7.79 (br, 1H), 7.69 (br, 1H), 3.90 (d, J=3.9 Hz, 1H), 3.32-3.18 (m, 4H), 1.88-1.73 (m, 4H).

Example 48: (S)—N-((1-((3-((5-(Aminomethyl)thiophen-2-yl)sulfonyl)phenyl)sulfonyl)pyrrolidin-2-yl)methyl)benzenesulfonamide

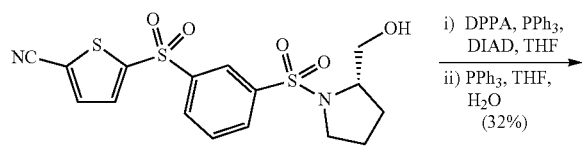

(See Example 43 for synthetic route)

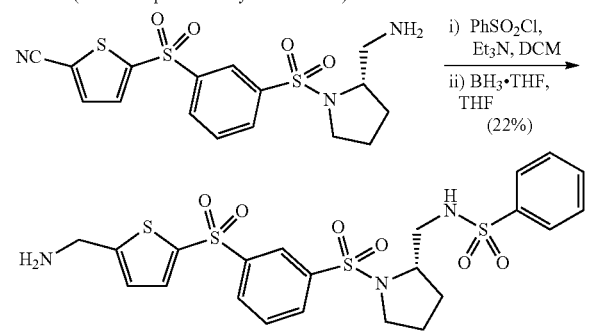

DIAD (467 µL, 2.37 mmol) was added to a solution of PPh₃ (622 mg, 2.37 mmol) in THF (8 mL) and the reaction was stirred at rt for 0.5 h. Diphenyl phosphoryl azide (DPPA) (681 µL, 3.16 mmol) and (S)-5-((3-((2-(hydroxymethyl)pyrrolidin-1-yl)sulfonyl)phenyl)sulfonyl)thiophene-2-carbonitrile (602 mg, 1.58 mmol) in THF (1 mL) were added and the reaction mixture was stirred at rt for a further 20 h. EtOAc (30 mL) was added and the organic phase was washed with H₂O (40 mL) and brine (40 mL), dried over MgSO₄, filtered and the solvent was removed under reduced pressure. The crude was purified by chromatography (EtOAc/cyclohexane 20→60%) to afford (S)-5-((3-((2-(azidomethyl)pyrrolidin-1-yl)sulfonyl)phenyl)sulfonyl)thiophene-2-carbonitrile a colourless oil, which was dissolved in THF (2.6 mL) and H₂O (0.3 mL). PPh₃ (207 mg, 0.791 mmol) was added and the mixture was stirred at rt for 16 h. The solvent was removed under reduced pressure. The crude was purified by chromatography (MeOH/DCM 0→15%) to afford (S)-5-((3-((2-(aminomethyl)pyrrolidin-1-yl)sulfonyl)phenyl)sulfonyl)thiophene-2-carbonitrile as a white foam (194 mg, 32% over 2 steps).

PhSO₂Cl (21 µL, 0.164 mmol) was added to a mixture of (S)-5-((3-((2-(aminomethyl)pyrrolidin-1-yl)sulfonyl)phenyl)sulfonyl)thiophene-2-carbonitrile (52 mg, 0.126 mmol), Et₃N (26 µL, 0.190 mmol) and DCM (1 mL) and the reaction was stirred at rt for 1 h. DCM (10 mL) was added and organic phase was washed with H₂O (10 mL), dried over MgSO₄, filtered and the solvent was removed under reduced pressure. The crude was dissolved in THF (1 mL), BH₃ (1.0 M in THF; 1.0 mL, 1.0 mmol) was added and the reaction was stirred at rt for 2 h. Ethanol (5 mL) was added and the mixture was heated at 70° C. for 1 h. The solvent was removed under reduced pressure and the crude was purified by chromatography (EtOH/cyclohexane 25, then 100%) to afford the title compound as a light yellow foam (11.2 mg, 22%). ¹H NMR (500 MHz, MeOD) δ 8.31 (t, J=1.7 Hz, 1H), 8.26 (ddd, J=7.9, 1.8, 1.0 Hz, 1H), 8.06 (ddd, J=7.9, 1.7, 1.2 Hz, 1H), 7.94-7.87 (m, 2H), 7.83 (t, J=7.9 Hz, 1H), 7.73 (d, J=3.8 Hz, 1H), 7.65 (m, 1H), 7.63-7.58 (m, 2H), 7.07 (dt, J=3.8, 0.9 Hz, 1H), 4.00 (d, J=0.8 Hz, 2H), 3.57 (m, 1H), 3.41 (m, 1H), 3.19 (dd, J=13.4, 3.9 Hz, 1H), 3.07 (m, 1H), 2.87 (dd, J=13.4, 8.7 Hz, 1H), 1.87-1.75 (m, 2H), 1.51-1.37 (m, 2H). ¹³C NMR (126 MHz, MeOD) δ 159.90, 145.36, 141.83, 140.39, 139.84, 136.11, 133.75, 133.13, 132.33, 132.22, 130.31, 128.03, 126.90, 126.60, 61.12, 50.91, 48.00, 41.69, 29.77, 24.52. HRMS (ESI) for C₂₂H₂₆N₃O₆S₄ ([M+H]⁺): Calculated 556.0699; Observed 556.0700.

Example 49: (S)—N-((1-((3-((5-(Aminomethyl)thiophen-2-yl)sulfonyl)phenyl)sulfonyl)pyrrolidin-2-yl)methyl)propane-2-sulfonamide

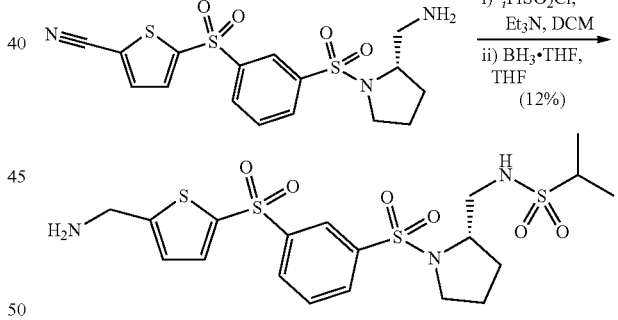

ⁱPrSO₂Cl (18 µL, 0.164 mmol) was added to a mixture of (S)-5-((3-((2-(aminomethyl)pyrrolidin-1-yl)sulfonyl)phenyl)sulfonyl)thiophene-2-carbonitrile (52 mg, 0.126 mmol), Et₃N (26 µL, 0.190 mmol) and DCM (1 mL) and the reaction was stirred at rt for 1 h. DCM (10 mL) was added and organic phase was washed with H₂O (10 mL), dried over MgSO₄, filtered and the solvent was removed under reduced pressure. The crude was dissolved in THF (1 mL), BH₃ (1.0 M in THF; 1.0 mL, 1.0 mmol) was added and the reaction was stirred at rt for 2 h. Ethanol (5 mL) was added and the mixture was heated at 70° C. for 1 h. The solvent was removed under reduced pressure and the crude was purified by chromatography (EtOH/cyclohexane 25, then 100%) to afford a white solid (6.5 mg, 13%). ¹H NMR (500 MHz, MeOD) δ 8.39 (t, J=1.6 Hz, 1H), 8.32 (m, 1H), 8.18 (m, 1H), 7.90 (t, J=7.9 Hz, 1H), 7.78 (d, J=3.9 Hz, 1H), 7.13 (m, 1H), 4.05 (s, 2H), 3.64 (m, 1H), 3.53 (m, 1H), 3.47 (dd, J=13.5, 3.9 Hz, 1H), 3.31 (hept, J=6.7 Hz, 1H), 3.21-3.11 (m, 2H), 1.99-1.84 (m, 2H), 1.57-1.47 (m, 2H), 1.42 (d, J=4.3 Hz, 3H), 1.41 (d, J=4.3 Hz, 3H). $^{13}$C NMR (126 MHz, MeOD) δ 159.91, 145.38, 140.43, 139.86, 136.10, 133.18, 132.33, 132.25, 126.92, 126.61, 61.80, 54.06, 50.94, 48.24, 41.68, 29.58, 24.55, 16.96, 16.85. HRMS (ESI) for $C_{19}H_{28}N_3O_6S_4$ ([M+H]$^+$): Calculated 522.0855; Observed 522.0850.

Example 50: 3-((5-(Aminomethyl)thiophen-2-yl)sulfonyl)-N-(2-hydroxyethyl)benzamide hydrochloride

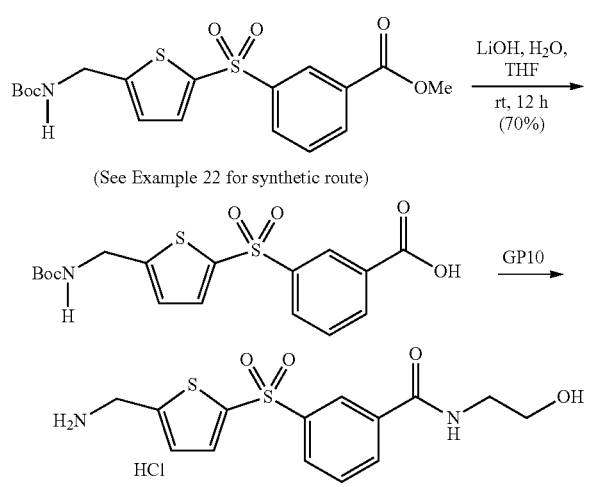

(See Example 22 for synthetic route)

A mixture of LiOH.H$_2$O (28 mg, 0.667 mmol), methyl 3-((5-(((tert-butoxycarbonyl)amino)methyl)thiophen-2-yl)sulfonyl)benzoate (250 mg, 0.608 mmol), H$_2$O (5.0 mL) and THF (10 mL) was stirred at rt for 12 h. The pH of the solution was adjusted to <4 and the aqueous phase was extracted with EtOAc. The combined organic phase was dried over MgSO$_4$, filtered and the solvent was removed under reduced pressure to afford 3-((5-(((tert-butoxycarbonyl)amino)methyl)thiophen-2-yl)sulfonyl)benzoic acid, which did not require further purification (170 mg, 70%). $^1$H NMR (500 MHz, CDCl$_3$) δ 8.62 (s, 1H), 8.25 (d, J=7.6 Hz, 1H), 8.16 (d, J=7.9 Hz, 1H), 7.51-7.69 (m, 2H), 6.92 (d, J=3.5 Hz, 1H), 4.92-5.64 (m, 1H), 4.44 (br. s., 2H), 1.42 (s, 9H).

The title compound was synthesised according to general procedures GP10—from i) 3-((5-(((tert-butoxycarbonyl)amino)methyl)thiophen-2-yl)sulfonyl)benzoic acid (50 mg, 0.126 mmol), HBTU (53 mg, 0.140 mmol), Et$_3$N (14.5 mg, 0.143 mmol), ethanolamine (8.5 μL, 0.141 mmol) and DMF (2.0 mL); rt, 12 h. ii) 4 M HCl in dioxane (1.0 mL); rt, 12 h. The crude was recrystallised from DCM/cyclohexane (36 mg, 76%). $^1$H NMR (500 MHz, CD$_3$OD) δ 6.89 (s, 1H), 6.37-6.67 (m, 1H), 6.21 (d, J=3.8 Hz, 1H), 6.14 (t, J=7.9 Hz, 1H), 5.75 (d, J=3.8 Hz, 1H), 2.82 (s, 1H), 2.15 (t, J=5.7 Hz, 1H), 1.95 (t, J=5.7 Hz, 1H). $^{13}$C NMR (126 MHz, CD$_3$OD) δ 168.3, 145.5, 145.4, 143.9, 137.5, 135.6, 133.5, 131.8, 131.3, 131.2, 127.6, 61.6, 43.9, 38.6. HRMS calcd for $C_{14}H_{16}N_2O_4S_2$ [M-NH$_2$]$^+$ 324.0364; found 324.0406.

Example 51: 3-((5-(Aminomethyl)thiophen-2-yl)sulfonyl)-N,N-dimethylbenzamide hydrochloride

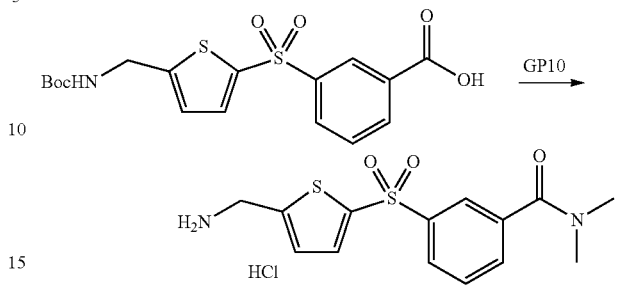

The title compound was synthesised according to general procedures GP10—from i) 3-((5-(((tert-butoxycarbonyl)amino)methyl)thiophen-2-yl)sulfonyl)benzoic acid (50 mg, 0.126 mmol), HBTU (53 mg, 0.140 mmol), Et$_3$N (14.5 mg, 0.143 mmol), Me$_2$NH (2.0 M in THF; 70 μL, 0.140 mmol) and DMF (2.0 mL); rt, 12 h. ii) 4 M HCl in dioxane (1.0 mL); rt, 12 h. The crude was recrystallised from DCM/cyclohexane (1.3 mg, 3%). $^1$H NMR (500 MHz, CD$_3$OD) δ 7.75 (d, J=7.6 Hz, 1H), 7.70 (s, 1H), 7.43 (d, J=3.8 Hz, 1H), 7.30-7.41 (m, 2H), 6.98 (d, J=3.5 Hz, 1H), 4.05 (s, 2H), 2.77 (s, 3H), 2.62 (s, 3H). $^{13}$C NMR (126 MHz, CD$_3$OD) δ 171.4, 145.6, 145.3, 143.8, 139.1, 135.6, 133.4, 131.9, 131.4, 129.7, 127.2, 40.1, 38.6, 35.9. HRMS calcd for $C_{14}H_{16}N_2O_3S_2$ [M-NH$_2$]$^+$ 308.0415; found 308.0564

Example 52: 3-((5-(Aminomethyl)thiophen-2-yl)sulfonyl)-N-(2-((4-methoxyphenyl)sulfonyl)-ethyl)benzamide hydrochoride

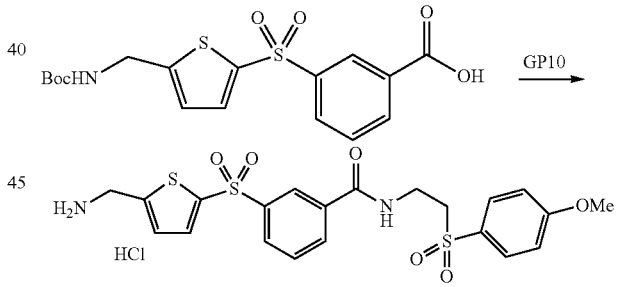

The title compound was synthesised according to general procedures GP10—from i) 3-((5-(((tert-butoxycarbonyl)amino)methyl)thiophen-2-yl)sulfonyl)benzoic acid (50 mg, 0.126 mmol), HBTU (53 mg, 0.140 mmol), Et$_3$N (14.5 mg, 0.143 mmol), 2-((4-methoxyphenyl)sulfonyl)ethanamine hydrochloride (36 mg, 0.143 mmol) and DMF (2.0 mL); rt, 12 h. ii) 4 M HCl in dioxane (1.0 mL); rt, 12 h. The crude was recrystallised from DCM/cyclohexane (1.2 mg, 2%). $^1$H NMR (500 MHz, CD$_3$OD) δ 8.34 (s, 1H), 8.14 (d, J=7.9 Hz, 1H), 7.96 (d, J=7.9 Hz, 1H), 7.85 (d, J=8.8 Hz, 2H), 7.78 (d, J=3.8 Hz, 1H), 7.67 (t, J=7.9 Hz, 1H), 7.33 (d, J=3.8 Hz, 1H), 7.04 (d, J=8.8 Hz, 2H), 4.39 (s, 2H), 3.80 (s, 3H), 3.75 (t, J=6.0 Hz, 2H), 3.56 (t, J=6.3 Hz, 2H). $^{13}$C NMR (126 MHz, CD$_3$OD) δ 167.6, 165.6, 145.6, 145.3, 143.9, 136.7, 135.6, 133.4, 132.2, 131.8, 131.5, 131.4, 131.2, 127.5, 115.8, 56.5, 55.4, 54.9, 391, 38.6, 35.9. HRMS calcd for $C_{21}H_{22}N_2O_6S_3$[M-NH$_2$]$^+$ 478.0453; found 478.0548

Example 53: (5-(Thiophen-2-ylsulfonyl)thiophen-2-yl)methanamine hydrochloride

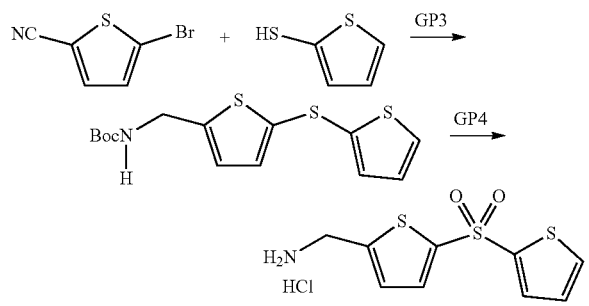

tert-Butyl ((5-(thiophen-2-ylthio)thiophen-2-yl)methyl)carbamate was synthesised according to general procedures GP3—from i) 5-bromothiophene-2-carbonitrile (406 mg, 2.83 mmol), thiophene-2-thiol (362 mg, 3.11 mmol), K$_2$CO$_3$ (781 mg, 5.66 mmol) and DMF (11 mL); 120° C., 16 h; chromatography (EtOAc/cyclohexane 2→10%), 442 mg, 70%. ii) 5-(thiophen-2-ylthio)thiophene-2-carbonitrile (326 mg, 1.46 mmol), BH$_3$ (1.0 M in THF; 4.4 mL, 4.40 mmol; rt, 1 h. iii) Boc$_2$O (478 mg, 2.19 mmol), Et$_3$N (0.31 mL, 2.22 mmol), DCM (40 mL); rt, 16 h. The crude was purified by chromatography (EtOAc/cyclohexane 2→20%) to afford tert-butyl ((5-(thiophen-2-ylthio)thiophen-2-yl)methyl)carbamate (258 mg, 54% over 2 steps). $^1$H NMR (500 MHz, CDCl$_3$) δ 8.58 (s, 1H), 8.22 (d, J=7.9 Hz, 1H), 8.13 (d, J=7.9 Hz, 1H), 7.60 (t, J=7.9 Hz, 1H), 7.56 (d, J=3.8 Hz, 1H), 6.91 (d, J=3.8 Hz, 1H), 5.20 (br. s., 1H), 4.43 (d, J=5.4 Hz, 2H), 3.94 (s, 3H), 1.42 (s, 9H). $^{13}$C NMR (126 MHz, CDCl$_3$) δ 155.4, 146.6, 135.1, 134.6, 132.7, 132.5, 129.6, 127.3, 125.4, 79.6, 39.7, 28.2. HRMS calcd for C$_{14}$H$_{17}$NO$_2$S$_3$ [M+H]$^+$ 328.0494; found 328.0516.

The title compound was synthesised according to general procedures GP4—from i) tert-butyl ((5-(thiophen-2-ylthio)thiophen-2-yl)methyl)carbamate (258 mg, 0.788 mmol), m-CPBA (77%; 340 mg, 1.52 mmol), DCM (5.0 mL); 50° C., 0.5 h; chromatography (MeOH/DCM 0→5%). ii) 4 M HCl in dioxane (1.0 mL); rt, 16 h. The white precipitate was filtered, washed with excess EtOA and dried under vacuum to afford a white solid (1.4 mg, 7% over two steps). $^1$H NMR (500 MHz, CDCl$_3$) δ 7.64 (dd, J=5.0, 1.3 Hz, 1H), 7.52 (dd, J=3.7, 1.3 Hz, 1H), 7.43 (d, J=3.7 Hz, 1H), 7.11 (dd, J=5.0, 3.7 Hz, 1H), 6.90 (dt, J=3.7, 0.9 Hz, 1H), 3.93 (s, 2H), 1.63 (br, 2H). $^{13}$C NMR (126 MHz, CDCl$_3$) δ 155.85, 147.91, 145.56, 131.64, 130.91, 129.86, 127.48, 123.47, 41.84.

Example 54: (R)-Methyl 1-(3-((5-(aminomethyl)thiophen-2-yl)sulfonyl)benzoyl)pyrrolidine-2-carboxylate hydrochloride

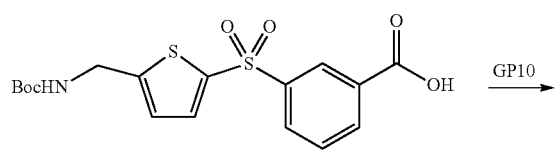

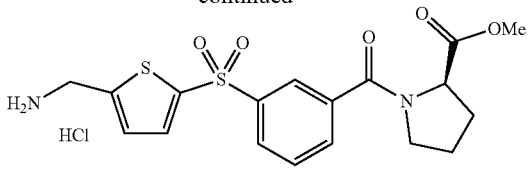

The title compound was synthesised according to general procedures GP10—from i) 3-((5-(((tert-butoxycarbonyl)amino)methyl)thiophen-2-yl)sulfonyl)benzoic acid (50 mg, 0.126 mmol), HBTU (53 mg, 0.140 mmol), Et$_3$N (14.5 mg, 0.143 mmol), L-proline methyl ester hydrochloride (24 mg, 0.145 mmol) and DMF (2.0 mL); rt, 12 h. ii) 4 M HCl in dioxane (1.0 mL); rt, 12 h. The crude was recrystallised from DCM/cyclohexane (1.2 mg, 2%). $^1$H NMR (500 MHz, (CD$_3$)$_2$SO) δ mixture of rotamers 8.14 (s, 1H), 7.94-8.08 (m, 1H), 7.78 (d, J=7.6 Hz, 1H), 7.45-7.65 (m, 2H), 6.91 (d, J=3.5 Hz, 1H), 5.04-5.26 (m, 1H), 4.65 (dd, J=8.2, 5.0 Hz, 1H), 4.44 (d, J=5.4 Hz, 2H), 3.78 (s, 3H), 3.58-3.69 (m, 2H), 3.38-3.58 (m, 2H), 2.26-2.40 (m, 1H), 1.97-2.14 (m, 4H), 1.86-1.96 (m, 1H), 1.43 (s, 9H). $^{13}$C NMR (126 MHz, CD$_3$OD) δ 174.2, 169.6, 145.7, 145.3, 143.8, 138.9, 135.6, 133.5, 131.9, 131.4, 130.4, 127.4, 61.1, 53.1, 51.4, 38.6, 30.5, 26.4. HRMS calcd for C$_{18}$H$_{20}$N$_2$O$_5$S$_2$ [M-NH$_2$]$^+$ 392.0626; found 392.0784.

Example 55: 4-((5-(Aminomethyl)thiophen-2-yl)sulfonyl)-N-methylbenzamide hydrochloride

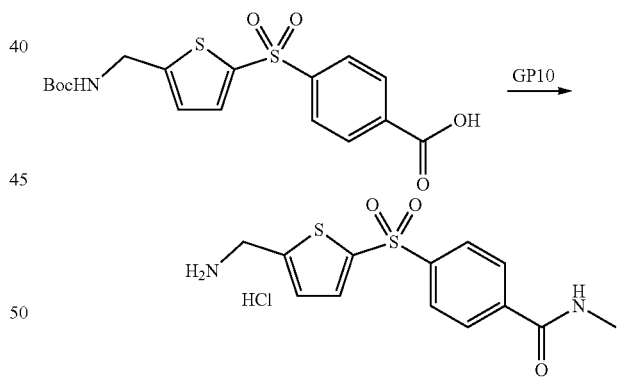

The title compound was synthesised according to general procedures GP10—from i) 4-((5-(((tert-butoxycarbonyl)amino)methyl)thiophen-2-yl)sulfonyl)benzoic acid (43 mg, 0.108 mmol), HBTU (46 mg, 0.121 mmol), Et$_3$N (20 µL, 0.143 mmol), MeNH$_2$ (2.0 M in MeOH; 60 µL, 0.120 mmol) and DMF (1.0 mL); rt, 12 h. ii) 4 M HCl in dioxane (1.5 mL); rt, 12 h. The solid product was triturated with Et$_2$O (10 mg, 27%). $^1$H NMR (500 MHz, CD$_3$OD) δ 8.03 (d, J=8.5 Hz, 2H), 7.92-7.99 (m, 2H), 7.73 (d, J=3.8 Hz, 1H), 7.30 (d, J=3.8 Hz, 1H), 4.36 (s, 2H), 2.88 (s, 3H). $^{13}$C NMR (126 MHz, CD$_3$OD) δ 168.8, 145.7, 145.6, 145.2, 140.6, 135.6, 131.8, 129.7, 128.8, 38.6, 27.2. HRMS calcd for C$_{13}$H$_{14}$N$_2$O$_3$S$_2$ [M-NH$_2$]$^+$ 294.0259; found 294.0307

4-((5-(((tert-Butoxycarbonyl)amino)methyl)thiophen-2-yl)sulfonyl)benzoic acid

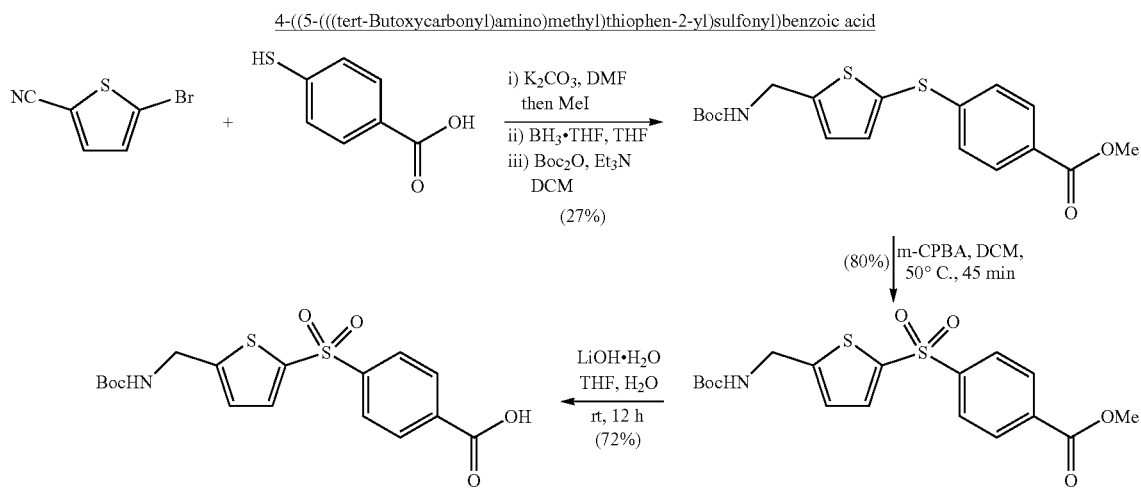

A mixture of 5-bromothiophene-2-carbonitrile (406 mg, 2.83 mmol), 4-mercaptobenzoic acid (479 mg, 3.11 mmol), and K$_2$CO$_3$ (781 mg, 5.65 mmol) in DMF (11 mL) was stirred at 120° C. for 2.5 h. After cooling to rt, MeI (750 μL, 11.32 mmol) was added and the mixture was stirred at 50° C. for 2 h. EtOAc was added and the organic phase was washed with H$_2$O/brine 1:1 (3×), dried over Na$_2$SO$_4$ and filtered. The solvent was removed under reduced pressure and the crude treated with BF$_3$.THF complex (1.0 M in THF; 7.0 mL, 7.0 mmol). The mixture was stirred for at rt for 1 h, and then quenched slowly with EtOH. The mixture was heated at reflux for 1 h before the solvent was removed under reduced pressure. DCM (40 mL) was added, followed by Et$_3$N (480 μL, 3.45 mmol) and Boc$_2$O (753 mg, 3.45 mmol). The mixture was stirred at rt for 12 h and then diluted with DCM. The organic phase was washed with H$_2$O, dried over Na$_2$SO$_4$, filtered and the solvent was removed under reduced pressure. The crude was purified by chromatography (EtOAc/cyclohexane 2→20%) to afford methyl 4-((5-(((tert-butoxycarbonyl)amino)methyl)thiophen-2-yl)thio)benzoate (288 mg, 27%). $^1$H NMR (500 MHz, CDCl$_3$) δ 7.90 (d, J=8.2 Hz, 2H), 7.09-7.22 (m, 3H), 6.96 (br. s, 1H), 4.83-5.09 (m, 1H), 4.48 (br. s, 1H), 3.89 (s, 3H), 1.47 (s, 9H).

m-CPBA (77%; 327 mg, 1.46 mmol) was added in portions to a solution of methyl 4-((5-(((tert-butoxycarbonyl)amino)methyl)thiophen-2-yl)thio)benzoate (288 mg, 0.76 mmol) in DCM (20 mL) and the mixture was stirred at 50° C. for 45 min. After cooling down to rt, the organic solution was washed with sat. NaHCO$_3$ (3×), dried over Na$_2$SO$_4$, filtered and the solvent was removed under reduced pressure. The crude was purified by chromatography (MeOH/DCM 0→5%) to afford methyl 4-((5-(((tert-butoxycarbonyl)amino)methyl)thiophen-2-yl)sulfonyl)benzoate (250 mg, 80%). $^1$H NMR (500 MHz, CDCl$_3$) δ 8.09 (d, J=8.5 Hz, 2H), 7.96 (d, J=8.5 Hz, 2H), 7.50 (d, J=3.5 Hz, 1H), 6.87 (d, J=3.8 Hz, 1H), 5.48 (br. s., 1H), 4.39 (d, J=5.4 Hz, 2H), 3.88 (s, 3H), 1.37 (s, 9H).

A mixture of methyl 4-((5-(((tert-butoxycarbonyl)amino)methyl)thiophen-2-yl)sulfonyl)benzoate (250 mg, 0.61 mmol), LiOH.H$_2$O (28 mg, 0.67 mmol), THF (10 mL) and H$_2$O (5 mL) was stirred at rt for 12 h. The pH was adjusted to <1 and the aqueous phase was extracted with EtOAc. The combined organic phase was dried over MgSO$_4$, filtered and the solvent was removed under reduced pressure to afford 4-((5-(((tert-butoxycarbonyl)amino)methyl)thiophen-2-yl)sulfonyl)benzoic acid (172 mg, 72%), which was used in the subsequent transformation without further purification. $^1$H NMR (500 MHz, CD$_3$OD) δ 8.19 (d, J=8.2 Hz, 2H), 8.06 (d, J=8.2 Hz, 2H), 7.66 (d, J=3.5 Hz, 1H), 7.02 (d, J=3.8 Hz, 1H), 4.40 (s, 2H), 1.44 (s, 9H).

Example 56: 4-((5-(Aminomethyl)thiophen-2-yl)sulfonyl)-N-(2-((4-methoxyphenyl)sulfonyl)ethyl)benzamide hydrochloride

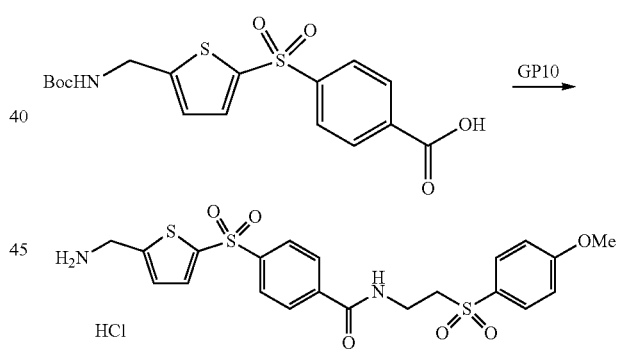

The title compound was synthesised according to general procedures GP10—from i) 4-((5-(((tert-butoxycarbonyl)amino)methyl)thiophen-2-yl)sulfonyl)benzoic acid (43 mg, 0.108 mmol), HBTU (46 mg, 0.121 mmol), Et$_3$N (20 μL, 0.143 mmol), 2-((4-methoxyphenyl)sulfonyl)ethanamine hydrochloride (30 mg, 0.119 mmol) and DMF (1.0 mL); rt, 12 h. ii) 4 M HCl in dioxane (1.5 mL); rt, 12 h. The solid product was triturated with Et$_2$O (45 mg, 78%). $^1$H NMR (500 MHz, CD$_3$OD) δ 8.00 (d, J=8.5 Hz, 2H), 7.81 (t, J=9.0 Hz, 4H), 7.73 (d, J=3.8 Hz, 1H), 7.29 (d, J=4.1 Hz, 1H), 7.00 (d, J=8.8 Hz, 2H), 4.35 (s, 2H), 3.75 (s, 3H), 3.69 (t, J=6.3 Hz, 2H), 3.46-3.55 (m, 2H). $^{13}$C NMR (126 MHz, CD$_3$OD) δ 168.0, 165.6, 145.8, 145.2, 140.0, 135.7, 132.2, 131.8, 131.5, 129.8, 128.7, 115.9, 56.5, 55.4, 38.6, 35.9. HRMS calcd for C$_{21}$H$_{23}$N$_2$O$_6$S$_3$ [M+H]$^+$ 495.0713; found 495.0685.

Example 57: 4-((5-(Aminomethyl)thiophen-2-yl)sulfonyl)-N,N-dimethylbenzamide hydrochloride

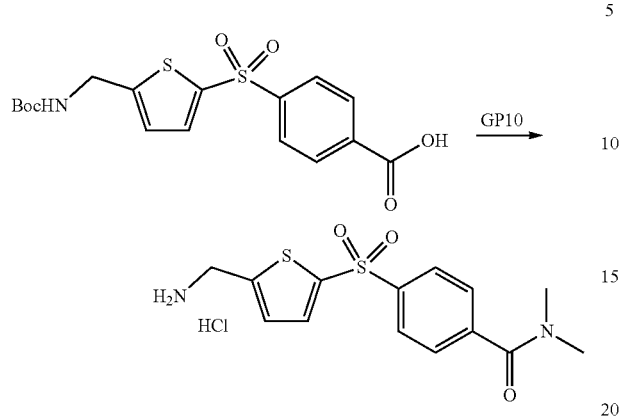

The title compound was synthesised according to general procedures GP10—from i) 4-((5-(((tert-butoxycarbonyl)amino)methyl)thiophen-2-yl)sulfonyl)benzoic acid (43 mg, 0.108 mmol), HBTU (46 mg, 0.121 mmol), Et$_3$N (20 μL, 0.143 mmol), Me$_2$NH.HCl (90 mg, 0.110 mmol) and DMF (1.0 mL); rt, 12 h. ii) 4 M HCl in dioxane (1.5 mL); rt, 10 h. The solid product was triturated with Et$_2$O (33 mg, 85%). $^1$H NMR (500 MHz, CD$_3$OD) δ 8.05 (d, J=6.6 Hz, 2H), 7.69-7.82 (m, 1H), 7.61 (d, J=6.6 Hz, 2H), 7.31 (br. s., 1H), 4.37 (br. s., 2H), 3.07 (br. s., 3H), 2.90 (br. s., 3H). $^{13}$C NMR (126 MHz, CD$_3$OD) δ 199.5, 173.5, 173.0, 172.1, 170.6, 163.4, 159.8, 157.3, 156.8, 67.8, 66.4, 63.7. HRMS calcd for C$_{14}$H$_{16}$N$_2$O$_3$S$_2$ [M-NH$_2$]$^+$ 308.0415; found 308.0587

Example 58: 4-((5-(Aminomethyl)thiophen-2-yl)sulfonyl)-N-(2-hydroxyethyl)benzamide hydrochloride

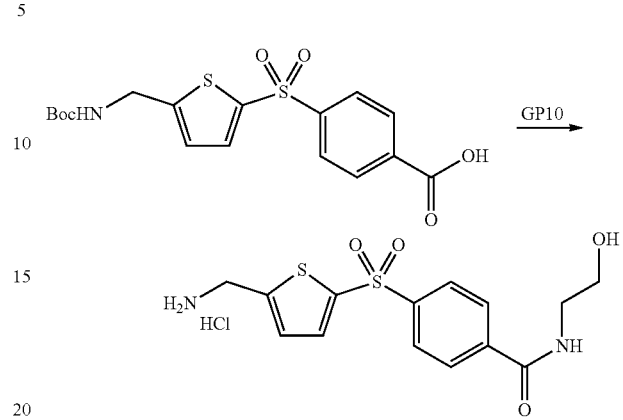

The title compound was synthesised according to general procedures GP10—from i) 4-((5-(((tert-butoxycarbonyl)amino)methyl)thiophen-2-yl)sulfonyl)benzoic acid (43 mg, 0.108 mmol), HBTU (46 mg, 0.121 mmol), Et$_3$N (20 μL, 0.143 mmol), ethanolamine (10 μL, 0.166 mmol) and DMF (1.0 mL); rt, 12 h. ii) 4 M HCl in dioxane (1.5 mL); rt, 10 h. The solid product was triturated with Et$_2$O (17 mg, 42%). $^1$H NMR (500 MHz, CD$_3$OD) δ 8.01-8.12 (m, 2H), 7.90-8.00 (m, 2H), 7.74 (d, J=3.8 Hz, 1H), 7.29 (d, J=3.8 Hz, 1H), 4.35 (s, 2H), 3.67 (t, J=5.7 Hz, 2H), 3.47 (t, J=5.8 Hz, 2H). $^{13}$C NMR (126 MHz, CD$_3$OD) δ 168.6, 145.7, 145.6, 145.2, 140.8, 135.6, 131.8, 129.8, 128.8, 61.5, 43.9, 38.6.

Example 59: (5-(6-(Methylsulfonyl)pyridin-2-ylsulfonyl)thiophen-2-yl)methanamine hydrochloride

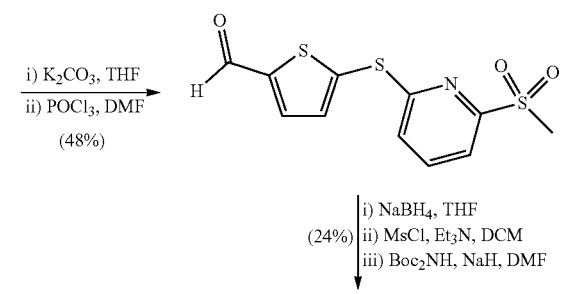

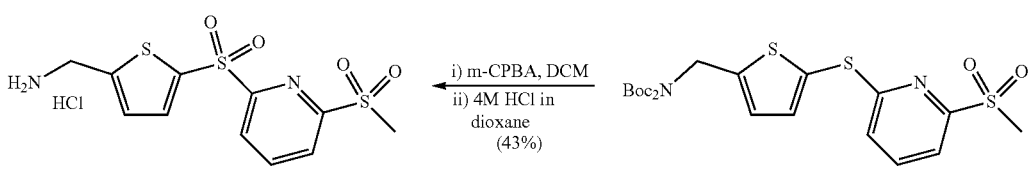

A mixture of thiophene-2-thiol (736 mg, 6.34 mmol), K$_2$CO$_3$ (903 mg, 6.64 mmol) and 2-chloro-6-(methylsulfonyl)pyridine [synthesised by the method previously reported by Kajino et al, patent no. EP1424336] (1.10 g, 5.76 mmol) in THF (30 mL) was stirred at rt for 12 h. EtOAc was added. The organic phase was washed with H$_2$O, dried over MgSO$_4$ and filtered. The solvent was removed under reduced pressure and the crude was dissolved in in DMF (1.02 mL). POCl$_3$ (1.3 mL, 14.0 mmol) was added dropwise and the mixture was stirred at 40° C. for 48 h. After cooling to room temperature, the reaction mixture was poured in ice and extracted with ethyl acetate. The organic phase was washed with brine, dried over Na$_2$SO$_4$, filtered and the solvent was removed under reduced pressure. The residue was purified by column chromatography (EtOAc/cyclohexane 0→30%) to give the 5-((6-(methylsulfonyl)pyridin-2-yl)thio)thiophene-2-carbaldehyde as a yellow solid (824 mg, 48% over 2 steps). $^1$H NMR (500 MHz, CDCl$_3$) δ 9.86 (s, 1H), 7.73-7.86 (m, 3H), 7.41 (d, J=3.8 Hz, 1H), 7.29 (dd, J=7.9, 0.9 Hz, 1H), 3.10 (s, 3H).

NaBH$_4$ (151 mg, 4.0 mmol) was added to a solution of 5-((6-(methylsulfonyl)pyridin-2-yl)thio)thiophene-2-carbaldehyde (986 mg, 3.64 mmol) in THF (20 mL) and the mixture was stirred at rt for 1 h. sat NH$_4$Cl was added and the aqueous phase was extracted with EtOAc. The organic phase was dried over Na$_2$SO$_4$ and filtered. The solvent was removed under reduced pressure and the crude (562 mg, 1.86 mmol) was dissolved in DCM (25 mL). Et$_3$N (290 µL, 2.05 mmol) and MsCl (160 µL, 2.05 mmol) were added and the mixture was stirred at rt for 1 h. DCM was added. The organic phase was washed with H$_2$O, dried over MgSO$_4$, filtered and the solvent was removed under reduced pressure to afford crude (5-((6-(methylsulfonyl)pyridin-2-yl)thio)thiophen-2-yl)methyl methanesulfonate. The crude mesylate was added to a solution of NaH (104 mg, 2.59 mmol) and di-tert-butyl-iminodicarboxylate (563 mg, 2.59 mmol) in DMF and the mixture was stirred at 50° C. for 24 h. After cooling to rt, 1N HCl was added and the aqueous phase was extracted with DCM. The combined organic phase was dried over MgSO$_4$, filtered and the solvent was removed under reduced pressure. The crude was purified by chromatography (EtOAc/cyclohexane 0→30%) to afford 2-(methylsulfonyl)-6-((5-(N,N-bis(tert-butoxycarbonyl)aminomethyl)thiophen-2-yl)thio)pyridine as a colourless oil (433 mg, 24% over 3 steps). $^1$H NMR (500 MHz, CDCl$_3$) δ 7.59-7.81 (m, 2H), 7.18 (d, J=3.8 Hz, 1H), 7.08-7.13 (m, 1H), 7.05 (d, J=3.5 Hz, 1H), 4.89 (s, 2H), 3.11 (s, 3H), 1.49 (s, 18H). $^{13}$C NMR (126 MHz, CDCl$_3$) δ 163.3, 157.5, 151.7, 148.2, 138.5, 137.3, 128.0, 125.6, 123.5, 116.4, 83.1, 44.5, 39.3, 27.9. HRMS calcd for C$_{21}$H$_{28}$N$_2$O$_6$S$_3$[M-N(Boc)$_2$]$^+$ 283.9874; found 283.9897.

m-CPBA (77%; 343 mg, 1.99 mmol) was added in small portions to a solution of 2-(methylsulfonyl)-6-((5-(N,N-bis(tert-butoxycarbonyl)aminomethyl)thiophen-2-yl)thio)pyridine (433 mg, 0.865 mmol) in DCM (10 mL) and the mixture was stirred at 50° C. for 38 h. The organic phase was washed with sat. NaHCO$_3$ (3×), dried over MgSO$_4$ and filtered. The solvent was removed under reduced pressure and the crude was purified by chromatography. The purified amine was treated with 4 M HCl in dioxane (5 mL) and the mixture was stirred at rt for 12 h. The precipitated solid was centrifuged and washed with Et$_2$O and EtOAc and dried under vacuum to afford the title compound as a yellow solid (136, 43% over 2 steps). $^1$H NMR (500 MHz, D$_2$O) δ 9.89 (br s, 1H), 9.73 (br s, 1H), 9.29 (br s, 1H), 8.80 (br s, 1H), 5.82 (br s, 1H), 4.69 (br s, 3H). $^{13}$C NMR (126 MHz, D$_2$O) δ 157.1, 156.8, 145.9, 142.9, 137.1, 130.8, 126.3, 125.7, 39.8, 37.3. HRMS calcd for C$_{11}$H$_{12}$N$_2$O$_4$S$_3$[M-NH$_2$]$^+$ 315.9771; found 315.9784

Example 60: (5-((5-(Methylsulfonyl)thiophen-2-yl)sulfonyl)thiophen-2-yl)methanamine

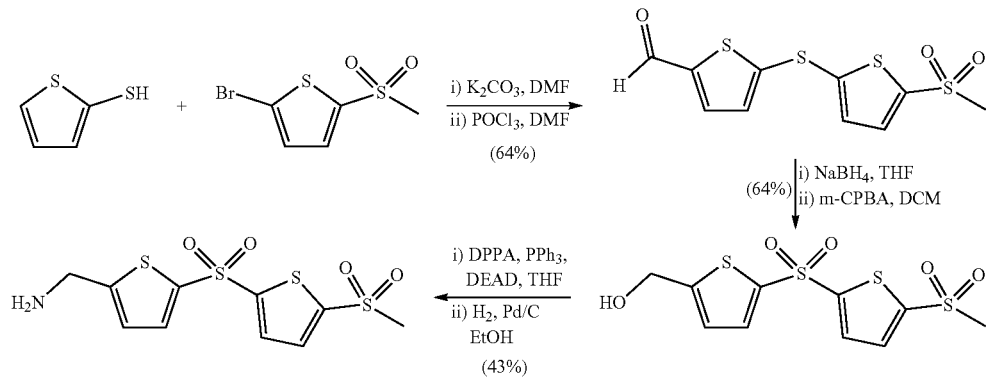

To a solution of 2-thiophenethiol (1.73 g, 14.9 mmol) and 2-bromo-5-(methylsulfonyl)thiophene (3.0 g, 12.4 mmol) in DMF (15 mL) was added potassium carbonate (2.58 g, 18.7 mmol). The reaction mixture was stirred at 150° C. (microwave) for 2 h. After cooling to rt, the reaction mixture was diluted with H$_2$O (100 mL) and extracted with Et$_2$O. The combined organic phase was dried MgSO$_4$, filtered and the solvent was removed under reduced pressure. The crude was purified by chromatography (EtOAc/cyclohexane 2→20%) to afford 2-(methylsulfonyl)-5-(thiophen-2-ylthio)thiophene. To this intermediate was added DMF (1.5 mL), followed by the dropwise addition of POCl$_3$ (3.0 mL, 19.5 mmol) at 0° C. The mixture was then stirred at 40° C. for 12 h. After cooling to rt, the reaction mixture was carefully poured onto ice and extracted with ethyl acetate. The organic phase was washed with brine, dried over Na$_2$SO$_4$, filtered and the solvent was removed under reduced pressure. The residue was purified by chromatography (EtOAc/cyclohexane (0→50%) to afford 5-((5-(methylsulfonyl)thiophen-2-yl)thio)thiophene-2-carbaldehyde (2.4 g, 64% over 2 steps). $^1$H NMR (500 MHz, CDCl$_3$) δ 9.85 (s, 1H), 7.68 (d, J=4.1 Hz, 1H), 7.63 (d, J=4.1 Hz, 1H), 7.26-7.32 (m, 2H), 3.21 (s, 3H). $^{13}$C NMR (126 MHz, CDCl$_3$) δ 182.5, 141.9, 136.2, 133.6, 132.3, 128.2, 128.1, 123.4, 45.9. HRMS calcd for C$_{10}$H$_8$O$_3$S$_4$ [M+H]$^+$ 304.9429; found 304.9462.

To a solution of 5-((5-(methylsulfonyl)thiophen-2-yl)thio)thiophene-2-carbaldehyde (2.4 g, 7.88 mmol) in THF (100 mL) at 0° C. was added sodium borohydride (895 mg, 23.7 mmol). The reaction mixture was stirred at room temperature for 2 h, before it was quenched with ice. The pH of the solution was adjusted to 4-5 with 1 M HCl and the aqueous phase was extracted with ethyl acetate. The combined organic phase was washed with brine, dried over Na$_2$SO$_4$, filtered and the solvent was removed under reduced pressure. The crude was purified by chromatography (EtOAc/cyclohexane 10→40%) to afford (5-((5-(methylsulfonyl)thiophen-2-yl)thio)thiophen-2-yl)methanol as a yellow solid (2.3 g, 95%). m-CPBA (77%; 1.82 g, 8.17 mmol) was added in small portions to a solution of (5-((5-(methylsulfonyl)thiophen-2-yl)thio)thiophen-2-yl)methanol (1.2 g, 3.92 mmol) in DCM (100 mL) at 0° C. and the mixture was stirred at rt for 12 h. The organic phase was washed with sat. NaHCO$_3$ (3×), dried over MgSO$_4$, filtered and the solvent was removed under reduced pressure. The crude was purified by chromatography (EtOAc/cyclohexane 0→60%) to afford (5-((5-(methylsulfonyl)thiophen-2-yl)sulfonyl)thiophen-2-yl)methanol (1.1 g, 83%). $^1$H NMR (500 MHz, CDCl$_3$) δ 7.68 (t, J=3.3 Hz, 2H), 7.63 (d, J=4.1 Hz, 1H), 7.01 (d, J=3.8 Hz, 1H), 4.90 (s, 2H), 2.81 (br s, OH), 3.22 (s, 3H). $^{13}$C NMR (126 MHz, CDCl$_3$) δ 158.1, 151.3, 148.5, 139.9, 134.8, 132.8, 132.2, 125.0, 60.1, 45.9. HRMS calcd for C$_{10}$H$_{10}$O$_5$S$_4$ [M-OH]$^+$ 320.9384; found 320.9397.

To a solution of (5-((5-(methylsulfonyl)thiophen-2-yl)sulfonyl)thiophen-2-yl)methanol (475 mg, 1.40 mmol) in THF (20 mL) at 0° C. was added PPh$_3$ (551 mg, 2.10 mmol) and DEAD (0.35 mL, 2.24 mmol). The mixture was stirred at 0° C. for 10 min, followed by the addition of DPPA (0.45 mL, 2.10 mmol). The reaction was warmed to rt over 16 h and the solvent was removed under reduced pressure. The crude was purified by chromatography (EtOAc/cyclohexane 0→50%) to afford 2-(azidomethyl)-5-((5-(methylsulfonyl)thiophen-2-yl)sulfonyl)thiophene. This was dissolved in EtOH (40 mL), followed by the addition of Pd/C (10%; 100 mg). The mixture was stirred at rt under H$_2$ pressure (balloon) for 10 h and then filtered through celite. The solvent was removed under reduced pressure and the crude was purified by chromatography (MeOH/EtOAc 0→10%) to afford the title compound as a pink gum (204 mg, 43% over 2 steps). $^1$H NMR (500 MHz, CDCl$_3$) δ 7.54-7.73 (m, 3H), 6.93 (d, J=3.8 Hz, 1H), 4.10 (s, 2H), 3.20 (s, 3H). $^{13}$C NMR (126 MHz, CDCl$_3$) δ 160.4, 151.4, 148.1, 138.3, 134.9, 132.7, 131.9, 123.9, 45.8, 41.5. HRMS calcd for CH$_{11}$NO$_4$S$_4$ [M-NH$_2$]$^+$ 320.9384; found 320.9425.

Example 61: (5-((3-(tert-Butyl)-5-(methylsulfonyl)phenyl)sulfonyl)thiophen-2-yl)methanamine

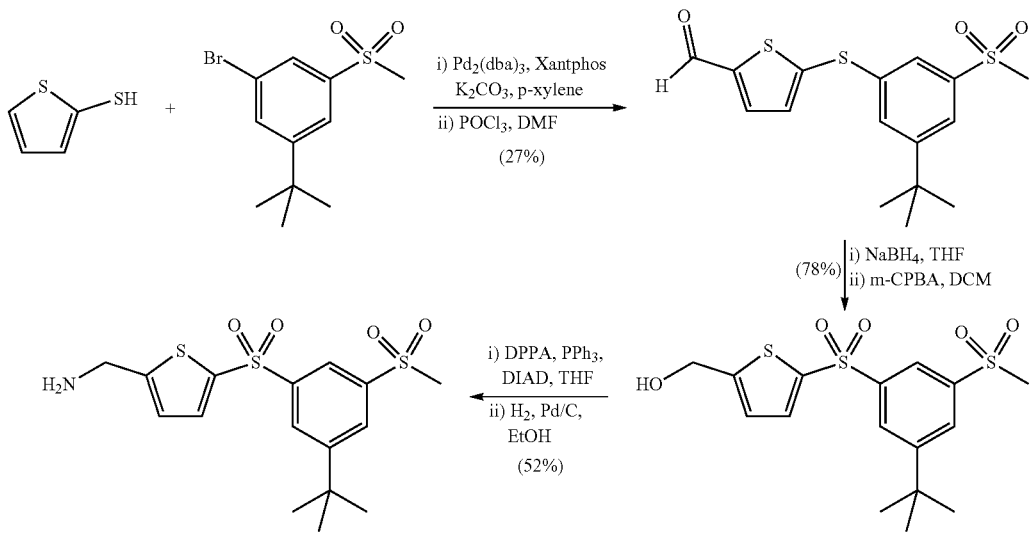

To a solution of 2-thiophenethiol (795 mg, 6.84 mmol) in p-xylene (30 mL) was added potassium carbonate (472 mg, 3.42 mmol). The reaction mixture was stirred at room temperature for 1 h. 1-bromo-3-(tert-butyl)-5-(methylsulfonyl)benzene (1.81 g, 6.22 mmol), Pd$_2$(dba)$_3$ (455 mg, 0.497 mmol) and Xantphos (324 mg, 0.560 mmol) were added. The reaction mixture was degassed with argon and stirred at 140° C. for 12 h. After cooling to room temperature, the reaction mixture was filtered through celite and the residue was washed with ethyl acetate. The solvent was removed under reduced pressure and the crude was purified by chromatography (EtOAc/cyclohexane 0→40%) to afford 2-((3-(tert-butyl)-5-(methylsulfonyl)phenyl)thio)thiophene. To this intermediate was added DMF (1.9 mL), followed by the dropwise addition of POCl$_3$ (3.80 mL, 24.5 mmol) at 0° C. The mixture was then stirred at 50° C. for 12 h. After cooling to rt, the reaction mixture was carefully poured onto ice and extracted with ethyl acetate. The organic phase was washed with brine, dried over Na$_2$SO$_4$, filtered and the solvent was removed under reduced pressure. The residue was purified by chromatography (EtOAc/cyclohexane (0→40%) to afford 5-((3-(tert-butyl)-5-(methylsulfonyl)phenyl)thio)thiophene-2-carbaldehyde (590 mg, 27%). $^1$H NMR (500 MHz, CDCl$_3$) δ 9.84 (s, 1H), 7.87 (t, J=1.6 Hz, 1H), 7.74 (t, J=1.6 Hz, 1H), 7.71 (d, J=3.8 Hz, 1H), 7.68 (t, J=1.6 Hz, 1H), 7.26-7.29 (m, 1H), 3.06 (s, 3H), 1.35 (s, 9H). $^{13}$C NMR (126 MHz, CDCl$_3$) δ 182.0, 154.7, 146.3, 141.8, 137.1, 136.6, 133.3, 132.3, 125.7, 123.7, 44.5, 35.4, 31.0. HRMS calcd for C$_{15}$H$_{18}$O$_2$S$_3$ [M+H]$^+$ 354.0418; found 354.0467.

To a solution of 5-((3-(tert-butyl)-5-(methylsulfonyl)phenyl)thio)thiophene-2-carbaldehyde (590 mg, 1.66 mmol) in THF (50 mL) at 0° C. was added sodium borohydride (141 mg, 3.72 mmol). The reaction mixture was stirred at room temperature for 2 h, before it was quenched with ice. The pH of the solution was adjusted to 4-5 with 1 M HCl and the aqueous phase was extracted with ethyl acetate. The combined organic phase was washed with brine, dried over Na$_2$SO$_4$, filtered and the solvent was removed under reduced pressure. The crude was purified by chromatography (EtOAc/cyclohexane 0→50%) to afford (5-((3-(tert-butyl)-5-(methylsulfonyl)phenyl)thio)thiophen-2-yl)methanol as a white solid (590 mg, quant.). DCM (50 mL) was added, followed by m-CPBA in small portions (77%; 742 mg, 3.31 mmol) at 0° C. The mixture was stirred at rt for 12 h, and the solvent was subsequently removed under reduced pressure. The crude was purified by chromatography (EtOAc/cyclohexane 0→60%) to afford (5-((3-(tert-butyl)-5-(methylsulfonyl)phenyl)sulfonyl)thiophen-2-yl)methanol (500 mg, 78% over 2 steps). $^1$H NMR (500 MHz, CDCl$_3$) δ 8.32 (t, J=1.4 Hz, 1H), 8.27 (t, J=1.7 Hz, 1H), 8.13 (t, J=1.6 Hz, 1H), 7.65 (d, J=3.8 Hz, 1H), 6.99 (d, J=3.8 Hz, 1H), 4.87 (s, 2H), 3.10 (s, 3H), 1.40 (s, 9H). $^{13}$C NMR (126 MHz, CDCl$_3$) δ 155.4, 155.3, 143.8, 142.0, 140.2, 134.3, 129.1, 128.7, 125.0, 123.7, 60.1, 44.4, 35.8, 31.0. HRMS calcd for C$_{16}$H$_{20}$O$_5$S$_3$ [M-OH]$^+$ 371.0445; found 371.0486

To a solution of (5-((3-(tert-butyl)-5-(methylsulfonyl)phenyl)sulfonyl)thiophen-2-yl)methanol (500 mg, 1.29 mmol) in THF (15 mL) at 0° C. was added PPh$_3$ (406 mg, 1.54 mmol) and DEAD (0.24 mL, 1.54 mmol). The mixture was stirred at 0° C. for 10 min, followed by the addition of DPPA (0.35 mL, 1.54 mmol). The reaction was warmed to rt over 16 h and the solvent was removed under reduced pressure. The crude was dissolved in EtOH (50 mL), and Pd/C (10%; 150 mg) was added. The mixture was stirred at rt under H$_2$ pressure (balloon) for 12 h and then filtered through celite. The solvent was removed under reduced pressure and the crude was was purified by chromatography (EtOH/cyclohexane 0→100%) to afford the title compound as an orange gum (262 mg, 52%). $^1$H NMR (500 MHz, CDCl$_3$) δ 8.28 (t, J=1.4 Hz, 1H), 8.23 (t, J=1.6 Hz, 1H), 8.09 (t, J=1.6 Hz, 1H), 7.60 (d, J=3.8 Hz, 1H), 6.90 (d, J=3.8 Hz, 1H), 4.06 (s, 2H), 3.08 (s, 3H), 1.36 (s, 9H). $^{13}$C NMR (126 MHz, CDCl$_3$) δ 159.4, 155.2, 143.9, 141.8, 138.6, 134.5, 128.9, 128.4, 123.9, 123.5, 44.3, 41.4, 35.6, 30.9. HRMS calcd for C$_{16}$H$_{21}$NO$_4$S$_3$ [M-NH$_2$]$^+$ 371.0445; found 371.0428.

1-Bromo-3-(tert-butyl)-5-(methylsulfonyl)benzene

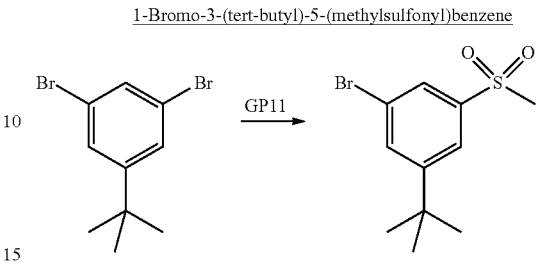

Synthesised according to general procedures GP11— from i) 1,3-dibromo-5-(tert-butyl)benzene (2.0 g, 6.85 mmol), $^t$BuLi (1.6 M in pentane; 8.5 mL, 13.6 mmol), THF (70 mL and 5 mL), dimethyl disulfide (0.74 mL, 8.22 mmol); −78° C.→rt; chromatography (EtOAc/cyclohexane 0→10%), 1.50 g, 85%. ii) (3-bromo-5-(tert-butyl)phenyl)(methyl)sulfane (1.50 g, 5.79 mmol), m-CPBA (77%; 2.50 g, 11.1 mmol), DCM (50 mL); rt, 12 h; chromatography (EtOAc/cyclohexane 0→30%), 1.40 g, 83%. $^1$H NMR (500 MHz, CDCl$_3$) δ 7.87 (t, J=1.6 Hz, 1H), 7.85 (t, J=1.6 Hz, 1H), 7.76 (t, J=1.7 Hz, 1H), 3.05 (s, 3H), 1.32 (s, 9H).

Example 62: (5-((3-(tert-Butyl)-5-(isopropylsulfonyl)phenyl)sulfonyl)thiophen-2-yl)methanamine

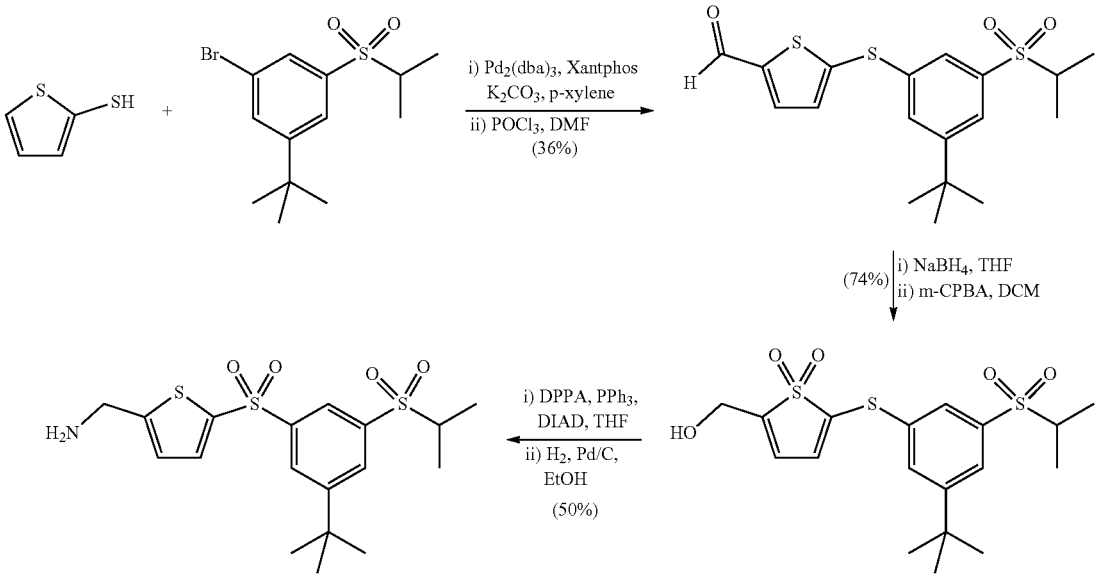 [SMILES: Sc1cccs1 ; CC(C)S(=O)(=O)c1cc(Br)cc(C(C)(C)C)c1 ; CC(C)S(=O)(=O)c1cc(Sc2ccc(C=O)s2)cc(C(C)(C)C)c1 ; CC(C)S(=O)(=O)c1cc(C(C)(C)C)cc(S(=O)(=O)c2ccc(CN)s2)c1 ; CC(C)S(=O)(=O)c1cc(SC2=CC=C(CO)S2(=O)=O)cc(C(C)(C)C)c1]

To a solution of 2-thiophenethiol (1.20 g, 10.3 mmol) in p-xylene (50 mL) was added potassium carbonate (714 mg, 5.17 mmol). The reaction mixture was stirred at room temperature for 1 h. 1-bromo-3-(tert-butyl)-5-(isopropylsulfonyl)benzene (3.0 g, 9.40 mmol), Pd$_2$(dba)$_3$ (689 mg, 0.750 mmol) and Xantphos (489 mg, 0.845 mmol) were added. The reaction mixture was degassed with argon and stirred at 140° C. for 12 h. After cooling to room temperature, the reaction mixture was filtered through celite and the residue was washed with ethyl acetate. The solvent was removed under reduced pressure and the crude was purified by chromatography (EtOAc/cyclohexane 0→40%) to afford 2-((3-(tert-butyl)-5-(isopropylsulfonyl)phenyl)thio)thiophene. To this intermediate was added DMF (2.0 mL), followed by the dropwise addition of POCl₃ (2.0 mL, 21.5 mmol) at 0° C. The mixture was then stirred at 40° C. for 12 h. After cooling to rt, the reaction mixture was carefully poured onto ice and extracted with ethyl acetate. The organic phase was washed with brine, dried over Na₂SO₄, filtered and the solvent was removed under reduced pressure. The residue was purified by chromatography (EtOAc/cyclohexane (0→40%) to afford the 5-((3-(tert-butyl)-5-(isopropylsulfonyl)phenyl)thio)thiophene-2-carbaldehyde (1.3 g, 36%). ¹H NMR (500 MHz, CDCl₃) δ 9.83 (s, 1H), 7.80 (t, J=1.4 Hz, 1H), 7.63-7.73 (m, 3H), 7.25 (d, J=3.8 Hz, 1H), 3.16 (dt, J=13.6, 6.9 Hz, 1H), 1.34 (s, 9H), 1.25-1.31 (m, 6H). ¹³C NMR (126 MHz, CDCl₃) δ 182.0, 154.3, 146.1, 145.3, 138.2, 136.7, 136.6, 132.9, 132.2, 127.5, 125.6, 55.7, 35.3, 31.0. HRMS calcd for C₁₈H₂₂O₃S₃ [M+H]⁺ 383.0804; found 383.0895

To a solution of 5-((3-(tert-butyl)-5-(isopropylsulfonyl)phenyl)thio)thiophene-2-carbaldehyde (1.30 g, 3.39 mmol) in THF (60 mL) at 0° C. was added sodium borohydride (295 mg, 7.82 mmol). The reaction mixture was stirred at room temperature for 2 h, before it was quenched with ice. The pH of the solution was adjusted to 4-5 with 1 M HCl and the aqueous phase was extracted with ethyl acetate. The combined organic phase was washed with brine, dried over Na₂SO₄, filtered and the solvent was removed under reduced pressure. The crude was purified by chromatography (EtOAc/cyclohexane 0→50%) to afford (5-((3-(tert-butyl)-5-(isopropylsulfonyl)phenyl)thio)thiophen-2-yl)methanol. DCM (50 mL) was added, followed by m-CPBA in small portions (77%; 1.40 g, 6.26 mmol) at 0° C. The mixture was stirred at rt for 2 h, and the solvent was subsequently removed under reduced pressure. The crude was purified by chromatography (EtOAc/cyclohexane 0→60%) to afford (5-((3-(tert-butyl)-5-(isopropylsulfonyl)phenyl)sulfonyl)thiophen-2-yl)methanol as a white solid (1.04 g, 74% over 2 steps). ¹H NMR (500 MHz, CDCl₃) δ 8.24 (d, J=0.9 Hz, 2H), 8.05 (t, J=1.6 Hz, 1H), 7.62 (d, J=3.8 Hz, 1H), 6.97 (d, J=3.8 Hz, 1H), 4.85 (s, 2H), 3.21 (spt, J=6.8 Hz, 1H), 1.38 (s, 9H), 1.29 (d, J=6.6 Hz, 6H). ¹³C NMR (126 MHz, CDCl₃) δ 155.5, 154.9, 143.5, 140.0, 138.5, 134.3, 130.5, 128.8, 125.1, 124.9, 59.9, 55.7, 35.6, 30.9, 26.9, 15.6. HRMS calcd for C₁₈H₂₄O₅S₃ [M-OH]⁺ 399.0758; found 399.0801

To a solution of (5-((3-(tert-butyl)-5-(isopropylsulfonyl)phenyl)sulfonyl)thiophen-2-yl)methanol (1.04 g, 2.49 mmol) in THF (30 mL) at 0° C. was added PPh₃ (657 mg, 3.25 mmol) and DEAD (0.51 mL, 3.25 mmol). The mixture was stirred at 0° C. for 10 min, followed by the addition of DPPA (0.73 mL, 3.25 mmol). The reaction was warmed to rt over over 16 h and the solvent was removed under reduced pressure. The crude was dissolved in EtOH (50 mL), and Pd/C (10%; 200 mg) was added. The mixture was stirred at rt under H₂ pressure (balloon) for 12 h and then filtered through celite. The solvent was removed under reduced pressure and the crude was recrystallised from EtOAc and a few drops of MeOH. The solid was centrifugated, washed with EtOAc and dried under vacuum to afford the title compound as a white solid (500 mg, 50%). ¹H NMR (500 MHz, CDCl₃) δ 8.33 (t, J=1.7 Hz, 1H), 8.23 (t, J=1.4 Hz, 1H), 8.15 (t, J=1.6 Hz, 1H), 7.86 (d, J=4.1 Hz, 1H), 7.32 (d, J=3.8 Hz, 1H), 4.38 (s, 2H), 3.42 (dt, J=13.6, 6.9 Hz, 1H), 1.40 (s, 9H), 1.25 (d, J=6.9 Hz, 6H). ¹³C NMR (126 MHz, CDCl₃) δ 157.1, 146.2, 144.8, 140.6, 136.0, 132.07, 132.01, 130.2, 126.2, 56.7, 38.6, 36.8, 31.3, 15.9. HRMS calcd for C₁₈H₂₅NO₄S₃ [M+H]⁺ 416.1018; found 416.1007

1-Bromo-3-(tert-butyl)-5-(isopropylsulfonyl)benzene

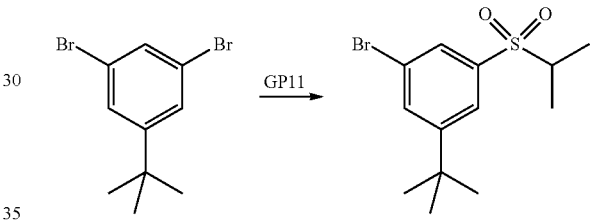

Synthesised according to general procedures GP11—from i) 1,3-dibromo-5-(tert-butyl)benzene (4.25 g, 14.5 mmol), ᵗBuLi (1.6 M in pentane; 20 mL, 32.0 mmol), THF (70 mL and 5 mL), diisopropyl disulfide (2.77 mL, 17.4 mmol); −78° C.→rt; chromatography (EtOAc/cyclohexane 0→10%), 3.54 g, 85%. ii) (3-bromo-5-(tert-butyl)phenyl)(isopropyl)sulfane (3.54 g, 12.3 mmol), m-CPBA (77%; 5.53 g, 24.7 mmol), DCM (200 mL); rt, 12 h; chromatography (EtOAc/cyclohexane 0→10%), 3.0 g, 76%. ¹H NMR (500 MHz, Chloroform-d) δ 7.84 (t, J=1.7 Hz, 1H), 7.81 (t, J=1.6 Hz, 1H), 7.78 (t, J=1.8 Hz, 1H), 3.20 (hept, J=6.9 Hz, 1H), 1.36 (s, 9H), 1.32 (s, 3H), 1.31 (s, 3H).

Example 63: (5-((3-(tert-Butyl)-5-(ethylsulfonyl)phenyl)sulfonyl)thiophen-2-yl)methanamine

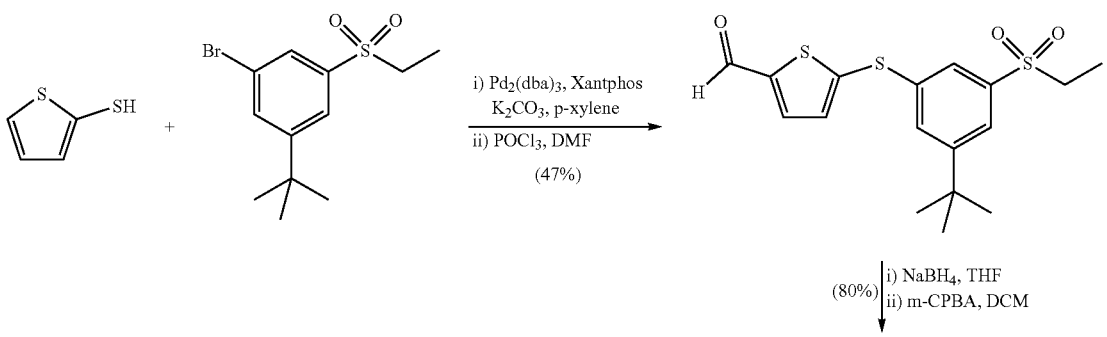

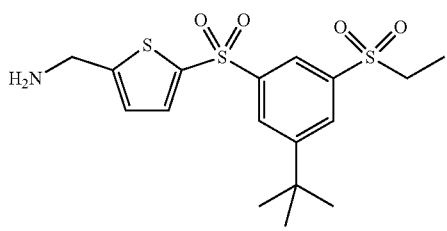 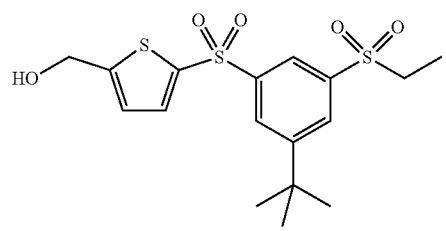

i) DPPA, PPh₃, DIAD, THF
ii) H₂, Pd/C, EtOH
(22%)

To a solution of 2-thiophenethiol (1.0 g, 8.65 mmol) in p-xylene (40 mL) was added potassium carbonate (597 mg, 4.32 mmol). The reaction mixture was stirred at room temperature for 1 h. 1-bromo-3-(tert-butyl)-5-(ethylsulfonyl)benzene (2.4 g, 7.86 mmol), Pd₂(dba)₃ (576 mg, 0.630 mmol) and Xantphos (408 mg, 0.706 mmol) were added. The reaction mixture was degassed with argon and stirred at 140° C. for 12 h. After cooling to room temperature, the reaction mixture was filtered through celite and the residue was washed with ethyl acetate. The solvent was removed under reduced pressure and the crude was purified by chromatography (EtOAc/cyclohexane 0→40%) to afford 2-((3-(tert-butyl)-5-(ethylsulfonyl)phenyl)thio)thiophene as a brown solid. To this intermediate was added DMF (2.0 mL), followed by the dropwise addition of POCl₃ (1.15 mL, 14.9 mmol) at 0° C. The mixture was then stirred at 40° C. for 12 h. After cooling to rt, the reaction mixture was carefully poured onto ice and extracted with ethyl acetate. The organic phase was washed with brine, dried over Na₂SO₄, filtered and the solvent was removed under reduced pressure. The residue was purified by chromatography (EtOAc/cyclohexane 0→40%) to afford the 5-((3-(tert-butyl)-5-(ethylsulfonyl)phenyl)thio)thiophene-2-carbaldehyde (1.37 g, 47%). ¹H NMR (500 MHz, CDCl₃) δ 9.83 (s, 1H), 7.82 (t, J=1.6 Hz, 1H), 7.69-7.72 (m, 1H), 7.66-7.68 (m, 1H), 7.24-7.28 (m, 1H), 3.10 (q, J=7.6 Hz, 2H), 1.34 (s, 9H), 1.28 (t, J=7.4 Hz, 3H). ¹³C NMR (126 MHz, CDCl₃) δ 182.0, 154.5, 146.2, 145.0, 139.8, 136.9, 136.7, 133.1, 132.3, 126.6, 124.6, 50.7, 35.4, 31.0, 26.9, 7.3. HRMS calcd for $C_{17}H_{20}O_3S_3$ [M+H]⁺ 369.0647; found 369.0636.

To a solution of 5-((3-(tert-butyl)-5-(ethylsulfonyl)phenyl)thio)thiophene-2-carbaldehyde (1.37 mg, 3.72 mmol) in THF (30 mL) at 0° C. was added sodium borohydride (309 mg, 8.18 mmol). The reaction mixture was stirred at room temperature for 2 h, before it was quenched with ice. The pH of the solution was adjusted to 4-5 with 1 M HCl and the aqueous phase was extracted with ethyl acetate. The combined organic phase was washed with brine, dried over Na₂SO₄, filtered and the solvent was removed under reduced pressure. The crude was purified by chromatography (EtOAc/cyclohexane 0→40%) to afford (5-((3-(tert-butyl)-5-(ethylsulfonyl)phenyl)thio)thiophen-2-yl)methanol as a white solid (1.37 g, quant.). DCM (200 mL) was added, followed by m-CPBA in small portions (77%; 1.70 g, 7.58 mmol) at 0° C. The mixture was stirred at rt for 12 h, and the solvent was subsequently removed under reduced pressure. The crude was purified by chromatography (EtOAc/cyclohexane 0→60%) to afford (5-((3-(tert-butyl)-5-(ethylsulfonyl)phenyl)sulfonyl)thiophen-2-yl)methanol as a colourless gum (1.2 g, 80% over 2 steps). ¹H NMR (500 MHz, CDCl₃) δ 8.27 (dt, J=8.5, 1.6 Hz, 1H), 8.09 (t, J=1.6 Hz, 1H), 7.64 (d, J=3.8 Hz, 1H), 6.99 (d, J=3.8 Hz, 1H), 4.87 (s, 2H), 3.75 (t, J=6.6 Hz, 1H), 3.15 (q, J=7.3 Hz, 2H), 1.86 (dt, J=6.6, 3.3 Hz, 1H), 1.39 (s, 9H), 1.31 (t, J=7.4 Hz, 3H). ¹³C NMR (126 MHz, CDCl₃) δ 155.3, 155.2, 143.7, 140.2, 140.1, 134.3, 129.6, 129.0, 125.0, 124.4, 68.0, 60.1, 50.6, 35.7, 31.0, 25.6, 7.3. HRMS calcd for $C_{17}H_{22}O_5S_3$ [M-OH]⁺ 385.0596; found 385.3065.

To a solution of (5-((3-(tert-butyl)-5-(ethylsulfonyl)phenyl)sulfonyl)thiophen-2-yl)methanol (1.2 g, 2.98 mmol) in THF (20 mL) at 0° C. was added PPh₃ (1.02 g, 3.88 mmol) and DEAD (0.61 mL, 3.88 mmol). The mixture was stirred at 0° C. for 10 min, followed by the addition of DPPA (0.87 mL, 3.88 mmol). The reaction was warmed to rt over over 16 h and the solvent was removed under reduced pressure. The crude was dissolved in EtOH (50 mL), and Pd/C (10%; 200 mg) was added. The mixture was stirred at rt under H₂ pressure (balloon) for 12 h and then filtered through celite. The solvent was removed under reduced pressure and the crude was was purified by chromatography (MeOH/EtOAc 0→100%) to afford the title compound (261 mg, 22%). ¹H NMR (500 MHz, CDCl₃) δ 8.18-8.38 (m, 2H), 8.08 (t, J=1.6 Hz, 1H), 7.64 (d, J=3.8 Hz, 1H), 6.93 (d, J=3.8 Hz, 1H), 4.10 (s, 2H), 3.15 (q, J=7.6 Hz, 2H), 1.65 (br. s., 2H), 1.39 (s, 9H), 1.31 (t, J=7.4 Hz, 3H). ¹³C NMR (126 MHz, CDCl₃) δ 159.2, 155.1, 143.9, 140.1, 138.9, 134.5, 129.4, 128.9, 124.3, 124.0, 50.6, 41.5, 35.7, 31.0, 7.3. HRMS calcd for $C_{17}H_{23}NO_4S_3$ [M-NH₂]⁺ 385.0602; found 385.0593.

1-Bromo-3-(tert-butyl)-5-(ethylsulfonyl)benzene

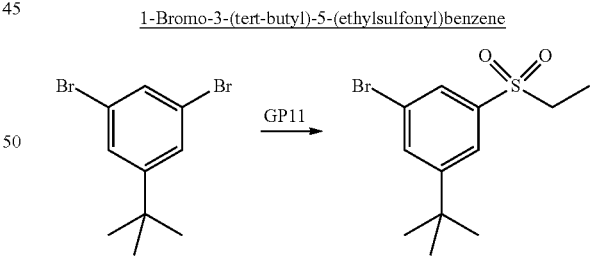

Synthesised according to general procedures GP11— from i) 1,3-dibromo-5-(tert-butyl)benzene (3.69 g, 12.6 mmol), ᵗBuLi (1.6 M in pentane; 15.8 mL, 25.3 mmol), THF (70 mL and 5 mL), diethyl disulfide (1.90 mL, 15.2 mmol); −78° C.→rt. ii) (3-bromo-5-(tert-butyl)phenyl)(ethyl)sulfane (crude), m-CPBA (77%; 5.60 g, 25.0 mmol), DCM (200 mL); rt, 12 h; chromatography (EtOAc/cyclohexane 0→10%), colourless oil, 2.4 g, 62% over 2 steps. ¹H NMR (500 MHz, CDCl₃) δ 7.87 (t, J=1.6 Hz, 1H), 7.83 (t, J=1.6 Hz, 1H), 7.79 (t, J=1.6 Hz, 1H), 3.13 (q, J=7.4 Hz, 2H), 1.36 (s, 9H), 1.31 (t, J=7.4 Hz, 3H).

Example 64: (5-((3-(tert-Butoxy)-5-(methylsulfonyl)phenyl)sulfonyl)thiophen-2-yl)methanamine

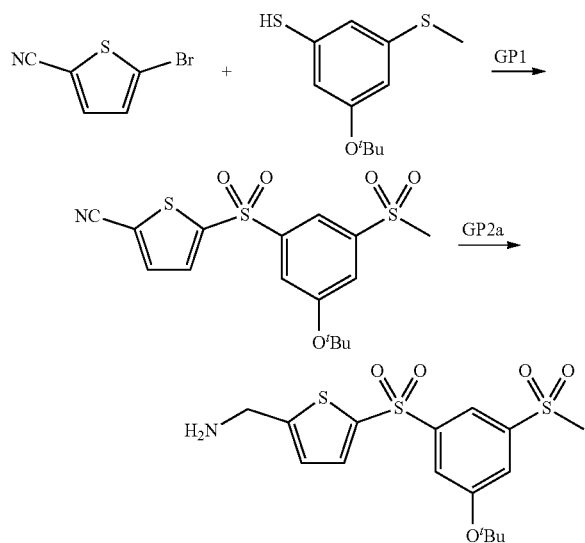

5-((3-(tert-Butoxy)-5-(methylsulfonyl)phenyl)sulfonyl)thiophene-2-carbonitrile was synthesised according to general procedures GP1—from i) 5-bromothiophene-2-carbonitrile (950 mg, 5.05 mmol), 3-(tert-butoxy)-5-(methylthio)benzenethiol (960 mg, 4.21 mmol), K$_2$CO$_3$ (872 mg, 6.32 mmol) and DMF (21 mL); 80° C., 16 h. ii) m-CPBA (77%; 4.74 g, 21.1 mmol) and DCM (28 mL); rt, 2 h. The crude was purified by chromatography (EtOAc/cyclohexane 0→60%) to afford a white solid (1.43 g, 85%). $^1$H NMR (500 MHz, CDCl$_3$) δ 8.17 (t, J=1.6 Hz, 1H), 7.81 (dd, J=2.2, 1.7 Hz, 1H), 7.76 (dd, J=2.2, 1.6 Hz, 1H), 7.71 (d, J=4.0 Hz, 1H), 7.60 (d, J=4.1 Hz, 1H), 3.10 (s, 3H), 1.46 (s, 9H).

The title compound was synthesised according to general procedures GP2a—from BH$_3$ (1.0 M in THF; 0.53 mL, 0.53 mmol), 3-(tert-butoxy)-5-(methylthio)benzenethiol (70 mg, 0.175 mmol) and THF (0.53 mL); 2 h, rt. The crude was purified by chromatography (EtOH/cyclohexane 30, then 100%) to afford a white foam (60 mg, 85%). $^1$H NMR (500 MHz, MeOD) δ 8.14 (t, J=1.6 Hz, 1H), 7.81 (m, 1H), 7.79-7.74 (m, 2H), 7.15 (m, 1H), 4.10 (s, 2H), 3.20 (s, 3H), 1.44 (s, 9H). $^{13}$C NMR (126 MHz, MeOD) δ 158.93, 157.22, 146.05, 144.77, 140.99, 136.12, 127.67, 126.97, 126.78, 120.47, 82.68, 43.97, 41.02, 28.83. HRMS (ESI) for C$_{16}$H$_{22}$NO$_5$S$_3$ ([M+H]$^+$): Calculated 404.0655; Observed 404.0651.

3-(tert-Butoxy)-5-(methylthio)benzenethiol

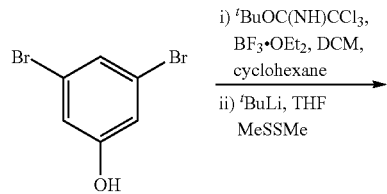

i) $^t$BuOC(NH)CCl$_3$, BF$_3$·OEt$_2$, DCM, cyclohexane
ii) $^t$BuLi, THF MeSSMe

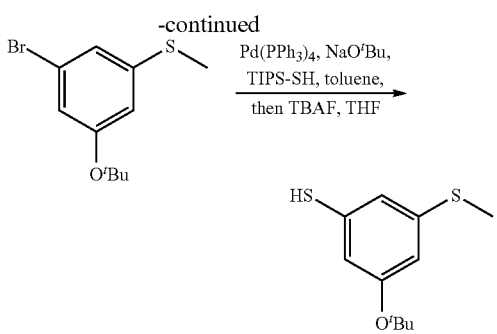

BF$_3$.OEt$_2$ (245 μL, 10%) was added to a solution of tert-butyl 2,2,2-trichloroacet-imidate (13.0 g, 59.5 mmol) and 3,5-dibromophenol (5.0 g, 19.9 mmol) in DCM/cyclohexane (1:1; 66 mL). The mixture was stirred at rt for 2 h. Cyclohexane (66 mL) was added and the flask was left in the fridge for 0.5 h. The solid was then filtered off. The organic solution was washed with sat. NaHCO$_3$ (3×130 mL), dried over MgSO$_4$, filtered and the solvent was removed under reduced pressure. The crude was purified by chromatography (EtOAc/cyclohexane 0→5%) to give 1,3-dibromo-5-(tert-butoxy)benzene as a colourless oil (5.65 g, 92%). $^t$BuLi (7.3 mL, 11.7 mmol) was added dropwise to a solution of 1,3-dibromo-5-(tert-butoxy)benzene (1.64 g, 5.32 mmol) in THF (35.5 mL) at −78° C., and the mixture was stirred at −78° C. for a further 0.5 h. (MeS)$_2$ (719 μL, 7.99 mmol) was added and the reaction was warmed to rt over 1 h. EtOAc was subsequently added. The organic solution was washed with 1:1 H$_2$O/brine, dried over MgSO$_4$, filtered and the solvent was removed under reduced pressure. The crude was purified by chromatography (EtOAc/cyclohexane 0→10%) to afford (3-bromo-5-(tert-butoxy)phenyl)(methyl)sulfane as a colourless oil (1.38 g, 94%). $^1$H NMR (500 MHz, CDCl$_3$) δ 7.08 (t, J=1.6 Hz, 1H), 6.93 (t, J=1.9 Hz, 1H), 6.80 (t, J=1.8 Hz, 1H), 2.46 (s, 3H), 1.36 (s, 9H).

NaO$^t$Bu (1.49 g, 15.5 mmol) was added to a solution of triisopropylsilanylthiol (3.32 mL, 15.5 mmol) and p-xylene (30 mL). The mixture was stirred at rt for 0.5 h. Pd(PPh$_3$)$_4$ (1.49 g, 10%) was subsequently added, followed by a solution of (3-bromo-5-(tert-butoxy)phenyl)(methyl)sulfane (3.53 g, 12.9 mmol) in p-xylene (34 mL). The mixture was thoroughly degassed with argon and then stirred at 130° C. for 16 h. After cooling to rt, TBAF (1.0 M in THF; 26.0 mL, 26.0 mmol) was added and the mixture was stirred at rt for a further hour. Et$_2$O (100 mL) was added the organic solution was extracted with IM NaOH (3×80 mL). The combined aqueous phase was neutralised with AcOH, and subsequently extracted with DCM (3×80 mL). The combined organic phase was dried over MgSO$_4$, filtered and the solvent was removed under reduced pressure. The crude was purified by chromatography (EtOAc/cyclohexane 0→40%) to afford 3-(tert-butoxy)-5-(methylthio)benzenethiol as a light yellow oil (498 mg, 16%). $^1$H NMR (500 MHz, CDCl$_3$) δ 6.86 (t, J=1.6 Hz, 1H), 6.70 (t, J=1.8 Hz, 1H), 6.68 (t, J=1.8 Hz, 1H), 3.44 (s, 1H), 2.45 (s, 3H), 1.35 (s, 9H).

Example 65: (5-((3-Ethoxy-5-(methylsulfonyl)phenyl)sulfonyl)thiophen-2-yl)methanamine

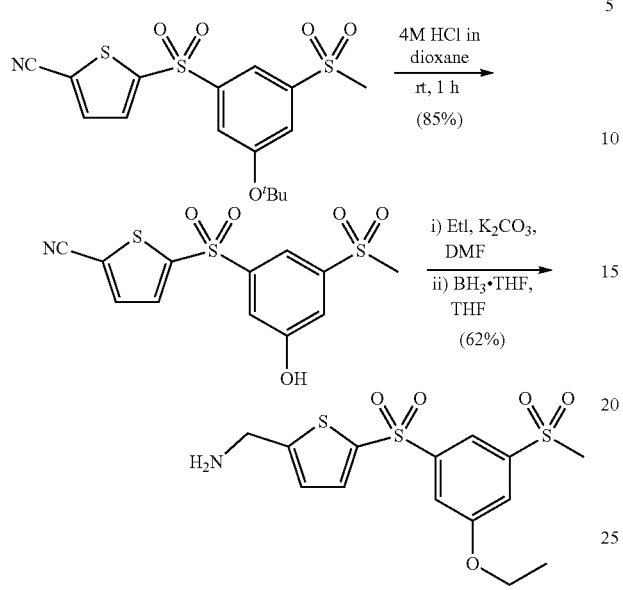

A mixture of 5-((3-(tert-butoxy)-5-(methylsulfonyl)phenyl)sulfonyl)thiophene-2-carbonitrile (1.40 g, 3.50 mmol), 4 M HCl in 1,4-dioxane (6 mL) and DCM (6 mL) was stirred at rt for 3 h. The solvent was removed under reduced pressure and the crude was purified by column chromatography (EtOAc/cyclohexane 10→100%) to afford 5-((3-hydroxy-5-(methylsulfonyl)phenyl)sulfonyl)thiophene-2-carbonitrile as a white foam (1.17 g, 95%). $^1$H NMR (500 MHz, CDCl$_3$) δ 10.00 (s, 1H), 8.05-7.98 (m, 2H), 7.97 (d, J=4.1 Hz, 1H), 7.75 (m, 1H), 7.69 (dd, J=2.2, 1.6 Hz, 1H), 3.22 (s, 3H).

A mixture of EtI (18.5 µL, 0.231 mmol), K$_2$CO$_3$ (34.5 mg, 0.245 mmol), 5-((3-hydroxy-5-(methylsulfonyl)phenyl)sulfonyl)thiophene-2-carbonitrile (66 mg, 0.192 mmol) and DMF (1.3 mL) was stirred at 40° C. for 5 h. The mixture was cooled to rt, diluted with EtOAc (30 mL). The organic phase was washed with 1:1 H$_2$O/brine (3×30 mL), dried over MgSO$_4$, filtered, and the solvent was removed under reduced pressure. The crude was dissolved in THF (0.65 mL). BH$_3$ (1.0 M in THF; 0.65 mL, 0.65 mmol) was added and the reaction was stirred at rt for 2 h. Ethanol (5 mL) was added slowly and the mixture was heated at 70° C. for 1 h. The solvent was removed under reduced pressure and the crude was purified by chromatography (EtOH/cyclohexane 30→100%, then 100%) to afford the title compound as a white powder (45 mg, 62%). $^1$H NMR (500 MHz, MeOD) δ 8.02 (t, J=1.5 Hz, 1H), 7.84 (d, J=3.9 Hz, 1H), 7.76 (m, 1H), 7.72 (m, 1H), 7.34 (d, J=3.9 Hz, 1H), 4.40 (s, 2H), 4.21 (q, J=7.0 Hz, 2H), 3.19 (s, 3H), 1.45 (t, J=7.0 Hz, 3H). $^{13}$C NMR (126 MHz, MeOD) δ 161.87, 145.99, 145.84, 145.33, 144.42, 135.99, 131.81, 119.27, 118.98, 118.41, 66.42, 43.97, 38.47, 14.72. HRMS (ESI) for C$_{14}$H$_{18}$NO$_5$S$_3$ ([M+H]$^+$): Calculated 376.0342; Observed 376.0336.

Example 66: 7-((5-(Aminomethyl)thiophen-2-yl)sulfonyl)-4,4-dimethylthiochroman 1,1-dioxide

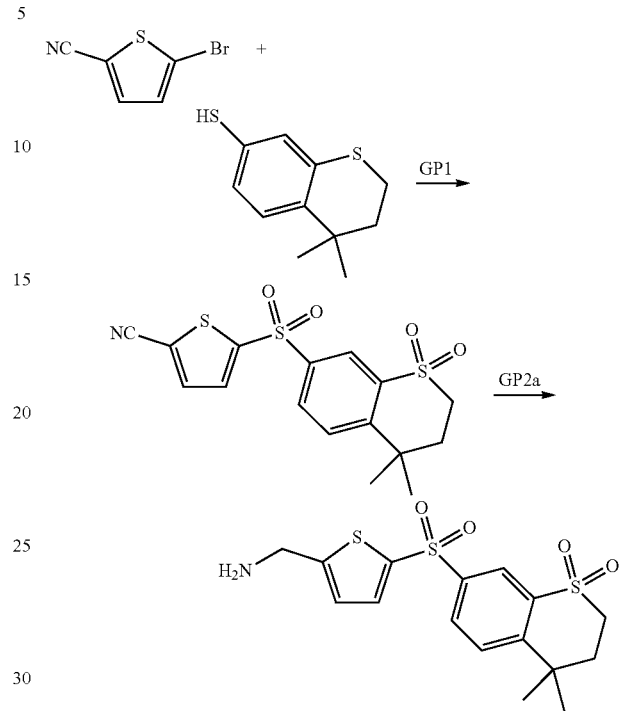

5-((4,4-Dimethyl-1,1-dioxidothiochroman-7-yl)sulfonyl)thiophene-2-carbonitrile was synthesised according to general procedures GP1—from i) 5-bromothiophene-2-carbonitrile (300 mg, 1.60 mmol), 4,4-dimethylthiochroman-7-thiol (280 mg, 1.33 mmol), K$_2$CO$_3$ (275 mg, 2.00 mol) and DMF (6.7 mL); 80° C., 16 h. ii) m-CPBA (70-75%; 1.43 g, ~5.99 mmol) and DCM (9 mL); rt, 4 h. The crude was purified by chromatography (EtOAc/cyclohexane 5→70%) to afford a white foam (288 mg, 57%). $^1$H NMR (500 MHz, CDCl$_3$) δ 8.53 (d, J=2.1 Hz, 1H), 8.09 (dd, J=8.5, 2.1 Hz, 1H), 7.70 (d, J=4.0 Hz, 1H), 7.66 (d, J=8.5 Hz, 1H), 7.59 (d, J=4.0 Hz, 1H), 3.48-3.40 (m, 2H), 2.48-2.39 (m, 2H), 1.45 (s, 6H).

The title compound was synthesised according to general procedures GP2a—from BH$_3$ (1.0 M in THF; 2.5 mL, 2.5 mmol), 5-((4,4-dimethyl-1,1-dioxidothiochroman-7-yl)sulfonyl)thiophene-2-carbonitrile (314 mg, 0.823 mmol) and THF (2.5 mL); rt, 1 h. The crude was purified by chromatography (EtOH/cyclohexane 30→100, then 100%) to afford a light yellow foam (124 mg, 39%). $^1$H NMR (500 MHz, CDCl$_3$) δ 8.45 (d, J=2.0 Hz, 1H), 8.05 (dd, J=8.5, 2.0 Hz, 1H), 7.67-7.54 (m, 2H), 6.89 (d, J=3.8 Hz, 1H), 4.06 (s, 2H), 3.48-3.35 (m, 2H), 2.45-2.35 (m, 2H), 1.69 (br, 2H), 1.41 (s, 6H). $^{13}$C NMR (126 MHz, CDCl$_3$) δ 159.45, 149.95, 141.99, 138.98, 138.77, 134.61, 130.65, 129.29, 124.08, 123.41, 47.00, 41.63, 35.32, 34.92, 30.62. HRMS (ESI) for C$_{16}$H$_{20}$NO$_4$S$_3$ ([M+H]$^+$): Calculated 386.0549; Observed 386.0546.

4,4Dimethylthiochromane-7-thiol

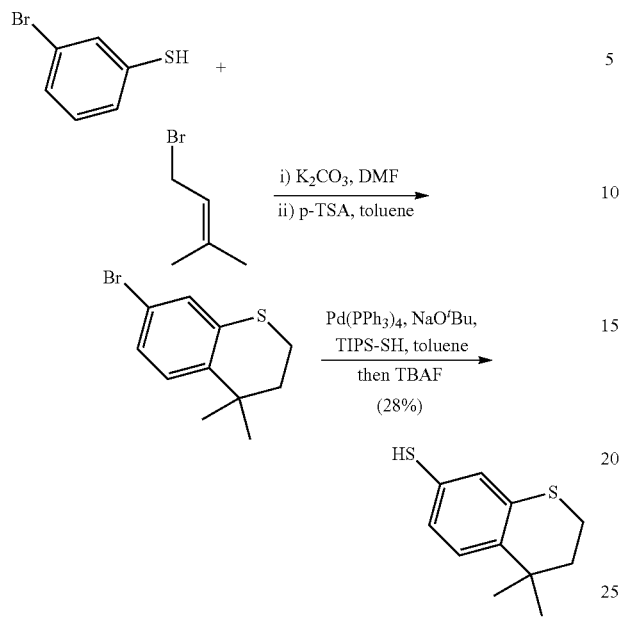

1-Bromo-3-methylbut-2-ene (1.94 mL, 16.8 mmol) was added to a mixture of 3-bromothiophenol (1.91 mL, 18.5 mmol), K$_2$CO$_3$ (138) and DMF (56 mL). The reaction was stirred at rt for 16 h. EtOAc (120 mL) was added. The organic phase was washed with 1:1 H$_2$O/brine (4×100 mL), dried over MgSO$_4$ and filtered. The solvent was removed under reduced pressure to give (3-bromophenyl)(3-methylbut-2-en-1-yl)sulfane as a colourless oil (4.29 g; quant). (3-bromophenyl)(3-methylbut-2-en-1-yl)sulfane (2.40 g, 9.33 mmol) was dissolved in toluene (10.4 mL). p-TSA (2.66 g, 14.0 mmol) was added and the mixture was stirred at 165° C. (microwave) for 45 min. After cooling to rt, EtOAc (80 mL) was added. The organic phase was washed with sat. NaHCO$_3$ (3×80 mL), dried over MgSO$_4$ and filtered. The solvent was removed under reduced pressure. The crude was purified by column chromatography (EtOAc/cyclohexane 0→5%) to afford a colourless oil containing mostly the desired 7-bromo-4,4-dimethylthiochroman and the regioisomer 5-bromo-4,4-dimethylthiochroman (2.42 g, 5.3:1; quant).

NaO$^t$Bu (365 mg, 3.79 mmol) was added to a solution of triisopropylsilanylthiol (814 µL, 3.79 mmol) and toluene (6.0 mL). The mixture was stirred at rt for 0.5 h. Pd(PPh$_3$)$_4$ (438 mg, 15%) was subsequently added, followed by a solution of the dimethylthiochroman mixture (650 mg, 2.53 mmol) in toluene (6.6 mL). The mixture was thoroughly degassed with argon and stirred at 110° C. for 16 h. After cooling to rt, TBAF (1.0 M in THF; 5.1 mL, 5.1 mmol) was added and the mixture was stirred at rt for a further hour. Et$_2$O (80 mL) was added, the organic phase was extracted with H$_2$O (80 mL) and 1 M NaOH (2×60 mL). The combined aqueous phase was neutralised with AcOH, extracted with DCM (3×60 mL). The combined organic phase was dried over MgSO$_4$, filtered and the solvent was removed under reduced pressure. The crude was purified by chromatography (EtOAc/cyclohexane 0→15%) to afford 4,4-dimethylthiochroman-7-thiol as a colourless oil (152 mg, 28%). $^1$H NMR (500 MHz, CDCl$_3$) δ 7.22 (d, J=8.3 Hz, 1H), 7.02 (d, J=2.1 Hz, 1H), 6.92 (dd, J=8.2, 2.1 Hz, 1H), 3.34 (s, 1H), 3.04-2.99 (m, 2H), 1.97-1.89 (m, 2H), 1.30 (s, 6H).

Example 67: (5-((3-Isopropoxy-5-(methylsulfonyl)phenyl)sulfonyl)thiophen-2-yl)methanamine

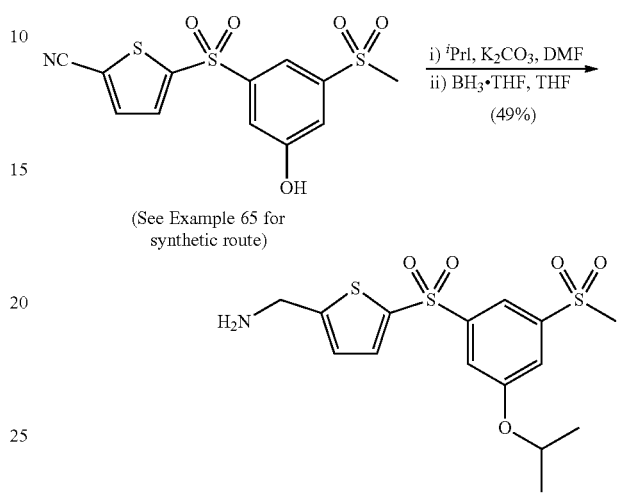

(See Example 65 for synthetic route)

A mixture of $^i$PrI (25.0 µL, 0.250 mmol), K$_2$CO$_3$ (37.4 mg, 0.271 mmol), 5-((3-hydroxy-5-(methylsulfonyl)phenyl)sulfonyl)thiophene-2-carbonitrile (71.6 mg, 0.209 mmol) and DMF (1.4 mL) was stirred at 40° C. for 5 h. The mixture was cooled to rt, diluted with EtOAc (30 mL). The organic phase was washed with 1:1 H$_2$O/brine (3×30 mL), dried over MgSO$_4$, filtered and the solvent was removed under reduced pressure. The crude was dissolved in THF (0.63 mL). BH$_3$ (1.0 M in THF; 0.63 mL, 0.63 mmol) was added and the reaction was stirred at rt for 2 h. Ethanol (5 mL) was added slowly and the mixture was heated at 70° C. for 1 h. The solvent was removed under reduced pressure and the crude was purified by chromatography (EtOH/cyclohexane 30→100%, then 100%) to afford a white powder (40 mg, 49%). $^1$H NMR (500 MHz, CDCl$_3$) δ 8.01 (t, J=1.5 Hz, 1H), 7.69 (dd, J=2.3, 1.6 Hz, 1H), 7.63 (d, J=3.8 Hz, 1H), 7.57 (dd, J=2.3, 1.6 Hz, 1H), 6.92 (br, 1H), 4.69 (hept, J=6.0 Hz, 1H), 4.10 (s, 2H), 3.08 (s, 3H), 1.65 (br, 2H), 1.39 (d, J=6.0 Hz, 6H). $^{13}$C NMR (126 MHz, CDCl$_3$) δ 159.65, 159.36, 145.59, 143.44, 138.85, 134.81, 124.13, 118.99, 118.57, 117.53, 71.93, 44.44, 41.73, 21.81. HRMS (ESI) for C$_{15}$H$_{20}$NO$_5$S$_3$ ([M+H]$^+$): Calculated 390.0498; Observed 390.0494.

Example 68: (5-((5-(Methylsulfonyl)-[1,1'-biphenyl]-3-yl)sulfonyl)thiophen-2-yl)methanamine

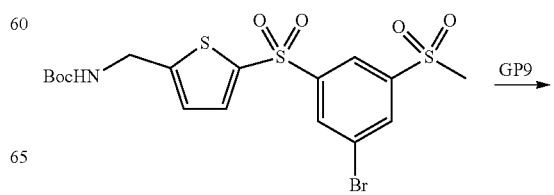

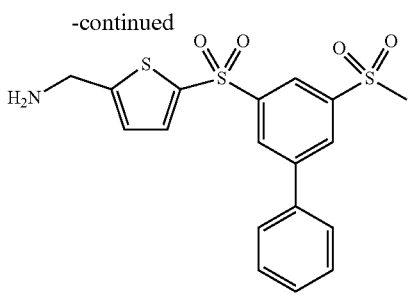

The title compound was synthesised according to general procedures GP9—from i) tert-butyl ((5-((3-bromo-5-(methylsulfonyl)phenyl)sulfonyl)thiophen-2-yl)methyl)carbamate (2.0 g, 3.92 mmol), Pd(PPh$_3$)$_4$ (453 mg, 10%), phenylboronic acid (574 mg, 4.71 mmol), Cs$_2$CO$_3$ (1.53 g, 4.71 mmol) and 1,4-dioxane (13 mL); 100° C., 16 h; Chromatography (EtOAc/cyclohexane 0→60), 1.59 g, 80%, brown foam. ii) 4 M HCl in dioxane (10.5 mL) and DCM (10.5 mL); rt, 16 h. The resultant amine hydrochloride was treated with 2N NH$_3$ in MeOH to liberate the free amine and the solvent was removed under reduced pressure to afford the title compound as a light brown solid (1.12 g, 88%). $^1$H NMR (500 MHz, CDCl$_3$) δ 8.46 (t, J=1.7 Hz, 1H), 8.44 (t, J=1.7 Hz, 1H), 8.32 (t, J=1.7 Hz, 1H), 7.67 (d, J=3.9 Hz, 1H), 7.65-7.61 (m, 2H), 7.55-7.45 (m, 3H), 6.93 (m, 1H), 4.09 (s, 2H), 3.14 (s, 3H), 1.68 (br, 2H). $^{13}$C NMR (126 MHz, CDCl$_3$) δ 145.00, 144.60, 142.82, 138.62, 137.33, 134.96, 130.41, 130.02, 129.54, 127.42, 124.66, 124.18, 44.56, 41.68. HRMS (ESI) for C$_{18}$H$_{18}$NO$_4$S$_3$ ([M+H]$^+$): Calculated 408.0392; Observed 408.0391.

mL), dried over MgSO$_4$, filtered and the solvent was removed under reduced pressure. The crude was recrystallised from DCM/cyclohexane to give 22.3 g of beige crystals containing a 4.5:1 mixture of the desired 1,3-dibromo-5-(methylsulfinyl)benzene and the by-product (5-bromo-1,3-phenylene)bis(methylsulfane). NaSMe (21% aq.; 27.5 mL, 82.3 mmol) was added to a solution of the sulfoxide mixture (22.3 g, 74.8 mmol) in DMF (374 mL), and the reaction was stirred at 40° C. for 6 h. After cooling to rt, EtOAc (400 mL) was added. The organic phase was washed with 1:1 H$_2$O/brine (3×400 mL), dried over MgSO$_4$, filtered and the solvent was removed under reduced pressure. The crude was purified by chromatography (EtOAc/cyclohexane 5→80%) to afford (3-bromo-5-(methylsulfinyl)phenyl)(methyl)sulfane as an orange oil (6.26 g, 19%). $^1$H NMR (500 MHz, CDCl$_3$) δ 7.46-7.41 (m, 3H), 2.75 (s, 3H), 2.53 (s, 3H).

TFAA (6.30 mL, 43.3 mmol) was added to a solution of (3-bromo-5-(methylsulfinyl)phenyl)(methyl)sulfane (4.0, 15.1 mmol) and 2,6-lutidine (7.04 mL, 60.4 mmol) in MeCN (101 mL). The reaction was stirred at rt for 0.5 h and all volatiles were removed under reduced pressure. 1:1 Et$_3$N/MeOH (100 mL) was then added. The solution was stirred at rt for 0.5 h and was subsequently acidified to pH<4 with 2 M HCl. The aqueous phase was extracted with EtOAc (400 mL). The organic phase was washed with 0.5 M HCl (200 mL) and brine (200 mL), dried over MgSO$_4$, filtered and the solvent was removed under reduced pressure. The crude was purified by chromatography (EtOAc/cyclohexane 0→30%) to afford 3-bromo-5-(methylthio)benzenethiol as an orange oil (3.42 g, 96%). $^1$H NMR (500 MHz, CDCl$_3$) δ 7.18 (t, J=1.6 Hz, 1H), 7.14 (t, J=1.6 Hz, 1H), 7.04 (t, J=1.6 Hz, 1H), 3.49 (s, 1H), 2.47 (s, 3H).

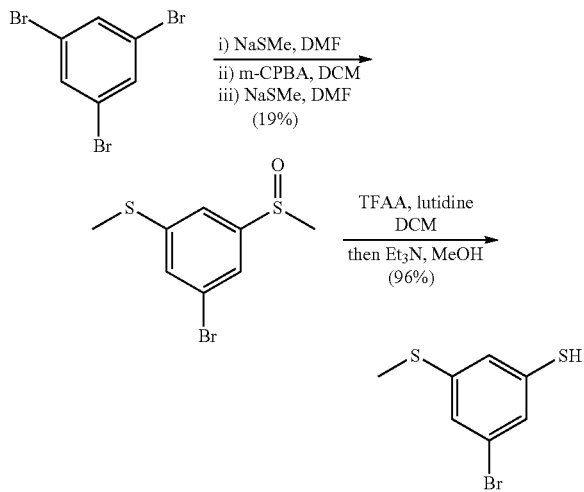

NaSMe (21% aq.; 50.8 mL, 152 mmol) was added to a solution of 1,3,5-tribromobenzene (40.0 g, 127 mmol) in DMF (508 mL), and the reaction was stirred at 100° C. for 16 h. After cooling to rt, EtOAc (1.5 L) was added. The organic phase was washed with H$_2$O (3×1.0 L), brine (1.0 L), dried over MgSO$_4$, filtered and the solvent was removed under reduced pressure. The intermediate sulfide was dissolved in DCM (400 mL) and cooled to 0° C. A solution of m-CPBA (34.2 g, 152 mmol) in DCM (234 mL) was slowly added and the mixture was stirred at 0° C. for 1 h before allowing to warm to rt over 1 h. EtOAc (800 mL) was added. The organic phase was washed with sat. NaHCO$_3$ (3×500

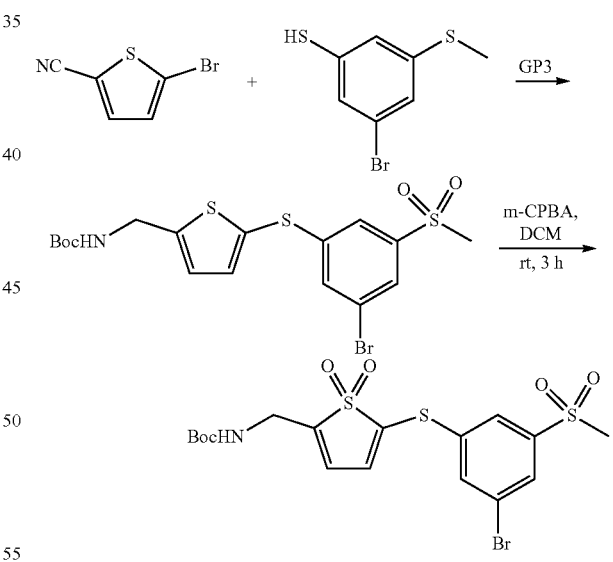

tert-Butyl ((5-((3-bromo-5-(methylsulfonyl)phenyl)thio)thiophen-2-yl)methyl)carbamate was synthesised according to general procedures GP3—from i) 5-bromothiophene-2-carbonitrile (5.20 g, 27.6 mmol), 3-bromo-5-(methylthio)benzenethiol (5.41 g, 23.0 mmol), K$_2$CO$_3$ (4.77 g, 34.5 mmol) and DMF (115 mL); 40° C., 16 h; Chromatography (EtOAc/cyclohexane 0→20%), 7.53 g, 96%. ii) BH$_3$ (1.0 M in THF; 66.1 mL, 66.1 mmol), THF (66 mL); rt, 1 h. iii) Boc$_2$O (7.60 mL, 33.0 mmol), Et$_3$N (9.21 mL, 66.1 mmol), DCM (110 mL); rt, 16 h. The crude was used in the subsequent transformation without further purification.

m-CPBA (50-55%; 32.6 g, ~99.1 mmol) was added in small portions to a solution of tert-butyl ((5-((3-bromo-5-(methylsulfonyl)phenyl)thio)thiophen-2-yl)methyl)carbamate (crude) in DCM (148 mL) at 0° C. and the mixture was stirred at rt for 3 h. When complete conversion was achieved, EtOAc was added (250 mL). The organic phase was washed with sat. NaHCO₃ (4×200 mL) and brine (200 mL), dried over MgSO₄ and filtered. The solvent was removed under reduced pressure. The crude was purified by column chromatography (EtOAc/cyclohexane 0→60%) to afford tert-butyl ((5-((3-bromo-5-(methylsulfonyl)phenyl)sulfonyl)thiophen-2-yl)methyl)carbamate as a yellow foam (3.83 g, 34%). ¹H NMR (500 MHz, CDCl₃) δ 8.43 (t, J=1.6 Hz, 1H), 8.34 (t, J=1.7 Hz, 1H), 8.26 (t, J=1.7 Hz, 1H), 7.64 (d, J=3.9 Hz, 1H), 6.99 (d, J=3.8 Hz, 1H), 5.05 (br, 1H), 4.48 (br, 2H), 3.12 (s, 3H), 1.46 (s, 9H).

Example 69: (5-((2'-Ethoxy-5-(methylsulfonyl)-[1,1'-biphenyl]-3-yl)sulfonyl)thiophen-2-yl)methanamine hydrochloride

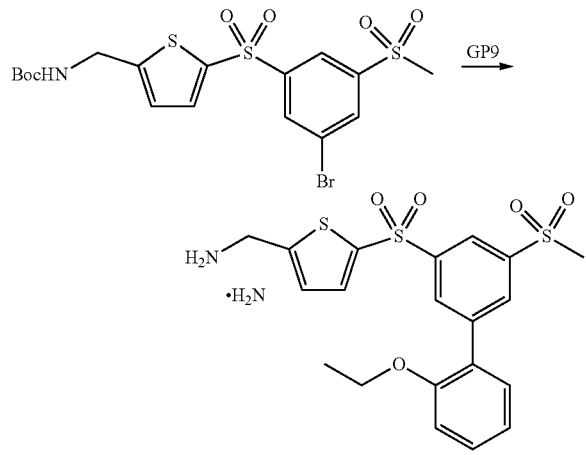

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh₃)₄ (22.6 mg, 10%), (2-ethoxyphenyl)boronic acid (39.1 mg, 0.235 mmol), Cs₂CO₃ (76.7 mg, 0.235 mmol) and 1,4-dioxane (1.3 mL); 90° C., 16 h. Chromatography (EtOAc/cyclohexane 0→60), 93 mg, 86%, yellow foam. ii) from 4 M HCl in dioxane (0.8 mL) and 1,4-dioxane (0.8 mL); rt, 16 h. The title compound (yellow foam; 62 mg, 74%) did not require further purification. ¹H NMR (500 MHz, MeOD) δ 8.48 (t, J=1.6 Hz, 1H), 8.41 (d, J=1.7 Hz, 2H), 7.85 (d, J=3.9 Hz, 1H), 7.47-7.39 (m, 2H), 7.34 (d, J=3.9 Hz, 1H), 7.13 (d, J=8.1 Hz, 1H), 7.09 (t, J=7.5 Hz, 1H), 4.39 (s, 2H), 4.11 (q, J=7.0 Hz, 2H), 3.22 (s, 3H), 1.36 (t, J=7.0 Hz, 3H). ¹³C NMR (126 MHz, MeOD) δ 157.11, 145.99, 144.65, 144.33, 143.78, 143.50, 135.91, 134.13, 133.85, 132.08, 131.82, 131.42, 127.46, 124.92, 122.36, 113.76, 65.26, 44.13, 38.43, 15.11. HRMS (ESI) for C₂₀H₂₂NO₅S₃ ([M+H]⁺): Calculated 452.0655; Observed 452.0653.

Example 70: (5-((2'-Ethyl-5-(methylsulfonyl)-[1,1'-biphenyl]-3-yl)sulfonyl)thiophen-2-yl)methanamine

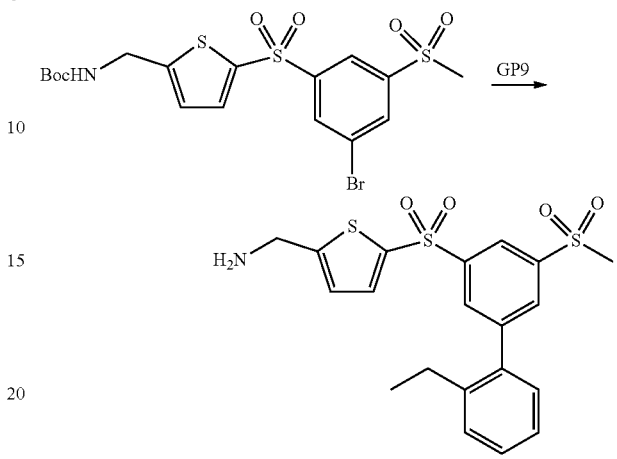

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh₃)₄ (22.6 mg, 10%), (2-ethylphenyl)boronic acid (35.3 mg, 0.235 mmol), Cs₂CO₃ (76.7 mg, 0.235 mmol) and 1,4-dioxane (1.3 mL); 90° C., 16 h. Chromatography (EtOAc/cyclohexane 0→60), 76 mg, 72%, yellow foam. ii) 4 M HCl in dioxane (0.7 mL) and 1,4-dioxane (0.7 mL); rt, 16 h. The amine hydrochloride product was basified with 2N NH₃ in MeOH, and purified by column chromatography (EtOH/cyclohexane 0→100% then 100%) to afford a white foam (42 mg, 68%). ¹H NMR (500 MHz, CDCl₃) δ 8.49 (t, J=1.7 Hz, 1H), 8.21 (t, J=1.6 Hz, 1H), 8.09 (t, J=1.6 Hz, 1H), 7.66 (d, J=3.8 Hz, 1H), 7.42 (td, J=7.6, 1.3 Hz, 1H), 7.37 (m, 1H), 7.30 (td, J=7.4, 1.4 Hz, 1H), 7.18 (dd, J=7.6, 1.2 Hz, 1H), 6.94 (d, J=3.9 Hz, 1H), 4.10 (s, 2H), 3.14 (s, 3H), 2.53 (q, J=7.5 Hz, 2H), 1.61 (s, 2H), 1.12 (t, J=7.6 Hz, 3H). ¹³C NMR (126 MHz, CDCl₃) δ 159.97, 145.25, 144.31, 142.19, 141.50, 138.66, 137.63, 134.95, 132.72, 132.24, 129.87, 129.41, 129.33, 126.37, 124.59, 124.15, 44.53, 41.73, 26.17, 15.73. HRMS (ESI) for C₂₀H₂₂NO₄S₃ ([M+H]⁺): Calculated 436.0705; Observed 436.0727.

Example 71: (5-((2',6'-Dimethyl-5-(methylsulfonyl)-[1,1'-biphenyl]-3-yl)sulfonyl)thiophen-2-yl)methanamine

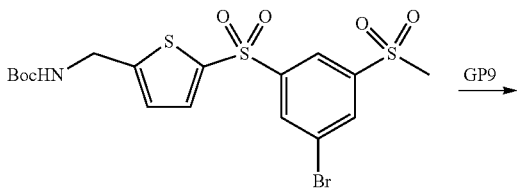

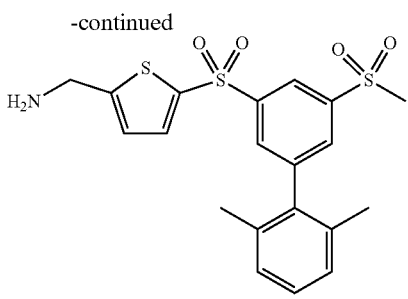

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), (2,6-dimethylphenyl)boronic acid (35.3 mg, 0.235 mmol), Cs$_2$CO$_3$ (76.7 mg, 0.235 mmol) and 1,4-dioxane (1.3 mL); 90° C., 16 h. Chromatography (EtOAc/cyclohexane 0→60), 93 mg, 89%, yellow foam. ii) 4 M HCl in dioxane (0.8 mL) and 1,4-dioxane (0.8 mL); rt, 16 h. The amine hydrochloride product was basified with 2N NH$_3$ in MeOH, and purified by column chromatography (EtOH/cyclohexane 0→100% then 100%) to afford a colourless oil (44 mg, 58%). $^1$H NMR (500 MHz, CDCl$_3$) δ 8.49 (t, J=1.7 Hz, 1H), 8.09 (t, J=1.6 Hz, 1H), 7.96 (t, J=1.5 Hz, 1H), 7.66 (d, J=3.8 Hz, 1H), 7.24 (d, J=7.6 Hz, 1H), 7.15 (d, J=7.6 Hz, 2H), 6.94 (d, J=3.9 Hz, 1H), 4.11 (s, 2H), 3.14 (s, 3H), 1.99 (s, 6H), 1.60 (br, 2H). $^{13}$C NMR (126 MHz, CDCl$_3$) δ 160.00, 144.72, 144.53, 142.54, 137.83, 135.61, 134.92, 133.15, 132.55, 128.81, 128.12, 124.70, 124.13, 44.54, 41.74, 21.08. HRMS (ESI) for C$_{20}$H$_{22}$NO$_4$S$_3$ ([M+H]$^+$): Calculated 436.0705; Observed 436.0709.

Example 72: (5-((3',5'-Dimethyl-5-(methylsulfonyl)-[1,1'-biphenyl]-3-yl)sulfonyl)thiophen-2-yl)methanamine

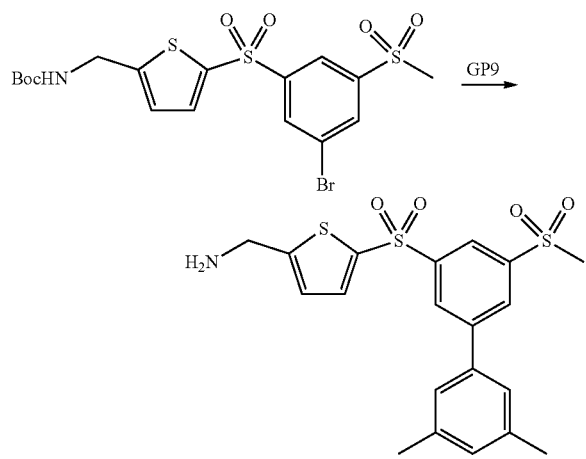

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), (3,5-dimethylphenyl)boronic acid (35.3 mg, 0.235 mmol), Cs$_2$CO$_3$ (76.7 mg, 0.235 mmol) and 1,4-dioxane (1.3 mL); 90° C., 16 h. Chromatography (EtOAc/cyclohexane 0→60), 70 mg, 67%, yellow foam. ii) 4 M HCl in dioxane (0.7 mL) and 1,4-dioxane (0.7 mL); rt, 16 h. The amine hydrochloride product was basified with 2N NH$_3$ in MeOH, and purified by column chromatography (EtOH/cyclohexane 0→100% then 100%) to afford a white solid (23 mg, 40%). $^1$H NMR (500 MHz, MeOD/CDCl$_3$) δ 8.41-8.35 (m, 2H), 8.30 (t, J=1.6 Hz, 1H), 7.68 (d, J=3.9 Hz, 1H), 7.22 (br, 2H), 7.09 (br, 1H), 7.03 (d, J=3.8 Hz, 1H), 4.04 (s, 2H), 3.17 (s, 3H), 2.38 (s, 6H). $^{13}$C NMR (126 MHz, MeOD/CDCl$_3$) δ 145.50, 144.81, 143.06, 139.62, 139.57, 137.51, 135.39, 131.47, 130.63, 130.52, 126.17, 125.50, 124.57, 44.43, 40.89, 21.44. HRMS (ESI) for C$_{20}$H$_{22}$NO$_4$S$_3$ ([M+H]$^+$): Calculated 436.0705; Observed 436.0700.

Example 73: (5-((3-(Methylsulfonyl)-5-(pyridin-4-yl)phenyl)sulfonyl)thiophen-2-yl)methanamine dihydrochloride

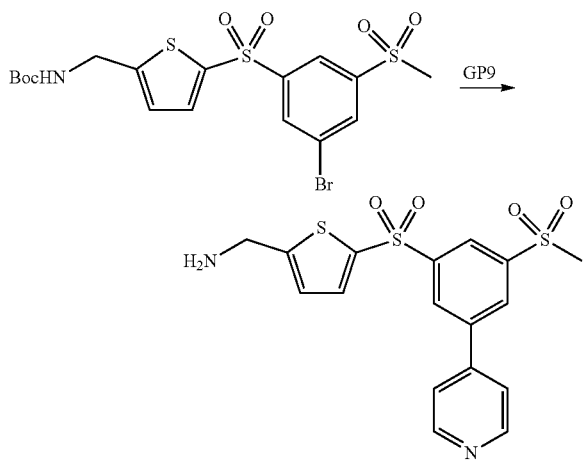

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), pyridine-4-boronic acid (57.8 mg, 0.470 mmol), Cs$_2$CO$_3$ (76.7 mg, 0.235 mmol) and 1,4-dioxane (1.3 mL); 90° C., 16 h. Chromatography (EtOAc/cyclohexane 0→100, then MeOH/DCM 0→15%), 47 mg, 47%, yellow foam. ii) 4 M HCl in dioxane (0.6 mL) and 1,4-dioxane (0.6 mL); rt, 16 h. The amine hydrochloride product was basified with 2N NH$_3$ in MeOH, and purified by column chromatography (MeOH/DCM 0→20%) to afford a yellow solid (35 mg, 93%). $^1$H NMR (500 MHz, MeOD/CDCl$_3$) δ 8.72-8.69 (m, 2H), 8.55 (t, J=1.6 Hz, 1H), 8.50 (t, J=1.6 Hz, 1H), 8.45 (t, J=1.6 Hz, 1H), 7.73-7.70 (m, 3H), 7.04 (d, J=3.9 Hz, 1H), 4.04 (s, 2H), 3.23 (s, 3H). $^{13}$C NMR (126 MHz, MeOD/CDCl$_3$) δ 158.47, 150.06, 145.33, 145.14, 143.36, 141.22, 138.23, 135.26, 130.28, 130.21, 126.22, 125.35, 122.13, 43.68, 40.64. HRMS (ESI) for C$_{17}$H$_{17}$N$_2$O$_4$S$_3$ ([M+H]$^+$): Calculated 409.0345; Observed 409.0340.

Example 74: (5-((3-(Methylsulfonyl)-5-(pyridin-3-yl)phenyl)sulfonyl)thiophen-2-yl)methanamine dihydrochloride

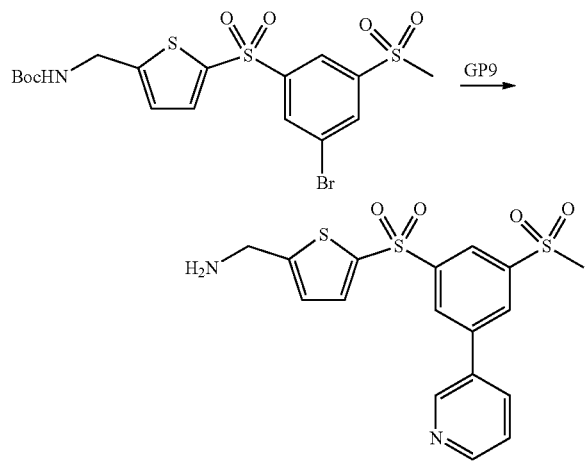

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), pyridine-3-boronic acid (57.8 mg, 0.470 mmol), Cs$_2$C$_{O3}$ (76.7 mg, 0.235 mmol) and 1,4-dioxane (1.3 mL); 90° C., 16 h. Chromatography (EtOAc/cyclohexane 0→100, then MeOH/DCM 0→15%), 47 mg, 47%, orange oil. ii) 4 M HCl in dioxane (0.6 mL) and 1,4-dioxane (0.6 mL); rt, 16 h. The amine hydrochloride product was basified with 2N NH$_3$ in MeOH, and purified by column chromatography (MeOH/DCM 0→20%) to afford a yellow solid (26 mg, 69%). $^1$H NMR (500 MHz, MeOD/CDCl$_3$) δ 8.88 (m, 1H), 8.64 (dd, J=4.9, 1.5 Hz, 1H), 8.50 (t, J=1.6 Hz, 1H), 8.48 (t, J=1.6 Hz, 1H), 8.45 (t, J=1.6 Hz, 1H), 8.17 (ddd, J=8.0, 2.3, 1.6 Hz, 1H), 7.75 (d, J=3.9 Hz, 1H), 7.59 (m, 1H), 7.06 (d, J=3.9 Hz, 1H), 4.02 (s, 2H), 3.25 (s, 3H). $^{13}$C NMR (126 MHz, MeOD) δ 158.24, 149.38, 147.44, 144.97, 143.40, 140.86, 138.55, 135.73, 135.15, 133.74, 130.29, 130.03, 125.48, 125.10, 124.42, 43.10, 40.38. HRMS (ESI) for C$_{17}$H$_{17}$N$_2$O$_4$S$_3$ ([M+H]$^+$): Calculated 409.0345; Observed 409.0371.

Example 75: (5-((3-(Methylsulfonyl)-5-((trimethylsilyl)ethynyl)phenyl)sulfonyl)thiophen-2-yl)methanamine hydrochloride

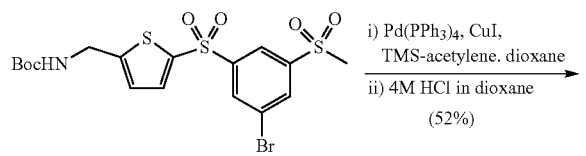

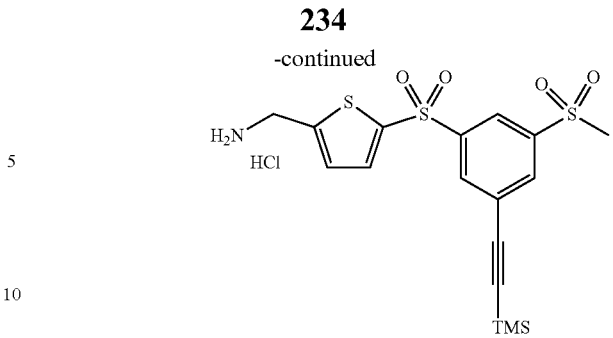

A mixture of tert-butyl ((5-((3-bromo-5-(methylsulfonyl)phenyl)sulfonyl)thiophen-2-yl)methyl)carbamate (170 mg, 0.333 mmol), Pd(PPh$_3$)$_4$ (38.5 mg, 10%), CuI (12.7 mg, 20%), trimethylsilylacetylene (70.6 μL, 0.500 mmol), Et$_3$N (0.5 mL) and 1,4-dioxane (0.5 mL) was degassed with argon and then stirred at rt for 16 h. The solvent was removed under reduced pressure and the crude was purified by chromatography (EtOAc/cyclohexane 0→60%) to afford tert-butyl ((5-((3-(methylsulfonyl)-5-((trimethylsilyl)ethynyl)phenyl)sulfonyl)thiophen-2-yl)methyl)carbamate as a brown oil (121 mg, 69%).

A mixture of tert-butyl ((5-((3-(methylsulfonyl)-5-((trimethylsilyl)ethynyl)phenyl)sulfonyl)thiophen-2-yl)methyl)carbamate (121 mg, 0.230 mmol) in DCM (1.0 mL) and 4 M HCl in dioxane (1.0 mL) was stirred at rt for 16 h. Cyclohexane (20 mL) was added to precipitate the solid product. The mixture was filtered, the solid was washed with EtOAC and dried under vacuum to afford the title compound, which did not require further purification (white powder; 80 mg, 75%). $^1$H NMR (500 MHz, MeOD) δ 8.42 (H, 1H), 8.29-8.21 (m, 2H), 7.88 (d, J=3.7 Hz, 1H), 7.33 (d, J=3.8 Hz, 1H), 4.39 (s, 2H), 3.21 (s, 3H), 0.28 (s, 9H). $^{13}$C NMR (126 MHz, MeOD) δ 146.34, 145.18, 144.58, 143.96, 136.34, 136.15, 135.52, 131.87, 127.82, 126.41, 101.83, 54.75, 43.85, 38.40. HRMS (ESI) for C$_{17}$H$_{22}$NO$_4$S$_3$Si ([M+H]$^+$): Calculated 428.0475; Observed 428.0477.

Example 76: (5-((4'-Methyl-5-(methylsulfonyl)-[1,1'-biphenyl]-3-yl)sulfonyl)thiophen-2-yl)methanamine

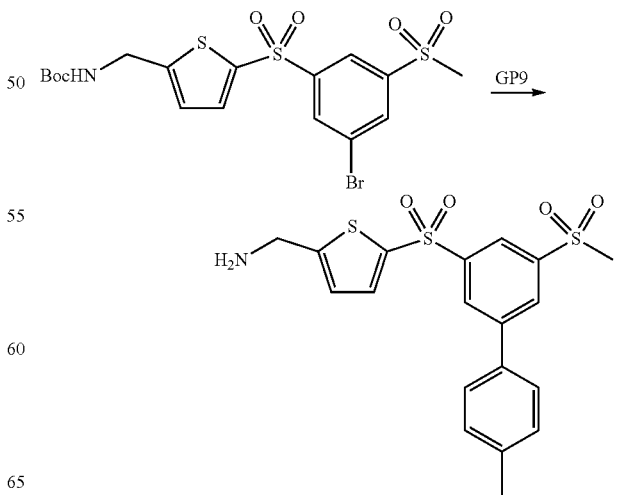

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), p-tolylboronic acid (32.0 mg, 0.235 mmol), Cs$_2$CO$_3$ (76.7 mg, 0.235 mmol) and 1,4-dioxane (1.3 mL); 90° C., 16 h. Chromatography (EtOAc/cyclohexane 0→60), 108 mg, quant., yellow oil. ii) 4 M HCl in dioxane (1.0 mL) and 1,4-dioxane (1.0 mL); rt, 3 h. The amine hydrochloride product was basified with 2N NH$_3$ in MeOH and purified by chromatography (acetone/DCM 0→40%) to afford a light yellow foam (20 mg, 24%). $^1$H NMR (500 MHz, CDCl$_3$) δ 8.45-8.39 (m, 2H), 8.30 (t, J=1.6 Hz, 1H), 7.67 (d, J=3.9 Hz, 1H), 7.54 (d, J=8.2 Hz, 2H), 7.33 (d, J=8.0 Hz, 2H), 6.93 (d, J=3.9 Hz, 1H), 4.09 (s, 2H), 3.14 (s, 3H), 2.44 (s, 3H), 1.61 (s, 2H). $^{13}$C NMR (126 MHz, CDCl$_3$) δ 144.95, 144.56, 142.77, 139.79, 138.73, 134.92, 134.43, 130.27, 130.15, 129.73, 127.25, 124.34, 124.16, 44.59, 41.71, 21.36. HRMS (ESI) for C$_{19}$H$_{20}$NO$_4$S$_3$ ([M+H]$^+$): Calculated 422.0549; Observed 422.0551.

Example 77: (5-((3-(1-Methyl-1H-pyrazol-4-yl)-5-(methylsulfonyl)phenyl)sulfonyl)thiophen-2-yl)methanamine

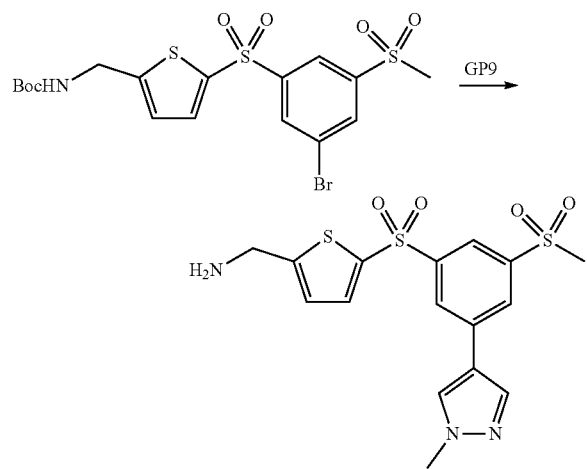

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), (1-methyl-1H-pyrazol-4-yl)boronic acid pinacol ester (48.9 mg, 0.235 mmol), Cs$_2$CO$_3$ (76.7 mg, 0.235 mmol) and 1,4-dioxane (1.3 mL); 90° C., 16 h. Chromatography (EtOAc/DCM 0→100%), light yellow gum; ii) 4M HCl in dioxane (1.0 mL) and DCM (1.0 mL); rt, 3 h. The reaction mixture was centrifuged for 10 min at 3000 RPM and the supernatant liquid was decanted. The amine hydrochloride salt was basified with 2N NH$_3$ in MeOH, and purified by chromatography (MeOH/DCM 0→25%) to afford the title compound as a light yellow solid (57 mg, 71% over 2 steps). $^1$H NMR (500 MHz, Methanol-d$_4$/Chloroform-d) δ 8.29 (t, J=1.7 Hz, 1H), 8.27-8.22 (m, 2H), 8.07 (s, 1H), 7.91 (s, 1H), 7.69 (d, J=3.9 Hz, 1H), 7.04 (d, J=3.7 Hz, 1H), 4.04 (s, 2H), 3.95 (s, 3H), 3.18 (s, 3H). $^{13}$C NMR (126 MHz, Methanol-d$_4$/Chloroform-d) δ 157.51, 145.17, 143.55, 139.75, 137.56, 137.06, 135.61, 129.87, 128.63, 128.57, 126.43, 123.50, 120.52, 44.25, 41.01, 39.31. HRMS (ESI) for C$_{16}$H$_{18}$N$_3$O$_4$S$_3$ ([M+H]$^+$): Calculated 412.0454; Observed 412.0444.

Example 78: (5-((4'-Fluoro-5-(methylsulfonyl)-[1,1'-biphenyl]-3-yl)sulfonyl)thiophen-2-yl)methanamine

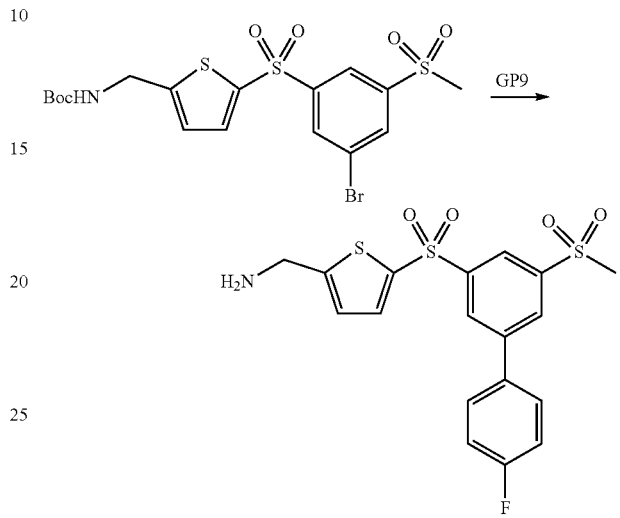

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh$_3$)$_4$ (22.6 mg, 10%), 4-fluorophenylboronic acid (32.9 mg, 0.235 mmol), Cs$_2$CO$_3$ (76.7 mg, 0.235 mmol) and 1,4-dioxane (1.3 mL); 90° C., 16 h. Chromatography (EtOAc/cyclohexane 0→60%), light brown gum; ii) 4M HCl in dioxane (1.0 mL) and DCM (1.0 mL); rt, 3 h. The reaction mixture was centrifuged for 10 min at 3000 RPM and the supernatant liquid was decanted. The amine hydrochloride salt was basified with 2N NH$_3$ in MeOH, and purified by chromatography (EtOH/Cyclohexane 0→100%) to afford the title compound as a light yellow solid (68 mg, 82% over 2 steps). $^1$H NMR (500 MHz, DMSO-d$_6$) δ 8.50 (dt, J=6.4, 1.7 Hz, 2H), 8.37 (t, J=1.6 Hz, 1H), 8.07 (d, J=3.9 Hz, 1H), 7.99-7.89 (m, 2H), 7.47-7.37 (m, 3H), 4.28 (s, 2H), 3.45 (s, 3H). $^{13}$C NMR (126 MHz, DMSO) δ 162.95 (d, J=248 Hz), 146.40, 143.35, 143.29, 142.59, 140.78, 135.35, 130.87, 130.46, 129.94, 129.87, 129.25, 123.48, 116.23 (d, J=21.4 Hz), 43.03, 36.67. HRMS (ESI) for C$_{18}$H$_{17}$FNO$_4$S$_3$ ([M+H]$^+$): Calculated 426.0298; Observed 426.0289.

Example 79: (5-((3-(Methylsulfonyl)-5-(thiophen-3-yl)phenyl)sulfonyl)thiophen-2-yl)methanamine

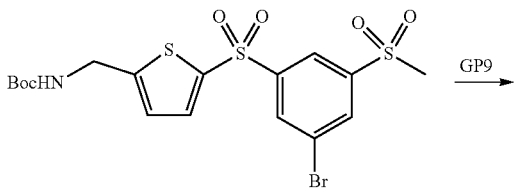

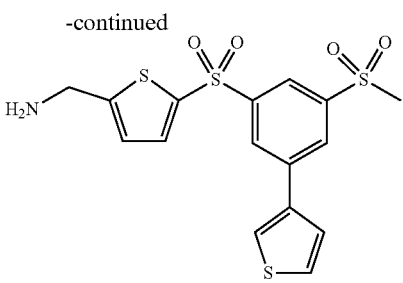

The title compound was synthesised according to general procedures GP9—from i) tert-butyl ((5-((3-bromo-5-(methylsulfonyl)phenyl)sulfonyl)thiophen-2-yl)methyl)carbamate (100 mg, 0.196 mmol), Pd(PPh₃)₄ (22.6 mg, 10%), thiophen-3-ylboronic acid (30.1 mg, 0.235 mmol), Cs₂CO₃ (76.7 mg, 0.235 mmol) and 1,4-dioxane (1.3 mL); 90° C., 16 h. Chromatography (EtOAc/cyclohexane 0→50%), light brown gum; ii) 4M HCl in dioxane (1.0 mL) and DCM (1.0 mL); rt, 3 h. The reaction mixture was centrifuged for 10 min at 3000 RPM and the supernatant liquid was decanted. The amine hydrochloride salt was basified with 2N NH₃ in MeOH, and purified by chromatography (EtOH/Cyclohexane 0→100%) to afford the title compound as a white solid (54 mg, 67% over 2 steps). ¹H NMR (500 MHz, DMSO-d₆) δ 8.53 (dt, J=5.5, 1.7 Hz, 2H), 8.37 (dd, J=2.9, 1.5 Hz, 1H), 8.25 (t, J=1.6 Hz, 1H), 8.01 (d, J=3.9 Hz, 1H), 7.79 (dd, J=5.1, 1.5 Hz, 1H), 7.76 (dd, J=5.1, 2.8 Hz, 1H), 7.33 (d, J=3.9 Hz, 1H), 4.14 (s, 2H), 3.43 (s, 3H). ¹³C NMR (126 MHz, DMSO) δ 143.61, 143.30, 138.41, 137.85, 135.44, 129.30, 128.61, 128.28, 126.41, 125.17, 122.67, 42.98, 38.07. HRMS (ESI) for C₁₆H₁₆NO₄S₄ ([M+H]⁺): Calculated 413.9957; Observed 413.9934.

Example 80: (5-((6-[Methylsulfonyl)-[1,1'-biphenyl]-3-yl)sulfonyl)thiophen-2-yl)methanamine

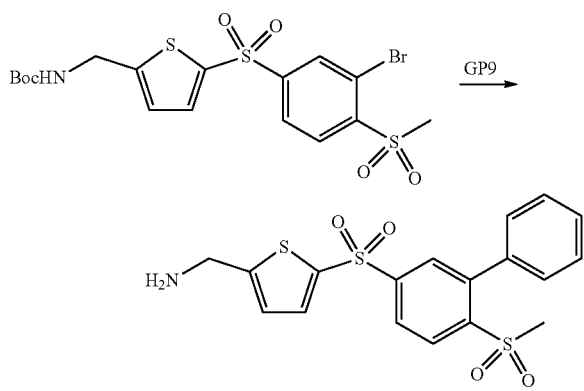

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh₃)₄ (34.0 mg, 10%), phenylboronic acid (43.1 mg, 0.353 mmol), Cs₂CO₃ (115 mg, 0.353 mmol) and 1,4-dioxane (2.0 mL); 90° C., 16 h. Chromatography (EtOAc/DCM 0→100%), white foam, 169 mg; ii) 4M HCl in dioxane (1.0 mL) and DCM (1.0 mL); rt, 3 h. The reaction mixture was centrifuged for 10 min at 3000 RPM and the supernatant liquid was decanted. The amine hydrochloride salt was treated with 7N NH₃ in MeOH. The solvent was removed under reduced pressure and the crude was purified by chromatography (EtOH/cyclohexane 0→100%) to afford the title compound as a white solid (66 mg, 55% over 2 steps). ¹H NMR (500 MHz, Chloroform-d) δ 8.37 (d, J=8.3 Hz, 1H), 8.11 (dd, J=8.3, 1.9 Hz, 1H), 7.97 (d, J=2.0 Hz, 1H), 7.63 (d, J=3.9 Hz, 1H), 7.55-7.41 (m, 5H), 6.93 (d, J=3.8 Hz, 1H), 4.10 (s, 2H), 2.61 (s, 3H), 1.63 (s, 2H). ¹³C NMR (126 MHz, Chloroform-d) δ 160.04, 146.65, 143.39, 142.92, 138.54, 136.79, 134.97, 131.05, 130.11, 129.70, 129.38, 128.43, 126.64, 124.12, 43.13, 41.67. HRMS (ESI) for C₁₈H₁₈NO₄S₃ ([M+H]⁺): Calculated 408.0392; Observed 408.0373.

tert-Butyl ((5-((3-bromo-4-(methylsulfonyl)phenyl)sulfonyl)thiophen-2-yl)methyl)carbamate

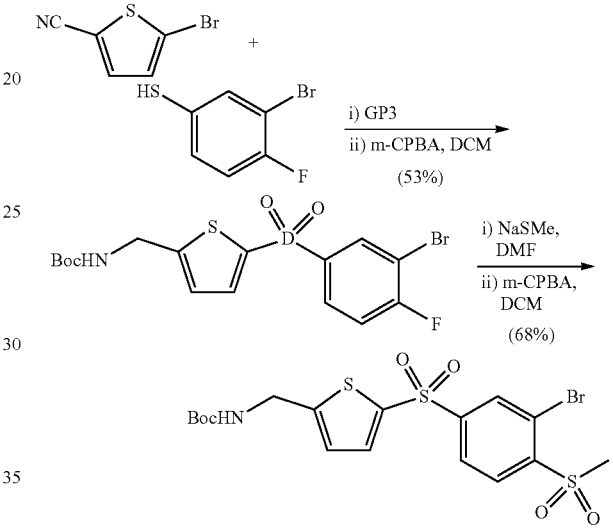

tert-Butyl ((5-((3-bromo-4-fluorophenyl)thio)thiophen-2-yl)methyl)carbamate was synthesised according to general procedures GP3—from i) 5-bromothiophene-2-carbonitrile (0.544 g, 2.90 mmol), 3-bromo-4-fluorobenzenethiol (0.5 g, 2.42 mmol), K₂CO₃ (0.394 g, 2.90 mmol) and DMF (8.0 mL); 90° C., 16 h. Chromatography (EtOAc/cyclohexane 0→20%), orange oil, 960 mg. ii) BH₃ (1.0 M in THF; 6.1 mL, 6.1 mmol), THF (6.1 mL); rt, 1 h. iii) Boc₂O (1.05 mL, 4.59 mmol), Et₃N (1.28 mL, 9.17 mmol), DCM (10.2 mL); rt, 16 h. Used immediately in the subsequent transformation.

m-CPBA (77%; 1.68 g, 7.49 mmol) was added in small portions to a solution of crude tert-butyl ((5-((3-bromo-4-fluorophenyl)thio)thiophen-2-yl)methyl)carbamate in DCM (20 mL). The mixture was stirred at rt for 16 h and then diluted with EtOAc (60 mL). The organic phase was washed with sat. NaHCO₃ (3×50 mL), dried over MgSO₄, filtered and the solvent was removed under reduced pressure. The crude was purified by chromatography (EtOAc/cyclohexane 0→60%) to afford tert-butyl ((5-((3-bromo-4-fluorophenyl)sulfonyl)thiophen-2-yl)methyl)carbamate as a yellow solid (658 mg, 53% over 4 steps). ¹H NMR (500 MHz, Chloroform-d) δ 8.18 (dd, J=6.2, 2.3 Hz, 1H), 7.92 (ddd, J=8.6, 4.4, 2.3 Hz, 1H), 7.57 (d, J=3.8 Hz, 1H), 7.25 (dd, J=8.7, 7.9 Hz, 1H), 6.94 (d, J=3.8 Hz, 1H), 5.03 (br, 1H), 4.47 (br, 2H), 1.46 (s, 9H).

NaSMe (111 mg, 1.59 mmol) was added to a solution of tert-butyl ((5-((3-bromo-4-fluorophenyl)sulfonyl)thiophen-2-yl)methyl)carbamate (650 mg, 1.44 mmol) in DMF (7.2 mL) and the mixture was stirred at rt for 16 h. After dilution with EtOAc (30 mL), the solution was washed with H$_2$O (3×30 mL) and brine (30 mL), dried over MgSO$_4$, filtered and the solvent was removed under reduced pressure. The crude sulfide was dissolved in DCM (9.6 m). m-CPBA (77%; 745 mg, 3.32 mmol) was added in small portions. The mixture was stirred at rt for 16 h and then diluted with EtOAc (30 mL). The organic phase was washed with sat. NaHCO$_3$ (3×30 mL), dried over MgSO$_4$, filtered and the solvent was removed under reduced pressure. The crude was purified by chromatography (EtOAc/cyclohexane 0→80%) to afford tert-butyl ((5-((3-bromo-4-(methylsulfonyl)phenyl)sulfonyl)thiophen-2-yl)methyl)carbamate as a white foam (461 mg, 68% over 2 steps). $^1$H NMR (500 MHz, Chloroform-d) δ 8.38-8.28 (m, 2H), 8.07 (dd, J=8.3, 1.8 Hz, 1H), 7.63 (d, J=3.9 Hz, 1H), 6.98 (dt, J=4.0, 1.0 Hz, 1H), 5.06 (br, 1H), 4.49 (d, J=6.0 Hz, 2H), 3.31 (s, 3H), 1.46 (s, 9H).

Example 81: (5-((3-(1-Methyl-1H-pyrazol-4-yl)-4-(methylsulfonyl)phenyl)sulfonyl)thiophen-2-yl)methanamine dihydrochloride

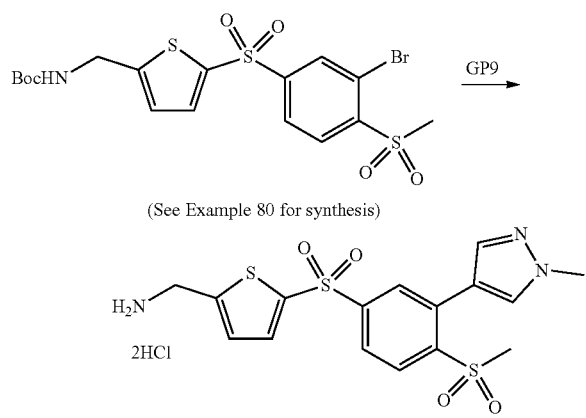

(See Example 80 for synthesis)

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh$_3$)$_4$ (34.0 mg, 10%), (1-methyl-1H-pyrazol-4-yl)boronic acid pinacol ester (73.0 mg, 0.353 mmol), Cs$_2$CO$_3$ (115 mg, 0.353 mmol) and 1,4-dioxane (2.0 mL); 90° C., 16 h. Chromatography (EtOAc/DCM 0→100%), white foam, 169 mg; ii) 4M HCl in dioxane (1.5 mL) and DCM (1.5 mL); rt, 3 h. The reaction mixture was centrifuged for 10 min at 3000 RPM and the supernatant liquid was decanted. The amine hydrochloride salt was washed with more EtOAc and dried under vacuum to afford the title compound as a white solid (111 mg, 92% over 2 steps). $^1$H NMR (500 MHz, D$_2$O) δ 8.32 (d, J=8.5 Hz, 1H), 8.16 (dd, J=8.6, 2.2 Hz, 1H), 8.05 (d, J=1.9 Hz, 1H), 7.92 (s, 1H), 7.84 (d, J=4.0 Hz, 1H), 7.74 (s, 1H), 7.33 (d, J=4.0 Hz, 1H), 4.44 (s, 2H), 3.96 (s, 3H), 2.96 (s, 3H). $^{13}$C NMR (126 MHz, D$_2$O) δ 144.87, 144.70, 142.07, 140.32, 139.70, 135.77, 134.00, 132.82, 131.38, 130.83, 130.08, 126.31, 116.55, 41.49, 38.31, 37.18. HRMS (ESI) for C$_{16}$H$_{18}$N$_3$O$_4$S$_3$ ([M+H]$^+$): Calculated 412.0454; Observed 412.0441.

Example 82: (5-((4'-Methyl-6-(methylsulfonyl)-[1,1'-biphenyl]-3-yl)sulfonyl)thiophen-2-yl)methanamine hydrochloride

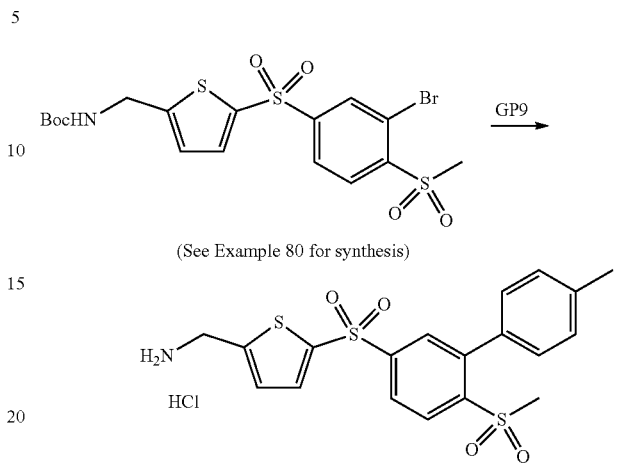

(See Example 80 for synthesis)

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh$_3$)$_4$ (34.0 mg, 10%), p-tolyl boronic acid (48.0 mg, 0.353 mmol), Cs$_2$CO$_3$ (115 mg, 0.353 mmol) and 1,4-dioxane (2.0 mL); 90° C., 16 h. Chromatography (EtOAc/cyclohexane 0→65%), white foam, 116 mg; ii) 4M HCl in dioxane (1.5 mL) and DCM (1.5 mL); rt, 3 h. The reaction mixture was centrifuged for 10 min at 3000 RPM and the supernatant liquid was decanted. The solids were dried under vacuum to afford the title compound as a beige solid (83 mg, 62% over 2 steps). $^1$H NMR (500 MHz, Methanol-d$_4$) δ 8.37 (d, J=8.4 Hz, 1H), 8.22 (dd, J=8.4, 2.0 Hz, 1H), 7.91 (d, J=2.0 Hz, 1H), 7.83 (d, J=3.9 Hz, 1H), 7.36-7.30 (m, 5H), 4.40 (s, 2H), 2.70 (s, 3H), 2.43 (s, 3H). $^{13}$C NMR (126 MHz, Methanol-d$_4$) δ 147.19, 146.22, 145.42, 144.67, 144.26, 140.58, 136.19, 135.38, 132.20, 131.88, 131.02, 130.91, 129.93, 127.80, 43.41, 38.43, 21.31. HRMS (ESI) for C$_{19}$H$_{20}$NO$_4$S$_3$ ([M+H]$^+$): Calculated 422.0549; Observed 422.0529.

Example 83: (5-((2'-Methyl-6-(methylsulfonyl)-[1,1'-biphenyl]-3-yl)sulfonyl)thiophen-2-yl)methanamine hydrochloride

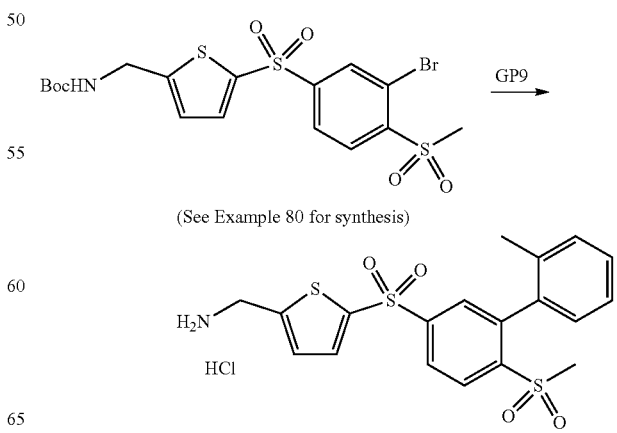

(See Example 80 for synthesis)

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh$_3$)$_4$ (34.0 mg, 10%), o-tolyl boronic acid (48.0 mg, 0.353 mmol), Cs$_2$CO$_3$ (115 mg, 0.353 mmol) and 1,4-dioxane (2.0 mL); 90° C., 16 h. Chromatography (EtOAc/cyclohexane 0→65%), beige solid, 118 mg; ii) 4M HCl in dioxane (1.5 mL) and DCM (1.5 mL); rt, 3 h. The reaction mixture was centrifuged for 10 min at 3000 RPM and the supernatant liquid was decanted. The solids were dried under vacuum to afford the title compound as a beige solid (78 mg, 58% over 2 steps). $^1$H NMR (500 MHz, Deuterium Oxide) δ 8.36 (d, J=8.5 Hz, 1H), 8.26 (m, 1H), 7.94 (s, 1H), 7.80 (d, J=3.8 Hz, 1H), 7.42 (t, J=7.5 Hz, 1H), 7.40-7.30 (m, 2H), 7.27 (t, J=7.5 Hz, 1H), 7.13 (d, J=7.4 Hz, 1H), 4.43 (s, 2H), 2.98 (s, 3H), 1.92 (s, 3H). $^{13}$C NMR (126 MHz, D$_2$O) δ 144.90, 144.82, 142.64, 142.21, 140.40, 136.71, 135.84, 135.76, 130.87, 130.67, 130.51, 130.13, 129.46, 129.25, 127.10, 125.28, 43.25, 37.17, 19.44. $^{13}$C NMR (126 MHz, D$_2$O) δ 144.90, 144.82, 142.64, 142.21, 140.40, 136.71, 135.84, 135.76, 130.87, 130.67, 130.51, 130.13, 129.46, 129.25, 127.10, 125.28, 43.25, 37.17, 19.44. HRMS (ESI) for C$_{19}$H$_{20}$NO$_4$S$_3$ ([M+H]$^+$): Calculated 422.0549; Observed 422.0519.

Example 84: (5-((4'-Fluoro-6-(methylsulfonyl)-[1,1'-biphenyl]-3-yl)sulfonyl)thiophen-2-yl)methanamine hydrochloride

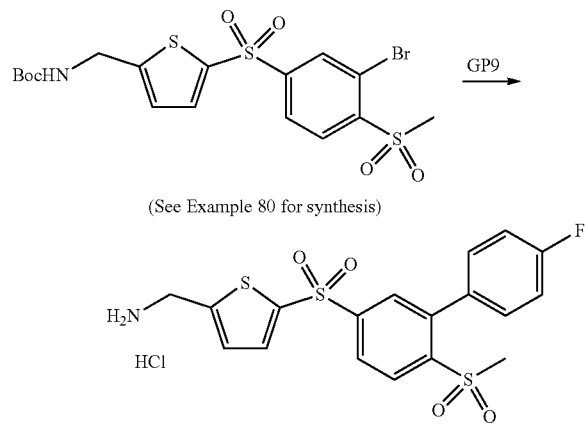

(See Example 80 for synthesis)

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh$_3$)$_4$ (34.0 mg, 10%), 4-fluorophenylboronic acid (49.4 mg, 0.353 mmol), Cs$_2$CO$_3$ (115 mg, 0.353 mmol) and 1,4-dioxane (2.0 mL); 90° C., 16 h. Chromatography (EtOAc/cyclohexane 0→65%), white foam, 110 mg; ii) 4M HCl in dioxane (1.5 mL) and DCM (1.5 mL); rt, 3 h. The reaction mixture was centrifuged for 10 min at 3000 RPM and the supernatant liquid was decanted. The solids were dried under vacuum to afford the title compound as a beige solid (85 mg, 63% over 2 steps). $^1$H NMR (500 MHz, Methanol-d$_4$) δ 8.38 (d, J=8.4 Hz, 1H), 8.25 (dd, J=8.4, 2.0 Hz, 1H), 7.95 (d, J=2.0 Hz, 1H), 7.84 (d, J=3.9 Hz, 1H), 7.51-7.45 (m, 2H), 7.35 (m, 1H), 7.27-7.19 (m, 2H), 4.40 (d, J=0.8 Hz, 2H), 2.77 (s, 3H). $^{13}$C NMR (126 MHz, MeOD) δ 164.62 (d, J=248.5 Hz), 147.31, 146.28, 145.41, 144.17, 143.63, 136.27, 134.40 (d, J=3.4 Hz), 134.39, 133.30 (d, J=8.5 Hz), 133.28, 132.26, 131.90, 131.24, 128.26, 116.23, 116.14 (d, J=22.1 Hz), 43.74, 38.43.

Example 85: (5-((3'-Methyl-6-(methylsulfonyl)-[1,1'-biphenyl]-3-yl)sulfonyl)thiophen-2-yl)methanamine hydrochloride

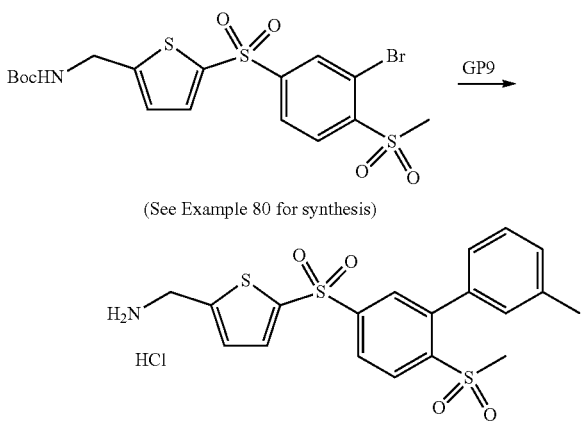

(See Example 80 for synthesis)

The title compound was synthesised according to general procedures GP9—from i) tert-butyl ((5-((3-bromo-4-(methylsulfonyl)phenyl)sulfonyl)thiophen-2-yl)methyl)carbamate (150 mg, 0.294 mmol), Pd(PPh$_3$)$_4$ (34.0 mg, 10%), m-tolyl boronic acid (48.0 mg, 0.353 mmol), Cs$_2$CO$_3$ (115 mg, 0.353 mmol) and 1,4-dioxane (2.0 mL); 90° C., 16 h. Chromatography (EtOAc/cyclohexane 0→65%), light brown gum, 27 mg; ii) 4M HCl in dioxane (1.5 mL) and DCM (1.5 mL); rt, 3 h. The reaction mixture was centrifuged for 10 min at 3000 RPM and the supernatant liquid was decanted. The solids were dried under vacuum to afford the title compound as a beige solid (18 mg, 13% over 2 steps). $^1$H NMR (500 MHz, Methanol-d$_4$/Chloroform-d) δ 8.35 (d, J=8.3 Hz, 1H), 8.13 (dd, J=8.4, 1.9 Hz, 1H), 7.93 (d, J=1.7 Hz, 1H), 7.71 (d, J=3.2 Hz, 1H), 7.39-7.28 (m, 3H), 7.26-7.19 (m, 2H), 4.31 (s, 2H), 2.66 (s, 3H), 2.40 (s, 3H). $^{13}$C NMR (126 MHz, Methanol-d$_4$/Chloroform-d) δ 146.19, 144.93, 144.26, 143.91, 143.10, 138.75, 137.03, 135.44, 131.54, 131.31, 131.01, 130.57, 130.21, 128.72, 127.44, 127.18, 43.41, 37.99, 21.51. HRMS (ESI) for C$_{19}$H$_{20}$NO$_4$S$_3$ ([M+H]$^+$): Calculated 422.0549; Observed 422.0543.

Non 5-Sulfonyl-AMT Compounds

Example 86: (5-(Phenylsulfinyl)thiophen-2-yl)methanamine

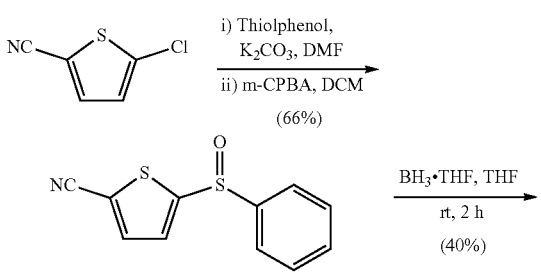

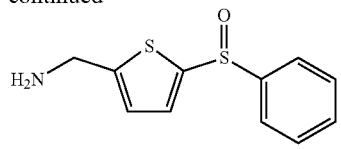

A mixture of 5-chlorothiophene-2-carbonitrile (95 µL, 0.901 mmol), K₂CO₃ (250 mg, 1.80 mmol) and thiophenol (102 µL, 0.991 mmol) in DMF (3.0 mL) was stirred at 120° C. for 16 h. After cooling to rt, EtOAc (15 mL) was added. The organic phase was washed with 1:1 H₂O/brine (3×15 mL), dried over MgSO₄ and filtered. The solvent was removed under reduced pressure and the crude was purified by chromatography (EtOAc/cyclohexane 0→15%) to afford 5-(phenylthio)thiophene-2-carbonitrile as a yellow oil (150 mg, 77%). m-CPBA (77%; 143 mg, 0.636 mmol) was added in small portions to a solution of 5-(phenylthio)thiophene-2-carbonitrile (138 mg, 0.636 mmol) in DCM (3 mL) and the mixture was stirred at rt for 16 h. DCM (10 mL) was added. The organic phase was washed with 1 M NaOH (10 mL), dried over MgSO₄ and filtered. The solvent was removed under reduced pressure and the crude was purified by chromatography (EtOAc/cyclohexane 0→20%) to afford 5-(phenylsulfinyl)thiophene-2-carbonitrile as a colourless oil (127 mg, 86%). ¹H NMR (500 MHz, CDCl₃) δ 7.76-7.70 (m, 2H), 7.60-7.50 (m, 4H), 7.44 (d, J=4.0 Hz, 1H).

A mixture of BH₃.THF (1.0M in THF; 1.70 mL, 1.70 mmol), 5-(phenylsulfinyl)thiophene-2-carbonitrile (132 mg, 0.568 mmol) and THF (2.8 mL) was stirred at rt for 2 h. MeOH was carefully added to quench the reaction. The solvent was removed under reduced pressure and the crude was purified by chromatography (MeOH/DCM 0→20%) to afford the title compound as a yellow oil (53 mg, 40%). ¹H NMR (500 MHz, CDCl₃) δ 7.72-7.65 (m, 2H), 7.54-7.43 (m, 4H), 6.86 (m, 1H), 4.00 (s, 2H), 1.80 (s, 2H). ¹³C NMR (126 MHz, CDCl₃) δ 156.03, 145.85, 145.18, 132.03, 131.13, 129.26, 124.42, 123.46, 41.74. HRMS (ESI) for C₁₁H₁₂NOS₂ ([M+H]⁺): Calculated 238.0355; Observed 238.0378.

Example 87: (2-(naphthalen-2-ylthio)thiazol-5-yl)methanamine hydrochloride

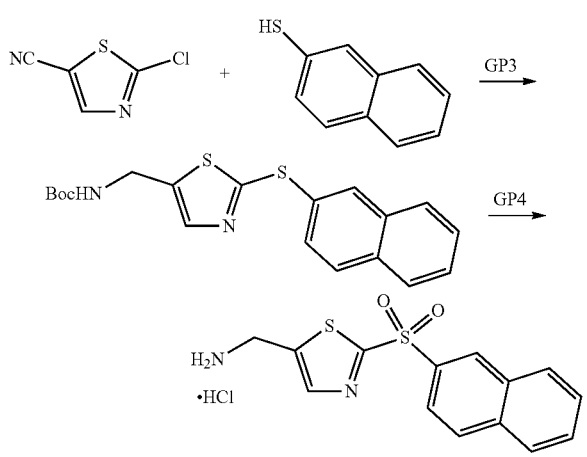

tert-Butyl ((2-(naphthalen-2-ylthio)thiazol-5-yl)methyl)carbamate was synthesised according to general procedures GP3—from i) 2-chlorothiazole-5-carbonitrile (580 mg, 4 mmol), 2-thionaphthol (640 mg, 4 mmol), K₂CO₃ (800 mg, 5.8 mmol) and DMF (10 mL); 60° C., 24 h. Chromatography (DCM/cyclohexane 0→100%) 400 mg, 37%. ii) 2-(naphthalen-2-ylthio)thiazole-5-carbonitrile (400 mg, 1.5 mmol), BH₃ (1.0 M in THF; 5 mL, 5 mmol), THF (20 mL); rt, 18 h. Chromatography (EtOAc/DCM 0→100%) 120 mg, 26% iii) (2-(naphthalen-2-ylthio)thiazol-5-yl)methanamine (120 mg, 0.4 mmol), Boc₂O (109 mg, 0.5 mmol), Et₃N (70 µL, 0.5 mmol), THF (5 mL); rt, 18 h. Chromatography (EtOAc/DCM 0→50%) to afford tert-butyl ((2-(naphthalen-2-ylthio)thiazol-5-yl)methyl)carbamate (110 mg, 74%). 1H NMR (500 MHz, DMSO-d₆) δ 8.79 (d, J=1.9 Hz, 1H), 8.29 (d, J=8.2 Hz, 1H), 8.20 (d, J=8.7 Hz, 1H), 8.09 (d, J=8.1 Hz, 1H), 7.95 (dd, J=8.6, 2.0 Hz, 1H), 7.91 (s, 1H), 7.82-7.75 (m, 1H), 7.72 (ddd, J=8.0, 6.9, 1.3 Hz, 1H), 7.65 (t, J=6.1 Hz, 1H), 4.36 (d, J=6.0 Hz, 2H), 1.38 (s, 9H).

The title compound was synthesised according to general procedures GP4—from i) tert-butyl ((2-(naphthalen-2-ylthio)thiazol-5-yl)methyl)carbamate (110 mg, 0.3 mmol), m-CPBA (77%; 340 mg, 1.2 mmol), DCM (5.0 mL); room temperature, 3 h; 105 mg (87%). ii) tert-butyl ((2-(naphthalen-2-ylsulfonyl)thiazol-5-yl)methyl)carbamate (105 mg, 0.26 mmol), 4 M HCl in dioxane (2.0 mL), dioxane (5 mL); rt, 16 h. The white precipitate was filtered, washed with excess dioxane and dried under vacuum to afford the desired amine hydrochloride as a white solid (33 mg, 42%). ¹H NMR (500 MHz, DMSO-d6) δ 8.82 (d, J=2.0 Hz, 1H), 8.49 (s, 3H), 8.31 (d, J=8.2 Hz, 1H), 8.23 (d, J=8.7 Hz, 1H), 8.15 (s, 1H), 8.10 (d, J=8.1 Hz, 1H), 7.97 (dd, J=8.6, 2.1 Hz, 1H), 7.84-7.77 (m, 1H), 7.77-7.71 (m, 1H), 4.39 (s, 2H). HRMS calcd for C₁₄H₁₃N₂O₂S₂ [M+H]⁺ 305.0413; found 305.0471.

Example 88: (5-(4-(Methylsulfonyl)phenylsulfonyl)thiazol-2-yl)methanamine hydrochloride

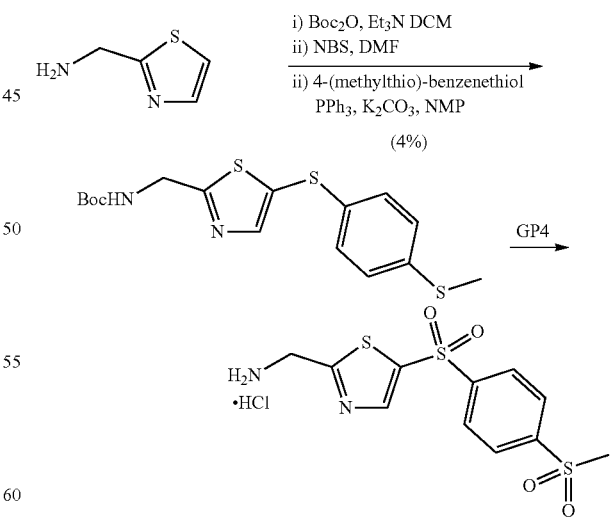

Boc₂O (2.86 g, 13.3 mmol) was added to a solution of thiazol-2-ylmethanamine (1.0 g, 8.76 mmol) and Et₃N (1.22 mL, 8.76 mmol) in DCM (50 mL). The mixture was stirred at rt for 3 h and then washed with sat. NH₄Cl. The organic phase was dried over MgSO₄, filtered and the solvent was removed under reduced pressure. The crude was purified by chromatography (EtOAc/cyclohexane 0→30%) to afford tert-butyl (thiazol-2-ylmethyl)carbamate as a yellow oil (1.9 g, quant.). ¹H NMR (500 MHz, CDCl₃) δ 7.58 (s, 1H), 5.40 (br. s., 1H), 4.55 (br. s., 2H), 1.47 (s, 9H).

A mixture of tert-butyl (thiazol-2-ylmethyl)carbamate (1.9 g, 8.88 mmol), NBS (2.05 g, 11.5 mmol) and DMF (10 mL) was stirred at 50° C. for 3 h. After cooling to rt, sat. NH₄Cl was added. The aqueous solution was extracted with EtOAc (3×). The combined organic phase was dried over MgSO₄ and filtered. The solvent was removed under reduced pressure and the crude was purified by chromatography (EtOAc/cyclohexane 0→20%) to afford tert-butyl ((5-bromothiazol-2-yl)methyl)carbamate (1.31 g, 50%). This was dissolved in NMP (6.0 mL), followed by the addition of $K_2CO_3$ (619 mg, 4.49 mmol), PPh₃ (235 mg, 0.896 mmol) and 4-(methylthio)benzenethiol (700 mg, 4.48 mmol). The mixture was stirred at 110° C. for 3 h. After cooling to rt, H₂O was added. The aqueous solution was extracted with EtOAc (3×). The combined organic phase was washed with sat. NaHCO₃ and brine, dried over MgSO₄ and filtered. The solvent was removed under reduced pressure and the crude was purified by chromatography (EtOAc/cyclohexane 0→40%) to afford tert-butyl ((5-((4-(methylthio)phenyl)thio)thiazol-2-yl)methyl)carbamate (132 mg, 8%). ¹H NMR (500 MHz, CDCl₃) δ 7.74 (s, 1H), 7.18-7.24 (m, 2H), 7.13-7.18 (m, 2H), 5.42 (br. s., 1H), 4.58 (d, J=4.7 Hz, 2H), 2.45 (s, 3H), 1.45 (s, 9H). ¹³C NMR (126 MHz, CDCl₃) δ 179.5, 168.4, 155.8, 145.6, 144.3, 142.3, 132.6, 128.8, 128.5, 80.5, 44.3, 41.9, 28.2. HRMS calcd for $C_{16}H_{20}N_2O_4S_3$ [M+H]⁺ 401.0658; found 401.0690

The title compound was synthesised according to general procedures GP4—from i) tert-butyl ((5-((4-(methylthio)phenyl)thio)thiazol-2-yl)methyl)carbamate (132 mg, 0.359 mmol), m-CPBA (77%; 314 mg, 1.40 mmol), DCM (10 mL); rt, 12 h; chromatography (EtOAc/cyclohexane 0→40%). ii) 4 M HCl in dioxane (1.0 mL); rt, 16 h. The mixture was centrifugated, the supernatant liquid discarded and the solid was washed with excess Et₂O and dried under vacuum to afford the amine hydrochloride as a white solid (1.35 mg, 1.5% over two steps). ¹H NMR (500 MHz, D₂O) δ 8.47 (s, 1H), 8.27 (d, J=8.5 Hz, 2H), 8.18 (d, J=8.2 Hz, 2H), 4.60 (s, 2H), 3.26 (s, 3H). ¹³C NMR (126 MHz, D₂O) δ 170.1, 162.1, 148.9, 144.6, 144.4, 138.3, 128.9, 128.7, 42.9, 39.8. HRMS calcd for $C_{11}H_{12}N_2O_4S_3$ [M+H]⁺ 333.0032; found 333.0026.

Example 89: (4-(Naphthalen-2-ylsulfonyl)thiophen-2-yl)methanamine

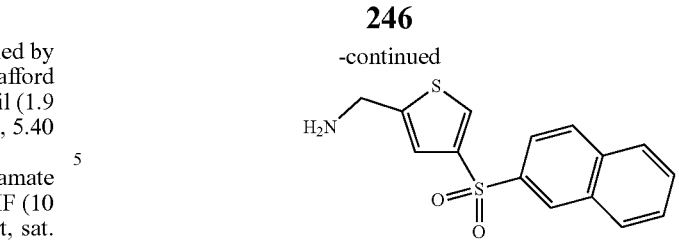

Xantphos (154 mg, 10%) was added to a mixture of 4-bromothiophene-2-carbonitrile (0.5 g, 2.66 mmol), NaO$^t$Bu (306 mg, 3.18 mmol), naphthalene-2-thiol (511 mg, 3.19 mmol), Pd₂dba₃ (244 mg, 10%) and toluene (13.3 mL). The mixture was thoroughly degassed with argon and stirred at 105° C. for 24 h. After cooling to rt, the mixture was filtered through celite and washed with EtOAc (50 mL). The organic phase was washed with 1:1 H₂O/brine (80 mL), dried over MgSO₄, filtered and the solvent was removed under reduced pressure. The crude was purified by chromatography (EtOAc/cyclohexane 0→5%) to afford the intermediate 4-(naphthalen-2-ylthio)thiophene-2-carbonitrile. This was dissolved in DCM (17.7 mL) and m-CPBA (70-75%; 1.90 g, ~7.98 mmol) was added portionwise. The mixture was allowed to stir at rt for 2 h. EtOAc (40 mL) was added and the organic phase was washed with sat NaHCO₃ (3×40 mL), dried over MgSO₄, filtered and the solvent was removed under reduced pressure. The crude was purified by chromatography (EtOAc/cyclohexane 0→70%) to afford 4-(naphthalen-2-ylsulfonyl)thiophene-2-carbonitrile as a white solid (509 mg, 64%).

The title compound was synthesised according to general procedures GP2b—from BH₃ (1.0 M in THF; 5.0 mL, 5.0 mmol), 4-(naphthalen-2-ylsulfonyl)thiophene-2-carbonitrile (501 mg, 1.68 mmol) and THF (5.0 mL); 2 h, rt. The crude was purified by chromatography (EtOH/cyclohexane 5→100%) to afford a light orange solid (256 mg, 51%). ¹H NMR (500 MHz, CDCl₃) δ 8.57 (s, 1H), 8.02 (s, 1H), 8.00-7.91 (m, 2H), 7.90-7.84 (m, 2H), 7.67-7.54 (m, 2H), 7.16 (s, 1H), 3.97 (s, 2H), 1.71 (s, 2H). ¹³C NMR (126 MHz, CDCl₃) δ 151.36, 141.20, 138.42, 135.07, 132.24, 130.33, 129.71, 129.44, 129.20, 128.89, 127.99, 127.70, 122.56, 121.52, 41.27. HRMS (ESI) for $C_{15}H_{14}NO_2S_2$ ([M+H]⁺): Calculated 304.0460; Observed 304.0444.

Example 90: (5-(Naphthalen-2-ylsulfonyl)thiazol-2-yl)methanamine hydrochloride

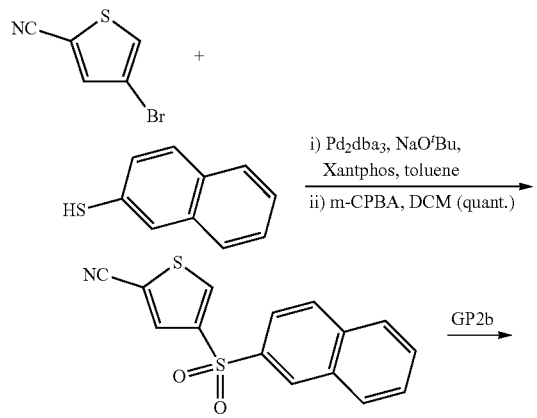

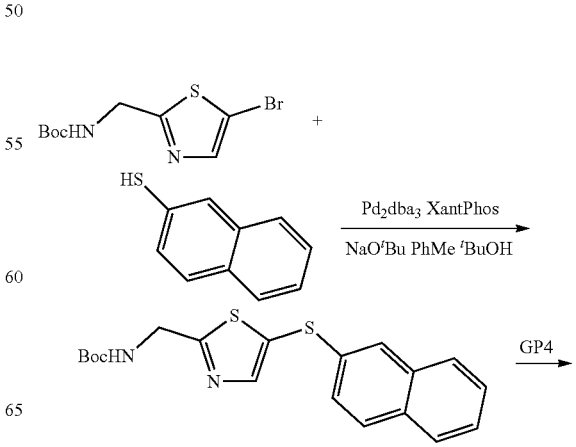

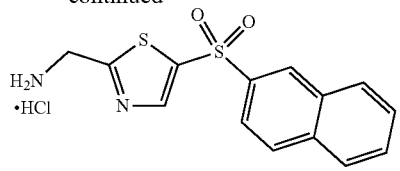

A solution of tert-Butyl ((5-bromothiazol-2-yl)methyl) carbamate (300 mg, 1.02 mmol) and naphthalene-2-thiol (180 mg, 1.13 mmol) in toluene:$^t$BuOH (5:1, 4.2 mL) was degassed with nitrogen for 5 minutes. Pd$_2$dba$_3$ (47 mg, 10 mol % Pd), XantPhos (118 mg, 20 mol %) and sodium tert-butoxide (118 mg, 1.23 mmol) were then added with stirring, and the solution was bubbled with nitrogen for a further 5 minutes before sealing the flask and heating to 110° C., with stirring for 18 hours. The reaction mixture was then diluted with ethyl acetate (20 mL) and washed with water (20 mL) and brine (20 mL), dried over anhydrous magnesium sulfate, filtered and the solvent was removed under reduced pressure. The crude was purified by chromatography (EtOAc/cyclohexane 10→60%) to afford the intermediate tert-butyl ((5-(naphthalen-2-ylthio)thiazol-2-yl)methyl)carbamate.

The title compound was synthesised according to general procedures GP4—from i) tert-butyl ((5-(naphthalen-2-ylthio)thiazol-2-yl)methyl)carbamate (200 mg, 0.537 mmol), m-CPBA (77%; 300 mg, 1.34 mmol), DCM (4 mL); rt, 18 h; chromatography (EtOAc/cyclohexane 0→60%). ii) 4 M HCl in dioxane (1.6 mL); rt, 4 h. The mixture was diluted with Et$_2$O and the precipitate collected using filtration, washing with excess Et$_2$O, and dried under vacuum to afford the amine hydrochloride as a white solid (106 mg, 31% over three steps). $^1$H NMR (DMSO-d$_6$, 500 MHz) δ 8.79 (d, 1H, J=1.8 Hz, ArH), 8.72 (br s, 3H, NH$_3$+), 8.65 (s, 1H, Thiazole-H), 8.27 (d, 1H, J=8.4 Hz, ArH), 8.21 (d, 1H, J=8.8 Hz, ArH), 8.09 (d, 1H, J=8.2 Hz, ArH), 8.00 (dd, 1H, J=8.7, 2.0 Hz, ArH), 7.78 (ddd, 1H, J=8.2, 6.9, 1.3 Hz, ArH), 7.73 (ddd, 1H, J=8.1, 6.9, 1.3 Hz, ArH), 4.46 (s, 2H, CH$_2$) ppm; $^{13}$C NMR (DMSO-d$_6$, 125 MHz) δ 170.3, 147.4, 140.2, 137.6, 134.9, 131.8, 130.4, 130.0, 129.7, 128.8, 128.2, 128.0, 121.8, 39.7 ppm; HRMS (ESI) m/z 305.0402 found (M+H)$^+$, 305.0413 calculated for C$_{14}$H$_{13}$N$_2$S$_2$O$_2$.

Example 91: (5-((4'-Methyl-[1,1'-biphenyl]-3-yl) sulfonyl)thiazol-2-yl)methanamine hydrochloride A solution of tert-Butyl ((5-bromothiazol-2-yl)methyl) carbamate (183 mg, 0.624 mmol) and 4'-methyl-[1,1'-biphenyl]-3-thiol (125 mg, 0.624 mmol) in toluene:$^t$BuOH (5:1, 4.8 mL) was degassed with nitrogen for 5 minutes. Pd$_2$dba$_3$ (29 mg, 10 mol % Pd), XantPhos (72 mg, 20 mol %) and sodium tert-butoxide (72 mg, 0.749 mmol) were then added with stirring, and the solution was bubbled with nitrogen for a further 5 minutes before sealing the flask and heating to 110° C., with stirring for 18 hours. The reaction mixture was then diluted with ethyl acetate (20 mL) and washed with water (20 mL) and brine (20 mL), dried over anhydrous magnesium sulfate, filtered and the solvent was removed under reduced pressure. The crude was purified by chromatography (EtOAc/cyclohexane 10→60%) to afford the intermediate tert-butyl ((5-((4'-methyl-[1,1'-biphenyl]-3-yl)thio) thiazol-2-yl)methyl)carbamate.

The title compound was synthesised according to general procedures GP4—from i) tert-butyl ((5-((4'-methyl-[1,1'-biphenyl]-3-yl)thio)thiazol-2-yl)methyl)carbamate (230 mg, 0.557 mmol), m-CPBA (77%; 312 mg, 1.39 mmol), DCM (6 mL); rt, 18 h; chromatography (EtOAc/cyclohexane 10→70%). ii) 4 M HCl in dioxane (1.7 mL); rt, 4 h. The mixture was diluted with Et$_2$O and the precipitate collected using filtration, washing with excess Et$_2$O, and dried under vacuum to afford the amine hydrochloride as a white solid (104 mg, 53% over three steps). $^1$H NMR (DMSO-d$_6$, 500 MHz) δ 8.82 (br s, 3H, NH$_3$+), 8.69 (s, 1H, Thiazole-H), 8.20 (t, 1H, J=1.7 Hz, ArH), 8.04 (ddd, 1H, J=7.8, 1.7, 1.0 Hz, ArH), 8.00 (ddd, 1H, J=7.9, 1.8, 1.0 Hz, ArH), 7.76 (t, 1H, J=7.9 Hz, ArH), 7.64 (d, 2H, J=8.2 Hz, ArH), 7.33 (d, 2H, J=7.9 Hz, ArH), 4.47 (s, 2H, CH$_2$N), 2.36 (s, 3H, CH$_3$) ppm; $^{13}$C NMR (DMSO-d$_6$, 125 MHz) δ 170.3, 147.7, 141.9, 141.5, 140.0, 138.2, 135.1, 132.4, 130.8, 129.8, 126.9, 125.7, 124.4, 39.7, 20.7 ppm; HRMS (ESI) m/z 345.0724 found (M+H)$^+$, 345.0726 calculated for C$_{17}$H$_{17}$N$_2$S$_2$O$_2$.

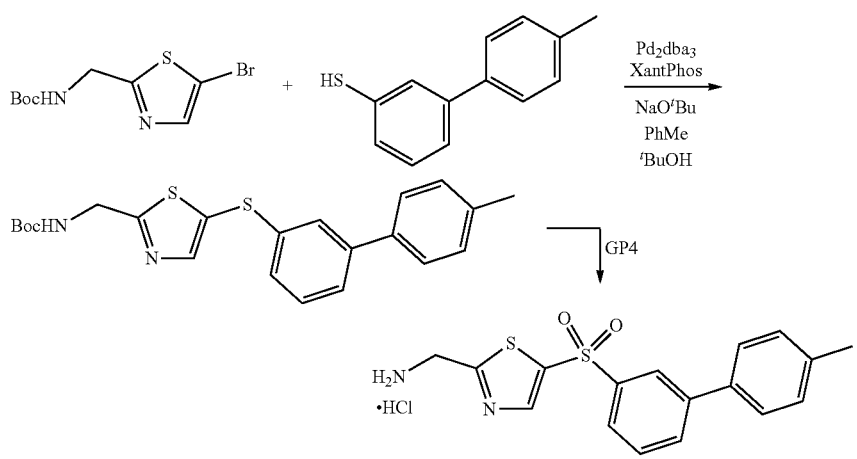

Example 92: (5-(Phenylsulfonyl)thiazol-2-yl)methanamine hydrochloride

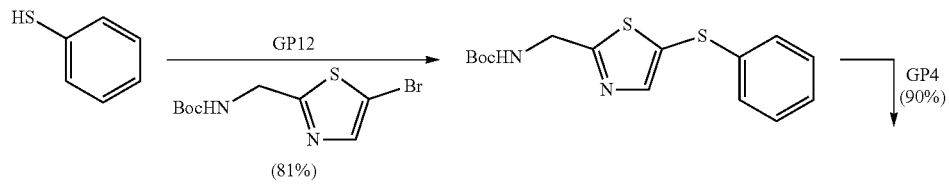

tert-Butyl ((5-(phenylthio)thiazol-2-yl)methyl)carbamate was synthesised according to general procedures GP12—from tert-butyl ((5-bromothiazol-2-yl)methyl)carbamate (275 mg, 0.938 mmol), benzenethiol (0.11 mL, 1.03 mmol), Pd$_2$(dba)$_3$ (43 mg, 10 mol % Pd), Xantphos (109 mg, 20 mol %), NaO$^t$Bu (108 mg, 1.126 mmol), toluene/$^t$BuOH (5:1, 3.0 mL); 110° C., 16 h. Chromatographic purification (5→60% EtOAc in hexane) afforded a yellow solid (246 mg, 81%). $^1$H NMR (CDCl$_3$, 500 MHz) δ 7.79 (s, 1H), 7.31-7.20 (m, 5H), 5.31 (br s, 1H), 4.61 (d, 2H, J=5.8 Hz), 1.47 (s, 9H). LCMS (ESI) m/z 323 (M+H)$^+$.

Example 92 was synthesised according to general procedures GP4—from i) tert-butyl ((5-(phenylthio)thiazol-2-yl)methyl)carbamate (220 mg, 0.68 mmol), m-CPBA (77%; 382 mg, 1.7 mmol), DCM (5.5 mL); rt, 18 h; chromatography (EtOAc/cyclohexane 10→70%). ii) 4 M HCl in dioxane (2.25 mL); rt, 4 h. The mixture was diluted with Et$_2$O and the precipitate collected using filtration, washing with excess Et$_2$O, and dried under vacuum to afford the amine hydrochloride as a white solid (132 mg, 90% over two steps). $^1$H NMR (DMSO-d$_6$, 500 MHz) δ 8.78 (br s, 3H), 8.60 (s, 1H), 8.04 (d, 2H, J=7.2 Hz), 7.78 (t, 1H, J=7.4 Hz), 7.69 (at, 2H, J=7.7 Hz), 4.47 (s, 2H). $^{13}$C NMR (DMSO-d$_6$, 125 MHz) δ 170.2, 147.4, 140.7, 140.1, 134.6, 130.1, 127.1, 39.7. HRMS (ESI) m/z 255.0255 found (M+H)$^+$, 255.0256 calculated for C$_{10}$H$_{11}$N$_2$S$_2$O$_2$.

Example 93: (5-((4-(tert-Butyl)phenyl)sulfonyl)thiazol-2-yl)methanamine tert-Butyl ((5-((4-(tert-butyl)phenyl)thio)thiazol-2-yl)methyl)carbamate was synthesised according to general procedures GP12—from tert-butyl ((5-bromothiazol-2-yl)methyl)carbamate (235 mg, 0.80 mmol), 4-(tert-butyl)benzenethiol (0.152 mL, 0.88 mmol), Pd$_2$(dba)$_3$ (37 mg, 10 mol % Pd), Xantphos (93 mg, 20 mol %), NaO$^t$Bu (92 mg, 0.96 mmol), toluene/$^t$BuOH (5:1, 4.8 mL); 110° C., 16 h. Chromatographic purification (0→50% EtOAc in hexane) afforded a yellow solid (303 mg, 100%). $^1$H NMR (CDCl$_3$, 500 MHz) δ 7.76 (s, 1H), 7.31 (d, 2H, J=8.6 Hz), 7.22 (d, 2H, J=8.6 Hz), 5.31 (s, 1H), 4.59 (d, 2H, J=5.7 Hz), 1.47 (s, 9H), 1.30 (s, 9H). LCMS (ESI) m/z 379.1497 found (M+H)$^+$, C$_{18}$H$_{26}$N$_2$S$_2$O$_2$.

Example 93 was synthesised according to general procedures GP4—from i) tert-butyl ((5-((4-(tert-butyl)phenyl)thio)thiazol-2-yl)methyl)carbamate (290 mg, 0.766 mmol), m-CPBA (77%; 429 mg, 1.91 mmol), DCM (6 mL); rt, 18 h; chromatography (EtOAc/cyclohexane 0→50%). ii) 4 M HCl in dioxane (3.0 mL); rt, 4 h. The mixture was diluted with Et$_2$O and the precipitate collected using filtration, washing with excess Et$_2$O, and dried under vacuum to afford the amine hydrochloride as a white solid (152 mg, 58% over two steps). $^1$H NMR (DMSO-d$_6$, 500 MHz) δ 8.82 (s, 3H), 8.57 (s, 1H), 7.95 (d, 2H, J=8.8 Hz), 7.70 (d, 2H, J=8.8 Hz), 4.47 (s, 2H), 1.29 (s, 9H). $^{13}$C NMR (DMSO-d$_6$, 125 MHz) δ 170.0, 157.8, 147.1, 140.5, 137.8, 127.1, 127.0, 39.7, 35.1, 30.6. HRMS (ESI) m/z 311.0878 found (M+H)$^+$, 311.0882 calculated for C$_{14}$H$_{19}$N$_2$S$_2$O$_2$.

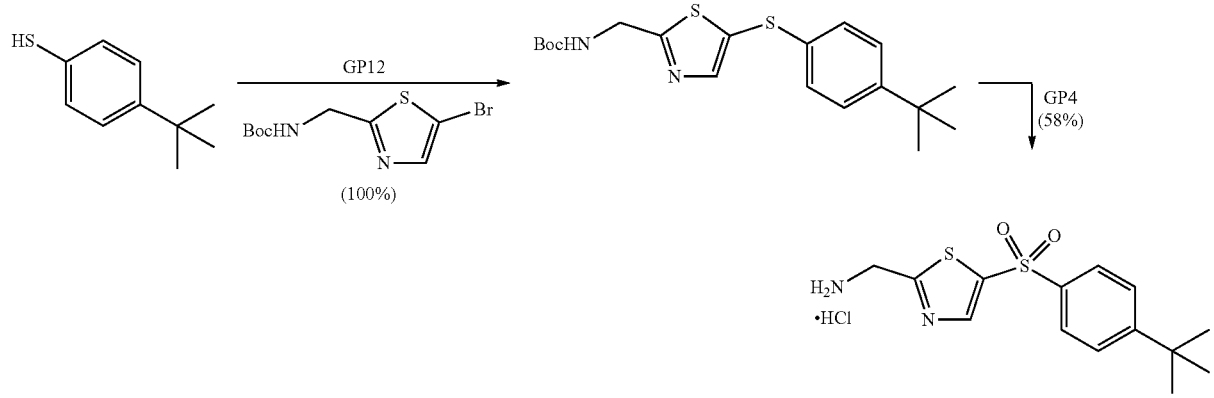

Example 94: (5-(Cyclohexylsulfonyl)thiazol-2-yl)methanamine hydrochloride

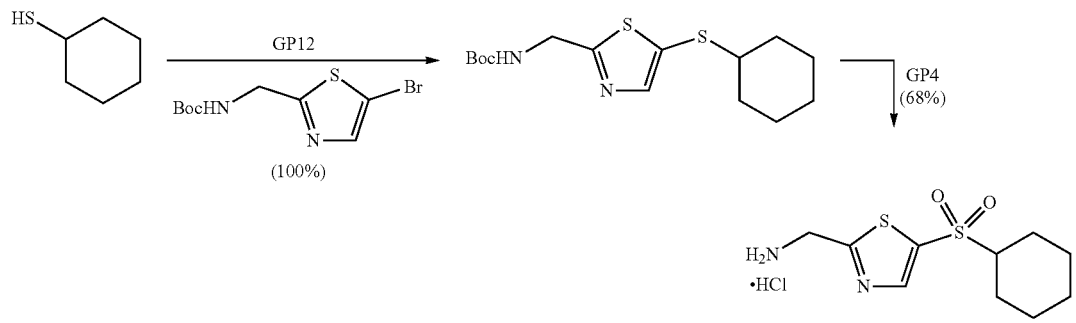

tert-Butyl ((5-(cyclohexylthio)thiazol-2-yl)methyl)carbamate was synthesised according to general procedures GP12—from tert-butyl ((5-bromothiazol-2-yl)methyl)carbamate (220 mg, 0.75 mmol), cyclohexanethiol (0.1 mL, 0.825 mmol), $Pd_2(dba)_3$ (35 mg, 10 mol % Pd), Xantphos (87 mg, 20 mol %), NaO$^t$Bu (87 mg, 0.90 mmol), toluene/BuOH (5:1, 4.8 mL); 110° C., 16 h. Chromatographic purification (5→60% EtOAc in hexane) afforded a yellow oil (247 mg, 100%). $^1$H NMR (CDCl$_3$, 500 MHz) δ 7.58 (s, 1H), 5.37 (br s, 1H), 4.57 (d, 2H, J=5.9 Hz), 2.86-2.80 (m, 1H), 1.96-1.94 (m, 2H), 1.78-1.75 (m, 2H), 1.62-1.58 (m, 1H), 1.47 (s, 9H), 1.37-1.16 (m, 5H). LCMS (ESI) m/z 329.1351 found (M+H)$^+$, $C_{15}H_{25}N_2S_2O_2$.

Example 94 was synthesised according to general procedures GP4—from i) tert-butyl ((5-(cyclohexylthio)thiazol-2-yl)methyl)carbamate (240 mg, 0.73 mmol), m-CPBA (77%; 409 mg, 1.826 mmol), DCM (7 mL); rt, 18 h; chromatography (EtOAc/cyclohexane 5→60%). ii) 4 M HCl in dioxane (2.8 mL); rt, 4 h. The mixture was diluted with Et$_2$O and the precipitate collected using filtration, washing with excess Et$_2$O, and dried under vacuum to afford the amine hydrochloride as a white solid (146 mg, 68% over two steps). $^1$H NMR (DMSO-d$_6$, 500 MHz) δ 8.86 (br s, 3H), 8.42 (s, 1H), 4.53 (d, 2H, J=5.4 Hz), 3.43-3.38 (m, 1H), 2.0-1.95 (m, 2H), 1.83-1.78 (m, 2H), 1.62-1.60 (m, 1H), 1.35-1.23 (m, 4H), 1.13-1.05 (m, 1H). $^{13}$C NMR (DMSO-d$_6$, 125 MHz) δ 170.0, 148.4, 135.5, 63.1, 39.7, 25.2, 24.6 24.1. HRMS (ESI) m/z 261.0723 found (M+H)$^+$, for $C_{10}H_{17}N_2O_2S_2$.

Example 95: (5-(Phenylsulfinyl)thiazol-2-yl)methanamine hydrochloride

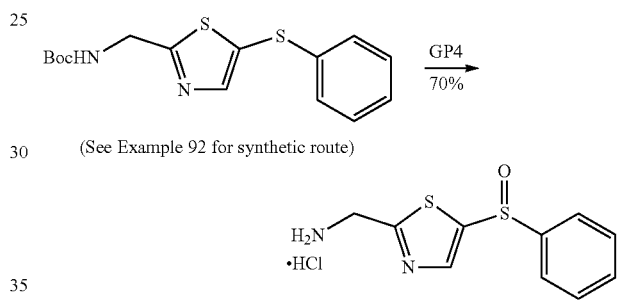

(See Example 92 for synthetic route)

Example 95 was synthesised according to general procedures GP4—from i) tert-butyl ((5-(phenylthio)thiazol-2-yl)methyl)carbamate (100 mg, 0.31 mmol), m-CPBA (77%; 70 mg, 0.31 mmol), DCM (3.5 mL); rt, 18 h; chromatography (EtOAc/cyclohexane 20→100%). ii) 4 M HCl in dioxane (1.25 mL); rt, 4 h. The mixture was diluted with Et$_2$O and the precipitate collected using filtration, washing with excess Et$_2$O, and dried under vacuum to afford the amine hydrochloride as a white solid (58 mg, 70% over two steps). $^1$H NMR (DMSO-d$_6$, 500 MHz) δ 8.79 (br s, 3H), 8.51 (s, 1H), 7.76-7.73 (m, 2H), 7.64-7.57 (m, 3H, ArH), 4.41 (q, 2H, J=5.7 Hz). $^{13}$C NMR (DMSO-d$_6$, 125 MHz) δ 168.5, 146.3, 145.0, 131.7, 129.8, 123.7, 39.8. HRMS (ESI) m/z 239.0308 found (M+H)$^+$, for $C_{10}H_{11}N_2S_2O$.

Example 96: 2-((2-(Aminomethyl)thiazol-5-yl)sulfonyl)ethan-1-amine hydrochloride

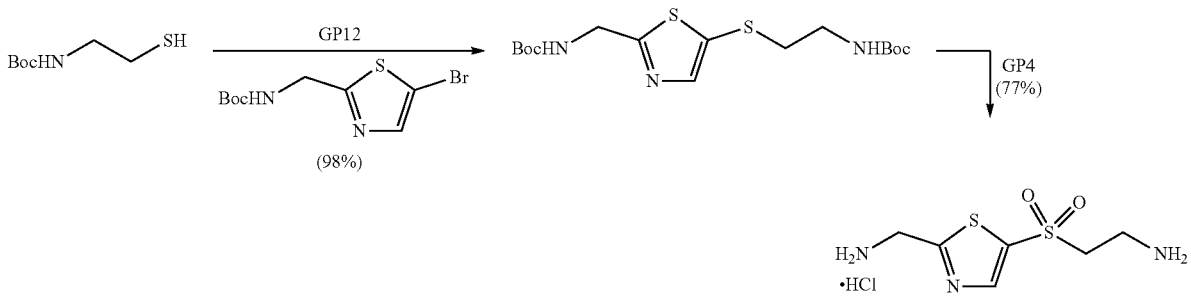

tert-Butyl ((5-((2-((tert-butoxycarbonyl)amino)ethyl)thio)thiazol-2-yl)methyl)carbamate was synthesised according to general procedures GP12—from tert-butyl ((5-bromothiazol-2-yl)methyl)carbamate (300 mg, 1.02 mmol), 2-(Boc-amino)ethanethiol (0.17 mL, 1.02 mmol), Pd$_2$(dba)$_3$ (23 mg, 5 mol % Pd), Xantphos (30 mg, 5 mol %), DIPEA (0.36 mL, 2.05 mmol), toluene (6.0 mL); 110° C., 16 h. Chromatographic purification (10→80% EtOAc in hexane) afforded a yellow oil (390 mg, 98%). $^1$H NMR (CDCl$_3$, 500 MHz) δ 7.61 (s, 1H), 5.36 (br s, 1H), 4.92 (br s, 1H), 4.54 (d, 2H, J=5.9 Hz), 3.29 (q, 2H, J=6.0 Hz), 2.85 (t, 2H, J=6.3 Hz), 1.45 (s, 9H), 1.42 (s, 9H). LCMS (ESI) m/z 390.1498 found (M+H)$^+$, $C_{16}H_{28}N_3S_2O_4$.

Example 96 was synthesised according to general procedures GP4—from i) tert-butyl ((5-((2-((tert-butoxycarbonyl)amino)ethyl)thio)thiazol-2-yl)methyl)carbamate (240 mg, 0.616 mmol), m-CPBA (77%; 345 mg, 1.54 mmol), DCM (5.0 mL); rt, 18 h; chromatography (EtOAc/cyclohexane 20→100%). ii) 4 M HCl in dioxane (2.1 mL); rt, 4 h. The mixture was diluted with Et$_2$O and the precipitate collected using filtration, washing with excess Et$_2$O, and dried under vacuum to afford the amine hydrochloride as a white solid (112 mg, 77% over two steps). $^1$H NMR (DMSO-d$_6$, 500 MHz) δ 8.94 (br s, 3H), 8.61 (s, 1H), 8.51 (br s, 3H), 4.56 (br s, 2H), 3.98-3.95 (m, 2H), 3.11 (br s, 2H). $^{13}$C NMR (DMSO-d$_6$, 125 MHz) δ 170.5, 148.6, 136.7, 53.6, 39.7, 33.1. HRMS (ESI) m/z 222.0377 found (M+H)$^+$, for $C_6H_{11}N_3S_2O_2$.

Example 97: (5-(Phenanthren-9-ylsulfonyl)thiazol-2-yl)methanamine hydrochloride tert-Butyl ((5-(phenanthren-9-ylthio)thiazol-2-yl)methyl)carbamate was synthesised according to general procedures GP12—from tert-butyl ((5-bromothiazol-2-yl)methyl)carbamate (200 mg, 0.68 mmol), phenanthrene-9-thiol (143 mg, 0.68 mmol), Pd$_2$(dba)$_3$ (31 mg, 10 mol % Pd), Xantphos (79 mg, 20 mol %), NaO$^t$Bu (79 mg, 0.819 mmol), toluene/$^t$BuOH (5:1, 4.8 mL); 110° C., 16 h. Chromatographic purification (5→60% EtOAc in hexane) afforded a yellow solid (102 mg, 35%). $^1$H NMR (CDCl$_3$, 500 MHz) δ 8.72-8.71 (m, 1H), 8.64 (d, 1H, J=8.2 Hz), 8.51-8.49 (m, 1H), 7.83 (s, 1H), 7.77 (dd, 1H, J=7.9, 1.2 Hz), 7.73-7.56 (m, 5H), 5.24 (br s, 1H), 4.57 (d, 2H, J=5.7 Hz), 1.43 (s, 9H). LCMS (ESI) m/z 423.1165 found (M+H)$^+$, $C_{23}H_{23}N_2S_2O_2$.

Example 97 was synthesised according to general procedures GP4—from i) tert-butyl ((5-(phenanthren-9-ylthio)thiazol-2-yl)methyl)carbamate (100 mg, 0.237 mmol), m-CPBA (77%; 133 mg, 0.59 mmol), DCM (4 mL); rt, 18 h; chromatography (EtOAc/cyclohexane 5-65%). ii) 4 M HCl in dioxane (0.9 mL); rt, 4 h. The mixture was diluted with Et$_2$O and the precipitate collected using filtration, washing with excess Et$_2$O, and dried under vacuum to afford the amine hydrochloride as a white solid (48 mg, 62% over two steps). $^1$H NMR (DMSO-d$_6$, 500 MHz) δ 9.03-9.00 (m, 2H), 8.95 (d, 1H, J=8.3 Hz), 8.84 (s, 1H), 8.78-8.76 (m, 1H), 8.70 (br s, 3H), 8.42 (d, 1H, J=8.0 Hz), 7.96 (ddd, 1H, J=8.4, 7.1, 1.3 Hz), 7.86-7.80 (m, 3H), 4.42 (s, 2H). $^{13}$C NMR (DMSO-d$_6$, 125 MHz) δ 170.1, 147.9, 140.0, 133.9, 133.0, 132.4, 131.3, 131.2, 130.8, 128.7, 128.4, 128.32, 128.26, 124.6, 124.42, 124.36, 123.3, 39.7. HRMS (ESI) m/z 355.0555 found (M+H)$^+$, 355.0569 calculated for $C_{18}H_{15}N_2S_2O_2$.

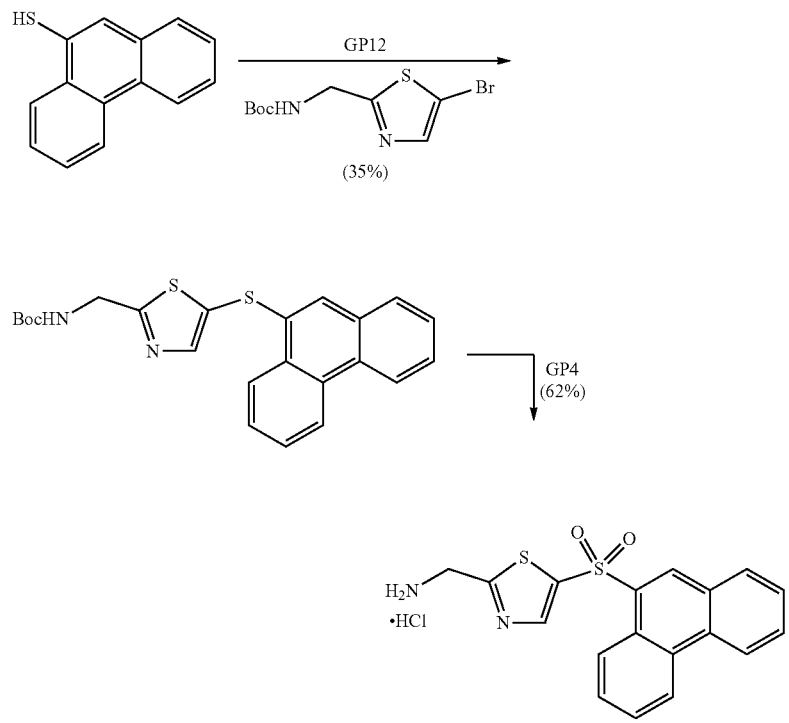

Example 98: (5-((3,4,5-Trimethoxyphenyl)sulfonyl)thiazol-2-yl)methanamine hydrochloride

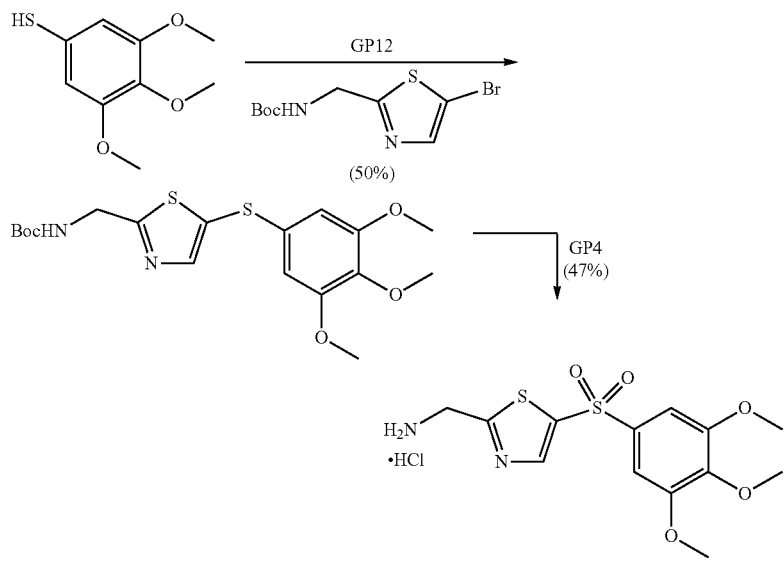

tert-Butyl ((5-((3,4,5-trimethoxyphenyl)thio)thiazol-2-yl)methyl)carbamate was synthesised according to general procedures GP12—from tert-butyl ((5-bromothiazol-2-yl)methyl)carbamate (290 mg, 0.989 mmol), 3,4,5-trimethoxybenzenethiol (198 mg, 0.989 mmol), Pd$_2$(dba)$_3$ (45 mg, 10 mol % Pd), Xantphos (114 mg, 20 mol %), NaO$^t$Bu (114 mg, 1.187 mmol), toluene/$^t$BuOH (5:1, 7.2 mL); 110° C., 16 h. Chromatographic purification (10→80% EtOAc in hexane) afforded a yellow oil (203 mg, 50%). $^1$H NMR (CDCl$_3$, 500 MHz) δ 7.74 (s, 1H), 6.53 (s, 2H), 5.32 (br s, 1H), 4.57 (d, 2H, J=5.9 Hz), 3.80 (s, 3H), 3.79 (s, 6H), 1.44 (s, 9H). LCMS (ESI) m/z 413.1182 found (M+H)$^+$, C$_{18}$H$_{25}$N$_2$S$_2$O$_5$.

Example 98 was synthesised according to general procedures GP4—from i) tert-butyl ((5-((3,4,5-trimethoxyphenyl)thio)thiazol-2-yl)methyl)carbamate (180 mg, 0.436 mmol), m-CPBA (77%; 244 mg, 1.09 mmol), DCM (7 mL); rt, 18 h; chromatography (EtOAc/cyclohexane 10→80%). ii) 4 M HCl in dioxane (1.3 mL); rt, 4 h. The mixture was diluted with Et$_2$O and the precipitate collected using filtration, washing with excess Et$_2$O, and dried under vacuum to afford the amine hydrochloride as a white solid (67 mg, 47% over two steps). $^1$H NMR (DMSO-d$_6$, 500 MHz) δ 8.73 (br s, 3H), 8.62 (s, 1H), 7.27 (s, 2H), 4.45 (s, 2H), 3.88 (s, 6H), 3.74 (s, 3H). $^{13}$C NMR (DMSO-d$_6$, 125 MHz) δ 170.3, 153.4, 147.3, 142.1, 140.3, 135.3, 104.6, 60.3, 56.6, 39.8. HRMS (ESI) m/z 345.0564 found (M+H)$^+$, 345.0573 calculated for C$_{13}$H$_{17}$N$_2$S$_2$O$_5$.

Example 99: (5-(Naphthalen-1-ylsulfonyl)thiazol-2-yl)methanamine hydrochloride

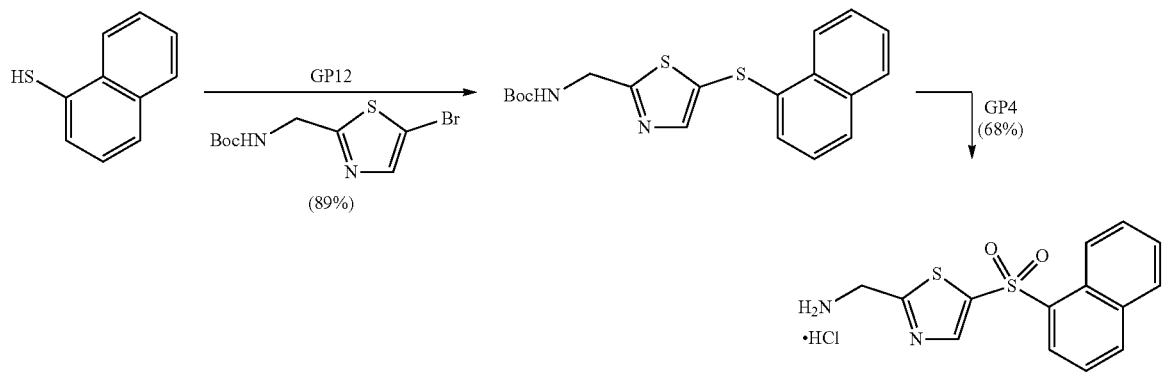

tert-Butyl ((5-(naphthalen-1-ylthio)thiazol-2-yl)methyl)carbamate was synthesised according to general procedures GP12—from tert-butyl ((5-bromothiazol-2-yl)methyl)carbamate (150 mg, 0.512 mmol), naphthalene-1-thiol (0.07 mL, 0.512 mmol), Pd$_2$(dba)$_3$ (23 mg, 10 mol % Pd), Xantphos (59 mg, 20 mol %), NaO$^t$Bu (59 mg, 0.614 mmol), toluene/$^t$BuOH (5:1, 3.6 mL); 110° C., 16 h. Chromatographic purification (10→60% EtOAc in hexane) afforded a yellow oil (170 mg, 89%). $^1$H NMR (CDCl$_3$, 500 MHz) δ 8.42 (d, 1H, J=8.4 Hz), 7.88 (d, 1H, J=7.6 Hz), 7.80-7.78 (m, 2H), 7.62-7.59 (m, 1H), 7.57-7.54 (m, 1H), 7.46 (d, 1H, J=6.9 Hz), 7.41-7.38 (m, 1H), 5.26 (br s, 1H), 4.57 (d, 2H, J=6.1 Hz), 1.45 (s, 9H). LCMS (ESI) m/z 373.1027 found (M+H)$^+$, C$_{19}$H$_{21}$N$_2$S$_2$O$_2$.

Example 99 was synthesised according to general procedures GP4—from i) tert-butyl ((5-(naphthalen-1-ylthio)thiazol-2-yl)methyl)carbamate (160 mg, 0.429 mmol), m-CPBA (77%; 240 mg, 1.07 mmol), DCM (8 mL); rt, 18 h; chromatography (EtOAc/cyclohexane 10→70%). ii) 4 M HCl in dioxane (1.8 mL); rt, 4 h. The mixture was diluted with Et$_2$O and the precipitate collected using filtration, washing with excess Et$_2$O, and dried under vacuum to afford the amine hydrochloride as a white solid (119 mg, 82% over two steps). $^1$H NMR (DMSO-d$_6$, 500 MHz) δ 8.80 (s, 1H), 8.77-8.68 (m, 4H), 8.48 (dd, 1H, J=7.4, 1.2 Hz), 8.41 (d, 1H, J=8.3 Hz), 8.17 (d, 1H, J=8.1 Hz), 7.82-7.78 (m, 2H), 7.72 (ddd, 1H, J=8.0, 7.0, 1.0 Hz), 4.42 (s, 2H). $^{13}$C NMR (DMSO-d$_6$, 125 MHz) δ 170.0, 147.6, 140.2, 136.5, 135.1, 133.9, 129.9, 129.7, 129.2, 127.5, 127.1, 125.2, 123.3, 39.7. HRMS (ESI) m/z 305.0402 found (M+H)$^+$, 305.0413 calculated for $C_{14}H_{13}N_2S_2O_2$.

Example 100: (5-((5-(Methylsulfonyl)-[1,1'-biphenyl]-3-yl)sulfonyl)thiazol-2-yl)methanamine hydrochloride (CDCl$_3$, 500 MHz) δ 7.55 (d, 2H, J=7.0 Hz), 7.44 (t, 2H, J=7.5 Hz), 7.37 (t, 1H, J=7.4 Hz), 7.32 (t, 1H, J=1.6 Hz), 7.29 (t, 1H, J=1.6 Hz), 7.21 (t, 1H, J=1.7 Hz), 4.05-3.99 (m, 2H), 3.22 (t, 2H, J=7.4 Hz), 2.67 (t, 2H, J=7.4 Hz), 2.53 (s, 3H), 1.59-1.54 (m, 1H), 1.38-1.32 (m, 2H), 1.31-1.26 (m, 6H), 0.88 (t, 6H, J=7.4 Hz).

tert-Butyl ((5-((5-(methylthio)-[1,1'-biphenyl]-3-yl)thio)thiazol-2-yl)methyl)carbamate was synthesised according to general procedures GP14 and GP12—from i) 2-ethylhexyl 3-((5-(methylthio)-[1,1'-biphenyl]-3-yl)thio)propanoate (500 mg, 1.20 mmol), NaOEt (21 wt % in EtOH; 0.78 mL, 2.40 mmol), toluene:EtOH (1:1, 12 mL); rt, 4 h; ii) tert-butyl ((5-bromothiazol-2-yl)methyl)carbamate (334 mg, 1.14 mmol), Pd$_2$(dba)$_3$ (104 mg, 10 mol %), Xantphos (132 mg, 20 mol %), NaO$^t$Bu (132 mg, 1.37 mmol), toluene/$^t$BuOH (5:1, 9.0 mL); 110° C., 16 h. Chromatographic purification (5→50% EtOAc in hexane) afforded a yellow oil (310 mg, 61%). $^1$H NMR (CDCl$_3$, 500 MHz) δ 7.81 (s, 1H), 7.48 (d, 2H, J=7.0 Hz), 7.42 (t, 2H, J=7.4 Hz), 7.36 (t, 1H, J=7.3 Hz), 7.26 (t, 1H, J=1.6 Hz), 7.19 (t, 1H, J=1.6 Hz), 7.07 (t, 1H,

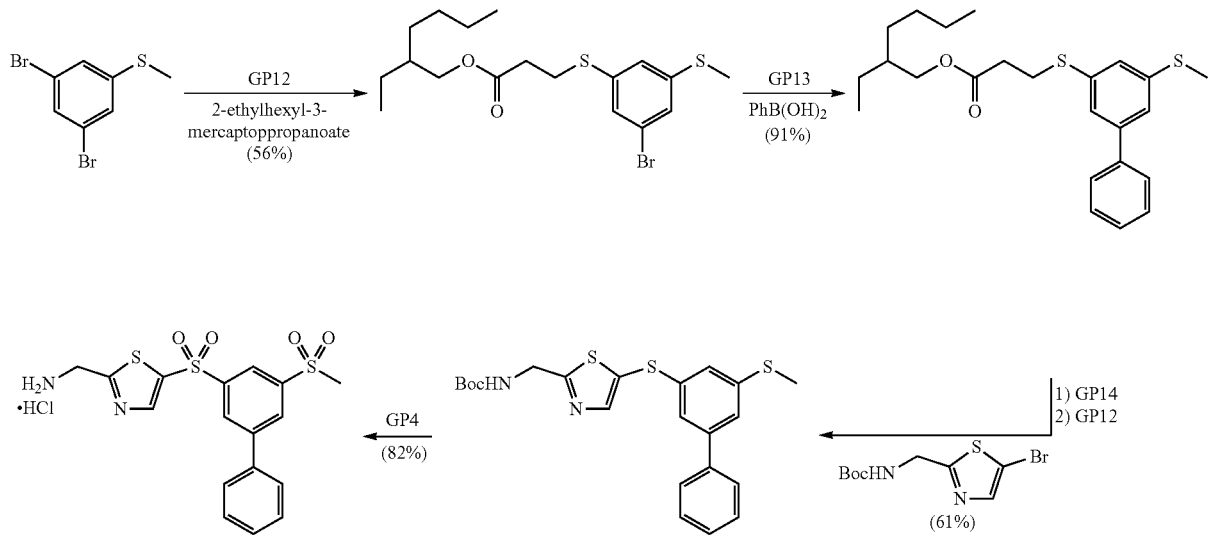

2-Ethylhexyl 3-((3-bromo-5-(methylthio)phenyl)thio)propanoate was synthesised according to general procedures GP12—from (3,5-dibromophenyl)(methyl)sulfane (3.0 g, 10.64 mmol), 2-ethylhexyl-3-mercaptopropionate (2.4 mL, 10.64 mmol), Pd$_2$(dba)$_3$ (244 mg, 2.5 mol %), Xantphos (308 mg, 5 mol %), DIPEA (3.7 mL, 21.28 mmol), toluene (45 mL); 110° C., 16 h. Chromatographic purification (1-10% EtOAc in hexane) afforded a pale yellow oil (2.503 g, 56%). $^1$H NMR (CDCl$_3$, 500 MHz) δ 7.21 (t, 1H, J=1.6 Hz), 7.16 (t, 1H, J=1.7 Hz), 7.10 (t, 1H, J=1.6 Hz), 4.05-3.99 (m, 2H), 3.17 (t, 2H, J=7.3 Hz), 2.64 (t, 2H, J=7.3 Hz), 2.46 (s, 3H), 1.59-1.54 (m, 1H), 1.38-1.32 (m, 2H), 1.31-1.27 (m, 6H), 0.89 (t, 6H, J=7.4 Hz). LCMS (ESI) m/z 419.036 found (M+H)$^+$, $C_{18}H_{28}S_2O_2Br$. 2-Ethylhexyl 3-((5-(methylthio)-[1,1'-biphenyl]-3-yl)thio)propanoate was synthesised according to general procedures GP13—from 2-ethylhexyl 3-((3-bromo-5-(methylthio) phenyl)thio)propanoate (1.0 g, 2.38 mmol), phenylboronic acid (320 mg, 2.62 mmol), Pd(PPh$_3$)$_4$ (275 mg, 0.238 mmol), K$_2$CO$_3$ (658 mg, 4.76 mmol), 1,2-DME:H$_2$O (5:1.18 mL); 100° C., 16 h. Chromatographic purification (1→12% EtOAc in hexane) afforded a clear colourless oil (900 mg, 91%). $^1$H NMR J=1.6 Hz), 5.31 (br s, 1H), 4.60 (d, 2H, J=5.8 Hz), 2.48 (s, 3H), 1.45 (s, 9H). LCMS (ESI) m/z 445.1263 found (M+H)$^+$, $C_{22}H_{25}N_2S_3O_2$.

Example 100 was synthesised according to general procedures GP4—from i) tert-butyl ((5-((5-(methylthio)-[1,1'-biphenyl]-3-yl)thio)thiazol-2-yl)methyl)carbamate (350 mg, 0.787 mmol), m-CPBA (77%; 776 mg, 3.46 mmol), DCM (15 mL); rt, 18 h; chromatography (EtOAc/cyclohexane 10→60%). ii) 4 M HCl in dioxane (2.0 mL); rt, 4 h. The mixture was diluted with Et$_2$O and the precipitate collected using filtration, washing with excess Et$_2$O, and dried under vacuum to afford the amine hydrochloride as a white solid (354 mg, 82% over two steps). $^1$H NMR (DMSO-d$_6$, 500 MHz) δ 8.83 (s, 1H), 8.72 (br s, 3H), 8.58 (t, 1H, J=1.7 Hz), 8.53 (t, 1H, J=1.6 Hz), 8.43 (t, 1H, J=1.7 Hz), 7.87 (d, 2H, J=7.0 Hz), 7.58 (t, 2H, J=7.3 Hz), 7.53 (t, 1H, J=7.3 Hz), 4.50 (br s, 2H), 3.45 (s, 3H). $^{13}$C NMR (DMSO-d$_6$, 125 MHz) δ 171.0, 148.8, 143.8, 143.4, 142.6, 138.9, 136.5, 130.9, 129.5, 129.4, 129.35, 127.5, 123.8, 43.0, 39.8. HRMS (ESI) m/z 409.0328 found (M+H)$^+$, 409.0345 calculated for $C_{17}H_{17}N_2S_3O_4$.

Example 101: (5-((5,6,7,8-Tetrahydronaphthalen-2-yl)sulfonyl)thiazol-2-yl)methanamine hydrochloride

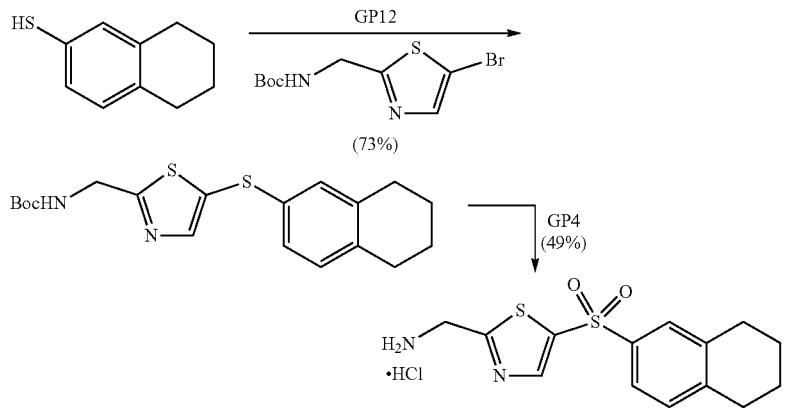

tert-Butyl ((5-((5,6,7,8-tetrahydronaphthalen-2-yl)thio)thiazol-2-yl)methyl)carbamate was synthesised according to general procedures GP12—from tert-butyl ((5-bromothiazol-2-yl)methyl)carbamate (160 mg, 0.546 mmol), 5,6,7,8-tetrahydronaphthalene-2-thiol (90 mg, 0.546 mmol), Pd$_2$(dba)$_3$ (25 mg, 10 mol % Pd), Xantphos (63 mg, 20 mol %), NaO$^t$Bu (63 mg, 0.65 mmol), toluene/$^t$BuOH (5:1, 4.8 mL); 110° C., 18 h. Chromatographic purification (5→60% EtOAc in hexane) afforded a yellow oil (150 mg, 73%). $^1$H NMR (CDCl$_3$, 500 MHz) δ 7.72 (s, 1H), 7.01-6.96 (m, 3H), 5.27 (br s, 1H), 4.57 (d, 2H, J=5.9 Hz), 2.72-2.68 (m, 4H), 1.77-1.74 (m, 4H), 1.45 (s, 9H). LCMS (ESI) m/z 377.1323 found (M+H)$^+$, C$_{19}$H$_{25}$N$_2$S$_2$O$_2$.

Example 101 was synthesised according to general procedures GP4—from i) tert-butyl ((5-((5,6,7,8-tetrahydronaphthalen-2-yl)thio)thiazol-2-yl)methyl)carbamate (140 mg, 0.37 mmol), m-CPBA (77%; 208 mg, 0.93 mmol), DCM (7 mL); rt, 18 h; chromatography (EtOAc/cyclohexane 10→60%). ii) 4 M HCl in dioxane (1.2 mL); rt, 4 h. The mixture was diluted with Et$_2$O and the precipitate collected using filtration, washing with excess Et$_2$O, and dried under vacuum to afford the amine hydrochloride as a white solid (61 mg, 49% over two steps). $^1$H NMR (DMSO-d$_6$, 500 MHz) δ 8.83 (br s, 3H), 8.54 (s, 1H), 7.72-7.69 (m, 2H), 7.35 (d, 1H, J=8.1 Hz), 4.46 (s, 2H), 2.80-2.78 (m, 4H), 1.74-1.71 (m, 4H). $^{13}$C NMR (DMSO-d$_6$, 125 MHz) δ 169.8, 146.9, 144.5, 140.7, 139.0, 137.6, 130.6, 127.4, 124.0, 39.7, 28.9, 28.6, 22.0, 21.9. HRMS (ESI) m/z 309.0721 found (M+H)$^+$, 309.0726 calculated for C$_{14}$H$_{16}$N$_2$S$_2$O$_2$.

Example 102: (5-(Quinolin-7-ylsulfonyl)thiazol-2-yl)methanamine hydrochloride

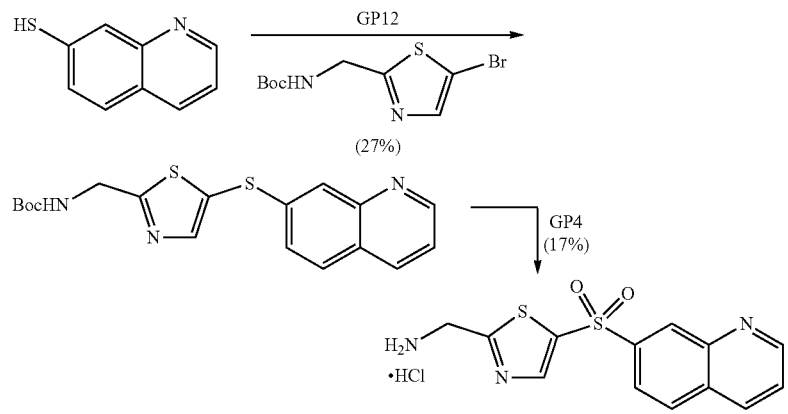

tert-Butyl ((5-(quinolin-7-ylthio)thiazol-2-yl)methyl)carbamate was synthesised according to general procedures GP12—from tert-butyl ((5-bromothiazol-2-yl)methyl)carbamate (145 mg, 0.496 mmol), quinoline-7-thiol (80 mg, 0.496 mmol), Pd$_2$(dba)$_3$ (23 mg, 10 mol % Pd), Xantphos (57 mg, 20 mol %), NaO$^t$Bu (57 mg, 0.82 mmol), toluene/$^t$BuOH (5:1, 4.8 mL); 120° C., 18 h. Chromatographic purification (40→100% EtOAc in hexane, then 0→10% MeOH in EtOAc) afforded a yellow oil (50 mg, 27%). $^1$H NMR (CDCl$_3$, 500 MHz) δ 8.88 (dd, 1H, J=4.3, 1.7 Hz), 8.13-8.10 (m, 1H), 7.89 (s, 1H), 7.81 (d, 1H, J=1.9 Hz), 7.74 (d, 1H, J=8.6 Hz), 7.40 (dd, 1H, J=8.6, 1.9 Hz), 7.37 (dd, 1H, J=4.2, 8.2 Hz), 5.34 (br s, 1H), 4.65 (d, 2H, J=5.9 Hz), 1.47 (s, 9H). LCMS m/z 374.1038 found (M+H)$^+$, C$_{19}$H$_{21}$N$_2$S$_2$O$_2$.

Example 102 was synthesised according to general procedures GP4—from i) tert-butyl ((5-(quinolin-7-ylthio)thiazol-2-yl)methyl)carbamate (50 mg, 0.134 mmol), m-CPBA (77%; 75 mg, 0.33 mmol), DCM (3 mL); rt, 18 h; chromatography (EtOAc/cyclohexane 50→100%, then MeOH/EtOAc 0→30%). ii) 4 M HCl in dioxane (0.25 mL); rt, 4 h. The mixture was diluted with Et$_2$O and the precipitate collected using filtration, washing with excess Et$_2$O, and dried under vacuum to afford the amine hydrochloride as a pale yellow solid (8 mg, 17% over two steps). $^1$H NMR (DMSO-d$_6$, 500 MHz) δ 9.13 (dd, 1H J=4.2, 1.7 Hz), 8.74 (s, 1H), 8.73 (br s, 3H), 8.66 (d, 1H J=1.9 Hz), 8.59 (d, 1H J=8.4 Hz), 8.34 (d, 1H J=8.6 Hz), 8.16 (dd, 1H J=8.6, 2.0 Hz), 7.80 (dd, 1H J=8.4, 4.2 Hz), 4.48 (q, 2H, J=5.5 Hz). $^{13}$C NMR (DMSO-d$_6$, 125 MHz) δ 170.7, 153.0, 148.1, 146.0, 141.2, 139.5, 136.8, 131.2, 130.7, 128.6, 124.7, 122.7, 39.7. HRMS (ESI) m/z 306.0354 found (M+H)$^+$, 306.0365 calculated for $C_{13}H_{12}N_3S_2O_2$.

Example 103: (5-((5-Ethyl-[1,1'-biphenyl]-3-yl)sulfonyl)thiazol-2-yl)methanamine hydrochloride 7.28 (t, 1H, J=1.6 Hz), 7.21 (t, 1H, J=1.6 Hz), 4.06-4.01 (m, 2H), 3.24 (t, 2H, J=7.4 Hz), 2.73-7.65 (m, 4H), 1.61-1.56 (m, 1H), 1.40-1.34 (m, 2H), 1.32-1.28 (m, 9H), 0.90 (t, 6H, J=7.4 Hz).

tert-Butyl ((5-((5-ethyl-[1,1'-biphenyl]-3-yl)thio)thiazol-2-yl)methyl)carbamate was synthesised according to general procedures GP14 and GP12—from i) 2-ethylhexyl 3-((5-ethyl-[1,1'-biphenyl]-3-yl)thio)propanoate (235 mg, 0.589 mmol), NaOEt (21 wt % in EtOH; 0.38 mL, 1.179 mmol), toluene:EtOH (1:1, 6 mL); rt, 4 h; ii) tert-butyl ((5-bromothiazol-2-yl)methyl)carbamate (134 mg, 0.457 mmol), Pd$_2$(dba)$_3$ (21 mg, 10 mol % Pd), Xantphos (53 mg, 20 mol %), NaO$^t$Bu (53 mg, 0.548 mmol), toluene/$^t$BuOH (5:1, 4.8 mL); 110° C., 18 h. Chromatographic purification (10→45% EtOAc in hexane) afforded a yellow oil (163 mg, 84%). $^1$H NMR (CDCl$_3$, 500 MHz) δ 7.80 (s, 1H), 7.52-7.49 (m, 2H), 7.42 (t, 2H, J=7.5 Hz), 7.34 (t, 1H, J=7.3 Hz), 7.28 (t, 1H, J=1.7 Hz), 7.26 (t, 1H, J=1.6 Hz), 7.08 (s, 1H), 5.27 (br s,

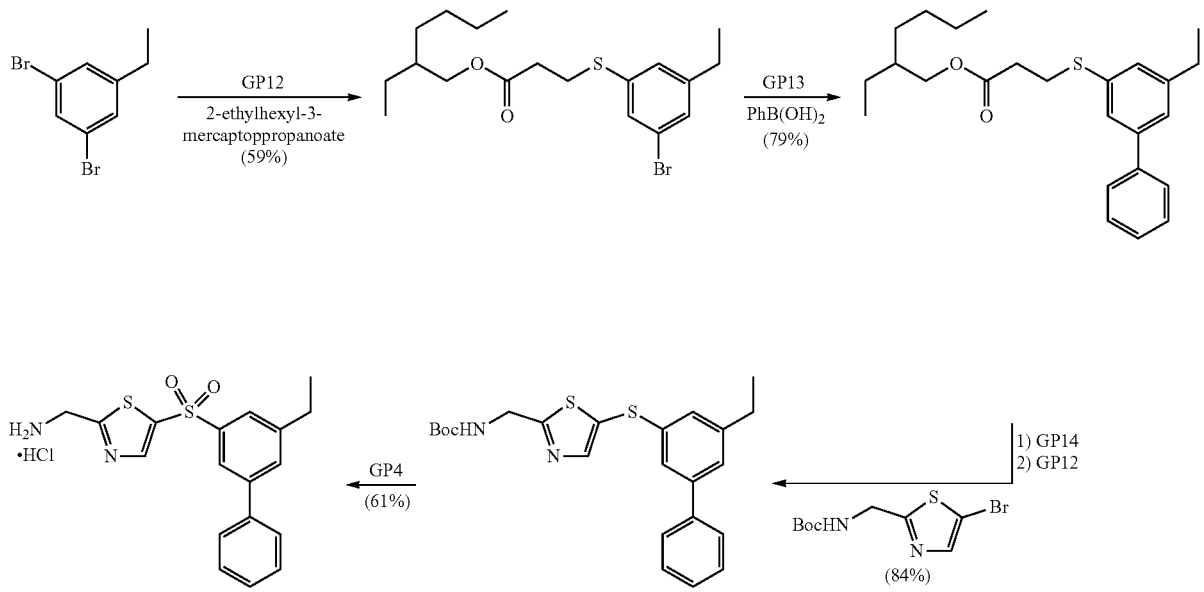

2-Ethylhexyl 3-((3-bromo-5-ethylphenyl)thio)propanoate was synthesised according to general procedures GP12—from 1,3-dibromo-5-ethylbenzene (3.0 g, 11.37 mmol), 2-ethylhexyl-3-mercaptopropionate (2.59 mL, 11.37 mmol), Pd$_2$(dba)$_3$ (260 mg, 2.5 mol %), Xantphos (329 mg, 5 mol %), DIPEA (3.96 mL, 22.73 mmol), toluene (50 mL); 110° C., 16 h. Chromatographic purification (1-15% EtOAc in hexane) afforded a pale yellow oil (2.69 g, 59%). $^1$H NMR (CDCl$_3$, 500 MHz) δ 7.29 (t, 1H, J=1.7 Hz), 7.17 (t, 1H, J=1.6 Hz), 7.09 (t, 1H, J=1.5 Hz), 4.04-3.99 (m, 2H), 3.17 (t, 2H, J=7.4 Hz), 2.63 (t, 2H, J=7.4 Hz), 2.59 (q, 2H, J=7.6 Hz), 1.59-1.55 (m, 1H), 1.38-1.32 (m, 2H), 1.30-1.26 (m, 6H), 1.21 (t, 3H, J=7.6 Hz), 0.89 (t, 6H, J=7.4 Hz). 2-Ethylhexyl 3-((5-ethyl-[1,1'-biphenyl]-3-yl)thio)propanoate was synthesised according to general procedures GP13—from 2-ethylhexyl 3-((3-bromo-5-ethylphenyl)thio)propanoate (300 mg, 0.747 mmol), phenylboronic acid (109 mg, 0.897 mmol), Pd(PPh$_3$)$_4$ (86 mg, 0.075 mmol), K$_2$CO$_3$ (206 mg, 1.494 mmol), 1,2-DME:H$_2$O (5:1, 6 mL); 100° C., 16 h. Chromatographic purification (2→15% EtOAc in hexane) afforded a clear colourless oil (235 mg, 79%). $^1$H NMR (CDCl$_3$, 500 MHz) E 7.59 (d, 2H, J=7.1 Hz), 7.45 (t, 2H, J=7.6 Hz), 7.42 (t, 1H, J=1.7 Hz), 7.37 (t, 1H, J=7.4 Hz), 1H), 4.60 (d, 2H, J=5.7 Hz), 2.66 (q, 2H, J=7.6 Hz), 1.45 (s, 9H), 1.24 (t, 3H, J=7.6 Hz). LCMS (ESI) m/z 427.161 found (M+H)$^+$, $C_{23}H_{27}N_2S_2O_2$.

Example 103 was synthesised according to general procedures GP4—from i) tert-butyl ((5-((5-ethyl-[1,1'-biphenyl]-3-yl)thio)thiazol-2-yl)methyl)carbamate (160 mg, 0.375 mmol), m-CPBA (77%; 210 mg, 0.938 mmol), DCM (8 mL); rt, 18 h; chromatography (EtOAc/cyclohexane 5→55%). ii) 4 M HCl in dioxane (1.5 mL); rt, 4 h. The mixture was diluted with Et$_2$O and the precipitate collected using filtration, washing with excess Et$_2$O, and dried under vacuum to afford the amine hydrochloride as a pale yellow solid (90 mg, 61% over two steps). $^1$H NMR (DMSO-d$_6$, 500 MHz) δ 8.86 (br s, 3H), 8.68 (s, 1H), 8.04 (s, 1H), 7.91 (s, 1H), 7.88 (s, 1H), 7.74 (d, 2H, J=7.2 Hz), 7.52 (t, 2H, J=7.5 Hz), 7.45 (t, 1H, J=7.3 Hz), 4.47 (s, 2H), 2.80 (q, 2H, J=7.6 Hz), 1.25 (t, 3H, J=7.6 Hz). $^{13}$C NMR (DMSO-d$_6$, 125 MHz) δ 170.2, 147.6, 147.1, 142.1, 141.6, 140.2, 138.2, 132.4, 129.2, 128.5, 127.1, 124.9, 122.4, 39.7, 27.9, 15.3. HRMS (ESI) m/z 359.0937 found (M+H)$^+$, 359.0882 calculated for $C_{18}H_{19}N_2S_2O_2$.

Example 104: (5-((2-Ethylphenyl)sulfonyl)thiazol-2-yl)methanamine hydrochloride

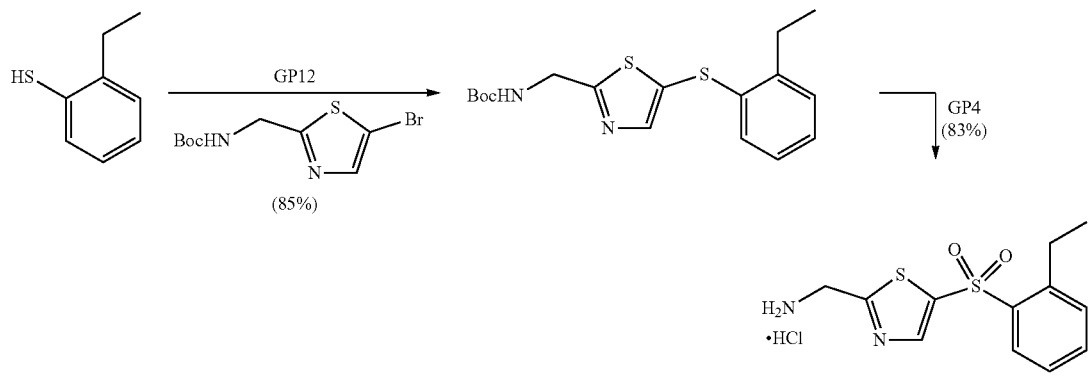

tert-Butyl ((5-((2-ethylphenyl)thio)thiazol-2-yl)methyl)carbamate was synthesised according to general procedures GP12—from tert-butyl ((5-bromothiazol-2-yl)methyl)carbamate (100 mg, 0.341 mmol), 2-ethylbenzenethiol (0.046 mL, 0.341 mmol), Pd$_2$(dba)$_3$ (16 mg, 10 mol % Pd), Xantphos (39 mg, 20 mol %), NaO$^t$Bu (39 mg, 0.409 mmol), toluene/BuOH (5:1, 3.6 mL); 110° C., 16 h. Chromatographic purification (5→40% EtOAc in hexane) afforded a yellow oil (102 mg, 85%). $^1$H NMR (CDCl$_3$, 500 MHz) δ 7.73 (s, 1H), 7.21-7.15 (m, 2H), 7.12-7.07 (m, 2H), 5.26 (br s, 1H), 4.59 (d, 2H, J=5.8 Hz), 2.83 (q, 2H, J=7.5 Hz), 1.45 (s, 9H), 1.26 (t, 3H, J=7.5 Hz). LCMS (ESI) m/z 351.1192 found (M+H)$^+$, C$_{17}$H$_{23}$N$_2$S$_2$O$_2$.

Example 104 was synthesised according to general procedures GP4—from i) tert-butyl ((5-((2-ethylphenyl)thio)thiazol-2-yl)methyl)carbamate (95 mg, 0.271 mmol), m-CPBA (77%; 152 mg, 0.678 mmol), DCM (6 mL); rt, 18 h; chromatography (EtOAc/cyclohexane 10→65%). ii) 4 M HCl in dioxane (1.2 mL); rt, 4 h. The mixture was diluted with Et$_2$O and the precipitate collected using filtration, washing with excess Et$_2$O, and dried under vacuum to afford the amine hydrochloride as a white solid (69 mg, 83% over two steps). $^1$H NMR (DMSO-d$_6$, 500 MHz) δ 8.82 (br s, 3H), 8.59 (s, 1H), 8.07 (d, 1H, J=8.1 Hz), 7.72 (td, 1H, J=7.6, 1.4 Hz), 7.55-7.52 (m, 2H), 4.48 (s, 2H), 2.96 (q, 2H, J=7.4 Hz), 1.14 (t, 3H, J=7.4 Hz). $^{13}$C NMR (DMSO-d$_6$, 125 MHz) δ 170.0, 147.1, 143.7, 140.6, 138.2, 135.0, 131.8, 128.8, 127.3, 39.7, 25.2, 15.7. HRMS (ESI) m/z 283.0564 found (M+H)$^+$, 283.0569 calculated for C$_{12}$H$_{14}$N$_2$S$_2$O$_2$.

Example 105: (5-((5-Methoxy-[1,1'-biphenyl]-3-yl)sulfonyl)thiazol-2-yl)methanamine hydrochloride

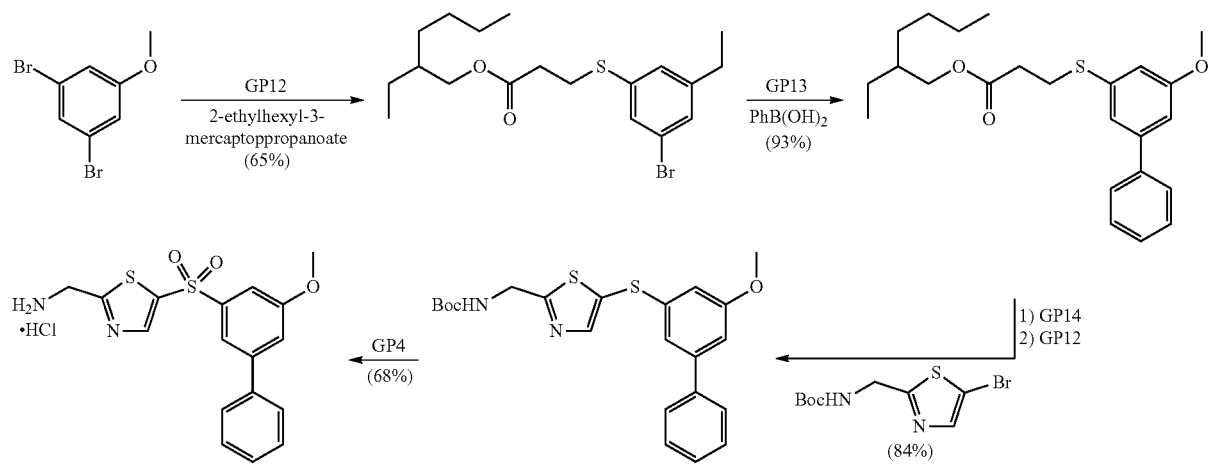

2-Ethylhexyl 3-((3-bromo-5-methoxyphenyl)thio)propanoate was synthesised according to general procedures GP12—from 1,3-dibromo-5-methoxybenzene (700 mg, 2.63 mmol), 2-ethylhexyl-3-mercaptopropionate (0.6 mL, 2.63 mmol), Pd$_2$(dba)$_3$ (60 mg, 2.5 mol %), Xantphos (76 mg, 5 mol %), DIPEA (0.92 mL, 5.26 mmol), toluene (15 mL); 110° C., 16 h. Chromatographic purification (5→30% EtOAc in hexane) afforded a pale yellow oil (685 mg, 65%). $^1$H NMR (CDCl$_3$, 500 MHz) δ 7.05 (t, 1H, J=1.6 Hz), 6.88 (dd, 1H, J=2.2, 1.7 Hz), 6.79 (dd, 1H, J=2.3, 1.6 Hz), 4.04-4.00 (m, 2H), 3.78 (s, 3H), 3.17 (t, 2H, J=7.3 Hz), 2.64 (t, 2H, J=7.3 Hz), 1.59-1.54 (m, 1H), 1.36-1.33 (m, 2H), 1.30-1.26 (m, 6H), 0.89 (t, 6H, J=7.5 Hz).

2-Ethylhexyl 3-((5-methoxy-[1,1'-biphenyl]-3-yl)thio)propanoate was synthesised according to general procedures GP13—2-ethylhexyl 3-((3-bromo-5-methoxyphenyl)thio)propanoate (320 mg, 0.79 mmol), phenylboronic acid (116 mg, 0.95 mmol), Pd(PPh$_3$)$_4$ (91 mg, 0.079 mmol), K$_2$CO$_3$ (218 mg, 1.58 mmol), 1,2-DME:H$_2$O (5:1, 6 mL); 100° C., 16 h. Chromatographic purification (1-12% EtOAc in hexane) afforded a clear yellow oil (295 mg, 93%). $^1$H NMR (CDCl$_3$, 500 MHz) δ 7.57-7.55 (m, 2H), 7.44 (t, 2H, J=7.5 Hz), 7.36 (t, 1H, J=7.3 Hz), 7.16 (t, 1H, J=1.5 Hz), 6.96 (dd, 1H, J=2.3, 1.5 Hz), 6.89 (dd, 1H, J=2.3, 1.6 Hz), 4.04-4.00 (m, 2H), 3.86 (s, 3H), 3.22 (t, 2H, J=7.4 Hz), 2.68 (t, 2H, J=7.4 Hz), 1.58-1.54 (m, 1H), 1.38-1.32 (m, 2H), 1.30-1.25 (m, 6H), 0.88 (t, 6H, J=7.5 Hz). LCMS (ESI) m/z 401.4660 found (M+H)$^+$, C$_{24}$H$_{33}$SO$_3$.

tert-Butyl ((5-((5-methoxy-[1,1'-biphenyl]-3-yl)thio)thiazol-2-yl)methyl)carbamate was synthesised according to general procedures GP14 and GP12—from i) 2-ethylhexyl 3-((5-methoxy-[1,1'-biphenyl]-3-yl)thio)propanoate (280 mg, 0.699 mmol), NaOEt (21 wt % in EtOH; 0.45 mL, 1.398 mmol), toluene:EtOH (1:1, 8 mL); rt, 4 h; ii) tert-butyl ((5-bromothiazol-2-yl)methyl)carbamate (176 mg, 0.60 mmol), Pd$_2$(dba)$_3$ (27 mg, 10 mol %), Xantphos (69 mg, 20 mol %), NaO$^t$Bu (69 mg, 0.72 mmol), toluene/$^t$BuOH (5:1, 6.0 mL); 110° C., 16 h. Chromatographic purification (10→50% EtOAc in hexane) afforded a yellow oil (218 mg, 84%). $^1$H NMR (CDCl$_3$, 500 MHz) δ 7.81 (s, 1H), 7.51-7.49 (m, 2H), 7.42 (t, 2H, J=7.5 Hz), 7. (t, 1H, J=7.3 Hz), 7.05 (t, 1H, J=1.5 Hz), 6.94 (dd, 1H, J=2.3, 1.5 Hz), 6.75 (t, 1H, J=2.0 Hz), 5.29 (br s, 1H), 4.60 (d, 2H, J=5.8 Hz), 3.81 (s, 3H), 1.45 (s, 9H). LCMS (ESI) m/z 429.1351 found (M+H)$^+$, C$_{22}$H$_{25}$N$_2$S$_2$O$_3$.

Example 105 was synthesised according to general procedures GP4—from i) tert-butyl ((5-((5-methoxy-[1,1'-biphenyl]-3-yl)thio)thiazol-2-yl)methyl)carbamate (200 mg, 0.467 mmol), m-CPBA (77%; 261 mg, 1.167 mmol), DCM (10 mL); rt, 18 h; chromatography (EtOAc/cyclohexane 10→70%). ii) 4 M HCl in dioxane (1.34 mL); rt, 4 h. The mixture was diluted with Et$_2$O and the precipitate collected using filtration, washing with excess Et$_2$O, and dried under vacuum to afford the amine hydrochloride as a white solid (124 mg, 68% over two steps). $^1$H NMR (DMSO-d$_6$, 500 MHz) δ 8.79 (br s, 3H), 8.71 (s, 1H), 7.80 (t, 1H, J=1.5 Hz), 7.76-7.74 (m, 2H), 7.57-7.56 (m, 1H), 7.53-7.49 (m, 3H), 7.46 (t, 1H, J=7.3 Hz), 4.47 (s, 2H), 3.93 (s, 3H). $^{13}$C NMR (DMSO-d$_6$, 125 MHz) δ 170.3, 160.5, 147.9, 143.7, 142.7, 139.9, 137.9, 129.1, 128.7, 127.2, 118.3, 117.1, 111.0, 56.1, 39.7. HRMS (ESI) m/z 361.00677 found (M+H)$^+$, 361.0675 calculated for C$_{17}$H$_{17}$N$_2$S$_2$O$_3$.

Example 106: (5-((3,5-Diethylphenyl)sulfonyl)thiazol-2-yl)methanamine hydrochloride

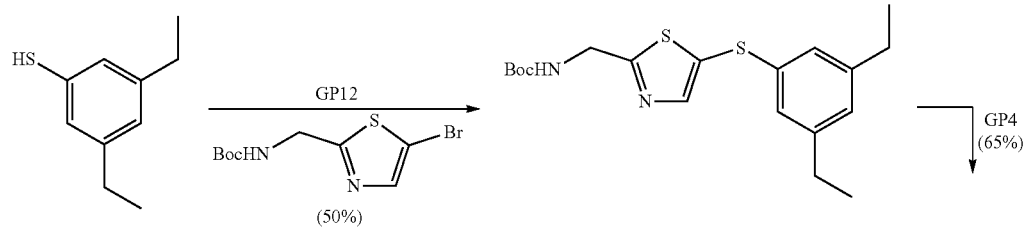

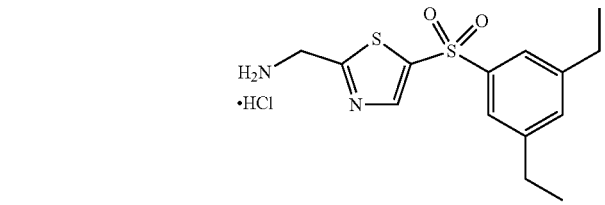

tert-Butyl ((5-((3,5-diethylphenyl)thio)thiazol-2-yl)methyl)carbamate was synthesised according to general procedures GP12—from tert-butyl ((5-bromothiazol-2-yl)methyl)carbamate (123 mg, 0.42 mmol), 3,5-diethylbenzenethiol (70 mg, 0.42 mmol), Pd$_2$(dba)$_3$ (19 mg, 10 mol %), Xantphos (49 mg, 20 mol %), NaO$^t$Bu (48 mg, 0.50 mmol), toluene/$^t$BuOH (5:1, 4.8 mL); 110° C., 16 h. Chromatographic purification (5→40% EtOAc in hexane) afforded a yellow oil (80 mg, 50%). $^1$H NMR (CDCl$_3$, 500 MHz) δ 7.75 (s, 1H), 6.91 (s, 2H), 6.88 (s, 1H), 5.26 (br s, 1H), 4.59 (d, 2H, J=5.9 Hz), 2.56 (q, 4H, J=7.6 Hz), 1.45 (s, 9H), 1.19 (t, 6H, J=7.6 Hz). LCMS (ESI) m/z 379.1493 found (M+H)$^+$, C$_{19}$H$_{27}$N$_2$S$_2$O$_2$.

Example 106 was synthesised according to general procedures GP4—from i) tert-butyl ((5-((3,5-diethylphenyl)thio)thiazol-2-yl)methyl)carbamate (80 mg, 0.21 mmol), m-CPBA (77%; 118 mg, 0.53 mmol), DCM (5 mL); rt, 18 h; chromatography (EtOAc/cyclohexane 10→45%). ii) 4 M HCl in dioxane (0.6 mL); rt, 4 h. The mixture was diluted with Et$_2$O and the precipitate collected using filtration, washing with excess Et$_2$O, and dried under vacuum to afford the amine hydrochloride as a white solid (47 mg, 65% over two steps). $^1$H NMR (DMSO-d$_6$, 500 MHz) δ 8.83 (br s, 3H), 8.59 (s, 1H), 7.69-7.66 (m, 2H), 7.47 (br s, 1H), 4.46 (s, 2H), 2.71-2.66 (m, 4H), 1.20-1.15 (m, 6H). $^{13}$C NMR (DMSO-d$_6$, 125 MHz) δ 170.0, 147.2, 146.2, 140.7, 140.4, 133.7, 123.6, 39.7, 27.8, 15.3. HRMS (ESI) m/z 311.0885 found (M+H)$^+$, 311.0882 calculated for C$_{14}$H$_{19}$N$_2$S$_2$O$_2$.

Example 107: (5-((3-Ethylphenyl)sulfonyl)thiazol-2-yl)methanamine hydrochloride

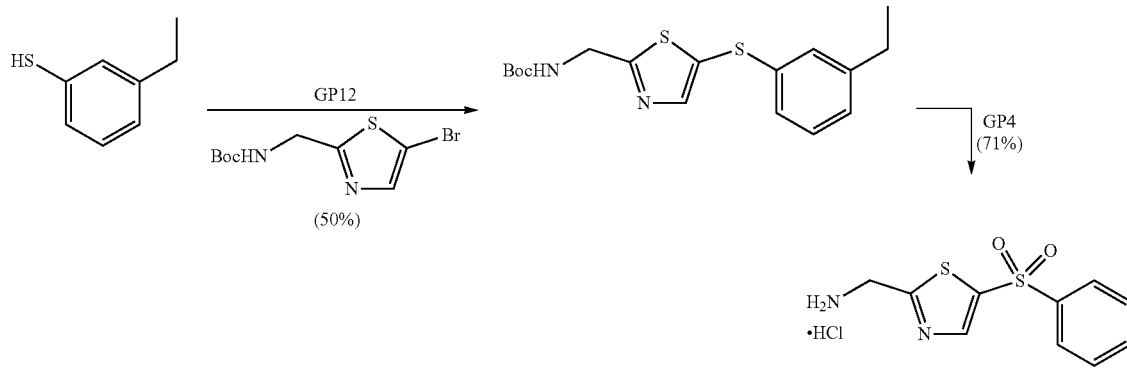

tert-Butyl ((5-((3-ethylphenyl)thio)thiazol-2-yl)methyl)carbamate was synthesised according to general procedures GP12—from tert-butyl ((5-bromothiazol-2-yl)methyl)carbamate (150 mg, 0.51 mmol), 3-ethylbenzenethiol (71 mg, 0.51 mmol), Pd$_2$(dba)$_3$ (23 mg, 10 mol %), Xantphos (59 mg, 20 mol %), NaO$^t$Bu (59 mg, 0.61 mmol), toluene/$^t$BuOH (5:1, 4.8 mL); 110° C., 16 h. Chromatographic purification (10→40% EtOAc in hexane) afforded a yellow oil (90 mg, 50%). $^1$H NMR (CDCl$_3$, 500 MHz) δ 7.76 (s, 1H), 7.20-7.17 (m, 1H), 7.10 (s, 1H), 7.04 (dd, 2H, J=7.7, 1.7 Hz), 5.26 (br s, 1H), 4.59 (d, 2H, J=5.9 Hz), 2.59 (q, 2H, J=7.6 Hz), 1.45 (s, 9H), 1.20 (t, 3H, J=7.6 Hz). LCMS (ESI) m/z 351.1172 found (M+H)$^+$, C$_{17}$H$_{23}$N$_2$S$_2$O$_2$.

Example 107 was synthesised according to general procedures GP4—from i) tert-butyl ((5-((3-ethylphenyl)thio)thiazol-2-yl)methyl)carbamate (90 mg, 0.257 mmol), m-CPBA (77%; 144 mg, 0.64 mmol), DCM (6 mL); rt, 18 h; chromatography (EtOAc/cyclohexane 10→50%). ii) 4 M HCl in dioxane (0.76 mL); rt, 4 h. The mixture was diluted with Et$_2$O and the precipitate collected using filtration, washing with excess Et$_2$O, and dried under vacuum to afford the amine hydrochloride as a white solid (58 mg, 71% over two steps). $^1$H NMR (DMSO-d$_6$, 500 MHz) δ 8.80 (br s, 3H), 8.60 (s, 1H), 7.87 (br s, 1H), 7.85 (dt, 1H, J=7.2, 1.8 Hz), 7.64-7.58 (m, 2H), 4.47 (s, 2H), 2.72 (q, 2H, J=7.6 Hz), 1.19 (t, 3H, J=7.6 Hz). $^{13}$C NMR (DMSO-d$_6$, 125 MHz) δ 170.1, 147.3, 146.2, 140.7, 140.3, 134.1, 130.1, 126.0, 124.6, 39.7, 27.8, 15.3. HRMS (ESI) m/z 283.0566 found (M+H)$^+$, 283.0569 calculated for C$_{12}$H$_{15}$N$_2$S$_2$O$_2$.

Example 108: (5-([1,1'-Biphenyl]-3-ylsulfonyl)thiazol-2-yl)methanamine hydrochloride

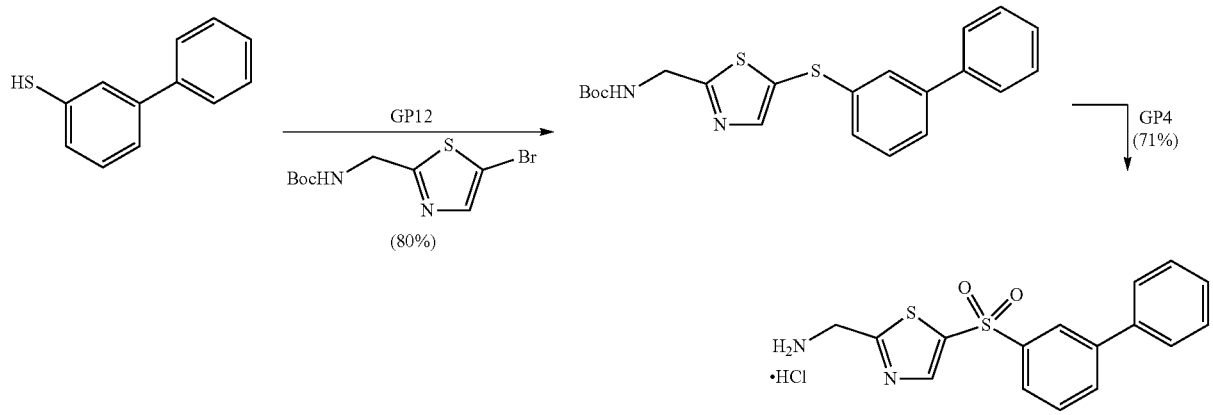 [SMILES: Sc1cccc(-c2ccccc2)c1 ; CC(C)(C)OC(=O)NCc1ncc(Br)s1 ; CC(C)(C)OC(=O)NCc1ncc(Sc2cccc(-c3ccccc3)c2)s1 ; NCc1ncc(S(=O)(=O)c2cccc(-c3ccccc3)c2)s1 ; Cl]

tert-Butyl ((5-([1,1'-biphenyl]-3-ylthio)thiazol-2-yl)methyl)carbamate was synthesised according to general procedures GP12—from tert-butyl ((5-bromothiazol-2-yl)methyl)carbamate (142 mg, 0.48 mmol), [1,1'-biphenyl]-3-thiol (90 mg, 0.48 mmol), Pd$_2$(dba)$_3$ (22 mg, 10 mol %), Xantphos (56 mg, 20 mol %), NaO$^t$Bu (56 mg, 0.58 mmol), toluene/$^t$BuOH (5:1, 4.8 mL); 110° C., 16 h. Chromatographic purification (5→45% EtOAc in hexane) afforded a yellow oil (154 mg, 80%). $^1$H NMR (CDCl$_3$, 500 MHz) δ 7.81 (s, 1H), 7.53-7.51 (m, 2H), 7.47 (t, 1H, J=1.7 Hz), 7.44-7.41 (m, 3H), 7.37-7.33 (m, 2H), 7.21 (ddd, 1H, J=7.8, 1.9, 1.1 Hz), 5.28 (br s, 1H), 4.60 (d, 2H, J=5.9 Hz), 1.45 (s, 9H). LCMS (ESI) m/z 399.1172 found (M+H)$^+$, C$_{21}$H$_{23}$N$_2$S$_2$O$_2$.

Example 108 was synthesised according to general procedures GP4—from i) tert-butyl ((5-([1,1'-biphenyl]-3-ylthio)thiazol-2-yl)methyl)carbamate (154 mg, 0.39 mmol), m-CPBA (77%; 216 mg, 0.97 mmol), DCM (10 mL); rt, 18 h; chromatography (EtOAc/cyclohexane 10→55%). ii) 4 M HCl in dioxane (1.2 mL); rt, 4 h. The mixture was diluted with Et$_2$O and the precipitate collected using filtration, washing with excess Et$_2$O, and dried under vacuum to afford the amine hydrochloride as a white solid (101 mg, 71% over two steps). $^1$H NMR (DMSO-$d_6$, 500 MHz) δ 8.74 (br s, 3H), 8.70 (s, 1H), 8.23 (t, 1H, J=1.8 Hz), 8.07 (ddd, 1H, J=7.8, 1.8, 1.0 Hz), 8.04 (ddd, 1H, J=7.9, 1.9, 1.0 Hz), 7.79 (t, 1H, J=7.9 Hz), 7.76-7.73 (m, 2H), 7.53 (t, 2H, J=7.5 Hz), 7.46 (t, 1H, J=7.3 Hz), 4.48 (s, 2H). $^{13}$C NMR (DMSO-$d_6$, 125 MHz) δ 170.3, 147.7, 142.0, 141.5, 140.0, 138.0, 132.8, 130.9, 129.2, 128.6, 127.1, 126.0, 124.8, 39.7. HRMS (ESI) m/z 331.0554 found (M+H)$^+$, 331.0569 calculated for $C_{16}H_{15}N_2S_2O_2$.

Example 109: (5-((5-Isopropyl-[1,1'-biphenyl]-3-yl)sulfonyl)thiazol-2-yl)methanamine hydrochloride tert-Butyl ((5-((5-isopropyl-[1,1'-biphenyl]-3-yl)thio)thiazol-2-yl)methyl)carbamate was synthesised according to general procedures GP14 and GP12—from i) 2-ethylhexyl 3-((5-isopropyl-[1,1'-biphenyl]-3-yl)thio)propanoate (265 mg, 0.64 mmol), NaOEt (21 wt % in EtOH; 0.42 mL, 1.28 mmol), toluene:EtOH (1:1, 8 mL); rt, 4 h; ii) tert-butyl ((5-bromothiazol-2-yl)methyl)carbamate (173 mg, 0.59 mmol), Pd$_2$(dba)$_3$ (27 mg, 10 mol % Pd), Xantphos (68 mg, 20 mol %), NaO$^t$Bu (68 mg, 0.71 mmol), toluene/$^t$BuOH (5:1, 6.0 mL); 110° C., 16 h. Chromatographic purification

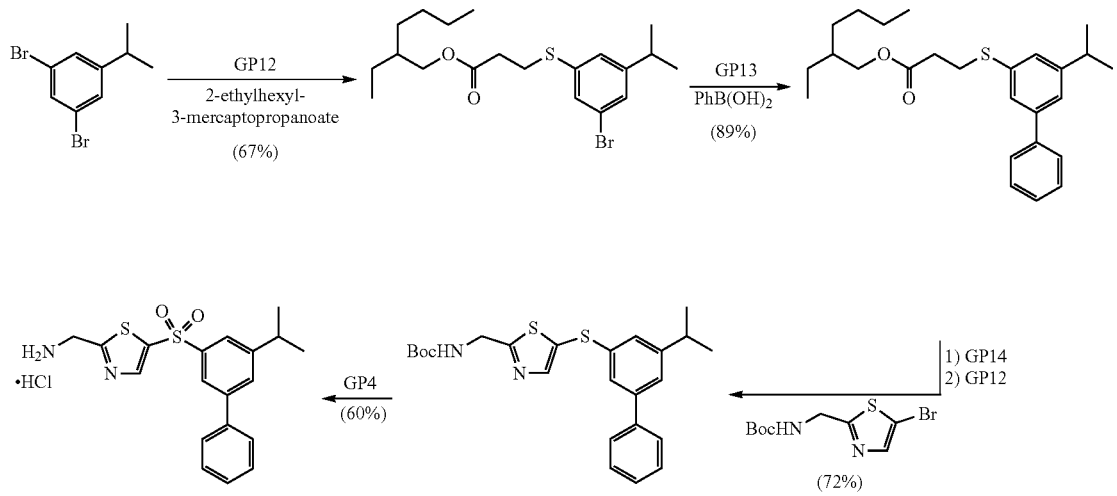

2-Ethylhexyl 3-((3-bromo-5-isopropylphenyl)thio)propanoate was synthesised according to general procedures GP12—from 1,3-dibromo-5-isopropylbenzene (300 mg, 1.08 mmol), 2-ethylhexyl-3-mercaptopropionate (0.25 mL, 1.08 mmol), Pd$_2$(dba)$_3$ (25 mg, 2.5 mol %), Xantphos (31 mg, 5 mol %), DIPEA (0.38 mL, 2.16 mmol), toluene (8 mL); 110° C., 16 h. Chromatographic purification (1→12% EtOAc in hexane) afforded a pale yellow oil (300 mg, 67%). $^1$H NMR (CDCl$_3$, 500 MHz) δ 7.29 (t, 1H, J=1.7 Hz), 7.19 (t, 1H, J=1.4 Hz), 7.11 (t, 1H, J=1.4 Hz), 4.05-3.99 (m, 2H), 3.17 (t, 2H, J=7.4 Hz), 2.83 (p, 1H, J=6.9 Hz), 2.63 (t, 2H, J=7.4 Hz), 1.58-1.55 (m, 1H), 1.38-1.34 (m, 2H), 1.31-1.28 (m, 6H), 1.22 0.89 (d, 6H, J=6.9 Hz), 0.89 (t, 6H, J=7.4 Hz). 2-Ethylhexyl 3-((5-isopropyl-[1,1'-biphenyl]-3-yl)thio)propanoate was synthesised according to general procedures GP13—from 2-ethylhexyl 3-((3-bromo-5-isopropylphenyl)thio)propanoate (300 mg, 0.72 mmol), phenylboronic acid (106 mg, 0.866 mmol), Pd(PPh$_3$)$_4$ (83 mg, 0.072 mmol), K$_2$CO$_3$ (200 mg, 1.44 mmol), 1,2-DME:H$_2$O (5:1, 6 mL); 100° C., 16 h. Chromatographic purification (1-12% EtOAc in hexane) afforded a clear colourless oil (266 mg, 89%). $^1$H NMR (CDCl$_3$, 500 MHz) δ 7.58-7.56 (m, 2H), 7.44 (t, 2H, J=7.6 Hz), 7.40 (t, 1H, J=1.7 Hz), 7.36 (t, 1H, J=7.4 Hz), 7.29 (t, 1H, J=1.5 Hz), 7.22 (t, 1H, J=1.5 Hz), 4.04-4.00 (m, 2H), 3.22 (t, 2H, J=7.4 Hz), 2.95 (p, 1H, J=6.9 Hz), 2.68 (t, 2H, J=7.4 Hz), 1.58-1.55 (m, 1H), 1.38-1.33 (m, 2H), 1.30-1.27 (m, 12H), 0.88 (t, 6H, J=7.4 Hz).

(5-45% EtOAc in hexane) afforded a yellow oil (188 mg, 72%). $^1$H NMR (CDCl$_3$, 500 MHz) δ 7.80 (s, 1H), 7.51-7.49 (m, 2H), 7.42 (t, 2H, J=7.5 Hz), 7.34 (t, 1H, J=7.3 Hz), 7.28-7.26 (m, 2H), 7.12 (t, 1H, J=1.5 Hz), 5.26 (br s, 1H), 4.59 (d, 2H, J=5.8 Hz), 2.92 (p, 1H, J=6.9 Hz), 1.44 (s, 9H), 1.26 (d, 6H, J=6.9 Hz). LCMS (ESI) m/z 441.1758 found (M+H)$^+$, $C_{24}H_{29}N_2S_2O_2$.

Example 109 was synthesised according to general procedures GP4—from i) tert-butyl ((5-((5-isopropyl-[1,1'-biphenyl]-3-yl)thio)thiazol-2-yl)methyl)carbamate (170 mg, 0.386 mmol), m-CPBA (77%; 216 mg, 0.96 mmol), DCM (7 mL); rt, 18 h; chromatography (Et$_2$O/cyclohexane 20→100%). ii) 4 M HCl in dioxane (1.2 mL); rt, 4 h. The mixture was diluted with Et$_2$O and the precipitate collected using filtration, washing with excess Et$_2$O, and dried under vacuum to afford the amine hydrochloride as a white solid (95 mg, 60% over two steps). $^1$H NMR (DMSO-$d_6$, 500 MHz) δ 8.83 (br s, 3H), 8.70 (s, 1H), 8.04 (t, 1H, J=1.7 Hz), 7.92 (t, 1H, J=1.4 Hz), 7.88 (t, 1H, J=1.5 Hz), 7.74 (d, 2H, J=7.1 Hz), 7.52 (t, 2H, J=7.5 Hz), 7.45 (t, 1H, J=7.3 Hz), 4.47 (s, 2H), 3.13 (p, 1H, J=6.9 Hz), 1.28 (d, 6H, J=6.9 Hz). $^{13}$C NMR (DMSO-$d_6$, 125 MHz) δ 170.2, 151.7, 147.7, 142.2, 141.6, 140.2, 138.2, 131.0, 129.2, 128.5, 127.2, 123.5, 122.7, 39.7, 33.4, 23.5. HRMS (ESI) m/z 373.103 found (M+H)$^+$, 373.1039 calculated for $C_{19}H_{21}N_2S_2O_2$.

Example 110: (4-(Naphthalen-2-ylsulfonyl)thiazol-2-yl)methanamine hydrochloride

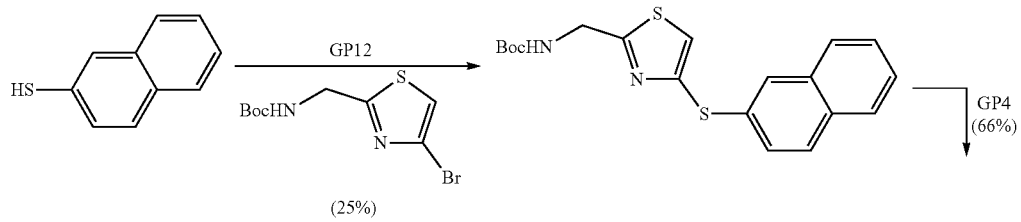
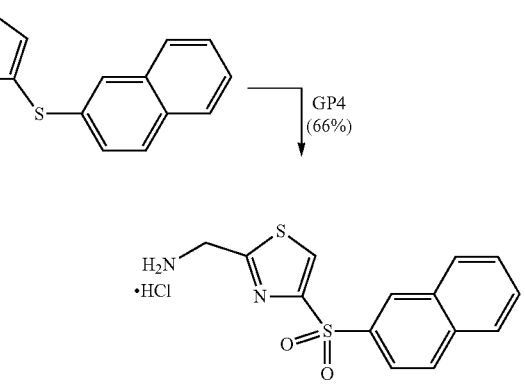

tert-Butyl ((4-(naphthalen-2-ylthio)thiazol-2-yl)methyl) carbamate was synthesised according to general procedures GP12—from tert-butyl ((4-bromothiazol-2-yl)methyl)carbamate (80 mg, 0.27 mmol), 5 naphthalene-2-thiol (44 mg, 0.27 mmol), Pd$_2$(dba)$_3$ (13 mg, 10 mol % Pd), Xantphos (32 mg, 20 mol %), NaO$^t$Bu (32 mg, 0.33 mmol), toluene/$^t$BuOH (5:1, 3.0 mL); 110° C., 18 h. Chromatographic purification (5→50% EtOAc in hexane) afforded a yellow oil (25 mg, 25%). $^1$H NMR (CDCl$_3$, 500 MHz) δ 7.87 (s, 1H), 7.81-7.74 (m, 3H), 7.48-7.46 (m, 2H), 7.43 (dd, 1H, J=8.6, 1.9 Hz), 7.14 (s, 1H), 5.25 (br s, 1H), 4.62-4.59 (m, 2H), 1.46 (s, 9H). LCMS (ESI) m/z 373.1030 found (M+H)$^+$, C$_{19}$H$_{21}$N$_2$S$_2$O$_2$.

Example 110 was synthesised according to general procedures GP4—from i) tert-butyl ((4-(naphthalen-2-ylthio)thiazol-2-yl)methyl)carbamate (25 mg, 0.067 mmol), m-CPBA (77%; 38 mg, 0.168 mmol), DCM (2 mL); rt, 18 h; chromatography (EtOAc/cyclohexane 10→55%). ii) 4 M HCl in dioxane (0.5 mL); rt, 4 h. The mixture was diluted with Et$_2$O and the precipitate collected using filtration, washing with excess Et$_2$O, and dried under vacuum to afford the amine hydrochloride as a white solid (16 mg, 66% over two steps). $^1$H NMR (DMSO-d$_6$, 500 MHz) δ 8.83 (s, 1H), 8.72 (d, 1H, J=1.5 Hz), 8.66 (br s, 3H), 8.26 (d, 1H, J=8.1 Hz), 8.18 (d, 1H, J=8.8 Hz), 8.08 (d, 1H, J=8.2 Hz), 7.95 (dd, 1H, J=8.7, 1.9 Hz), 7.77 (t, 1H, J=6.9 Hz), 7.72 (t, 1H, J=6.9 Hz), 4.42 (s, 2H). $^{13}$C NMR (DMSO-d$_6$, 125 MHz) δ 166.1, 152.3, 136.3, 134.9, 131.7, 130.5, 129.9, 129.7, 129.6, 129.4, 127.9 (2×C), 122.7, 39.3. HRMS (ESI) m/z 305.0403 found (M+H)$^+$, 305.0413 calculated for C$_{14}$H$_{13}$N$_2$S$_2$O$_2$.

Example 111: (5-((3-Ethyl-5-(1-methyl-1H-pyrazol-4-yl)phenyl)sulfonyl)thiazol-2-yl)methanamine hydrochloride

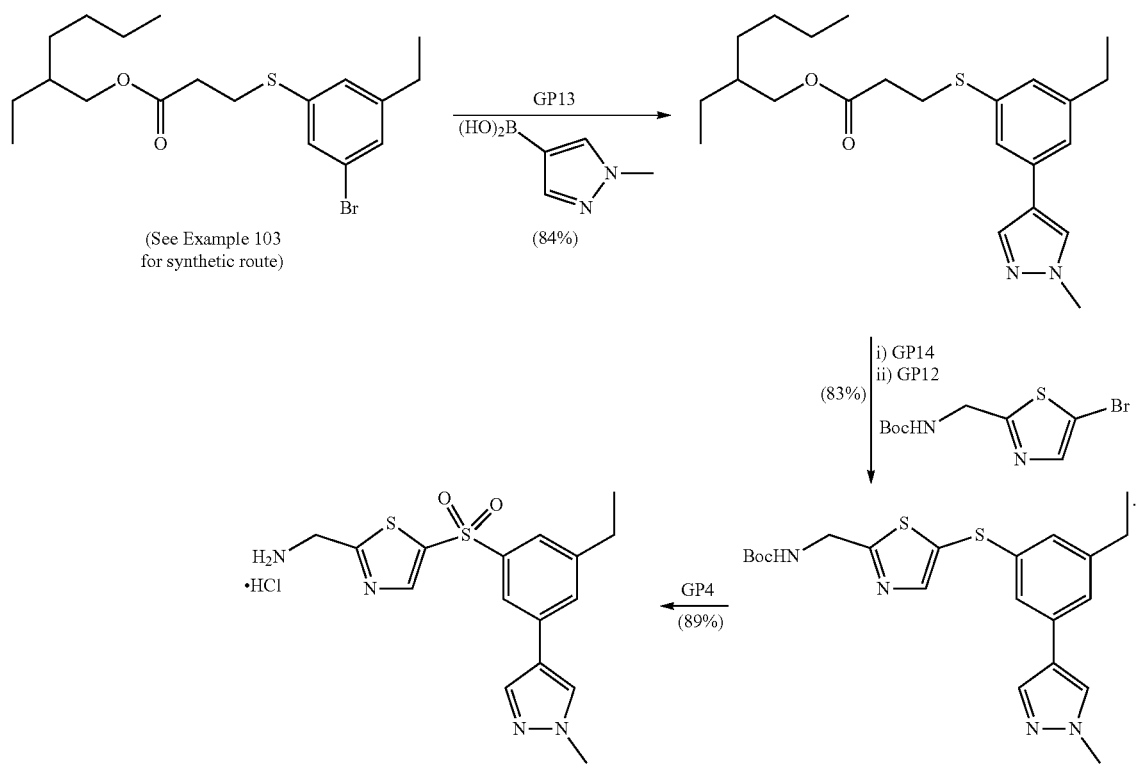

2-Ethylhexyl 3-((3-ethyl-5-(1-methyl-1H-pyrazol-4-yl)phenyl)thio)propanoate was synthesised according to general procedures GP13—from 2-ethylhexyl 3-((3-bromo-5-ethylphenyl)thio)propanoate (500 mg, 1.245 mmol), 1-methyl-1H-pyrazole-4-boronic acid (188 mg, 1.49 mmol), Pd(PPh$_3$)$_4$ (144 mg, 0.125 mmol), K$_2$CO$_3$ (344 mg, 2.49 mmol), 1,2-DME:H$_2$O (5:1, 12 mL); 100° C., 16 h. Chromatographic purification (15→65% EtOAc in hexane) afforded a pale yellow oil (419 mg, 84%). $^1$H NMR (CDCl$_3$, 500 MHz) δ 7.74 (d, 1H, J=0.7 Hz), 7.60 (s, 1H), 7.28 (t, 1H, J=1.6 Hz), 7.14 (t, 1H, J=1.5 Hz), 7.06 (t, 1H, J=1.6 Hz), 4.04-3.98 (m, 2H), 3.94 (s, 3H), 3.19 (t, 2H, J=7.4 Hz), 2.66-2.61 (m, 4H), 1.58-1.52 (m, 1H), 1.38-1.32 (m, 2H), 1.29-1.24 (m, 9H), 0.88 (t, 6H, J=7.4 Hz). LCMS (ESI) m/z 403.4904 found (M+H)$^+$ for C$_{23}$H$_{35}$N$_2$SO$_2$.

tert-Butyl ((5-((3-ethyl-5-(1-methyl-1H-pyrazol-4-yl)phenyl)thio)thiazol-2-yl)methyl) carbamate was synthesised according to general procedures GP14 and GP12—from i) 2-ethylhexyl 3-((3-ethyl-5-(1-methyl-1H-pyrazol-4-yl)phenyl)thio)propanoate (800 mg, 1.99 mmol), NaO$^t$Bu (477 mg, 4.97 mmol), toluene:$^t$BuOH (4:1, 20 mL); rt, 4 h (work-up not performed); ii) To the reaction mixture were added tert-butyl ((5-bromothiazol-2-yl)methyl)carbamate (583 mg, 1.99 mmol), Pd$_2$(dba)$_3$ (91 mg, 10 mol % Pd), Xantphos (230 mg, 20 mol %); 110° C., 16 h. Chromatographic purification (20→100% EtOAc in hexanes, then 0→5% MeOH in EtOAc) afforded a yellow oil (148 mg, 73%). $^1$H NMR (CDCl$_3$, 500 MHz) δ 7.78 (s, 1H), 7.69 (d, 1H, J=0.7 Hz), 7.55 (s, 1H), 7.15 (br s, 1H), 7.13 (br s, 1H), 6.94 (t, 1H, J=1.6 Hz), 5.30 (br s, 1H), 4.59 (d, 2H, J=5.8 Hz), 3.92 (s, 3H), 2.60 (q, 2H, J=7.6 Hz), 1.44 (s, 9H), 1.21 (t, 3H, J=7.6 Hz). LCMS (ESI) m/z 431.1559 found (M+H)$^+$, C$_{21}$H$_{27}$N$_4$S$_2$O$_2$.

Example 111 was synthesised according to general procedures GP4—from i) tert-butyl ((5-((3-ethyl-5-(1-methyl-1H-pyrazol-4-yl)phenyl)thio)thiazol-2-yl)methyl) carbamate (140 mg, 0.325 mmol), m-CPBA (77%; 182 mg, 0.813 mmol), DCM (7 mL); rt, 18 h; chromatography (EtOAc/cyclohexane 40→100%, then MeOH/EtOAc 0→5%). ii) 4 M HCl in dioxane (1.36 mL); rt, 4 h. The mixture was diluted with Et$_2$O and the precipitate collected using filtration, washing with excess Et$_2$O, and dried under vacuum to afford the amine hydrochloride as a white solid (106 mg, 89% over two steps). $^1$H NMR (DMSO-d$_6$, 500 MHz) δ 8.87 (br s, 3H), 8.63 (s, 1H), 8.37 (s, 1H), 8.01 (d, 1H, J=0.7 Hz), 7.97 (t, 1H, J=1.7 Hz), 7.81 (t, 1H, J=1.5 Hz), 7.66 (t, 1H, J=1.5 Hz), 4.46 (q, 2H, J=5.6 Hz), 3.87 (s, 3H), 2.72 (q, 2H, J=7.6 Hz), 1.22 (t, 3H, J=7.6 Hz). $^{13}$C NMR (DMSO-d$_6$, 125 MHz) δ 170.1, 147.4, 146.8, 141.5, 140.3, 136.5, 134.7, 130.1, 129.0, 123.3, 120.4, 120.1, 39.7, 38.8, 27.9, 15.3. HRMS (ESI) m/z 363.094 found (M+H)$^+$, 363.0944 calculated for C$_{16}$H$_{19}$N$_4$S$_2$O$_2$.

Example 112: (5-((3-(3,5-Dimethylisoxazol-4-yl)-5-ethylphenyl)sulfonyl)thiazol-2-yl)methanamine hydrochloride

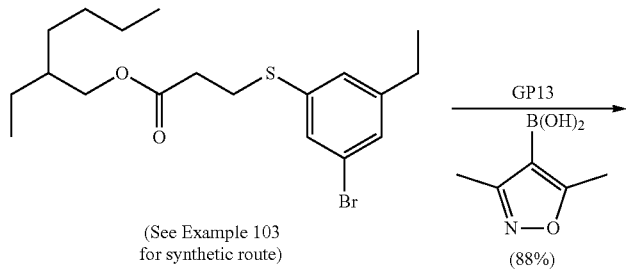

(See Example 103 for synthetic route)

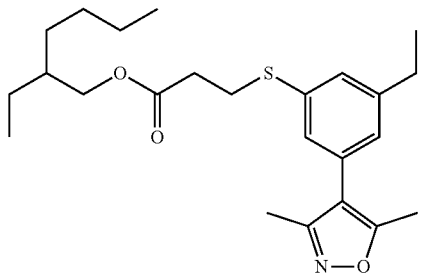

(88%)

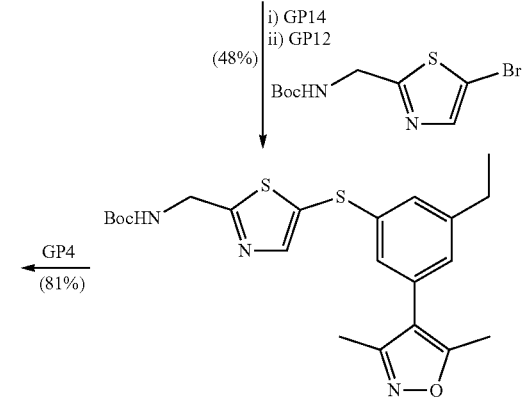

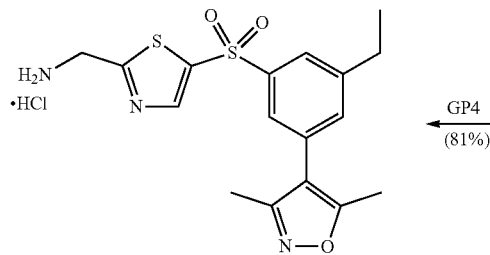

2-Ethylhexyl 3-((3-(3,5-dimethylisoxazol-4-yl)-5-ethylphenyl)thio)propanoate was synthesised according to general procedures GP13—from 2-ethylhexyl 3-((3-bromo-5-ethylphenyl)thio)propanoate (250 mg, 0.623 mmol), (3,5-dimethylisoxazol-4-yl)boronic acid (105 mg, 0.747 mmol), Pd(PPh$_3$)$_4$ (72 mg, 0.062 mmol), K$_2$CO$_3$ (172 mg, 1.246 mmol), 1,2-DME:H$_2$O (5:1, 6 mL); 100° C., 16 h. Chromatographic purification (2→40% EtOAc in hexane) afforded a yellow oil (228 mg, 88%). $^1$H NMR (CDCl$_3$, 500 MHz) δ 7.18 (t, 1H, J=1.6 Hz), 7.04 (t, 1H, J=1.6 Hz), 6.91 (t, 1H, J=1.5 Hz), 4.05-3.99 (m, 2H), 3.19 (t, 2H, J=7.4 Hz), 2.68-2.64 (m, 4H), 2.40 (s, 3H), 2.27 (s, 3H), 1.59-1.54 (m, 1H), 1.37-1.32 (m, 2H), 1.29-1.24 (m, 9H), 0.89-0.86 (m, 6H).

tert-Butyl ((5-((3-(3,5-dimethylisoxazol-4-yl)-5-ethylphenyl)thio)thiazol-2-yl)methyl) carbamate was synthesised according to general procedures GP14 and GP12—from i) 2-ethylhexyl 3-((3-(3,5-dimethylisoxazol-4-yl)-5-ethylphenyl)thio)propanoate (225 mg, 0.539 mmol), NaO$^t$Bu (129 mg, 1.347 mmol), toluene:$^t$BuOH (4:1, 5 mL); rt, 4 h (work-up not performed); ii) To the reaction mixture were added tert-butyl ((5-bromothiazol-2-yl)methyl)carbamate (158 mg, 0.539 mmol), Pd$_2$(dba)$_3$ (25 mg, 10 mol % Pd), Xantphos (62 mg, 20 mol %); 110° C., 16 h. Chromatographic purification (10→50% EtOAc in hexane) afforded a yellow oil (115 mg, 48%). $^1$H NMR (CDCl$_3$, 500 MHz) δ 7.78 (s, 1H), 7.06 (t, 1H, J=1.7 Hz), 6.90 (t, 1H, J=1.4 Hz), 6.86 (t, 1H, J=1.7 Hz), 5.31 (br s, 1H), 4.59 (d, 2H, J=5.9 Hz), 2.63 (q, 2H, J=7.6 Hz), 2.35 (s, 3H), 2.21 (s, 3H), 1.44 (s, 9H), 1.22 (t, 3H, J=7.6 Hz). LCMS (ESI) m/z 446.1539 found (M+H)$^+$, C$_{22}$H$_{28}$N$_3$S$_2$O$_3$.

Example 112 was synthesised according to general procedures GP4—from i) tert-butyl ((5-((3-(3,5-dimethylisoxazol-4-yl)-5-ethylphenyl)thio)thiazol-2-yl)methyl) carbamate (110 mg, 0.247 mmol), m-CPBA (77%; 138 mg, 0.617 mmol), DCM (5 mL); rt, 18 h; chromatography (EtOAc/cyclohexane 15→65%). ii) 4 M HCl in dioxane (1.05 mL); rt, 4 h. The mixture was diluted with Et$_2$O and the precipitate collected using filtration, washing with excess Et$_2$O, and dried under vacuum to afford the amine hydrochloride as a white solid (78 mg, 81% over two steps). $^1$H NMR (DMSO-d$_6$, 500 MHz) δ 8.84 (br s, 3H), 8.67 (s, 1H), 7.89 (t, 1H, J=1.6 Hz), 7.82 (t, 1H, J=1.7 Hz), 7.65 (t, 1H, J=1.5 Hz), 4.48 (br s, 2H), 2.78 (q, 2H, J=7.6 Hz), 2.42 (s, 3H), 2.24 (s, 3H), 1.23 (t, 3H, J=7.6 Hz). $^{13}$C NMR (DMSO-d$_6$, 125 MHz) δ 170.3, 166.2, 158.0, 147.7, 147.1, 141.4, 140.0, 134.3, 131.9, 125.1, 124.4, 114.5, 39.7, 27.8, 15.3, 11.4, 10.4. HRMS (ESI) m/z 378.0935 found (M+H)$^+$, 378.0941 calculated for C$_{17}$H$_{20}$N$_3$S$_2$O$_3$.

Example 113: 3-(3-((2-((Aminomethyl)thiazol-5-yl)sulfonyl)-5-ethylphenyl)pyridine 1-oxide hydrochloride 2-Ethylhexyl 3-((3-ethyl-5-(pyridin-3-yl)phenyl)thio)propanoate was synthesised according to general procedures GP13—from 2-ethylhexyl 3-((3-bromo-5-ethylphenyl)thio)propanoate (250 mg, 0.623 mmol), pyridin-3-ylboronic acid (92 mg, 0.747 mmol), Pd(PPh$_3$)$_4$ (72 mg, 0.062 mmol), K$_2$CO$_3$ (172 mg, 1.246 mmol), 1,2-DME:H$_2$O (5:1, 6 mL); 100° C., 16 h. Chromatographic purification (10→80% EtOAc in hexane) afforded a dark yellow oil (231 mg, 93%). $^1$H NMR (CDCl$_3$, 500 MHz) δ 8.82 (dd, 1H, J=2.4, 0.8 Hz), 8.59 (dd, 1H, J=4.8, 1.6 Hz), 7.85 (ddd, 1H, J=7.9, 2.3, 1.7 Hz), 7.37-7.34 (m, 2H), 7.23 (d, 2H, J=1.7 Hz), 4.04-3.98 (m, 2H), 3.22 (t, 2H, J=7.4 Hz), 2.72-2.65 (m, 4H), 1.58-1.54 (m, 1H), 1.37-1.31 (m, 2H), 1.30-1.26 (m, 9H), 0.87 (t, 6H, J=7.5 Hz). LCMS (ESI) m/z 400.4766 found (M+H)$^+$ for C$_{24}$H$_{34}$NSO$_2$.

tert-Butyl ((5-((3-ethyl-5-(pyridin-3-yl)phenyl)thio)thiazol-2-yl)methyl)carbamate was synthesised according to general procedures GP14 and GP12—from i) 2-ethylhexyl 3-((3-ethyl-5-(pyridin-3-yl)phenyl)thio)propanoate (220 mg, 0.55 mmol), NaO$^t$Bu (132 mg, 1.38 mmol), toluene:$^t$BuOH (4:1, 5 mL); rt, 4 h (work-up not performed); ii) To the reaction mixture were added tert-butyl ((5-bromothiazol-2-yl)methyl)carbamate (161 mg, 0.55 mmol), Pd$_2$(dba)$_3$ (25 mg, 10 mol % Pd), Xantphos (64 mg, 20 mol %); 110° C., 16 h. Chromatographic purification (20→100% EtOAc in hexane) afforded a yellow oil (105 mg, 45%). $^1$H NMR (CDCl$_3$, 500 MHz) δ 8.76 (dd, 1H, J=2.4, 0.8 Hz), 8.58 (dd, 1H, J=4.8, 1.6 Hz), 7.81 (s, 1H), 7.79 (ddd, 1H, J=7.9, 2.3, 1.7 Hz), 7.34 (ddd, 1H, J=7.9, 4.8, 0.8 Hz), 7.24-7.23 (m, 2H), 7.12 (t, 1H, J=1.6 Hz), 5.32 (br s, 1H), 4.60 (d, 2H, J=5.8 Hz), 2.67 (q, 2H, J=7.6 Hz), 1.44 (s, 9H), 1.25 (t, 3H, J=7.6 Hz). LCMS (ESI) m/z 428.1429 found (M+H)$^+$, C$_{22}$H$_{26}$N$_3$S$_2$O$_2$.

Example 113 was synthesised according to general procedures GP4—from i) 3-(3-((2-(((tert-butoxycarbonyl)amino)methyl)thiazol-5-yl)thio)-5-ethylphenyl)pyridine

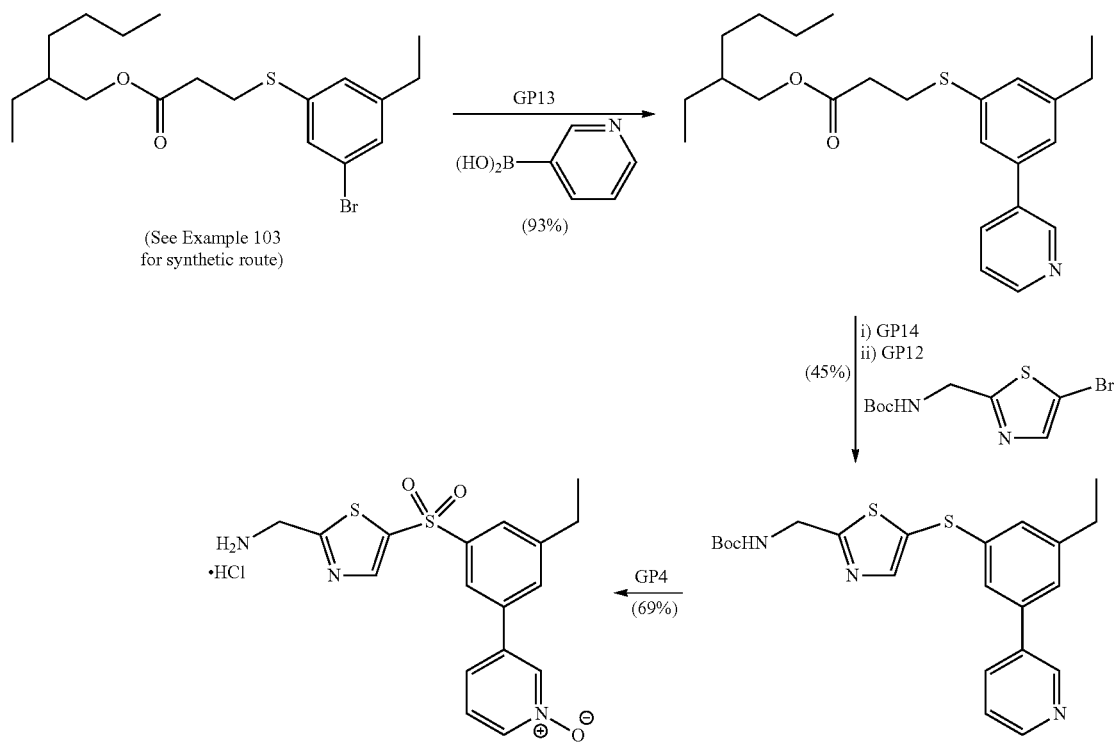

1-oxide (105 mg, 0.246 mmol), m-CPBA (77%; 138 mg, 0.614 mmol), DCM (5 mL); rt, 18 h; chromatography (EtOAc/cyclohexane 80→100%, then MeOH/EtOAc 0→50%). ii) 4 M HCl in dioxane (0.9 mL); rt, 4 h. The mixture was diluted with Et$_2$O and the precipitate collected using filtration, washing with excess Et$_2$O, and dried under vacuum to afford the amine hydrochloride as a white solid (68 mg, 69% over two steps). $^1$H NMR (DMSO-d$_6$, 500 MHz) δ 8.96 (s, 1H), 8.84 (br s, 3H), 8.70 (s, 1H), 8.50 (d, 1H, J=6.3 Hz), 8.22 (s, 1H), 8.04-7.98 (m, 3H), 7.72-7.69 (m, 1H), 4.47 (d, 2H, J=5.4 Hz), 2.80 (q, 2H, J=7.6 Hz), 1.25 (t, 3H, J=7.6 Hz). $^{13}$C NMR (DMSO-d$_6$, 125 MHz) δ 170.3, 148.0, 147.5, 141.9, 139.9, 138.5, 137.7, 137.4, 136.3, 133.0, 128.0, 127.1, 126.8, 123.2, 39.7, 27.9, 15.2. HRMS (ESI) m/z 376.0793 found (M+H)$^+$, 376.0784 calculated for $C_{17}H_{18}N_3S_2O_3$.

Example 114: (5-((5-(tert-Butyl)-[1,1'-biphenyl]-3-yl)sulfonyl)thiazol-2-yl)methanamine hydrochloride 3H), 4.05-3.99 (m, 2H), 3.23 (t, 2H, J=7.4 Hz), 2.68 (t, 2H, J=7.4 Hz), 1.59-1.55 (m, 1H), 1.37 (s, 9H), 1.34-1.30 (m, 2H), 1.30-1.26 (m, 6H), 0.88 (t, 6H, J=7.4 Hz). LCMS m/z 427.2577 found (M+H)$^+$ for $C_{27}H_{39}SO_2$.

tert-Butyl ((5-((5-(tert-butyl)-[1,1'-biphenyl]-3-yl)thio)thiazol-2-yl)methyl)carbamate was synthesised according to general procedures GP14 and GP12—from i) 2-ethylhexyl 3-((5-(tert-butyl)-[1,1'-biphenyl]-3-yl)thio)propanoate (250 mg, 0.59 mmol), NaOBu (141 mg, 1.46 mmol), toluene:$^t$BuOH (4:1, 5 mL); rt, 4 h (work-up not performed); ii) To the reaction mixture were added tert-butyl ((5-bromothiazol-2-yl)methyl)carbamate (172 mg, 0.59 mmol), Pd$_2$(dba)$_3$ (27 mg, 10 mol % Pd), Xantphos (68 mg, 20 mol %); 110° C., 16 h. Chromatographic purification (5→20% EtOAc in hexane) afforded a yellow oil (171 mg, 64%). $^1$H NMR (CDCl$_3$, 500 MHz) δ 8.80 (s, 1H), 7.51-7.49 (m, 2H), 7.44-7.41 (m, 3H), 7.36-7.33 (m, 1H), 7.31 (s, 1H), 7.25 (t, 1H, J=1.6 Hz), 5.30 (br s, 1H), 4.59 (d, 2H, J=5.9 Hz), 1.44

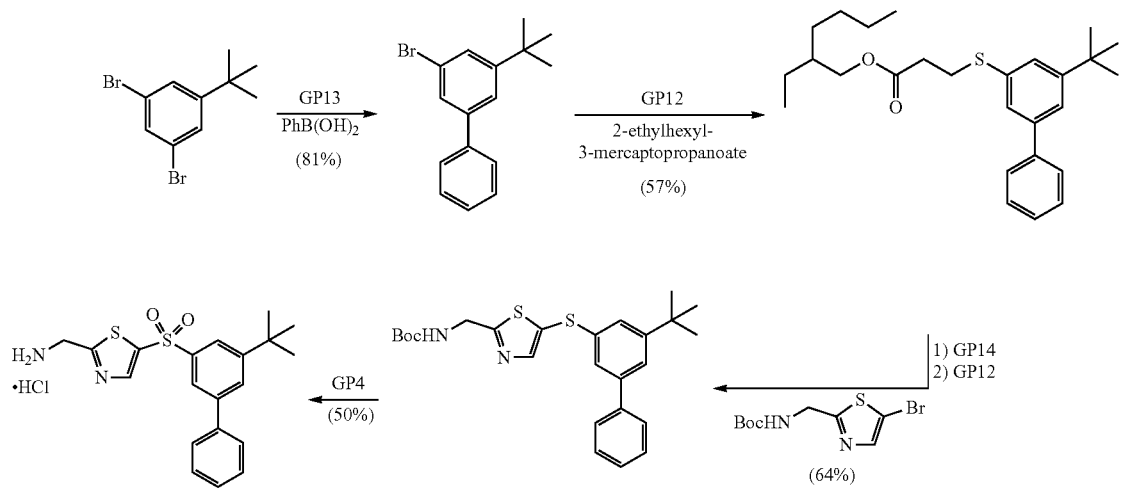

3-Bromo-5-(tert-butyl)-1,1'-biphenyl was synthesised according to general procedures GP13—from 1,3-dibromo-5-(tert-butyl)benzene (1.0 g, 3.42 mmol), phenylboronic acid (459 mg, 3.77 mmol), Pd(PPh$_3$)$_4$ (393 mg, 0.34 mmol), K$_2$CO$_3$ (947 mg, 6.85 mmol), 1,2-DME:H$_2$O (5:1, 12 mL); 100° C., 16 h. Chromatographic purification (1-10% EtOAc in hexane) afforded a clear colourless oil (85 mg, 81%). $^1$H NMR (CDCl$_3$, 500 MHz) δ 7.58-7.56 (m, 3H), 7.53-7.52 (m, 2H), 7.46-7.45 (m, 2H), 7.38 (t, 1H, J=7.4 Hz), 1.38 (s, 9H). 2-Ethylhexyl 3-((5-(tert-butyl)-[1,1'-biphenyl]-3-yl)thio)propanoate was synthesised according to general procedures GP12—from 3-bromo-5-(tert-butyl)-1,1'-biphenyl (300 mg, 1.04 mmol), 2-ethylhexyl-3-mercaptopropionate (0.23 mL, 1.04 mmol), Pd$_2$(dba)$_3$ (24 mg, 2.5 mol %), Xantphos (30 mg, 5 mol %), DIPEA (0.36 mL, 2.074 mmol), toluene (10 mL); 110° C., 16 h. Chromatographic purification (10→100% dichloromethane in hexane) afforded a clear colourless yellow oil (254 mg, 57%). $^1$H NMR (CDCl$_3$, 500 MHz) δ 7.58-7.56 (m, 2H), 7.46-7.43 (m, 3H), 7.40-7.34 (m, 3H), 4.05-3.99

(s, 9H), 1.33 (s, 9H). LCMS (ESI) m/z 455.1922 found (M+H)$^+$, $C_{25}H_{31}N_2S_2O_2$.

Example 114 was synthesised according to general procedures GP4—from i) tert-butyl ((5-((5-(tert-butyl)-[1,1'-biphenyl]-3-yl)thio)thiazol-2-yl)methyl)carbamate (170 mg, 0.37 mmol), m-CPBA (77%; 209 mg, 0.93 mmol), DCM (8 mL); rt, 18 h; chromatography (EtOAc/cyclohexane 5→55%). ii) 4 M HCl in dioxane (1.0 mL); rt, 4 h. The mixture was diluted with Et$_2$O and the precipitate collected using filtration, washing with excess Et$_2$O, and dried under vacuum to afford the amine hydrochloride as a white solid (79 mg, 50% over two steps). $^1$H NMR (DMSO-d$_6$, 500 MHz) δ 8.75 (br s, 3H), 8.72 (s, 1H), 8.04 (t, 1H, J=1.7 Hz), 8.01 (t, 1H, J=1.7 Hz), 7.97 (t, 1H, J=1.7 Hz), 7.74 (d, 2H, J=7.1 Hz), 7.52 (t, 2H, J=7.5 Hz), 7.46 (t, 1H, J=7.3 Hz), 4.47 (s, 2H), 1.38 (s, 9H). $^{13}$C NMR (DMSO-d$_6$, 125 MHz) δ 170.2, 153.9, 147.7, 142.1, 141.5, 140.2, 138.5, 130.0, 129.2, 128.5, 127.3, 122.5, 122.2, 39.7, 35.2, 30.8. HRMS (ESI) m/z 409.1007 found (M+Na)$^+$, 409.1015 calculated for $C_{20}H_{22}N_2S_2O_2Na$.

Example 115: (5-((3-Ethyl-5-(thiophen-3-yl)phenyl)sulfonyl)thiazol-2-yl)methanamine hydrochloride

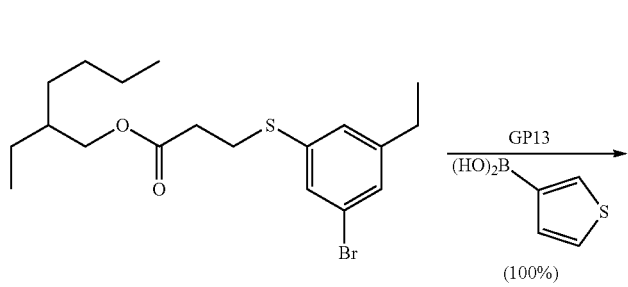

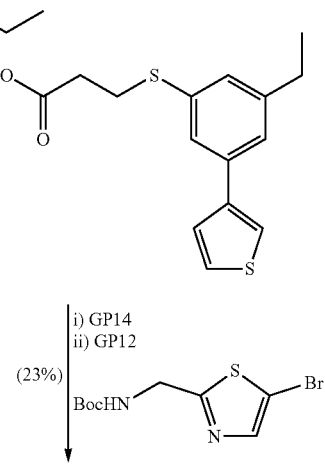

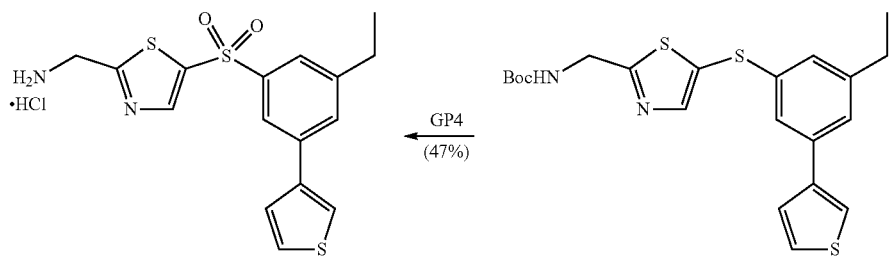

2-Ethylhexyl 3-((3-ethyl-5-(thiophen-3-yl)phenyl)thio)propanoate was synthesised according to general procedures GP13—from 2-ethylhexyl 3-((3-bromo-5-ethylphenyl)thio)propanoate (200 mg, 0.498 mmol), thiophen-3-ylboronic acid (76 mg, 0.598 mmol), Pd(PPh$_3$)$_4$ (58 mg, 0.05 mmol), K$_2$CO$_3$ (138 mg, 0.996 mmol), 1,2-DME:H$_2$O (5:1, 4.8 mL); 100° C., 16 h. Chromatographic purification (2→20% EtOAc in hexane) afforded a clear colourless oil (202 mg, 100%). $^1$H NMR (CDCl$_3$, 500 MHz) δ 7.45 (dd, 1H, J=2.8, 1.4 Hz), 7.42 (t, 1H, J=1.7 Hz), 7.39-7.36 (m, 2H), 7.27 (t, 1H, J=1.5 Hz), 7.14 (t, 1H, J=1.5 Hz), 4.05-3.99 (m, 2H), 3.23 (t, 2H, J=7.4 Hz), 2.69-2.65 (m, 4H), 1.59-1.54 (m, 1H), 1.38-1.32 (m, 2H), 1.30-1.26 (m, 9H), 0.88 (t, 6H, J=7.5 Hz).

tert-Butyl ((5-((3-ethyl-5-(thiophen-3-yl)phenyl)thio)thiazol-2-yl)methyl)carbamate was synthesised according to general procedures GP14 and GP12—from i) 2-ethylhexyl 3-((3-ethyl-5-(thiophen-3-yl)phenyl)thio)propanoate (200 mg, 0.494 mmol), NaOBu (119 mg, 1.24 mmol), toluene:$^t$BuOH (4:1, 5 mL); rt, 4 h (work-up not performed); ii) To the reaction mixture were added tert-butyl ((5-bromothiazol-2-yl)methyl)carbamate (145 mg, 0.494 mmol), Pd$_2$(dba)$_3$ (23 mg, 10 mol % Pd), Xantphos (57 mg, 20 mol %); 110° C., 16 h. Chromatographic purification (10→55% EtOAc in hexane) afforded a yellow oil (50 mg, 23%). $^1$H NMR (CDCl$_3$, 500 MHz) δ 7.79 (s, 1H), 7.40 (dd, 1H, J=3.0, 1.4 Hz), 7.36 (dd, 1H, J=5.0, 3.0 Hz), 7.30 (dd, 1H, J=5.0, 1.4 Hz), 7.28 (t, 1H, J=1.7 Hz), 7.26-7.25 (m, 1H), 7.02 (t, 1H, J=1.5 Hz), 5.25 (br s, 1H), 4.59 (d, 2H, J=5.8 Hz), 2.63 (q, 2H, J=7.6 Hz), 1.45 (s, 9H), 1.23 (t, 3H, J=7.6 Hz). LCMS (ESI) m/z 433.1099 found (M+H)$^+$, C$_{21}$H$_{25}$N$_2$S$_3$O$_2$.

Example 115 was synthesised according to general procedures GP4—from i) tert-butyl ((5-((3-ethyl-5-(thiophen-3-yl)phenyl)thio)thiazol-2-yl)methyl)carbamate (50 mg, 0.116 mmol), m-CPBA (77%; 65 mg, 0.29 mmol), DCM (3 mL); rt, 18 h; chromatography (EtOAc/cyclohexane 15→45%). ii) 4 M HCl in dioxane (0.5 mL); rt, 4 h. The mixture was diluted with Et$_2$O and the precipitate collected using filtration, washing with excess Et$_2$O, and dried under vacuum to afford the amine hydrochloride as a white solid (21 mg, 47% over two steps). $^1$H NMR (DMSO-d$_6$, 500 MHz) δ 8.75 (br s, 3H), 8.68 (s, 1H), 8.13 (dd, 1H, J=2.9, 1.3 Hz), 8.10 (s, 1H), 7.97 (s, 1H), 7.79 (s, 1H), 7.71 (dd, 1H, J=5.0, 2.9 Hz), 7.67 (dd, 1H, J=5.0, 1.3 Hz), 4.47 (s, 2H), 2.76 (q, 2H, J=7.6 Hz), 1.24 (t, 3H, J=7.6 Hz). $^{13}$C NMR (DMSO-d$_6$, 125 MHz) δ 170.1, 147.6, 147.0, 141.6, 140.2, 139.4, 136.9, 131.5, 127.7, 126.3, 124.5, 123.2, 121.7, 39.7, 27.9, 15.3. HRMS (ESI) m/z 365.0516 found (M+H)$^+$, 365.0447 calculated for C$_{16}$H$_{17}$N$_2$S$_3$O$_2$.

Example 116: (5-((3-(1-Methyl-1H-pyrazol-4-yl)phenyl)sulfonyl)thiazol-2-yl)methanamine

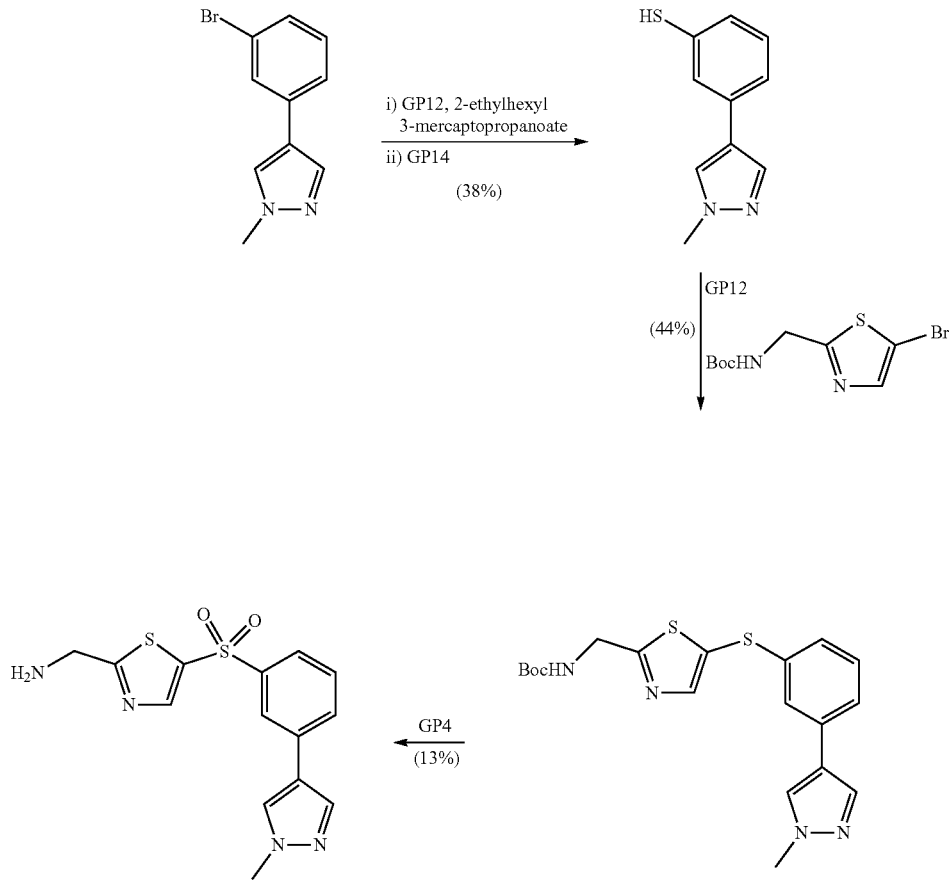

2-Ethylhexyl 3-((3-(1-methyl-1H-pyrazol-4 yl)phenyl)thio)propanoate was synthesised according to general procedures GP12—from 4-(3-bromophenyl)-1-methyl-1H-pyrazole (2.5 g, 10.5 mmol), Pd$_2$(dba)$_3$ (0.24 g, 2.5 mol %), Xanthphos (0.3 g, 5 mol %), 2-ethylhexyl-3-mercaptopropionate (2.29 g, 10.5 mmol), DIPEA (4.8 ml, 27.6 mmol) and toluene (30 ml); 110° C., 16 h. Chromatographic purification (28% EtOAc in hexane) afforded a yellow oil (0.60 g, 44%). $^1$H NMR (400 MHz, DMSO-d$_6$) δ: 8.20 (s, 1H), 7.87 (s, 1H), 7.51-7.50 (m, 1H), 7.40-7.38 (m, 1H), 7.39-7.28 (m, 1H), 7.15-7.13 (m, 1H), 3.95-3.93 (m, 2H), 3.85 (s, 3H), 3.22-3.19 (m, 2H), 2.64-2.61 (m, 2H), 1.52-1.50 (m, 1H), 1.31-1.29 (m, 7H), 1.18-1.16 (m, 1H), 0.85-0.83 (m, 6H). LCMS (ESI) m/z 375 (M+H)$^+$.

3-(1-Methyl-1H-pyrazol-4-yl)benzenethiol was synthesised according to general procedures GP14—from 2-ethylhexyl 3-((3-(1-methyl-1H-pyrazol-4 yl)phenyl)thio)propanoate (1.80 g, 4.81 mmol), KO$^t$Bu (1.0 M in THF; 14.5 mL, 14.5 mmol), THF (25 mL); rt, 1 h. Yellow oil (0.8 g, 87%). $^1$H NMR (400 MHz, DMSO-d$_6$) δ: 8.79 (s, 1H), 8.16 (s, 1H), 8.11 (s, 1H), 7.84 (d, J=11.3 Hz, 1H), 7.37 (t, J=7.3 Hz, 1H), 7.30 (d, J=7.3 Hz, 1H), 5.34 (s, 1H), 3.85 (s, 3H). LCMS (ESI) m/z 191 (M+H)$^+$.

tert-Butyl ((5-((3-(1-methyl-1H-pyrazol-4-yl)phenyl)thio)thiazol-2-yl)methyl)carbamate was synthesised according to general procedures GP12—from tert-butyl ((5-bromothiazol-2-yl)methyl)carbamate (1.0 g, 3.41 mmol), 3-(1-methyl-1H-pyrazol-4-yl)benzenethiol (0.74 g, 3.89 mmol), Pd$_2$(dba)$_3$ (0.10 g, 3 mol %), Xantphos (0.10 g, 6 mol %), NaO$^t$Bu (0.60 g, 6.24 mmol), toluene/BuOH (5:1, 36 mL); 110° C., 16 h. Chromatographic purification (70% EtOAc in hexane) afforded a yellow liquid (0.60 g, 44%). $^1$H NMR (400 MHz, DMSO-d$_6$) δ 8.12 (s, 1H), 7.93-7.83 (m, 1H), 7.78-7.75 (t, J=5.8 Hz, 1H), 7.33-7.31 (m, 1H), 7.78-7.43 (m, 2H), 7.33-7.29 (m, 1H), 7.01 (d, J=7.8 Hz, 1H), 4.39-4.38 (m, 2H), 3.84 (s, 3H), 1.37 (s, 9H). LCMS (ESI) m/z 403 (M+H)$^+$.

Example 116 was synthesised according to general procedures GP4—from i) m-CPBA (55%; 0.72 g, 2.18 mmol), tert-butyl ((5-((3-(1-methyl-1H-pyrazol-4-yl)phenyl)thio)thiazol-2-yl)methyl)carbamate (0.40 g, 0.995 mmol) and DCM (10 mL); rt, 3 h. Chromatography (72% EtOAc in cyclohexane), brown oil (280 mg, 65%); ii) 2 M HCl in Et$_2$O (3.0 ml), tert-butyl ((5-((3-(1-methyl-1H-pyrazol-4-yl)phenyl)sulfonyl)thiazol-2-yl)methyl)carbamate (280 mg, 0.644 mmol) and DCM (3.0 mL); rt, 3 h. The hydrochloride salt was diluted with DCM and washed with sat. NaHCO$_3$ to afford the free base. The crude amine was purified by preparative TLC (10% MeOH in DCM) to afford a brown semi-solid (40 mg, 20%). $^1$H NMR (500 MHz, Chloroform-d) δ 8.23 (s, 1H), 8.04 (m, 1H), 7.86-7.77 (m, 2H), 7.75-7.65 (m, 2H), 7.52 (t, J=7.8 Hz, 1H), 4.17 (s, 2H), 3.97 (s, 3H), 1.78 (s, 2H). $^{13}$C NMR (126 MHz, Chloroform-d) δ 184.34, 148.12, 142.32, 138.57, 136.98, 134.60, 130.48, 130.17, 127.68, 125.03, 123.98, 121.41, 44.28, 39.40. HRMS (ESI) for C$_{14}$H$_{15}$N$_4$O$_2$S$_2$ ([M+H]$^+$): Calculated 335.0631; Observed 335.0621.

Example 117: (5-((1-Phenyl-1H-pyrazol-4-yl)sulfonyl)thiophen-2-yl)methanamine dihydrochloride

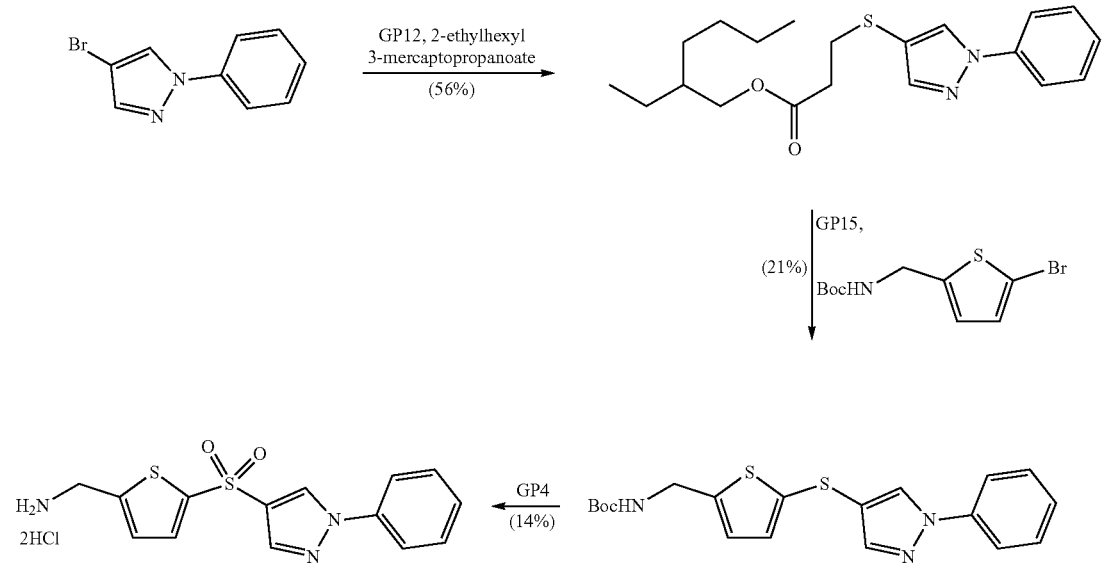

2-Ethylhexyl 3-((1-phenyl-1H-pyrazol-4-yl)thio)propanoate was synthesised according to general procedures GP12—from 4-bromo-1-phenyl-1H-pyrazole (2.20 g, 9.86 mmol), Pd$_2$(dba)$_3$ (0.220 g, 2.5 mol %), Xantphos (0.285 g, 5 mol %), 2-ethylhexyl-3-mercaptopropionate (2.15 g, 9.86 mmol), DIPEA (1.59 mL, 19.7 mmol) and toluene (10 mL) 110° C., 16 h. Chromatographic purification (EtOAc/hexane 5→8%) afforded a yellow oil (2.0 g, 56%). $^1$H NMR (400 MHz, DMSO-d$_6$) δ 7.98 (s, 1H), 7.72 (s, 1H), 7.67-7.65 (m, 2H), 7.46 (t, J=8.2 Hz, 2H), 7.31 (t, J=7.3 Hz, 1H), 4.00 (t, J=2.9 Hz, 2H), 2.93 (t, J=7.1 Hz, 2H), 2.60 (t, J=7.1 Hz, 2H), 1.58-1.55 (m, 2H), 1.38-1.25 (m, 7H), 0.90-0.86 (m, 6H). LCMS (ESI) m/z 361 (M+H$^+$).

tert-Butyl ((5-((1-phenyl-1H-pyrazol-4-yl)thio)thiophen-2-yl)methyl)carbamate was synthesised according to general procedures GP15—from 2-ethylhexyl 3-((1-phenyl-1H-pyrazol-4-yl)thio)propanoate (1.50 g, 4.16 mmol), NaO$^t$Bu (1.19 g, 12.4 mmol), toluene/$^t$BuOH (5:1, 60 mL); rt, 4 h, then tert-butyl ((5-bromothiophen-2-yl)methyl)carbamate (1.21 g, 4.16 mmol), Pd$_2$(dba)$_3$ (0.380 g, 10 mol %) and Xantphos (0.480 g, 20 mol %); 110° C., 16 h. Chromatographic purification (EtOAc/hexane 10→12%) afforded a yellow oil (0.34 g, 21%). $^1$H NMR (400 MHz, Chloroform-d) δ 8.00 (s, 1H), 7.73 (s, 1H), 7.64 (d, J=7.8 Hz, 2H), 7.47 (t, J=8.0 Hz, 2H), 7.36-7.26 (m, 2H), 7.01 (d, J=3.4 Hz, 1H), 6.76 (br s, 1H), 4.37 (d, J=5.4 Hz, 2H), 1.43 (s, 9H). LCMS (ESI) m/z 388 (M+H$^+$).

Example 117 was synthesised according to general procedures GP4—from i) m-CPBA (55%; 0.606 g, 1.93 mmol), tert-butyl ((5-((1-phenyl-1H-pyrazol-4-yl)thio)thiophen-2-yl)methyl)carbamate (0.340 g, 0.880 mmol) and DCM (10 ml); rt, 3 h. Chromatography (20% EtOAc in cyclohexane), brown oil (110 mg, 30%); ii) 2 M HCl in Et$_2$O (3.0 ml), tert-butyl ((5-((1-phenyl-1H-pyrazol-4-yl)sulfonyl)thiophen-2-yl)methyl)carbamate (0.11 g, 0.262 mmol) and DCM (7.0 ml); rt, 4 h. The desired amine hydrochloride salt was obtained as a white solid (43 mg, 46%) and did not require further purification. $^1$H NMR (500 MHz, DMSO-d$_6$) δ 9.37 (s, 1H), 8.82 (s, 3H), 8.28 (s, 1H), 7.94-7.87 (m, 2H), 7.81 (d, J=3.9 Hz, 1H), 7.60-7.49 (m, 2H), 7.46-7.37 (m, 2H), 4.28 (s, 2H). $^{13}$C NMR (126 MHz, DMSO-d$_6$) δ 144.26, 143.96, 139.84, 138.46, 132.97, 130.71, 130.32, 129.70, 128.00, 126.08, 119.41, 36.63. HRMS (ESI) for C$_{14}$H$_{11}$N$_2$O$_2$S$_2$ ([M-NH$_2$]$^+$): Calculated 303.0262; Observed 303.0262.

Example 118: (5-((2-Phenylpyrimidin-5-yl)sulfonyl)thiazol-2-yl)methanamine trihydrochloride

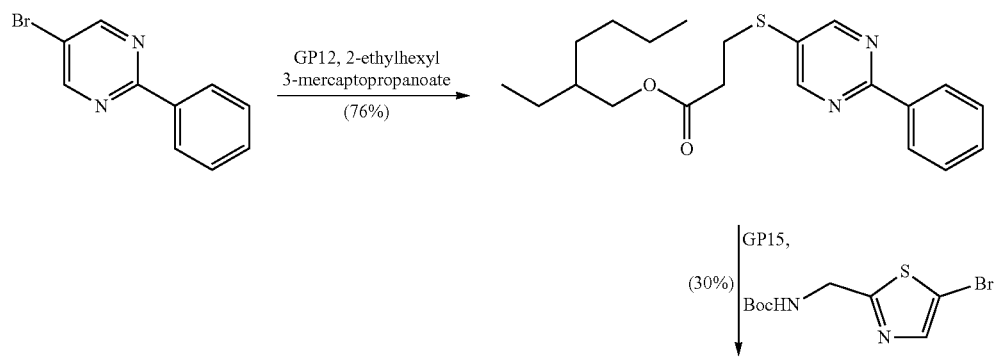

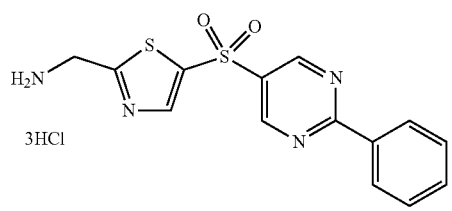 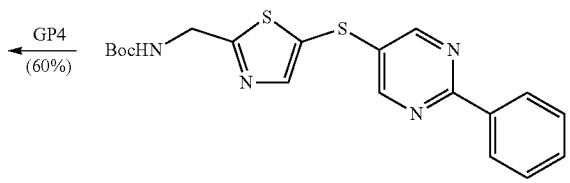

2-Ethylhexyl 3-((2-phenylpyrimidin-5-yl)thio)propanoate was synthesised according to general procedures GP12—from 5-bromo-2-phenylpyrimidine (1.0 g, 4.25 mmol), Pd$_2$(dba)$_3$ (90 mg, 2.5 mol %), Xantphos (200 mg, 5 mol %), 2-ethylhexyl-3-mercaptopropionate (0.91 g, 4.25 mmol), DIPEA (1.5 mL, 8.61 mmol) and toluene (25 mL), 110° C., 16 h. Chromatographic purification (4% EtOA in hexane) afforded a yellow oil (1.2 g, 76%). LCMS (ESI) m/z 373 (M+H)$^+$.

tert-Butyl ((5-((2-phenylpyrimidin-5-yl)thio)thiazol-2-yl)methyl)carbamate was synthesised according to general procedures GP15—from 2-ethylhexyl 3-((2-phenylpyrimidin-5-yl)thio)propanoate (1.0 g, 2.68 mmol), NaO$^t$Bu (0.640 g, 6.72 mmol), toluene/$^t$BuOH (4:1, 25 mL); rt, 4 h, then tert-butyl ((5-bromothiazol-2-yl)methyl)carbamate (0.780 g, 2.68 mmol), Pd$_2$(dba)$_3$ (0.240 g, 10 mol %) and XantPhos (0.30 g, 20 mol %); 110° C., 16 h. Chromatographic purification (40% EtOAc in hexane) afforded a yellow oil (0.30 g, 30%). $^1$H NMR (400 MHz, DMSO-d$_6$) δ 8.67 (s, 2H), 8.40-8.38 (m, 2H), 7.86 (s, 1H), 7.49-7.48 (m, 3H), 7.25 (s, 1H), 4.59 (d, J=5.8 Hz, 2H), 1.45 (s, 9H). LCMS (ESI) m/z 401 (M+H)$^+$.

Example 118 was synthesised according to general procedures GP4—from i) m-CPBA (55%; 0.34 g, 0.99 mmol), tert-butyl ((5-((2-phenylpyrimidin-5-yl)thio)thiazol-2-yl)methyl)carbamate (0.180 g, 0.450 mmol) and DCM (10 mL); rt, 3 h. Chromatography (50% EtOAc in cyclohexane), yellow solid (140 mg, 70%); ii) 2 M HCl in Et$_2$O (3.0 mL), tert-butyl ((5-((2-phenylpyrimidin-5-yl)sulfonyl)thiazol-2-yl)methyl)carbamate (0.140 g, 0.320 mmol) and DCM (10.0 mL); rt, 3 h. The desired amine hydrochloride salt was obtained as a white solid (50 mg, 50%) and did not require further purification. $^1$H NMR (500 MHz, DMSO-d$_6$) b 9.50 (s, 2H), 9.01 (s, 3H), 8.74 (s, 1H), 8.44 (d, J=7.2 Hz, 2H), 7.69-7.53 (m, 3H), 4.51 (s, 2H). $^{13}$C NMR (126 MHz, DMSO-d$_6$) δ 171.05, 166.62, 156.84, 148.64, 139.07, 135.32, 133.50, 132.74, 129.12, 128.87, 39.69. HRMS (ESI) for C$_{14}$H$_{13}$N$_4$O$_2$S$_2$ ([M+H]$^+$): Calculated 333.0480; Observed 333.0472.

Example 119: (5-((5-Methoxy-[1,1'-biphenyl]-3-yl)sulfonyl)thiophen-2-yl)methanamine hydrochloride

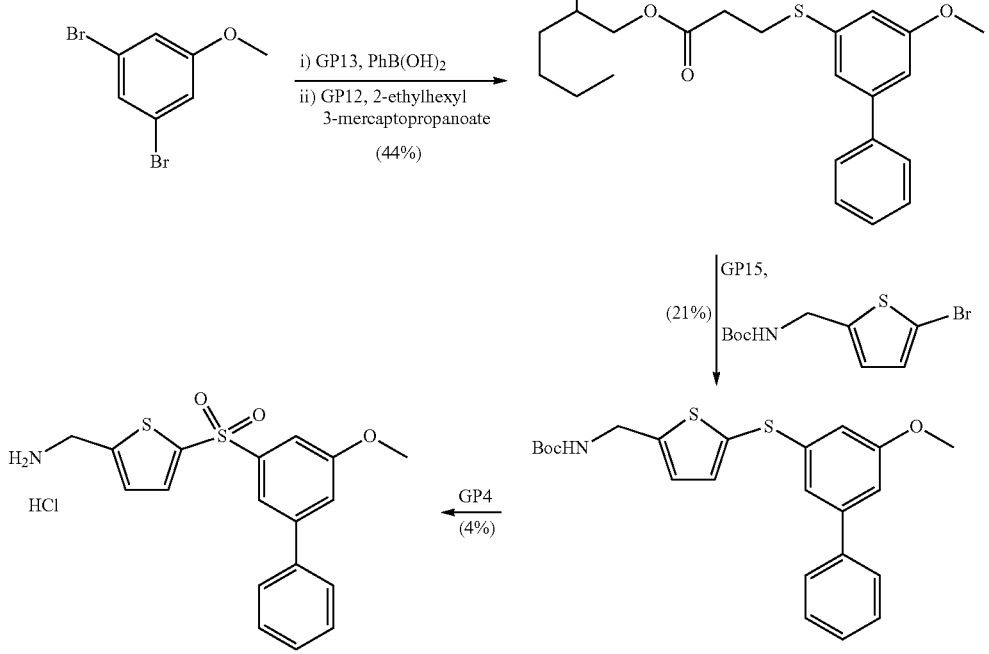

3-Bromo-5-methoxy-1,1'-biphenyl was synthesised according to general procedures GP13—from 1,3-dibromo-5-methoxybenzene (6.50 g, 24.4 mmol), phenylboronic acid (2.08 g, 17.0 mmol), Pd(PPh$_3$)$_4$ (1.40 g, 5 mol %), Na$_2$CO$_3$ (6.47 g, 61.0 mmol), toluene (70 mL), ethanol (7.0 mL) and water (7.0 mL); 100° C., 16 h. Chromatographic purification (hexane) afforded a colourless oil (4.1 g, contained a small amount of impurity), which is used in the subsequent transformation as an impure mixture. ¹H NMR of a pure chromatography fraction (400 MHz, DMSO-$d_6$) δ: 7.55-7.53 (m, 2H), 7.43-7.42 (m, 2H), 7.37 (d, J=7.3 Hz, 1H), 7.32-7.31 (m, 1H), 7.03 (d, J=1.4 Hz, 2H), 3.85 (s, 3H).

2-Ethylhexyl 3-((5-methoxy-[1,1'-biphenyl]-3-yl)thio)propanoate was synthesised according to general procedures GP12—from $Pd_2(dba)_3$ (0.356 g, 2.5 mol %), Xantphos (0.450 g, 5 mol %), 2-ethylhexyl-3-mercaptopropionate (3.40 g, 15.6 mmol), DIPEA (5.40 mL, 31.1 mmol) and toluene (40 mL); 110° C., 16 h. Chromatography (EtOAc/hexane 0→1%) afforded a yellow oil (3.0 g, 44% over 2 steps). ¹H NMR (400 MHz, DMSO-$d_6$) δ 7.66 (d, J=7.8 Hz, 2H), 7.46 (t, J=7.6 Hz, 2H), 7.27-7.25 (m, 1H), 7.13 (s, 1H), 7.02 (s, 1H), 6.88 (s, 1H), 3.94 (d, J=5.8 Hz, 2H), 3.83 (s, 3H), 3.25 (t, J=6.8 Hz, 2H), 2.65 (t, J=6.8 Hz, 2H), 1.51-1.49 (m, 1H), 1.30-1.22 (m, 8H), 0.84-0.81 (m, 6H). LCMS (ESI) m/z 401.2 (M+H)⁺.

tert-Butyl ((5-((5-methoxy-[1,1'-biphenyl]-3-yl)thio)thiophen-2-yl)methyl)carbamate was synthesised according to general procedures GP15—from 2-ethylhexyl 3-((5-methoxy-[1,1'-biphenyl]-3-yl)thio)propanoate (1.50 g, 3.74 mmol), NaO$^t$Bu (1.19 g, 12.4 mmol), toluene/$^t$BuOH (5:1, 60 mL); rt, 4 h, then tert-butyl ((5-bromothiophen-2-yl)methyl)carbamate (1.21 g, 4.14 mmol), $Pd_2(dba)_3$ (0.38 g, 10 mol %), Xantphos (0.48 g, 20 mol %); 110° C., 16 h. Chromatographic purification (EtOAc/hexane 10→12%) afforded a yellow oil (0.34 g, 21%). LCMS (ESI) m/z 311 (M-BocNH)⁺.

Example 119 was synthesised according to general procedures GP4—from i) m-CPBA (55%; 0.53 g, 1.70 mmol), tert-butyl ((5-((5-methoxy-[1,1'-biphenyl]-3-yl)thio)thiophen-2-yl)methyl)carbamate (0.33 g, 0.771 mmol) and DCM (10 mL); rt, 3 h. Chromatography (EtOAc/hexane 20%), brown oil (24 mg, 6.8%); ii) 2 M HCl in $Et_2O$ (3.0 ml), tert-butyl ((5-((5-methoxy-[1,1'-biphenyl]-3-yl)sulfonyl)thiophen-2-yl)methyl)carbamate (24 mg, 52.2 mol) and DCM (3.0 ml). rt, 4 h. White solid obtained (12 mg, 59%) without further purification. ¹H NMR (500 MHz, Methanol-$d_4$) δ 7.79 (d, J=3.8 Hz, 1H), 7.74 (t, J=1.6 Hz, 1H), 7.64-7.59 (m, 2H), 7.51-7.45 (m, 3H), 7.44-7.39 (m, 2H), 7.31 (d, J=3.9 Hz, 1H), 4.38 (s, 2H), 3.92 (s, 3H). ¹³C NMR (126 MHz, Methanol-$d_4$) δ 162.23, 145.77, 145.70, 145.11, 144.81, 140.20, 135.16, 131.54, 130.20, 129.64, 128.13, 118.99, 118.87, 112.01, 56.53, 38.47. HRMS (ESI) for $C_{18}H_{15}O_3S_2$ ([M-NH$_2$]⁺): Calculated 343.0462; Observed 343.0466.

Example 120: (5-((5-Ethyl-[1,1'-biphenyl]-3-yl)sulfonyl)thiophen-2-yl)methanamine hydrochloride

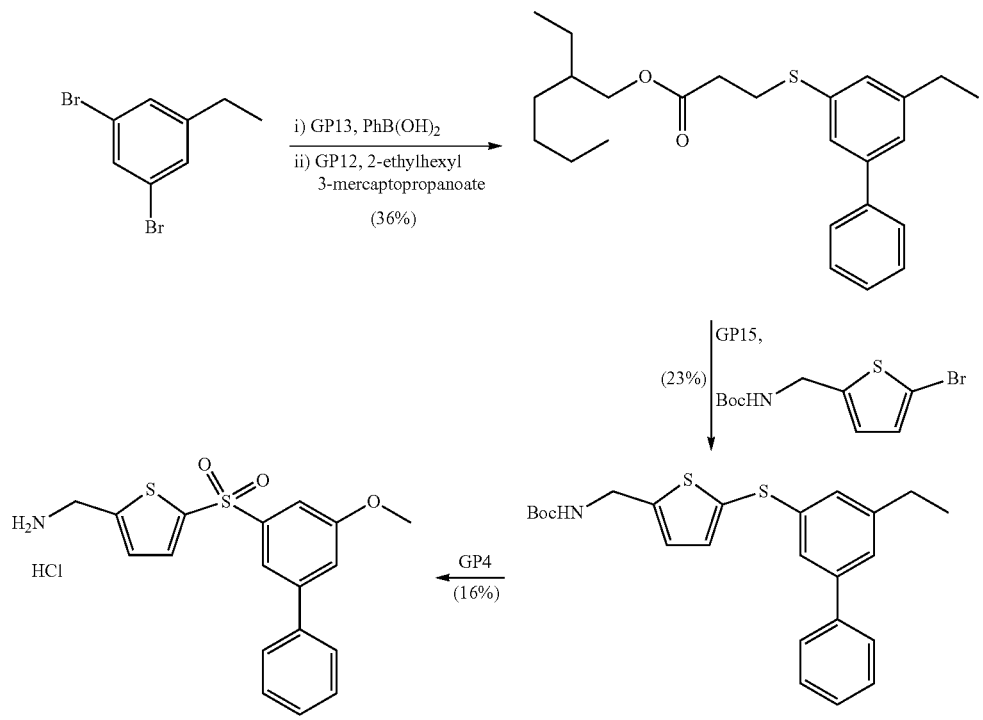

3-Bromo-5-ethyl-1,1'-biphenyl was synthesised according to general procedures GP13—from 1,3-dibromo-5-ethybenzene (1.50 g, 5.68 mmol), phenylboronic acid (0.62 g, 5.08 mmol), $Pd(PPh_3)_4$ (0.65 g, 10 mol %), $Na_2CO_3$ (1.20 g, 11.3 mmol), 1,4-dioxane (15 mL), ethanol (7.0 mL) and water (5.6 ml); 100° C., 16 h. Chromatographic purification (hexane) afforded a yellow oil (0.63 g, 47%). ¹H NMR (400 MHz, DMSO-$d_6$) δ: 7.68-7.64 (m, 3H), 7.51-7.39 (m, 5H), 2.68-2.66 (m, 2H), 1.22 (t, J=7.6 Hz, 3H).

2-Ethylhexyl 3-((5-ethyl-[1,1'-biphenyl]-3-yl)thio)propanoate was synthesised according to general procedures GP12—from 3-bromo-5-ethyl-1,1'-biphenyl (0.90 g, 3.42 mmol), $Pd_2(dba)_3$ (79.0 mg, 2.5 mol %), Xantphos (100 mg, 5 mol %), 2-ethylhexyl-3-mercaptopropionate (0.750 g, 3.44 mmol), DIPEA (1.18 ml, 6.79 mmol) and toluene (12 ml); 110° C., 16 h. Chromatography (EtOAc/hexane 4-8%) afforded a yellow oil (1.35 g, 98%). ¹H NMR (400 MHz, Chloroform-d) δ: 7.56 (d, J=7.3 Hz, 2H), 7.45-7.34 (m, 5H), 7.19 (s, 1H), 4.05-3.97 (m, 2H), 3.22 (t, J=7.3 Hz, 2H), 2.72-2.64 (m, 4H), 1.51-1.49 (m, 1H), 1.38-1.26 (m, 11H), 0.91→086 (m, 6H). LCMS (ESI) m/z 399 (M+H)+.

tert-Butyl ((5-((5-ethyl-[1,1'-biphenyl]-3-yl)thio)thiophen-2-yl)methyl)carbamate was synthesised according to general procedures GP15—from 2-ethylhexyl 3-((5-ethyl-[1,1'-biphenyl]-3-yl)thio)propanoate (1.40 g, 3.51 mmol), NaO<sup>t</sup>Bu (1.01 g, 10.5 mmol), toluene/BuOH (5:1, 60 mL); rt, 4 h, then tert-butyl ((5-bromothiophen-2-yl)methyl)carbamate (1.03 g, 3.53 mmol), Pd₂(dba)₃ (0.320 g, 10 mol %), Xantphos (0.407 g, 20 mol %); 110° C., 16 h. Chromatographic purification (EtOAc/hexane 10→12%) afforded a yellow oil (0.35 g, 23%). ¹H NMR (400 MHz, DMSO-d₆) δ 7.56 (d, J=7.6 Hz, 2H), 7.44 (t, J=7.5 Hz, 2H), 7.38-7.28 (m, 3H), 7.23 (s, 1H), 7.05 (s, 1H), 6.95 (m, 1H), 4.29 (dd, J=22.8, 5.6 Hz, 2H), 2.61 (q, J=8.0 Hz, 2H), 1.36 (s, 9H), 1.16 (t, J=13.6 Hz, 3H). LCMS (ESI) m/z 309 (M-BocNH)+.

Example 120 was synthesised according to general procedures GP4—from i) m-CPBA (55%; 0.567 g, 1.81 mmol), tert-butyl ((5-((5-ethyl-[1,1'-biphenyl]-3-yl)thio)thiophen-2-yl)methyl)carbamate (0.350 g, 0.822 mmol) and DCM (15 mL); rt, 3 h. Chromatographic purification (20% EtOAc in hexane) afforded a brown oil (100 mg, 27%); ii) 2 M HCl in Et₂O (6.0 mL), tert-butyl ((5-((5-ethyl-[1,1'-biphenyl]-3-yl) sulfonyl)thiophen-2-yl)methyl)carbamate (75 mg, 0164 mmol) and DCM (3.0 mL); rt, 4 h. White solid obtained (35 mg, 59%) without further purification. ¹H NMR (500 MHz, Methanol-d₄) δ 7.98 (m, 1H), 7.81 (m, 1H), 7.78 (d, J=3.8 Hz, 1H), 7.75 (m, 1H), 7.64-7.58 (m, 2H), 7.51-7.44 (m, 2H), 7.41 (m, 1H), 7.32 (d, J=3.9 Hz, 1H), 4.38 (s, 2H), 2.79 (q, J=7.6 Hz, 2H), 1.29 (t, J=7.6 Hz, 3H). ¹³C NMR (126 MHz, Methanol-d₄) δ 148.46, 146.00, 144.99, 144.33, 143.76, 140.40, 134.99, 133.03, 131.51, 130.21, 129.45, 128.13, 126.18, 124.13, 38.46, 29.68, 15.89. HRMS (ESI) for C₁₉H₁₇O₂S₂ ([M-NH₂]+): Calculated 341.0670; Observed 341.0667.

Example 121: (5-((4'-Methyl-5-(methylsulfonyl)-[1,1'-biphenyl]-3-yl)sulfonyl)thiazol-2-yl)methanamine dihydrochloride

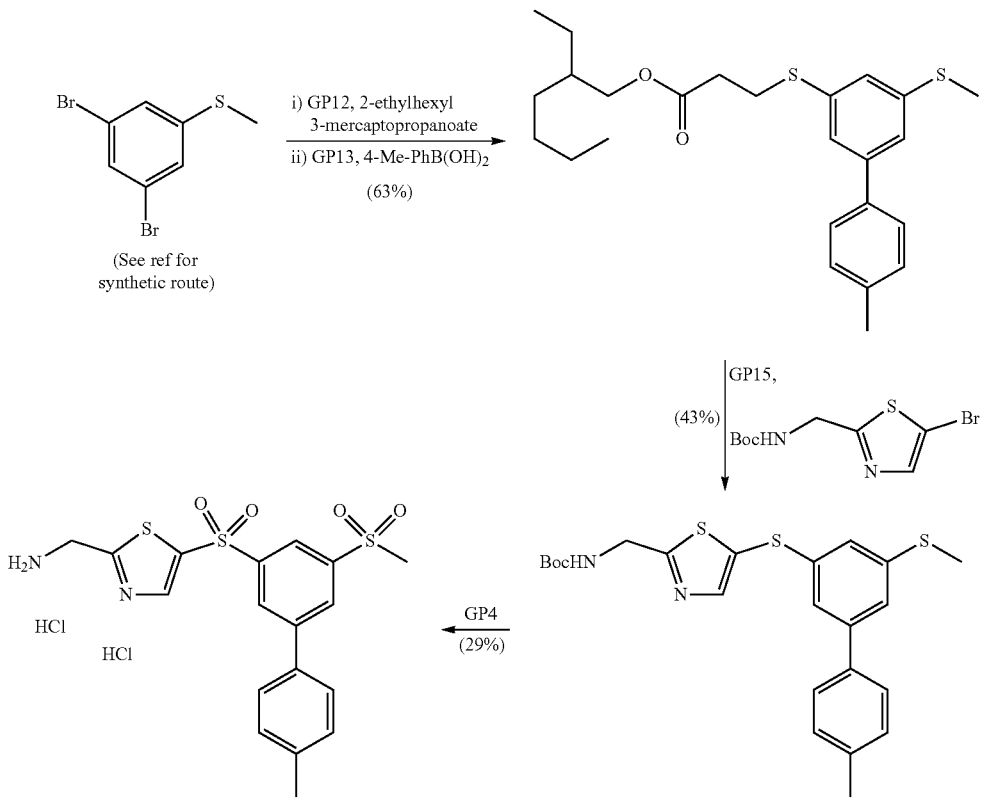

Ref - (Van Bierbeek et al 1998).

2-Ethylhexyl 3-((3-bromo-5-(methylthio)phenyl)thio) propanoate was synthesised according to general procedures GP12—from (3,5-dibromophenyl)(methyl)sulfane (3.0 g, 10.6 mmol), Pd₂(dba)₃ (243 mg, 2.5 mol %), Xantphos (300 mg, 5 mol %), 2-ethylhexyl-3-mercaptopropionate (1.85 g, 8.49 mmol), DIPEA (2.73 mL, 15.7 mmol) and toluene (30 mL); 110° C., 16 h. Chromatography (5% EtOAc in hexane) afforded a yellow oil (2.50 g, 70%). ¹H NMR (400 MHz, DMSO-d₆) δ 7.25 (d, J=5.6 Hz, 2H), 7.14 (s, 1H), 3.94 (d, J=5.6 Hz, 2H), 3.23 (t, J=6.8 Hz, 2H), 2.63 (t, J=7.2 Hz, 2H), 2.50 (s, 3H), 1.51 (m, 1H), 1.31-1.24 (m, 8H), 0.86-0.82 (m, 6H). LCMS (ESI) m/z 419 (M+H)+.

2-Ethylhexyl 3-((4'-methyl-5-(methylthio)-[1,1'-biphenyl]-3-yl)thio)propanoate was synthesised according to general procedures GP13—from 2-ethylhexyl 3-((3-bromo-5-(methylthio)phenyl)thio)propanoate (1.30 g, 3.10 mmol), phenylboronic acid (0.500 g, 4.10 mmol), Pd(PPh₃)₄ (0.350 g, 10 mol %), 2M Na₂CO₃ (3 mL, 6.0 mmol), 1,4-dioxane (15 mL); 100° C., 16 h. Chromatographic purification (30% EtOAc/hexane) afforded a yellow oil (1.20 g, 90%). ¹H NMR (400 MHz, DMSO-d₆) δ 7.55 (d, J=8.0 Hz, 2H), 7.28-7.24 (m, 4H), 7.12 (s, 1H), 3.92 (d, J=6.0 Hz, 2H), 3.24 (t, J=6.8 Hz, 2H), 2.63 (t, J=6.8 Hz, 2H), 2.52 (s, 3H), 2.33

(s, 3H), 1.51 (m, 1H), 1.26-1.16 (m, 8H), 0.83-0.79 (m, 6H). LCMS (ESI) m/z 431 (M+H)⁺.

tert-Butyl ((5-((4'-methyl-5-(methylthio)-[1,1'-biphenyl]-3-yl)thio)thiazol-2-yl)methyl)carbamate was synthesised according to general procedures GP15—from 2-ethylhexyl 3-((4'-methyl-5-(methylthio)-[1,1'-biphenyl]-3-yl)thio)propanoate (700 mg, 1.62 mmol), NaO^tBu (390 mg, 4.06 mmol), toluene/^tBuOH (3:1, 40 mL); rt, 4 h, then tert-butyl ((5-bromothiazol-2-yl)methyl)carbamate (470 mg, 1.60 mmol), Pd₂(dba)₃ (14 mg, 1 mol %), Xantphos (18 mg, 2 mol %); 110° C., 16 h. Chromatographic purification (45% EtOAc in hexane) afforded a yellow oil (320 mg, 43%). ¹H NMR (400 MHz, DMSO-d₆) δ 7.99 (s, 1H), 7.79 (br, 1H), 7.50 (d, J=7.6 Hz, 2H), 7.32 (s, 1H), 7.25 (d, J=8.0 Hz, 2H), 7.19 (s, 1H), 7.04 (s, 1H), 4.38 (d, J=6.0 Hz, 2H), 2.50 (s, 3H), 2.33 (s, 3H), 1.37 (s, 9H). LCMS (ESI) m/z 459 (M+H)⁺.

Example 121 was synthesised according to general procedures GP4—from i) m-CPBA (55%; 1.09 g, 3.47 mmol), tert-butyl ((5-((4'-methyl-5-(methylthio)-[1,1'-biphenyl]-3-yl)thio)thiazol-2-yl)methyl)carbamate (0.320 g, 0.697 mmol) and DCM (10 mL); rt, 3 h. Chromatographic purification (50% EtOAc in hexane) afforded a brown oil (0.160 g, 44%); ii) 2 M HCl in Et₂O (4.0 mL), tert-butyl ((5-((4'-methyl-5-(methylsulfonyl)-[1,1'-biphenyl]-3-yl)sulfonyl)thiazol-2-yl)methyl)carbamate (80 mg, 0153 mmol) and DCM (10.0 mL); rt, 4 h. White solid obtained (50 mg, 66%) without further purification. ¹H NMR (500 MHz, Methanol-d₄) δ 8.56 (s, 1H), 8.49 (t, J=1.6 Hz, 1H), 8.48-8.41 (m, 2H), 7.66-7.59 (m, 2H), 7.35 (d, J=7.9 Hz, 2H), 4.56 (s, 2H), 3.26 (s, 3H), 2.40 (s, 3H). ¹³C NMR (126 MHz, Methanol-d₄) δ 171.15, 149.57, 146.12, 144.89, 144.70, 141.58, 140.98, 135.43, 131.70, 131.17, 130.85, 128.22, 125.25, 44.00, 41.18, 21.19. HRMS (ESI) for C₁₈H₁₉N₂O₄S₃ ([M+H]⁺): Calculated 423.0507; Observed 423.0496.

Example 122: 5-((2-(Aminomethyl)thiazol-5-yl)sulfonyl)-N-methyl-[1,1'-biphenyl]-3-amine trihydrochloride A mixture of tert-butyl (3,5-dibromophenyl)carbamate (3.00 g, 8.54 mmol), KOH (1.70 g, 30.4 mmol) were taken in DMF (15 mL) then MeI (0.80 mL, 12.8 mmol) was added stirred at rt for 16 h. The mixture was diluted with EtOAc. The organic layer was washed with H₂O and brine, dried over Na₂S₂SO₄ and filtered. The solvent was removed under reduced pressure and the crude was purified by combi flash (10% EtOAc in hexane) to afford tert-butyl (3,5-dibromophenyl)(methyl)carbamate as a colourless oil (2.70 g, 87%). ¹H NMR (400 MHz, DMSO-d₆) δ 7.63-7.62 (m, 1H), 7.58-7.57 (m, 2H), 3.18 (s, 3H), 1.41 (s, 9H). LCMS (ESI) m/z 264 (M-Boc+2H)⁺.

2-Ethylhexyl 3-((3-bromo-5-((tert-butoxycarbonyl)amino)phenyl)thio)propanoate was synthesised according to general procedures GP12—from tert-butyl (3,5-dibromophenyl)(methyl)carbamate (2.00 g, 5.48 mmol), Pd₂(dba)₃ (125 mg, 2.5 mol %), Xantphos (150 mg, 5 mol %), 2-ethylhexyl-3-mercaptopropionate (1.19 g, 5.45 mmol), DIPEA (2.0 mL, 11.5 mmol) and toluene (30 mL); 110° C., 16 h. Chromatography (12% EtOAc in hexane) afforded a yellow oil (1.30 g, 47%). LCMS (ESI) m/z 446 (M-Boc+2H)⁺.

2-Ethylhexyl 3-((5-((tert-butoxycarbonyl)(methyl)amino)-[1,1'-biphenyl]-3-yl)thio)propanoate was synthesised according to general procedures GP13—from 2-ethylhexyl 3-((3-bromo-5-((tert-butoxycarbonyl)amino)phenyl)thio)propanoate (1.30 g, 2.58 mmol), phenylboronic acid (0.470 g, 3.88 mmol), Pd(PPh₃)₄ (0.350 g, 10 mol %), 2M Na₂CO₃ (2.58 mL, 5.16 mmol), 1,4-toluene (20 mL); 100° C., 16 h. Chromatographic purification (15% EtOAc in hexane) afforded a white solid (1.20 g, 93%). ¹H NMR (400 MHz, DMSO-d₆) δ 7.56 (d, J=7.3 Hz, 2H), 7.46-7.37 (m, 4H), 7.31-7.23 (m, 2H), 4.01 (s, 2H), 3.29 (s, 3H), 3.22 (t, J=7.4 Hz, 2H), 2.67 (t, J=7.4 Hz, 2H), 1.51-1.49 (m, 1H), 1.47 (s, 9H), 1.36-1.27 (m, 8H), 0.89-0.86 (m, 6H). LCMS (ESI) m/z 444 (M-Boc+2H)⁺.

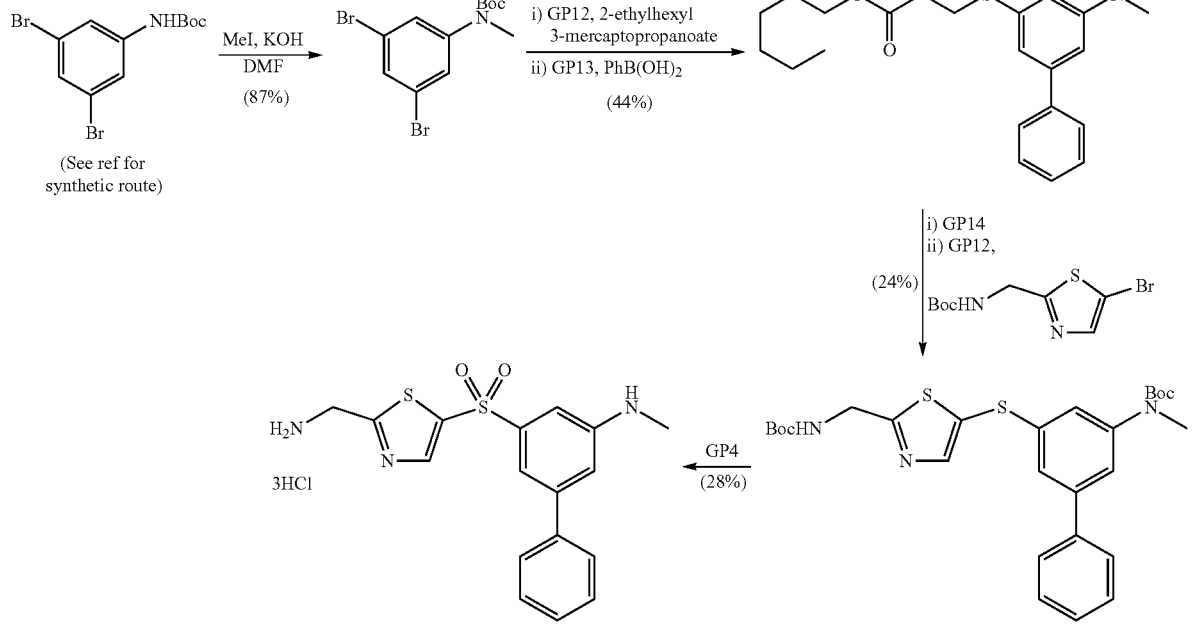

Ref - (Schweighauser et al, 2015)

tert-Butyl (5-((2-(((tert-butoxycarbonyl)amino)methyl) thiazol-5-yl)thio)-[1,1'-biphenyl]-3-yl)(methyl)carbamate was synthesised according to general procedures GP14 and GP12—from i) 2-ethylhexyl 3-((5-(((tert-butoxycarbonyl) (methyl)amino)-[1,1'-biphenyl]-3-yl)thio)propanoate (0.80 g, 1.60 mmol), KO$^t$Bu (1.0 M in THF; 4.70 mL, 4.70 mmol), THF (25 mL); rt, 1 h; ii) Pd$_2$(dba)$_3$ (150 mg, 0.170 mmol), Xantphos (190 mg, 0.330 mmol), tert-butyl ((5-bromothiazol-2-yl)methyl)carbamate (0.50 g, 1.71 mmol), NaO$^t$Bu (0.40 g, 4.17 mmol) and toluene/$^t$BuOH (4:1; 25 mL); 110° C., 16 h. Chromatography (35% EtOAc in hexane) afforded a brown oil (200 mg, 24%). $^1$H NMR (400 MHz, DMSO-d$_6$) δ 7.99 (s, 1H), 7.78-7.76 (m, 1H), 7.60 (d, J=7.4 Hz, 2H), 7.59-7.37 (m, 4H), 7.29 (s, 1H), 7.14 (s, 1H), 4.38 (d, J=5.9 Hz, 2H), 3.20 (s, 3H), 1.36 (s, 18H). %). LCMS (ESI) m/z 528 (M+H)$^+$.

Example 122 was synthesised according to general procedures GP4—from i) from m-CPBA (55%; 0.280 g, 0.892 mmol), tert-butyl (5-((2-(((tert-butoxycarbonyl)amino) methyl)thiazol-5-yl)thio)-[1,1'-biphenyl]-3-yl)(methyl)carbamate (200 mg, 0.379 mmol) and DCM (10 mL); rt, 3 h. Chromatographic purification (40% EtOAc in hexane) afforded a yellow solid (110 mg, 52%); ii) 2 M HCl in Et$_2$O (3.0 mL), tert-butyl (5-((2-(((tert-butoxycarbonyl)amino) methyl)thiazol-5-yl)sulfonyl)-[1,1'-biphenyl]-3-yl)(methyl) carbamate (110 mg, 0196 mmol) and DCM (10.0 mL); rt, 4 h. White solid obtained (50 mg, 53%) without further purification. $^1$H NMR (500 MHz, Methanol-d$_4$) δ 8.53 (s, 1H), 8.23 (s, 1H), 8.11 (s, 1H), 8.03 (s, 1H), 7.71 (t, 2H), 7.56-7.50 (m, 2H), 7.47 (t, J=7.3 Hz, 1H), 4.60 (s, 2H), 3.17 (s, 3H). $^{13}$C NMR (126 MHz, Methanol-d$_4$) δ 170.95, 149.41, 146.60, 145.10, 141.90, 141.63, 138.69, 130.44, 130.36, 128.32, 126.18, 125.77, 119.59, 41.34, 37.04. HRMS (ESI) for C$_{17}$H$_{18}$N$_3$O$_2$S$_2$ ([M+H]$^+$): Calculated 360.0840; Observed 360.0848.

Example 123: (1-Methyl-5-(naphthalen-2-ylsulfonyl)-1H-imidazol-2-yl)methanamine dihydrochloride

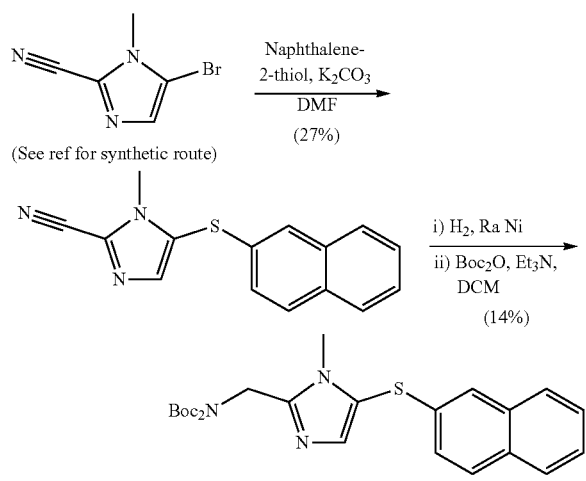

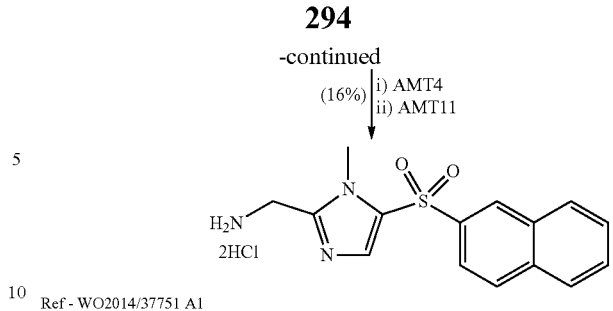

Ref - WO2014/37751 A1

A solution of 5-bromo-1-methyl-1H-imidazole-2-carbonitrile (1.80 g, 9.68 mmol), K$_2$CO$_3$ (1.97 g, 14.3 mmol) and naphthalene-2-thiol (1.82 g, 11.4 mmol) in DMF (20 ml) was stirred at 120° C. for 16 h. After coming to RT, the mixture was diluted with EtOAc, washed with water, saturated brine solution, dried over Na$_2$S$_2$O$_4$ and the solvent was removed under reduced pressure. The crude was purified by chromatography (20% EtOAc in hexane) to afford 1-methyl-5-(naphthalen-2-ylthio)-1H-imidazole-2-carbonitrile as light yellow solid (0.70 g, 27%). $^1$H NMR (400 MHz, DMSO-d$_6$) δ 7.90-7.84 (m, 3H), 7.68 (d, J=6.8 Hz, 2H), 7.52-7.48 (m, 2H), 7.29 (d, J=8.0 Hz, 1H), 3.71 (s, 3H); LCMS (ESI) m/z 266 [M+H]$^+$.

A mixture of 1-methyl-5-(naphthalen-2-ylthio)-1H-imidazole-2-carbonitrile (0.70 g, 2.64 mmol) and Raney-Ni (slurry in H$_2$O; 0.7 g) in MeOH (20 mL) was stirred under H$_2$ pressure (50 psi) at rt for 16 h and then filtered through celite. The solvent was removed under reduced pressure and the crude amine was dissolved in DCM (20 ml). Et$_3$N (0.71 ml, 5.09 mmol) and DMAP (0.31 g, 2.54 mmol) were added, followed by Boc$_2$O (1.13 g, 5.18 mmol) and the mixture was stirred at rt for 16 h before diluted with DCM. The solution was washed with saturated NaHCO$_3$, H$_2$O and brine, dried over Na$_2$S$_2$O$_4$ and filtered. The solvent was removed under reduced pressure and the crude was purified by chromatography (30% EtOAc in hexane) to afford di-tert-butyl((1-methyl-5-(naphthalen-2-ylthio)-1H-imidazol-2-yl) methyl) carbamate (0.17 g, 14%) as a light yellow oil. $^1$H NMR (400 MHz, DMSO-d$_6$) δ 7.89-7.85 (m, 2H), 7.76 (d, J=7.2 Hz, 1H), 7.55 (br, 1H), 7.51-7.47 (m, 2H), 7.38 (s, 1H), 7.20 (dd, J=8.4, 2.0 Hz, 1H), 4.81 (s, 2H), 3.50 (s, 3H), 1.40 (s, 18H). LCMS (ESI) m/z 470 [M+H]$^+$.

Example 123 was synthesised according to general procedures AMT4 and GP4- from i) di-tert-butyl((1-methyl-5-(naphthalen-2-ylthio)-1H-imidazol-2-yl) methyl)carbamate (0.17 g, 0.362 mmol), m-CPBA (55%; 0.160 g, 0.510 mmol), DCM (20 ml); rt, 3 h. ii) 1 M HCl in Et$_2$O (4.0 mL), DCM (10 mL); rt, 2 h. Light brown solid obtained (22 mg, 16%) without further purification. $^1$H NMR (400 MHz, Methanol-d$_4$) δ 8.66 (br, 1H), 8.14-8.06 (m, 2H), 7.99 (d, J=8.0 Hz, 1H), 7.88-7.84 (m, 2H), 7.77-7.64 (m, 2H), 4.23 (s, 2H), 3.71 (s, 3H). HRMS (ESI) for C$_{15}$H$_{13}$N$_2$O$_2$S ([M-NH$_2$]$^+$): Calculated 285.0698; Observed 285.0692.

Example 124: (5-((3-((2-Phenylpyrrolidin-1-yl)sulfonyl)phenyl)sulfonyl)thiophen-2-yl)methanamine hydrochloride

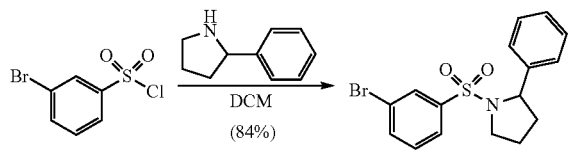

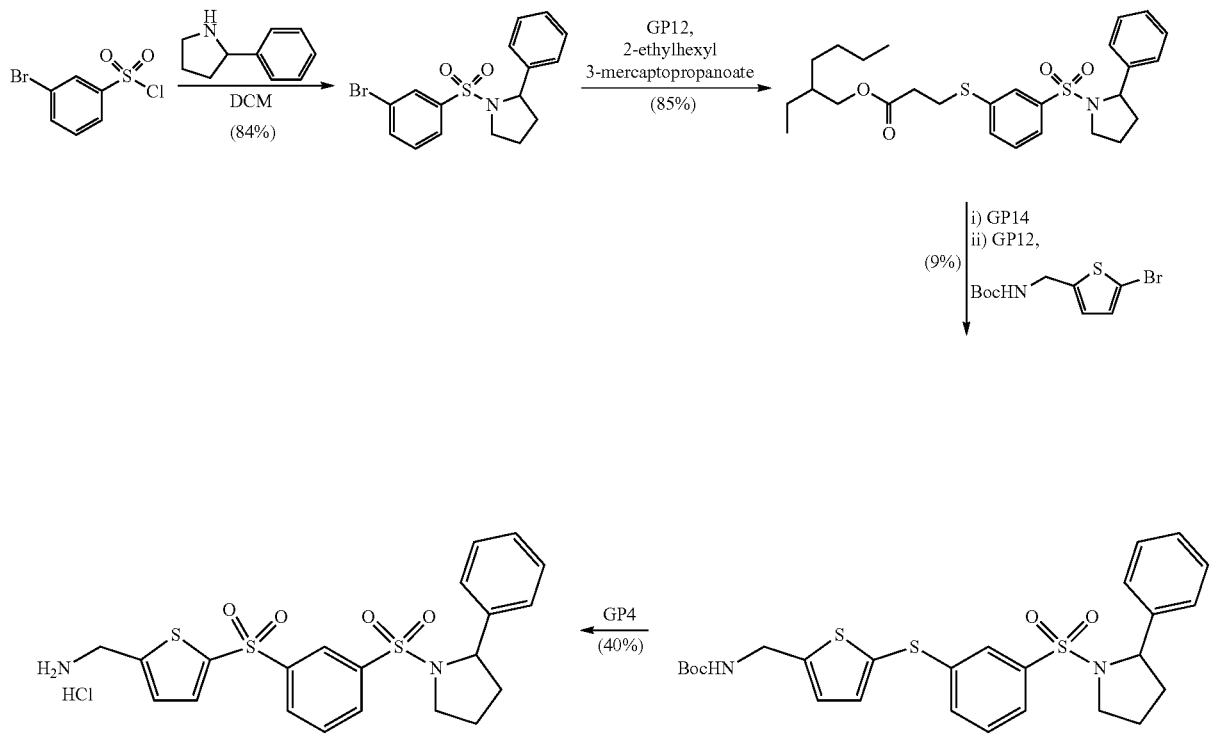

2-Phenylpyrrolidine (1.72 g, 11.7 mmol) was added to a solution of 3-bromobenzenesulfonyl chloride (1.50 g, 5.88 mmol) in DCM (25 ml) at 0° C. and the mixture was stirred at rt for 4 h before it was diluted with DCM. The organic solution was washed with $H_2O$ and brine, dried over $Na_2S_2O_4$ and filtered. The solvent was removed under reduced pressure and the crude was purified by chromatography (20% EtOAc in hexane) to afford 1-((3-bromophenyl)sulfonyl)-2-phenylpyrrolidine as yellow liquid (1.80 g, 84%). $^1$H NMR (400 MHz, DMSO-$d_6$) δ 7.91 (d, J=6.8 Hz, 1H), 7.86-7.82 (m, 2H), 7.58 (t, J=8.2 Hz, 1H), 7.32-7.30 (m, 4H), 7.26-7.22 (m, 1H), 4.83-4.80 (m, 1H), 3.60-3.55 (m, 1H), 3.40-3.31 (m, 1H), 2.00-1.95 (m, 1H), 1.80-1.69 (m, 2H), 1.61-1.56 (m, 1H). LCMS (ESI) m/z 366 (M+H)$^+$.

2-Ethylhexyl 3-((3-((2-phenylpyrrolidin-1-yl)sulfonyl)phenyl)thio)propanoate was synthesised according to general procedures GP12—from 1-((3-bromophenyl)sulfonyl)-2-phenylpyrrolidine (1.80 g, 4.92 mmol), $Pd_2(dba)_3$ (112 mg, 0.122 mmol), Xantphos (140 mg, 0.242 mmol), 2-ethylhexyl 3-mercaptopropanoate (1.07 g, 4.91 mmol), DIPEA (1.80 mL, 10.4 mmol) and toluene (25 mL); 110° C., 16 h. Chromatography (25% EtOAc in hexane) afforded a yellow oil (2.10 g, 85%). $^1$H NMR (400 MHz, DMSO-$d_6$) δ 7.66-7.55 (m, 4H), 7.32-7.29 (m, 4H), 7.26-7.21 (m, 1H), 4.79-4.76 (m, 1H), 3.93 (d, J=5.4 Hz, 2H), 3.58-3.53 (m, 1H), 3.39-3.30 (m, 1H), 3.26 (t, J=6.9 Hz, 2H), 2.66 (t, J=6.9 Hz, 2H), 1.94-1.87 (m, 1H), 1.76-1.65 (m, 2H), 1.56-1.50 (m, 2H), 1.33-1.22 (m, 8H), 0.84-0.81 (m, 6H). LCMS (ESI) m/z 504 (M+H)$^+$.

tert-Butyl ((5-((3-((2-phenylpyrrolidin-1-yl)sulfonyl)phenyl)thio)thiophen-2-yl)methyl)carbamate was synthesised according to general procedures GP14 and GP12—from i) 2-ethylhexyl 3-((3-((2-phenylpyrrolidin-1-yl)sulfonyl)phenyl)thio)propanoate (1.50 g, 2.98 mmol), KO$^t$Bu (1.0 M in THF; 8.92 mL, 8.92 mmol), THF (25 mL); rt, 1 h. ii) $Pd_2(dba)_3$ (220 mg, 0.241 mmol), Xantphos (280 mg, 0.484 mmol), tert-butyl ((5-bromothiophene-2-yl)methyl)carbamate (0.730 g, 2.50 mmol), NaO$^t$Bu (0.360 g, 3.75 mmol) and toluene/$^t$BuOH (4:1; 25 mL); 110° C., 16 h. Chromatography (50% EtOAc in hexane) afforded a brown solid (120 mg, 9%). $^1$H NMR (400 MHz, DMSO-$d_6$) δ 7.62-7.52 (m, 4H), 7.43-7.38 (m, 2H), 7.32-7.23 (m, 5H), 7.05 (d, J=3.4 Hz, 1H), 4.60-4.55 (m, 1H), 4.30 (d, J=5.9 Hz, 2H), 3.55-3.40 (m, 1H), 3.30-3.22 (m, 1H), 1.90-1.86 (m, 1H), 1.74-1.64 (m, 2H), 1.49-1.39 (m, 1H), 1.37 (s, 9H). LCMS (ESI) m/z 431 (M-Boc+2H)$^+$.

Example 124 was synthesised according to general procedures GP4—from i) tert-Butyl ((5-((3-((2-phenylpyrrolidin-1-yl)sulfonyl)phenyl)thio)thiophen-2-yl)methyl)carbamate (0.120 g, 0.226 mmol), m-CPBA (55%; 0.150 g, 0.478 mmol), DCM (10 ml); rt, 3 h. ii) 1 M HCl in $Et_2O$ (5.0 mL), DCM (10 mL); rt, 3 h. White solid obtained (45 mg, 40%) without further purification. $^1$H NMR (500 MHz, Methanol-$d_4$) δ 8.26-8.16 (m, 2H), 7.98 (d, J=8.6 Hz, 1H), 7.83-7.69 (m, 2H), 7.35 (d, J=3.8 Hz, 1H), 7.26-7.13 (m, 5H), 4.78 (dd, J=7.9, 4.6 Hz, 1H), 4.39 (s, 2H), 3.64 (ddd, J=10.0, 7.0, 5.5 Hz, 1H), 3.51 (dt, J=10.1, 7.0 Hz, 1H), 2.08 (m, 1H), 1.91 (m, 1H), 1.81 (m, 1H), 1.70 (m, 1H). $^{13}$C NMR (126 MHz, Methanol-$d_4$) δ 145.83, 144.44, 144.15, 143.69, 141.65, 135.75, 133.18, 132.21, 131.79, 129.29, 128.24, 127.37, 126.73, 65.15, 50.72, 49.21, 49.00, 48.82, 38.37, 37.05, 25.05. HRMS (ESI) for $C_{21}H_{20}NO_4S_3$ ([M-$NH_2$]$^+$): Calculated 446.0554; Observed 446.0537.

Example 125: 5-((2-(Aminomethyl)thiazol-5-yl)sulfonyl)-N,N-dimethyl-[1,1'-biphenyl]-3-carboxamide dihydrochloride

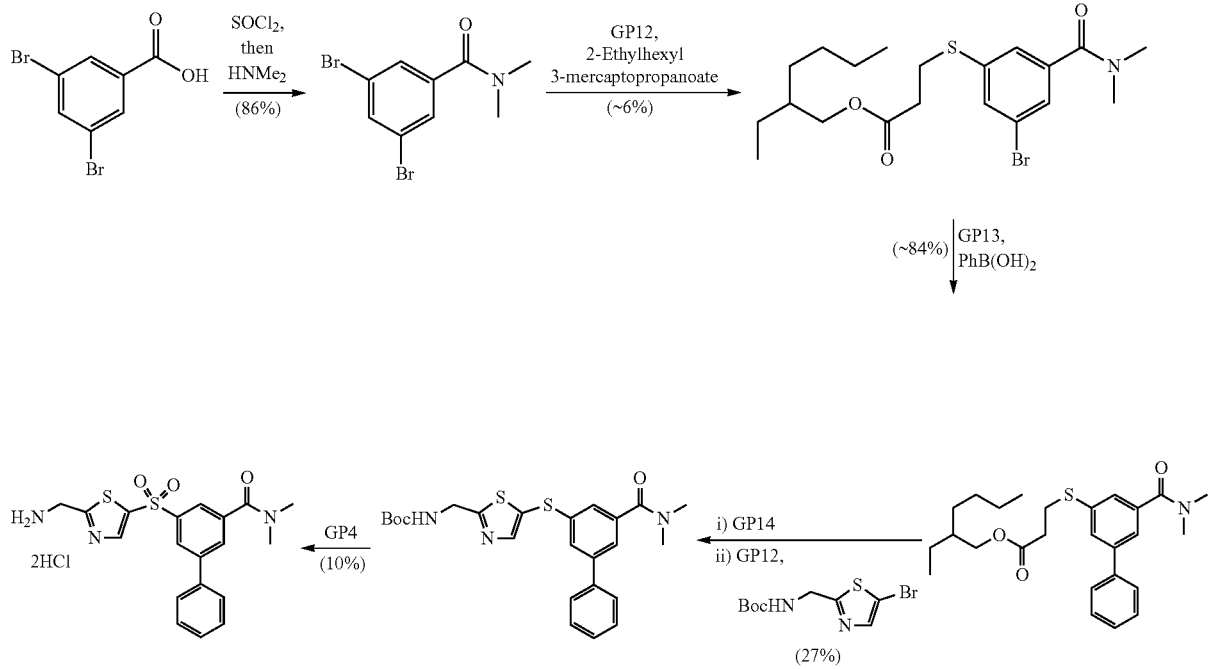

SOCl$_2$ (20.6 ml, 286 mmol) was added to 3,5-dibromobenzoic acid (4.0 g, 14.3 mmol) at rt, and the mixture was stirred at reflux for 4 h before it was cooled to rt. The solvent was removed under reduced pressure to give the corresponding acid chloride. 40% dimethyl amine solution in water (40 mL) was added drop-wise at 0° C., and the mixture was stirred at rt for 16 h before it was diluted with EtOAc. The organic solution was washed with water and brine, dried over Na$_2$S$_2$O$_4$ and filtered. The solvent was removed under reduced pressure and the crude was purified by chromatography (50% EtOAc in hexane) to afford the desired 3,5-dibromo-N,N-dimethylbenzamide (3.70 g, 86%). $^1$H NMR (400 MHz, DMSO-d$_6$) δ 7.93 (s, 1H), 7.63 (d, J=1.6 Hz, 2H), 2.96 (s, 3H), 2.87 (s, 3H). LCMS (ESI) m/z 307 (M+H)$^+$.

2-Ethylhexyl 3-((3-bromo-5-(dimethylcarbamoyl)phenyl)thio)propanoate was synthesised according to general procedures GP12—from 3,5-dibromo-N,N-dimethylbenzamide (3.7 g, 12.1 mmol), Pd$_2$(dba)$_3$ (0.27 g, 2.5 mol %), Xantphos (0.35 g, 5 mol %), 2-ethylhexyl-3-mercaptopropionate (2.64 g, 12.1 mmol), DIPEA (4.47 mL, 24.2 mmol) and toluene (40 mL); 110° C., 16 h. Chromatography (55% EtOAc in hexane) afforded the desired compound as a yellow oil (~50% purity; 6.0 g, ~56%). LCMS (ESI) m/z 444 (M+H)$^+$.

2-Ethylhexyl 3-(5-(dimethylcarbamoyl)-[1,1'-biphenyl]-3-yl)thio)propanoate was synthesised according to general procedures GP13—from 2-ethylhexyl 3-((3-bromo-5-(dimethylcarbamoyl)phenyl)thio)propanoate (~50% purity; 2.0 g, ~2.25 mmol), phenylboronic acid (0.81 g, 6.75 mmol), Pd(PPh$_3$)$_4$ (0.26 g, 5 mol %), 2 M Na$_2$CO$_3$ (4.5 mL, 9.0 mmol), toluene (25 mL); 100° C., 16 h. Preparative HPLC (0.1% TFA in CH$_3$CN) afforded a colourless oil (0.80 g, ~84%). $^1$H NMR (400 MHz, DMSO-d$_6$) δ 7.70 (d, J=7.6 Hz, 2H), 7.62 (s, 1H), 7.49-7.40 (m, 4H), 7.31 (s, 1H), 3.95 (d, J=5.9 Hz, 2H), 3.29 (t, J=6.8 Hz, 2H), 3.00 (s, 3H), 2.93 (s, 3H), 2.66 (t, J=6.8 Hz, 2H), 1.52-1.50 (m, 1H), 1.29-1.21 (m, 8H), 0.83-0.80 (m, 6H). LCMS (ESI) m/z 442 (M+H)$^+$.

tert-Butyl ((5-((5-(dimethylcarbamoyl)-[1,1'-biphenyl]-3-yl)thio)thiazol-2-yl)methyl)carbamate was synthesised according to general procedures GP14 and GP12—from i) 2-ethylhexyl 3-((5-(dimethylcarbamoyl)-[1,1'-biphenyl]-3-yl)thio)propanoate (0.70 g, 1.58 mmol), KOtBu (1.0 M in THF; 4.76 mL, 4.76 mmol), THF (25 mL); −78° C., 30 min. ii) Pd$_2$(dba)$_3$ (0.24 g, 10 mol %), Xantphos (0.31 g, 20 mol %), tert-butyl ((5-bromothiazol-2-yl)methyl)carbamate (0.79 g, 2.72 mmol), sodium tert-butoxide (0.39 g, 4.08 mmol) and toluene/BuOH (4:1, 25 mL); 110° C., 16 h. Chromatography (64% EtOAc in hexane) afforded a brown solid (0.30 g, 27%). $^1$H NMR (400 MHz, DMSO-d$_6$) δ 8.02 (s, 1H), 7.83 (s, 1H), 7.65 (d, J=8.8 Hz, 2H), 7.58 (t, J=1.6 Hz, 1H), 7.53 (s, 1H), 7.49-7.40 (m, 3H), 7.16 (t, J=1.6 Hz, 1H), 4.40 (d, J=6.3 Hz, 2H), 2.97 (s, 3H), 2.88 (s, 3H), 1.37 (s, 9H). LCMS (ESI) m/z 370 (M-Boc+H)$^+$.

Example 125 was synthesised according to general procedures GP4—from i) m-CPBA (55%; 0.43 g, 1.41 mmol), tert-butyl ((5-((5-(dimethylcarbamoyl)-[1,1'-biphenyl]-3-yl)thio)thiazol-2-yl)methyl)carbamate (0.30 g, 0.640 mmol) and DCM (15 mL); rt, 3 h. Chromatography (66% EtOAc in cyclohexane), pale yellow solid (0.10 g, 31%); ii) 1 M HCl in Et$_2$O (3.0 mL), tert-butyl ((5-((5-(dimethylcarbamoyl)-[1,1'-biphenyl]-3-yl)sulfonyl)thiazol-2-yl)methyl)carbamate (0.10 g, 0.199 mmol) and DCM (10 mL); rt, 3 h. Solid obtained (25 mg, 31%) without further purification. $^1$H NMR (500 MHz, Methanol-d$_4$) δ 8.48 (br, 1H), 8.27 (s, 1H), 8.14-7.90 (m, 2H), 7.76-7.58 (m, 2H), 7.56-7.36 (m, 3H), 4.54 (s, 2H), 3.14 (s, 3H), 3.03 (br, 3H). $^{13}$C NMR (126 MHz, Methanol-d$_4$) δ 170.51, 149.15, 144.76, 143.62, 142.13, 139.75, 139.01, 132.09, 130.32, 129.92, 128.26, 127.49, 125.75, 42.20, 40.63, 36.09. HRMS (ESI) for C$_{19}$H$_{20}$N$_3$O$_3$S$_2$ ([M+H]$^+$): Calculated 402.0946; Observed 402.0938.

Example 126: 5-((2-(Aminomethyl)thiazol-5-yl)sulfonyl)-[1,1'-biphenyl]-3-carboxylic acid ditrifluoroacetate

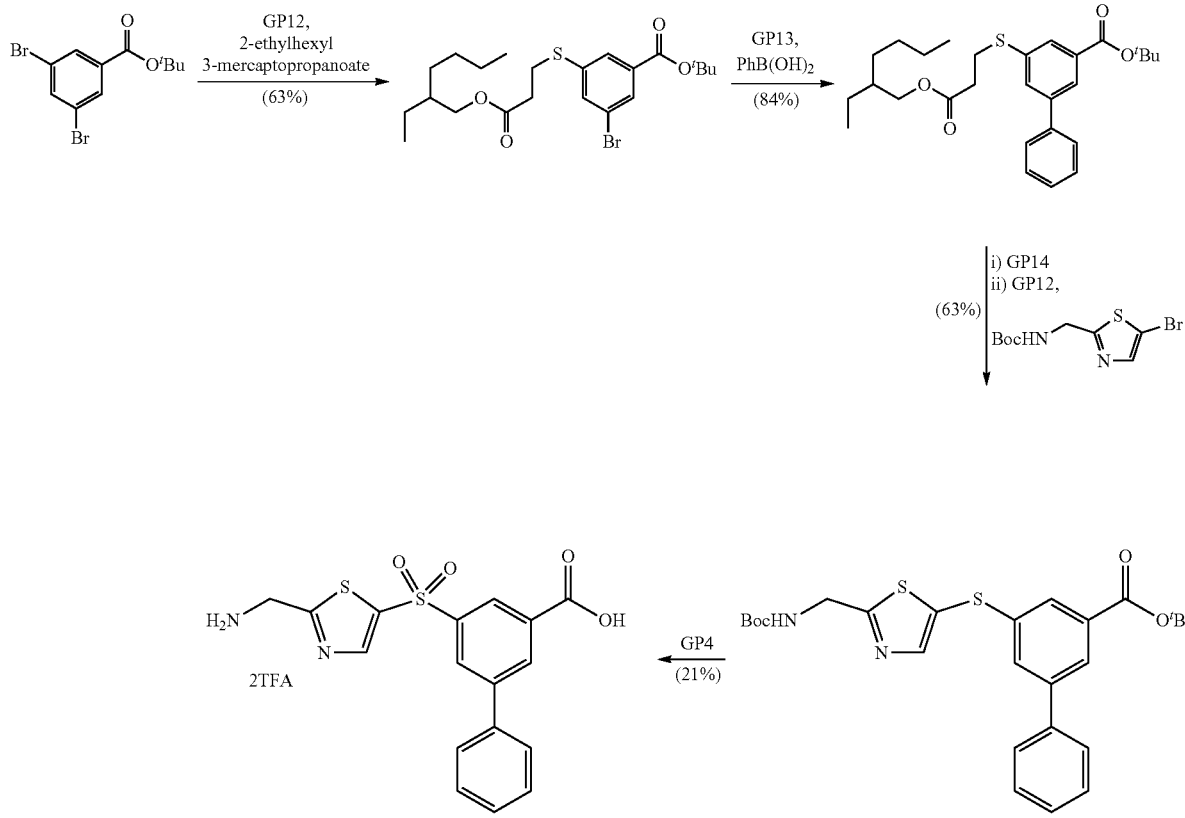

tert-Butyl 3-bromo-5-((3-((2-ethylhexyl)oxy)-3-oxopropyl)thio)benzoate was synthesised according to general procedures GP12—from tert-butyl 3,5-dibromobenzoate (2.7 g, 8.03 mmol), Pd$_2$(dba)$_3$ (0.18 g, 2.5 mol %), Xantphos (0.23 g, 5 mol %), 2-ethylhexyl-3-mercaptopropionate (1.75 g, 8.03 mmol), DIPEA (2.96 mL, 16.06 mmol) and toluene (30 mL); 110° C., 16 h. Chromatography (5% EtOAc in hexane) afforded a pale orange solid (2.4 g, 63%). $^1$H NMR (400 MHz, DMSO-d$_6$) δ 7.70 (t, J=2.0 Hz, 2H), 7.73 (s, 1H), 3.94 (d, J=5.6 Hz, 2H), 3.27 (t, J=6.8 Hz, 2H), 2.65 (t, J=6.8 Hz, 2H), 1.54 (s, 9H), 1.40-1.30 (m, 1H), 1.30-1.22 (m, 8H), 0.86-0.81 (m, 6H). LCMS (ESI) m/z 417 (M-$^t$Bu+2H)$^+$.

tert-Butyl 5-((3-((2-ethylhexyl)oxy)-3-oxopropyl)thio)-[1,1'-biphenyl]-3-carboxylate was synthesised according to general procedures GP13—from tert-butyl 3-bromo-5-((3-((2-ethylhexyl)oxy)-3-oxopropyl)thio)benzoate (2.4 g, 5.07 mmol), phenylboronic acid (0.73 g, 6.08 mmol), Pd(PPh$_3$)$_4$ (0.29 g, 5 mol %), 2 M Na$_2$CO$_3$ (5 mL, 10.14 mmol), toluene (30 mL); 100° C., 16 h. Chromatographic purification (8% EtOAc in hexane) afforded a colourless oil (2.0 g, 84%). $^1$H NMR (400 MHz, DMSO-d6) δ 8.03 (t, J=1.6 Hz, 1H), 7.93 (t, J=1.6 Hz, 1H), 7.71 (t, J=2.0 Hz, 1H), 7.60-7.58 (m, 2H), 7.45 (t, J=7.2 Hz, 2H), 7.39-7.38 (m, 1H), 4.04-4.0 (m, 2H), 3.25 (t, J=7.2 Hz, 2H), 2.67 (t, J=8.0 Hz, 2H), 1.57 (s, 9H), 1.40-1.38 (m, 1H), 1.38-1.27 (m, 8H), 0.89-0.85 (m, 6H). LCMS (ESI) m/z 415 (M-$^t$Bu+2H)$^+$.

tert-Butyl 5-((2-(((tert-butoxycarbonyl)amino)methyl)thiazol-5-yl)thio)-[1,1'-biphenyl]-3-carboxylate was synthesised according to general procedures GP14 and GP12— from i) tert-butyl 5-((3-((2-ethylhexyl)oxy)-3-oxopropyl)thio)-[1,1'-biphenyl]-3-carboxylate (1.8 g, 3.82 mmol), KOtBu (1.0 M in THF; 11.4 mL, 11.4 mmol), THF (25 mL); −78° C., 1 h. ii) Pd$_2$(dba)$_3$ (0.41 g, 10 mol %), Xantphos (0.52 g, 20 mol %), tert-butyl ((5-bromothiazol-2-yl)methyl)carbamate (1.33 g, 4.54 mmol), NaO$^t$Bu (0.72 g, 7.50 mmol) and toluene/$^t$BuOH (4:1, 25 mL); 110° C., 16 h. Chromatography (30% EtOAc in hexane) afforded a yellow oil (1.2 g, 63%). $^1$H NMR (400 MHz, DMSO-d$_6$) 8.05 (s, 1H), 7.95 (t, J=1.6 Hz, 1H), 7.86-7.82 (m, 1H), 7.75 (t, J=1.6 Hz, 1H), 7.76-7.65 (m, 3H), 7.51-7.21 (m, 3H), 4.40 (d, J=6.0 Hz, 2H), 1.40 (s, 9H), 1.37 (s, 9H). LCMS (ESI) m/z 499 (M+H)$^+$.

Example 126 was synthesised according to general procedures GP4—from i) m-CPBA (55%; 1.65 g, 5.28 mmol), tert-butyl 5-((2-(((tert-butoxycarbonyl)amino)methyl)thiazol-5-yl)thio)-[1,1'-biphenyl]-3-carboxylate (1.2 g, 2.40 mmol) and DCM (20 mL); rt, 3 h. Chromatography (35% EtOAc in cyclohexane), pale yellow solid (0.60 g, 47%); ii) TFA (3.0 mL), tert-butyl 5-((2-(((tert-butoxycarbonyl)amino)methyl)thiazol-5-yl)sulfonyl)-[1,1'-biphenyl]-3-carboxylate (50 mg, 0.094 mmol) and DCM (10 mL); rt, 6 h. The precipitate formed was collected using filtration, washing with diethyl ether, to afford a white solid (25 mg, 44%) as a TFA salt. $^1$H NMR (500 MHz, Methanol-d$_4$) δ 8.57-8.49 (m, 3H), 8.41 (t, J=1.8 Hz, 1H), 7.70-7.65 (m, 2H), 7.55-7.50 (m, 2H), 7.46 (m, 1H), 4.55 (s, 2H). $^{13}$C NMR (126 MHz, Methanol-d$_4$) δ 170.84, 167.32, 149.10, 145.01, 143.96, 142.16, 139.18, 134.79, 134.27, 130.43, 130.22, 130.06, 128.20, 127.92, 41.13. HRMS (ESI) for C$_{17}$H$_{12}$NO$_4$S$_2$ ([M-NH$_2$]$^+$): Calculated 358.0208; Observed 358.0211.

Example 127: (5-((3-(Methylsulfonyl)-5-(1H-pyrazol-4-yl)phenyl)sulfonyl)thiophen-2-yl)methanamine dihydrochloride

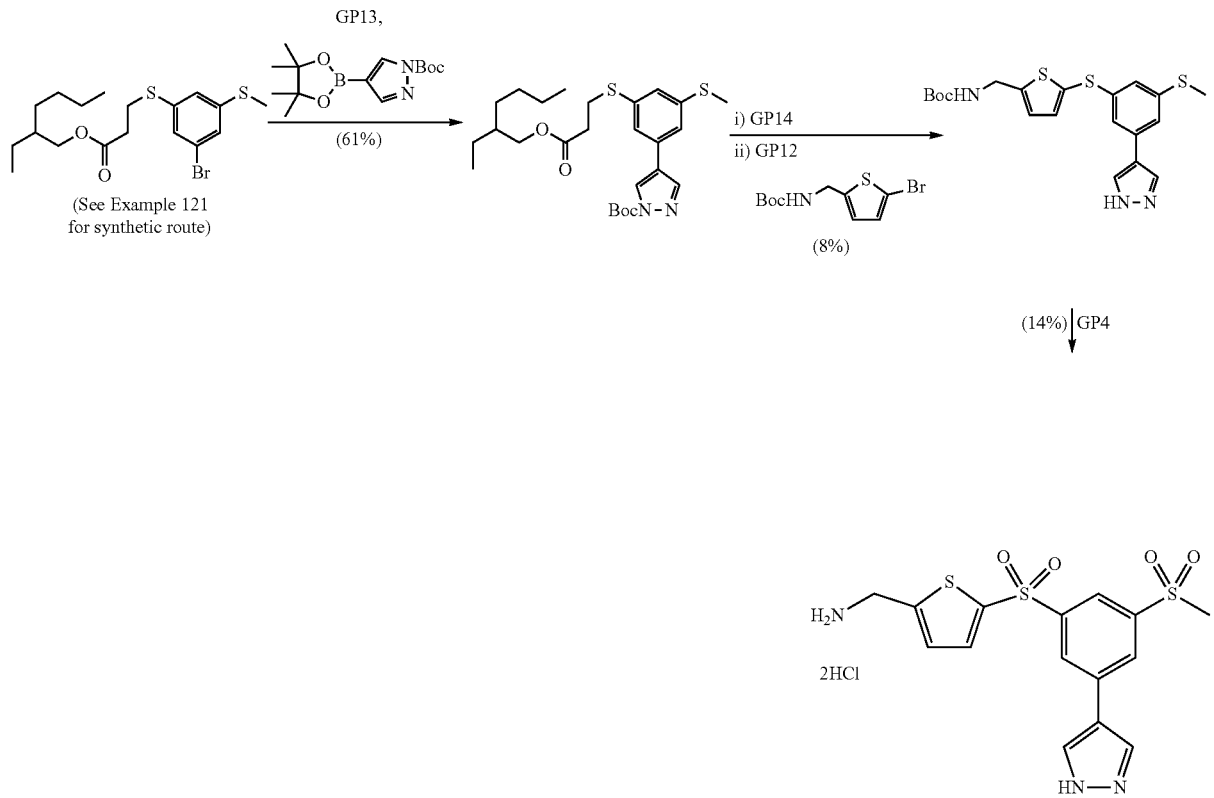

tert-Butyl 4-(3-((3-((2-ethylhexyl)oxy)-3-oxopropyl)thio)-5-(methylthio)phenyl)-1H-pyrazole-1-carboxylate was synthesised according to general procedures GP13—from 2-ethylhexyl 3-((3-bromo-5-(methylthio)phenyl)thio)propanoate (3.0 g, 7.15 mmol), 1-Boc-pyrazole-4-boronic acid pinacol ester (5.25 g, 17.8 mmol), PdCl$_2$(dppf)$_2$·DCM (0.58 g, 10 mol %), 2 M Na$_2$CO$_3$ (14.1 mL, 28.2 mmol), 1,4-dioxane/water (35:15 mL); 100° C., 16 h. Chromatographic purification (30% EtOAc in hexane) afforded a brown oil (2.2 g, 61%). $^1$H NMR (400 MHz, DMSO-d$_6$) δ 8.29 (br, 1H), 7.99 (br, 1H), 7.33 (s, 2H), 6.97 (s, 1H), 3.95 (s, 5H), 3.24 (t, J=6.8 Hz, 2H), 2.64 (t, J=7.2 Hz, 2H), 1.51-1.50 (m, 1H), 1.40-1.19 (m, 17H), 0.84-0.81 (m, 6H). LCMS (ESI) m/z 407 (M-Boc+H)$^+$.

tert-Butyl ((5-((3-(methylthio)-5-(1H-pyrazol-4-yl)phenyl)thio)thiophen-2-yl)methyl) carbamate was synthesised according to general procedures GP14 and GP12—from i) tert-butyl 4-(3-((3-((2-ethylhexyl)oxy)-3-oxopropyl)thio)-5-(methylthio)phenyl)-1H-pyrazole-1-carboxylate (2.2 g, 4.35 mmol), KO$^t$Bu (1.0 M in THF; 13 mL, 13.0 mmol), THF (13 mL); −78° C., 20 min. ii) Pd$_2$(dba)$_3$ (0.156 g, 2.5 mol %), Xantphos (0.193 g, 5 mol %), tert-butyl ((5-bromothiophen-2-yl)methyl)carbamate (1.98 g, 6.78 mmol), DIPEA (2.38 mL, 13.6 mmol) and toluene/$^t$BuOH (3:1, 40 mL); 110° C., 16 h. Chromatography (50% EtOAc in hexane) afforded a pale yellow solid (0.15 g, 8%). $^1$H NMR (400 MHz, DMSO-d$_6$) δ 13.0 (s, 1H), 8.24 (s, 1H), 7.90 (s, 1H), 7.55 (t, J=5.6 Hz, 1H), 7.32-7.29 (m, 2H), 7.25 (s, 1H), 6.97 (d, J=3.6 Hz, 1H), 6.74 (s, 1H), 4.27 (d, J=6.4 Hz, 2H), 2.44 (s, 3H), 1.37 (s, 9H). LCMS (ESI) m/z 434 (M+H)$^+$.

Example 127 was synthesised according to general procedures GP4—from i) m-CPBA (55%; 0.408 g, 1.30 mmol), tert-butyl ((5-((3-(methylthio)-5-(1H-pyrazol-4-yl)phenyl)thio)thiophen-2-yl)methyl)carbamate (0.15 g, 0.346 mmol) and DCM (20 mL); rt, 3 h. Chromatography (50% EtOAc in cyclohexane), pale yellow solid (65 mg, 38%); ii) 1 M HCl in Et$_2$O (4.0 mL), tert-butyl ((5-((3-(methylsulfonyl)-5-(1H-pyrazol-4-yl)phenyl) sulfonyl)thiophen-2-yl)methyl)carbamate (65 mg, 0.140 mmol) and DCM (5.0 mL); rt, 2 h. Off-white solid obtained (24 mg, 37%) without further purification. $^1$H NMR (500 MHz, DMSO-d$_6$) δ 8.89-8.38 (m, 8H), 8.24-7.94 (m, 3H), 7.45 (m, 1H), 4.27 (s, 2H), 3.34 (s, 3H). $^{13}$C NMR (126 MHz, DMSO-d$_6$) b 146.10, 143.26, 143.21, 141.04, 136.82, 135.07, 132.47 (br), 130.82, 128.10, 127.18, 121.31, 118.39, 42.97, 36.68. HRMS (ESI) for C$_{15}$H$_{13}$N$_2$O$_4$S$_3$ ([M-NH$_2$]$^+$): Calculated 381.0037; Observed 381.0031.

Example 128: (5-((3-Methoxy-5-(1-methyl-1H-pyrazol-4-yl)phenyl)sulfonyl)thiazol-2-yl)methanamine trihydrochloride

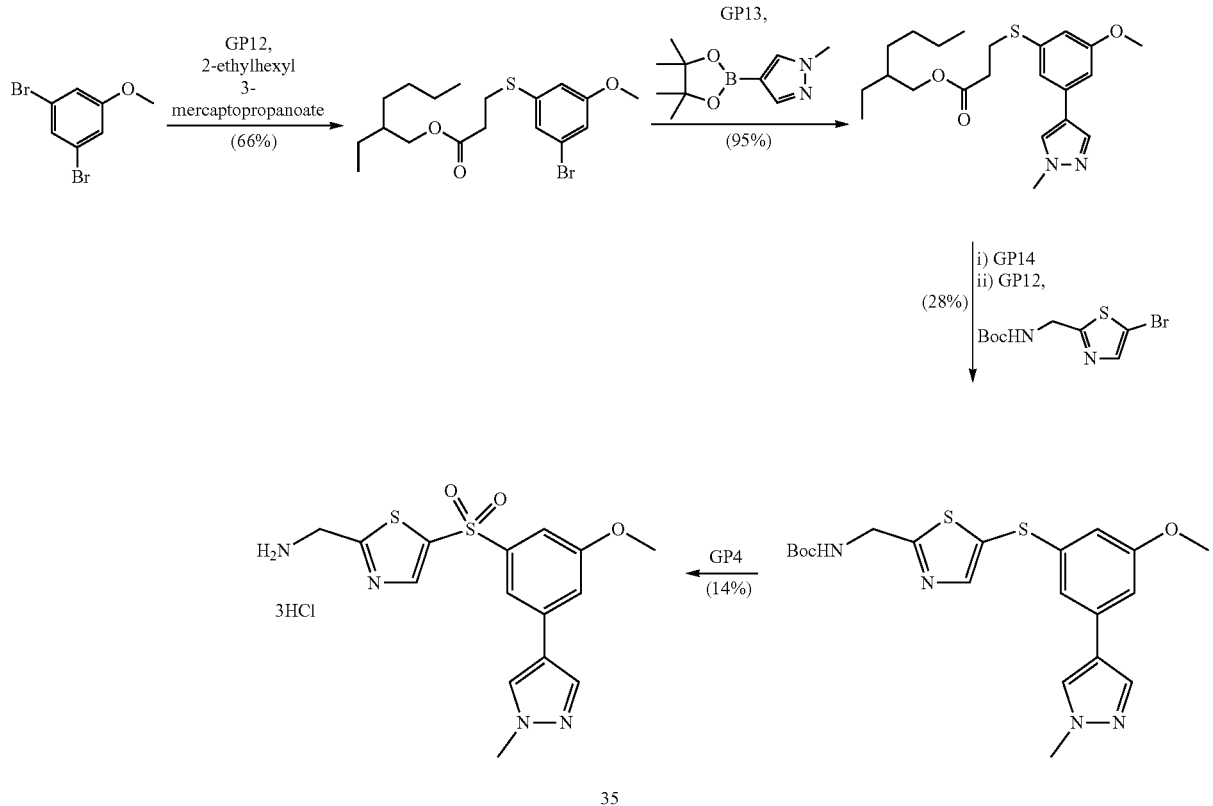

2-Ethylhexyl 3-((3-bromo-5-methoxyphenyl)thio)propanoate was synthesised according to general procedures GP12—from 1,3-dibromo-5-methoxybenzene (3.0 g, 11.3 mmol), Pd$_2$(dba)$_3$ (0.25 mg, 2.5 mol %), Xantphos (0.32 mg, 5 mol %), 2-ethylhexyl-3-mercaptopropionate (1.96 g, 9.02 mmol), DIPEA (4.15 mL, 23.9 mmol) and toluene (30 mL); 110° C., 8 h. Chromatography (12% EtOAc in hexane) afforded a pale orange solid (2.4 g, 66%). $^1$H NMR (400 MHz, DMSO-d$_6$) δ 7.05 (t, J=1.6 Hz, 1H), 6.99 (d, J=2.0 Hz, 1H), 6.87 (t, J=2.0 Hz, 1H), 3.95 (d, J=5.6 Hz, 2H), 3.76 (s, 3H), 3.21 (t, J=6.4 Hz, 2H), 2.63 (t, J=6.8 Hz, 2H), 1.52-1.50 (m, 1H), 1.29-1.24 (m, 8H), 0.87-0.82 (m, 6H). LCMS (ESI, −ve) m/z 217/219 (M-C$_{11}$H$_{21}$O$_2$)$^-$.

2-Ethylhexyl 3-((3-methoxy-5-(1-methyl-1H-pyrazol-4-yl)phenyl)thio)propanoate was synthesised according to general procedures GP13—from 2-ethylhexyl 3-((3-bromo-5-methoxyphenyl)thio)propanoate (2.0 g, 4.96 mmol), 1-methylpyrazole-4-boronic acid pinacol ester (1.50 g, 7.44 mmol), Pd(dppf)Cl$_2$ (0.20 g, 5 mol %), Cs$_2$CO$_3$ (4.0 g, 12.4 mmol), 1,4-dioxane:H$_2$O (6:1, 35 mL); 100° C., 16 h. Chromatographic purification (52% EtOAc in hexane) afforded a colourless oil (1.9 g, 95%). $^1$H NMR (400 MHz, DMSO-d$_6$) δ 8.18 (s, 1H), 7.88 (s, 1H), 7.08 (t, J=1.6 Hz, 1H), 6.97-6.96 (m, 1H), 6.69 (t, J=1.6 Hz, 1H), 3.94 (d, J=5.2 Hz, 2H), 3.85 (s, 3H), 3.78 (s, 3H), 3.21 (t, J=6.8 Hz, 2H), 2.63 (t, J=6.8 Hz, 2H), 1.51-1.50 (m, 1H), 1.30-1.22 (m, 8H), 0.85-0.81 (m, 6H). LCMS (ESI) m/z 405 (M+H)$^+$.

tert-Butyl ((5-((3-methoxy-5-(1-methyl-1H-pyrazol-4-yl)phenyl)thio)thiazol-2-yl)methyl) carbamate was synthesised according to general procedures GP14 and GP12—from i) from 2-ethylhexyl 3-((3-methoxy-5-(1-methyl-1H-pyrazol-4-yl)phenyl)thio)propanoate (1.9 g, 4.70 mmol), KOtBu (1.0 M in THF; 14.1 mL, 14.1 mmol), THF (25 mL); −78° C., 1 h. 1.5 g of crude obtained and used immediately without further purification. ii) 3-Methoxy-5-(1-methyl-1H-pyrazol-4-yl)benzenethiol (0.80 g of the 1.5 g crude), Pd$_2$(dba)$_3$ (0.33 g, ~10 mol %), Xantphos (0.42 mg, ~20 mol %), tert-butyl ((5-bromothiazol-2-yl)methyl)carbamate (0.85 g, 2.90 mmol), NaO$^t$Bu (0.52 g, 5.44 mmol) and toluene:$^t$BuOH (4:1; 25 mL); 110° C., 16 h. Chromatography (62% EtOAc in hexane) afforded a yellow oil (0.30 g, 28% over 2 steps). $^1$H NMR (400 MHz, DMSO-d$_6$) δ 8.14 (s, 1H), 7.94 (s, 1H), 7.92 (s, 1H), 7.90-7.84 (m, 1H), 7.44-7.35 (m, 2H), 7.01 (t, J=1.6 Hz, 1H), 4.39 (d, J=6.0 Hz, 2H), 3.84 (s, 3H), 3.74 (s, 3H), 1.33 (s, 9H). LCMS (ESI) m/z 433 (M+H)$^+$.

Example 128 was synthesised according to general procedures GP4—from i) m-CPBA (55%; 0.47 g, 1.52 mmol), tert-butyl ((5-((3-methoxy-5-(1-methyl-1H-pyrazol-4-yl)phenyl)thio)thiazol-2-yl)methyl)carbamate (0.30 g, 0.69 mmol) and DCM (20 mL); rt, 3 h. Chromatography (82% EtOAc in hexane), pale yellow solid (0.12 g, 37%); ii) 1 M HCl in Et$_2$O (4 mL), tert-butyl ((5-((3-methoxy-5-(1-methyl-1H-pyrazol-4-yl)phenyl)sulfonyl)thiazol-2-yl)methyl)carbamate (0.12 g, 0.25 mmol) and DCM (10 mL); rt, 4 h. White solid obtained (35 mg, 37%) without further purification. $^1$H NMR (500 MHz, Methanol-d$_4$) δ 8.62-8.36 (m, 3H), 7.80 (s, 1H), 7.48 (s, 1H), 7.40 (s, 1H), 4.57 (s, 2H), 4.10 (s, 3H), 3.92 (s, 3H). $^{13}$C NMR (126 MHz, Methanol-d$_4$) δ 170.31, 162.37, 148.87, 144.47, 142.35, 135.59, 135.28, 133.24, 123.14, 117.90, 117.48, 112.27, 56.91, 41.52, 39.50. HRMS (ESI) for C$_{15}$H$_{17}$N$_4$O$_3$S$_2$ ([M+H]$^+$): Calculated 365.0742; Observed 365.0736.

Example 129: (5-((2-(Methylsulfonyl)-[1,1'-biphenyl]-4-yl)sulfonyl)thiophen-2-yl)methanamine hydrochloride

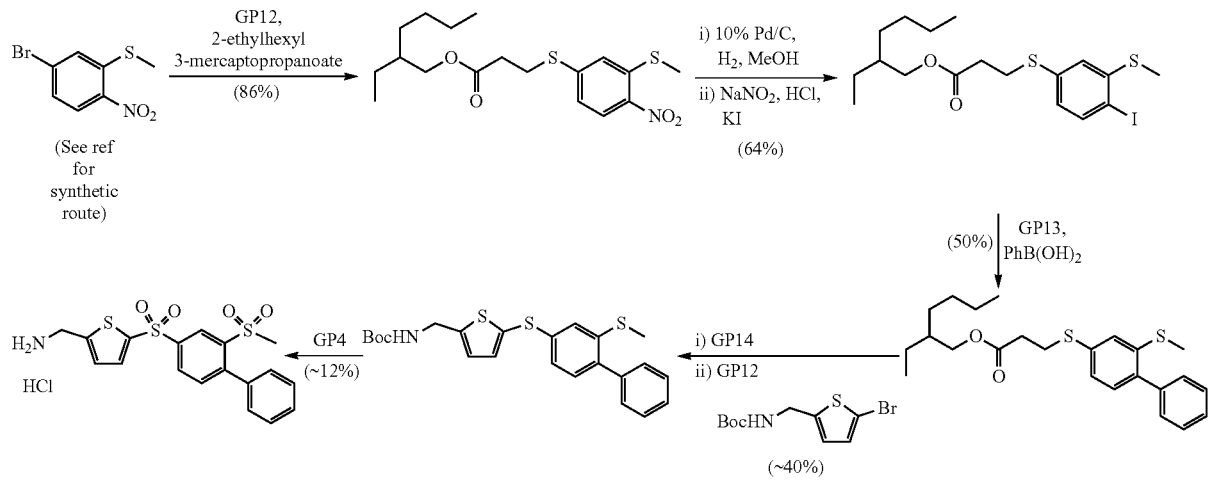

Ref - (Romero, F. et al, 2016)

2-Ethylhexyl 3-((3-(methylthio)-4-nitrophenyl)thio)propanoate was synthesised according to general procedures GP12—from (5-bromo-2-nitrophenyl)(methyl)sulfane (0.30 g, 1.21 mmol), $Pd_2(dba)_3$ (27 mg, 2.5 mol %), Xantphos (35 mg, 5 mol %), 2-ethylhexyl-3-mercaptopropionate (0.26 g, 1.21 mmol), DIPEA (0.42 mL, 2.42 mmol) and toluene (5 mL); 110° C., 16 h. Chromatography (5% EtOAc in hexane) afforded a yellow oil (0.40 g, 86%). $^1$H NMR (400 MHz, DMSO-$d_6$) δ 8.17 (d, J=8.8 Hz, 1H), 7.27 (d, J=1.5 Hz, 1H), 7.24 (d, J=2.0 Hz, 1H), 3.95 (d, J=7.4 Hz, 2H), 3.36 (t, J=6.8 Hz, 2H), 2.75 (t, J=6.8 Hz, 2H), 2.54 (s, 3H), 1.55-1.45 (m, 1H), 1.38-1.20 (m, 8H), 0.90-0.80 (m, 6H). LCMS (ESI, −ve) m/z 200 (M-$C_{11}H_{21}O_2$)$^-$.

Pd/C (10%, 50 mg) was added to a solution of 2-ethylhexyl 3-((3-(methylthio)-4-nitrophenyl)thio)propanoate (0.10 g, 0.260 mmol) in methanol (3.0 mL), and the reaction mixture was stirred for 4 h under $H_2$ atmosphere (40 psi). The reaction mixture was then filtered through a pad of celite and the solvent was removed under reduced pressure to afford 2-ethylhexyl 3-((4-amino-3-(methylthio)phenyl)thio)propanoate (80 mg, 87%) as an amber-coloured oil. $^1$H NMR (400 MHz, DMSO-d6) δ 7.23 (d, J=1.9 Hz, 1H), 7.05 (dd, J=2.0 Hz, 8.3 Hz, 1H), 6.66 (d, J=8.3 Hz, 1H), 5.41 (br, 2H), 3.93 (d, J=5.8 Hz, 2H), 2.91 (t, J=6.8 Hz, 2H), 2.49-2.46 (m, 2H), 2.32 (s, 3H), 1.53-1.50 (m, 1H), 1.33-1.25 (m, 8H), 0.87-0.82 (m, 6H). LCMS (ESI) m/z 356 (M+H)$^+$.

2-Ethylhexyl 3-((4-amino-3-(methylthio)phenyl)thio)propanoate (0.210 g, 0.592 mmol) was dissolved in aq. HCl (2.5 N, 10 mL) and the solution was cooled to 0° C. $NaNO_2$ (81 mg, 1.18 mmol) was added and the resulting mixture was stirred at 0° C. for 1 h. A solution of KI (196 mg, 1.18 mmol) in water (6 mL) was then added and the mixture was stirred at rt for 16 h. The reaction mixture was subsequently extracted with EtOAc (30 mL), dried over $Na_2SO_4$, filtered and the solvent was removed under reduced pressure. The crude was purified using chromatography (5% EtOAc in hexane) to afford 2-ethylhexyl 3-((4-iodo-3-(methylthio)phenyl)thio)propanoate as a yellow oil (0.20 g, 73%). $^1$H NMR (400 MHz, DMSO-$d_6$) δ 7.70 (d, J=7.9 Hz, 1H), 7.03 (d, J=2.0 Hz, 1H), 6.87 (dd, J=1.9 Hz, 2.0 Hz, 1H), 3.93 (d, J=5.9 Hz, 2H), 3.21 (t, J=6.6 Hz, 2H), 2.63 (t, J=6.8 Hz, 2H), 2.51 (s, 3H), 1.52-1.49 (m, 1H), 1.32-1.23 (m, 8H), 0.87-0.81 (m, 6H). LCMS (ESI) m/z 378 (M+Na)$^+$.

2-Ethylhexyl 3-((2-(methylthio)-[1,1'-biphenyl]-4-yl)thio)propanoate was synthesised according to general procedures GP13—from 2-ethylhexyl 3-((4-iodo-3-(methylthio)phenyl)thio)propanoate (0.20 g, 0.429 mmol), phenylboronic acid (63 mg, 0.514 mmol), Pd(PPh$_3$)$_4$ (25 mg, 5 mol %), Na$_2$CO$_3$ (0.114 g, 1.07 mmol), toluene:H$_2$O (5:1, 6 mL); 100° C., 16 h. Chromatographic purification (10-15% EtOAc in hexane) afforded a yellow oil (90 mg, 50%). $^1$H NMR (400 MHz, DMSO-$d_6$) δ 7.42-7.31 (m, 5H), 7.16-7.10 (m, 3H), 3.93 (d, J=5.9 Hz, 2H), 3.21 (t, J=6.8 Hz, 2H), 2.64 (t, J=6.8 Hz, 2H), 2.36 (s, 3H), 1.55-1.45 (m, 1H), 1.29-1.22 (m, 8H), 0.84-0.70 (m, 6H). LCMS (ESI, −ve) m/z 415 (M−H)$^-$.

tert-Butyl ((5-((2-(methylthio)-[1,1'-biphenyl]-4-yl)thio)thiophen-2-yl)methyl)carbamate was synthesised according to general procedures GP14 and GP12—from i) 2-Ethylhexyl 3-((2-(methylthio)-[1,1'-biphenyl]-4-yl)thio)propanoate (0.50 g, 1.20 mmol), KO$^t$Bu (1.0 M in THF; 3.60 mL, 3.60 mmol), THF (10 mL); −78° C., 1 h. ii) Pd$_2$(dba)$_3$ (0.11 g, 0.12 mmol), Xantphos (0.149 mg, 0.24 mmol), tert-butyl ((5-bromothiophen-2-yl)methyl)carbamate (0.352 g, 1.20 mmol), NaO$^t$Bu (0.17 g, 1.81 mmol) and toluene/$^t$BuOH (5:1; 12 mL); 110° C., 16 h. Chromatography (25% EtOAc in hexane) afforded a yellow oil (0.22 g, ~41%), which contained impurities that was carried over to the subsequent transformation. $^1$H NMR (400 MHz, DMSO-$d_6$) δ 7.55-7.50 (m, 1H), 7.43-7.41 (m, 6H), 7.12 (d, J=8.3 Hz, 1H), 7.07 (s, 1H), 6.99-6.95 (m, 2H), 4.48 (d, J=5.4 Hz, 2H), 2.28 (s, 3H), 1.38 (s, 9H). LCMS (ESI) m/z 327 (M-BocNH)$^+$.

Example 129 was synthesised according to general procedures GP4—from i) m-CPBA (55%; 0.78 g, 2.48 mmol), tert-butyl ((5-((2-(methylthio)-[1,1'-biphenyl]-4-yl)thio)thiophen-2-yl)methyl)carbamate (0.22 g, 0.497 mmol) and DCM (10 mL); rt, 3 h. Chromatography (60% EtOAc in hexane), pale yellow oil (0.10 g, ~40%); ii) 2 M HCl in Et$_2$O (10 mL), tert-butyl ((5-((2-(methylsulfonyl)-[1,1'-biphenyl]-4-yl)sulfonyl)thiophen-2-yl)methyl) carbamate (0.10 g, 0.197 mmol) and DCM (10 mL); rt, 4 h. White solid obtained (27 mg, 31%) without further purification. $^1$H NMR (500 MHz, Methanol-$d_4$) δ 8.70 (d, J=1.9 Hz, 1H), 8.34 (dd, J=8.0, 2.0 Hz, 1H), 7.86 (d, J=3.8 Hz, 1H), 7.68 (d, J=8.0 Hz, 1H), 7.56-7.44 (m, 5H), 7.39 (d, J=3.8 Hz, 1H), 4.43 (s, 2H), 2.72 (s, 3H). $^{13}$C NMR (126 MHz, Methanol-$d_4$) δ 148.21, 146.02, 144.52, 143.07, 142.42, 138.31, 135.90, 135.83, 132.70, 131.92, 130.90, 130.29, 129.23, 128.16, 43.56, 38.49. HRMS (ESI) for $C_{18}H_{18}NO_4S_3$ ([M-NH$_2$]$^+$): Calculated 391.0132; Observed 391.0124.

Example 130: (5-((3-(1-Ethyl-1H-pyrazol-4-yl)-5-methoxyphenyl)sulfonyl)thiazol-2-yl)methanamine trihydrochloride phenyl)thio)propanoate (2.20 g, 5.26 mmol), KO$^t$Bu (1.0 M in THF; 15.8 mL, 15.8 mmol), THF (25 mL); −78° C., 30 min. Crude thiol (2.0 g, 91%); ii) 3-(1-ethyl-1H-pyrazol-4-yl)-5-methoxybenzenethiol (1.0 g, ~4.27 mmol), tert-butyl ((5-bromothiazol-2-yl)methyl)carbamate (1.0 g, 3.41 mmol), Pd$_2$(dba)$_3$ (390 mg, 0.426 mmol), Xantphos (490 mg, 0.846 mmol), NaO$^t$Bu (610 mg, 6.35 mmol) and toluene/$^t$BuOH (4:1; 25 mL); 110° C., 16 h. Chromatography (52% EtOAc in hexane) afforded a yellow oil (0.50 g, 33%). $^1$H NMR (400 MHz, DMSO-$d_6$) δ 8.18 (s, 1H), 7.92 (s, 1H), 7.83 (s, 1H), 7.77-7.76 (m, 1H), 7.05 (s, 1H), 7.01 (s, 1H), 6.52 (s, 1H), 4.38 (d, J=5.6 Hz, 2H), 4.11 (q, J=7.2 Hz, 2H),

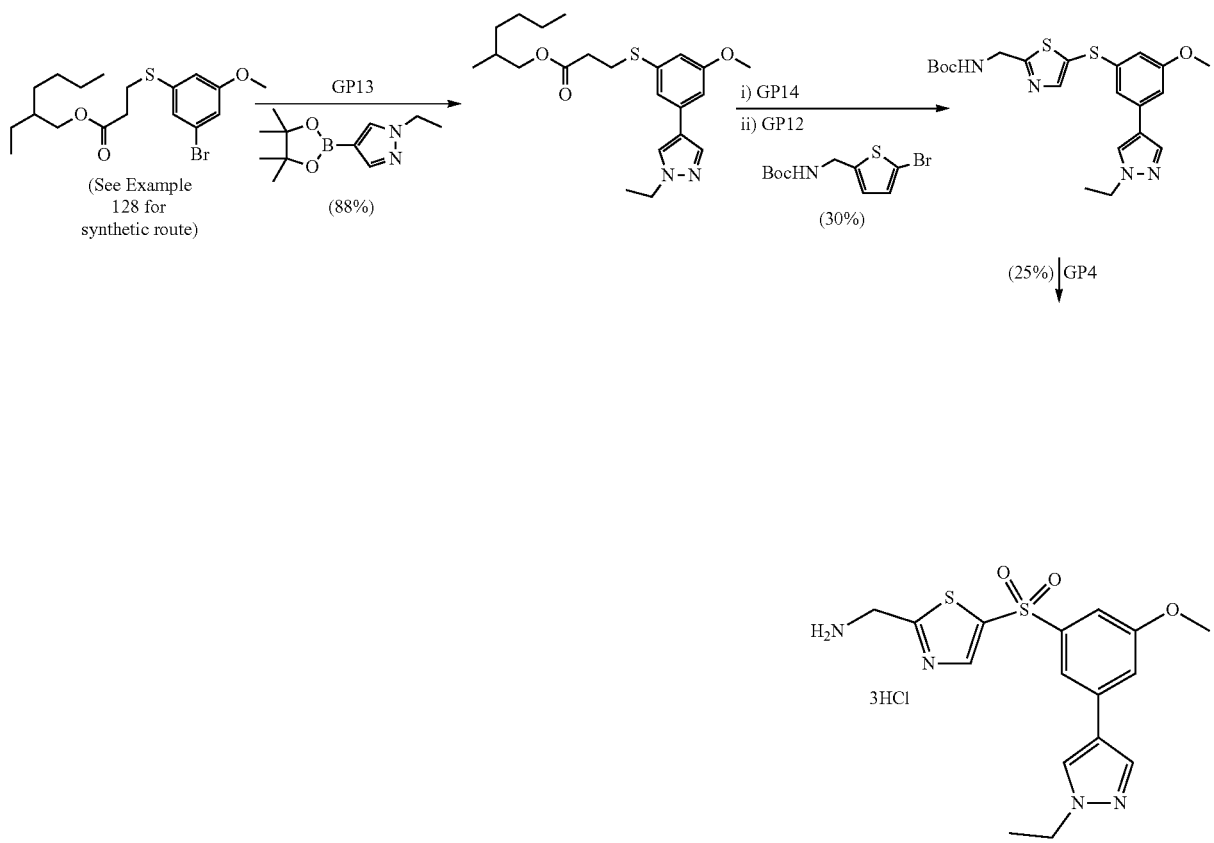

2-Ethylhexyl 3-((3-(1-ethyl-1H-pyrazol-4-yl)-5-methoxyphenyl)thio)propanoate was synthesised according to general procedures GP13—from 2-ethylhexyl 3-((3-bromo-5-methoxyphenyl)thio)propanoate (2.40 g, 5.95 mmol), 1-ethyl-4-(4,4,5,5-tetramethyl-1,3,2-dioxaborolan-2-yl)-1H-pyrazole (1.98 g, 8.92 mmol), Pd(dppf)Cl$_2$ (240 mg, 5 mol %), Cs$_2$CO$_3$ (4.85 g, 14.9 mmol), 1,4-dioxane/H$_2$O (6:1; 35 mL); 100° C., 16 h. Chromatographic purification (28% EtOAc in hexane) afforded a colourless oil (2.20 g, 88%). $^1$H NMR (400 MHz, DMSO-$d_6$) δ 8.25 (s, 1H), 7.90 (s, 1H), 7.10 (s, 1H), 6.98 (d, J=2.0 Hz, 1H), 6.68 (t, J=2.0 Hz, 1H), 4.13 (q, J=7.2 Hz, 2H) 3.94 (d, J=6.4 Hz, 2H), 3.78 (s, 3H), 3.22 (t, J=6.8 Hz, 2H), 2.66 (t, J=5.6 Hz, 2H), 1.52-1.41 (m, 1H), 1.38 (t, J=7.2 Hz, 3H), 1.30-1.22 (m, 8H), 0.84-0.81 (m, 6H). LCMS (ESI) m/z 419 (M+H)$^+$.

tert-Butyl ((5-((3-(1-ethyl-1H-pyrazol-4-yl)-5-methoxyphenyl)thio)thiazol-2-yl)methyl)carbamate was synthesised according to general procedures GP14 and GP12—from i) 2-ethylhexyl 3-((3-(1-ethyl-1H-pyrazol-4-yl)-5-methoxy- 3.73 (s, 3H), 1.51 (s, 9H), 1.37 (t, J=8.0 Hz, 3H). LCMS (ESI) m/z 447 (M+H)$^+$.

Example 130 was synthesised according to general procedures GP4—from i) m-CPBA (55%; 0.770 g, 2.45 mmol), tert-butyl ((5-((3-(1-ethyl-1H-pyrazol-4-yl)-5-methoxyphenyl)thio)thiazol-2-yl)methyl)carbamate (0.50 g, 1.12 mmol) and DCM (20 mL); rt, 3 h. Chromatography (53% EtOAc in cyclohexane), yellow solid (0.30 g, 56%); ii) 1 M HCl in Et$_2$O (5.0 ml), tert-butyl ((5-((3-(1-ethyl-1H-pyrazol-4-yl)-5-methoxyphenyl)sulfonyl)thiazol-2-yl)methyl)carbamate (200 mg, 0.418 mmol) and DCM (10 mL); rt, 3 h. White solid (90 mg, 44%) obtained and required no further purification. $^1$H NMR (500 MHz, Methanol-$d_4$) δ 8.91-8.27 (m, 3H), 7.82 (s, 1H), 7.51 (s, 1H), 7.39 (s, 1H), 4.73-4.31 (m, 4H), 3.92 (s, 3H), 1.60 (br, 3H). $^{13}$C NMR (126 MHz, Methanol-$d_4$) δ 170.34, 162.34, 148.87, 144.43, 142.21, 135.24, 135.07, 132.09, 123.07, 117.86, 117.47, 112.46, 56.92, 48.73, 41.42, 15.38. HRMS (ESI) for $C_{16}H_{19}N_4O_3S_2$ ([M+H]$^+$): Calculated 379.0898; Observed 379.0905.

Example 131: (5-((3-Fluoro-5-(1-methyl-1H-pyrazol-4-yl)phenyl)sulfonyl)thiazol-2-yl)methanamine trihydrochloride

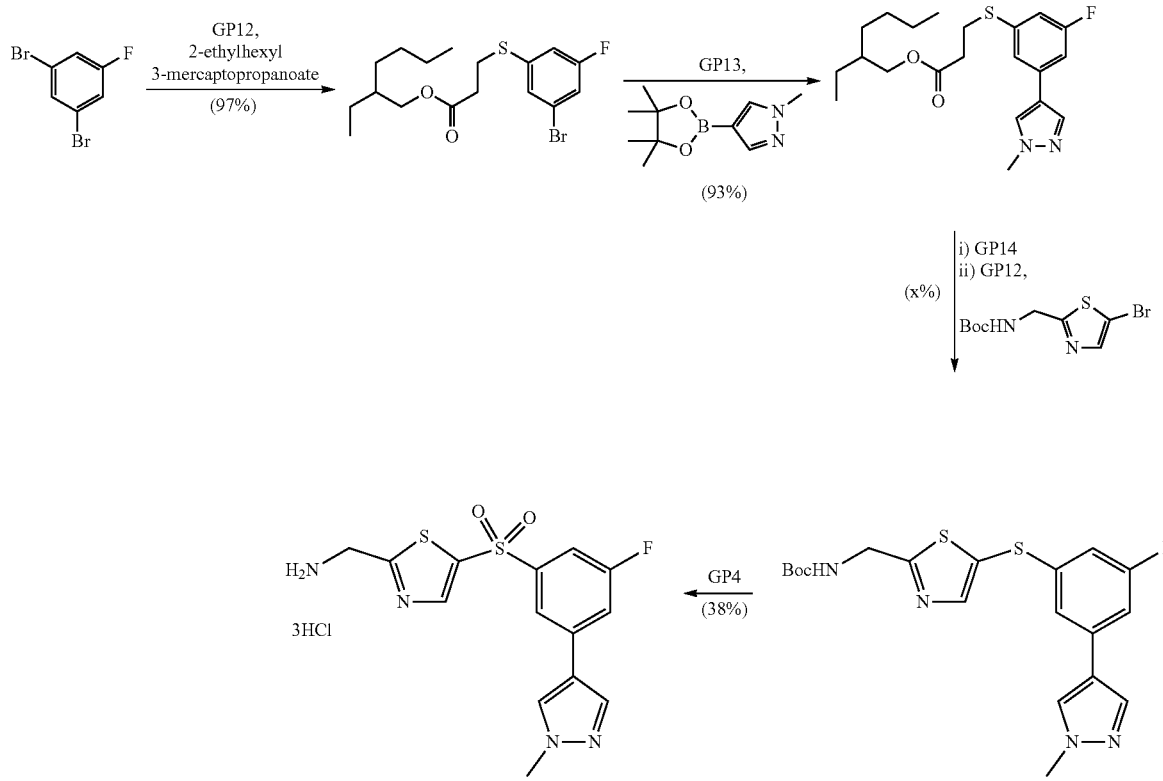

2-Ethylhexyl 3-((3-bromo-5-fluorophenyl)thio)propanoate was synthesised according to general procedures GP12—from 1,3-dibromo-5-fluorobenzene (1.0 g, 3.94 mmol), $Pd_2(dba)_3$ (90 mg, 2.5 mol %), Xanthphos (0.114 g, 5 mol %), 2-ethylhexyl-3-mercaptopropionate (0.860 g, 3.94 mmol), DIPEA (1.36 ml, 7.82 mmol) and toluene (20 ml); 110° C., 6 h. Chromatographic purification (8% EtOAc in hexane) afforded a yellow solid (1.50 g, 97%). $^1$H NMR (400 MHz, DMSO-$d_6$) δ 7.38-7.37 (m, 1H), 7.35 (d, J=2.0 Hz, 1H), 7.27-7.24 (m, 1H), 3.94 (d, J=5.4 Hz, 2H), 3.26 (t, J=6.8 Hz, 2H), 2.65 (t, J=5.6 Hz, 2H), 1.53-1.50 (m, 1H), 1.33-1.25 (m, 8H), 0.87-0.80 (m, 6H). LCMS (ESI, -ve) m/z 388.9 (M−H)$^-$.

2-Ethylhexyl 3-((3-fluoro-5-(1-methyl-1H-pyrazol-4-yl)phenyl)thio)propanoate was synthesised according to general procedures GP13- from 2-ethylhexyl 3-((3-bromo-5-fluorophenyl)thio)propanoate (1.50 g, 3.83 mmol), 1-methyl-4-(4,4,5,5-tetramethyl-1,3,2-dioxaborolan-2-yl)-1H-pyrazole (0.960 g, 4.62 mmol), Pd(dppf)$Cl_2 \cdot CH_2Cl_2$ (140 mg, 5 mol %), $Cs_2CO_3$ (2.49 g, 7.64 mmol), 1,4-dioxane/$H_2O$ (6:1; 35 mL); 105° C., 16 h. Chromatographic purification (40% EtOAc in hexane) afforded a colourless oil (1.40 g, 93%). $^1$H NMR (400 MHz, DMSO-$d_6$) δ 8.25 (s, 1H), 7.95 (s, 1H), 7.34 (s, 1H), 7.26 (d, J=9.3 Hz, 1H), 6.99 (d, J=8.8 Hz, 1H), 3.95 (d, J=1.9 Hz, 2H), 3.94 (s, 3H), 3.26 (t, J=6.8 Hz, 2H), 2.67-2.64 (m, 2H), 1.51-1.49 (m, 1H), 1.32-1.26 (m, 8H), 0.85-0.81 (m, 6H). LCMS (ESI) m/z 393 (M+H)$^+$.

tert-Butyl ((5-((3-fluoro-5-(1-methyl-1H-pyrazol-4-yl)phenyl)thio)thiazol-2-yl)methyl)carbamate was synthesised according to general procedures GP14 and GP12—from i) 2-ethylhexyl 3-((3-fluoro-5-(1-methyl-1H-pyrazol-4-yl)phenyl)thio)propanoate (2.20 g, 5.61 mmol), KO$^t$Bu (1.0 M in THF; 16.8 mL, 16.8 mmol), THF (22 mL); −78° C., 30 min; ii) tert-butyl ((5-bromothiazol-2-yl)methyl)carbamate (1.407 g, 4.80 mmol), $Pd_2(dba)_3$ (440 mg, 10 mol %), Xantphos (550 mg, 20 mol %), NaO$^t$Bu (690 mg, 7.20 mmol) and toluene/$^t$BuOH (4:1; 30 mL); 110° C., 16 h. Chromatography (50% EtOAc in hexane) afforded a yellow oil (0.470 g, 20%). $^1$H NMR (400 MHz, DMSO-$d_6$) δ 8.20 (s, 1H), 7.99 (s, 1H), 7.93 (s, 1H), 7.80-7.78 (m, 1H), 7.33-7.31 (m, 1H), 6.74 (d, J=9.3 Hz, 1H) 4.40 (d, J=5.9 Hz, 2H), 3.85 (s, 3H), 1.38 (s, 9H). LCMS (ESI) m/z 421.0 (M+H)$^+$.

Example 131 was synthesised according to general procedures GP4—from i) m-CPBA (55%; 0.620 g, 1.98 mmol), tert-butyl ((5-((3-fluoro-5-(1-methyl-1H-pyrazol-4-yl)phenyl)thio)thiazol-2-yl)methyl)carbamate (0.380 g, 0.904 mmol) and DCM (10 mL); rt, 4 h. Chromatography (55% EtOAc in cyclohexane), yellow oil (0.290 g, 71%); ii) 2 M HCl in $Et_2O$ (5.0 ml), tert-butyl ((5-((3-fluoro-5-(1-methyl-1H-pyrazol-4-yl)phenyl)sulfonyl)thiazol-2-yl)methyl)carbamate (200 mg, 0.442 mmol) and DCM (5.0 mL); rt, 3 h. Yellow solid (110 mg, 54%) obtained and required no further purification. $^1$H NMR (500 MHz, Methanol-$d_4$/Chloroform-d) δ 8.40 (s, 1H), 8.17 (br, 1H), 8.01-7.90 (m, 2H), 7.65-7.48 (m, 2H), 4.53 (s, 2H), 3.98 (s, 3H). $^{13}$C NMR (126 MHz, Methanol-$d_4$/Chloroform-d) δ 169.90, 163.89 (d, J=252 Hz), 148.66, 144.34 (d, J=7.6 Hz), 141.33, 137.62 (d, J=10.1 Hz), 136.99, 130.68, 121.23, 120.57, 118.51 (d, J=23 Hz), 112.79 (d, J=25 Hz), 40.99, 39.30. $^{19}$F NMR (471 MHz, Methanol-$d_4$/Chloroform-d) δ−109.29. HRMS (ESI) for $C_{14}H_{14}FN_4O_2S_2$ ([M+H]$^+$): Calculated 353.0542; Observed 353.0541.

311

Example 132: (5-((3-(1-Cyclopropyl-1H-pyrazol-4-yl)-5-methoxyphenyl)sulfonyl)thiazol-2-yl)methanamine trihydrochloride

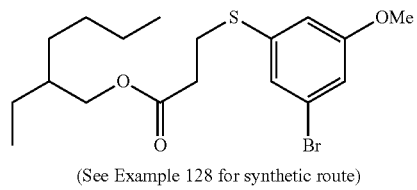

(See Example 128 for synthetic route)

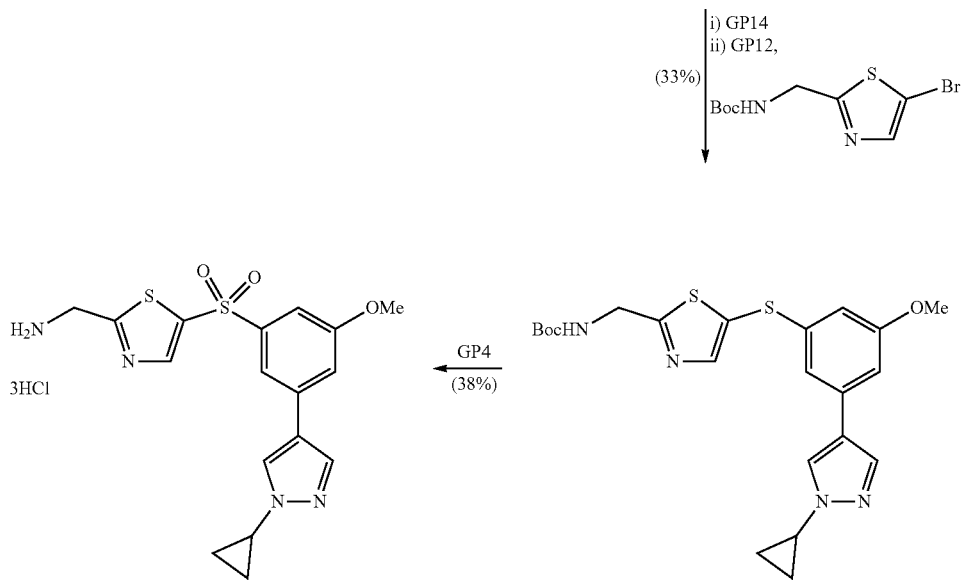

2-Ethylhexyl 3-((3-(1-cyclopropyl-1H-pyrazol-4-yl)-5-methoxyphenyl)thio)propanoate was synthesised according to general procedures GP13—from 2-ethylhexyl 3-((3-bromo-5-methoxyphenyl)thio)propanoate (2.23 g, 5.55 mmol), 1-cyclopropyl-4-(4,4,5,5-tetramethyl-1,3,2-dioxaborolan-2-yl)-1H-pyrazole (1.00 g, 4.27 mmol), Pd(dppf)Cl$_2$ (220 mg, 5 mol %), Cs$_2$CO$_3$ (4.48 g, 13.7 mmol), 1,4-dioxane/H$_2$O (5:1; 30 mL); 90° C., 16 h. Chromatographic purification (0→10% EtOAc/hexane) afforded a yellow oil (1.46 g, 80%). $^1$H NMR (400 MHz, DMSO-d$_6$) δ 8.23 (s, 1H), 7.90 (s, 1H), 7.11 (br, 1H), 6.99 (br, 1H), 6.68 (t, J=1.6 Hz, 1H), 3.94 (d, J=5.6 Hz, 2H), 3.78 (s, 3H), 3.73-3.71 (m, 1H), 1.51-1.47 (m, 1H), 3.23-3.20 (m, 2H), 2.63 (t, J=6.8 Hz, 2H), 1.30-1.22 (m, 8H), 1.07-1.04 (m, 2H), 1.00-0.97 (m, 2H), 0.85-0.81 (m, 6H). LCMS (ESI) m/z 431 (M+H)$^+$.

tert-Butyl ((5-((3-(1-cyclopropyl-1H-pyrazol-4-yl)-5-methoxyphenyl)thio)thiazol-2-yl)methyl)carbamate GP14 and GP12—from i) 2-ethylhexyl 3-((3-(1-cyclopropyl-1H-pyrazol-4-yl)-5-methoxyphenyl)thio)propanoate (1.36 g, 3.16 mmol), KOtBu (1.0 M in THF; 9.5 mL, 9.50 mmol), THF (20 mL); −78° C., 30 min; ii) tert-butyl ((5-bromothiazol-2-yl)methyl)carbamate (0.70 g, 2.38 mmol), Pd$_2$(dba)$_3$ (290 mg, 13 mol %), Xantphos (360 mg, 26 mol %), NaO$^t$Bu

312

(460 mg, 4.79 mmol) and toluene/$^t$BuOH (4:1; 25 mL); 110° C., 16 h. Chromatography (0→33% EtOAc/hexane) afforded a yellow oil (0.36 g, 33%). $^1$H NMR (400 MHz, DMSO-d$_6$) δ 8.25 (s, 1H), 7.94 (s, 1H), 7.84 (s, 1H), 7.78 (br, 1H), 7.09 (s, 1H), 7.04 (s, 1H), 6.53 (s, 1H), 4.39 (d, J=5.2 Hz, 2H), 3.77 (s, 3H), 3.74-3.70 (m, 1H), 1.41 (s, 9H), 1.06-1.04 (m, 2H), 1.01-0.97 (m, 2H). LCMS (ESI) m/z 459 (M+H)$^+$.

Example 132 was synthesised according to general procedures GP4—from i) m-CPBA (55%; 0.30 g, 0.96 mmol), tert-butyl ((5-((3-(1-cyclopropyl-1H-pyrazol-4-yl)-5-methoxyphenyl)thio)thiazol-2-yl)methyl)carbamate (0.20 g, 0.436 mmol) and DCM (15 mL); rt, 3 h. Chromatography (52% EtOAc in cyclohexane), yellow solid (120 mg, 56%); ii) 1 M HCl in Et$_2$O (4.0 ml), tert-butyl ((5-((3-(1-cyclopropyl-1H-pyrazol-4-yl)-5-methoxyphenyl)sulfonyl)thiazol-2-yl)methyl)carbamate (80 mg, 0.163 mmol) and DCM (2.0 mL); rt, 3 h. Yellow solid (55 mg, 68%) obtained and required no further purification. $^1$H NMR (500 MHz, Methanol-d$_4$) δ 8.59 (s, 1H), 8.47 (s, 1H), 8.36 (s, 1H), 7.81 (s, 1H), 7.49 (s, 1H), 7.39 (s, 1H), 4.58 (s, 2H), 3.92 (s, 3H), 3.84 (m, 1H), 1.32-1.16 (m, 4H). $^{13}$C NMR (126 MHz, Methanol-d$_4$) δ 170.35, 162.42, 148.84, 144.47, 142.40, 136.17, 135.59, 132.22, 122.75, 117.76, 117.41, 112.25, 56.76, 41.28, 33.75, 7.37. HRMS (ESI) for C$_{17}$H$_{19}$N$_4$O$_3$S$_2$ ([M+H]$^+$): Calculated 391.0898; Observed 391.0897.

Example 133: (5-((4'-Fluoro-5-(methylsulfonyl)-[1,1'-biphenyl]-3-yl)sulfonyl)thiazol-2-yl)methanamine

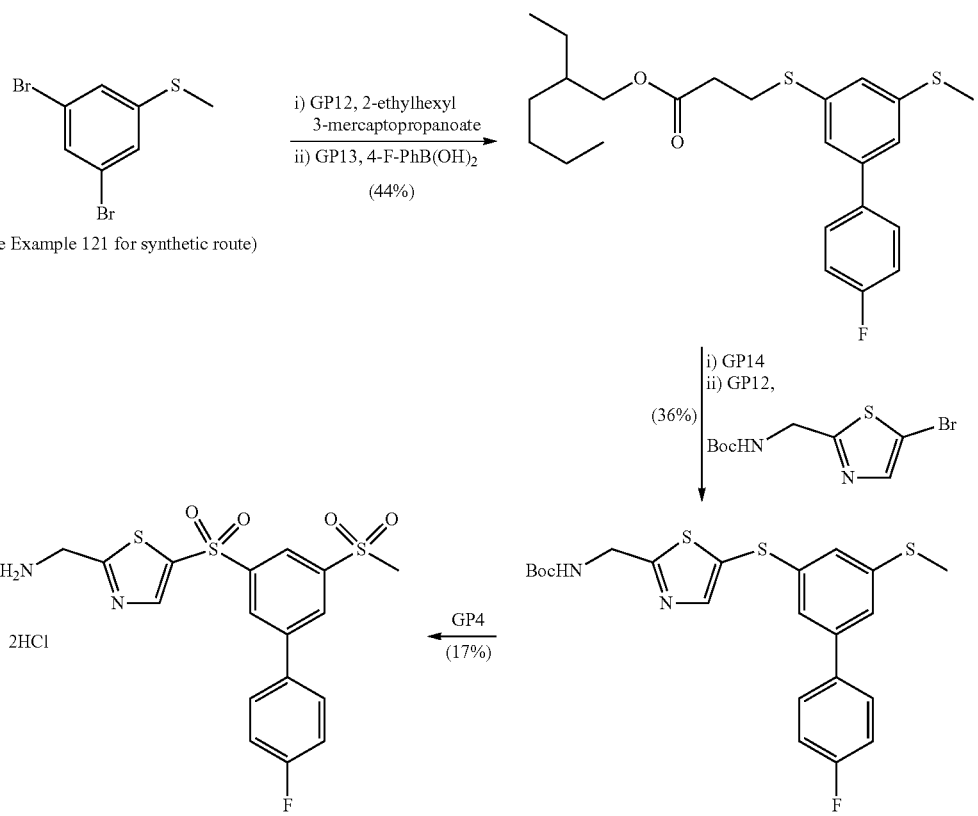

2-Ethylhexyl 3-((3-bromo-5-(methylthio)phenyl)thio)propanoate was synthesised according to general procedures GP12—from (3,5-dibromophenyl)(methyl)sulfane (3.0 g, 10.6 mmol), Pd$_2$(dba)$_3$ (243 mg, 2.5 mol %), Xanthphos (0.30 g, 5 mol %), 2-ethylhexyl-3-mercaptopropionate (1.85 g, 8.49 mmol), DIPEA (3.72 ml, 21.4 mmol) and toluene (30 ml); 110° C., 6 h. Chromatographic purification (5% EtOAc in hexane) afforded a yellow oil (2.50 g, 70%). $^1$H NMR (400 MHz, DMSO-d$_6$) δ 7.24 (d, J=5.6 Hz, 2H), 7.14 (s, 1H), 3.94 (d, J=5.6 Hz, 2H), 3.22 (t, J=6.8 Hz, 2H), 2.62 (t, J=7.2 Hz, 2H), 2.50 (s, 3H), 1.50 (m, 1H), 1.29-1.24 (m, 8H), 0.86-0.82 (m, 6H). LCMS (ESI, −ve) m/z 233/235 (M-C$_{11}$H$_{21}$O$_2$)$^-$.

2-Ethylhexyl 3-((4'-fluoro-5-(methylthio)-[1,1'-biphenyl]-3-yl)thio)propanoate was synthesised according to general procedures GP13—from 2-ethylhexyl 3-((3-bromo-5-(methylthio)phenyl)thio)propanoate (2.0 g, 4.77 mmol), 4-fluorophenylboronic acid (0.80 g, 5.71 mmol), Pd(PPh$_3$)$_4$ (0.27 g, 0.24 mmol, 5 mol %), aq. Na$_2$CO$_3$ (2.0 M; 4.7 mL, 9.40 mmol), toluene (5:1; 30 mL); 100° C., 16 h. Chromatographic purification (10% EtOAc in hexane) afforded a colourless oil (1.30 g, 63%). $^1$H NMR (400 MHz, DMSO-d6) δ 7.75-7.70 (m, 2H), 7.30-7.26 (m, 4H), 7.16 (t, J=1.6 Hz, 1H), 3.94 (d, J=5.2 Hz, 2H), 3.25 (t, J=4.0 Hz, 2H), 2.64 (t, J=5.6 Hz, 2H), 2.51 (s, 3H), 1.51-1.47 (m, 1H), 1.31-1.22 (m, 8H), 0.84-0.80 (m, 6H). LCMS (ESI, −ve) m/z 249 (M-C$_{11}$H$_{21}$O$_2$)$^-$.

tert-Butyl ((5-((4'-fluoro-5-(methylthio)-[1,1'-biphenyl]-3-yl)thio)thiazol-2-yl)methyl)carbamate was synthesised according to general procedures GP14 and GP12—from i) 2-ethylhexyl 3-((4'-fluoro-5-(methylthio)-[1,1'-biphenyl]-3-yl)thio)propanoate (1.30 g, 2.99 mmol), KO$^t$Bu (1.0 M in THF; 8.92 mL, 8.92 mmol), THF (25 mL); −78° C., 30 min. ii) tert-butyl ((5-bromothiazol-2-yl)methyl)carbamate (0.93 g, 3.17 mmol), Pd$_2$(dba)$_3$ (360 mg, 13 mol %), Xantphos (460 mg, 27 mol %), NaO$^t$Bu (570 mg, 5.94 mmol) and toluene/$^t$BuOH (4:1; 25 mL); 110° C., 16 h. Chromatography (28% EtOAc in hexane) afforded a yellow oil (0.50 g, 36%). $^1$H NMR (400 MHz, DMSO-d$_6$) δ 7.99 (s, 1H), 7.78 (br, 1H), 7.60-7.68 (m, 2H), 7.33 (s, 1H), 7.27 (t, J=2.0 Hz, 2H), 7.25 (s, 1H), 7.05 (s, 1H), 4.39 (d, J=6.0 Hz, 2H), 3.26 (s, 3H), 1.37 (s, 9H). LCMS (ESI) m/z 463 (M+H)$^+$.

Example 133 was synthesised according to general procedures GP4—from i) m-CPBA (55%; 0.74 g, 2.36 mmol), tert-butyl ((5-((4'-fluoro-5-(methylthio)-[1,1'-biphenyl]-3-yl)thio)thiazol-2-yl)methyl)carbamate (0.25 g, 0.540 mmol) and DCM (20 mL); rt, 8 h. Chromatography (32% EtOAc in cyclohexane), a yellow solid (110 mg, 39%); 1 M HCl in Et$_2$O (5.0 ml), tert-butyl ((5-((4'-fluoro-5-(methylsulfonyl)-[1,1'-biphenyl]-3-yl)sulfonyl)thiazol-2-yl)methyl)carbamate (110 mg, 0.209 mmol) and DCM (10 mL); 0° C., 5 h. white solid (45 mg, 43%) obtained and required no further purification. $^1$H NMR (500 MHz, Methanol-d$_4$) δ 8.79-8.32 (m, 4H), 7.79 (br, 2H), 7.28 (br, 2H), 4.58 (s, 2H), 3.28 (s, 3H). $^{13}$C NMR (126 MHz, Methanol-d$_4$) δ 173.79, 167.59 (d, J=249.5 Hz), 152.53, 147.74, 147.61, 147.40, 144.20, 137.27, 134.82, 133.97, 133.55 (d, J=7.6 Hz), 128.42, 120.05 (d, J=22.7 Hz), 47.48, 45.02. HRMS (ESI) for C$_{17}$H$_{16}$FN$_2$O$_4$S$_3$ ([M+H]$^+$): Calculated 427.0256; Observed 427.0242.

Example 134: (5-((3'-Fluoro-5-(methylsulfonyl)-[1,1'-biphenyl]-3-yl)sulfonyl)thiazol-2-yl)methanamine

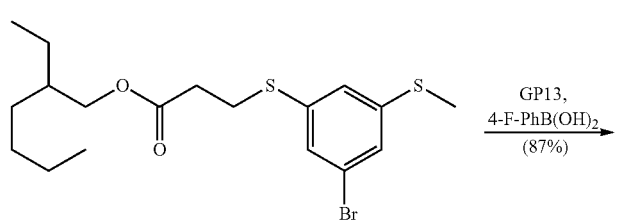

(See Example 133 for synthetic route)

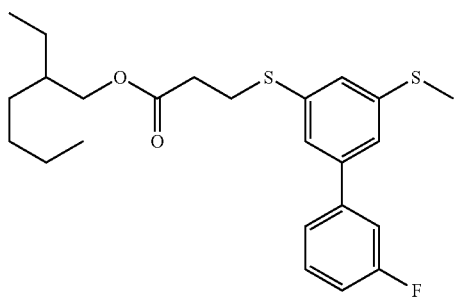

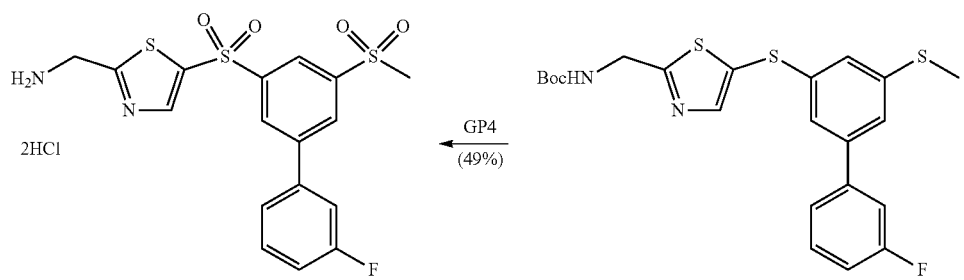

2-Ethylhexyl 3-((3'-fluoro-5-(methylthio)-[1,1'-biphenyl]-3-yl)thio)propanoate was synthesised according to general procedures GP13—from 2-ethylhexyl 3-((3-bromo-5-(methylthio)phenyl)thio)propanoate (2.0 g, 4.77 mmol), (3-fluorophenyl)boronic acid (0.80 g, 5.71 mmol), Pd(PPh$_3$)$_4$ (0.27 g, 5 mol %), aq. Na$_2$CO$_3$ (2.0 M, 4.7 mL, 9.40 mmol), toluene (35 mL); 100° C., 16 h. Chromatographic purification (13% EtOAc in hexane) afforded a colourless liquid (1.8 g, 87%). $^1$H NMR (400 MHz, DMSO-d$_6$) δ 7.58-7.49 (m, 3H), 7.36-7.34 (m, 2H), 7.23 (d, J=1.6 Hz, 1H), 7.18 (t, J=1.2 Hz, 1H), 3.94 (d, J=5.2 Hz, 2H), 3.27 (t, J=7.2 Hz, 2H), 2.65 (t, J=7.2 Hz, 2H), 2.55 (s, 3H), 1.51-1.47 (m, 1H), 1.29-1.26 (m, 8H), 0.84-0.80 (m, 6H). LCMS (ESI) m/z 435 (M+H)$^+$.

tert-Butyl ((5-((3'-fluoro-5-(methylthio)-[1,1'-biphenyl]-3-yl)thio)thiazol-2-yl)methyl)carbamate was synthesised according to general procedures GP14 and GP12—from i) 2-ethylhexyl 3-((3'-fluoro-5-(methylthio)-[1,1'-biphenyl]-3-yl)thio)propanoate (1.8 g, 4.14 mmol), KO$^t$Bu (1.0 M in THF; 12.4 mL, 12.4 mmol), THF (25 mL); −78° C., 1 h. ii) Pd$_2$(dba)$_3$ (0.36 g, 12 mol %), Xantphos (0.46 g, 25 mol %), tert-butyl ((5-bromothiazol-2-yl)methyl)carbamate (0.93 g, 3.17 mmol), NaO$^t$Bu (0.57 g, 5.93 mmol) and toluene/$^t$BuOH (4:1, 25 mL); 110° C., 16 h. Chromatography (25% EtOAc in hexane) afforded a yellow oil (0.50 g, 34%). $^1$H NMR (400 MHz, DMSO-d$_6$) δ 7.99 (s, 1H), 7.78 (br, 1H), 7.51 (s, 1H), 7.45-7.49 (m, 2H), 7.39 (d, J=1.2 Hz, 1H), 7.28 (s, 1H), 7.20-7.25 (m, 1H), 7.07 (s, 1H), 4.39 (d, J=6.0 Hz, 2H), 3.26 (s, 3H), 1.39 (s, 9H). LCMS (ESI) m/z 463 (M+H)$^+$.

Example 134 was synthesised according to general procedures GP4—from i) m-CPBA (55%, 1.48 g, 4.76 mmol), tert-butyl ((5-((3'-fluoro-5-(methylthio)-[1,1'-biphenyl]-3-yl)thio)thiazol-2-yl)methyl)carbamate (0.50 g, 1.08 mmol) and DCM (20 mL); rt, 3 h. Chromatography (46% EtOAc in cyclohexane), yellow solid (0.40 g, 70%); ii) 2 M HCl in Et$_2$O (5.0 mL), tert-butyl ((5-((3'-fluoro-5-(methylsulfonyl)-[1,1'-biphenyl]-3-yl)-(methylene)sulfinyl)thiazol-2-yl)methyl)carbamate (0.12 g, 0.228 mmol) and DCM (10 mL); rt, 24 h. Beige solid obtained (80 mg, 70%) without further purification. $^1$H NMR (500 MHz, Methanol-d$_4$) δ 8.59 (s, 1H), 8.56 (t, J=1.7 Hz, 1H), 8.53 (t, J=1.6 Hz, 1H), 8.51 (t, J=1.6 Hz, 1H), 7.63-7.53 (m, 3H), 7.29-7.21 (m, 1H), 4.59 (s, 2H), 3.30 (s, 3H). $^{13}$C NMR (126 MHz, Methanol-d$_4$) δ 171.29, 164.73 (d, J=247.0 Hz), 149.76, 145.04, 144.88, 144.78, 141.37, 140.68 (d, J=7.6 Hz), 132.45 (d, J=8.8 Hz), 132.28, 131.41, 126.24, 124.48, 124.45, 117.23 (d, J=21.4 Hz), 115.35 (d, J=23.9 Hz), 44.02, 41.24. $^{19}$F NMR (471 MHz, Methanol-d$_4$) δ−113.74. HRMS (ESI) for C$_{17}$H$_{16}$FN$_2$O$_4$S$_3$ ([M+H]$^+$): Calculated 427.0256; Observed 427.0247.

Example 135: (5-((4-Methoxy-3-(1-methyl-1H-pyrazol-4-yl)phenyl)sulfonyl)thiazol-2-yl)methanamine trihydrochloride

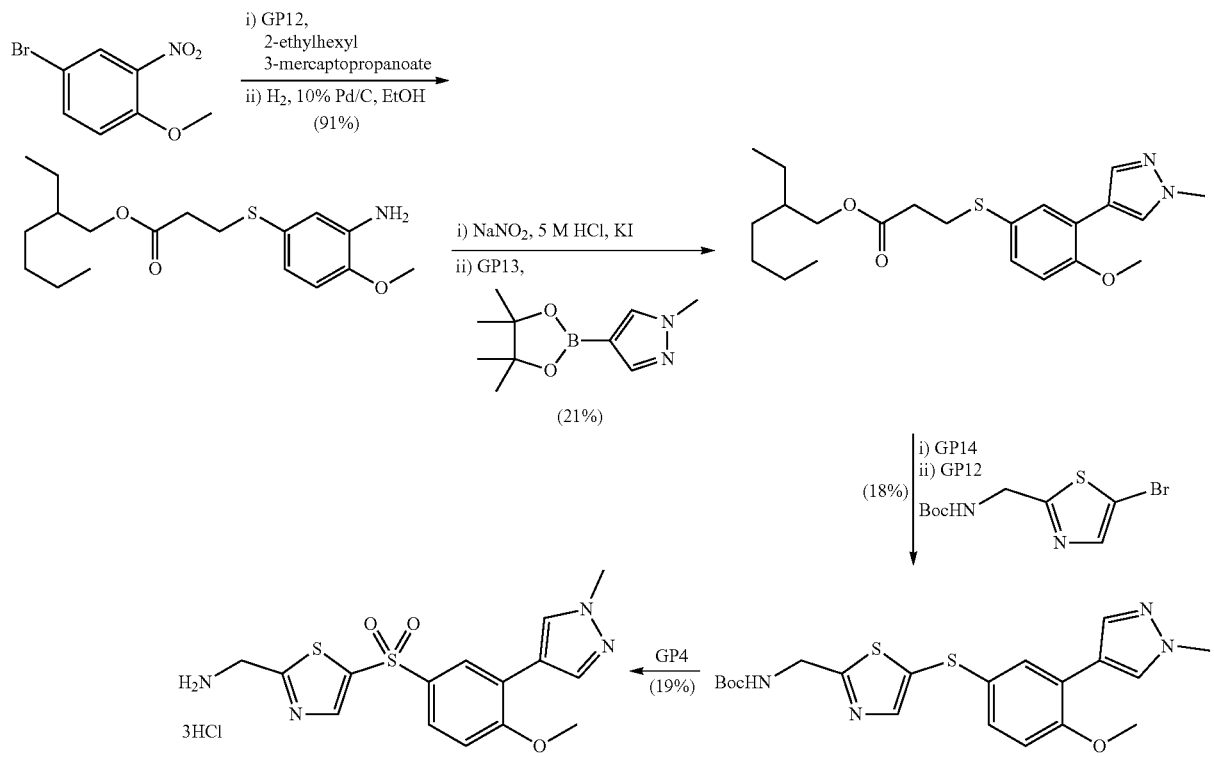

2-Ethylhexyl 3-((4-methoxy-3-nitrophenyl)thio)propanoate was synthesised according to general procedures GP12—from 4-bromo-1-methoxy-2-nitrobenzene (5.0 g, 21.6 mmol), Pd$_2$(dba)$_3$ (0.49 g, 2.5 mol %), Xantphos (0.62 g, 5 mol %), 2-ethylhexyl-3-mercaptopropionate (4.7 g, 21.5 mmol), DIPEA (7.49 mL, 43.1 mmol) and toluene (50 mL); 110° C., 6 h. Chromatography (5% EtOAc in hexane) afforded a yellow oil (7.7 g, 97%). $^1$H NMR (400 MHz, DMSO-d$_6$) δ 7.86 (d, J=2.0 Hz, 1H), 7.66 (dd, J=2.5 Hz, 8.8 Hz, 1H), 7.34 (d, J=8.8 Hz, 1H), 3.93 (d, J=6.3 Hz, 2H), 3.91 (s, 3H), 3.15 (t, J=6.8 Hz, 2H), 2.59 (t, J=6.8 Hz, 2H), 1.53-1.48 (m, 1H), 1.33-1.23 (m, 8H), 0.87-0.82 (m, 6H). LCMS (ESI, −ve) m/z 184 (M-C$_{11}$H$_{21}$O$_2$)$^−$.

Pd/C (10%, 1.8 g) was added to a solution of 2-ethylhexyl 3-((4-methoxy-3-nitrophenyl)thio)propanoate (3.6 g, 9.74 mmol) in ethanol (40 mL), and the reaction mixture was stirred for 20 h at rt under H$_2$ atmosphere (40 psi). The reaction mixture was then filtered through a pad of celite and the solvent was removed under reduced pressure to afford 2-ethylhexyl 3-((3-amino-4-methoxyphenyl)thio)propanoate (3.1 g, 94%) as yellow oil. $^1$H NMR (400 MHz, DMSO-d$_6$) δ 6.74 (d, J=8.3 Hz, 1H), 6.67 (d, J=2.5 Hz, 1H) 6.54 (dd, J=1.9 Hz, 8.3 Hz, 1H), 4.83 (s, 2H), 3.93 (d, J=5.4 Hz, 2H), 3.74 (s, 3H), 2.96 (t, J=6.8 Hz, 2H), 2.55-2.53 (m, 2H), 1.52-1.50 (m, 1H), 1.35-1.24 (m, 8H), 0.87-0.79 (m, 6H). LCMS (ESI) m/z 340 (M+H)$^+$.

2-Ethylhexyl 3-((3-amino-4-methoxyphenyl)thio)propanoate (1.5 g, 4.42 mmol) was dissolved in aq. HCl (5 N, 10 mL) and the solution was cooled to 0° C. A solution of NaNO$_2$ (0.609 g, 8.84 mmol) in water (10 mL) was then added and the resulting mixture was stirred at 0° C. for 1 h. A solution of KI (1.47 g, 8.84 mmol) in water (10 mL) was then added and the mixture was stirred at rt for 3 h. The reaction mixture was subsequently diluted with water (80 mL) and extracted with EtOAc (2×70 mL), dried over Na$_2$SO$_4$, filtered and the solvent was removed under reduced pressure. The crude was purified by chromatography (1-3% EtOAc in hexane) to afford 2-ethylhexyl 3-((3-iodo-4-methoxyphenyl)thio)propanoate as a yellow solid (0.60 g, 30%). $^1$H NMR (400 MHz, DMSO-d$_6$) δ 7.76 (d, J=1.9 Hz, 1H), 7.41 (dd, J=2.2 Hz, 8.6 Hz, 1H), 6.98 (d, J=8.8 Hz, 1H), 3.94 (d, J=5.4 Hz, 2H), 3.81 (s, 3H), 3.06 (t, J=6.8 Hz, 2H), 2.53-2.52 (m, 2H), 1.53-1.48 (m, 1H), 1.33-1.24 (m, 8H), 0.87-0.82 (m, 6H).

2-Ethylhexyl 3-((4-methoxy-3-(1-methyl-1H-pyrazol-4-yl)phenyl)thio)propanoate was synthesised according to general procedures GP13—from 2-ethylhexyl 3-((3-iodo-4-methoxyphenyl)thio)propanoate (1.25 g, 2.77 mmol), 1-methyl-pyrazole-4-boronic acid pinacol ester (0.577 g, 2.77 mmol), PdCl$_2$(dppf)$_2$.DCM (0.10 g, 5 mol %), Cs$_2$CO$_3$ (1.81 g, 5.55 mmol), 1,4-dioxane/water (5:1, 16 mL); 105° C., 16 h. Chromatographic purification (30-40% EtOAc in hexane) afforded a yellow oil (0.78 g, 70%). $^1$H NMR (400 MHz, DMSO-d$_6$) δ 8.12 (s, 1H), 7.89 (s, 1H), 7.60 (d, J=2.4 Hz, 1H), 7.21 (dd, J=2.2 Hz, 8.5 Hz, 1H), 7.03 (d, J=2.3 Hz, 1H), 3.92 (d, J=5.9 Hz, 2H), 3.86 (s, 6H), 3.08 (t, J=6.8 Hz, 2H), 2.55 (t, J=6.8 Hz, 2H), 1.55-1.47 (m, 1H), 1.30-1.22 (m, 8H), 0.84-0.81 (m, 6H). LCMS (ESI) m/z 405 (M+H)$^+$.

tert-Butyl ((5-((4-methoxy-3-(1-methyl-1H-pyrazol-4-yl)phenyl)thio)thiazol-2-yl)methyl) carbamate was synthesised according to general procedures GP14 and GP12—from i) 2-ethylhexyl 3-((4-methoxy-3-(1-methyl-1H-pyrazol-4-yl)phenyl)thio)propanoate (0.55 g, 1.36 mmol), KO$^t$Bu (1.0 M in THF; 3.4 mL, 3.40 mmol), THF (6 mL); −78° C., 1 h; ii) Pd$_2$(dba)$_3$ (0.104 g, 11 mol %), Xantphos (0.131 g, 22 mol %), tert-butyl ((5-bromothiazol-2-yl)methyl)carbamate (0.299 g, 1.02 mmol), DIPEA (0.391 mL, 2.27 mmol) and 1,4-dioxane (10 mL); 105° C., 8 h. Chromatography (40% EtOAc in hexane) afforded a yellow oil (80 mg, 18%). $^1$H NMR (400 MHz, DMSO-d$_6$) δ 8.11 (s, 1H), 7.85 (d, J=6.9 Hz, 2H), 7.70 (t, J=5.9 Hz, 1H), 7.64 (d, J=2.5 Hz, 1H), 7.19 (dd, J=2.2 Hz, 8.5 Hz, 1H), 7.05 (d, J=8.8 Hz, 1H), 4.32 (d, J=5.9 Hz, 2H), 3.86 (s, 6H), 1.37 (s, 9H). LCMS (ESI) m/z 433 (M+H)$^+$.

Example 135 was synthesised according to general procedures GP4—from i) m-CPBA (55%; 0.127 g, 0.407 mmol), tert-butyl ((5-((4-methoxy-3-(1-methyl-1H-pyrazol-4-yl)phenyl) thio)thiazol-2-yl)methyl) carbamate (80 mg, 0.185 mmol) and DCM (10 mL); rt, 4 h. Chromatography (60% EtOAc in cyclohexane) followed by preparative HPLC (0.1% aq. TFA/CH$_3$CN gradient) afforded a white solid (20 mg, 23%); ii) 2 M HCl in Et$_2$O (3.0 mL), tert-butyl ((5-((4-methoxy-3-(1-methyl-1H-pyrazol-4-yl)phenyl) sulfonyl) thiazol-2-yl)methyl) carbamate (17 mg, 0.039 mmol) and DCM (3 mL); rt, 4 h. Solid obtained (12 mg, 82%) without further purification. $^1$H NMR (500 MHz, Methanol-d$_4$) δ 8.62-8.31 (m, 3H), 8.21 (s, 1H), 7.95 (s, 1H), 7.32 (s, 1H), 4.54 (s, 2H), 4.08 (s, 3H), 4.05 (s, 3H). $^{13}$C NMR (126 MHz, Methanol-d$_4$) δ 169.71, 161.64, 148.29, 143.59, 137.49, 134.66, 134.20, 129.70, 127.97, 122.54, 118.95, 113.70, 57.54, 42.06, 39.77. HRMS (ESI) for C$_{15}$H$_{17}$N$_4$O$_3$S$_2$ ([M+H]$^+$): Calculated 365.0742; Observed 365.0742

Example 136: (5-((3-(1-Methyl-1H-pyrazol-4-yl)-4-(methylsulfonyl)phenyl)sulfonyl)thiazol-2-yl)methanamine g, 8.10 mmol), Pd$_2$(dba)$_3$ (0.185 g, 2.5 mol %), Xantphos (0.234 g, 5 mol %), 2-ethylhexyl-3-mercaptopropionate (1.76 g, 8.10 mmol), DIPEA (2.90 mL, 16.2 mmol) and toluene (20 mL); 110° C., 16 h. Chromatography (5% EtOAc in hexane) afforded a yellow oil (1.6 g, 51%). $^1$H NMR (400 MHz, DMSO-d$_6$) δ 8.10 (d, J=2.5 Hz, 1H), 7.70 (d, J=2.4 Hz, 1H), 7.53 (d, J=8.8 Hz, 1H), 3.93 (d, J=5.9 Hz, 2H), 3.25 (t, J=6.9 Hz, 2H), 2.65 (t, J=6.9 Hz, 2H), 2.53 (s, 3H), 1.50-1.49 (m, 1H), 1.38-1.20 (m, 8H), 0.90-0.80 (m, 6H). Pd/C (10%, 0.25 g) was added to a solution of 2-ethylhexyl 3-((4-(methylthio)-3-nitrophenyl)thio)propanoate (0.50 g, 1.29 mmol) in methanol (10 mL), and the reaction mixture was stirred for 4 h at rt under H$_2$ atmosphere (40 psi). The reaction mixture was then filtered through a pad of celite and the solvent was removed under reduced pressure to afford 2-ethylhexyl 3-((3-amino-4-(methylthio)phenyl)thio)propanoate (0.40 g, 87%) as an yellow oil. $^1$H NMR (400 MHz, DMSO-d$_6$) δ 7.13 (d, J=8.3 Hz, 1H), 6.67 (d, J=2.0 Hz, 1H), 6.49 (dd, J=2.0 Hz, 7.8 Hz, 1H), 5.27 (br, 2H), 3.95 (d, J=5.4 Hz, 2H), 3.05 (t, J=6.8 Hz, 2H), 2.61 (t, J=6.8 Hz, 2H), 2.28 (s, 3H), 1.53-1.50 (m, 1H), 1.33-1.24 (m, 8H), 0.87-0.82 (m, 6H). LCMS (ESI) m/z 356 (M+H)$^+$.

2-Ethylhexyl 3-((3-amino-4-(methylthio)phenyl)thio) propanoate (4.0 g, 11.3 mmol) was dissolved in aq. HCl (5 N, 40 mL) and the solution was cooled to 0° C. A solution of NaNO$_2$ (2.33 g, 33.8 mmol) in water (20 mL) was then added and the resulting mixture was stirred at 0° C. for 1 h. A solution of KI (5.6 g, 33.8 mmol) in water (10 mL) was then added and the mixture was stirred at rt for 16 h. The reaction mixture was subsequently extracted with EtOAc (2×50 mL), dried over Na$_2$SO$_4$, filtered and the solvent was

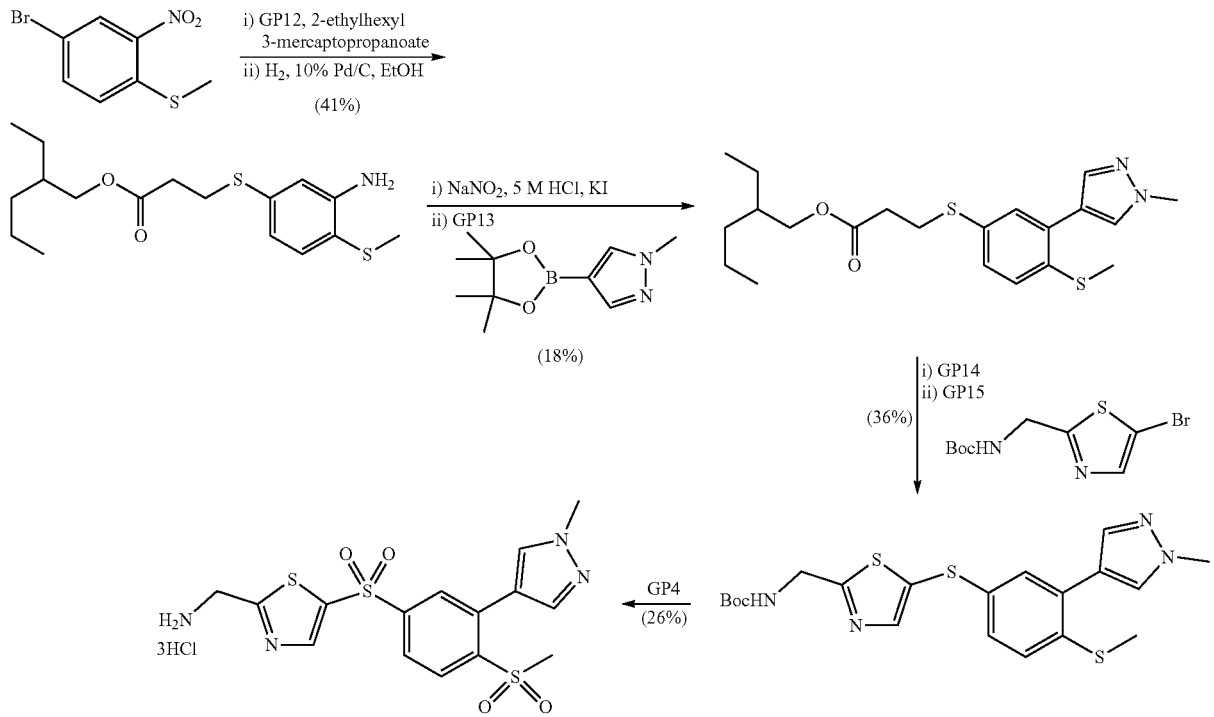

2-Ethylhexyl 3-((4-(methylthio)-3-nitrophenyl)thio)propanoate was synthesised according to general procedures GP12—from (4-bromo-2-nitrophenyl)(methyl)sulfane (2.0 removed under reduced pressure. The crude was purified using chromatography (5% EtOAc in hexane) to afford 2-ethylhexyl 3-((3-iodo-4-(methylthio)phenyl)thio)propanoate as a yellow oil (1.4 g, 27%). $^1$H NMR (400 MHz, DMSO-d$_6$) δ 7.76 (d, J=1.9 Hz, 1H), 7.40 (dd, J=1.9 Hz, 8.4 Hz, 1H), 7.13 (d, J=8.3 Hz, 1H), 3.93 (d, J=5.9 Hz, 2H), 3.13 (t, J=2.8 Hz, 2H), 2.58 (t, J=6.8 Hz, 2H), 2.49 (s, 3H), 1.52 (m, 1H), 1.31-1.24 (m, 8H), 0.87-0.82 (m, 6H). LCMS (ESI, -ve) m/z 281 (M-C$_{11}$H$_{21}$O$_2$)$^-$.

2-Ethylhexyl 3-((3-(1-methyl-1H-pyrazol-4-yl)-4-(methylthio)phenyl)thio)propanoate was synthesised according to general procedures GP13—from 2-ethylhexyl 3-((3-iodo-4-(methylthio)phenyl)thio)propanoate (1.3 g, 2.79 mmol), 1-methyl-pyrazole-4-boronic acid pinacol ester (0.64 g, 3.08 mmol), PdCl$_2$(dppf)$_2$.DCM (0.12 g, 5 mol %), Cs$_2$CO$_3$ (2.27 g, 6.97 mmol), 1,4-dioxane/water (5:1, 10 mL); 100° C., 4 h. Chromatographic purification (12% EtOAc in hexane) afforded a amber-coloured oil (0.80 g, 68%). $^1$H NMR (400 MHz, DMSO-d$_6$) δ 8.00 (s, 1H), 7.69 (s, 1H), 7.28 (s, 1H), 7.26-7.25 (m, 2H), 3.92 (t, J=5.9 Hz, 2H), 3.88 (s, 3H), 3.15 (t, J=6.8 Hz, 2H), 2.60 (t, J=6.8 Hz, 2H), 2.49 (s, 3H), 1.55-1.45 (m, 1H), 1.30-1.22 (m, 8H), 0.84-0.80 (m, 6H). LCMS (ESI) m/z 421.2 (M+H)$^+$.

tert-Butyl ((5-((3-(1-methyl-1H-pyrazol-4-yl)-4-(methylthio)phenyl)thio)thiazol-2-yl)methyl) carbamate was synthesised according to general procedures GP14 and GP12—from i) 2-ethylhexyl 3-((3-(1-methyl-1H-pyrazol-4-yl)-4-(methylthio)phenyl)thio)propanoate (0.50 g, 1.19 mmol), KO$^t$Bu (1.0 M in THF; 3.6 mL, 3.60 mmol), THF (10 mL); –78° C., 1 h; ii) Pd$_2$(dba)$_3$ (0.16 g, 10 mol %), Xantphos (0.2 g, 20 mol %), tert-butyl ((5-bromothiazol-2-yl)methyl)carbamate (0.50 g, 1.71 mmol), NaO$^t$Bu (0.25 g, 2.60 mmol) and toluene/BuOH (5:1, 12 mL); 110° C., 16 h. Chromatography (58% EtOAc in hexane) afforded a yellow oil (0.16 g, 36%). $^1$H NMR (400 MHz, DMSO-d$_6$) δ 7.98 (s, 1H), 7.91 (s, 1H), 7.75 (s, 1H), 7.65 (s, 1H), 7.26 (d, J=8.0 Hz, 2H), 7.18 (dd, J=2.0 Hz, 8.4 Hz, 1H), 4.36 (d, J=6.4 Hz, 2H), 3.88 (s, 3H), 2.41 (s, 3H), 1.41 (s, 9H). LCMS (ESI) m/z 449 (M+H)$^+$.

Example 136 was synthesised according to general procedures GP4—from i) m-CPBA (55%; 0.56 g, 1.62 mmol), tert-butyl ((5-((3-(1-methyl-1H-pyrazol-4-yl)-4-(methylthio)phenyl)thio)thiazol-2-yl)methyl)carbamate (0.16 g, 0.36 mmol) and DCM (10 mL); rt, 4 h. Chromatographic purification (72% EtOAc in cyclohexane) afforded a pale yellow solid (85 mg, 55%); ii) 2 M HCl in Et$_2$O (10 mL), tert-butyl ((5-((3-(1-methyl-1H-pyrazol-4-yl)-4-(methylsulfonyl)phenyl) sulfonyl)thiazol-2-yl)methyl)carbamate (85 mg, 0.166 mmol) and DCM (10 mL); rt, 4 h. Solid obtained (30 mg, 47%) without further purification. $^1$H NMR (500 MHz, Methanol-d$_4$/Deuterium Oxide) δ 8.47 (m, 1H), 8.32 (m, 1H), 8.18 (m, 1H), 8.04 (m, 1H), 7.94 (m, 1H), 7.73 (m, 1H), 4.58 (s, 2H), 3.94 (s, 3H), 2.91 (s, 3H). $^{13}$C NMR (126 MHz, Methanol-d$_4$/Deuterium Oxide) δ 171.22, 149.83, 145.65, 143.93, 140.48, 139.70, 135.24, 133.79, 132.45, 131.39, 127.61, 117.68, 42.40, 40.91, 39.32. HRMS (ESI) for C$_{15}$H$_{17}$N$_4$O$_4$S$_3$ ([M+H]$^+$): Calculated 413.0412; Observed 413.0409.

Example 137: (5-((3-(1-Methyl-1H-imidazol-4-yl)-5-(methylsulfonyl)phenyl)sulfonyl)thiophen-2-yl)methanamine dihydrochloride

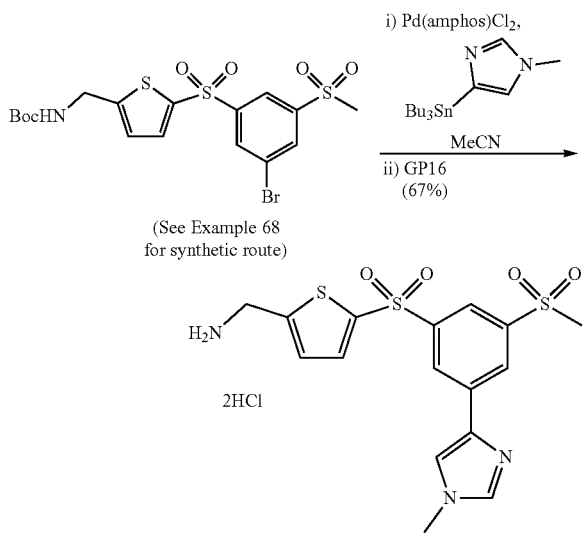

(See Example 68 for synthetic route)

A mixture of tert-butyl ((5-((3-bromo-5-(methylsulfonyl)phenyl)sulfonyl)thiophen-2-yl)methyl)carbamate (0.17 g, 0.333 mmol), 1-methyl-4-(tributylstannyl)-1H-imidazole (0.24 g, 0.645 mmol), Pd(amphos)Cl$_2$ (23 mg, 10 mol %) and acetonitrile (20 mL) was degassed with nitrogen and then stirred at 80° C. for 16 h. After cooling to rt, the mixture was diluted with EtOAc (250 mL). The organic layer was washed with H$_2$O (40 mL) and brine (25 mL), dried over Na$_2$S$_2$O$_4$ and filtered. The solvent was removed under reduced pressure and the crude was purified by chromatography (83% EtOAc in hexane) to afford tert-butyl ((5-((3-(1-methyl-1H-imidazol-4-yl)-5-(methylsulfonyl)phenyl)sulfonyl)thiophen-2-yl)methyl)carbamate as a colourless liquid (0.15 g, 88%). $^1$H NMR (400 MHz, DMSO-d$_6$) δ 8.53 (s, 1H), 8.49 (s, 1H), 8.15 (s, 1H), 8.05 (s, 1H), 7.84 (d, J=4.0 Hz, 1H), 7.76 (s, 1H), 7.62 (br, 1H), 7.06 (d, J=4.0 Hz, 1H), 4.30 (d, J=6.0 Hz, 2H), 3.72 (s, 3H), 3.36 (s, 3H), 1.37 (s, 9H). LCMS (ESI) m/z 512 (M+H)$^+$.

Example 137 was synthesised according to general procedures GP16—from 1 M HCl in Et$_2$O (5.0 ml), tert-butyl ((5-((3-(1-methyl-1H-imidazol-4-yl)-5-(methylsulfonyl)phenyl)sulfonyl)thiophen-2-yl)methyl)carbamate (140 mg, 0.273 mmol) and DCM (10 mL); rt, 4 h. White solid (100 mg, 83%) obtained and required no further purification. $^1$H NMR (500 MHz, Methanol-d$_4$) δ 9.12 (s, 1H), 8.71 (s, 1H), 8.61 (s, 1H), 8.51 (d; J=3.7 Hz, 1H), 8.33 (br, 1H), 7.93 (d, J=3.6 Hz, 1H), 7.38 (br, 1H), 4.41 (s, 2H), 4.04 (s, 3H), 3.28 (s, 3H). $^{13}$C NMR (126 MHz, Methanol-d$_4$) δ 149.66, 132.36, 131.09, 131.05, 129.94, 128.00, 43.38, 41.21, 21.30. HRMS (ESI) for C$_{16}$H$_{18}$N$_3$O$_4$S$_3$ ([M+H]$^+$): Calculated 412.0459; Observed 412.0450.

Example 138: (5-((4'-Methyl-6-(methylsulfonyl)-[1,1'-biphenyl]-3-yl)sulfonyl)thiazol-2-yl)methanamine dihydrochloride

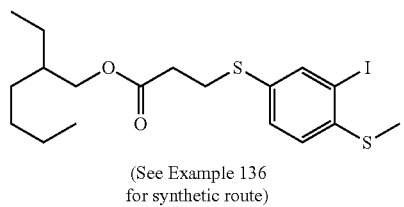 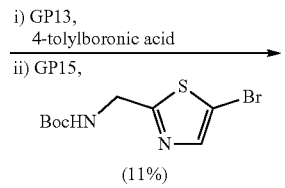 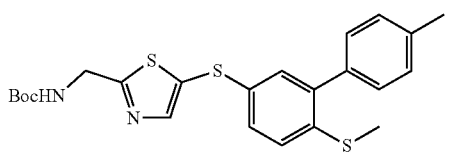

2-Ethylhexyl 3-((4'-methyl-6-(methylthio)-[1,1'-biphenyl]-3-yl)thio)propanoate was synthesised according to general procedures GP13—2-ethylhexyl 3-((3-iodo-4-(methylthio)phenyl)thio)propanoate (1.00 g, 2.14 mmol), p-tolylboronic acid (437 mg, 3.22 mmol), Pd(PPh$_3$)Cl$_2$ (150 mg, 10 mol %), sodium bicarbonate (0.540 g, 6.43 mmol) and DMF/H$_2$O (10:1, 11 mL); 80° C., 6 h. Chromatographic purification (15% EtOAc in hexane) afforded 2-ethylhexyl 3-((4'-methyl-6-(methylthio)-[1,1'-biphenyl]-3-yl)thio)propanoate as a yellow oil (0.50 g, 54%). $^1$H NMR (400 MHz, DMSO-d$_6$) δ 7.36 (d, J=2.0 Hz, 1H), 7.34 (d, J=2.0 Hz, 1H), 7.31-7.22 (m, 4H), 7.11 (d, J=1.9 Hz, 1H) 3.92 (d, J=5.9 Hz, 2H), 3.14 (t, J=6.8 Hz, 2H), 2.60 (t, J=6.9 Hz, 2H), 2.35 (s, 6H), 1.51-1.48 (m, 1H), 1.27-1.22 (m, 8H), 0.85-0.80 (m, 6H). LCMS (ESI) m/z 431 (M+H)$^+$.

tert-Butyl ((5-((4'-methyl-6-(methylthio)-[1,1'-biphenyl]-3-yl)thio)thiazol-2-yl)methyl)carbamate was synthesised according to general procedures GP15—from 2-ethylhexyl 3-((4'-methyl-6-(methylthio)-[1,1'-biphenyl]-3-yl)thio)propanoate as (0.50 g, 1.16 mmol), tert-butyl ((5-bromothiazol-2-yl)methyl)carbamate (0.34 g, 1.16 mmol), NaO$^t$Bu (223 mg, 2.32 mmol), Pd$_2$(dba)$_3$ (53 mg, 5 mol %), Xantphos (67 mg, 0.116 mmol) and toluene/BuOH (5:1, 10 mL); 110° C., 16 h. Chromatography (30% EtOAc in hexane) afforded a yellow oil (0.11 g, 21%). $^1$H NMR (400 MHz, DMSO-d$_6$) δ 7.91 (s, 1H), 7.89 (t, J=4.0 Hz, 1H), 7.29 (s, 1H), 7.28-7.11 (m, 5H), 7.05 (s, 1H), 4.35 (d, J=5.9 Hz, 2H), 2.34 (s, 6H), 1.38 (s, 9H). LCMS (ESI) m/z 459 (M+H)$^+$.

Example 138 was synthesised according to general procedures GP4—from i) m-CPBA (55%; 0.34 g, 1.08 mmol), tert-butyl ((5-((4'-methyl-6-(methylthio)-[1,1'-biphenyl]-3-yl)thio)thiazol-2-yl)methyl)carbamate (0.11 g, 0.240 mmol) and DCM (40 mL); rt, 4 h. Chromatography (30% EtOAc in cyclohexane), yellow oil (77 mg, 61%); ii) 1 M HCl in Et$_2$O (5.0 ml), tert-butyl ((5-((4'-methyl-6-(methylsulfonyl)-[1,1'-biphenyl]-3-yl)sulfonyl)thiazol-2-yl)methyl)carbamate (75 mg, 0.144 mmol) and DCM (5.0 mL); rt, 4 h. Yellow solid (55 mg, 78%) obtained and required no further purification. $^1$H NMR (500 MHz, Methanol-d$_4$) δ 8.50 (s, 1H), 8.41 (d, J=8.4 Hz, 1H), 8.26 (dd, J=8.4, 2.0 Hz, 1H), 7.97 (d, J=1.9 Hz, 1H), 7.39-7.30 (m, 4H), 4.56 (s, 2H), 2.71 (s, 3H), 2.44 (s, 3H). $^{13}$C NMR (126 MHz, Methanol-d$_4$) δ 171.23, 149.67, 146.55, 145.92, 144.88, 141.50, 140.66, 135.27, 132.37, 131.10, 131.05, 129.95, 128.01, 43.41, 41.24, 21.31. HRMS (ESI) for C$_{18}$H$_{19}$N$_2$O$_4$S$_3$ ([M+H]$^+$): Calculated 423.0507; Observed 423.0507.

Example 139: (5-((3-Methoxy-5-(1-methyl-1H-imidazol-4-yl)phenyl)sulfonyl)thiazol-2-yl)methanamine trihydrochloride

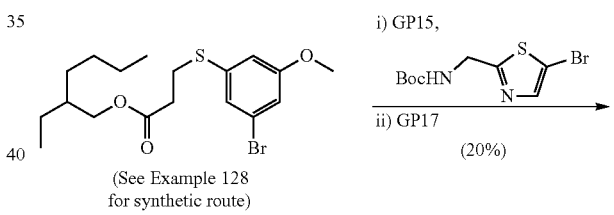

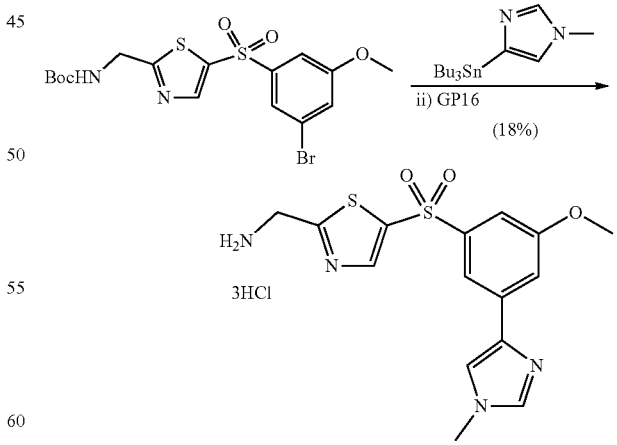

tert-Butyl ((5-((3-bromo-5-methoxyphenyl)thio)thiazol-2-yl)methyl)carbamate was synthesised according to general procedures GP15—from 2-ethylhexyl 3-((3-bromo-5-methoxyphenyl)thio)propanoate (0.70 g, 1.74 mmol), tert-butyl ((5-bromothiazol-2-yl)methyl)carbamate (1.02 g, 3.47 mmol), NaO^tBu (330 mg, 3.47 mmol), Pd$_2$(dba)$_3$ (160 mg, 10 mol %), Xantphos (200 mg, 10 mol %) and toluene/^tBuOH (5:1, 12 mL); 110° C., 16 h. Chromatography (20% EtOAc in hexane) afforded a yellow oil (0.50 g, 67%). $^1$H NMR (400 MHz, DMSO-d$_6$) δ 7.99 (s, 1H), 7.80 (br, 1H), 7.05 (s, 1H), 6.89 (s, 1H), 6.77 (s, 1H), 4.40 (d, J=6.9 Hz, 2H), 3.74 (s, 3H), 1.39 (s, 9H). LCMS (ESI) m/z 430.9 (M+H)$^+$.

tert-Butyl ((5-((3-bromo-5-methoxyphenyl)sulfonyl)thiazol-2-yl)methyl)carbamate was synthesised according to general procedures GP17—from m-CPBA (55%; 0.48 g, 1.53 mmol), tert-butyl ((5-((3-bromo-5-methoxyphenyl)thio)thiazol-2-yl)methyl)carbamate (0.30 g, 0.695 mmol) and DCM (15 mL); rt, 3 h. Chromatographic purification (35% EtOAc in cyclohexane) afforded a pale yellow oil (97 mg, 30%). $^1$H NMR (400 MHz, DMSO-d$_6$) δ 8.51 (s, 1H), 7.87 (br, 1H), 7.70 (s, 1H), 7.55-7.54 (m, 1H), 7.49-7.48 (m, 1H), 4.42 (d, J=5.2 Hz, 2H), 3.86 (s, 3H), 1.38 (s, 9H). LCMS (ESI) m/z 463/465 (M+H)$^+$.

A suspension of tert-butyl ((5-((3-bromo-5-methoxyphenyl)sulfonyl)thiazol-2-yl)methyl) carbamate (145 mg, 0.313 mmol) and 1-methyl-4-(tributylstannyl)-1H-imidazole (348 mg, 0.939 mmol) in acetonitrile (5 mL) was degassed for 10 min with nitrogen. Pd(amphos)Cl$_2$ (22 mg, 10%) was then added and the vessel sealed and heated at 90° C. for 16 h. After cooling to rt, the mixture was diluted with ethyl acetate (100 mL), washed with water (2×50 mL) and brine (50 mL), dried over anhydrous sodium sulfate, filtered and concentrated under reduced pressure. Chromatographic purification (4% MeOH in dichloromethane) afforded tert-butyl ((5-((3-methoxy-5-(1-methyl-1H-imidazol-4-yl)phenyl)sulfonyl)thiazol-2-yl)methyl)carbamate as a pale yellow solid (40 mg, 28%). $^1$H NMR (400 MHz, DMSO-d$_6$) δ 8.44 (s, 1H), 7.90 (t, J=1.4 Hz, 1H), 7.86-7.84 (m, 2H), 7.68 (s, 1H), 7.59-7.58 (m, 1H), 7.27 (s, 1H), 4.39 (d, J=5.8 Hz, 2H), 3.87 (s, 3H), 3.69 (s, 3H), 1.38 (s, 9H). LCMS (ESI) m/z 465.0 (M+H)$^+$.

Example 139 was synthesised according to general procedures GP16—from 2 M HCl in Et$_2$O (10 mL), tert-butyl ((5-((3-methoxy-5-(1-methyl-1H-imidazol-4-yl)phenyl)sulfonyl)thiazol-2-yl)methyl)carbamate (36 mg, 0.0776 mmol) and MeOH/DCM (1:2, 10 mL); rt, 6 h. Beige solid (20 mg, 65%) obtained and required no further purification. $^1$H NMR (500 MHz, Methanol-d$_4$) δ 9.07 (s, 1H), 8.49 (s, 1H), 8.20 (br, 1H), 7.99 (s, 1H), 7.71-7.54 (m, 2H), 4.58 (s, 2H), 4.03 (s, 3H), 3.96 (s, 3H). $^{13}$C NMR (126 MHz, Methanol-d$_4$) δ 170.68, 162.62, 149.24, 145.19, 141.93, 138.33, 133.21, 130.95, 122.38, 117.79, 117.38, 114.76, 57.15, 41.51, 37.10. HRMS (ESI) for C$_{15}$H$_{17}$N$_4$O$_3$S$_2$ ([M+H]$^+$): Calculated 365.0742; Observed 365.0736.

Example 140: (5-((5-(Methylsulfonyl)-4'-(trifluoromethyl)-[1,1'-biphenyl]-3-yl)sulfonyl)thiazol-2-yl)methanamine dihydrochloride

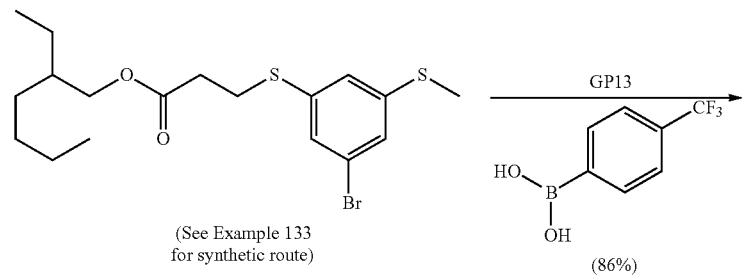

(See Example 133 for synthetic route)

(86%)

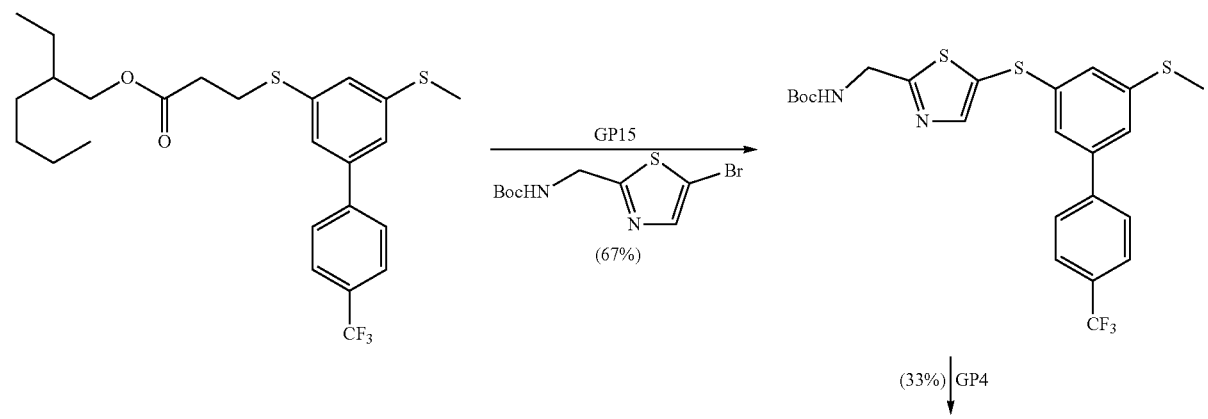

(67%)

(33%) GP4

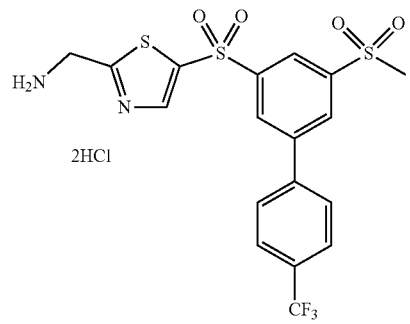

2-Ethylhexyl 3-((5-(methylthio)-4'-(trifluoromethyl)-[1,1'-biphenyl]-3-yl)thio)propanoate was synthesised according to general procedures GP13—from 2-ethylhexyl 3-((3-bromo-5-(methylthio)phenyl)thio)propanoate (1.20 g, 2.85 mmol), 4-(trifluoromethyl)phenylboronic acid (0.81 g, 4.28 mmol), Pd(dppf)Cl$_2$·DCM (0.11 g, 5 mol %), 2 M Na$_2$CO$_3$ (3.5 mL, 7.0 mmol), toluene (35 mL); 100° C., 16 h. Chromatographic purification (10% EtOAc in cyclohexane) afforded a colourless oil (1.20 mg, 86%). $^1$H NMR (400 MHz, DMSO-d$_6$) δ 7.92 (d, J=8.0 Hz, 2H), 7.80 (d, J=8.4 Hz, 2H), 7.38 (t, J=2.0 Hz, 2H), 7.23 (t, J=2.0 Hz, 1H), 3.93 (d, J=6.0 Hz, 2H), 3.27 (d, J=6.8 Hz, 2H), 2.66 (t, J=4.0 Hz, 2H), 2.55 (s, 3H), 1.51-1.47 (m, 1H), 1.31-1.22 (m, 8H), 0.85-0.79 (m, 6H). LCMS (ESI, −ve) m/z 299 (M-C$_{11}$H$_{21}$O$_2$)$^-$.

tert-Butyl ((5-((5-(methylthio)-4'-(trifluoromethyl)-[1,1'-biphenyl]-3-yl)thio)thiazol-2-yl)methyl)carbamate was synthesised according to general procedures GP15—from 2-ethylhexyl 3-((5-(methylthio)-4'-(trifluoromethyl)-[1,1'-biphenyl]-3-yl)thio)propanoate (1.20 g, 2.47 mmol), tert-butyl ((5-bromothiazol-2-yl)methyl)carbamate (0.72 g, 2.47 mmol), NaO$^t$Bu (0.47 g, 4.94 mmol), Pd$_2$(dba)$_3$ (110 mg, 5 mol %), Xantphos (140 mg, 10 mol %) and toluene/BuOH (4:1, 30 mL); 110° C., 16 h. Chromatography (35% EtOAc in hexane) afforded a yellow oil (0.50 g, 67%). $^1$H NMR (400 MHz, DMSO-d$_6$) δ 8.00 (s, 1H), 7.85 (d, J=7.6 Hz, 2H), 7.79 (d, J=7.6 Hz, 3H), 7.42 (d, J=1.6 Hz, 1H), 7.27 (t, J=1.6 Hz, 1H), 7.13 (s, 1H), 4.39 (d, J=6.4 Hz, 2H), 3.31 (s, 3H), 1.35 (s, 9H). LCMS (ESI) m/z 513 (M+H)$^+$.

Example 140 was synthesised according to general procedures GP4—from i) m-CPBA (55%; 0.62 g, 1.97 mmol), tert-butyl ((5-((5-(methylthio)-4'-(trifluoromethyl)-[1,1'-biphenyl]-3-yl)thio)thiazol-2-yl)methyl)carbamate (0.23 g, 0.45 mmol) and DCM (20 mL); rt, 3 h. Chromatography (58% EtOAc in cyclohexane), yellow oil (120 mg, 46%); ii) 2 M HCl in Et$_2$O (5 mL), tert-butyl ((5-((5-(methylsulfonyl)-4'-(trifluoromethyl)-[1,1'-biphenyl]-3-yl)sulfonyl)thiazol-2-yl)methyl)carbamate (110 mg, 0.191 mmol) and DCM (10 mL); rt, 4 h. Beige solid (70 mg, 72%) obtained and required no further purification. $^1$H NMR (500 MHz, Methanol-d$_4$) δ 8.64-8.55 (m, 4H), 7.98 (d, J=8.0 Hz, 2H), 7.86 (d, J=7.8 Hz, 2H), 4.59 (s, 2H), 3.30 (s, 3H). $^{13}$C NMR (126 MHz, Methanol-d$_4$) δ 171.30, 149.78, 145.16, 144.98, 144.53, 142.17, 141.36, 132.60, 132.22 (q, J=32.8 Hz), 131.63, 129.33, 127.63 (q, J=272.2 Hz), 127.34 (q, J=3.8 Hz), 126.63, 44.01, 41.23. $^{19}$F NMR (471 MHz, Methanol-d$_4$) δ -61.78. HRMS (ESI) for C$_{18}$H$_{16}$F$_3$N$_2$O$_4$S$_3$ ([M+H]$^+$): Calculated 477.0224; Observed 477.0230.

Example 141: (5-((3-Methoxy-5-(1-(methoxymethyl)-1H-pyrazol-4-yl)phenyl)sulfonyl)thiazol-2-yl)methanamine tri-trifluoroacetate and Example 142: (5-((3-methoxy-5-(1H-pyrazol-4-yl)phenyl)sulfonyl)thiazol-2-yl)methanamine tri-trifluoroacetate

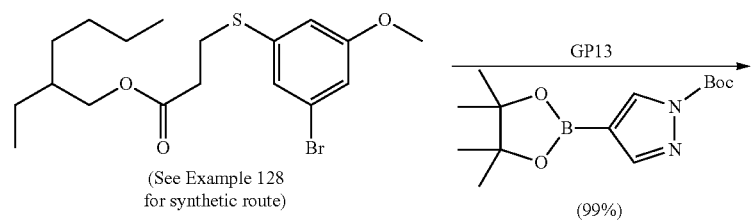

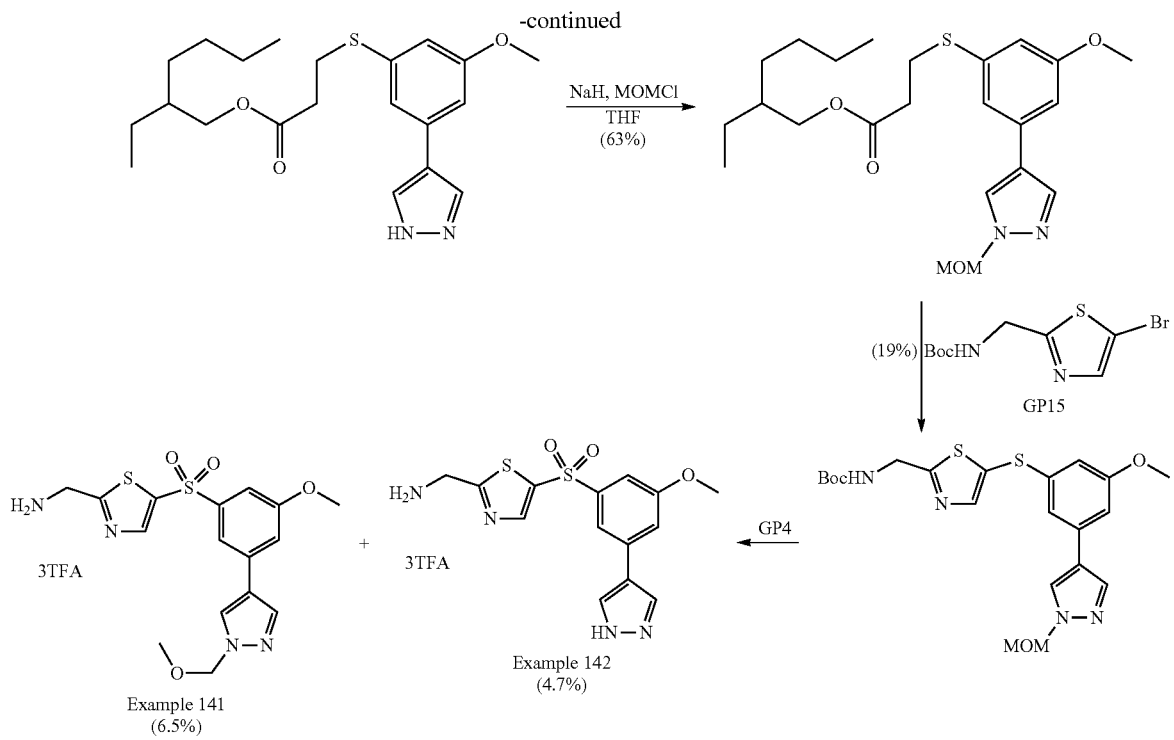

2-Ethylhexyl 3-((3-methoxy-5-(1H-pyrazol-4-yl)phenyl)thio)propanoate was synthesised according to general procedures GP13—from 2-ethylhexyl 3-((3-bromo-5-methoxyphenyl)thio)propanoate (4.50 g, 11.2 mmol), tert-butyl 4-(4,4,5,5-tetramethyl-1,3,2-dioxaborolan-2-yl)-1H-pyrazole-1-carboxylate (4.92 g, 16.7 mmol), Pd(dppf)Cl$_2$.DCM (0.45 g, 5 mol %), aq. Na$_2$CO$_3$ (2.0 M; 11.2 mL, 22.4 mmol), 1,4-dioxane (35 mL); 100° C., 16 h. Chromatographic purification (52% EtOAc in hexane) afforded a colourless oil (4.31 g, 99%). $^1$H NMR (400 MHz, DMSO-d$_6$) δ 12.94 (br, 1H), 8.23 (s, 1H), 7.94 (s, 1H), 7.14 (s, 1H), 7.02 (s, 1H), 6.78 (s, 1H), 3.95 (d, J=5.4 Hz, 2H), 3.84 (s, 3H), 3.22 (t, J=6.4 Hz, 2H), 2.63 (t, J=6.8 Hz, 2H), 1.51-1.50 (m, 1H), 1.30-1.22 (m, 8H), 0.85-0.81 (m, 6H). LCMS (ESI) m/z 391 (M+H)$^+$.

2-Ethylhexyl 3-((3-methoxy-5-(1H-pyrazol-4-yl)phenyl)thio)propanoate (4.30 g, 11.0 mmol) was dissolved in dry THF (50 mL) and NaH (60% in mineral oil; 0.66 g, 16.5 mmol) was added portionwise over 2 min at 0° C. MOMCl (1.76 mL, 23.1 mmol) was then added and the mixture was stirred at 0° C. for 15 min. The reaction mixture was poured onto crushed ice and extracted with EtOAc (2×125 mL). The organic extracts were combined and washed with brine (30 mL), dried over NaSO$_4$, filtered and the solvent was removed under reduced pressure. The crude was purified by chromatography (30% EtOAc in hexane) to afford 2-ethylhexyl 3-((3-methoxy-5-(1-(methoxymethyl)-1H-pyrazol-4-yl)phenyl)thio)propanoate as a colourless oil (3.0 g, 63%). $^1$H NMR (400 MHz, DMSO-d$_6$) δ 8.41 (s, 1H), 8.03 (s, 1H), 7.15 (d, J=1.2 Hz, 1H), 7.03 (t, J=2.0 Hz, 1H), 6.72 (t, J=2.0 Hz, 1H), 5.37 (s, 2H), 3.94 (d, J=5.8 Hz, 2H), 3.79 (s, 3H), 3.27 (s, 3H), 3.23 (t, J=5.4 Hz, 2H), 2.66 (t, J=4.0 Hz, 2H), 1.51-1.50 (m, 1H), 1.30-1.22 (m, 8H), 0.85-0.81 (m, 6H). LCMS (ESI) m/z 435 (M+H)$^+$.

tert-Butyl ((5-((3-methoxy-5-(1-(methoxymethyl)-1H-pyrazol-4-yl)phenyl)thio)thiazol-2-yl)methyl)carbamate was synthesised according to general procedures GP15—from 2-ethylhexyl 3-((3-methoxy-5-(1-(methoxymethyl)-1H-pyrazol-4-yl)phenyl)thio)propanoate (3.00 g, 6.91 mmol), tert-butyl ((5-bromothiazol-2-yl)methyl)carbamate (2.02 g, 6.90 mmol), NaO$^t$Bu (1.32 g, 13.82 mmol), Pd$_2$(dba)$_3$ (0.32 g, 5 mol %), Xantphos (0.40 g, 10 mol %) and toluene/$^t$BuOH (4:1, 25 mL); 110° C., 16 h. Chromatography (62% EtOAc in hexane) afforded a yellow oil (0.60 g, 19%). $^1$H NMR (400 MHz, DMSO-d$_6$) δ 8.38 (s, 1H), 7.99 (s, 1H), 7.95 (s, 1H), 7.77 (br, 1H), 7.13 (s, 1H), 7.08 (d, J=2.4 Hz, 1H), 6.56 (d, J=2.0 Hz, 1H), 5.36 (s, 2H), 4.39 (d, J=6.0 Hz, 2H), 3.75 (s, 3H), 3.26 (s, 3H), 1.37 (s, 9H). LCMS (ESI) m/z 463 (M+H)$^+$.

Examples 141 and 142 were synthesised according to general procedures GP4—from i) m-CPBA (55%, 0.89 g, 2.85 mmol), tert-butyl ((5-((3-methoxy-5-(1-(methoxymethyl)-1H-pyrazol-4-yl)phenyl)thio)thiazol-2-yl)methyl)carbamate (0.60 g, 1.29 mmol) and DCM (20 mL); rt, 3 h. Chromatography (68% EtOAc in cyclohexane), yellow solid (0.32 g, 50%); ii) 2 M HCl in Et$_2$O (4.0 ml), tert-butyl ((5-((3-methoxy-5-(1-(methoxymethyl)-1H-pyrazol-4-yl)phenyl)sulfonyl)thiazol-2-yl)methyl)carbamate (0.10 g, 0.202 mmol) and DCM (10 mL); rt, 3 h. The hydrochloride salt was diluted with DCM and washed with sat. NaHCO$_3$ to afford the free base. The crude amine mixture was purified by HPLC (0.1% TFA in H$_2$O:MeCN gradient) to afford amine tri-trifluoroacetates 10125 (18 mg, 13%) and 10126 (12 mg, 9.3%) both as beige solids.

Data for Example 141

$^1$H NMR (500 MHz, Methanol-d$_4$) δ 8.46 (s, 1H), 8.33 (d, J=0.8 Hz, 1H), 8.02 (d, J=0.8 Hz, 1H), 7.77 (t, J=1.6 Hz, 1H), 7.46 (dd, J=2.5, 1.5 Hz, 1H), 7.37 (dd, J=2.4, 1.6 Hz, 1H), 5.43 (s, 2H), 4.54 (s, 2H), 3.91 (s, 3H), 3.34 (s, 3H). $^{13}$C NMR (126 MHz, Methanol-d$_4$) δ 170.33, 162.45, 148.69, 144.35, 142.67, 139.01, 137.17, 130.00, 123.23, 117.61, 117.28, 111.40, 83.00, 57.07, 56.53, 41.10. HRMS (ESI) for $C_{16}H_{18}N_4O_4S_2$ ([M+H]$^+$): Calculated 395.0847; Observed 395.0849.

Data for Example 142

$^1$H NMR (500 MHz, Methanol-d$_4$) δ 8.45 (s, 1H), 8.08 (s, 2H), 7.76 (t, J=1.6 Hz, 1H), 7.45 (dd, J=2.4, 1.5 Hz, 1H), 7.35 (dd, J=2.4, 1.6 Hz, 1H), 4.54 (s, 2H), 3.90 (s, 3H). $^{13}$C NMR (126 MHz, Methanol-d$_4$) δ 170.29, 162.41, 148.65, 144.25, 142.73, 137.78, 132.80, 121.67, 117.58, 117.27, 111.03, 56.49, 41.09. HRMS (ESI) for $C_{14}H_{14}N_4O_3S_2$ ([M+H]$^+$): Calculated 351.0585; Observed 351.0594.

Example 143: (5-((3-(1-Methyl-1H-pyrazol-4-yl)-5-(trifluoromethyl)phenyl)sulfonyl)thiazol-2-yl)methanamine

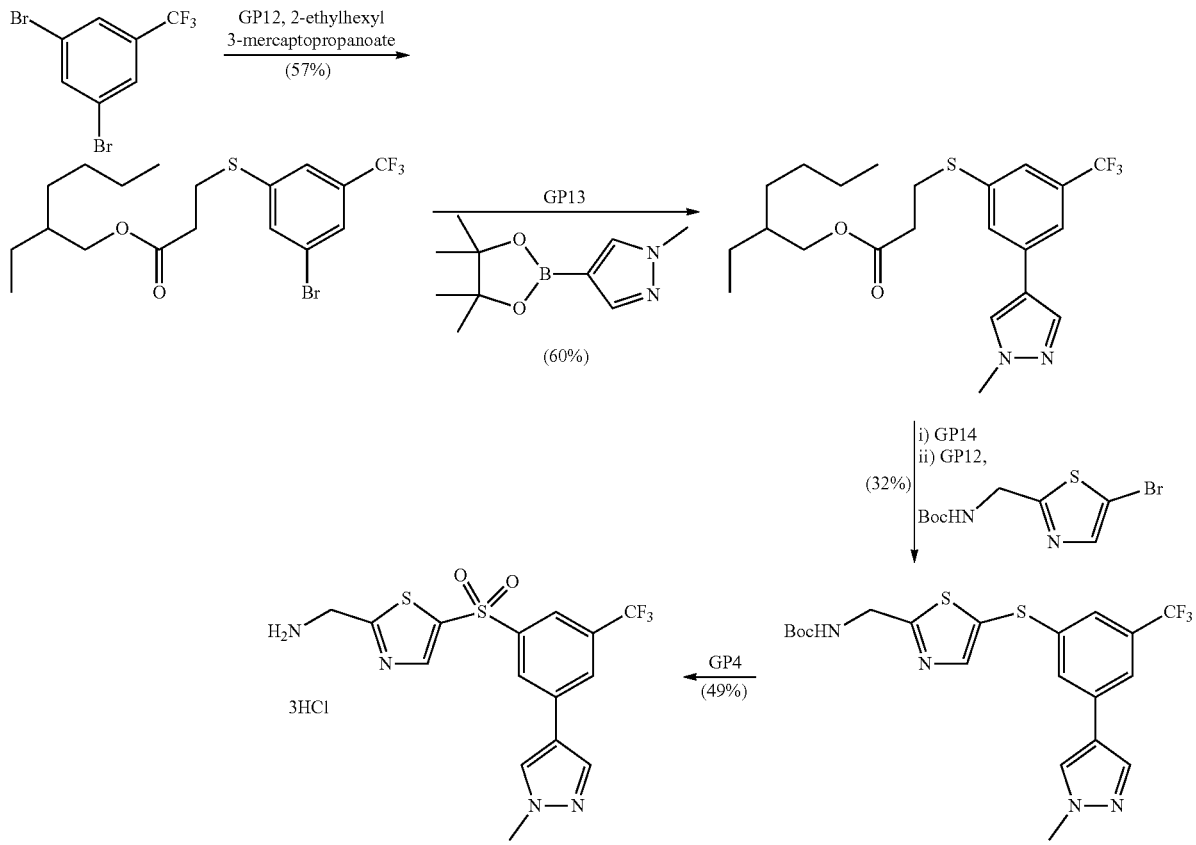

2-Ethylhexyl-3-((3-bromo-5-(trifluoromethyl)phenyl)thio)propanoate was synthesised according to general procedures GP12—from 1,3-dibromo-5-(trifluoromethyl)benzene (2.0 g, 6.58 mmol), Pd$_2$(dba)$_3$ (0.15 g, 2.5 mol %), Xantphos (0.19 g, 5 mol %), 2-ethylhexyl-3-mercaptopropionate (1.44 g, 6.58 mmol), DIPEA (2.29 mL, 13.16 mmol) and toluene (20 mL); 110° C., 8 h. Chromatography (6-8% EtOAc in hexane) afforded a pale yellow oil (1.65 g, 57%). $^1$H NMR (400 MHz, DMSO-d$_6$) δ 7.85 (s, 1H), 7.76 (s, 1H), 7.64 (s, 1H), 3.94 (d, J=5.3 Hz, 2H), 3.34-3.32 (m, 2H), 2.66 (t, J=6.6 Hz, 2H), 1.51-1.49 (m, 1H), 1.30-1.23 (m, 8H), 0.85-0.82 (m, 6H). 2-Ethylhexyl-3-((3-(1-methyl-1H-pyrazol-4-yl)-5-(trifluoromethyl)phenyl)thio)propanoate was synthesised according to general procedures GP13—from 2-ethylhexyl 3-((3-bromo-5-(trifluoromethyl)phenyl)thio)propanoate (0.33 g, 0.75 mmol), 1-methylpyrazole-4-boronic acid pinacol ester (0.172 g, 0.83 mmol), Pd(dppf)Cl$_2$—CH$_2$Cl$_2$ (31 mg, 5 mol %), Na$_2$CO$_3$ (0.197 g, 1.88 mmol), toluene/H$_2$O (5:1, 12 mL); 110° C., 16 h. Chromatographic purification (10% EtOAc in hexane) afforded a pale yellow oil (0.20 g, 60%). $^1$H NMR (400 MHz, DMSO-d$_6$) δ 8.37 (s, 1H), 8.05 (s, 1H), 7.80 (s, 1H), 7.72 (s, 1H), 7.39 (s, 1H), 3.95-3.91 (m, 2H), 3.87 (s, 3H), 3.32 (t, J=6.8 Hz, 2H), 2.66 (m, 2H), 1.52-1.48 (m, 1H), 1.29-1.23 (m, 8H), 0.84-0.80 (m, 6H); LCMS (ESI) m/z 443 (M+H)$^+$.

tert-Butyl ((5-((3-(1-methyl-1H-pyrazol-4-yl)-5-(trifluoromethyl)phenyl)thio)thiazol-2-yl)methyl)carbamate was synthesised according to general procedures GP14 and GP12—from i) 2-ethylhexyl 3-((3-(1-methyl-1H-pyrazol-4-yl)-5-(trifluoromethyl)phenyl)thio) propanoate (0.6 g, 1.36 mmol), KOtBu (1.0 M in THF; 2.7 mL, 2.71 mmol), THF (10 mL); −78° C., 1 hour. ii) tert-butyl ((5-bromothiazol-2-yl)methyl)carbamate (0.46 g, 1.57 mmol), Pd$_2$(dba)$_3$ (206 mg, 14 mol %), Xantphos (268 mg, 28 mol %), NaO$^t$Bu (430 mg, 4.49 mmol) and toluene/BuOH (5:1; 24 mL); 110° C., 16 h. Chromatography (40% EtOAc in hexane) afforded an orange oil (0.24 g, 32%). $^1$H NMR (400 MHz, DMSO-d$_6$) δ 8.31 (s, 1H), 8.04 (s, 1H), 7.99 (s, 1H), 7.79-7.77 (m, 3H), 7.23 (s, 1H), 4.40 (d, J=5.9 Hz, 2H), 3.86 (s, 3H), 1.37 (s, 9H). LCMS (ESI) m/z 471 (M+H)$^+$.

Example 143 was synthesised according to general procedures GP4—from i) m-CPBA (55%; 0.35 g, 1.22 mmol), tert-butyl ((5-((3-(1-methyl-1H-pyrazol-4-yl)-5-(trifluoromethyl)phenyl)thio)thiazol-2-yl)methyl)carbamate (0.24 g, 0.51 mmol) and DCM (10 mL); rt, 4 h. Chromatography (50% EtOAc in cyclohexane), yellow oil (130 mg, 51%); ii) 2 M HCl in Et$_2$O (8 mL), tert-butyl ((5-((3-(1-methyl-1H-pyrazol-4-yl)-5-(trifluoromethyl)phenyl)sulfonyl) thiazol-2-yl)methyl)carbamate (90 mg, 0.18 mmol) and DCM (8 mL); rt, 3 h. Pale yellow solid obtained (70 mg, 97%) without further purification. $^1$H NMR (500 MHz, Methanol-d$_4$) δ 8.56 (s, 1H), 8.45 (s, 1H), 8.41 (s, 1H), 8.23-8.21 (m, 2H), 8.11 (s, 1H), 4.57 (s, 2H), 4.01 (s, 3H); $^{13}$C NMR (126 MHz, Methanol-d$_4$) δ 171.1, 149.6, 144.8, 141.7, 137.3, 137.2, 134.0 (q, J=34.0 Hz), 131.7, 128.34, 128.31, 124.5 (q, J=272.2 Hz), 122.6 (q, J=3.8 Hz), 121.4, 41.3, 39.3; $^{19}$F NMR (470 MHz, Methanol-d$_4$) δ−64.40 (s). HRMS (ESI) for C$_{15}$H$_{14}$F$_3$N$_4$O$_2$S$_2$ ([M+H]$^+$): Calculated 403.0510; Observed 403.0517.

Example 144: (5-((5-(Methylsulfonyl)-[1,1'-biphenyl]-2-yl)sulfonyl)thiazol-2-yl)methanamine

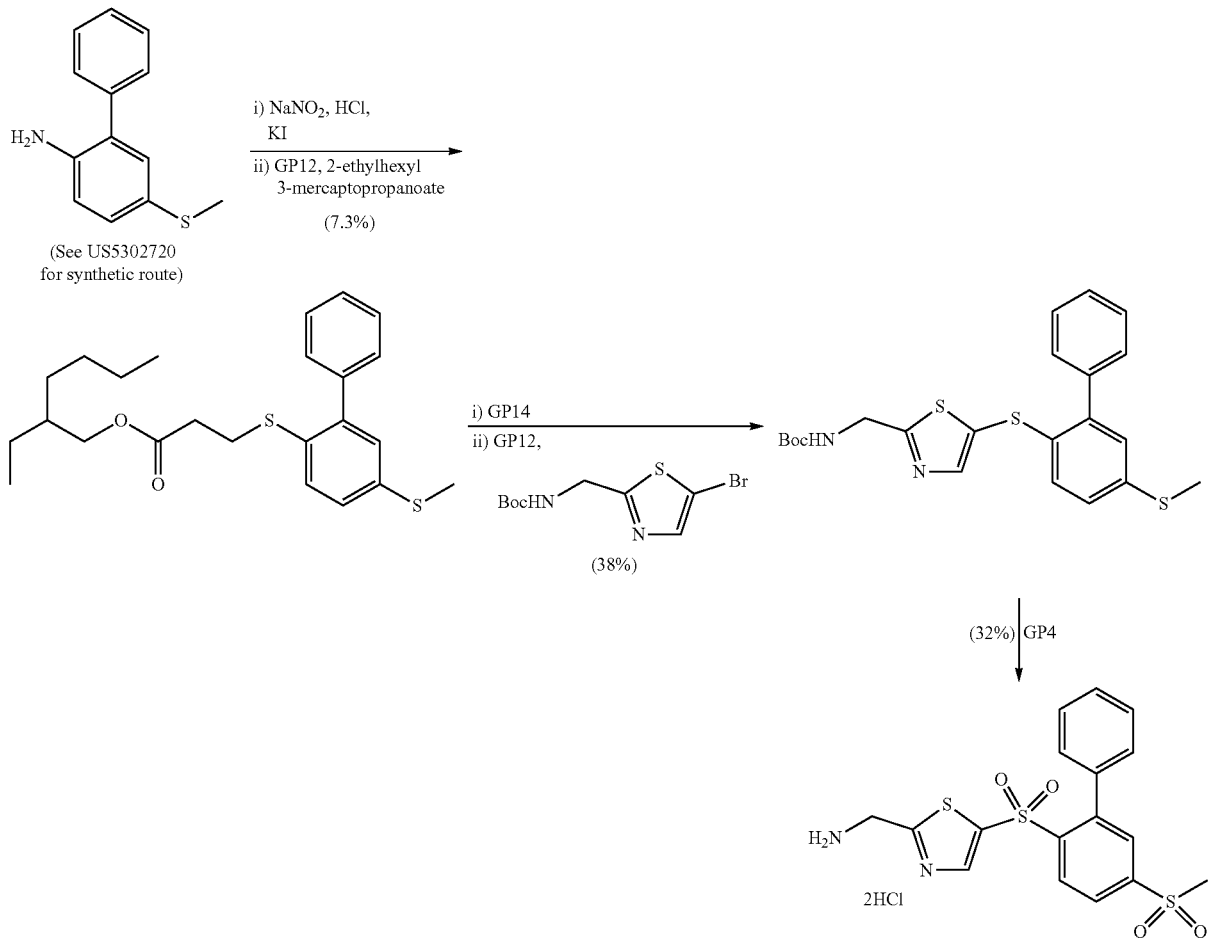

Ref-(Gopalan Balasubramanian, 1994).

As solution of NaNO$_2$ (2.84 g, 41.16 mmol) in water (30 mL) was added to a solution of 5-(methylthio)-[1,1'-biphenyl]-2-amine (2.95 g, 13.70 mmol) in aq. HCl (5 M, 35 mL) at 0° C., and the resulting solution was stirred at 0° C. for 1 h. A solution of KI (6.83 g, 41.2 mmol) in water (30 mL) was then added and stirring was continued for a further 2 h at 0° C. After completion of the reaction, the reaction mixture was extracted with ethyl acetate (30 mL), dried over anhydrous sodium sulfate and filtered. The solvent was removed under reduced pressure and the crude product was purified using combi flash column chromatography (100% Hexanes) to give (6-iodo-[1,1'-biphenyl]-3-yl)(methyl)sulfane (2.5 g, 56%) as a brown-coloured oil. $^1$H NMR (400 MHz, DMSO-d$_6$) δ 7.86 (d, J=8.3 Hz, 1H), 7.52-7.41 (m, 3H), 7.33-7.31 (m, 2H), 7.14 (d, J=2.3 Hz, 1H), 7.04-7.10 (m, 1H), 2.50 (s, 3H). LCMS (ESI, −ve) m/z 325 (M−H)$^+$.

2-Ethylhexyl 3-((5-(methylthio)-[1,1'-biphenyl]-2-yl)thio)propanoate was synthesised according to general procedures GP12—from (6-iodo-[1,1'-biphenyl]-3-yl)(methyl) sulfane (2.4 g, 7.36 mmol), Pd$_2$(dba)$_3$ (0.17 g, 2.5 mol %), Xantphos (0.21 g, 5 mol %), 2-ethylhexyl-3-mercaptopropionate (1.28 g, 5.88 mmol), DIPEA (2.17 mL, 14.72 mmol) and toluene (30 mL); 110° C., 16 h. Chromatography (5% EtOAc in hexane) afforded a pale yellow oil (0.40 g, 13%). $^1$H NMR (400 MHz, DMSO-d$_6$) δ 7.43-7.35 (m, 5H), 7.27-7.25 (m, 2H), 7.08 (d, J=2.0 Hz, 1H), 3.95 (d, J=5.6 Hz, 2H), 3.21 (t, J=6.4 Hz, 2H), 2.63 (t, J=6.8 Hz, 2H), 2.50 (s, 3H), 1.52-1.50 (m, 1H), 1.29-1.24 (m, 8H), 0.87-0.82 (m, 6H); LCMS (ESI) m/z 417 (M+H)$^+$.

tert-Butyl ((5-((5-(methylthio)-[1,1'-biphenyl]-2-yl)thio) thiazol-2-yl)methyl)carbamate was synthesised according to general procedures GP14 and GP12—from i) 2-Ethylhexyl 3-((5-(methylthio)-[1,1'-biphenyl]-2-yl)thio)propanoate (0.4 g, 0.96 mmol), KO'Bu (1.0 M in THF; 2.88 mL, 2.88 mmol), THF (10 mL); −78° C., 30 min. ii) tert-butyl ((5-bromothiazol-2-yl)methyl)carbamate (0.45 g, 1.55 mmol), Pd₂(dba)₃ (70 mg, 5 mol %), Xantphos (80 mg, 10 mol %), NaO'Bu (290 mg, 3.10 mmol) and toluene/'BuOH (4:1; 20 mL); 110° C., 16 h. Chromatography (38% EtOAc in hexane) afforded a brown solid (0.16 g, 38%). ¹H NMR (400 MHz, DMSO-d₆) δ 7.73 (br, 1H), 7.69 (s, 1H), 7.52-7.40 (m, 5H), 7.24 (d, J=8.8 Hz, 1H), 7.13 (d, J=1.9 Hz, 1H), 7.08 (d, J=8.3 Hz, 1H), 4.34 (d, J=5.9 Hz, 2H), 2.49 (s, 3H), 1.38 (s, 9H). LCMS (ESI) m/z 445 (M+H)⁺.

Example 144 was synthesised according to general procedures GP4—from i) m-CPBA (55%; 0.46 g, 1.48 mmol), tert-butyl ((5-((5-(methylthio)-[1,1'-biphenyl]-2-yl)thio)thiazol-2-yl)methyl)carbamate (0.15 g, 0.33 mmol) and DCM (15 mL); rt, 3 h. Chromatography (65% EtOAc in cyclohexane), yellow solid (70 mg, 41%); ii) 2 M HCl in Et₂O (4 mL), tert-butyl ((5-((5-(methylsulfonyl)-[1,1'-biphenyl]-2-yl)sulfonyl)thiazol-2-yl)methyl)carbamate (60 mg, 0.12 mmol) and DCM (10 mL); rt, 3 h. White solid obtained (40 mg, 77%) without further purification. ¹H NMR (500 MHz, Methanol-d₄) δ 8.59 (d, J=8.2 Hz, 1H), 8.25 (d, J=8.0 Hz, 1H), 7.88 (s, 1H), 7.48 (t, J=7.3 Hz, 1H), 7.44-7.36 (m, 3H), 7.19 (d, J=7.2 Hz, 2H), 4.48 (s, 2H), 3.22 (s, 3H). ¹³C NMR (126 MHz, Methanol-d₄) δ 170.41, 149.64, 146.99, 145.23, 144.88, 140.59, 137.70, 132.80, 131.21, 130.93, 130.11, 129.11, 128.37, 43.98, 41.26.

Example 145: (3-Chloro-5-((5-(methylsulfonyl)-[1,1'-biphenyl]-3-yl)sulfonyl)thiophen-2-yl)methanamine hydrochloride Synthesis of tert-butyl ((5-bromo-3-chlorothiophen-2-yl)methyl) carbamate (intermediate 1)

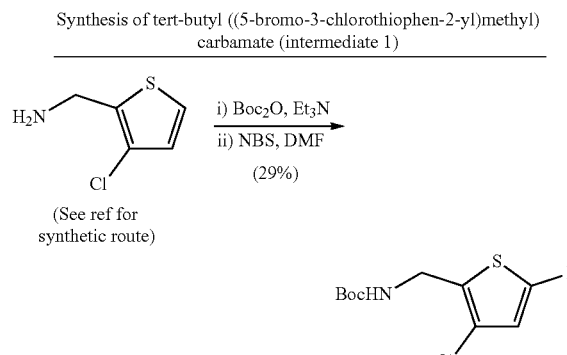

Ref-(Crowley, V. et al. 2016).

To a stirred solution of (3-chlorothiophen-2-yl)methanamine (1.0 g, 6.80 mmol) and Et₃N (1.43 mL, 10.2 mmol) in DCM (10 mL), was added Boc₂O (1.78 g, 7.76 mmol) drop-wise. The mixture was stirred at rt for 16 h before it was diluted with DCM (100 mL), washed with brine (2×50 mL), water (50 mL), dried over Na₂SO₄ and filtered. The solvent was removed under reduced pressure and the crude was purified by chromatography (12% EtOAc in hexanes) to afford tert-butyl ((3-chlorothiophen-2-yl)methyl)carbamate (0.70 g, 42%) as a colorless oil. ¹H NMR (400 MHz, DMSO-d₆) δ 7.56-7.54 (m, 1H), 7.51 (d, J=5.4 Hz, 1H), 6.98 (d, J=4.9 Hz, 1H), 4.23 (d, J=5.9 Hz, 2H), 1.24 (s, 9H). LCMS (ESI) m/z 148/150 (M-Boc+2H)⁺.

To a stirred solution of tert-butyl ((3-chlorothiophen-2-yl)methyl)carbamate (0.10 g, 0.405 mmol) in DMF (2.0 ml) was added N-bromosuccinimide (79 mg, 0.443 mmol) at 0° C. The mixture was stirred at rt for 3 h before it was diluted with Et₂O (80 ml), washed with chilled water (3×30 ml), dried over Na₂SO₄ and filtered. The solvent was removed under reduced pressure and the crude was purified by chromatography (8% EtOAc in hexanes) to afford tert-butyl ((5-bromo-3-chlorothiophen-2-yl)methyl)carbamate as a yellow solid (90 mg, 69%). ¹H NMR (400 MHz, DMSO-d₆) δ 7.61 (t, J=5.7 Hz, 1H), 7.20 (s, 1H), 4.17 (d, J=5.8 Hz, 2H), 1.39 (s, 9H). LCMS (ESI) m/z 209/211 (M-BocNH)⁺.

Synthesis of Example 145

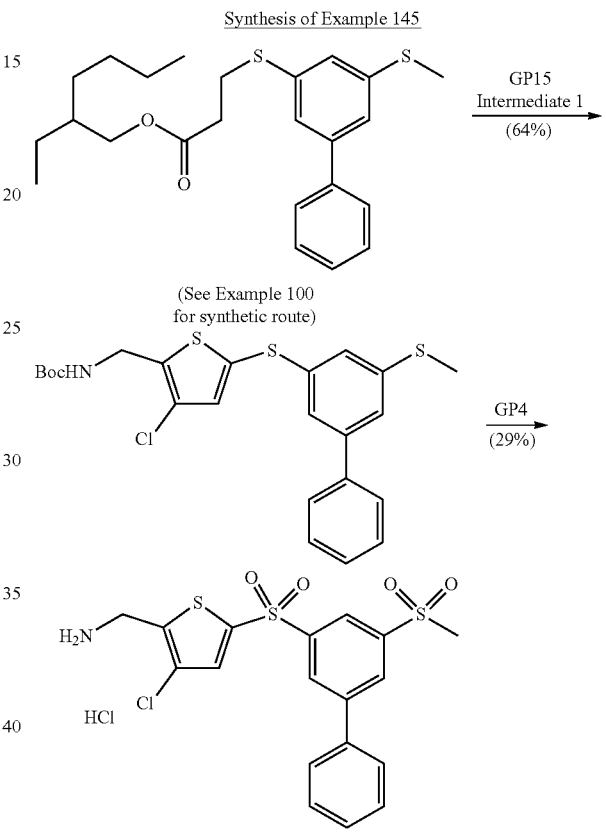

tert-Butyl ((3-chloro-5-((5-(methylthio)-[1,1'-biphenyl]-3-yl)thio)thiophen-2-yl)methyl) carbamate was synthesised according to general procedures GP15—from 2-ethylhexyl 3-((5-(methylthio)-[1,1'-biphenyl]-3-yl)thio)propanoate (204 mg, 0.490 mmol), tert-butyl ((5-bromo-3-chlorothiophen-2-yl)methyl)carbamate (160 mg, 0.490 mmol), Pd₂(dba)₃ (45 mg, 10 mol %), Xantphos (0.14 g, 20 mol %), NaO'Bu (94 mg, 0.979 mmol), toluene/'BuOH (5:1, 6 mL), 110° C., 16 h. Chromatography (20% EtOAc in hexane), a yellow oil (0.15 g, 64%). ¹H NMR (400 MHz, Methanol-d) δ 7.52-7.50 (m, 2H), 7.44-7.43 (m, 3H), 7.30 (s, 1H), 7.20-7.18 (m, 2H), 7.07 (s, 1H), 4.35 (s, 2H), 2.47 (s, 3H), 1.41 (s, 9H). LCMS (ESI) m/z 422 (M-'Bu+2H)⁺.

Example 145 was synthesised according to general procedures GP4—from i) m-CPBA (55%; 295 mg, 0.940 mmol), tert-butyl ((3-chloro-5-((5-(methylthio)-[1,1'-biphenyl]-3-yl)thio)thiophen-2-yl)methyl)carbamate (90 mg, 0.188 mmol) and DCM (10 mL); rt, 3 h. Chromatography (60% EtOAc in cyclohexane), off-white solid (45 mg, 44%); ii) 2 M HCl in Et₂O (4 mL), tert-butyl ((3-chloro-5-((5-(methylthio)-[1,1'-biphenyl]-3-yl)sulfonyl)thiophen-2-yl) methyl) carbamate (40 mg, 0.0738 mmol) and DCM (4 mL);

rt, 3 h. Yellow solid obtained (23 mg, 66%) without further purification. ¹H NMR (500 MHz, Methanol-d₄/Chloroform-d) δ 8.52-8.45 (m, 3H), 7.94 (s, 1H), 7.76-7.70 (m, 2H), 7.58-7.53 (m, 2H), 7.52-7.47 (m, 1H), 4.37 (s, 2H), 3.27 (s, 3H). ¹³C NMR (126 MHz, Methanol-d₄/Chloroform-d) δ 146.03, 144.53, 144.28, 143.73, 138.08, 137.97, 135.13, 131.81, 131.23, 130.39, 130.35, 129.33, 128.23, 125.55, 44.17, 36.07. HRMS (ESI) for C₁₈H₁₄ClO₄S₃ ([M-NH₂]⁺): Calculated 424.9743; Observed 424.9734.

Example 146: (5-((4-(Methylsulfonyl)-[1,1'-biphenyl]-2-yl)sulfonyl)thiazol-2-yl)methanamine dihydrochloride

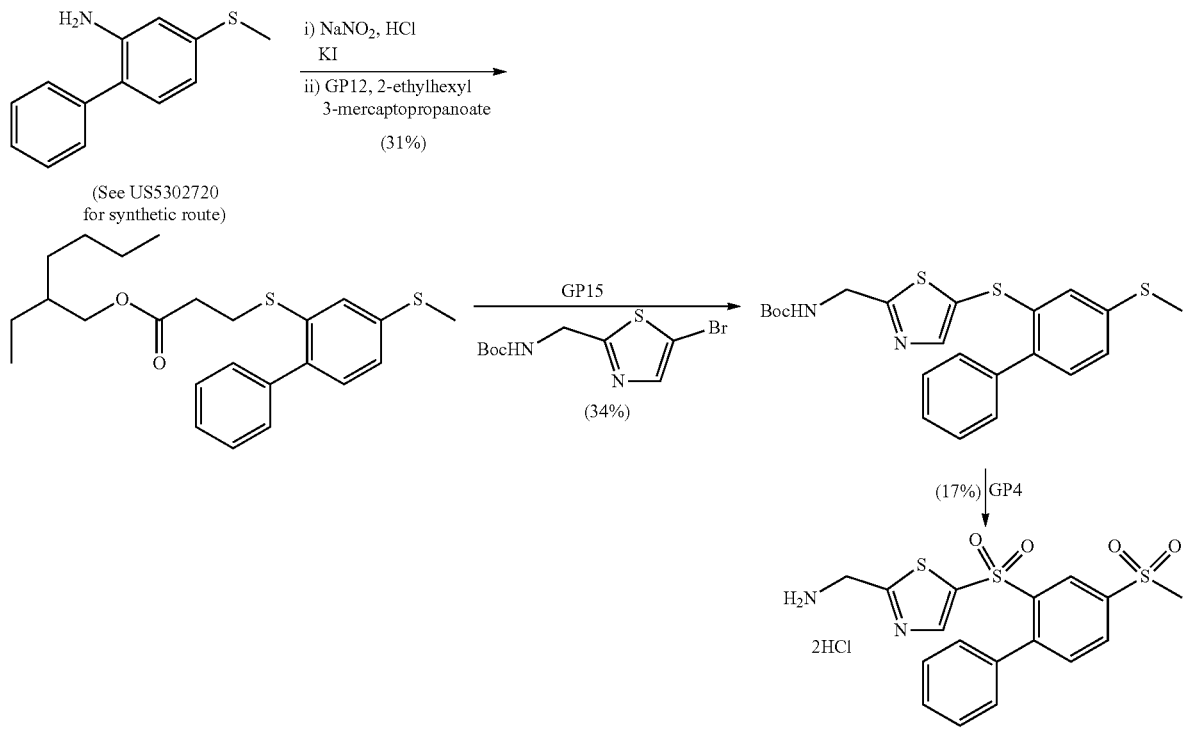

Ref-(Gopalan Balasubramanian, 1994).

A solution of 4-(methylthio)-[1,1'-biphenyl]-2-amine (1.40 g, 6.50 mmol) in 5 N aq. HCl (10 mL) was cooled to 0° C. and a solution of NaNO₂ (1.35 g, 19.5 mmol) in water (20 mL) was then added. The resultant mixture was stirred at 0° C. for 1 h, before adding KI (3.24 g, 19.5 mmol) in water (30 mL) with continued stirring for a further 2 h at the same temperature. After completion, the reaction mixture was extracted with EtOAc (2×30 mL) and the combined organic extracts were dried over anhydrous sodium sulfate, filtered and concentrated under reduced pressure. Chromatographic purification (2% EtOAc in hexane) afforded (2-iodo-[1,1'-biphenyl]-4-yl)(methyl)sulfane (1.20 g, 57%) as a black oil. 2-Ethylhexyl 3-((4-(methylthio)-[1,1'-biphenyl]-2-yl)thio)propanoate was synthesised according to general procedures GP12—from (2-iodo-[1,1'-biphenyl]-4-yl)(methyl)sulfane (1.20 g, 3.68 mmol), Pd₂(dba)₃ (84 mg, 2.5 mol %), Xanthphos (106 mg, 5 mol %), 2-ethylhexyl-3-mercaptopropionate (0.80 g, 3.68 mmol), DIPEA (1.28 mL, 7.36 mmol) and toluene (15 mL); 110° C., 16 h. Chromatographic purification (6% EtOAc in hexane) afforded a yellow oil (0.86 g, 56%). ¹H NMR (400 MHz, Chloroform-d) δ 7.40-7.38 (m, 5H), 7.35 (d, J=6.9 Hz, 1H), 7.18-7.14 (m, 2H), 3.98-3.96 (m, 2H), 2.99-2.91 (m, 2H), 2.76-2.74 (m, 1H), 2.53 (s, 3H), 2.52-2.49 (m, 1H), 1.37-1.25 (m, 9H), 0.91-0.85 (m, 6H). LCMS (ESI) m/z 417 (M+H)⁺.

tert-Butyl ((5-((4-(methylthio)-[1,1'-biphenyl]-2-yl)thio)thiazol-2-yl)methyl)carbamate was synthesised according to general procedures GP15—from 2-Ethylhexyl 3-((4-(methylthio)-[1,1'-biphenyl]-2-yl)thio)propanoate (0.50 g, 1.20 mmol), tert-butyl ((5-bromothiazol-2-yl)methyl)carbamate (0.35 g, 1.20 mmol), NaOʳBu (230 mg, 2.40 mmol), Pd₂(dba)₃ (110 mg, 10 mol %), Xantphos (140 mg, 20 mol %) and toluene/ʳBuOH (5:1, 12 mL); 110° C., 16 h. Chromatography (38% EtOAc in hexane) afforded a brown solid (0.18 g, 34%). ¹H NMR (400 MHz, DMSO-d₆) δ 7.81 (s, 1H), 7.78 (brs, 1H), 7.49-7.41 (m, 5H), 7.24-7.19 (m, 2H), 6.83 (s, 1H) 4.37 (d, J=6.4 Hz, 2H), 2.39 (s, 3H), 1.35 (s, 9H). LCMS (ESI) m/z 445 (M+H)⁺.

Example 146 was synthesised according to general procedures GP4—from i) m-CPBA (55%; 0.53 g, 1.69 mmol), tert-butyl ((5-((4-(methylthio)-[1,1'-biphenyl]-2-yl)thio)thiazol-2-yl)methyl)carbamate (0.15 g, 0.337 mmol) and DCM (10 mL); rt, 3 h. Chromatography (60% EtOAc in cyclohexane), white solid (40 mg, 24%); ii) 2 M HCl in Et₂O (6.0 mL), tert-butyl ((5-((4-(methylsulfonyl)-[1,1'-biphenyl]-2-yl)sulfonyl)thiazol-2-yl)methyl)carbamate (40 mg, 0.079 mmol) and DCM (5 mL); rt, 3 h. Yellow solid obtained (25 mg, 71%) without further purification. ¹H NMR (500 MHz, Methanol-d₄) δ 8.84 (d, J=1.9 Hz, 1H), 8.32 (dd, J=8.0, 2.0 Hz, 1H), 7.63 (d, J=8.0 Hz, 1H), 7.48 (m, 1H), 7.43-7.36 (m, 3H), 7.20-7.14 (m, 2H), 4.49 (s, 2H), 3.28 (s, 3H). ¹³C NMR (126 MHz, Methanol-d₄) δ 170.39, 149.62, 148.72, 142.39, 142.08, 140.55, 137.68, 135.91, 133.77, 130.90, 130.16, 129.07, 128.53, 44.21, 41.03. HRMS (ESI) for C₁₇H₁₇N₂O₄S₃ ([M+H]⁺): Calculated 409.0350; Observed 409.0339.

Example 147: 3-((2-(Aminomethyl)thiazol-5-yl)sulfonyl)-5-ethylbenzoic acid dihydrochloride

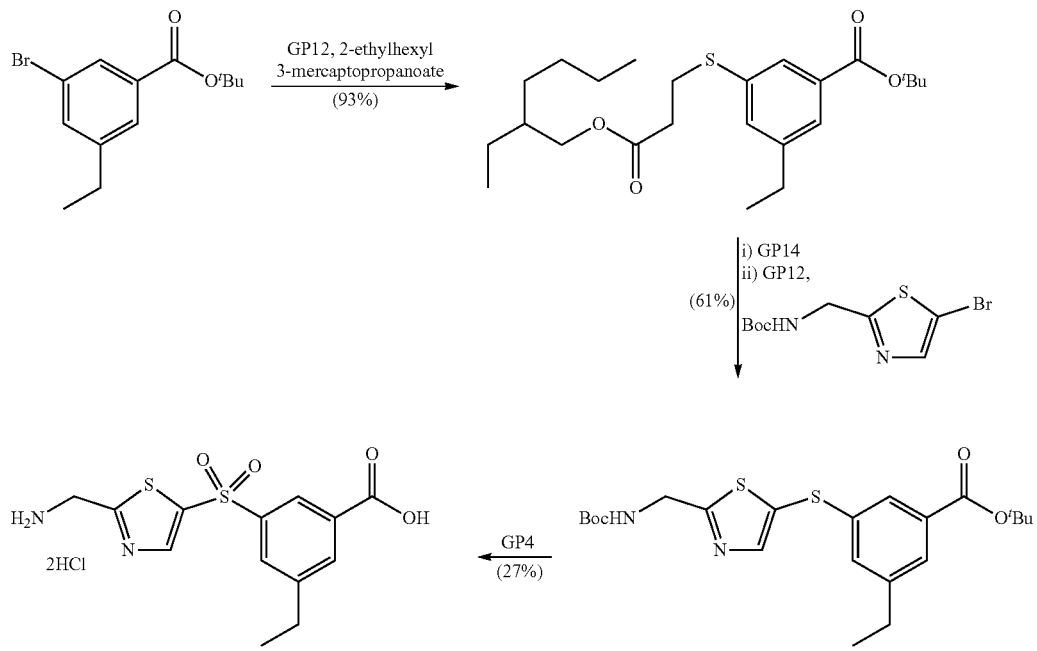 [SMILES: CCc1cc(Br)cc(C(=O)OC(C)(C)C)c1 ; CCCCC(CC)COC(=O)CCSc1cc(CC)cc(C(=O)OC(C)(C)C)c1 ; CC(C)(C)OC(=O)NCc1ncc(Br)s1 ; CCc1cc(C(=O)O)cc(S(=O)(=O)c2cnc(CN)s2)c1 ; CCc1cc(Sc2cnc(CNC(=O)OC(C)(C)C)s2)cc(C(=O)OC(C)(C)C)c1]

tert-Butyl 3-ethyl-5-((3-((2-ethylhexyl)oxy)-3-oxopropyl)thio)benzoate was synthesised according to general procedures GP12—from tert-butyl 3-bromo-5-ethylbenzoate (1.30 g, 4.57 mmol), $Pd_2(dba)_3$ (100 mg, 2.5 mol %), Xanthphos (130 mg, 5 mol %), 2-ethylhexyl-3-mercaptopropionate (1.0 g, 4.57 mmol), DIPEA (1.0 mL, 5.49 mmol) and toluene (15 mL); 110° C., 16 h. Chromatographic purification (5% EtOAc in hexane) afforded a yellow oil (1.8 g, 93%). $^1$H NMR (400 MHz, DMSO-$d_6$) δ 7.60 (s, 1H), 7.56 (s, 1H), 7.43 (s, 1H), 3.94 (d, J=5.6 Hz, 2H), 3.20 (t, J=6.8 Hz, 2H), 2.67-2.61 (m, 4H), 1.54 (s, 9H), 1.32-1.16 (m, 12H), 0.85-0.81 (m, 6H). LCMS (ESI, -ve) m/z 365.1 (M-$^t$Bu)$^-$.

tert-Butyl 3-((2-(((tert-butoxycarbonyl)amino)methyl)thiazol-5-yl)thio)-5-ethylbenzoate was synthesised according to general procedures GP14 and GP12—from i) tert-butyl 3-ethyl-5-((3-((2-ethylhexyl)oxy)-3-oxopropyl)thio)benzoate (0.60 g, 1.42 mmol), KO$^t$Bu (1.0 M in THF; 2.8 mL, 2.80 mmol), THF (15 mL); −78° C., 1 h. ii) Pd$_2$(dba)$_3$ (0.12 g, 10 mol %), Xantphos (0.16 g, 20 mol %), tert-butyl ((5-bromothiazol-2-yl)methyl)carbamate (0.32 g, 1.09 mmol), NaO$^t$Bu (0.266 g, 2.70 mmol) and toluene/$^t$BuOH (4:1; 8.6 mL); 110° C., 16 h. Chromatography (17% EtOAc in hexane) afforded a yellow oil (0.38 g, 61%). $^1$H NMR (400 MHz, DMSO-$d_6$) δ 7.97 (s, 1H), 7.80 (s, 1H), 7.59 (s, 1H), 7.51 (s, 1H), 7.37 (s, 1H), 4.39 (d, J=6.0 Hz, 2H), 2.63-2.51 (m, 2H), 1.51 (s, 9H), 1.38 (s, 9H), 1.14 (d, J=7.2 Hz, 3H). LCMS (ESI) m/z 451 (M+H)$^+$.

Example 147 was synthesised according to general procedures GP4—from i) m-CPBA (55%, 0.58 g, 1.84 mmol), tert-butyl 3-((2-(((tert-butoxycarbonyl)amino)methyl)thiazol-5-yl)thio)-5-ethylbenzoate (0.38 g, 0.843 mmol) and DCM (10 mL); rt, 4 h. Chromatography (27% EtOAc in cyclohexane), off-white solid (0.16 g, 39%); ii) 2 M HCl in Et$_2$O (5.0 ml), tert-butyl 3-((2-(((tert-butoxycarbonyl)amino)methyl)thiazol-5-yl)sulfonyl)-5-ethylbenzoate (0.16 g, 0.33 mmol) and DCM (2.0 mL); rt, 16 h. White solid (75 mg, 69%) obtained and required no further purification. $^1$H NMR (500 MHz, Methanol-$d_4$) δ 8.46 (s, 1H), 8.40 (m, 1H), 8.19 (m, 1H), 8.10 (m, 1H), 4.56 (s, 2H), 2.83 (q, J=7.6 Hz, 2H), 1.29 (t, J=7.6 Hz, 3H). $^{13}$C NMR (126 MHz, Methanol-$d_4$) δ 170.57, 167.51, 148.82, 148.79, 143.26, 142.45, 135.65, 134.09, 131.55, 127.02, 41.14, 29.41, 15.65. HRMS (ESI) for $C_{13}H_{15}N_2O_4S_2$ ([M+H]$^+$): Calculated 327.0473; Observed 327.0484.

Example 148: 3-((2-(Aminomethyl)thiazol-5-yl)sulfonyl)-5-bromobenzoic acid dihydrochloride

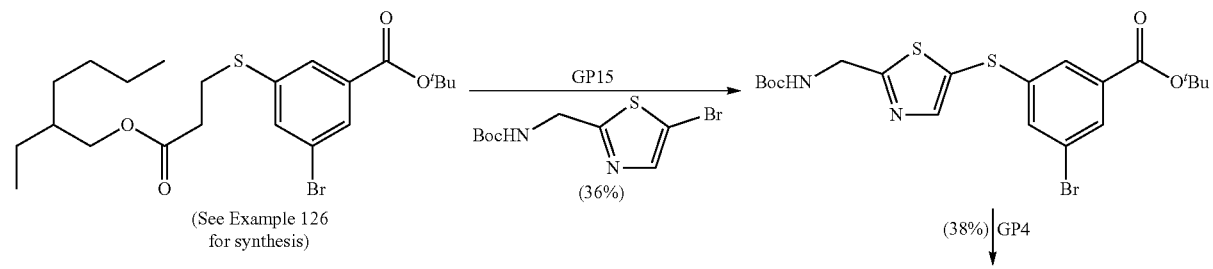

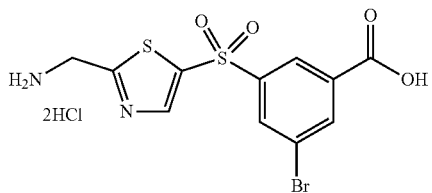

tert-Butyl 3-bromo-5-((2-(((tert-butoxycarbonyl)amino)methyl)thiazol-5-yl)thio)benzoate was synthesised according to general procedures GP15—from tert-butyl 3-bromo-5-((3-((2-ethylhexyl)oxy)-3-oxopropyl)thio)benzoate (1.0 g, 2.1 mmol), tert-butyl ((5-bromothiazol-2-yl)methyl)carbamate (0.49 g, 1.69 mmol), NaO$^t$Bu (407 mg, 4.23 mmol), Pd$_2$(dba)$_3$ (195 mg, 10 mol %), Xantphos (245 mg, 20 mol %) and toluene/$^t$BuOH (4:1, 10 mL); 110° C., 16 h. Chromatography (15% EtOAc in hexane) afforded a yellow oil (0.30 g, 36%). LCMS (ESI) m/z 501 (M+H)$^+$.

Example 148 was synthesised according to general procedures GP4—from i) m-CPBA (55%, 0.25 g, 0.797 mmol), tert-butyl 3-bromo-5-((2-(((tert-butoxycarbonyl)amino)methyl)thiazol-5-yl)thio) benzoate (0.30 g, 0.599 mmol) and DCM (15 mL); rt, 3 h. Chromatography (20% EtOAc in cyclohexane), yellow solid (0.16 g, 76%); ii) 2 M HCl in Et$_2$O (6.0 mL) and 1 M HCl in dioxane (3.0 mL), tert-butyl 3-bromo-5-((2-(((tert-butoxycarbonyl)amino)methyl)thiazol-5-yl)sulfonyl)benzoate (0.16 g, 0.300 mmol) and DCM (2.0 mL); rt, 6 h. White solid (60 mg, 50%) obtained and required no further purification. $^1$H NMR (500 MHz, Methanol-d$_4$) δ 8.57-8.47 (m, 2H), 8.46-8.35 (m, 2H), 4.57 (s, 2H). $^{13}$C NMR (126 MHz, Methanol-d$_4$) δ 169.81, 164.55, 148.19, 143.61, 140.09, 137.53, 134.57, 133.53, 126.73, 123.33, 40.14. HRMS (ESI) for C$_{13}$H$_{15}$N$_2$O$_4$S$_2$ ([M+H]$^+$): Calculated 327.9265; Observed 376.9219.

Example 149: (5-((2-(Aminomethyl)thiazol-5-yl)sulfonyl)-[1,1'-biphenyl]-3-yl)(3-hydroxypyrrolidin-1-yl)methanone dihydrochloride

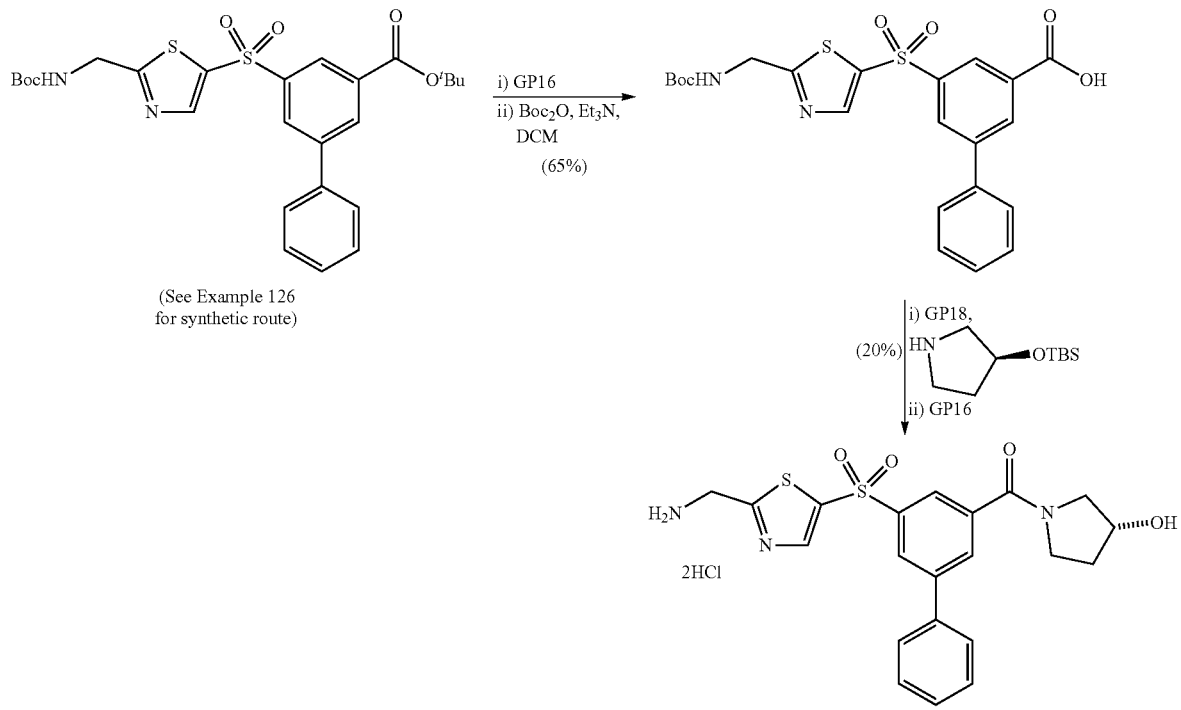

5-((2-(Aminomethyl)thiazol-5-yl)sulfonyl)-[1,1'-biphenyl]-3-carboxylic acid hydrochloride was synthesised according to general procedures GP16—from 2 M HCl in Et$_2$O (12 ml), tert-butyl 5-((2-(((tert-butoxycarbonyl)amino)methyl)thiazol-5-yl)sulfonyl)-[1,1'-biphenyl]-3-carboxylate (450 mg, 0.849 mmol) and DCM (5.0 mL); rt, 16 h. White solid (348 mg, quantitative). $^1$H NMR (400 MHz, DMSO-d$_6$) δ 13.9 (br, 1H), 8.69 (br, 4H), 8.48-8.47 (m, 2H), 8.43-8.422 (m, 1H), 7.81-7.79 (m, 2H), 7.58-7.48 (m, 3H), 4.49 (s, 2H). LCMS (ESI) m/z 375 (M+H)$^+$.

Boc$_2$O (220 mg, 0.959 mmol) was added to a solution of 5-((2-(aminomethyl)thiazol-5-yl)sulfonyl)-[1,1'-biphenyl]-3-carboxylic acid dihydrochloride (345 mg, 0.841 mmol) and Et$_3$N (0.82 mL, 5.88 mmol) in DCM (30 mL) added at 0° C. and the mixture was stirred at rt for 16 h. The reaction mixture was diluted with EtOAc (50 mL), washed with aq. HCl (1 N, 10 mL), water (50 mL×2), brine (50 mL) and dried over Na$_2$SO$_4$. The solvent was removed under pressure and the crude was washed with Et$_2$O (20 mL) and hexanes (20 mL×2) to obtain 5-((2-(((tert-butoxycarbonyl)amino)

methyl)thiazol-5-yl)sulfonyl)-[1,1'-biphenyl]-3-carboxylic acid as a white solid (260 mg, 65%). ¹H NMR (400 MHz, DMSO-d₆) δ 13.80 (br, 1H), 8.57 (s, 1H), 8.44-8.39 (m, 3H), 7.86 (br, 1H), 7.79-7.76 (m, 2H), 7.56-7.47 (m, 3H), 4.41 (d, J=5.6 Hz, 2H), 1.37 (s, 9H). LCMS (ESI) m/z 475 (M+H)⁺.

tert-Butyl (R)-((5-((5-(3-((tert-butyldimethylsilyl)oxy)pyrrolidine-1-carbonyl)-[1,1'-biphenyl]-3-yl)sulfonyl)thiazol-2-yl)methyl)carbamate was synthesised according to general procedures GP18—from 5-((2-(((tert-butoxycarbo- 128.24, 127.83, 125.81, 125.72, 71.50, 70.21, 58.36, 55.77, 48.56, 45.68, 41.29, 35.34, 33.42. HRMS (ESI) for C₂₁H₂₂N₃O₄S₂ ([M+H]⁺): Calculated 444.1052; Observed 444.1043.

Example 150: 3-((2-(Aminomethyl)thiazol-5-yl)sulfonyl)-5-(1-methyl-1H-pyrazol-4-yl)benzoic acid trihydrochloride

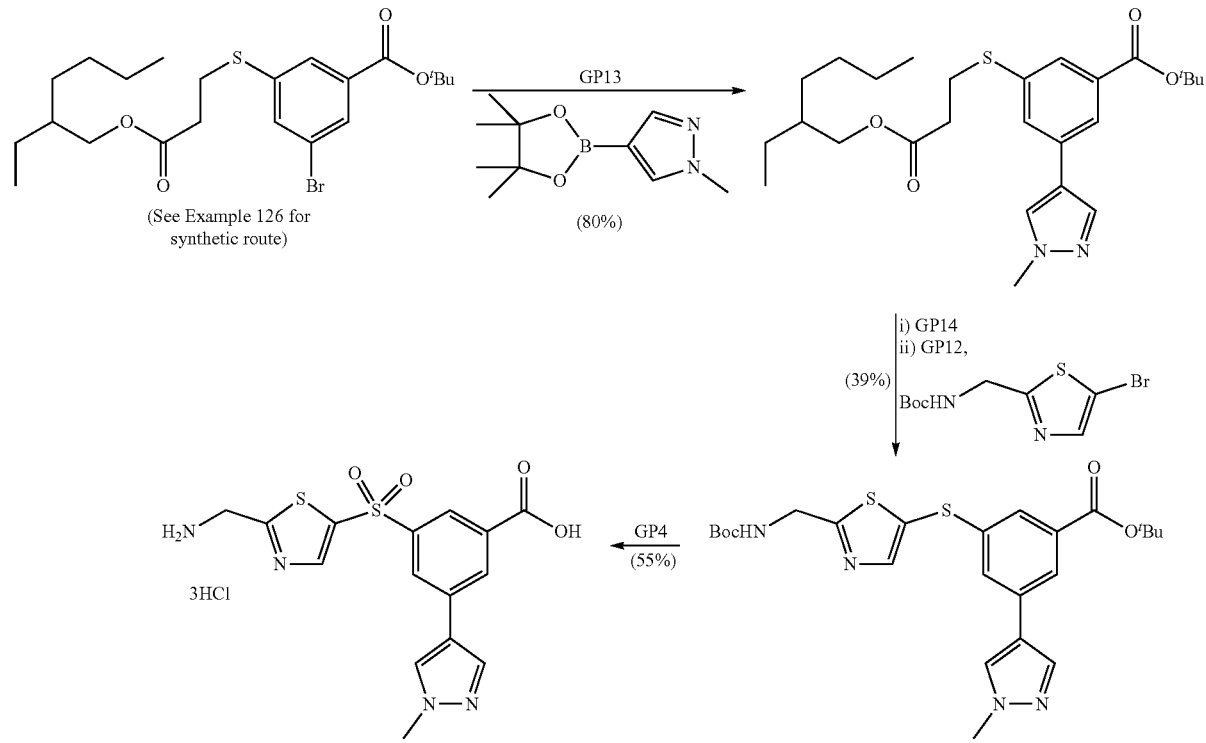

nyl)amino)methyl)thiazol-5-yl)sulfonyl)-[1,1'-biphenyl]-3-carboxylic acid (200 mg, 0.422 mmol), HATU (192 mg, 0.505 mmol), (R)-3-((tert-butyldimethylsilyl)oxy)pyrrolidine (127 mg, 0.632 mmol), DIPEA (0.22 mL, 1.26 mmol) and DMF (5.0 mL); rt, 16 h. Yellow oil (120 mg, 43%). ¹H NMR (400 MHz, Chloroform-d) for a mixture of rotamers δ 8.22-8.18 (m, 2H), 8.08-8.02 (m, 1H), 7.99-7.96 (m, 1H), 7.59 (d, J=7.2 Hz, 2H), 7.51-7.42 (m, 3H), 5.26 (br, 1H), 4.59 (d, J=5.6 Hz, 2H), 4.52-4.41 (br, 1H), 3.84-3.65 (m, 2H), 3.60-3.54 (m, 1H), 3.52-3.43 and 3.30-3.27 (1×m each, 1H), 2.01-1.91 (m, 2H), 1.44 (s, 9H), 0.92-0.85 (m, 9H), 0.12-0.07 (m, 6H). LCMS (ESI, −ve) m/z 656 (M−H)⁻

Example 149 was synthesised according to general procedures GP16—from 2 M HCl in dioxane (10 ml), tert-butyl (R)-((5-((5-(3-((tert-butyldimethylsilyl)oxy)pyrrolidine-1-carbonyl)-[1,1'-biphenyl]-3-yl)sulfonyl)thiazol-2-yl) methyl)carbamate (120 mg, 0.182 mmol); rt, 16 h. Crude was purified by washing with DCM (5.0 mL×2) and diethyl ether (5.0 mL×3) and dried under high vacuum to afford a white solid (44 mg, 47%). ¹H NMR (500 MHz, Methanol-d₄) for a mixture of rotamers δ 8.50 (s, 1H), 8.31 (s, 1H), 8.20-8.03 (m, 2H), 7.75-7.63 (m, 2H), 7.56-7.40 (m, 3H), 4.68-4.32 (m, 3H), 3.94-3.46 (m, 4H), 2.28-1.85 (m, 2H). ¹³C NMR (126 MHz, Methanol-d₄) for a pair of rotamers δ 170.73, 169.56, 169.50, 149.11, 144.86, 143.75, 142.14, 140.31, 140.27, 139.18, 132.12, 132.06, 130.39, 130.04, tert-Butyl 3-((3-((2-ethylhexyl)oxy)-3-oxopropyl)thio)-5-(1-methyl-1H-pyrazol-4-yl)benzoate was synthesised according to general procedures GP13—from tert-butyl 3-bromo-5-((3-((2-ethylhexyl)oxy)-3-oxopropyl)thio)benzoate (1.0 g, 2.11 mmol), 1-methyl-4-(4,4,5,5-tetramethyl-1,3,2-dioxaborolan-2-yl)-1H-pyrazole (0.53 g, 2.54 mmol), Pd(PPh₃)₄ (0.24 g, 10 mol %), Na₂CO₃ (0.45 g, 4.23 mmol), toluene (20 mL) and water (4.0 mL); 100° C., 16 h. Chromatographic purification (13% EtOAc in hexane) afforded a colourless oil (0.80 g, 80%). ¹H NMR (400 MHz, DMSO-d₆) δ8.28 (s, 1H), 7.95 (s, 1H), 7.84 (s, 1H), 7.76 (s, 1H) 7.58 (s, 1H), 3.94-3.87 (m, 2H), 3.86 (s, 3H), 3.27 (t, J=6.8 Hz, 2H), 2.65 (t, J=6.8 Hz, 2H), 1.56 (s, 9H), 1.29-1.27 (m, 9H), 0.84-0.80 (m, 6H). LCMS (ESI) m/z 475 (M+H)⁺.

tert-Butyl 3-((2-(((tert-butoxycarbonyl)amino)methyl)thiazol-5-yl)thio)-5-(1-methyl-1H-pyrazol-4-yl)benzoate was synthesised according to general procedures GP14 and GP12—from i) tert-butyl 3-((3-((2-ethylhexyl)oxy)-3-oxopropyl)thio)-5-(1-methyl-1H-pyrazol-4-yl)benzoate (0.80 g, 1.68 mmol), KOᵗBu (1.0 M in THF; 3.37 mL, 3.37 mmol), THF (15 mL); −78° C., 1 h; ii) tert-butyl ((5-bromothiazol-2-yl)methyl)carbamate (0.36 g, 1.24 mmol), Pd₂(dba)₃ (0.12 g, 10 mol %), Xantphos (0.15 g, 20 mol %), DIPEA (0.50 mL, 2.88 mmol), toluene (15 mL); 110° C., 16 h. Chromatographic purification (46% EtOAc in hexane) afforded a yellow liquid (0.24 g, 39%). $^1$H NMR (400 MHz, DMSO-$d_6$) δ 8.26 (s, 1H), 8.01 (s, 1H), 7.92 (s, 1H), 7.87 (s, 1H), 7.83 (t, J=8.0 Hz, 1H), 7.73 (s, 1H), 7.45 (s, 1H), 4.40 (d, J=5.6 Hz, 2H), 3.86 (s, 3H), 1.52 (s, 9H), 1.37 (s, 9H). LCMS (ESI) m/z 503 (M+H)$^+$.

Example 150 was synthesised according to general procedures GP4—from i) m-CPBA (55%; 0.33 g, 1.05 mmol), tert-butyl 3-((2-(((tert-butoxycarbonyl)amino)methyl)thiazol-5-yl)thio)-5-(1-methyl-1H-pyrazol-4-yl)benzoate (0.24 g, 0.478 mmol) and DCM (10 mL); rt, 3 h. Chromatography (48% EtOAc in cyclohexane), white solid (0.20 g, 78%); ii) 2 M HCl in Et$_2$O (10 mL), tert-butyl 3-((2-(((tert-butoxycarbonyl)amino)methyl)thiazol-5-yl)sulfonyl)-5-(1-methyl-1H-pyrazol-4-yl)benzoate (200 mg, 0.375 mmol) and DCM (1.0 mL); rt, 16 h. The precipitate was filtered and washed with Et$_2$O to afford a white solid (130 mg, 71%). $^1$H NMR (500 MHz, Methanol-$d_4$) for a mixture of rotamers δ 8.49 and 8.50 (s, 1H), 8.45-8.25 (m, 4H), 8.05 and 8.04 (s, 1H), 4.57 and 4.56 (s, 2H), 3.98 and 3.97 (s, 3H). $^{13}$C NMR (126 MHz, Methanol-$d_4$) for a mixture of rotamers δ 170.77, 167.25, 149.11, 143.96, 142.03 (br), 137.28 (br), 136.20 (br), 134.68, 132.38, 131.21 (br), 128.33, 126.87, 121.76, 41.29 (br), 39.28 (br). HRMS (ESI) for $C_{15}H_{15}N_4O_4S_2$ ([M+H]$^+$): Calculated 379.0535; Observed 379.537.

Example 151: 5-((2-(Aminomethyl)thiazol-5-yl)sulfonyl)-N-ethyl-[1,1'-biphenyl]-3-carboxamide dihydrochloride

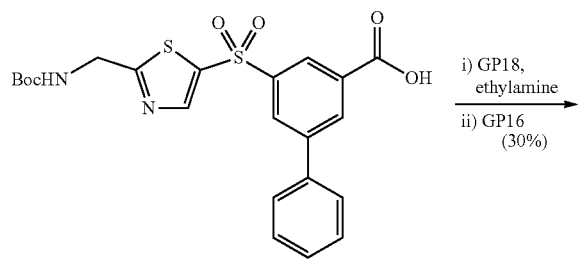

(See Example 149 for synthetic route)

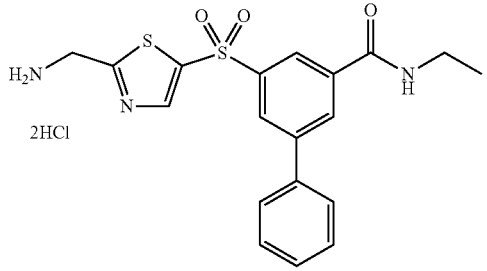

tert-Butyl ((5-((5-(ethylcarbamoyl)-[1,1'-biphenyl]-3-yl)sulfonyl)thiazol-2-yl)methyl)carbamate was synthesised according to general procedures GP18—from 5-((2-(((tert-butoxycarbonyl)amino)methyl)thiazol-5-yl)sulfonyl)-[1,1'-biphenyl]-3-carboxylic acid (100 mg, 0.211 mmol), HATU (104 mg, 0.274 mmol), ethanamine hydrochloride (34 mg, 0.425 mmol), DIPEA (0.11 mL, 0.633 mmol) and DMF (3.0 mL); rt, 16 h. Chromatography (50% EtOAc in hexanes) afforded a yellow oil (45 mg, 43%). $^1$H NMR (400 MHz, Chloroform-d) δ 8.28-8.27 (m, 2H), 8.23 (s, 1H), 8.22 (br, 1H), 7.61 (d, J=7.2 Hz, 2H), 7.51-7.42 (m, 3H), 6.34 (br, 1H), 5.29 (br, 1H), 4.58 (d, J=6.0 Hz, 2H), 3.55 (q, J=7.6 Hz, 2H), 1.44 (s, 9H), 1.277 (t, J=7.6 Hz, 3H). LCMS (ESI, −ve) m/z 500 (M−H)$^−$.

Example 151 was synthesised according to general procedures GP16—from 2 M HCl in Et$_2$O (3.0 mL), tert-butyl ((5-((5-(ethylcarbamoyl)-[1,1'-biphenyl]-3-yl)sulfonyl)thiazol-2-yl)methyl)carbamate (45 mg, 0.090 mmol) and DCM (2.0 mL); rt, 16 h. The precipitate was filtered and washed with Et$_2$O to afford a white solid (30 mg, 70%). $^1$H NMR (500 MHz, Methanol-$d_4$) δ 8.52 (s, 1H), 8.45 (s, 1H), 8.40 (s, 1H), 8.36 (s, 1H), 7.75-7.68 (m, 2H), 7.56-7.50 (m, 2H), 7.47 (m, 1H), 4.58 (s, 2H), 3.47 (q, J=7.1 Hz, 2H), 1.27 (t, J=7.3 Hz, 3H). $^{13}$C NMR (126 MHz, Methanol-$d_4$) δ 170.69, 167.33, 149.07, 144.84, 143.85, 142.19, 139.32, 138.23, 132.11, 130.37, 130.00, 128.90, 128.26, 126.04, 41.20, 36.13, 14.76. HRMS (ESI) for $C_{19}H_{20}N_3O_3S_2$ ([M+H]$^+$): Calculated 402.0946; Observed 402.0951.

Example 152: 5-((2-(Aminomethyl)thiazol-5-yl)sulfonyl)-N-(2-hydroxyethyl)-[1,1'-biphenyl]-3-carboxamide dihydrochloride

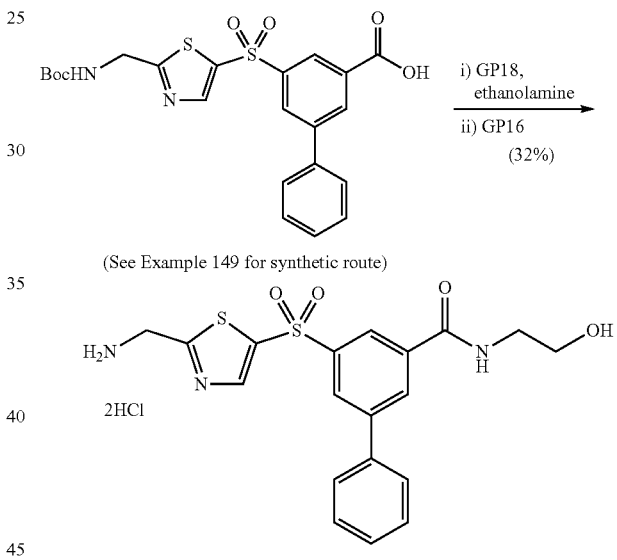

(See Example 149 for synthetic route)

tert-Butyl ((5-((5-((2-(((tert-butyldimethylsilyl)oxy)ethyl)carbamoyl)-[1,1'-biphenyl]-3-yl)sulfonyl)thiazol-2-yl)methyl)carbamate was synthesised according to general procedures GP18—from 5-((2-(((tert-butoxycarbonyl)amino)methyl)thiazol-5-yl)sulfonyl)-[1,1'-biphenyl]-3-carboxylic acid (200 mg, 0.421 mmol), HATU (192 mg, 0.505 mmol), 2-((tert-butyldimethylsilyl)oxy)ethan-1-amine (111 mg, 0.634 mmol), DIPEA (0.22 mL, 1.26 mmol) and DMF (6.0 mL); rt, 16 h. Chromatography (50% EtOAc in hexanes) afforded a yellow oil (144 mg, 54%). $^1$H NMR (400 MHz, Chloroform-d) δ 8.26-8.24 (m, 3H), 8.19 (s, 1H), 7.60-7.58 (m, 2H), 7.50-7.41 (m, 3H), 6.76 (br, 1H), 5.36 (br, 1H), 4.57 (d, J=6.0 Hz, 2H), 3.82 (t, J=4.8 Hz, 2H), 3.63-3.59 (m, 2H), 1.45 (s, 9H), 0.91 (s, 9H), 0.21 (s, 6H). LCMS (ESI, −ve) m/z 630 (M−H)$^−$.

Example 152 was synthesised according to general procedures GP16—from 2 M HCl in dioxane (10 mL), tert-butyl ((5-((5-((2-(((tert-butyldimethylsilyl)oxy)ethyl)carbamoyl)-[1,1'-biphenyl]-3-yl)sulfonyl)thiazol-2-yl)methyl)carbamate (144 mg, 0.236 mmol) and DCM (2.0 mL); rt, 16 h. The precipitate was filtered and washed with Et$_2$O to afford a white solid (68 mg, 59%). ¹H NMR (500 MHz, Methanol-d₄) δ 8.55-8.30 (m, 4H), 7.77-7.62 (m, 2H), 7.55-7.40 (m, 3H), 4.56 (s, 2H), 3.81-3.49 (m, 4H). ¹³C NMR (126 MHz, Methanol-d₄) δ 170.60, 167.89, 149.08, 144.74, 143.75, 142.17, 139.22, 138.09, 132.22, 130.34, 129.96, 128.90, 128.25, 126.11, 61.43, 43.79, 41.60. HRMS (ESI) for $C_{19}H_{20}N_3OS_2$ ([M+H]⁺): Calculated 418.0895; Observed 402.0893.

Example 153: 3-((2-(Aminomethyl)thiazol-5-yl)sulfonyl)-5-(1-methyl-1H-pyrazol-4-yl)benzoic acid trihydrochloride

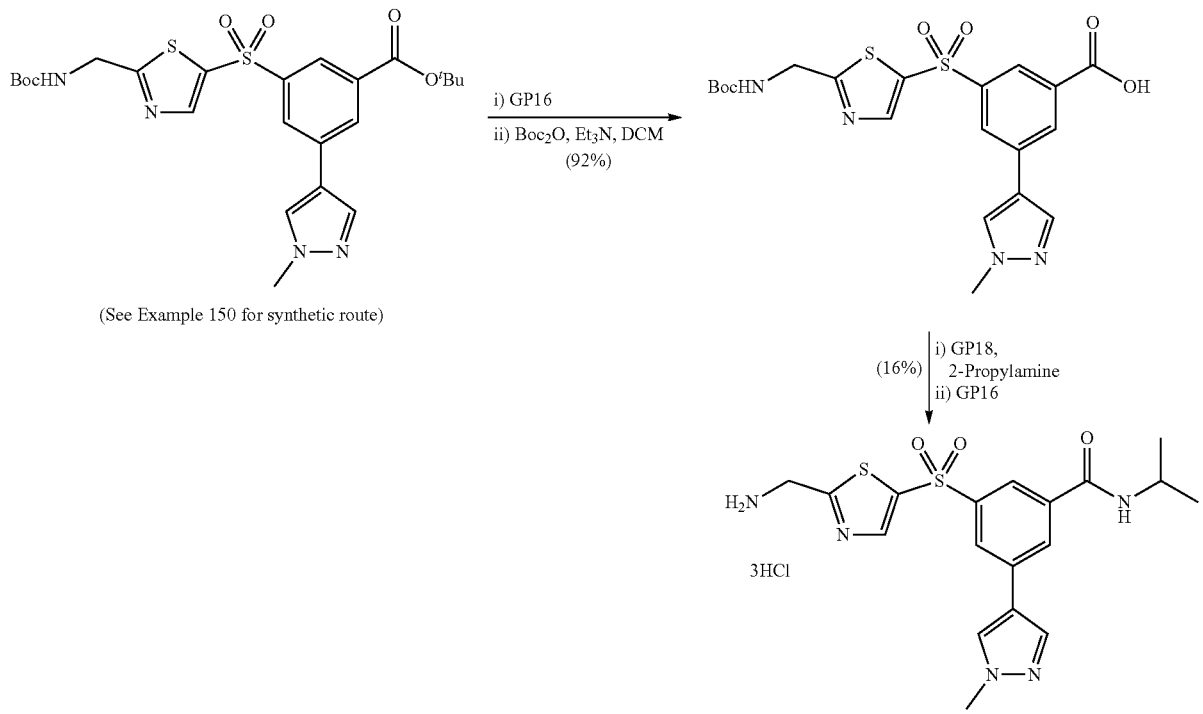

(See Example 150 for synthetic route)

3-((2-(Aminomethyl)thiazol-5-yl)sulfonyl)-5-(1-methyl-1H-pyrazol-4-yl)benzoic acid hydrochloride was synthesised according to general procedures GP16—from 2 M HCl in diethyl ether (10 mL), tert-butyl 3-((2-(((tert-butoxycarbonyl)amino)methyl)thiazol-5-yl)sulfonyl)-5-(1-methyl-1H-pyrazol-4-yl)benzoate (200 mg, 0.375 mmol) and DCM (1.0 mL); rt, 16 h. The precipitate was filtered and washed with Et₂O to afford a white solid (130 mg, 92%). ¹H NMR (400 MHz, DMSO-d₆) δ 13.9 (br, 1H), 8.73 (s, 1H), 8.58 (br, 3H), 8.49 (s, 1H), 8.40 (s, 1H), 8.38 (s, 1H), 8.22 (s, 1H), 8.11 (s, 1H), 4.49 (s, 2H), 3.88 (s, 3H). LCMS (ESI) m/z 379 (M+H)⁺.

Triethylamine (0.78 mL, 5.60 mmol) and Boc₂O (0.20 g, 0.917 mmol) were added sequentially to a solution of 3-((2-(aminomethyl)thiazol-5-yl)sulfonyl)-5-(1-methyl-1H-pyrazol-4-yl)benzoic acid hydrochloride (330 mg, 0.792 mmol) in DCM (10 mL), with stirring at 0° C. for 16 hours, warming to room temperature. After completion of the reaction the solvent was removed under reduced pressure to afford the 3-((2-(((tert-butoxycarbonyl)amino)methyl)thiazol-5-yl)sulfonyl)-5-(1-methyl-1H-pyrazol-4-yl)benzoic acid (425 mg, crude), which was used in the next step without further purification. ¹H NMR (400 MHz, DMSO-d₆) δ 10.9 (br, 1H), 8.46 (s, 1H), 8.39 (s, 1H), 8.30 (s, 1H), 8.19 (d, J=4.8 Hz, 2H), 8.09 (s, 1H), 7.85 (br, 1H), 4.40 (d, J=5.2 Hz, 2H), 3.87 (s, 3H), 1.37 (s, 9H). LCMS (ESI) m/z 423 (M−ᵗBu+2H)⁺.

tert-Butyl ((5-((3-(isopropylcarbamoyl)-5-(1-methyl-1H-pyrazol-4-yl)phenyl)sulfonyl)thiazol-2-yl)methyl)carbamate was synthesised according to general procedures GP18—from 3-((2-(((tert-butoxycarbonyl)amino)methyl)thiazol-5-yl)sulfonyl)-5-(1-methyl-1H-pyrazol-4-yl) benzoic acid (175 mg, ~0.36 mmol), HATU (180 mg, 0.473 mmol), isopropylamine (0.043 g, 0.727 mmol), DIPEA (0.20 mL, 1.12 mmol) and DMF (3.0 mL); rt, 1 h. Chromatography (1.5% MeOH in DCM) afforded a white solid (40 mg, 21%). ¹H NMR (400 MHz, DMSO-d₆) δ 8.53 (d, J=7.2 Hz, 1H), 8.48 (s, 1H), 8.40 (s, 1H), 8.30 (s, 1H), 8.24 (t, J=1.6 Hz, 1H), 8.19 (s, 1H), 8.05 (s, 1H), 7.85 (br, 1H), 4.40 (d, J=5.6 Hz, 2H), 4.14-4.09 (m, 1H), 3.86 (s, 3H), 1.37 (s, 9H), 1.20 (d, J=6.8 Hz, 6H). LCMS (ESI) m/z 464 (M−ᵗBu+2H)⁺.

Example 153 was synthesised according to general procedures GP16—from 2 M HCl in diethyl ether (5.0 mL), tert-butyl ((5-((3-(isopropylcarbamoyl)-5-(1-methyl-1H-pyrazol-4-yl)phenyl)sulfonyl)thiazol-2-yl)methyl)carbamate (40 mg, 0.0771 mmol) and DCM (1.0 mL); rt, 16 h. The precipitate was filtered and washed with Et₂O to afford a white solid (25 mg, 78%). ¹H NMR (500 MHz, Methanol-d₄) δ ¹H NMR (500 MHz, Methanol-d₄) δ 8.50 (s, 1H), 8.44-8.17 (m, 5H), 4.57 (s, 2H), 4.23 (m, 1H), 4.03 (s, 3H), 1.29 (d, J=6.4 Hz, 6H). ¹³C NMR (126 MHz, Methanol-d₄) δ 170.61, 166.63, 149.16, 143.90, 142.18, 138.45, 137.00, 135.67, 131.76, 130.44, 127.18, 125.38, 122.19, 43.58, 41.47, 39.45, 22.46. HRMS (ESI) for $C_{18}H_{21}N_5O_3S_2$ ([M+H]⁺): Calculated 420.1164; Observed 420.1159.

Example 154: 3-((2-(Aminomethyl)thiazol-5-yl)sulfonyl)-5-(1-methyl-1H-pyrazol-4-yl)benzoic acid

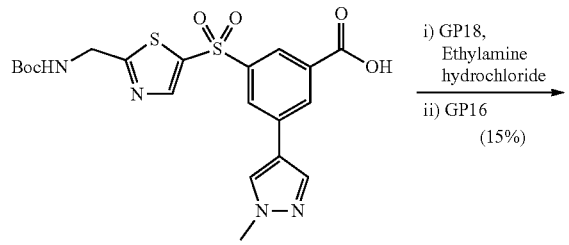

(See Example 153 for synthetic route)

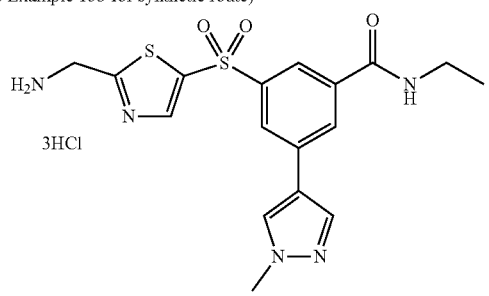

tert-Butyl ((5-((3-(ethylcarbamoyl)-5-(1-methyl-1H-pyrazol-4-yl)phenyl)sulfonyl)thiazol-2-yl)methyl)carbamate was synthesised according to general procedures GP18—from 3-((2-(((tert-butoxycarbonyl)amino)methyl)thiazol-5-yl)sulfonyl)-5-(1-methyl-1H-pyrazol-4-yl)benzoic acid (175 mg, 0.366 mmol), HATU (180 mg, 0.474 mmol), ethylamine hydrochloride (60 mg, 0.736 mmol), DIPEA (0.20 mL, 1.09 mmol) and DMF (3.0 mL); rt, 1 h. Chromatography (1.5% MeOH in DCM) afforded a white solid (40 mg, 22%). $^1$H NMR (400 MHz, DMSO-$d_6$) δ 8.78 (t, J=4.8 Hz, 1H), 8.51 (s, 1H), 8.40 (s, 1H), 8.32 (s, 1H), 8.25 (s, 1H), 8.19 (s, 1H), 8.06 (s, 1H), 7.84 (br, 1H), 4.40 (d, J=5.2 Hz, 2H), 3.88 (s, 3H), 3.36-3.30 (m, 2H), 1.37 (s, 9H), 1.15 (t, J=7.2 Hz, 3H). LCMS (ESI) m/z 450 (M-$^t$Bu+2H)$^+$.

Example 154 was synthesised according to general procedures GP16—from 2 M HCl in diethyl ether (5.0 mL), tert-butyl ((5-((3-(ethylcarbamoyl)-5-(1-methyl-1H-pyrazol-4-yl)phenyl)sulfonyl)thiazol-2-yl)methyl)carbamate (40 mg, 0.07 mmol) and DCM (1.0 mL); rt, 16 h. The precipitate was filtered and washed with Et$_2$O to afford a white solid (25 mg, 70%). $^1$H NMR (500 MHz, Methanol-$d_4$) δ 8.50 (s, 1H), 8.36-8.25 (m, 4H), 8.09 (s, 1H), 4.56 (s, 2H), 3.99 (s, 3H), 3.45 (q, J=7.2 Hz, 2H), 1.26 (t, J=7.2 Hz, 3H). $^{13}$C NMR (126 MHz, Methanol-$d_4$) δ 170.62, 167.28, 149.12, 143.95, 142.22, 138.23, 137.38, 136.14, 131.18, 130.23, 127.06, 125.06, 122.02, 41.35, 39.35, 36.13, 14.78. HRMS (ESI) for $C_{17}H_{20}N_5O_3S_2$ ([M+H]$^+$): Calculated 406.1007; Observed 406.1017.

Example 155: (4-((3-Ethyl-5-(1-methyl-1H-pyrazol-4-yl)phenyl)sulfonyl)thiazol-2-yl)methanamine trihydrochloride

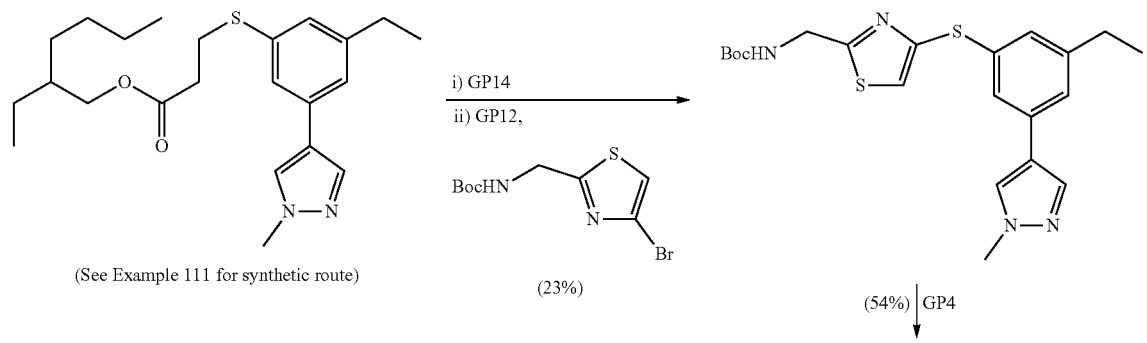

(See Example 111 for synthetic route)

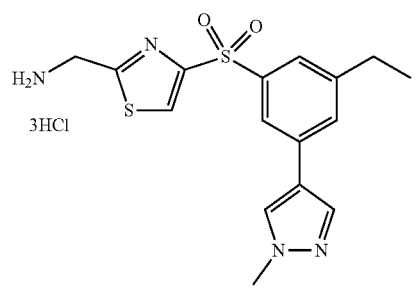

tert-Butyl ((4-((3-ethyl-5-(1-methyl-1H-pyrazol-4-yl)phenyl)thio)thiazol-2-yl)methyl) carbamate was synthesised according to general procedures GP14 and GP12—from i) 2-ethylhexyl 3-((3-ethyl-5-(1-methyl-1H-pyrazol-4-yl)phenyl)thio)propanoate (0.95 g, 2.36 mmol), KO$^t$Bu (1.0 M in THF; 4.71 mL, 4.71 mmol), THF (20 mL); −78° C., 1 h. ii) Pd$_2$(dba)$_3$ (78 mg, 5 mol %), Xantphos (99 mg, 10 mol %), tert-butyl ((4-bromothiazol-2-yl)methyl)carbamate (0.50 g, 1.71 mmol), DIPEA (0.74 mL, 4.26 mmol) and toluene (20 mL); 110° C., 16 h. Chromatography (45% EtOAc in hexanes) afforded a pale yellow oil (0.17 g, 23%). $^1$H NMR (400 MHz, DMSO-d$_6$) δ 8.17 (s, 1H), 7.82 (s, 1H), 7.76 (t, J=5.9 Hz, 1H), 7.57 (s, 1H), 7.33 (d, J=1.5 Hz, 2H), 6.97 (s, 1H), 4.37 (d, J=5.9 Hz, 2H), 3.84 (s, 3H), 2.58 (q, J=7.6 Hz, 2H), 1.40 (s, 9H), 1.19-1.15 (m, 3H). LCMS (ESI) m/z 431 (M+H)$^+$.

Example 155 was synthesised according to general procedures GP4—from i) m-CPBA (55%; 272 mg, 0.867 mmol), tert-butyl ((4-((3-ethyl-5-(1-methyl-1H-pyrazol-4-yl)phenyl)thio)thiazol-2-yl)methyl)carbamate (0.17 g, 0.395 mmol) and DCM (10 mL); rt, 3 h. Chromatography (25% EtOAc in cyclohexane), off-white solid (140 mg, 77%); ii) 2 M HCl in Et$_2$O (6 mL), tert-butyl ((4-((3-ethyl-5-(1-methyl-1H-pyrazol-4-yl)phenyl)sulfonyl)thiazol-2-yl)methyl)carbamate (140 mg, 0.303 mmol) and DCM (6 mL); rt, 3 h. White solid obtained (100 mg, 70%) without further purification. $^1$H NMR (500 MHz, Methanol-d$_4$) δ 8.70 (s, 1H), 8.36-7.98 (m, 3H), 7.83-7.72 (m, 2H), 4.53 (s, 2H), 4.08-3.92 (m, 3H), 2.78 (q, J=7.6 Hz, 2H), 1.30 (t, J=7.6 Hz, 3H). $^{13}$C NMR (126 MHz, Methanol-d$_4$) δ 166.38, 155.19, 148.39, 141.75, 136.26, 134.47, 131.72, 131.62, 130.54, 126.83, 123.52, 123.14, 40.85, 39.11, 29.58, 15.76. HRMS (ESI) for C$_{16}$H$_{19}$N$_4$O$_2$S$_2$ ([M+H]$^+$): Calculated 363.0949; Observed 363.0956.

Example 156: (R)-(3-((2-(Aminomethyl)thiazol-5-yl)sulfonyl)-5-(1-methyl-1H-pyrazol-4-yl)phenyl)(3-hydroxypyrrolidin-1-yl)methanone trihydrochloride

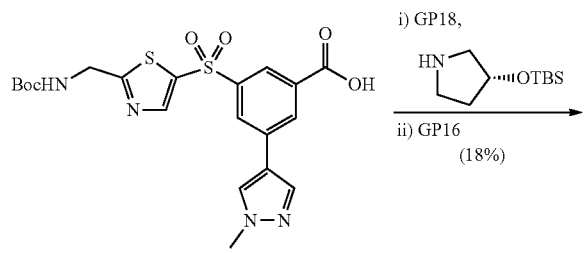

(See Example 153 for synthetic route)

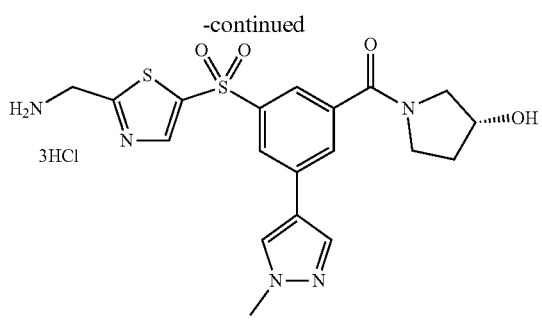

tert-Butyl (R)-((5-((3-(3-((tert-butyldimethylsilyl)oxy)pyrrolidine-1-carbonyl)-5-(1-methyl-1H-pyrazol-4-yl)phenyl)sulfonyl)thiazol-2-yl)methyl)carbamate was synthesised according to general procedures GP18—from 3-((2-(((tert-butoxycarbonyl)amino)methyl)thiazol-5-yl)sulfonyl)-5-(1-methyl-1H-pyrazol-4-yl)benzoic acid (200 mg, 0.418 mmol), HATU (200 mg, 0.526 mmol), (R)-3-((tert-butyldimethylsilyl)oxy)pyrrolidine (100 mg, 0.498 mmol), DIPEA (0.21 mL, 1.25 mmol) and DMF (4.0 mL); rt, 1 h. Chromatography (1.5% MeOH in DCM) afforded a light brown oil (70 mg, 25%). $^1$H NMR (400 MHz, DMSO-d$_6$) δ 8.50 (d, J=3.6 Hz, 1H), 8.44 (s, 1H), 8.20 (s, 1H), 8.08 (s, 1H), 8.01 (s, 1H), 7.85 (br, 1H), 7.79 (d, J=8.8 Hz, 2H), 4.50-4.40 (m, 3H), 3.87 (s, 3H), 3.61-3.44 (m, 4H), 2.04-2.01 (m, 2H), 1.38 (s, 9H), 0.89-0.79 (m, 8H), 0.10-0.09 (m, 6H). LCMS (ESI −ve) m/z 660 (M−H)$^-$.

Example 156 was synthesised according to general procedures GP16—from 2 M HCl in diethyl ether (5.0 mL), tert-butyl (R)-((5-((3-(3-((tert-butyldimethylsilyl)oxy)pyrrolidine-1-carbonyl)-5-(1-methyl-1H-pyrazol-4-yl)phenyl)sulfonyl)thiazol-2-yl)methyl)carbamate (70 mg, 0.10 mmol) and DCM (1.0 mL); rt, 16 h. The precipitate was filtered and washed with Et$_2$O to afford a white solid (40 mg, 70%). $^1$H NMR (500 MHz, Methanol-d$_4$) for a mixture of rotamers δ 8.50 (s, 1H), 8.34 (s, 1H), 8.28 (s, 1H), 8.15 (s, 1H), 8.09-8.03 (m, 1H), 8.03-7.97 (m, 1H), 4.58 (s, 2H), 4.52 (br, 0.5H), 4.41 (br, 0.5H), 4.00 (s, 3H), 3.81-3.59 (m, 2.5H), 3.52-3.44 (m, 1H), 3.33-3.27 (m, 0.5H), 2.22-1.84 (m, 2H). $^{13}$C NMR (126 MHz, Methanol-d$_4$) for a mixture of rotamers δ 170.69, 169.51, 149.14, 143.88, 142.11, 140.39, 140.35, 137.16, 136.03, 131.38, 130.21, 130.15, 126.00, 124.85, 124.76, 121.92, 71.49, 70.22, 66.88, 58.33, 55.75, 45.67, 41.23, 39.23, 35.33, 33.44. HRMS (ESI) for C$_{19}$H$_{22}$N$_5$O$_4$S$_2$ ([M+H]$^+$): Calculated 448.1113; Observed 448.1112.

Example 157: 5-((2-(Aminomethyl)thiazol-4-yl)sulfonyl)-[1,1'-biphenyl]-3-carboxylic acid dihydrochloride

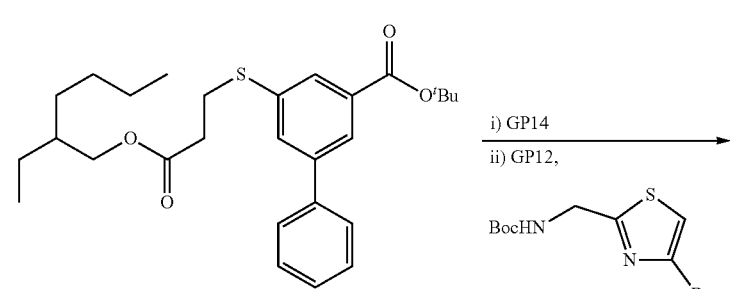

(See Example 126 for synthetic route)

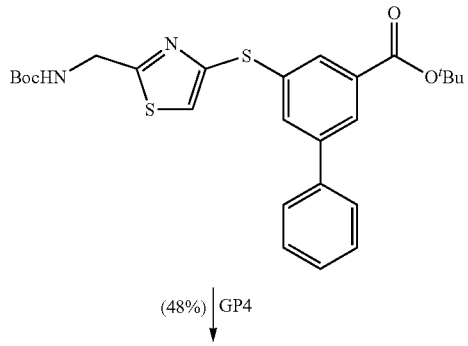

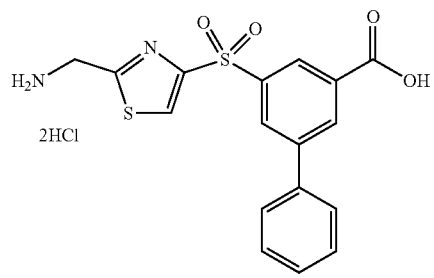

2HCl tert-Butyl 5-((2-(((tert-butoxycarbonyl)amino)methyl)thiazol-4-yl)thio)-[1,1'-biphenyl]-3-carboxylate was synthesised according to general procedures GP14 and GP12—from i) tert-butyl 5-((3-((2-ethylhexyl)oxy)-3-oxopropyl)thio)-[1,1'-biphenyl]-3-carboxylate (1.0 g, 2.12 mmol), KO$^t$Bu (1.0 M in THF; 4.25 mL, 4.25 mmol), THF (10 mL); −78° C., 1 h. ii) Pd$_2$(dba)$_3$ (78 mg, 5 mol %), Xantphos (99 mg, 10 mol %), tert-butyl ((4-bromothiazol-2-yl)methyl)carbamate (0.50 g, 1.71 mmol), DIPEA (0.59 mL, 3.41 mmol) and toluene (20 mL); 110° C., 16 h. Chromatography (8-10% EtOAc in hexanes) afforded a pale yellow oil (0.17 g, 20%). $^1$H NMR (400 MHz, DMSO-d$_6$) δ 7.97 (s, 1H), 7.96 (s, 1H), 7.87-7.78 (m, 2H), 7.70 (s, 1H), 7.65 (d, J=7.3 Hz, 2H), 7.49 (t, J=7.3 Hz, 2H), 7.44-7.40 (m, 1H), 4.39 (d, J=5.9 Hz, 2H), 1.54 (s, 9H), 1.40 (s, 9H). LCMS (ESI) m/z 499 (M+H)$^+$.

Example 157 was synthesised according to general procedures GP4—from i) m-CPBA (55%; 234 mg, 0.746 mmol), tert-butyl 5-((2-(((tert-butoxycarbonyl)amino)methyl)thiazol-4-yl)thio)-[1,1'-biphenyl]-3-carboxylate (0.17 g, 0.341 mmol) and DCM (5 mL); rt, 3 h. Chromatography (25% EtOAc in cyclohexane), off-white solid (120 mg, 66%); ii) 2 M HCl in Et$_2$O (10 mL), tert-butyl 5-((2-(((tert-butoxycarbonyl)amino)methyl)thiazol-4-yl)sulfonyl)-[1,1'-biphenyl]-3-carboxylate (120 mg, 0.226 mmol) and DCM (6.0 mL); rt, 3 h. White solid obtained (74 mg, 73%) without further purification. $^1$H NMR (500 MHz, Methanol-d$_4$) δ 8.76 (s, 1H), 8.58 (s, 1H), 8.51 (s, 1H), 8.43 (s, 1H), 7.71-7.64 (m, 2H), 7.54-7.42 (m, 3H), 4.53 (s, 2H). $^{13}$C NMR (126 MHz, Methanol-d$_4$) δ 167.50, 166.67, 154.61, 144.54, 142.28, 139.26, 134.34, 134.11, 131.24, 131.08, 130.39, 129.95, 128.98, 128.16, 40.87. HRMS (ESI) for C$_{17}$H$_{15}$N$_2$O$_4$S$_2$ ([M+H]$^+$): Calculated 375.0473; Observed 375.0480.

Example 158: 3-((2-(Aminomethyl)thiazol-5-yl)sulfonyl)-5-(6-methylpyridin-3-yl)benzoic acid trihydrochloride

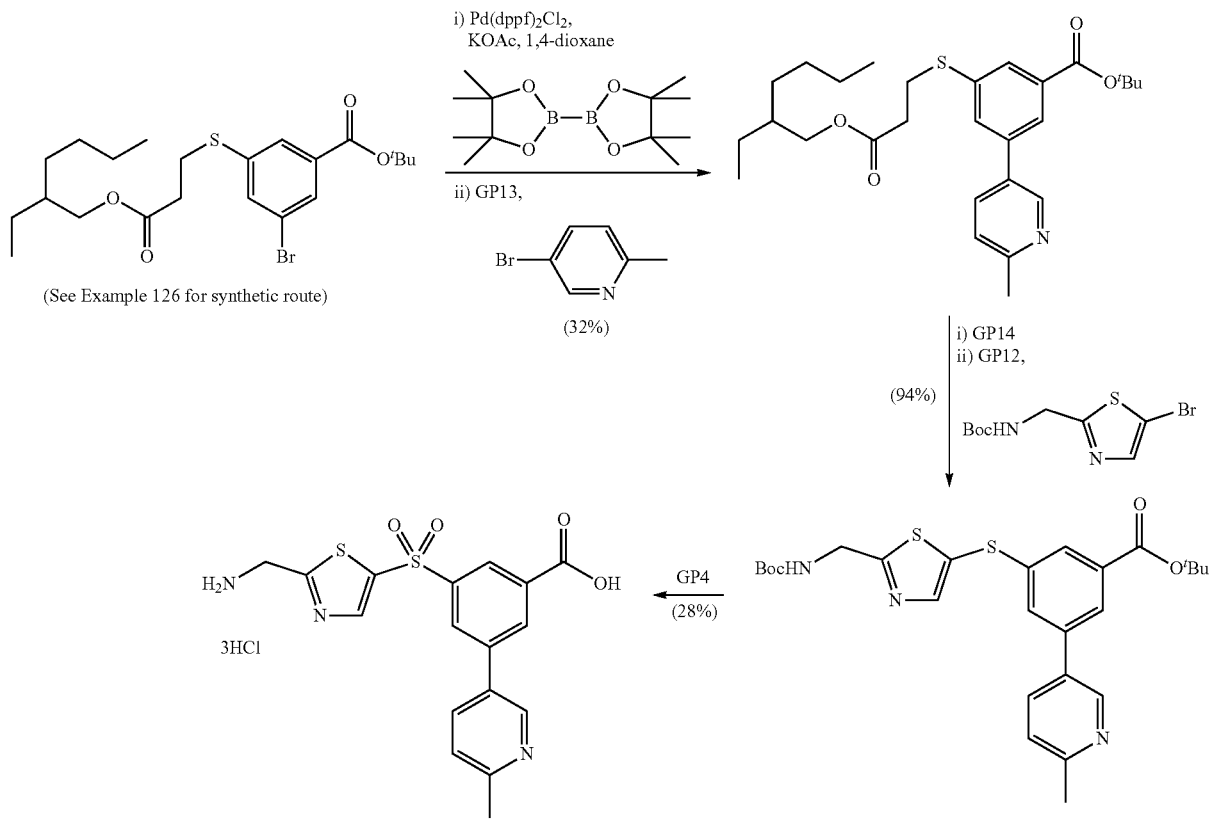

A mixture of tert-butyl 3-bromo-5-((3-((2-ethylhexyl)oxy)-3-oxopropyl)thio)benzoate (4.2 g, 8.89 mmol), bis(pinacolato)diboron (2.8 g, 10.7 mmol), Pd(dppf)₂Cl₂ (0.73 g, 10 mol %), KOAc (1.8 g, 17.8 mmol) and 1,4-dioxane (45 mL) was degassed with N₂ for 10 min, then heated at 100° C. with stirring for 15 h. After cooling to room temperature, the reaction mixture was diluted with ethyl acetate (200 mL) and washed with water (50 mL) and brine (30 mL), dried over anhydrous sodium sulfate, filtered and concentrated under reduced pressure. Chromatography (9% EtOAc in hexanes) afforded tert-butyl 3-((3-((2-ethylhexyl)oxy)-3-oxopropyl)thio)-5-(4,4,5,5-tetramethyl-1,3,2-dioxaborolan-2-yl)benzoate as a colourless semi-solid (3.8 g, 79%). ¹H NMR (400 MHz, DMSO-d₆) δ 7.98 (s, 1H), 7.92 (s, 1H), 7.76 (s, 1H), 3.93 (d, J=5.8 Hz, 2H), 3.22 (t, J=6.6 Hz, 2H), 2.66-2.61 (m, 2H), 1.55 (s, 9H), 1.31-1.67 (m, 21H), 0.85-0.81 (m, 6H), LCMS (ESI) m/z 521 (M+H)⁺.

tert-Butyl 3-((3-((2-ethylhexyl)oxy)-3-oxopropyl)thio)-5-(6-methylpyridin-3-yl)benzoate was synthesised according to general procedures GP13—from tert-butyl 3-((3-((2-ethylhexyl)oxy)-3-oxopropyl)thio)-5-(4,4,5,5-tetramethyl-1,3,2-dioxaborolan-2-yl)benzoate (2.1 g, 4.04 mmol), 5-bromo-2-methylpyridine (0.70 g, 4.04 mmol), Pd(PPh₃)₄ (0.47 g, 10 mol %), Cs₂CO₃ (2.6 g, 8.1 mmol), 1,4-dioxane (20 mL), water (4 mL); 100° C., 16 h. Chromatographic purification (34% EtOAc in hexane) afforded a white semi-solid (0.9 g, 47%). ¹H NMR (400 MHz, DMSO-d₆) δ 8.78 (d, J=2.0 Hz, 1H), 8.02 (dd, J=8.0 Hz, 7.6 Hz, 1H), 7.93 (s, 1H), 7.86 (s, 1H), 7.76 (s, 1H), 7.48-7.41 (m, 1H), 3.93 (d, J=6.0 Hz, 2H), 3.34-3.25 (m, 2H), 2.67 (t, J=6.4 Hz, 2H), 2.50 (s, 3H), 1.56 (s, 9H), 1.3-1.27 (m, 9H), 0.83-0.79 (m, 6H). LCMS (ESI) m/z 486 (M+H)⁺.

tert-Butyl 3-((2-(((tert-butoxycarbonyl)amino)methyl)thiazol-5-yl)thio)-5-(6-methylpyridin-3-yl)benzoate was synthesised according to general procedures GP14 and GP12—from i) tert-butyl 3-((3-((2-ethylhexyl)oxy)-3-oxopropyl)thio)-5-(6-methylpyridin-3-yl)benzoate (0.5 g, 1.03 mmol), KOᵗBu (1.0 M in THF; 2.1 mL, 2.1 mmol), THF (10 mL); −78° C., 1 h. ii) Pd₂(dba)₃ (47 mg, 5 mol %), Xantphos (60 mg, 10 mol %), tert-butyl ((4-bromothiazol-2-yl)methyl)carbamate (301 mg, 1.02 mmol), DIPEA (0.40 mL, 2.06 mmol) and toluene (15 mL); 110° C., 16 h. Chromatography (42% EtOAc in hexanes) afforded a brown semi-solid (0.50 g, 94%). ¹H NMR (400 MHz, DMSO-d₆) δ 8.72 (d, J=2.0 Hz, 1H), 8.04 (s, 1H), 7.98-7.92 (m, 2H), 7.82-7.80 (m, 2H), 7.78-7.66 (m, 1H), 7.36 (d, J=7.8 Hz, 1H), 4.4 (d, J=6.0 Hz, 2H), 2.52 (s, 3H), 1.53 (s, 9H), 1.37 (s, 9H). LCMS (ESI) m/z 514 (M+H)⁺.

Example 158 was synthesised according to general procedures GP4—from i) m-CPBA (55%; 687 mg, 2.19 mmol), tert-butyl 3-((2-(((tert-butoxycarbonyl)amino)methyl)thiazol-5-yl)thio)-5-(6-methylpyridin-3-yl)benzoate (0.45 g, 0.870 mmol) and DCM (20 mL); rt, 16 h. Chromatography (55% EtOAc in cyclohexane), yellow semi-solid (180 mg, 38%); ii) 2 M HCl in Et₂O (4.0 mL), tert-butyl 3-((2-(((tert-butoxycarbonyl)amino)methyl)thiazol-5-yl)sulfonyl)-5-(6-methylpyridin-3-yl)benzoate (70 mg, 0.128 mmol) and DCM (2.0 mL); rt, 16 h. The precipitate was filtered and washed with Et₂O to afford a white solid (45 mg, 91%) without further purification. ¹H NMR (500 MHz, Methanol-d₄) δ 9.20 (s, 1H), 8.87 (s, 1H), 8.78-8.64 (m, 3H), 8.56 (s, 1H), 8.08 (s, 1H), 4.60 (s, 2H), 2.90 (s, 3H). ¹³C NMR (126 MHz, Methanol-d₄) δ 171.05, 166.63, 155.37, 149.61, 145.95, 144.66, 141.62, 141.20, 137.91, 136.31, 135.42, 134.95, 131.25, 130.15, 129.60, 41.43, 19.78. HRMS (ESI) for C₁₇H₁₆N₃O₄S₂ ([M+H]⁴): Calculated 390.0582; Observed 390.0585.

Example 159: 3-((2-(Aminomethyl)thiazol-5-yl)sulfonyl)-5-(pyrrolidin-1-yl)benzoic acid trihydrochloride

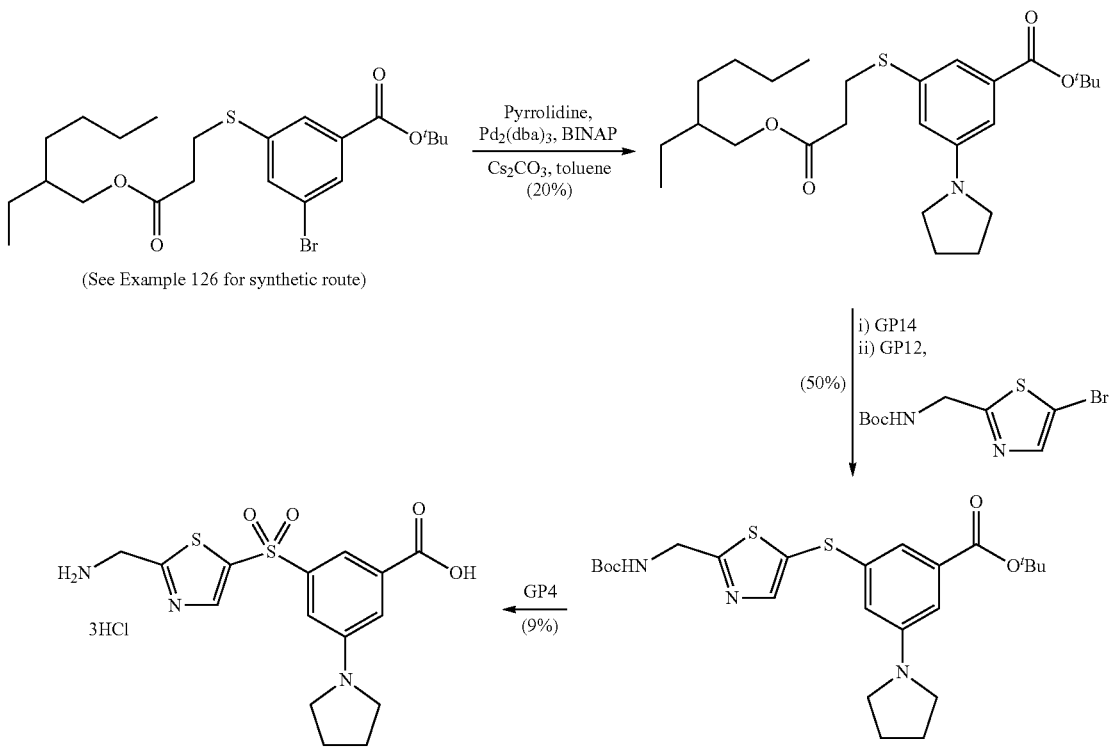

(See Example 126 for synthetic route)

A mixture of tert-butyl 3-bromo-5-((3-((2-ethylhexyl)oxy)-3-oxopropyl)thio)benzoate (4.0 g, 8.47 mmol), pyrrolidine (0.72 g, 10.2 mmol), BINAP (0.27 g, 0.42 mmol), Pd$_2$(dba)$_3$ (0.78 g, 10 mol %), Cs$_2$CO$_3$ (5.5 g, 16.9 mmol) and toluene (40 mL) was degassed with N$_2$ for 10 min, then heated at 100° C. with stirring for 16 h. After cooling to room temperature, the reaction mixture was diluted with ethyl acetate (200 mL) and washed with water (50 mL) and brine (50 mL), dried over anhydrous sodium sulfate, filtered and concentrated under reduced pressure. Chromatography (18% EtOAc in hexanes) afforded tert-butyl 3-((3-((2-ethylhexyl)oxy)-3-oxopropyl)thio)-5-(pyrrolidin-1-yl)benzoate as a yellow semi-solid (0.8 g, 20%). $^1$H NMR (400 MHz, DMSO-d$_6$) δ 7.02 (s, 1H), 6.87 (s, 1H), 6.64 (s, 1H), 3.95 (d, J=6.0 Hz, 2H), 3.3-3.23 (m, 4H), 3.17 (t, J=6.8 Hz, 2H), 2.62 (t, J=6.8 Hz, 2H), 1.97-1.94 (m, 4H), 1.57-1.46 (m, 9H), 1.23 (s, 9H), 0.85-0.81 (m, 6H). LCMS (ESI) m/z 464 (M+H)$^+$.

azol-5-yl)thio)-5-(pyrrolidin-1-yl)benzoate (0.40 g, 0.813 mmol) and DCM (15 mL); rt, 16 h. Chromatography (31% EtOAc in cyclohexane) then preparative TLC (20% EtOAc in cyclohexane), yellow semi-solid (53 mg, 12%); ii) 2 M HCl in diethyl ether (2.0 mL), tert-butyl 3-((2-(((tert-butoxycarbonyl)amino)methyl)thiazol-5-yl)sulfonyl)-5-(pyrrolidin-1-yl)benzoate (50 mg, 0.095 mmol) and DCM (1.0 mL); rt, 8 h. The precipitate was filtered and washed with Et$_2$O to afford a white solid (30 mg, 71%). $^1$H NMR (400 MHz, DMSO-d$_6$) δ 13.47 (br, 1H), 8.61 (br, 3H), 7.60 (s, 1H), 7.30 (s, 1H), 7.18 (s, 1H), 4.49 (s, 2H), 3.38-3.29 (m, 4H), 2.06-1.94 (m, 4H). LCMS (ESI) m/z 368 (M+H)$^+$.

Example 160: 5-((2-(Aminomethyl)oxazol-5-yl)sulfonyl)-[1,1'-biphenyl]-3-carboxylic acid dihydrochloride

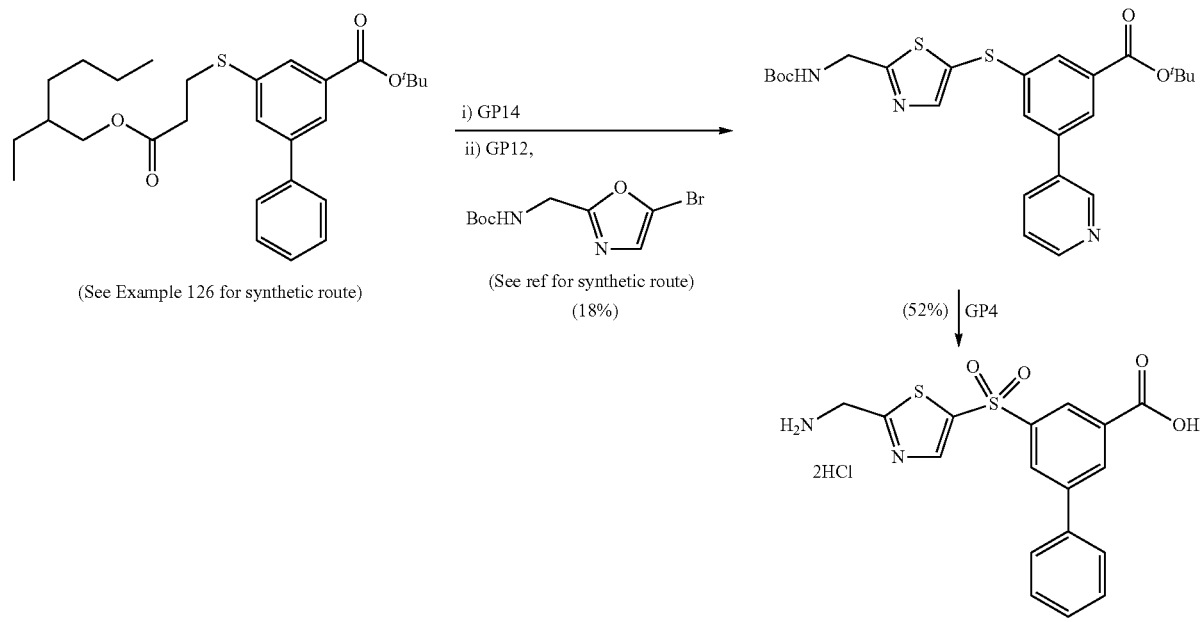

(See Example 126 for synthetic route)

(See ref for synthetic route)
(18%)

(52%) GP4

Ref - (Curtis, M. et al, 2013).

tert-Butyl 3-((2-(((tert-butoxycarbonyl)amino)methyl)thiazol-5-yl)thio)-5-(pyrrolidin-1-yl) benzoate was synthesised according to general procedures GP14 and GP12—from i) tert-butyl 3-((3-((2-ethylhexyl)oxy)-3-oxopropyl)thio)-5-(pyrrolidin-1-yl)benzoate (0.80 g, 1.73 mmol), KO$^t$Bu (1.0 M in THF; 3.5 mL, 3.5 mmol), THF (15 mL); −78° C., 1 h. ii) Pd$_2$(dba)$_3$ (80 mg, 5 mol %), Xantphos (100 mg, 10 mol %), tert-butyl ((5-bromothiazol-2-yl)methyl)carbamate (0.5 g, 1.73 mmol), DIPEA (0.6 mL, 3.4 mmol) and toluene (15 mL); 110° C., 16 h. Chromatography (26% EtOAc in hexanes) afforded a brown semi-solid (0.42 g, 50%). $^1$H NMR (400 MHz, DMSO-d$_6$) δ 7.94 (s, 1H), 7.78 (t, J=6 Hz, 1H), 6.92 (s, 1H), 6.88 (s, 1H), 6.56 (s, 1H), 4.37 (d, J=5.6 Hz, 2H), 3.19 (t, J=6.4 Hz, 4H), 1.93 (t, J=6.4 Hz, 4H), 1.49 (s, 9H), 1.38 (s, 9H). LCMS (ESI) m/z 492 (M+H)$^+$.

Example 159 was synthesised according to general procedures GP4—from i) m-CPBA (55%; 1.0 g, 3.24 mmol), tert-butyl 3-((2-(((tert-butoxycarbonyl)amino)methyl)thitert-Butyl 5-((2-(((tert-butoxycarbonyl)amino)methyl)oxazol-5-yl)thio)-[1,1'-biphenyl]-3-carboxylate was synthesised according to general procedures GP14 and GP12—from i) tert-butyl 5-((3-((2-ethylhexyl)oxy)-3-oxopropyl)thio)-[1,1'-biphenyl]-3-carboxylate (0.30 g, 0.638 mmol), KO$^t$Bu (1.0 M in THF; 1.27 mL, 1.27 mmol), THE (5 mL); −78° C., 1 h. ii) Pd$_2$(dba)$_3$ (12 mg, 5 mol %), Xantphos (15 mg, 10 mol %), tert-butyl ((5-bromooxazol-2-yl)methyl)carbamate (70 mg, 0.252 mmol), DIPEA (0.11 mL, 0.637 mmol) and toluene (10 mL); 110° C., 16 h. Chromatography (40% EtOAc in hexanes) afforded an amber-coloured oil (22 mg, 18%). $^1$H NMR (400 MHz, DMSO-d$_6$) δ 7.98 (s, 1H), 7.72 (br, 3H), 7.65 (d, J=6.8 Hz, 2H), 7.51-7.48 (m, 4H), 4.26 (d, J=6.0 Hz, 2H), 1.55 (s, 9H), 1.31 (s, 9H). LCMS (ESI) m/z 483 (M+H)$^+$.

Example 160 was synthesised according to general procedures GP4—from i) m-CPBA (55%; 31 mg, 0.0988 mmol), tert-butyl 5-((2-(((tert-butoxycarbonyl)amino)methyl)oxazol-5-yl)thio)-[1,1'-biphenyl]-3-carboxylate (22 mg, 0.0456 mmol) and DCM (3 mL); rt, 3 h. Chromatography (25% EtOAc in cyclohexane) afforded an off-white solid (15 mg, 62%); ii) 2 M HCl in Et$_2$O (3 mL), tert-butyl 5-((2-(((tert-butoxycarbonyl)amino)methyl)oxazol-5-yl)sulfonyl)-[1,1'-biphenyl]-3-carboxylate (15 mg, 0.0291 mmol) and DCM (0.5 mL); rt, 16 h. White solid obtained (6 mg, 52%) without further purification. $^1$H NMR (500 MHz, Methanol-d$_4$) δ 8.62-8.54 (m, 2H), 8.45 (m, 1H), 8.10 (s, 1H), 7.72 (d, J=7.0 Hz, 2H), 7.55 (t, J=7.5 Hz, 2H), 7.49 (t, J=7.3 Hz, 1H), 4.40 (s, 2H). $^{13}$C NMR (126 MHz, Methanol-d$_4$) δ 167.25, 162.97, 150.80, 145.06, 141.75, 139.15, 135.10, 134.78, 130.95, 130.48, 130.12, 128.69, 128.23, 37.20. HRMS (ESI) for C$_{17}$H$_{15}$N$_2$O$_5$S ([M+H]$^+$): Calculated 359.0702; Observed 359.0701.

Example 161: (3-Fluoro-5-((5-(methylsulfonyl)-[1,1'-biphenyl]-3-yl)sulfonyl)thiophen-2-yl)methanamine Synthesis of tert-butyl ((5-bromo-3-fluorothiophen-2-yl)methyl)carbamate (intermediate 1)

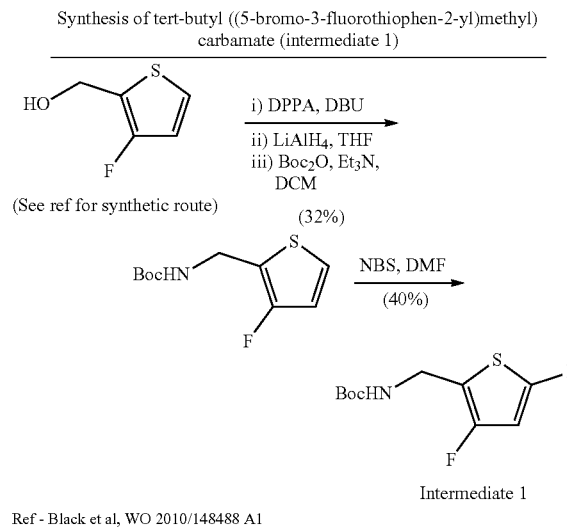

Ref - Black et al, WO 2010/148488 A1

DBU (1.34 g, 8.82 mmol) was added to a mixture (3-fluorothiophen-2-yl)methanol (0.97 g, 7.34 mmol) and diphenyl phosphoryl azide (DPPA; 2.42 g, 8.80 mmol) in toluene (10 mL) at 0° C. and the reaction was stirred for 1 h at rt. The mixture was diluted with EtOAc (200 mL). The organic layer was washed with water (2×100 mL), dried over Na$_2$SO$_4$, filtered and the solvent was removed under reduced pressure. The crude was purified by chromatography (1% EtOAc in hexanes) to afford 2-(azidomethyl)-3-fluorothiophene (1.2 g, quant.) as a colourless oil. $^1$H NMR (400 MHz, Chloroform-d) δ 7.20 (dd, J=5.3, 3.9 Hz, 1H), 6.81 (d, J=5.4 Hz, 1H), 4.44 (s, 2H). LCMS (ESI) m/z did not ionise. A solution of 2-(azidomethyl)-3-fluorothiophene (1.2 g, ~7.34) in THF (11 mL) was added dropwise to a stirred suspension of LiAlH$_4$ (0.58 g, 15.3 mmol) in THF (4.0 mL) at 0° C. The mixture was stirred for at rt for 1 h, and the reaction was quenched with EtOAc (3 mL), aq. NaOH (10%, 3 mL), and water (2 mL). The precipitate was filtered off and washed with EtOAc (100 mL). The filtrate was washed with water (80 mL), dried over Na$_2$SO$_4$, filtered and the solvent was removed under reduced pressure to afford (3-fluorothiophen-2-yl)methanamine (1.0 g) as a colourless oil. DCM was added (10 mL) followed by and Et$_3$N (2.64 mL, 19.1 mmol) and then Boc$_2$O (2.49 g, 11.4 mmol) and the mixture was stirred for at rt for 16 h before it was diluted with DCM (100 mL). The organic phase was washed with water (100 mL), brine (2×100 mL) and the solvent was removed under reduced pressure. The crude was purified by chromatography (10% EtOAc in hexanes) to afford tert-butyl ((3-fluorothiophen-2-yl)methyl)carbamate as a colourless oil (0.56 g, 32%). $^1$H NMR (400 MHz, DMSO-d$_6$) δ 7.45-7.37 (m, 2H), 6.88 (d, J=5.4 Hz, 1H), 4.17 (d, J=5.8 Hz, 2H), 1.38 (s, 9H). N-Bromosuccinimide (NBS; 474 mg, 2.67 mmol) was added to a solution of tert-butyl ((3-fluorothiophen-2-yl)methyl)carbamate (0.56 g, 2.42 mmol) in DMF (7.0 mL) at 0° C. and the mixture was stirred at rt for 3 h before it was diluted with Et$_2$O (80 mL). The organic phase was washed with cold water (3×30 mL), dried over Na$_2$SO$_4$, filtered and the solvent was removed under reduced pressure. The crude was purified by chromatography (8% EtOAc in hexanes) to afford tert-butyl ((5-bromo-3-fluorothiophen-2-yl)methyl)carbamate as a pale yellow solid (300 mg, 40%). $^1$H NMR (400 MHz, DMSO-d$_6$) δ 7.51 (br, 1H), 7.18 (s, 1H), 4.11 (d, J=5.9 Hz, 2H), 1.39 (s, 9H).

Synthesis of compound Example 161

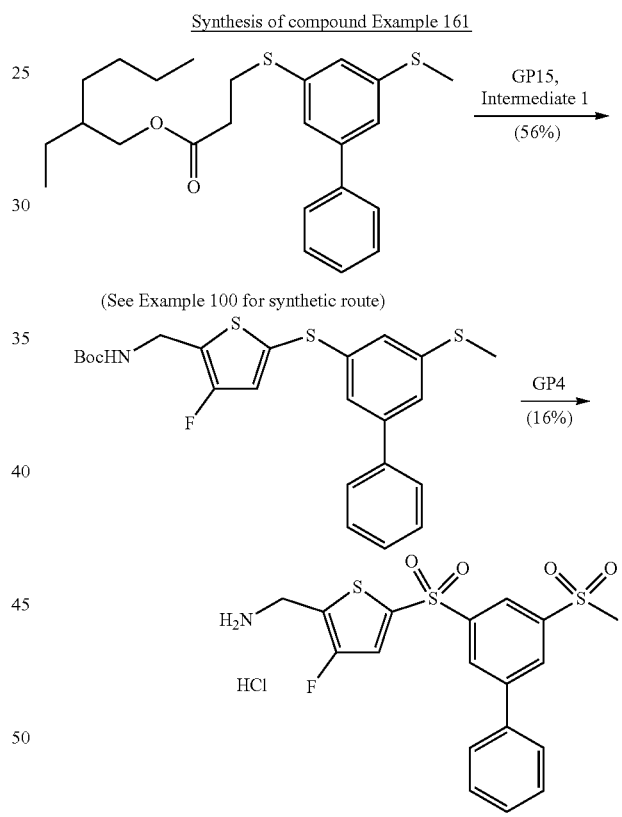

(See Example 100 for synthetic route)

tert-Butyl ((3-fluoro-5-((5-(methylthio)-[1,1'-biphenyl]-3-yl)thio)thiophen-2-yl)methyl)carbamate was synthesised according to general procedures GP15—from 2-ethylhexyl 3-((5-(methylthio)-[1,1'-biphenyl]-3-yl)thio)propanoate (0.419 g, 1.01 mmol), NaO$^t$Bu (223 mg, 2.32 mmol), toluene/BuOH (4:1, 10 mL); rt, 4 h, then tert-butyl ((5-bromo-3-fluorothiophen-2-yl)methyl)carbamate intermediate 1 (240 mg, 0.769 mmol), Pd$_2$(dba)$_3$ (106 mg, 15 mol %) and Xantphos (134 mg, 30 mol %); 110° C., 16 h. Chromatographic purification (15% EtOAc in hexane) afforded a yellow oil as (200 mg, 56%). $^1$H NMR (400 MHz, Chloroform-d) δ 7.52-7.51 (m, 2H), 7.50-7.44 (m, 2H), 7.42-7.38 (m, 1H), 7.31 (t, J=1.4 Hz, 1H), 7.27 (t, J=1.8 Hz, 1H), 7.40

(t, J=4.2 Hz, 1H), 6.98 (s, 1H), 4.89 (br, 1H), 4.38 (d, J=4.8 Hz, 2H), 2.49 (s, 3H), 1.47 (s, 9H). LCMS (ESI) m/z 345 (M-NHBoc)+.

Example 161 was synthesised according to general procedures GP4—from i) m-CPBA (55%; 544 mg, 1.74 mmol), tert-butyl ((3-fluoro-5-((5-(methylthio)-[1,1'-biphenyl]-3-yl)thio)thiophen-2-yl)methyl)carbamate (200 mg, 0.434 mmol) and DCM (10 mL); rt, 3 h. Chromatography (35% in EtOAc in hexanes), off-white solid (53 mg, 23%); ii) 2 M HCl in dioxane (4.0 mL), tert-butyl ((3-fluoro-5-((5-(methylsulfonyl)-[1,1'-biphenyl]-3-yl)sulfonyl)thiophen-2-yl) methyl)carbamate (43 mg, 0.0819 mmol) and DCM (2.0 mL); rt, 5 h. The precipitate was filtered and washed with Et$_2$O to afford a white solid (25 mg, 66%). $^1$H NMR (500 MHz, DMSO-d$_6$) δ 8.65 (br, 3H), 8.59-8.49 (m, 2H), 8.39 (s, 1H), 8.27 (s, 1H), 7.99-7.81 (m, 2H), 7.68-7.45 (m, 3H), 4.20 (s, 2H), 3.46 (s, 3H). $^{13}$C NMR (126 MHz, DMSO-d$_6$) δ 155.78 (d, J=265.9 Hz), 144.21, 143.82, 142.92, 139.39 (d, J=7.6 Hz), 137.00, 131.30, 130.08, 129.88, 129.81, 128.00, 124.96 (d, J=17.6 Hz), 124.57 (d, J=25 Hz), 124.28, 43.51, 32.77. $^{19}$F NMR (471 MHz, DMSO-d$_6$) δ −122.29. HRMS (ESI) for C$_{18}$H$_{14}$FO$_4$S$_3$ ([M-NH$_2$]+): Calculated 409.0038; Observed 409.0026.

Example 162: 5-((2-(Aminomethyl)thiazol-4-yl)sulfonyl)-N,N-dimethyl-[1,1'-biphenyl]-3-carboxamide hydrochloride

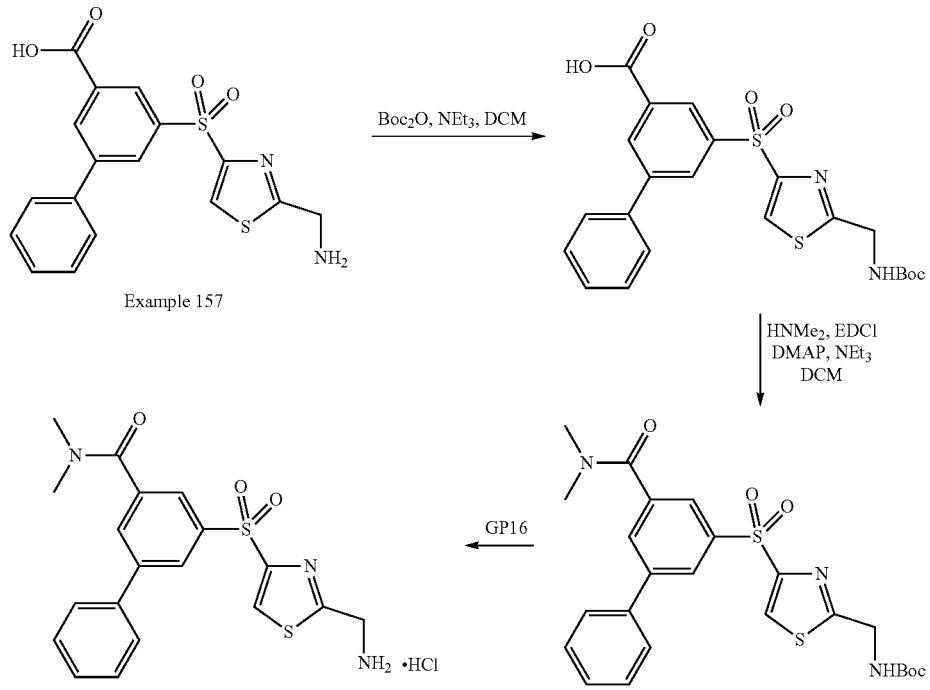 [SMILES: NCc1nc(S(=O)(=O)c2cc(C(=O)O)cc(-c3ccccc3)c2)cs1 ; CC(C)(C)OC(=O)NCc1nc(S(=O)(=O)c2cc(C(=O)O)cc(-c3ccccc3)c2)cs1 ; CN(C)C(=O)c1cc(-c2ccccc2)cc(S(=O)(=O)c2csc(CN)n2)c1 ; Cl ; CN(C)C(=O)c1cc(-c2ccccc2)cc(S(=O)(=O)c2csc(CNC(=O)OC(C)(C)C)n2)c1]

Example 157

Triethylamine (0.17 mL, 1.25 mmol) was added to a suspension of Example 157 (123 mg, 0.25 mmol) in dichloromethane (5 mL), with stirring at room temperature for 5 minutes, before adding Boc$_2$O (60 mg, 0.28 mmol), with continued stirring for 18 hours. The reaction mixture was then diluted with ethyl acetate (25 mL) and washed with 0.5 M aq. HCl (20 mL), water (20 mL) and brine (20 mL), dried over anhydrous magnesium sulfate, filtered and concentrated to give the crude product, which was washed with 1:1 diethyl ether:hexanes to give 5-((2-(((tert-butoxycarbonyl)amino)methyl)thiazol-4-yl)sulfonyl)-[1,1'-biphenyl]-3-carboxylic acid (95 mg, 79% yield) as a white solid. $^1$H NMR (DMSO-d$_6$, 500 MHz) δ 13.77 (s, 1H), 8.75 (s, 1H), 8.44 (s, 1H), 8.42 (s, 1H), 8.35 (t, 1H, J=1.7 Hz), 7.82 (t, 1H, J=6.0 Hz), 7.75 (d, 2H, J=7.3 Hz), 7.54 (t, 2H, J=7.8 Hz), 7.48 (t, 1H, J=7.3 Hz), 4.36 (d, 2H, J=6.0 Hz), 1.36 (s, 9H) ppm; LCMS (ESI) m/z 497.0807 found (M+Na)+, C$_{22}$H$_{22}$N$_2$S$_2$O$_6$Na. Triethylamine (0.13 mL, 0.95 mmol) and DMAP (23 mg, 0.19 mmol) were added to a solution of 5-((2-(((tert-butoxycarbonyl)amino)methyl)thiazol-4-yl) sulfonyl)-[1,1'-biphenyl]-3-carboxylic acid (90 mg, 0.19 mmol) and dimethylamine (33% in EtOH (~5.6 M), 0.05 mL, 0.29 mmol) in anhydrous dichloromethane (4 mL), with stirring at 0° C. under nitrogen for 10 mins. EDCI-HCl (40 mg, 0.20 mmol) was then added in one portion and the reaction mixture was allowed to stir for 24 hours warming to room temperature. The reaction mixture was then diluted with ethyl acetate (20 mL) and washed with saturated aq. NaHCO$_3$ (20 mL) and brine (20 mL), dried over anhydrous magnesium sulfate, filtered and concentrated to give the crude product. Chromatographic purification (40→100% EtOAc in hexane then 0→20% methanol in EtOAc) afforded a yellow oil (22 mg, 23%). $^1$H NMR (CDCl$_3$, 500 MHz) δ 8.31 (t, 1H, J=1.7 Hz), 8.19 (s, 1H), 8.02 (t, 1H, J=1.6 Hz), 7.89 (t, 1H, J=1.6 Hz), 7.61 (d, 2H, J=7.0 Hz), 7.48 (t, 2H, J=7.4 Hz), 7.42 (t, 1H, J=7.3 Hz), 5.23 (br s, 1H), 4.55 (d, 2H, J=6.1 Hz), 3.15 (s, 3H), 3.02 (s, 3H), 1.43 (s, 9H) ppm; LCMS (ESI) m/z 402.0932 found (M-Boc+H)+, C$_{24}$H$_{28}$N$_3$O$_5$S$_2$.

Example 162 was synthesised according to general procedures GP16—from tert-butyl ((4-((5-(dimethylcarbamoyl)-[1,1'-biphenyl]-3-yl)sulfonyl)thiazol-2-yl)methyl) carbamate (20 mg, 0.04 mmol), 4 M HCl in dioxane (0.5 mL); rt, 4 h. The mixture was concentrated in vacuo and dried under vacuum to afford the amine hydrochloride as an off-white solid (16 mg, 92%). $^1$H NMR (MeOD-d$_4$, 500 MHz) δ 8.75 (s, 1H), 8.33 (t, 1H, J=1.7 Hz), 8.09 (t, 1H, J=1.5 Hz), 8.03 (t, 1H, J=1.6 Hz), 7.70 (d, 2H, J=7.1 Hz), 7.53 (t, 2H, J=7.5 Hz), 7.47 (t, 1H, J=7.4 Hz), 4.54 (s, 2H), 3.17 (s, 3H), 3.05 (s, 3H) ppm; $^{13}$C NMR (MeOD-d$_4$, 125 MHz) δ 171.4, 166.6, 154.7, 144.5, 142.3, 139.5, 139.4, 131.8, 130.9, 130.4, 130.0, 128.5, 128.3, 126.8, 40.8, 40.0, 35.8 ppm; HRMS (ESI) m/z 402.0916 found (M+H)$^+$, 402.0941 calculated for C$_1$H$_2$ON$_3$S$_2$O$_3$.

Example 163: 3-((2-(Aminomethyl)thiazol-4-yl)sulfonyl)-5-(1-methyl-1H-pyrazol-4-yl)benzoic acid trifluoroacetate

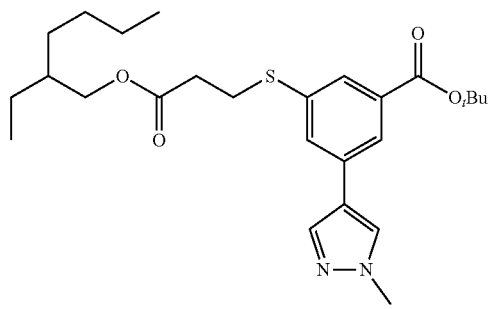

(See Example 150 for synthetic route)

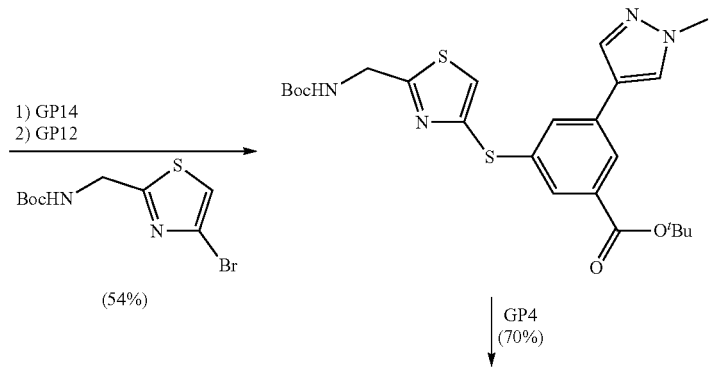

(CDCl$_3$, 500 MHz) δ 7.92 (t, 1H, J=1.6 Hz), 7.77 (s, 1H), 7.73 (s, 1H), 7.62 (s, 1H), 7.58 (s, 1H), 7.21 (s, 1H), 5.36 (br s, 1H), 4.59 (d, 2H, J=5.9 Hz), 3.92 (s, 3H), 1.57 (s, 9H), 1.44 (s, 9H) ppm; LCMS (ESI) m/z 403.1239 found (M-Boc+H)$^+$, C$_{24}$H$_{31}$N$_4$S$_2$O$_4$.

Example 163 was synthesised according to general procedures GP4—from i) tert-butyl 3-((2-(((tert-butoxycarbonyl)amino)methyl)thiazol-4-yl)thio)-5-(1-methyl-1H-pyrazol-4-yl)benzoate (460 mg, 0.915 mmol), m-CPBA (77%; 451 mg, 2.01 mmol), DCM (20 mL); rt, 18 h; chromatography (EtOAc/cyclohexane 25→100%, then MeOH/EtOAc 0→10%). ii) TFA (3.22 mL), DCM (6.5 mL); rt, 4 h. The mixture was concentrated then diluted with Et$_2$O and the

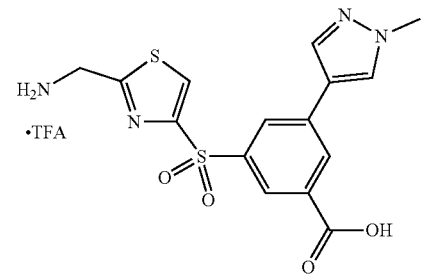

tert-Butyl 3-((2-(((tert-butoxycarbonyl)amino)methyl)thiazol-4-yl)thio)-5-(1-methyl-1H-pyrazol-4-yl)benzoate was synthesised according to general procedures GP14 and GP12—from i) tert-butyl 3-((3-((2-ethylhexyl)oxy)-3-oxopropyl)thio)-5-(1-methyl-1H-pyrazol-4-yl)benzoate (800 mg, 1.685 mmol), NaO$^t$Bu (405 mg, 4.21 mmol), toluene:$^t$BuOH (4:1, 20 mL); rt, 4 h (work-up not performed); ii) To the reaction mixture were added tert-butyl ((4-bromothiazol-2-yl)methyl)carbamate (494 mg, 1.685 mmol), Pd$_2$(dba)$_3$ (156 mg, 10 mol %), Xantphos (197 mg, 20 mol %); 110° C., 16 h. Chromatographic purification (15→90% EtOAc in hexanes) afforded a yellow oil (461 mg, 54%). $^1$H NMR precipitate collected using filtration, washing with excess Et$_2$O, and dried under vacuum to afford the amine trifluoroacetate as a white solid (311 mg, 70% over two steps). $^1$H NMR (MeOD-d$_4$, 500 MHz) E 8.75 (s, 1H), 8.44-8.42 (m, 2H), 8.34 (t, 1H, J=1.8 Hz), 8.17 (s, 1H), 7.94 (d, 1H, J=0.7 Hz), 4.51 (s, 2H), 3.95 (s, 3H) ppm; $^{13}$C NMR (MeOD-d$_4$, 125 MHz) δ 167.6, 166.7, 154.8, 142.3, 137.8, 136.4, 134.4, 132.2, 130.9, 130.3, 129.2, 127.8, 121.7, 40.8, 39.2 ppm; HRMS (ESI) m/z 379.0505 found (M+H)$^+$, 379.0529 calculated for C$_{15}$H$_{15}$N$_4$S$_2$O$_4$.

Example 164: 3-((2-(Aminomethyl)thiazol-4-yl)sulfonyl)-N,N-dimethyl-5-(1-methyl-1H-pyrazol-4-yl)benzamide hydrochloride

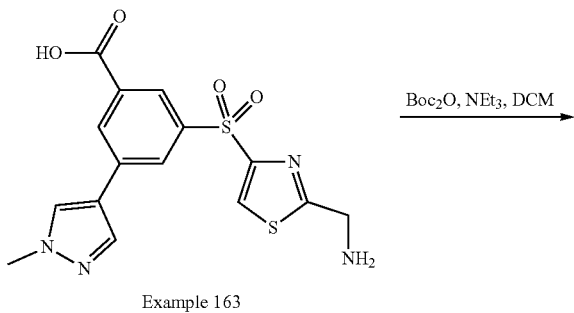

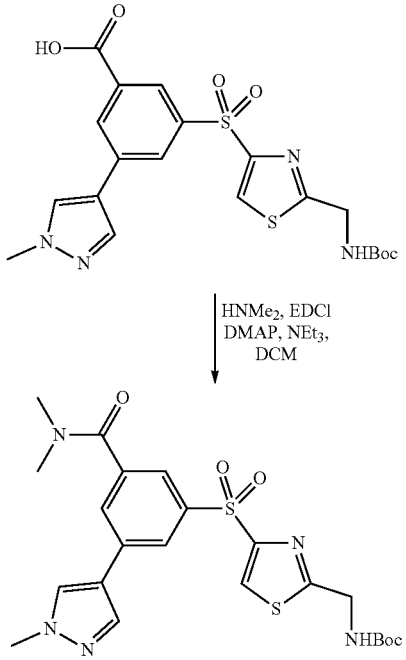

Triethylamine (0.34 mL, 2.485 mmol) was added to a suspension of Example 163 (245 mg, 0.497 mmol) in dichloromethane (6 mL), with stirring at room temperature for 5 minutes, before adding Boc$_2$O (119 mg, 0.547 mmol), with continued stirring for 18 hours. The reaction mixture was then diluted with ethyl acetate (25 mL) and washed with 0.5 M aq. HCl (20 mL), water (20 mL) and brine (20 mL), dried over anhydrous magnesium sulfate, filtered and concentrated to give the crude product, which was washed with 1:1 diethyl ether:hexanes to give 3-((2-(((tert-butoxycarbonyl)amino)methyl)thiazol-4-yl)sulfonyl)-5-(1-methyl-1H-pyrazol-4-yl)benzoic acid (207 mg, 87% yield) as an off-white solid. $^1$H NMR (DMSO-d$_6$, 500 MHz) δ 13.64 (s, 1H), 8.70 (s, 1H), 8.45 (s, 1H), 8.36 (s, 1H), 8.26 (t, 1H, J=1.7 Hz), 8.21 (s, 1H), 8.05 (s, 1H), 7.82 (t, 1H, J=6.0 Hz), 4.35 (d, 2H, J=6.0 Hz), 3.88 (s, 3H), 1.37 (s, 9H) ppm; LCMS m/z 501.0890 found (M+Na)$^+$ for C$_{20}$H$_{22}$N$_4$S$_2$O$_6$Na.

Triethylamine (0.27 mL, 1.93 mmol) and DMAP (47 mg, 0.387 mmol) were added to a solution of 3-((2-(((tert-butoxycarbonyl)amino)methyl)thiazol-4-yl)sulfonyl)-5-(1-methyl-1H-pyrazol-4-yl)benzoic acid (185 mg, 0.387 mmol) and dimethylamine (33% in EtOH (~5.6 M), 0.1 mL, 0.58 mmol) in anhydrous dichloromethane (6 mL), with stirring at 0° C. under nitrogen for 10 mins. EDC-HCl (82 mg, 0.425 mmol) was then added in one portion and the reaction mixture was allowed to stir for 24 hours warming to room temperature. The reaction mixture was then diluted with ethyl acetate (20 mL) and washed with saturated aq. NaHCO$_3$ (20 mL) and brine (20 mL), dried over anhydrous magnesium sulfate, filtered and concentrated to give the crude product. Chromatographic purification (75→100% EtOAc in hexane then 0→30% methanol in EtOAc) afforded a yellow oil (9 mg, 5%). $^1$H NMR (CDCl$_3$, 500 MHz) δ 8.18 (s, 1H), 8.14 (t, 1H, J=1.7 Hz), 7.84 (t, 1H, J=1.6 Hz), 7.81 (s, 1H), 7.75 (t, 1H, J=1.6 Hz), 7.73 (s, 1H), 5.24 (br s, 1H), 4.54 (d, 2H, J=6.2 Hz), 3.13 (s, 3H), 3.01 (s, 3H), 1.44 (s, 9H) ppm; LCMS (ESI) m/z 406.0986 found (M-Boc+H)$^+$ for C$_{22}$H$_{28}$N$_5$O$_5$S$_2$.

Example 164 was synthesised according to general procedures GP16—from tert-butyl ((4-((3-(dimethylcarbamoyl)-5-(1-methyl-1H-pyrazol-4-yl)phenyl)sulfonyl)thiazol-2-yl)methyl)carbamate (9 mg, 0.018 mmol), 4 M HCl in dioxane (0.5 mL); rt, 4 h. The mixture was concentrated in vacuo, washed with diethyl ether and dried under vacuum to afford the amine hydrochloride as an off-white solid (7 mg, 89%). $^1$H NMR (MeOD-d$_4$, 500 MHz), 8.73 (s, 1H), 8.27 (s, 1H), 8.26 (t, 1H, J=1.6 Hz), 8.09 (s, 1H), 7.97 (t, 1H, J=1.5 Hz), 7.94 (t, 1H, J=1.5 Hz), 4.54 (s, 2H), 4.00 (s, 3H), 3.16 (s, 3H), 3.04 (s, 3H) ppm; HRMS (ESI) m/z 406.0964 found (M+H)$^+$, 406.1002 calculated for C$_{17}$H$_{20}$N$_5$S$_2$O$_3$.

Materials and Methods
LOX Enzyme Activity Assay

Compounds were assessed by an enzyme kinetic assay performed according to the following protocol.
The following reagents were prepared:
Reagents
500 mM CHES, pH 9 (with NaOH), filtered (MW=207.29)
20.7 g in 200 ml in dH$_2$O
10% Pluronic F-127 (store at 4° C.)
1 g in 10 ml in dH$_2$O
10% BSA (store at 4° C.)
~2.5 g in 25 ml dH$_2$O
1 M MgCl$_2$.6H$_2$O (MW=203)
5.1 g in 25 ml dH$_2$O
5 M Urea (MW=60.06)
60 g in 200 ml dH$_2$O
5 M NaCl (MW=58.44)
14.6 g in 50 ml dH$_2$O
8.5 M Cadaverine Dihydrochloride (MW=175.10): Sigma, Cat No: C8561
1.49 g in 1 ml dH$_2$O
10 mM Na$_3$VO$_4$, pH 10 (with HCl), boil to activate (MW=183.91): Sigma, Cat No: S6508

0.1839 g in 10 ml dH$_2$O
20 mM Amplex Red (MW=257.25): Invitrogen, Cat No: A12222.
5 mg in 1 ml DMSO (aliquot into 40 μl and store at −20° C.)
1000 U/ml HRP in dH$_2$O (store at 4° C.): Sigma, Cat No: P2088
H$_2$O$_2$ (store at 4° C.): Sigma, Cat No: H1009
DMSO
LOX Assay Buffer:

| Reagent | Volume (μl) 1 x plate | Final Conc$^n$ |
|---|---|---|
| 500 mM CHES, pH9 | 5000 | 100 mM |
| 10% Pluronic F-127 | 125 | 0.05% |
| 10% BSA | 1250 | 0.5% |
| 1M MgCl$_2$ | 25 | 1 mM |
| 5M Urea | 5000 | 1M |
| 5M NaCl | 500 | 100 mM |
| dH$_2$O | 13100 | — |
| Total Volume | 25 000 | — |

Inhibitors (Test Compounds):
  10 mM stock diluted to 10, 3, 1, 0.3, 0.1, 0.03, 0.01, 0.003, 0.001, and 0.0003 mM in drug plate, resulting in a concentration of 100, 30, 10, 3, 1, 0.3, 0.1, 0.03, 0.01, and 0.003 uM in the assay.
LOX Enzyme:
  LOX enzyme was obtained from pig skin by the method of Shackleton et al 1990.
Assay Plates:
  Black, flat bottom 96 well plates
Procedure:
1. Dilute LOX enzyme in Assay Buffer (~4 ml for one plate, 8 ml for two plates) (dilution dependent on batch activity)
2. Add 0.5 μl test compound serial dilutions, in duplicate
3. Add 0.5 μl serial dilutions of positive control, BAPN, down column 11 (no duplication)
4. Add following controls:
  0.5 μl DMSO (100% activity control)
5. Cover plate and incubate for 20 min at room temperature on a plate shaker
6. Prepare Start Mix:

| Reagent | Volume 1 x plate | 2 x plate | Final Conc$^n$ |
|---|---|---|---|
| Assay Buffer | 2 ml | 3 ml | — |
| 8.5M Cadaverine | 23 μl | 34.5 μl | 97.8 mM |
| 20 mM Amplex Red | 10 μl | 15 μl | 100 μM |
| 1000 U/ml HRP | 10 μl | 15 μl | 35 U/ml |

7. Add 10 μl Start Mix to No HRP control wells
8. Add HRP to the Start Mix. Add 10 ul to all wells EXCEPT No HRP control wells
9. Incubate for 45 min at room temp on a plate shaker, protected from light
10. Measure fluorescence using a plate reader:
  Excitation wavelength: 545 nm
  Emission wavelength: 585 nm
HRP Counter Assay Protocol
1. Dilute 5 μl H$_2$O$_2$ in 640 μl dH$_2$O. Add 1 μl diluted H$_2$O$_2$ to 10 ml Assay Buffer. Vortex
2. Add 40 μl H$_2$O$_2$+Assay Buffer into every well on the counter assay plate EXCEPT no H$_2$O$_2$ control wells (add 40 μl Assay Buffer only)
3. Add 0.5 μl test compound serial dilutions, in duplicate
4. Add 0.5 μl serial dilutions of positive control, Na$_3$VO$_4$, down column 11 (no duplication)
5. Add following controls:
  0.5 μl DMSO (100% activity control)
  1 μl diluted H$_2$O$_2$ (blow out control)
6. Incubate for 20 min at room temp on a plate shaker
7. Prepare Start Mix:

| Reagent | Volume 1 x plate | 2 x plate | Final Concn |
|---|---|---|---|
| Assay Buffer | 2 ml | 3 ml | — |
| 20 mM Amplex Red | 10 μl | 15 μl | 100 μM |
| 1000 U/ml HRP | 10 μl | 15 μl | 5 U/ml |

8. Add 10 μl Start Mix to No HRP control wells
9. Add HRP to the Start Mix. Add 10 ul to all wells EXCEPT No HRP control wells
10. Incubate for 5 min at room temp on a plate shaker, protected from light (almost instant reaction)
11. Measure fluorescence using a plate reader:
  Excitation wavelength: 545 nm
  Emission wavelength: 585 nm
  Values for the blank (no LOX/no H$_2$O$_2$ controls) are subtracted from all samples. The DMSO controls are set as 100% activity and samples are calculated as a % of the DMSO control. Data is plotted using Graph pad Prism software, and a non-linear regression line is calculated using a variable slope sigmoidal dose response equation:

$$Y=\text{Bottom}+(\text{Top}-\text{Bottom})/(1+10^{((\text{LogIC50}-X)*\text{HillSlope})}).$$

Where X is the logarithm of concentration and Y is the response. The IC50 is the concentration of the drug that produces a percentage control fluorescence value midway between the saturation and zero effect plateaus. Two independent assays are usually performed, and the mean IC50 is reported.
LOX Assay Plate Layout is described in FIG. 23.
HRP Counter Assay Plate Layout is described in FIG. 24.
LOX inhibition data for compounds described in this invention are shown in Table 1.
HRP counterscreen inhibition does not reach IC50 at the top concentration used in the assay (IC50>100 uM) for all the compounds shown in table 1.
LOXL2 Enzyme Activity Assay:
Compounds were assessed by an enzyme kinetic assay performed according to the following protocol.
The following reagents were prepared:
Reagents
500 mM CHES, pH 9 (with NaOH), filtered (MW=207.29)
20.7 g in 200 ml in dH$_2$O
10% Pluronic F-127 (store at 4° C.)
1 g in 10 ml in dH$_2$O
10% BSA (store at 4° C.)
−2.5 g in 25 ml dH$_2$O
1 M MgCl$_2$.6H$_2$O (MW=203)
5.1 g in 25 ml dH$_2$O
5 M Urea (MW=60.06)
60 g in 200 ml dH$_2$O
5 M NaCl (MW=58.44)
14.6 g in 50 ml dH$_2$O
8.5 M Cadaverine Dihydrochloride (MW=175.10): Sigma, Cat No: C8561
1.49 g in 1 ml dH$_2$O Promega ROS-Glo H$_2$O$_2$ Assay Kit, 50 ml
Cat No. G8821
DMSO
LOXL2 Assay Buffer:

| Reagent | Volume (µl) 1 x plate | Final Conc" |
|---|---|---|
| 500 mM CHES, pH9 | 5000 | 100 mM |
| 10% Pluronic F-127 | 125 | 0.05% |
| 10% BSA | 1250 | 0.5% |
| 1M MgCl$_2$ | 25 | 1 mM |
| 5M Urea | 5000 | 1M |
| 5M NaCl | 500 | 100 mM |
| dH$_2$O | 13100 | — |
| Total Volume | 25 000 | — |

Inhibitors (Test compounds):
10 mM stock diluted to 10, 3, 1, 0.3, 0.1, 0.03, 0.01, 0.003, 0.001, and 0.0003 mM in drug plate, resulting in a concentration of 100, 30, 10, 3, 1, 0.3, 0.1, 0.03, 0.01, and 0.003 uM in the assay.
LOXL2:
LOXL2 batch is obtained from R&D systems/Bio-techne
Assay Plates:96 well white polystyrene, flat bottom plates, no lid: Fisher, Cat No. DPS-134-050A
Procedure:
1. Dilute LOXL2 enzyme in Assay Buffer (~4 ml for one plate, 8 ml for two plates) (dilution dependent on batch activity)
1. Add 0.5 µl test compound serial dilutions, in duplicate
2. Add 0.5 µl serial dilutions of positive control, BAPN, down column 11 (no duplication)
3. Add following controls:
   0.5 µl DMSO (100% activity control)
4. Cover plate and incubate for 20 minutes (Method (a) in Table 1), 60 minutes (Method (b) in Table 1) or 20 hours (Method (c) in Table 1), at room temp on a plate shaker
5. Prepare Start Mix:

| Reagent | Volume 1 x plate | 2 x plate | Final Conc" |
|---|---|---|---|
| Assay Buffer | 2 ml | 3 ml | — |
| 8.5M Cadaverine | 23 µl | 34.5 µl | 97.8 mM |
| H$_2$O$_2$ Substrate (1:80) | 25 µl | 37.5 µl | 125 µM |

6. Add 10 µl Start Mix to all wells
7. Incubate for 60 min at room temp on a plate shaker
8. Prepare Detection Reagent:

| Reagent | Volume 1 x plate | 2 x plate |
|---|---|---|
| Luciferin | 5 ml | 10 ml |
| D-cysteine (1:100) | 50 µl | 100 µl |
| Signal Enhancer (1:100) | 50 µl | 100 µl |

9. Add 50 µl Detection Regent to each well EXCEPT No Luciferin controls (add 50 µl assay buffer)
10. Incubate for 20 min at room temp on a plate shaker, protected from light
11. Measure luminescence using a plate reader (integration 500 ms)

Values for the blank (no LOXL2 controls) are subtracted from all samples. The DMSO controls are set as 100% activity and samples are calculated as a % of the DMSO control. Data is plotted using Graph pad Prism software, and a non-linear regression line is calculated using a variable slope sigmoidal dose response equation:

$$Y = \text{Bottom} + (\text{Top} - \text{Bottom})/(1 + 10^{((\text{LogIC50} - X)*\text{Hill-Slope})}).$$

Where X is the logarithm of concentration and Y is the response. The IC50 is the concentration of the drug that produces a percentage control fluorescence value midway between the saturation and zero effect plateaus. Two independent assays are usually performed, and the mean IC50 is reported. ROS-Glo LOX Assay Plate Layout is described in FIG. 25

LOX Activity in Cysts Assay
Cell Culture and Transfection
All cell lines used in this study was purchased from American Type Culture Collection (ATCC). *Mycoplasma* contamination was routinely monitored by PCR. Cells used were not found to be *Mycoplasma* positive. MDCK cell lines were cultured in Dulbecco's Modified Eagle Medium (DMEM) supplemented with 10% fetal bovine serum (FBS) and 1% Penicillin Streptomycin solution (Pen Strep). For GFP constructs transfection in MDCK cells, lipofectamine 3000 was used according to manufactures protocols. Cells were either selected with G418 (Life Technologies) at 5 mg/ml. All cell culture reagents were purchased from Life Technologies.

To produce MDCK cysts, cells were cultured on Matrigel (Corning) with 2% Matrigel supplemented in DMEM with 10% FBS. Cysts were allowed to form for 10 days before subsequent studies.

Cloning of LOX Expression Constructs
Mouse LOX cDNA was purchased from OriGene. Full length LOX cDNA was then PCR cloned into pEGFP-N1 (Clonetech), or biosensor vector proGFP2-N1 (Hanson, 2004) using the following primers, GAGAGAGCTAGCATGCGTTTCGCCTGGG (SEQ. ID NO. 1) (forward primer) and TCTCTCCTCGAGATACGGTGAAATTGTGCAGCC (SEQ. ID NO. 2) (reverse primer). For the insertion into pEGFP-N1 or proGFP2-N1, NheI and XhoI restriction sites were added to forward and reverse primers accordingly. Mutant LOX constructs were made using QuickChange II site-directed mutagenesis kit (Agilent Technologies) following manufacture's protocol using LOX-GFP as template. To generate, roGFP2 versions of LOX mutant constructs, LOX mutant cDNA was transferred from pEGFP-N1 to proGFP2-N$_1$ using NheI and XhoI.

Confocal Imaging and Imaging Analysis
All photomicrographs were taken with a Leica TCS SP8 X confocal system. For LOX biosensor imaging, live MDCK cysts were used. The oxidised biosensor was excited using a 405 nm laser, while the reduced biosensor was excited with a 488 nm laser. Emission of the biosensor was recorded at 500 nm-530 nm range using sequential scans. Ratio images were generated following a published protocol {Kardash, 2011 #376}. Note, while the published protocol generates YFP/CFP ratio images, we used it to generate Oxidised/Reduced (roGFP2 ratio) ratio images. The roGFP2 ratio at the basal surface of MDCK cysts was used to indicate LOX inhibition. LOX inhibitors were added 30 min prior to imaging at 20 uM.

The inhibition of LOX in cysts assay by LOX inhibitors as compared to control (DMSO vehicle treated) cysts is shown in Table A.

TABLE A

A Cellular inhibition of LOX and downstream signalling

| Compound* | % inhibition of LOX - roGFP2 sensor in MOCK cysts | pAKT/AKT % inhibited vs control in MDA-MB231 cells |
|---|---|---|
| Example 14 | 69% | 48% |
| Example 68 | 74% | 39% |

*All results at 20 µM compound

AKT Activation Assay

MDA-MB-231 cells were cultured in Dulbecco's Modified Eagle Medium (DMEM) supplemented with 10% fetal bovine serum (FBS) and 1% Penicillin Streptomycin solution (Pen Strep). Serum starved MDA-MB-231 cells were stimulated with 100 ng/ml EGF (Peprotech) for 3 minutes. Cells were then lysed using cell lysis buffer with the addition of protease and phosphatase inhibitor cocktails. Equal amounts of proteins were then used for AKT activation analysis using pS473AKT/total AKT ELISA kit (Abcam) following manufacture's protocol.

The inhibition of EGF-stimulated AKT phosphorylation by LOX inhibitors in MDA-MB231 cells is shown in Table A.

Monoamine Oxidase A (MAO-A) Selectivity Assay
Compounds were assessed for MAO-A activity according to the following protocol.
The following reagents were prepared:
Reagents
MAO-Glo Assay Kit: Promega, Cat No. V1402
MAO-A Enzyme: Promega, Cat No. V1452
Clorgyline: Sigma, Cat No. M3778 (50 mg)
Assay Plates:96 well white polystyrene, flat bottom plates, no lid: Fisher, Cat No. DPS-134-050A
Inhibitors (Test compounds):
10 mM stock diluted to 10, 3, 1, 0.3, 0.1, 0.03, 0.01, 0.003, 0.001, and 0.0003 mM in drug plate, resulting in a concentration of 100, 30, 10, 3, 1, 0.3, 0.1, 0.03, 0.01, and 0.003 uM in the assay.
Procedure:
1. Dilute MAO substrate 1:50 with MAO A reaction buffer and add 25 µl to each well of a 96 well plate
   Require 2.8 ml: 56 µl MAO substrate+2744 µl reaction buffer
2. Add 0.5 µl test compound serial dilutions, in duplicate
3. Add 0.5 µl serial dilutions of Clorgyline (positive control) down column 11 (no duplication)
4. Add 25 µl specific MAO enzyme dilution:
   dilute 1:520 with MAO-A specific reaction buffer (5.3 µl MAO-A+2750.7 µl reaction buffer)
5. Add following controls, in duplicate, down column 12:
   No Luciferin: 25 µl MAO enzyme
   DMSO: 0.5 µl DMSO+25 µl MAO enzyme
   Blow Out: 1 µl undiluted MAO-A enzyme+24 µl reaction buffer
6. Incubate for 1 hour at room temp on a plate shaker
7. Add 50 µl Luciferin detection reagent to each well EXCEPT no luciferin control wells (add 50 µl reaction buffer)
8. Incubate for 20 min at room temp on a plate shaker, protected from light
9. Measure the luminescence using a plate reader (read mode: luminescence 500 ms/well)

Values for the blank (no MAO-enzyme controls) are subtracted from all samples. The DMSO controls are set as 100% activity and samples are calculated as a % of the DMSO control. Data is plotted using Graph pad Prism software, and a non-linear regression line is calculated using a variable slope sigmoidal dose response equation:

$$Y = \text{Bottom} + (\text{Top} - \text{Bottom})/(1 + 10^{((\text{LogIC50} - X) * \text{HillSlope})}).$$

Where X is the logarithm of concentration and Y is the response. The IC50 is the concentration of the drug that produces a percentage control fluorescence value midway between the saturation and zero effect plateaus. Two independent assays are usually performed, and the mean IC50 is reported.

MAO-A Assay Plate Layout is Described in FIG. 26.
Monoamine oxidase B (MAO-B) Selectivity Assay
Compounds were assessed for MAO-B activity according to the following protocol.
The following reagents were prepared:
Reagents
MAO-Glo Assay Kit: Promega, Cat No. V1402
MAO-B Enzyme: Sigma, Cat No. M7441
Deprenyl: Sigma, Cat No. M003

Assay Plates: 96 well white polystyrene, flat bottom plates, no lid: Fisher, Cat No. DPS-134-050A Inhibitors (Test compounds):

10 mM stock diluted to 10, 3, 1, 0.3, 0.1, 0.03, 0.01, 0.003, 0.001, and 0.0003 mM in drug plate, resulting in a concentration of 100, 30, 10, 3, 1, 0.3, 0.1, 0.03, 0.01, and 0.003 uM in the assay.

Procedure:

1. Dilute MAO substrate 1:50 with MAO A reaction buffer and add 25 µl to each well of a 96 well plate Require 2.8 ml: 56 µl MAO substrate+2744 µl reaction buffer 2. Add 0.5 µl test compound serial dilutions, in duplicate
3. Add 0.5 µl serial dilutions of Deprenyl (positive control) down column 11 (no duplication)
4. Add 25 µl specific MAO enzyme dilution:

MAO-B (plate 2): dilute 1:52 with MAO-B specific reaction buffer (53 µl MAO-B+2703 µl reaction buffer)

5. Add following controls, in duplicate, down column 12:

No Luciferin: 25 µl MAO enzyme

DMSO: 0.5 µl DMSO+25 µl MAO enzyme

Blow Out: 1 µl undiluted MAO-A enzyme+24 µl reaction buffer

6. Incubate for 1 hour at room temp on a plate shaker
7. Add 50 µl Luciferin detection reagent to each well EXCEPT no luciferin control wells (add 50 µl reaction buffer)
8. Incubate for 20 min at room temp on a plate shaker, protected from light
9. Measure the luminescence using a plate reader (read mode: luminescence 500 ms/well)

Values for the blank (no MAO enzyme controls) are subtracted from all samples. The DMSO controls are set as 100% activity and samples are calculated as a % of the DMSO control. Data is plotted using Graph pad Prism software, and a non-linear regression line is calculated using a variable slope sigmoidal dose response equation:

$$Y = \text{Bottom} + (\text{Top} - \text{Bottom})/(1 + 10^{((\text{LogIC50} - X) * \text{Hill-Slope})}).$$

Where X is the logarithm of concentration and Y is the response. The IC50 is the concentration of the drug that produces a percentage control fluorescence value midway between the saturation and zero effect plateaus. Two independent assays are usually performed, and the mean IC50 is reported.

MAO-B Assay Plate Layout is described in FIG. 27.

Compounds of this invention show selectivity >10 fold for LOX vs MAO-A and MAO-B, with the exception of Example 91, which has >5 fold selectivity for LOX vs MAO-A and MAO-B (Table 1)

Diamine oxidase (DAO) selectivity assay

Reagents

Promega ROS-Glo $H_2O_2$ Assay Kit, 50 ml. Cat No. G8821

Inhibitors (Test compounds):

10 mM stock diluted to 10, 3, 1, 0.3, 0.1, 0.03, 0.01, 0.003, 0.001, and 0.0003 mM in drug plate, resulting in a concentration of 100, 30, 10, 3, 1, 0.3, 0.1, 0.03, 0.01, and 0.003 uM in the assay.

Positive Control (Aminoguanidine):

1 mM stock diluted to 1 to 0.0001 and 0.00003 mM in drug plate, resulting in a concentration of 3 to 0.001 and 0.0003 uM in the assay.

DAO:

DAO batch is obtained from Sigma Enzyme is reconstituted in sodium phosphate buffer at 10 mg/mL Assay Plates: 96 well white polystyrene, flat bottom plates: Fisher, Cat No. DPS-134-050A Procedure:

1. Dilute 400 ul DAO enzyme in 4 mL Assay Buffer (enough for one plate). Add 40 ul DAO enzyme to all wells (excluding G+H 12, assay buffer only)
3. Add 0.5 µl test compound serial dilutions, in duplicate
4. Add 0.5 µl serial dilutions of Aminoguanidine down column 11 and to E+F 12
5. Add 0.5 µl DMSO (100% activity control) to C+D 12
6. Cover plate and incubate for 20 minutes at room temp on a plate shaker
7. Prepare Start Mix:

| Reagent | Volume | | Final Conc$^n$ |
|---|---|---|---|
| | 1 x plate | 2 x plate | |
| Assay Buffer | 2 ml | 3 ml | — |
| 8.5M Cadaverine | 23 µl | 34.5 µl | 97.8 mM |
| $H_2O_2$ Substrate (1:80) | 25 µl | 37.5 µl | 125 µM |

8. Add 10 µl Start Mix to all wells
9. Incubate for 60 min at room temp on a plate shaker
10. Prepare Detection Reagent:

| Reagent | Volume | |
|---|---|---|
| | 1 x plate | 2 x plate |
| Luciferin | 5 ml | 10 ml |
| D-cysteine (1:100) | 50 µl | 100 µl |
| Signal Enhancer (1:100) | 50 µl | 100 µl |

11. Add 50 µl Detection Regent to each well EXCEPT No Luciferin controls (A+B 12, add 50PI assay buffer)
12. Incubate for 20 min at room temp on a plate shaker, protected from light
13. Measure luminescence using a plate reader (integration 500 ms)

Values for the blank (no DAO controls) are subtracted from all samples. DMSO controls are set as 100% activity and samples are calculated as a % of the DMSO control. Data is plotted using Graphpad Prism software, and a non-linear regression line is calculated using a variable slope sigmoidal dose response equation:

$$Y = \text{Bottom} + (\text{Top} - \text{Bottom})/(1 + 10^{((\text{LogIC50} - X) * \text{Hill-Slope})}).$$

Where X is the logarithm of concentration and Y is the response. The IC50 is the concentration of the drug that produces a percentage control fluorescence value midway between the saturation and zero effect plateaus. Two independent assays are usually performed, and the mean IC50 is reported.

DAO Assay Plate Layout is Described in FIG. 28.

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 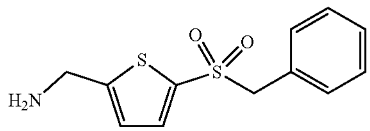 [SMILES: NCc1ccc(S(=O)(=O)Cc2ccccc2)s1] | Example 1 | 2.7 | \ | a) 2.2 c) 2.4 | \ | \ | \ |
| 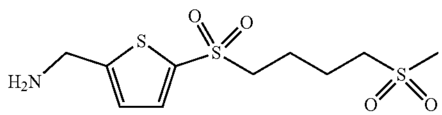 [SMILES: CS(=O)(=O)CCCCS(=O)(=O)c1ccc(CN)s1] | Example 8 | 11 | \ | \ | \ | \ | \ |
| 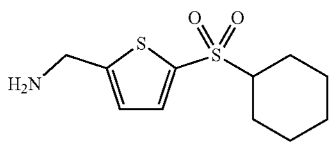 [SMILES: NCc1ccc(S(=O)(=O)C2CCCCC2)s1] | Example 3 | 2.1 | \ | a) 5.1 | \ | \ | \ |
| 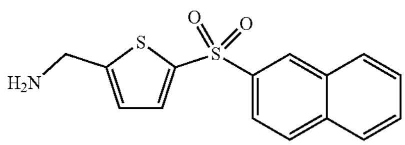 [SMILES: NCc1ccc(S(=O)(=O)c2ccc3ccccc3c2)s1] | Example 2 | 1 | \ | a) 4.0 c) 0.2 | 37 | >100 | \ |
| 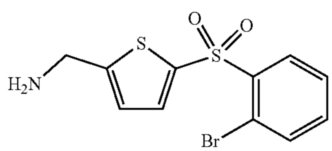 [SMILES: NCc1ccc(S(=O)(=O)c2ccccc2Br)s1] | Example 4 | 9.4 | \ | \ | \ | \ | \ |
| 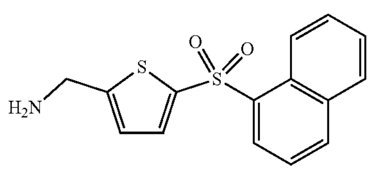 [SMILES: NCc1ccc(S(=O)(=O)c2cccc3ccccc23)s1] | Example 7 | 3 | \ | \ | 66 | \ | \ |
| 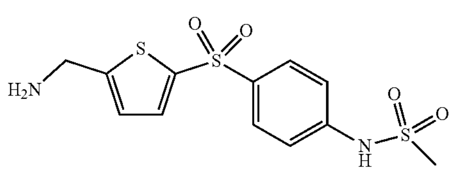 [SMILES: CS(=O)(=O)Nc1ccc(S(=O)(=O)c2ccc(CN)s2)cc1] | Example 11 | 2.9 | \ | \ | \ | \ | \ |
| 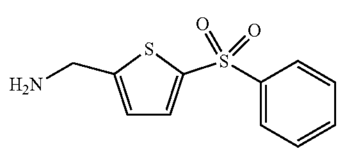 | Example 18 | 3 | \ | a) 2.2 | 53 | \ | \ |
| 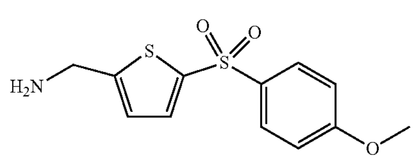 [SMILES: COc1ccc(S(=O)(=O)c2ccc(CN)s2)cc1] | Example 19 | 2 | \ | \ | \ | \ | \ |
| 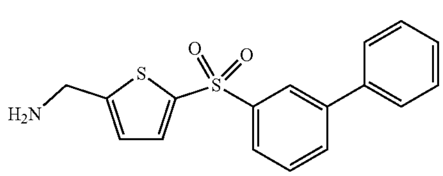 [SMILES: NCc1ccc(S(=O)(=O)c2cccc(-c3ccccc3)c2)s1] | Example 20 | 6.3 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 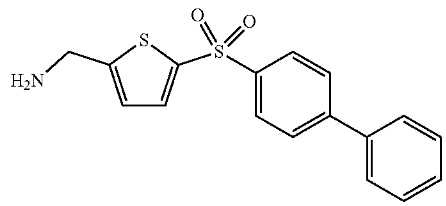 [SMILES: NCc1ccc(S(=O)(=O)c2ccc(-c3ccccc3)cc2)s1] | Example 21 | 1.8 | \ | \ | \ | \ | \ |
| 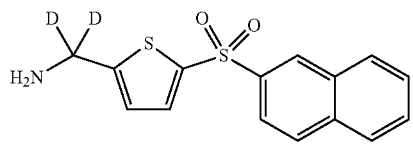 [SMILES: [2H]C([2H])(N)c1ccc(S(=O)(=O)c2ccc3ccccc3c2)s1] | Example 24 | 3.6 | \ | \ | \ | \ | \ |
| 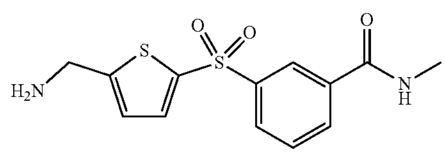 [SMILES: CNC(=O)c1cccc(S(=O)(=O)c2ccc(CN)s2)c1] | Example 22 | 1.6 | \ | \ | \ | \ | \ |
| 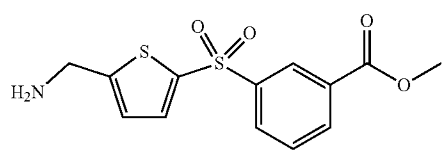 [SMILES: COC(=O)c1cccc(S(=O)(=O)c2ccc(CN)s2)c1] | Example 23 | 2.4 | \ | \ | \ | \ | \ |
| 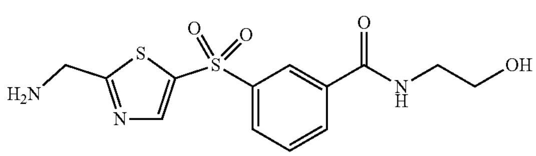 [SMILES: NCc1ncc(S(=O)(=O)c2cccc(C(=O)NCCO)c2)s1] | Example 50 | 0.74 | \ | \ | \ | \ | \ |
| 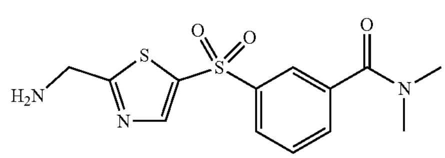 [SMILES: CN(C)C(=O)c1cccc(S(=O)(=O)c2cnc(CN)s2)c1] | Example 51 | 2.4 | \ | \ | \ | \ | \ |
| 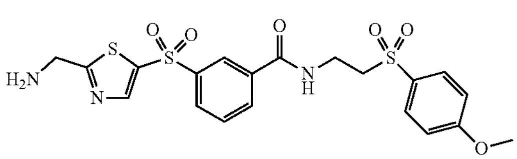 [SMILES: COc1ccc(S(=O)(=O)CCNC(=O)c2cccc(S(=O)(=O)c3cnc(CN)s3)c2)cc1] | Example 52 | 0.76 | \ | \ | \ | \ | \ |
| 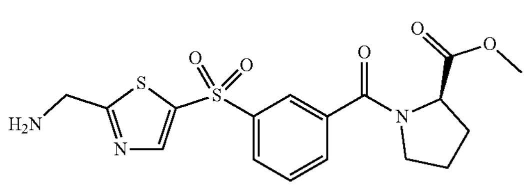 [SMILES: COC(=O)[C@H]1CCCN1C(=O)c1cccc(S(=O)(=O)c2cnc(CN)s2)c1] | Example 54 | 1.5 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| (aminomethyl-thiophene-sulfonyl-phenyl-N-methylcarboxamide) | Example 55 | 4.6 | \ | \ | \ | \ | \ |
| (aminomethyl-thiophene-sulfonyl-phenyl-carboxamide-ethyl-methoxyphenyl-sulfonyl) | Example 56 | 2.2 | \ | \ | \ | \ | \ |
| (aminomethyl-thiophene-sulfonyl-phenyl-N,N-dimethylcarboxamide) | Example 57 | 3.5 | \ | \ | \ | \ | \ |
| (aminomethyl-thiophene-sulfonyl-phenyl-carboxamide-ethanol) | Example 58 | 2.7 | \ | a) 9.5 | \ | \ | \ |
| (aminomethyl-thiophene-sulfonyl-phenyl-methylsulfonyl) | Example 5 | 0.48 | \ | a) 2.6 | >100 | >100 | \ |
| (aminomethyl-thiophene-sulfonyl-phenyl-methylsulfonyl meta) | Example 9 | 0.34 | \ | a) 1.5 c) 0.27 | >100 | >100 | \ |
| (aminomethyl-thiophene-sulfonyl-phenyl-methylsulfonyl ortho) | Example 10 | 1.7 | \ | \ | >100 | >100 | \ |
| (aminomethyl-thiophene-sulfonyl-phenyl-sulfonyl-ethanol) | Example 16 | 0.3 | \ | \ | >100 | >100 | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 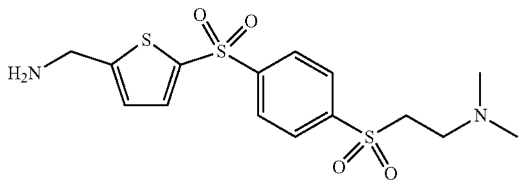 [SMILES: CN(C)CCS(=O)(=O)c1ccc(S(=O)(=O)c2ccc(CN)s2)cc1] | Example 17 | 0.45 | \ | \ | \ | \ | \ |
| 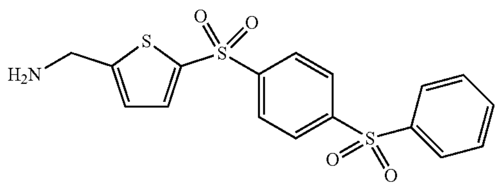 [SMILES: NCc1ccc(S(=O)(=O)c2ccc(S(=O)(=O)c3ccccc3)cc2)s1] | Example 25 | 1.9 | \ | \ | \ | \ | \ |
| 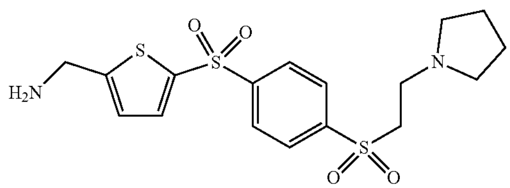 [SMILES: NCc1ccc(S(=O)(=O)c2ccc(S(=O)(=O)CCN3CCCC3)cc2)s1] | Example 26 | 0.55 | \ | \ | \ | \ | \ |
| 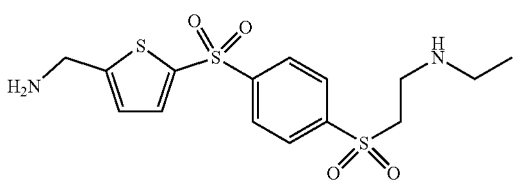 [SMILES: CCNCCS(=O)(=O)c1ccc(S(=O)(=O)c2ccc(CN)s2)cc1] | Example 27 | 0.4 | \ | \ | >100 | >100 | \ |
| 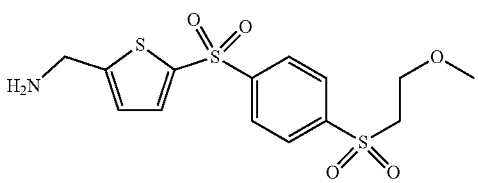 [SMILES: COCCS(=O)(=O)c1ccc(S(=O)(=O)c2ccc(CN)s2)cc1] | Example 28 | 1.3 | \ | \ | \ | \ | \ |
| 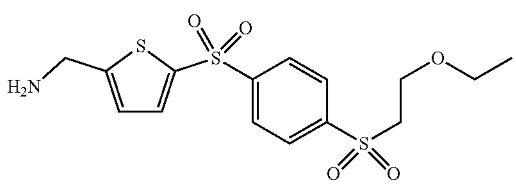 [SMILES: CCOCCS(=O)(=O)c1ccc(S(=O)(=O)c2ccc(CN)s2)cc1] | Example 29 | 2.3 | \ | \ | \ | \ | \ |
| 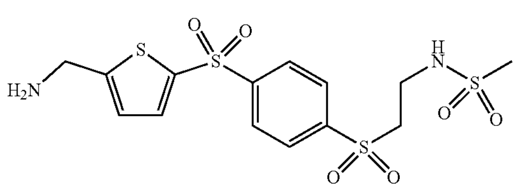 [SMILES: CS(=O)(=O)NCCS(=O)(=O)c1ccc(S(=O)(=O)c2ccc(CN)s2)cc1] | Example 30 | 1.8 | \ | \ | \ | \ | \ |
| 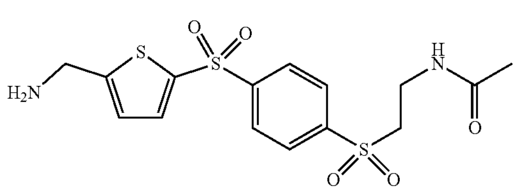 [SMILES: CC(=O)NCCS(=O)(=O)c1ccc(S(=O)(=O)c2ccc(CN)s2)cc1] | Example 31 | 0.91 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 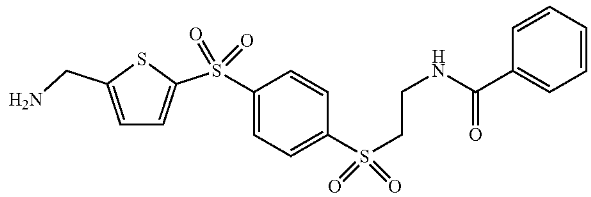 [SMILES: NCc1ccc(S(=O)(=O)c2ccc(S(=O)(=O)CCNC(=O)c3ccccc3)cc2)s1] | Example 32 | 0.72 | \ | \ | \ | \ | \ |
| 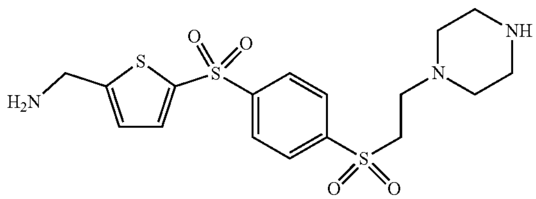 [SMILES: NCc1ccc(S(=O)(=O)c2ccc(S(=O)(=O)CCN3CCNCC3)cc2)s1] | Example 33 | 1.1 | \ | \ | \ | \ | \ |
| 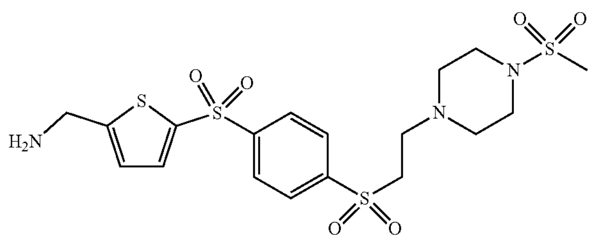 [SMILES: CS(=O)(=O)N1CCN(CCS(=O)(=O)c2ccc(S(=O)(=O)c3ccc(CN)s3)cc2)CC1] | Example 34 | 0.53 | \ | \ | \ | \ | \ |
| 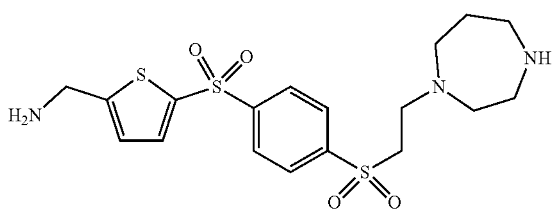 [SMILES: NCc1ccc(S(=O)(=O)c2ccc(S(=O)(=O)CCN3CCCNCC3)cc2)s1] | Example 35 | 0.45 | \ | \ | \ | \ | \ |
| 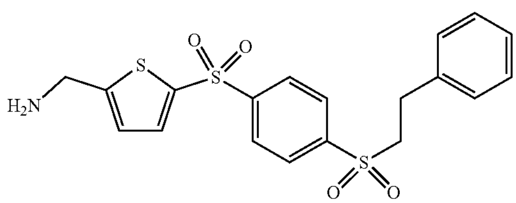 [SMILES: NCc1ccc(S(=O)(=O)c2ccc(S(=O)(=O)CCc3ccccc3)cc2)s1] | Example 36 | 2.2 | \ | \ | \ | \ | \ |
| 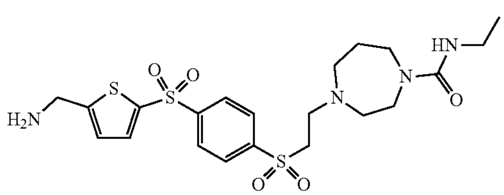 [SMILES: CCNC(=O)N1CCCN(CCS(=O)(=O)c2ccc(S(=O)(=O)c3ccc(CN)s3)cc2)CC1] | Example 37 | 1.1 | \ | \ | \ | \ | \ |
| 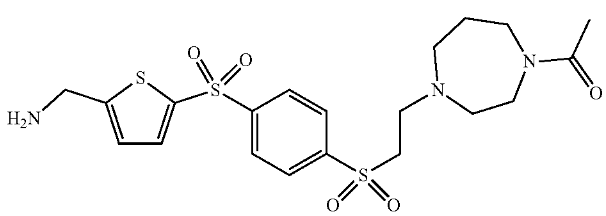 [SMILES: CC(=O)N1CCCN(CCS(=O)(=O)c2ccc(S(=O)(=O)c3ccc(CN)s3)cc2)CC1] | Example 38 | 0.59 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 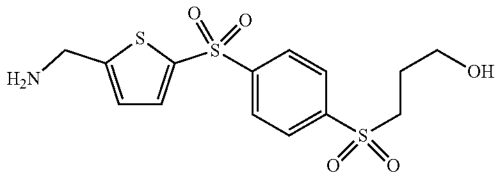 [SMILES: NCc1ccc(S(=O)(=O)c2ccc(S(=O)(=O)CCCO)cc2)s1] | Example 39 | 0.44 | \ | \ | >100 | >100 | \ |
| 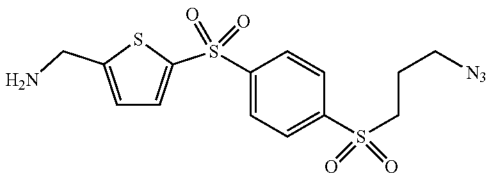 [SMILES: [N-]=[N+]=NCCCS(=O)(=O)c1ccc(S(=O)(=O)c2ccc(CN)s2)cc1] | Example 40 | 0.47 | \ | \ | >100 | >100 | \ |
| 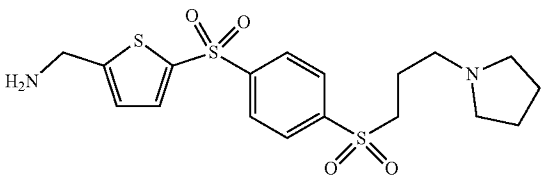 [SMILES: NCc1ccc(S(=O)(=O)c2ccc(S(=O)(=O)CCCN3CCCC3)cc2)s1] | Example 41 | 0.69 | \ | \ | \ | \ | \ |
| 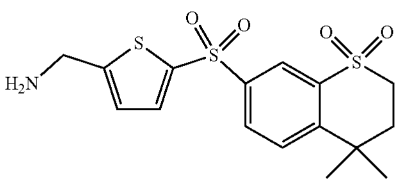 [SMILES: CC1(C)CCS(=O)(=O)c2cc(S(=O)(=O)c3ccc(CN)s3)ccc21] | Example 66 | 2.5 | \ | \ | >100 | >100 | \ |
| 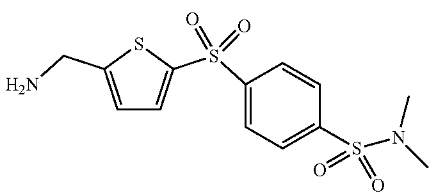 [SMILES: CN(C)S(=O)(=O)c1ccc(S(=O)(=O)c2ccc(CN)s2)cc1] | Example 12 | 0.51 | \ | \ | >100 | >100 | \ |
| 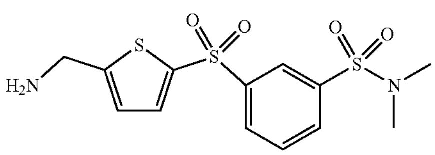 [SMILES: CN(C)S(=O)(=O)c1cccc(S(=O)(=O)c2ccc(CN)s2)c1] | Example 13 | 0.82 | \ | \ | >100 | >100 | \ |
| 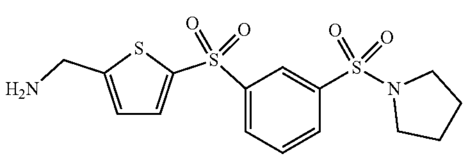 [SMILES: NCc1ccc(S(=O)(=O)c2cccc(S(=O)(=O)N3CCCC3)c2)s1] | Example 14 | 0.62 | \ | a) 1.8  c) 0.056 | >100 | >100 | \ |
| 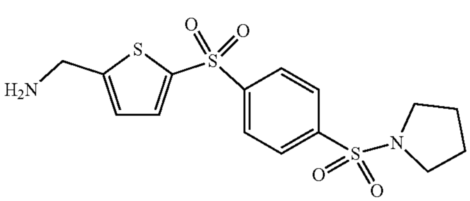 [SMILES: NCc1ccc(S(=O)(=O)c2ccc(S(=O)(=O)N3CCCC3)cc2)s1] | Example 15 | 0.93 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| [structure] | Example 42 | 1.4 | \ | a) 5.0 c) 0.4 | \ | \ | \ |
| [structure] | Example 43 | 0.42 | \ | \ | >100 | >100 | \ |
| [structure] | Example 44 | 1.2 | \ | \ | 83 | >100 | \ |
| [structure] | Example 45 | 1 | \ | \ | \ | \ | \ |
| [structure] | Example 46 | 2.1 | \ | \ | \ | \ | \ |
| [structure] | Example 48 | 1.7 | \ | \ | >100 | >100 | \ |
| [structure] | Example 49 | 1.6 | \ | \ | >100 | >100 | \ |
| [structure] | Example 47 | 1.1 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 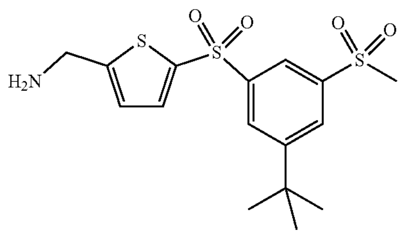 [SMILES: CC(C)(C)c1cc(S(C)(=O)=O)cc(S(=O)(=O)c2ccc(CN)s2)c1] | Example 61 | 1.9 | \ | \ | >100 | >100 | \ |
| 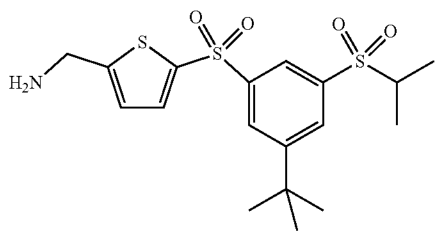 [SMILES: CC(C)S(=O)(=O)c1cc(C(C)(C)C)cc(S(=O)(=O)c2ccc(CN)s2)c1] | Example 62 | 3.2 | \ | \ | >100 | >100 | \ |
| 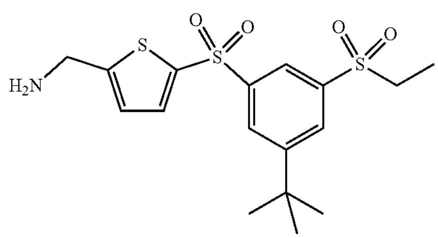 [SMILES: CCS(=O)(=O)c1cc(C(C)(C)C)cc(S(=O)(=O)c2ccc(CN)s2)c1] | Example 63 | 3.4 | \ | \ | >100 | >100 | \ |
| 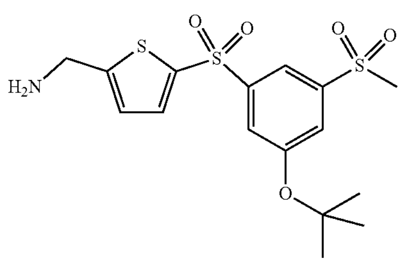 [SMILES: CC(C)(C)Oc1cc(S(C)(=O)=O)cc(S(=O)(=O)c2ccc(CN)s2)c1] | Example 64 | 1.6 | \ | \ | >100 | >100 | \ |
| 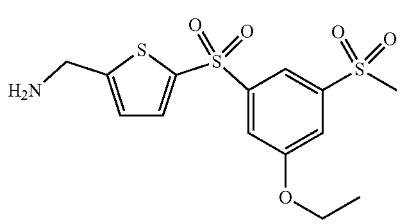 [SMILES: CCOc1cc(S(C)(=O)=O)cc(S(=O)(=O)c2ccc(CN)s2)c1] | Example 65 | 3.1 | \ | \ | >100 | >100 | \ |
| 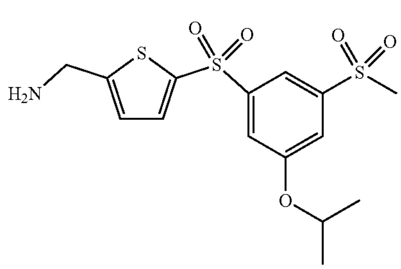 [SMILES: CC(C)Oc1cc(S(C)(=O)=O)cc(S(=O)(=O)c2ccc(CN)s2)c1] | Example 67 | 3.2 | \ | \ | >100 | >100 | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 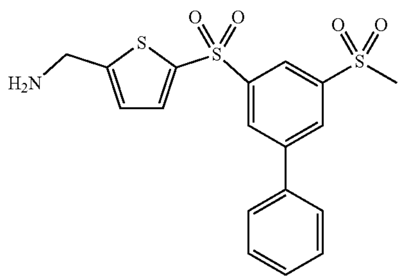 [SMILES: CS(=O)(=O)c1cc(-c2ccccc2)cc(S(=O)(=O)c2ccc(CN)s2)c1] | Example 68 | 0.89 | 2.5 | a) 3.8 b) 0.26 | >100 | >100 | \ |
| 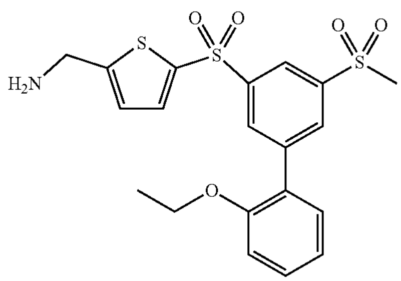 [SMILES: CCOc1ccccc1-c1cc(S(C)(=O)=O)cc(S(=O)(=O)c2ccc(CN)s2)c1] | Example 69 | 7.8 | \ | \ | \ | \ | \ |
| 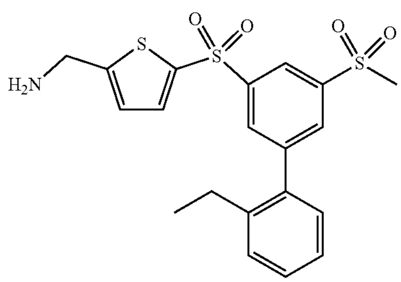 [SMILES: CCc1ccccc1-c1cc(S(C)(=O)=O)cc(S(=O)(=O)c2ccc(CN)s2)c1] | Example 70 | 6.1 | \ | \ | \ | \ | \ |
| 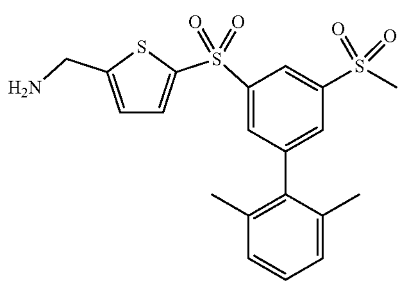 [SMILES: Cc1cccc(C)c1-c1cc(S(C)(=O)=O)cc(S(=O)(=O)c2ccc(CN)s2)c1] | Example 71 | 3.1 | \ | \ | \ | \ | \ |
| 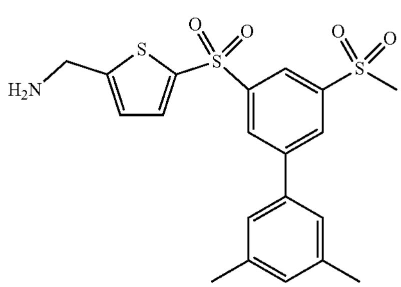 [SMILES: Cc1cc(C)cc(-c2cc(S(C)(=O)=O)cc(S(=O)(=O)c3ccc(CN)s3)c2)c1] | Example 72 | 4.5 | \ | \ | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| [structure] | Example 73 | 2.1 | \ | \ | \ | \ | \ |
| [structure] | Example 74 | 1.4 | \ | \ | >100 | >100 | \ |
| [structure] | Example 75 | 2.5 | \ | \ | \ | \ | \ |
| [structure] | Example 76 | 1.1 | \ | a) 2.0 c) 0.19 | >100 | | >100 |
| [structure] | Example 77 | 1.6 | \ | \ | >100 | >100 | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 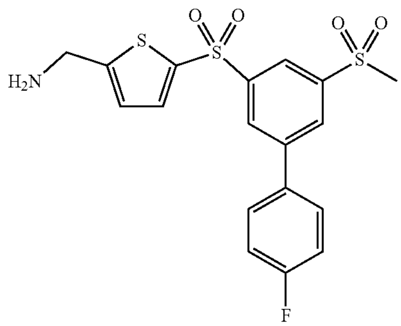 [SMILES: CS(=O)(=O)c1cc(-c2ccc(F)cc2)cc(S(=O)(=O)c2ccc(CN)s2)c1] | Example 78 | 1.9 | \ | \ | 66 | >100 | \ |
| 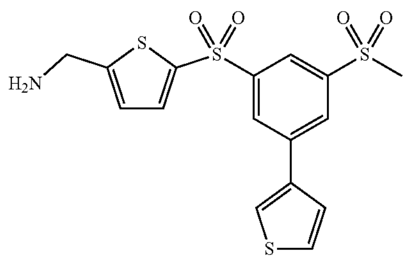 [SMILES: CS(=O)(=O)c1cc(-c2ccsc2)cc(S(=O)(=O)c2ccc(CN)s2)c1] | Example 79 | 3.0 | \ | \ | \ | \ | \ |
| 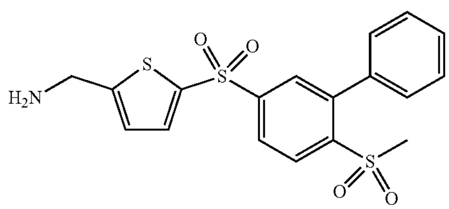 [SMILES: CS(=O)(=O)c1ccc(S(=O)(=O)c2ccc(CN)s2)cc1-c1ccccc1] | Example 80 | 0.77 | \ | \ | 68 | >100 | \ |
| 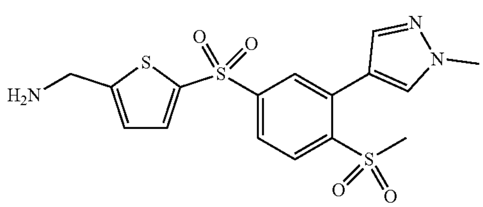 [SMILES: Cn1cc(-c2cc(S(=O)(=O)c3ccc(CN)s3)ccc2S(C)(=O)=O)cn1] | Example 81 | 0.83 | \ | c) 0.38 | >100 | >100 | \ |
| 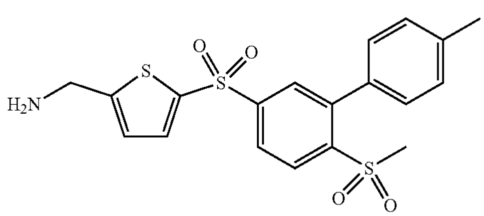 [SMILES: Cc1ccc(-c2cc(S(=O)(=O)c3ccc(CN)s3)ccc2S(C)(=O)=O)cc1] | Example 82 | 0.77 | <0.18 | a) 2.3 c) 0.26 | 31 | >100 | >100 |
| 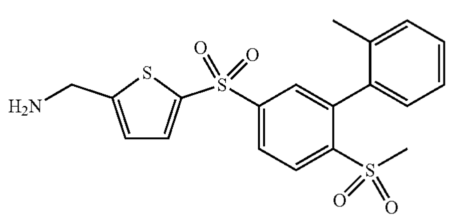 [SMILES: Cc1ccccc1-c1cc(S(=O)(=O)c2ccc(CN)s2)ccc1S(C)(=O)=O] | Example 83 | 1.8 | \ | \ | >100 | >100 | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| [Structure] | Example 84 | 0.91 | \ | c) 0.22 | 12 | >100 | \ |
| [Structure] | Example 85 | 1.4 | \ | \ | >100 | >100 | \ |
| [Structure] | Example 6 | 2.9 | \ | \ | 49 | 100 | \ |
| [Structure] | Example 53 | 1.1 | \ | \ | \ | \ | \ |
| [Structure] | Example 59 | 2.6 | \ | \ | >100 | >100 | \ |
| [Structure] | Example 60 | 1.5 | \ | \ | >100 | >100 | \ |
| [Structure] | Example 86 | 7 | \ | \ | >100 | \ | \ |
| [Structure] | Example 89 | 11 | \ | a) 13 | \ | \ | \ |
| [Structure] | Example 90 | 1.4 | \ | a) 0.77 c) 0.09 | >100 | >100 | \ |

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 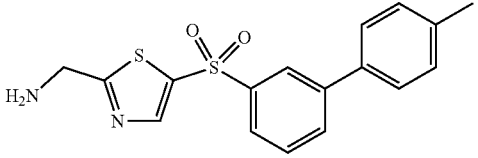 [SMILES: Cc1ccc(-c2cccc(S(=O)(=O)c3cnc(CN)s3)c2)cc1] | Example 91 | 3.3 | \ | c) 0.07 | 27 | 17 | \ |
| 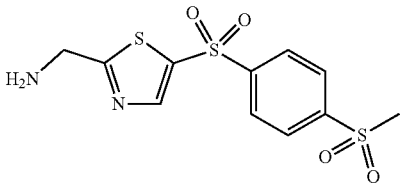 [SMILES: CS(=O)(=O)c1ccc(S(=O)(=O)c2cnc(CN)s2)cc1] | Example 88 | 4.8 | \ | a) 1.5<br>c) 1.3 | \ | \ | \ |
| 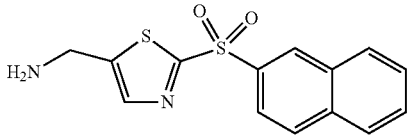 [SMILES: NCc1cnc(S(=O)(=O)c2ccc3ccccc3c2)s1] | Example 87 | 26 | \ | a) 27 | \ | \ | \ |
| 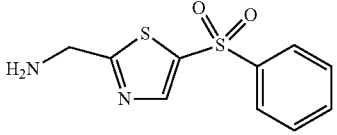 [SMILES: NCc1ncc(S(=O)(=O)c2ccccc2)s1] | Example 92 | \ | \ | a) 2.2<br>c) 0.26 | \ | \ | \ |
| 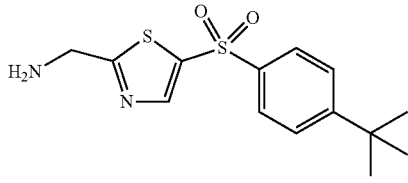 [SMILES: CC(C)(C)c1ccc(S(=O)(=O)c2cnc(CN)s2)cc1] | Example 93 | \ | \ | a) 3.0<br>c) 0.50 | \ | \ | \ |
| 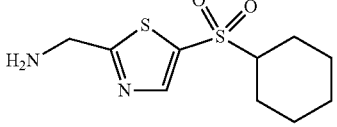 | Example 94 | \ | \ | a) 4.0<br>c) 0.68 | \ | \ | \ |
| 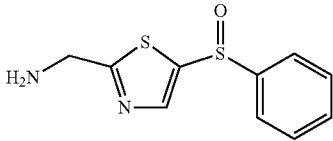 [SMILES: NCc1ncc(S(=O)c2ccccc2)s1] | Example 95 | \ | \ | c) 1.0 | \ | \ | \ |
| 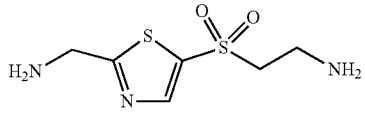 [SMILES: NCCS(=O)(=O)c1cnc(CN)s1] | Example 96 | \ | \ | c) 0.2 | \ | \ | \ |
| 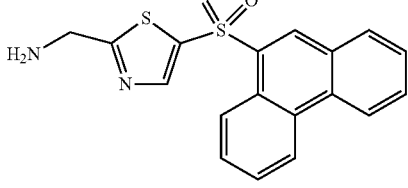 | Example 97 | \ | \ | c) 0.2 | 46 | >100 | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 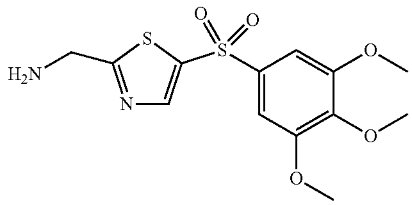 [SMILES: COc1cc(S(=O)(=O)c2cnc(CN)s2)cc(OC)c1OC] | Example 98 | \ | \ | c) 0.64 | \ | \ | \ |
| 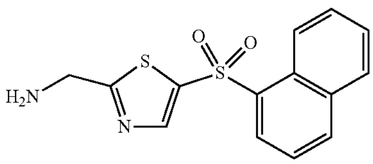 [SMILES: NCc1ncc(S(=O)(=O)c2cccc3ccccc23)s1] | Example 99 | \ | \ | c) 0.068 | \ | \ | \ |
| 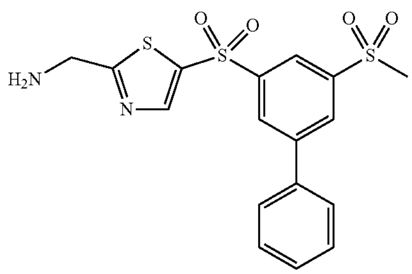 [SMILES: CS(=O)(=O)c1cc(-c2ccccc2)cc(S(=O)(=O)c2cnc(CN)s2)c1] | Example 100 | \ | \ | c) 0.09 | \ | \ | >100 |
| 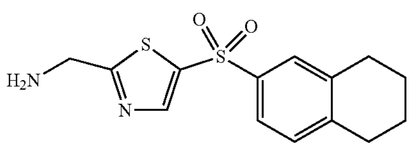 [SMILES: NCc1ncc(S(=O)(=O)c2ccc3c(c2)CCCC3)s1] | Example 101 | \ | \ | c) 0.1 | \ | \ | \ |
| 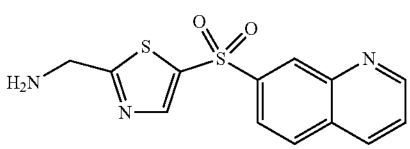 [SMILES: NCc1ncc(S(=O)(=O)c2ccc3cccnc3c2)s1] | Example 102 | \ | \ | c) 0.23 | \ | \ | \ |
| 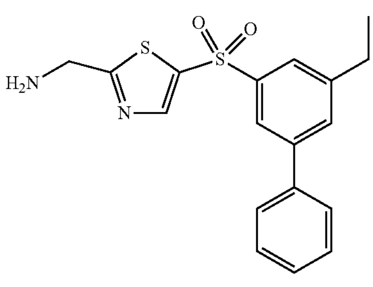 [SMILES: CCc1cc(-c2ccccc2)cc(S(=O)(=O)c2cnc(CN)s2)c1] | Example 103 | \ | \ | c) 0.065 | \ | \ | >100 |
| 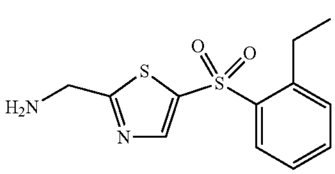 [SMILES: CCc1ccccc1S(=O)(=O)c1cnc(CN)s1] | Example 104 | \ | \ | c) 0.074 | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 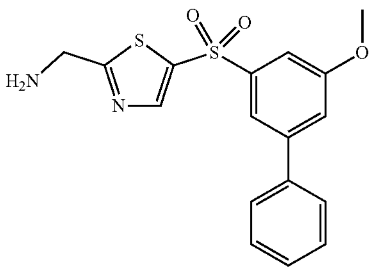 [SMILES: COc1cc(-c2ccccc2)cc(S(=O)(=O)c2cnc(CN)s2)c1] | Example 105 | \ | \ | c) 0.11 | \ | \ | \ |
| 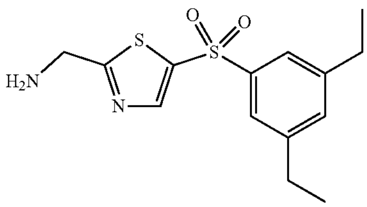 [SMILES: CCc1cc(CC)cc(S(=O)(=O)c2cnc(CN)s2)c1] | Example 106 | \ | \ | c) 0.045 | \ | \ | \ |
| 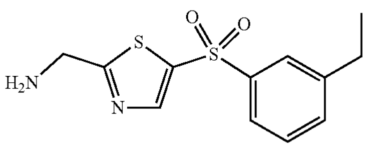 [SMILES: CCc1cccc(S(=O)(=O)c2cnc(CN)s2)c1] | Example 107 | \ | \ | c) 0.056 | \ | \ | \ |
| 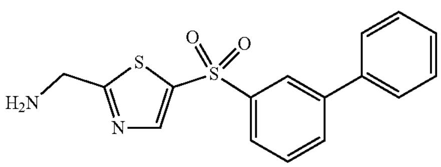 [SMILES: NCc1ncc(S(=O)(=O)c2cccc(-c3ccccc3)c2)s1] | Example 108 | \ | \ | c) 0.06 | \ | \ | \ |
| 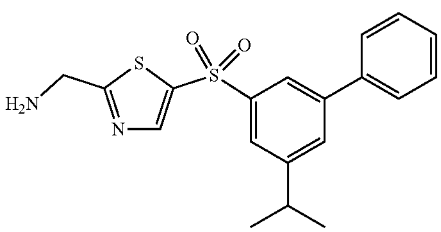 [SMILES: CC(C)c1cc(-c2ccccc2)cc(S(=O)(=O)c2cnc(CN)s2)c1] | Example 109 | \ | \ | c) 0.082 | \ | \ | \ |
| 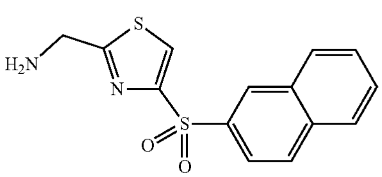 [SMILES: NCc1nc(S(=O)(=O)c2ccc3ccccc3c2)cs1] | Example 110 | \ | \ | c) 0.23 | \ | \ | \ |
| 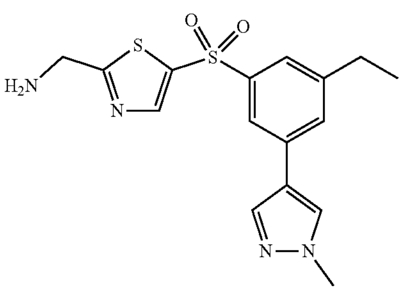 [SMILES: CCc1cc(-c2cnn(C)c2)cc(S(=O)(=O)c2cnc(CN)s2)c1] | Example 111 | \ | 0.19 | c) 0.13 | >100 | >100 | >100 |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 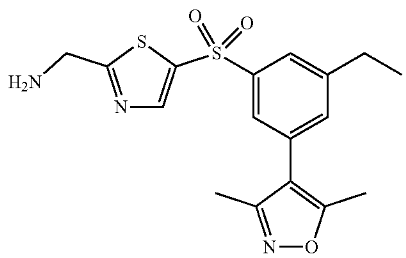 [SMILES: CCc1cc(-c2c(C)noc2C)cc(S(=O)(=O)c2cnc(CN)s2)c1] | Example 112 | \ | \ | b) 0.28 c) 0.15 | \ | \ | \ |
| 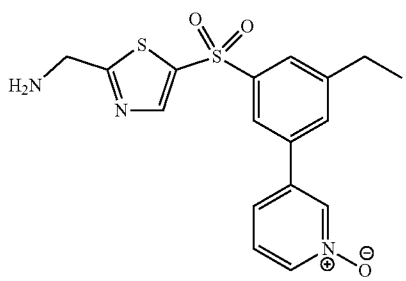 [SMILES: CCc1cc(-c2ccc[n+]([O-])c2)cc(S(=O)(=O)c2cnc(CN)s2)c1] | Example 113 | \ | \ | b) 0.15 c) 0.07 | \ | \ | >100 |
| 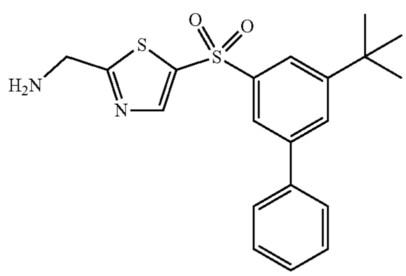 [SMILES: CC(C)(C)c1cc(-c2ccccc2)cc(S(=O)(=O)c2cnc(CN)s2)c1] | Example 114 | \ | \ | b) 1.26 c) 0.17 | \ | \ | \ |
| 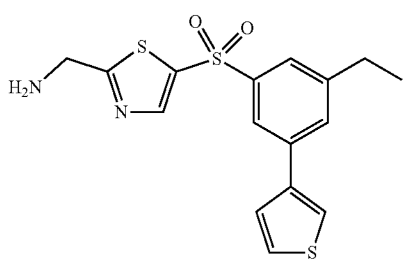 [SMILES: CCc1cc(-c2ccsc2)cc(S(=O)(=O)c2cnc(CN)s2)c1] | Example 115 | \ | \ | b) 0.29 c) 0.14 | \ | \ | \ |
| 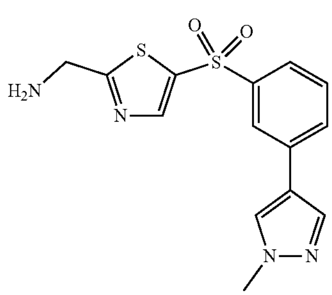 [SMILES: Cn1cc(-c2cccc(S(=O)(=O)c3cnc(CN)s3)c2)cn1] | Example 116 | \ | \ | c) 0.074 | \ | \ | >100 |
| 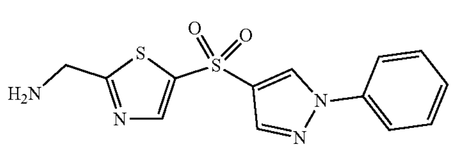 [SMILES: NCc1ncc(S(=O)(=O)c2cnn(-c3ccccc3)c2)s1] | Example 117 | \ | \ | c) 1.0 | \ | \ | \ |

-continued
| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 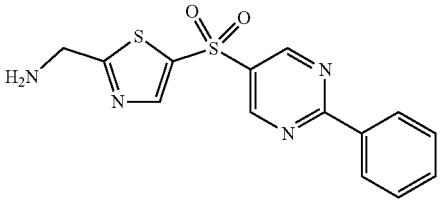 [SMILES: NCc1ncc(S(=O)(=O)c2cnc(-c3ccccc3)nc2)s1] | Example 118 | \ | \ | c) 0.11 | \ | \ | \ |
| 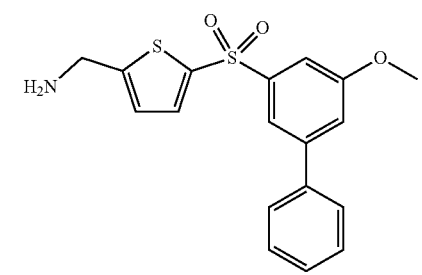 [SMILES: COc1cc(-c2ccccc2)cc(S(=O)(=O)c2ccc(CN)s2)c1] | Example 119 | \ | \ | c) 0.42 | \ | \ | \ |
| 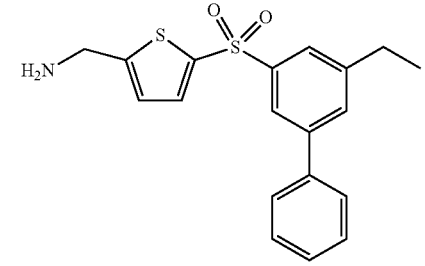 [SMILES: CCc1cc(-c2ccccc2)cc(S(=O)(=O)c2ccc(CN)s2)c1] | Example 120 | \ | \ | c) 0.37 | \ | \ | \ |
| 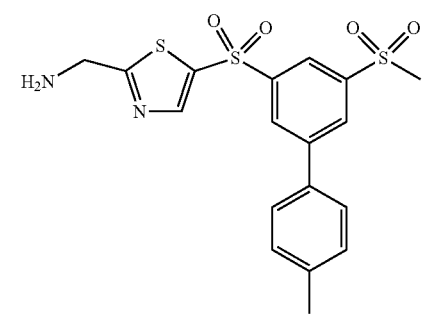 [SMILES: Cc1ccc(-c2cc(S(C)(=O)=O)cc(S(=O)(=O)c3cnc(CN)s3)c2)cc1] | Example 121 | \ | \ | c) 0.028 | 18 | 65 | >100 |
| 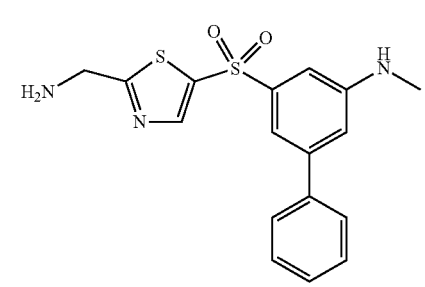 [SMILES: CNc1cc(-c2ccccc2)cc(S(=O)(=O)c2cnc(CN)s2)c1] | Example 122 | \ | \ | c) 0.058 | \ | \ | \ |
| 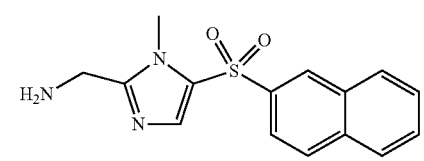 [SMILES: Cn1c(S(=O)(=O)c2ccc3ccccc3c2)cnc1CN] | Example 123 | \ | \ | b) 19 | \ | \ | \ |

-continued
| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 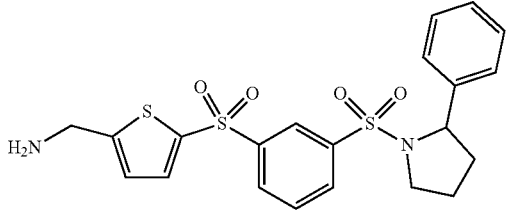 [SMILES: NCc1ccc(S(=O)(=O)c2cccc(S(=O)(=O)N3CCCC3c3ccccc3)c2)s1] | Example 124 | \ | \ | b) 0.12 | \ | \ | \ |
| 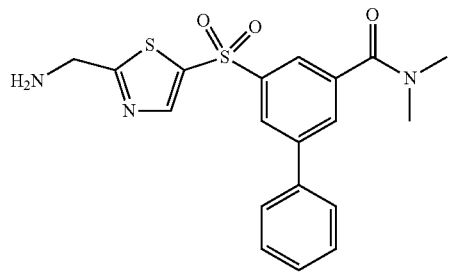 [SMILES: CN(C)C(=O)c1cc(-c2ccccc2)cc(S(=O)(=O)c2cnc(CN)s2)c1] | Example 125 | \ | \ | b) 0.18 | >100 | >100 | >100 |
| 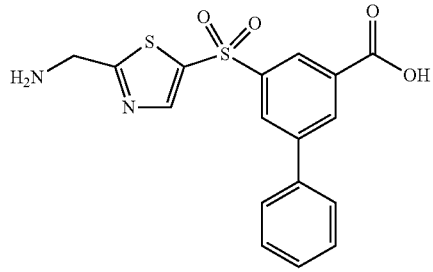 [SMILES: NCc1ncc(S(=O)(=O)c2cc(C(=O)O)cc(-c3ccccc3)c2)s1] | Example 126 | \ | 0.7 | b) 0.24 | >100 | >100 | >100 |
| 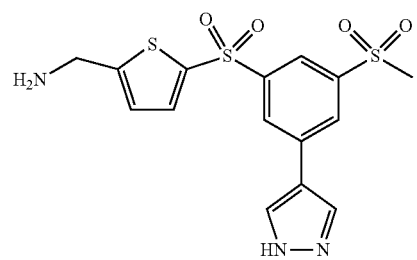 [SMILES: CS(=O)(=O)c1cc(-c2cn[nH]c2)cc(S(=O)(=O)c2ccc(CN)s2)c1] | Example 127 | \ | \ | b) 0.18 | \ | \ | \ |
| 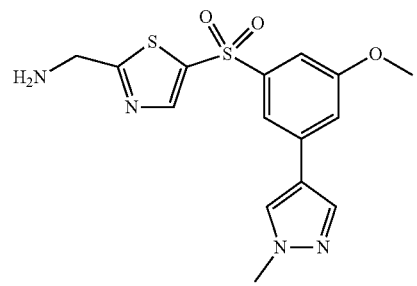 [SMILES: COc1cc(-c2cnn(C)c2)cc(S(=O)(=O)c2cnc(CN)s2)c1] | Example 128 | \ | \ | b) 0.082 | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 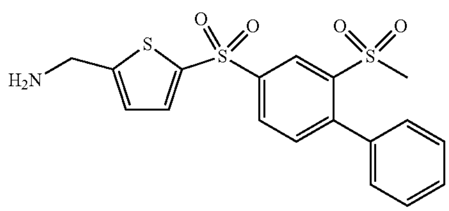 [SMILES: CS(=O)(=O)c1cc(S(=O)(=O)c2ccc(CN)s2)ccc1-c1ccccc1] | Example 129 | \ | \ | b) 0.48 | \ | \ | \ |
| 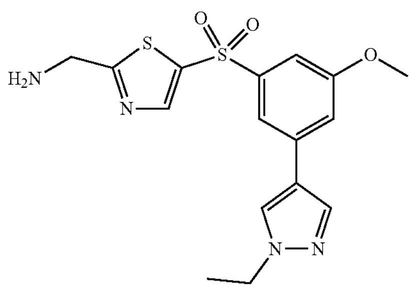 [SMILES: CCn1cc(-c2cc(OC)cc(S(=O)(=O)c3cnc(CN)s3)c2)cn1] | Example 130 | \ | \ | b) 0.094 | \ | \ | \ |
| 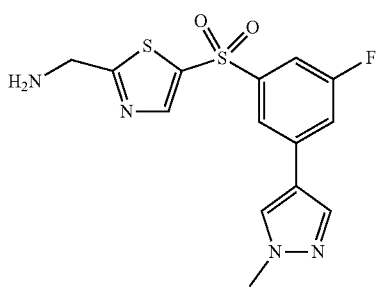 [SMILES: Cn1cc(-c2cc(F)cc(S(=O)(=O)c3cnc(CN)s3)c2)cn1] | Example 131 | \ | \ | b) 0.085 | >100 | >100 | >100 |
| 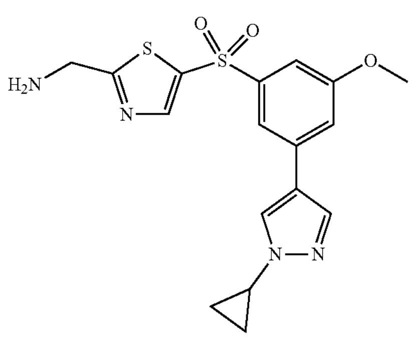 [SMILES: COc1cc(-c2cnn(C3CC3)c2)cc(S(=O)(=O)c2cnc(CN)s2)c1] | Example 132 | \ | \ | b) 0.074 | \ | \ | \ |
| 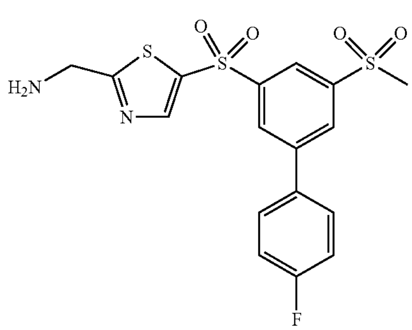 [SMILES: CS(=O)(=O)c1cc(-c2ccc(F)cc2)cc(S(=O)(=O)c2cnc(CN)s2)c1] | Example 133 | \ | \ | b) 0.14 | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 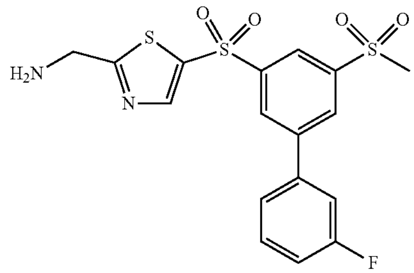 [SMILES: CS(=O)(=O)c1cc(-c2cccc(F)c2)cc(S(=O)(=O)c2cnc(CN)s2)c1] | Example 134 | \ | \ | b) 0.066 | \ | \ | \ |
| 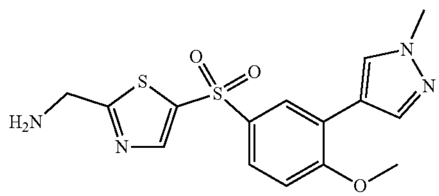 [SMILES: COc1ccc(S(=O)(=O)c2cnc(CN)s2)cc1-c1cnn(C)c1] | Example 135 | \ | \ | b) 0.096 | \ | \ | \ |
| 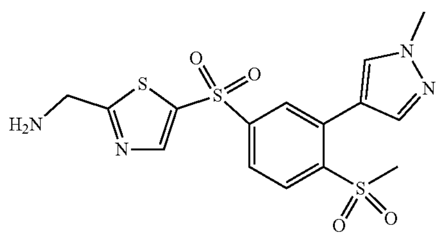 [SMILES: Cn1cc(-c2cc(S(=O)(=O)c3cnc(CN)s3)ccc2S(C)(=O)=O)cn1] | Example 136 | \ | \ | b) 0.089 | \ | \ | \ |
| 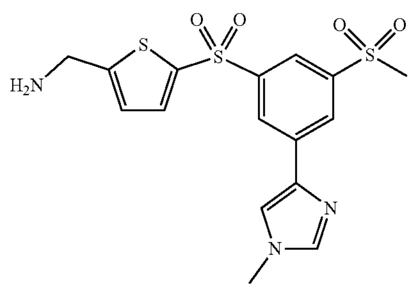 [SMILES: Cn1cnc(-c2cc(S(C)(=O)=O)cc(S(=O)(=O)c3ccc(CN)s3)c2)c1] | Example 137 | \ | \ | b) 0.079 | \ | \ | \ |
| 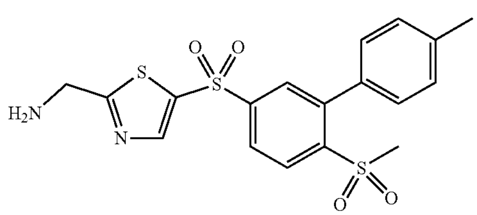 [SMILES: Cc1ccc(-c2cc(S(=O)(=O)c3cnc(CN)s3)ccc2S(C)(=O)=O)cc1] | Example 138 | \ | \ | b) 0.26 | \ | \ | \ |
| 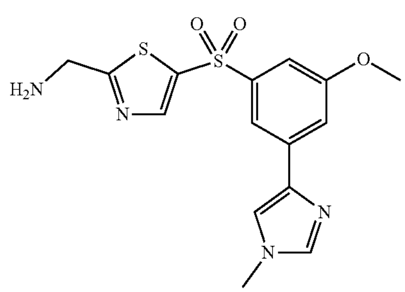 [SMILES: COc1cc(-c2cn(C)cn2)cc(S(=O)(=O)c2cnc(CN)s2)c1] | Example 139 | \ | \ | b) 0.14 | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 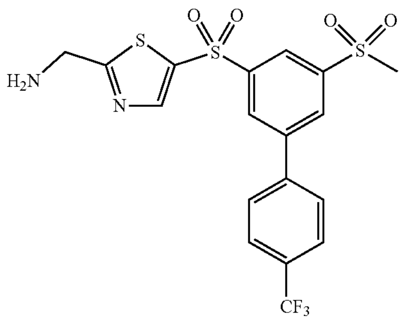 [SMILES: CS(=O)(=O)c1cc(-c2ccc(C(F)(F)F)cc2)cc(S(=O)(=O)c2cnc(CN)s2)c1] | Example 140 | \ | \ | b) 0.17 | \ | \ | \ |
| 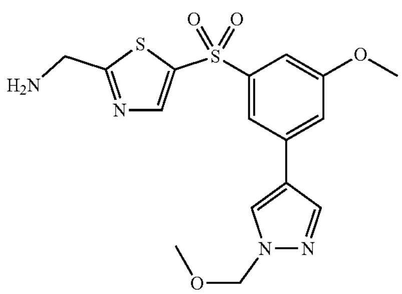 [SMILES: COCn1cc(-c2cc(OC)cc(S(=O)(=O)c3cnc(CN)s3)c2)cn1] | Example 141 | \ | \ | b) 0.072 | \ | \ | \ |
| 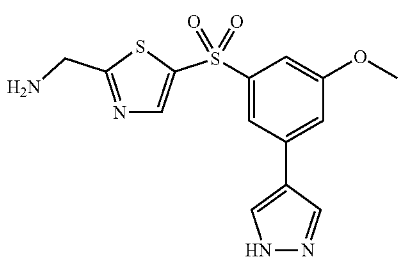 [SMILES: COc1cc(-c2cn[nH]c2)cc(S(=O)(=O)c2cnc(CN)s2)c1] | Example 142 | \ | \ | b) 0.41 | \ | \ | \ |
| 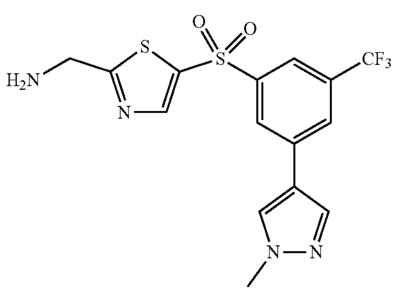 [SMILES: Cn1cc(-c2cc(C(F)(F)F)cc(S(=O)(=O)c3cnc(CN)s3)c2)cn1] | Example 143 | \ | \ | b) 0.31 | \ | \ | \ |
| 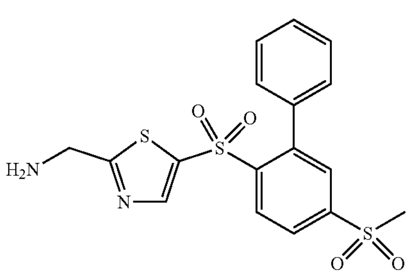 [SMILES: CS(=O)(=O)c1ccc(S(=O)(=O)c2cnc(CN)s2)c(-c2ccccc2)c1] | Example 144 | \ | \ | b) 0.22 | \ | \ | \ |

-continued
| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 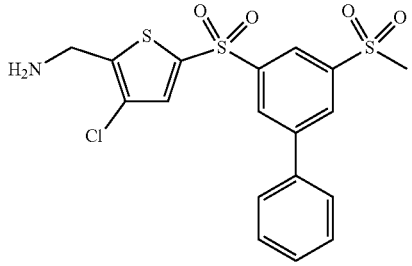 [SMILES: CS(=O)(=O)c1cc(-c2ccccc2)cc(S(=O)(=O)c2cc(Cl)c(CN)s2)c1] | Example 145 | \ | \ | b) 1.8 | \ | \ | \ |
| 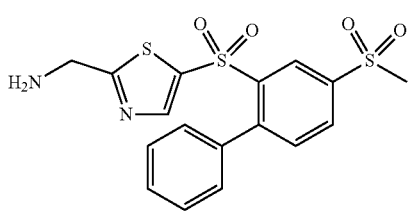 [SMILES: CS(=O)(=O)c1ccc(-c2ccccc2)c(S(=O)(=O)c2cnc(CN)s2)c1] | Example 146 | \ | \ | b) 0.80 | \ | \ | \ |
| 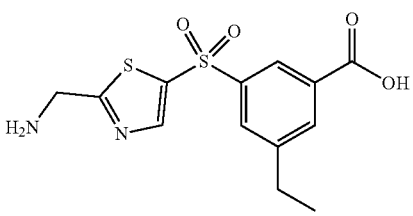 [SMILES: CCc1cc(C(=O)O)cc(S(=O)(=O)c2cnc(CN)s2)c1] | Example 147 | \ | \ | b) 1.9 | \ | \ | \ |
| 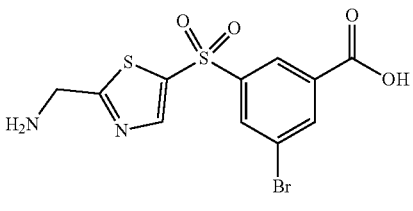 [SMILES: NCc1ncc(S(=O)(=O)c2cc(Br)cc(C(=O)O)c2)s1] | Example 148 | \ | \ | b) 5.0 | \ | \ | \ |
| 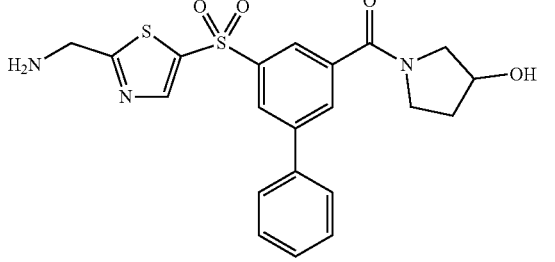 | Example 149 | \ | \ | b) 0.26 | \ | \ | \ |
| 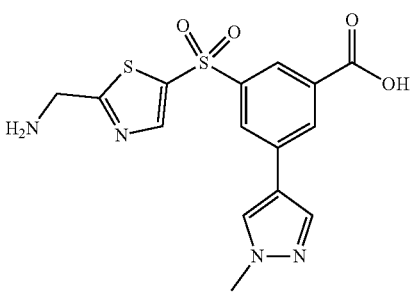 [SMILES: Cn1cc(-c2cc(C(=O)O)cc(S(=O)(=O)c3cnc(CN)s3)c2)cn1] | Example 150 | \ | \ | b) 0.24 | >100 | >100 | >100 |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 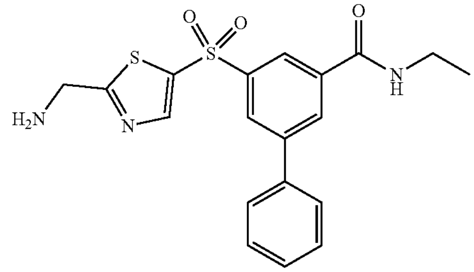 [SMILES: CCNC(=O)c1cc(-c2ccccc2)cc(S(=O)(=O)c2cnc(CN)s2)c1] | Example 151 | \ | \ | b) 0.077 | \ | \ | \ |
| 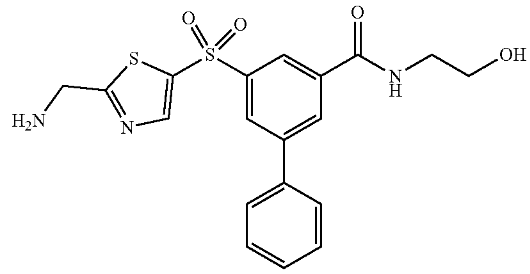 [SMILES: NCc1ncc(S(=O)(=O)c2cc(C(=O)NCCO)cc(-c3ccccc3)c2)s1] | Example 152 | \ | \ | b) 0.56 | \ | \ | \ |
| 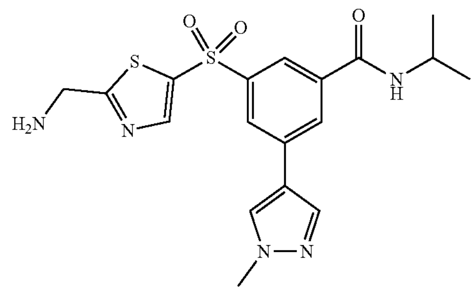 [SMILES: CC(C)NC(=O)c1cc(-c2cnn(C)c2)cc(S(=O)(=O)c2cnc(CN)s2)c1] | Example 153 | \ | \ | b) 0.17 | \ | \ | \ |
| 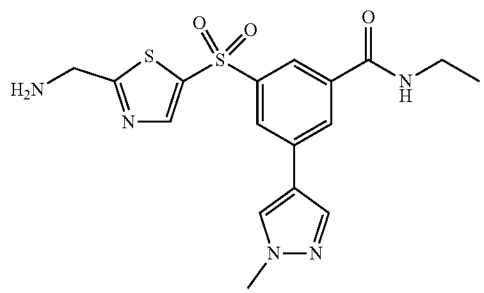 [SMILES: CCNC(=O)c1cc(-c2cnn(C)c2)cc(S(=O)(=O)c2cnc(CN)s2)c1] | Example 154 | \ | \ | b) 0.15 | \ | \ | \ |
| 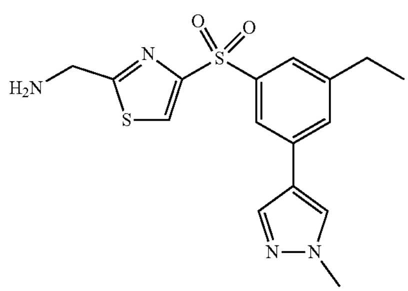 [SMILES: CCc1cc(-c2cnn(C)c2)cc(S(=O)(=O)c2csc(CN)n2)c1] | Example 155 | \ | \ | b) 0.32 | \ | \ | \ |

-continued

| Structure | Example | LOX IC$_{50}$ (μM) | Cyst LOX IC$_{50}$ (μM) | LOXL2 IC$_{50}$ (μM) a) 20 min b) 1 hr c) 20 hr | MAO A IC$_{50}$ (μM) | MAO B IC$_{50}$ (μM) | DAO IC$_{50}$ (μM) |
|---|---|---|---|---|---|---|---|
| 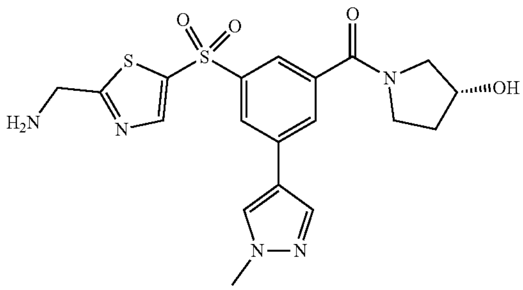 [SMILES: Cn1cc(-c2cc(C(=O)N3CC[C@@H](O)C3)cc(S(=O)(=O)c3cnc(CN)s3)c2)cn1] | Example 156 | \ | \ | b) 0.20 | \ | \ | \ |
| 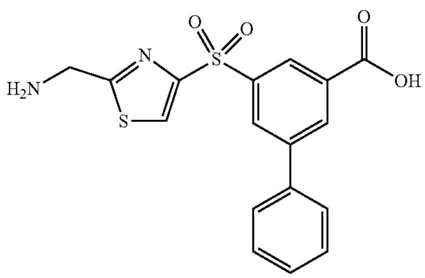 [SMILES: NCc1nc(S(=O)(=O)c2cc(C(=O)O)cc(-c3ccccc3)c2)cs1] | Example 157 | \ | \ | b) 1.6 | \ | \ | \ |
| 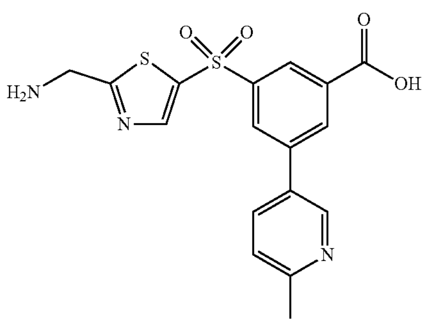 [SMILES: Cc1ccc(-c2cc(C(=O)O)cc(S(=O)(=O)c3cnc(CN)s3)c2)cn1] | Example 158 | \ | \ | b) 0.064 | \ | \ | \ |
| 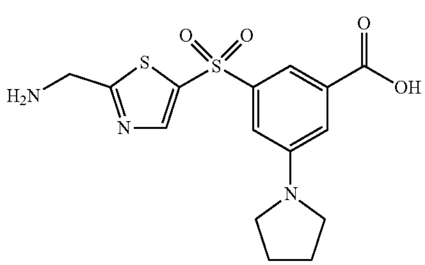 [SMILES: NCc1ncc(S(=O)(=O)c2cc(C(=O)O)cc(N3CCCC3)c2)s1] | Example 159 | \ | \ | b) 0.28 | \ | \ | \ |
| 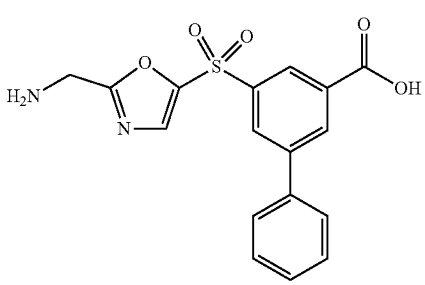 [SMILES: NCc1ncc(S(=O)(=O)c2cc(C(=O)O)cc(-c3ccccc3)c2)o1] | Example 160 | \ | \ | b) 1.1 | \ | \ | \ |

-continued

| Structure | Example | LOX IC$_{50}$ (µM) | Cyst LOX IC$_{50}$ (µM) | LOXL2 IC$_{50}$ (µM) a) 20 min b) 1 hr c) 20 hr | MAO A IC$_{50}$ (µM) | MAO B IC$_{50}$ (µM) | DAO IC$_{50}$ (µM) |
|---|---|---|---|---|---|---|---|
| 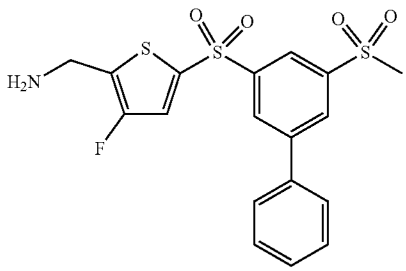 [SMILES: CS(=O)(=O)c1cc(-c2ccccc2)cc(S(=O)(=O)c2cc(F)c(CN)s2)c1] | Example 161 | \ | \ | b) 0.46 | \ | \ | \ |
| 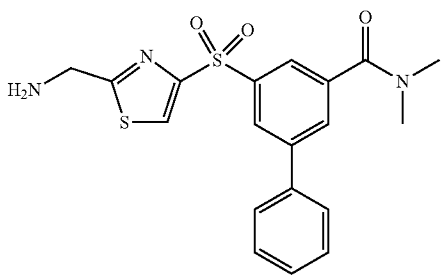 [SMILES: CN(C)C(=O)c1cc(-c2ccccc2)cc(S(=O)(=O)c2csc(CN)n2)c1] | Example 162 | \ | \ | b) 0.31 | \ | \ | \ |
| 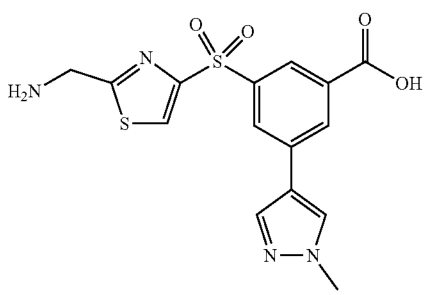 [SMILES: Cn1cc(-c2cc(C(=O)O)cc(S(=O)(=O)c3csc(CN)n3)c2)cn1] | Example 163 | \ | \ | b) 1.9 | \ | \ | \ |
| 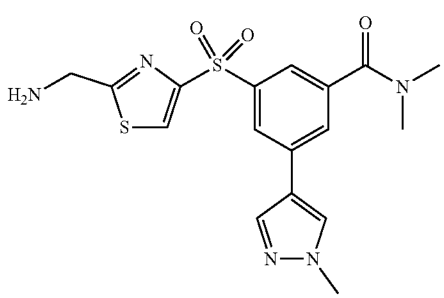 [SMILES: CN(C)C(=O)c1cc(-c2cnn(C)c2)cc(S(=O)(=O)c2csc(CN)n2)c1] | Example 164 | \ | \ | b) 1.2 | \ | \ | \ |

Pharmacokinetic Analysis

Method 1—Dry Blood Spots

For pharmacokinetic analyses, test compound (50 mg/kg in 5% DMSO/aq, 1:19 vv, po n=3 or 10 mg/kg in 10% DMSO/Tween20/saline 10:1:89 vv, iv n=3, were administered to 6 weeks old female, Balb/C and CD1 nude mice from Charles River. Test compound micro blood samples were collected at time points from 5 min-8 h post dose from the tail vein using 20 µl heparinised capillaries then pipetted onto Whatman FTA DMPK-B cards (GE Healthcare) and left to dry overnight.

Test compound solutions (10 mM in DMSO) were used to make stock Standard Curve (SC) and Quality Control (QC) solutions at appropriate concentrations. Blank blood was spiked with stock solutions to produce a final SC concentration of 10, 50, 100, 500 1000, 5000 and 10000 nM; with final QC concentrations of 250 and 7500 nM. SC blood (20 µl) and QC blood (20 µl) was pipetted onto Whatman FTA DMPK-B cards (GE Healthcare) and left to dry overnight. To extract, samples, SC and QC blood spots were punched from Whatman cards with Harris unicore 6 mm punch (GE Healthcare) and placed in a 1 ml 96-well plate. Methanol (200 µl) containing internal standard was added. Samples were vortex mixed for 10 min then centrifuged at 3700 rpm, 4° C. for 5 min. The samples were evaporated under nitrogen and then reconstituted in 30 µl methanol:water (30:70). The plate was vortex mixed and centrifuged for 5 min at 3700 rpm. Extracted samples from test compound were then diluted for analysis by liquid chromatography mass spectrometry (LC-MS/MS) for the compound concentrations. Non-compartmental analysis was performed on concentration data by computer software WinNonlin v6.3.

Method 2—Standard Volume Sampling

Test compound (50 mg/kg in 5% DMSO/aq, 1:19 vv, po n=21 or 10 mg/kg in 10% DMSO/Tween20/saline 10:1:89 vv, iv n=24, were administered to 6 weeks old female, Balb/C and CD1 nude mice from Charles River. Test compound blood samples were collected at time points from 5 min-8 h post by terminal cardic puncture, centrifuged for 3 min at 13000 rpm, plasma collected and snap frozen in Liquid Nitrogen. Samples placed at −80 degrees centigrade until being analysed. Test compound solutions (10 mM in DMSO) were used to make stock Standard Curve (SC) and Quality Control (QC) solutions at appropriate concentrations.

Blank plasma (10 μl) was added to a 96 well plate and spiked with 1 μl of stock solution to produce a final SC concentration of 10, 50, 100, 500 1000, 5000 and 10000 nM; with final QC concentrations of 250 and 7500 nM. Plasma PK samples (10 μl) were added to the 96 well plate and DMSO (1 μl) was added to these samples. SC, QC and plasma samples were extracted with methanol (30 μl) containing internal standard. Following protein precipitation, the samples were centrifuged for 20 minutes in a refrigerated centrifuge (4° C.) at 3700 rpm. The supernatant was diluted and analysed by Liquid Chromatography Mass Spectrometry (LC-MS/MS) for the compound plasma concentrations. Non-compartmental analysis was performed on plasma concentration data by computer software WinNonlin v5.3 or Phoenix WinNonlin v6.3.

TABLE 1a

In vivo pharmacokinetics
PK doses (Mouse = M; Rat = R)
po-50 mg/kg (M); 20 mg/kg (R)
iv-10 mg/kg (M); 4 mg/kg (R)

|  | Example 68 | Example 76 | Example 82 | Example 111 | Example 121 | Example 126 | Example 150 |
|---|---|---|---|---|---|---|---|
| AUC (po, μM · hr) | 15 (M) 0.22 (R) | 11 (M) | 12 (M) | 18 (M) 19 (R) | 46 (M) | 413 (M) 106 (R) | 38 (M) |
| Cmax (po, μM) | 17 (M) 0.34 (R) | 6.7 (M) | 9.4 (M) | 27 (M) 6.5 (R) | 31 (M) | 100 (M) 35 (R) | 10 (M) |
| T1/2 (po, hr) | 0.6 (M) 0.5 (R) | 1.3 (M) | 1.0 (M) | 1.1 (M) 1.3 (R) | 1.1 (M) | 2.3 (M) 1.8 (R) | 2.0 (M) |
| F (%) | — | 45 (M) | 39 (M) | 74 (M) | 48 (M) 68 (R) | — | 67 (M) 33 (R) | — |

AUC = Area under curve
Cmax = Maximum concentration
T1/2 = Half life
F = Bioavailability Blank plasma (50 μl) was added to a 96 well plate and spiked with 5 μl of stock solution to produce a final SC concentration of 10, 50, 100, 500 1000, 5000 and 10000 nM; with final QC concentrations of 250 and 7500 nM. Plasma PK samples (50 μl) were added to the 96 well plate and DMSO (5 μl) was added to these samples. SC, QC and plasma samples were extracted with methanol (150 μl) containing internal standard. Following protein precipitation, the samples were centrifuged for 20 minutes in a refrigerated centrifuge (4° C.) at 3700 rpm. The supernatant was diluted and analysed by Liquid Chromatography Mass Spectrometry (LC-MS/MS) for the compound plasma concentrations. Non-compartmental analysis was performed on plasma concentration data by computer software WinNonlin v5.3 or Phoenix WinNonlin v6.3.

Method 3—Reduced Volume Sampling

Test compound (50 mg/kg in 5% DMSO/aq, 1:19 vv, po n=6 or 10 mg/kg in 10% DMSO/Tween20/saline 10:1:89 vv, iv n=6), were administered to 6 weeks old female, Balb/C and CD1 nude mice from Charles River. Test compound blood samples were collected at time points from 5 min-8 h post from the tail vein using 50 μl heparinised capillaries, centrifuged for 3 min at 13000 rpm, plasma collected and snap frozen in Liquid Nitrogen. Samples placed at −80 degrees centigrade until being analysed. Test compound solutions (10 mM in DMSO) were used to make stock Standard Curve (SC) and Quality Control (QC) solutions at appropriate concentrations.

In Vivo Assessment of LOX Inhibitors

Animal Procedures

All procedures involving animals were approved by the Animal Welfare and Ethical Review Body of the Institute of Cancer Research and Cancer Research UK Manchester Institute in accordance with National Home Office regulations under the Animals (Scientific Procedures) Act 1986 and according to the guidelines of the Committee of the National Cancer Research Institute Tumour size was determined by caliper measurements of tumour length, width and depth and volume was calculated as volume=0.5236× length×width×depth (mm). In accordance with our licence to perform animal experiments, animals were excluded from the experiments if they displayed signs of distress, excessive bodyweight loss (>20%) or illness. Oral tolerability of LOX inhibitors Two CD1 nude female mice at 6 weeks of age from Charles River Labs, dosed po by metal gavage once a day for 4 days with suspension of the test compound at the dose planned for therapy (70 mg/kg/day for the compound of Example 68 and 100 mg/kg/day for the compounds of Examples 76 and 82) in 5.25% Tween20/saline (v:v) at 0.2 ml per 20 g bodyweight.

The mice were observed for up to 15 days after last dose and their bodyweight measured every 4 days. A compound is considered tolerated if the bodyweight does not fall by >20% for >3 days.

Compounds of this invention tested in vivo show good tolerability at the dose tested and <5% bodyweight loss or show bodyweight gain in the tolerability study and in further longer therapy studies.

In Vivo Tumour Models Studies

PDAC allografts: CD1 nu/nu mice at 6 weeks of age, from Charles River Laboratories, were inoculated subcutaneously in the right flank with 2×10$^6$ PDAC TRP53 R172H (p53 mut) cells at 100 ul suspension per animal. Groups of 7-8 mice were assigned to treatment following stratified allocation of tumour volumes with a median size of circa 100 mm$^3$. Dosing commenced around day 10, at 0.2 ml/20 g bodyweight per animal once daily for 2 weeks, with compound dissolved in 5.25% tween20 saline. Control animals received a similar dosage of vehicle (5.25% tween20/saline)

SW620 xenografts: NCr mice were inoculated subcutaneously in the right flank with 5×10$^6$ SW620 cells at 100 ul suspension per animal. Groups of 7-8 mice were assigned to treatment following stratified allocation of tumour volumes with a median size of circa 100 mm$^3$. Dosing commenced around day 10-13 at 0.2 ml/20 g bodyweight per animal once daily for 2 weeks. Dosing administrated by metal gavage orally, at 0.2 ml/20 g bodyweight, compound dissolved in 5.25% tween20 saline. Control animals received a similar dosage of vehicle (5.25% tween20/saline).

MDA-MB-231 xenografts. Ncr nude female mice at 6 weeks old from Charles River were injected into the right mammary fat pad with MDA-MB-231 Luc 4×10$^{\wedge}$6 in 100 ul PB (50:50 Matrigel). When tumours reach a mean of 80 mm$^3$ around 10 days post cell inoculation the animals are allocated in 4 groups of 8. LOX inhibitor treatment is then administrated by oral gavage dosing, at 0.2 ml/20 g bodyweight once daily for up to 28 consecutive days. Tumours and weights are measured twice weekly using calipers and the animals can be imaged using non invasive method by bioluminescence using IVIS 200 imaging machine, weekly using 150 mg/kg luciferin administrate intraperitoneal or subcutaneous. At the end of the study the animals are culled, and samples taken, fixed and or snap frozen in liquid nitrogen. Frozen samples kept at −80 degree centigrade until being analyzed and the fixed will be stain accordingly to our interests.

LOX Inhibitor Treatment of a Transgenic Mouse Breast Cancer Model

MMTV-PyMT (Guy et al, 1992) (FVB) female mice were selected randomly for LOX inhibitor treatments from day 70 post-birth, when animals had no detectable tumour. Mice were treated daily with LOX inhibitor (for example 70 mg/kg of the compound of Example 68) in vehicle, or daily vehicle (5% DMSO/2.5% Tween20 in water) by oral gavage. Mammary tumours and lungs were collected when the primary tumours reached ethical limits.

For therapeutic efficacy assessment, the ratio of average tumour volume between compound treated and vehicle control treated (T/C) is calculated. Reduction in tumour volume in the compound treated group compared to vehicle-treated control group results in T/C<1. The efficacy of LOX inhibitors described in this invention, as measured by T/C in a pancreatic cancer model, a colorectal cancer model and a breast cancer model is shown in Table 2 and is significant ($p<0.05$) for all the data presented.

For lung metastases quantification, samples were sectioned and H&E stained. Samples were imaged with a Leica SCN400 slide scanner. Lung mets were manually selected using Pen tool in ImageScope. Lung mets number was counted and area was measured using ImageScope. The ratio of average metastases surface between compound treated and vehicle control treated (T/C) is calculated. Reduction in metastases area in the compound treated group compared to vehicle-treated control group results in T/C<1. The antimetastaticefficacy of LOX inhibitors described in this invention, as measured by T/C in a model of breast cancer metastasising to lungs is shown in Table 2 and is significant ($p<0.05$) for all the data presented.

TABLE 2

Tumour Model Studies
Therapeutic Efficacy:
Primary tumour: Ratio of Tumour Volume (treated)/Tumour Volume (Control)
Metastasis: Ratio of metastatic surface area (treated)/metastatic surface area (Control)

| Model | Example 68 | Example 76 | Example 82 | Example 111 | Example 121 | Example 126 | Example 118 |
|---|---|---|---|---|---|---|---|
| PDAC R172H (p53 mut) (mouse pancreatic carcinoma)-primary tumour | 0.53 (70 mg/kg qd) | | | | | | |
| SW620 human colorectal carcinoma cells (mutant RAS)-primary tumour | | 0.56 (100 mg/kg qd) | 0.48 (100 mg/kg qd) | | | | |
| MDA-MB-231 (human breast adenocarcinoma)-primary tumour | 0.46 (100 mg/kg qd) | | | 0.53 (100 mg/kg qd) | 0.55 (100 mg/kg qd) | 0.46 (100 mg/kg qd) | 0.48 (100 mg/kg qd) |
| MMT-PyMT breast transgenic model-primary tumour | 0.40 (70 mg/kg qd) | | | | 0.26 (100 mg/kg qd) | 0.44 (100 mg/kg qd) | |

TABLE 2-continued

Tumour Model Studies
Therapeutic Efficacy:
Primary tumour: Ratio of Tumour Volume (treated)/Tumour Volume (Control)
Metastasis: Ratio of metastatic surface area (treated)/metastatic surface area (Control)

| Model | Example 68 | Example 76 | Example 82 | Example 111 | Example 121 | Example 126 | Example 118 |
|---|---|---|---|---|---|---|---|
| MMT-PyMT breast transgenic model-metastasis | 0.57 (70 mg/kg qd) | | | 0.14 (100 mg/kg qd) | | | |

Significant, p < 0.05

Immunofluorescence

All samples were fixed in 4% paraformaldehyde (EMS). Fixed cells were then subjected to incubation with primary antibodies followed by fluorescence secondary antibodies (Life Technologies) to visualise extracellular proteins. Anti-human MATN2 (R&D) antibody was used at 1:100 dilutions. DAPI (Sigma) was used to stain DNA.

RNA Interference

To generate stable LOX depleted MDA-MB-231 and U87 cell lines, shLOXA (TTGTTATTGAAAACAGTCC, V3LHS_406838, Dharmacon) targeting human LOX, and shLOXB (ACATCTGTAATATCAATCC, V3LHS_348880, Dharmacon) targeting mouse and human LOX was used. GIPZ non-silencing shRNA from Dharmacon was used as control (shCtl) in MDA-MB-231 and U87 cells. Stable LOX depletion in BJ fibroblasts was achieved by using a lentivirus (shLOXC) containing human specific LOX targeting shRNA (CGACAACCCTTATTACAACTA, TRCN00-00045991, Sigma). For BJ fibroblasts, a lentivirus containing pLKO.1 non-targeting shRNA (shCtl) from Sigma was used as control.

For transient reduction of protein expressions, MDA-MB-231 or U87 cells were transfected with specific siRNAs from Qiagen. For LOX reduction, human specific siLOX #1 (AAGCTGGCTACTCGACATC, S100036120), or mouse and human specific siLOX #2 (CTGCACAATTT-CACCGTAT, S100036113) was used. To reduce MATN2 protein expression, siMATN2 (ATGCCGAA-GACTTCAGCACAA, S104169795) was used. AllStars negative control siRNA (siCtl) from Qiagen was used as a control.

Western Blotting

Proteins were extracted from cultured cells using cell lysis buffer (Cell Signalling Technology) with the addition of protease and phosphatase inhibitor cocktails (Pierce). Protein concentrations were measured using Pierce 660 nm protein assay reagent and SpectaMax M5 plate reader. Equal amounts of proteins were then separated using NuPAGE 4-12% Bis-Tris gels with NuPAGE MOPS SDS running buffer (Life Technologies). Separated proteins were transferred to nitrocellulose membranes using a Trans-Blot turbo transfer system (Bio-Rad). Following blocking with Odyssey blocking buffer (Li—COR), membranes were incubated with two primary antibodies of different species at 4° C. over night. Corresponding fluorescence secondary antibodies (Li—COR) of different excitation and emission wavelengths were used to visualize the protein of interest on an Odyssey CLx infrared imaging system (Li—COR). Quantification of band fluorescence intensity was achieved using Li-COR ImageStudio. The following primary antibodies were used, anti-LOX (Sigma), anti-human MATN2 (R&D), anti-EGFR and anti-pY1068EGFR (Cell Signalling Technology), and anti-GAPDH (Millipore).

Homotrimeric HTRA1 in cell culture medium was resolved using NativePAGE (Life Technologies). Extracellular proteins in 15 ml serum free cell culture medium with protease inhibitors was first concentrated using Vivaspin protein concentrator spin columns (GE Healthcare Life Sciences). Proteins in concentrated culture medium was then separated using NativePAGE 3-12% Bis-Tris Gel and NativePAGE running buffer (Life Technologies). Separated proteins were transferred to nitrocellulose membranes using a Trans-Blot turbo transfer system (Bio-Rad) as normal. Followed by standard blotting procedures as described above. Anti-human HTRA1 antibody (R&D) was then used to detect native HTRA1 proteins.

Quantitative Real Time PCR

RNA was extracted with Trizol (Life Technologies) according to the manufacturer's instruction. RNA was reverse-transcribed to generate complementary DNA using M-MLV Reverse Transcriptase (Sigma). Real-time qRT-PCR was performed with FastStart Universal Probe Master (Rox) (Roche) and TaqMan Gene Expression Assay probes on an Applied Biosystems 7900HT Fast Real Time machine. Relative MATN2 (hs00242753_m1, Life Technologies) expression was calculated using the $\Delta Ct$ method and housekeeping genes (GAPDH) as an internal control.

PathScan RTK Signalling Antibody Array

Cell lysates of MDA-MB-231 cells cultured either on plastic or in 3D collagen gel was collected using cell lysis buffer (Cell Signalling Technology) with protease and phosphatase inhibitor cocktails (Pierce). PathScan RTK signalling antibody array (Cell Signalling Technology) was then performed according to manufacture's instructions using equal amounts of proteins. The fluorescent readout was recorded on an Odyssey CLx infrared imaging system (Li—COR). Quantification of the array fluorescent intensity was achieved using Li-COR ImageStudio.

Labelling and Detection of Surface EGFR

Following 100 ng/ml EGF stimulation cells were washed with ice cold PBS and then incubated with ice cold 0.24 mg/ml Sulfo-NHS-SS-Biotin (Pierce) in PBS for 30 min at 4° C. Excessive Sulfo-NHS-SS-Biotin was then blocked using 50 mM $NH_4Cl$ in PBS and washed using ice cold PBS. Cells were subsequently lysed using cell lysis buffer (Cell Signalling Technology) with the addition of protease and phosphatase inhibitor cocktails (Pierce). Protein concentrations were determined as described above. Equal amount of protein was used for immunoprecipitation at room temperature using NeutrAvidin Agarose beads (Pierce) for 1 h. Precipitated surface proteins were subjected to Western blotting.

Cell Viability Assay

2000 MDA-MB-231 or U87 cells were seeded on Day 0 in 96-well plates. Cells were culture in EGF only culture medium. Cell viability was then tested using CellTiter-Glo luminescent assay (Promage) corroding to manufacture's protocol on indicated days. Student's t-Test was used to calculate the statistical significance. Data were normalised to the reading on Day 1.

Lung Deposition Assay

Female CD1 nude mice (Charles River) were tail vein injected to study lung deposition of control or LOX depleted MDA-MB-231 cells. Each animal was tail vein injected with $1\times10^5$ MDA-MB-231 cells in PBS. Lungs were collected when animals had lost 10% body weight or had developed breathing difficulties. Otherwise lungs were collected 50 days post-injection.

Histology and Immunohistochemistry

All mouse tissue samples were fixed in 10% formalin (Sigma) and embedded in paraffin. Samples were then sectioned, and hematoxylin and eosin (H&E) stained using standard protocols. H&E stained samples were imaged with a Leica DM4000 upright microscope. To quantify malignant deposits in the lungs following tail vein injection of MDA-MB-231 cells, the proportion of lung parenchyma occupied was assessed and scored according to the proportion of occupied lung parenchyma. For spontaneous lung metastasis in MMTV-PyMT animals treated with either water or LOX inhibitors, we counted the number of lung metastasis in the lung parenchyma ranked by size, and a lung metastasis score was assigned accordingly (Table 3).

TABLE 3

Tumour Model Studies
Therapeutic Efficacy in Metastatic model:
MMTV-PyMT breast transgenic model
Number and score of lung metastasis

|  | Mouse | Number of metastases | | | Score |
|---|---|---|---|---|---|
|  |  | Small | Medium | Large |  |
| DMSO control | 1 | 7 | 0 | 5 | 22 |
|  | 2 | 2 | 1 | 4 | 16 |
|  | 3 | 7 | 4 | 1 | 18 |
|  | 4 | 1 | 2 | 9 | 32 |
|  | 5 | 0 | 4 | 15 | 53 |
|  | 6 | 1 | 4 | 0 | 9 |
| Example 68 | 7 | 0 | 0 | 0 | 0 |
|  | 8 | 0 | 0 | 0 | 0 |
|  | 9 | 0 | 1 | 0 | 2 |
|  | 10 | 0 | 1 | 0 | 2 |
|  | 11 | 0 | 1 | 0 | 2 |
|  | 12 | 1 | 1 | 0 | 3 |

Legend:

| Size | | Score |
|---|---|---|
| None | 0 | 0 |
| Small | <100 μm | 1 |
| Medium | 100 μm-200 μm | 2 |
| Large | >200 μm | 3 |

To visualise MATN2 and EGFR in mouse tissue samples, sectioned samples were processed as previously described (Viros, 2014). Anti-Mouse MATN2 (R&D) was used at 1.100 dilution. Anti-EGFR (Abcam) was used at 1:200 dilution. Corresponding fluorescence secondary antibodies (Life Technologies) were then used for confocal imaging of tissue samples.

REFERENCES

Guy, C. T., Cardiff, R. D. & Muller, W. J. Induction of mammary tumors by expression of polyomavirus middle T oncogene: a transgenic mouse model for metastatic disease. Mol Cell Biol 12, 954-961 (1992)

Hanson, G. T., Aggeler, R., Oglesbee, D., Cannon, M., Capaldi, R. A., Tsien, R. Y., Remington J. S. (2004). Investigating mitochondrial redox potential with redox-sensitive green fluorescent protein indicators. J. Biol. Chem. 279, 13044-13053.

Viros A, Sanchez-Laorden B, Pedersen M, Furney S J, Rae J, Hogan K, Ejiama S, Girotti M R, Cook M, Dhomen N, Marais R. Ultraviolet radiation accelerates BRAF-driven melanomagenesis by targetin Results LOX Inhibition Reduces EGFR Pathway Signalling LOX Depletion Reduces EGFR Phosphorylation To discover new functions for LOX, we examined how LOX depletion by short-hairpin RNA (shRNA) affects cancer cell signalling. Using a receptor tyrosine kinase (RTK) antibody array, we find that when LOX is depleted in MDA-MB-231 breast cancer cells grown in standard plastic (2D) culture conditions, phosphorylation of several receptor tyrosine kinases (RTKs) including the EGF receptor (EGFR) is reduced (FIG. 1a). We repeated the analysis in collagen gels (3D) and again observed consistent reduction of EGFR phosphorylation when LOX was depleted (FIG. 1b).

Figure 2:
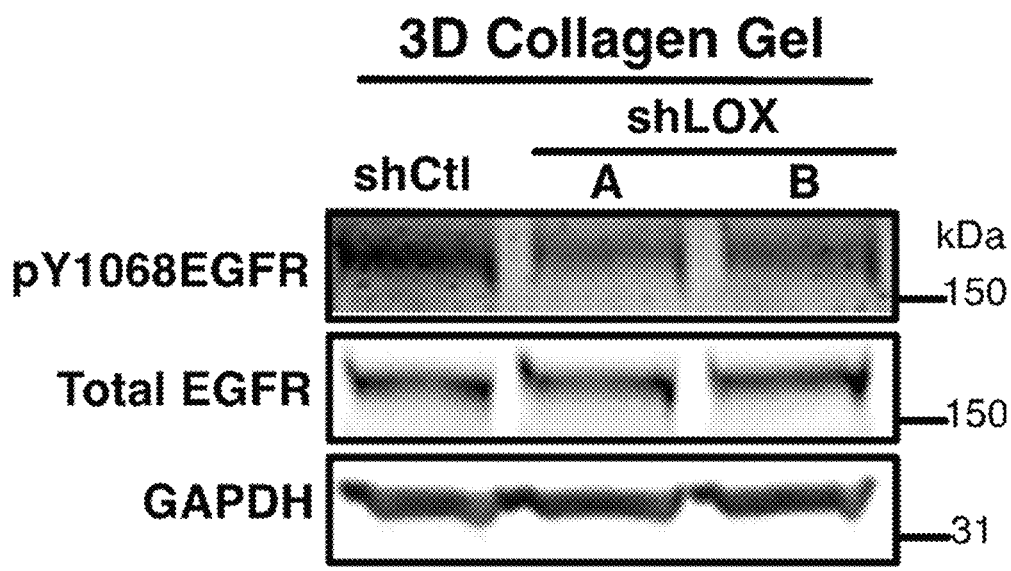
FIG. 2 shows a western blot of phospho-EGFR, EGFR and GAPDH in control (shCtl) or LOX-depleted (shLOXA, shLOXB) MDA-MB-231 breast cancer cells in collagen gels.

Western blot of phospho-EGFR, EGFR and GAPDH in control (shCtl) or LOX-depleted (shLOXA, shLOXB) MDA-MB-231 cells in collagen gels confirmed the effect of LOX depletion in reducing EGFR phosphorylation (pY1068EGFR; FIG. 2).

LOX Drives EGF Signalling by Trapping EGFR on the Cell Surface

Figure 3:
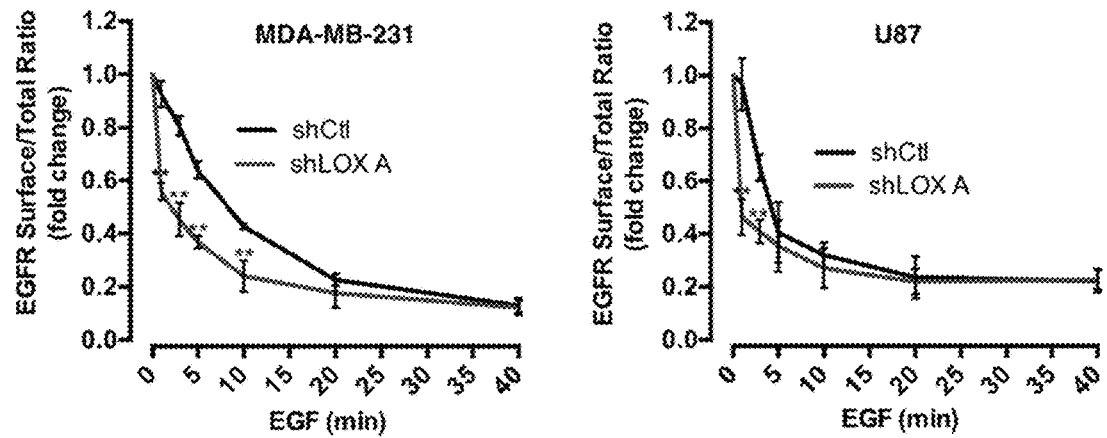
FIG. 3 shows the EGFR surface/total ratio (fold change) in control (shCtl) and Lox-depleted (shLOX) in EGF stimulated and subsequent surface protein biotin labelled: a) MDA-MB-231 breast cancer cells and b) U87 glioblastoma cells.

MDA-MB-231 breast cancer cells and U87 glioblastoma cells had LOX stably depleted with shLOX, stimulated with EGF and then surface proteins were labelled with biotin. LOX depletion does not affect cell surface levels of EGFR in serum free conditions in MDA-MB-231 cells or U87 glioblastoma cells, but when the cells were EGF stimulated, EGFR was internalised more rapidly in LOX deficient cells (FIG. 3a,b).

Figure 4:
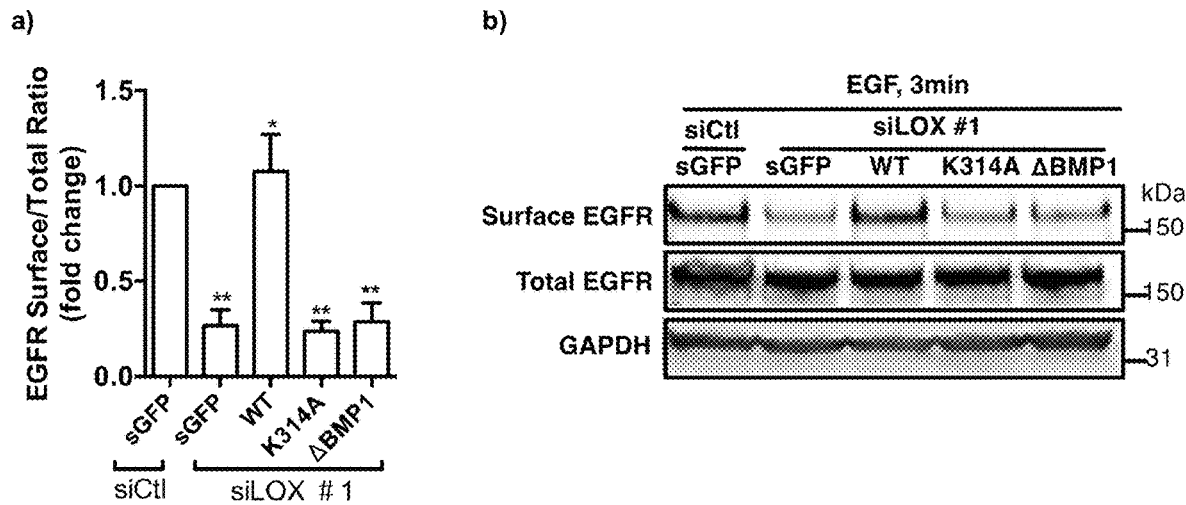
FIG. 4 shows the EGFR surface/total ratio (fold change) in control (siCtl) and siRNA-insensitive active LOX-GFP and inactive mutants LOXK314A-GFP and LOXΔBMP-1-GFP in MDA-MB-231 cells.

Critically, the stabilisation of surface EGFR requires enzymatically active LOX. In LOX-depleted cells, EGFR retention at the plasma membrane of MDA-MB-231 cells can only be rescued by a siRNA-insensitive active LOX-GFP, whereas inactive mutants LOXK314A-GFP and LOXΔBMP-1-GFP did not rescue EGFR membrane retention (FIG. 4a,b).

Figure 5:
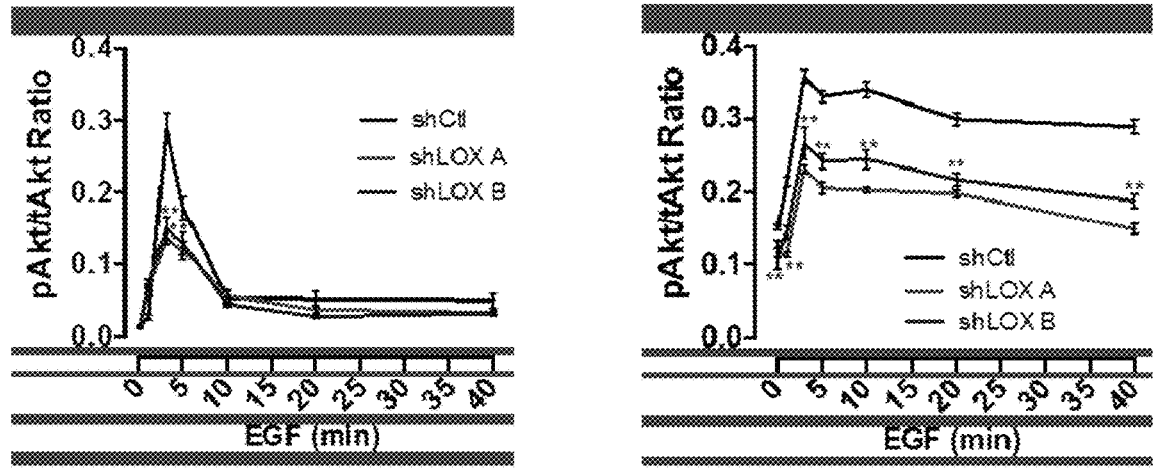
FIG. 5 shows the ratio of phosphorylated to total AKt for EGF stimulated control (shCtl) and LOX-depleted (shLOX A and shLOXB): a) MDA-MB-231 cells and b) U87 glioblastoma cells.

EGFR signal downstream through a number of signalling cascades, notably PI3K/Akt. The phosphorylation of Akt was reduced by LOX depletion in EGF-stimulated MDA-MB-231 breast cancer cells and U87 glioblastoma cells, in agreement with faster loss of EGFR from cell surface leading to inhibition of downstream signalling. (FIG. 5a,b).

Figure 6:
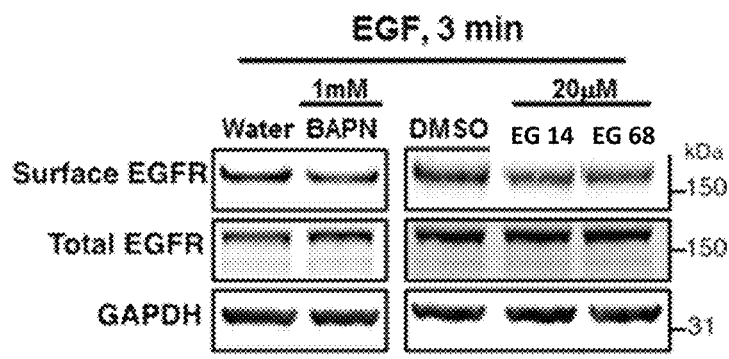
FIG. 6 shows surface EGFR, total EGFR and GAPDH in water, DMSO and LOX inhibited (BAPN, Example 14 and Example 68) MDA-MB-231 cells following stimulation with EGF for 3 minutes.

The LOX inhibitors described herein display similar effects of inhibition of the EGFR signalling. Exemplification of LOX inhibitors reduction of surface EGFR in EGF-stimulated MDA-MB-231 cell line is shown in FIG. 6.

Figure 7:
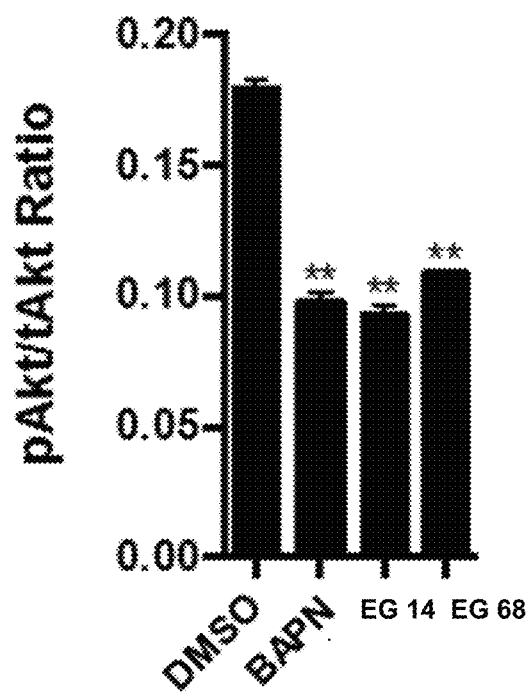
FIG. 7 shows the ratio of phosphorylated to total AKT in MDA-MB-231 cells treated with DMSO or a LOX inhibitor (BAPN, Example 14, Example 68). The compounds of Examples 14 and 68 were tested at 20 μM concentration; BAPN was used at 1 mM. A

Similarly, LOX inhibitors show reduced Akt phosphorylation in EGF stimulated MDA-MB-231 cell line compared to vehicle control (FIG. 7, Table A with cellular data for compounds).

Thus, LOX modulates retention of EGFR at the cell surface, and when LOX is depleted, EGF signalling is impaired. Critically, when endogenous LOX is depleted, an siRNA-insensitive LOX-GFP (data not shown) rescues EGFR plasma membrane retention, and EGFR and Akt activation, whereas a LOX catalytic activity mutant (LOXK314A-GFP) or LOX lacking the BMP1 site necessary for maturation (LOXΔBMP-1-GFP)6 do not rescue these events (FIG. 1g-i).

Thus, EGFR cell surface retention is dependent on LOX maturation and catalytic activity.

Figure 8:
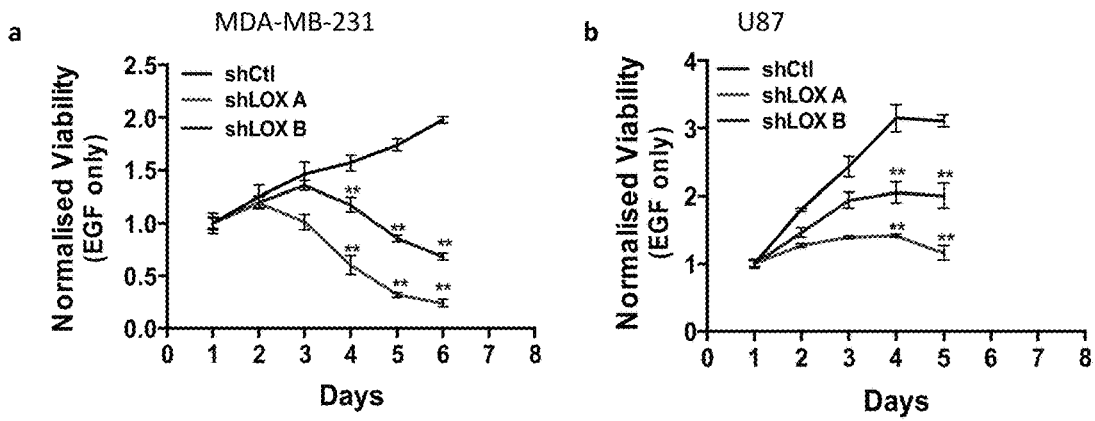
FIG. 8 shows the normalised viability of control (shCtl) and LOX-depleted (shLOX A and shLOXB): a) MDA-MB-231 cells and b) U87 glioblastoma cells cultured in medium with EGF as the only growth factor.

LOX Inhibition Blocks the Proliferation of Breast Cancer and Glioblastoma Models When cultured in medium with EGF as the only growth factor, LOX-depleted MDA-MB-231 or U87 cells have a significantly reduced proliferation compared to non-transfected cells (FIG. 8a,b).

Figure 9:
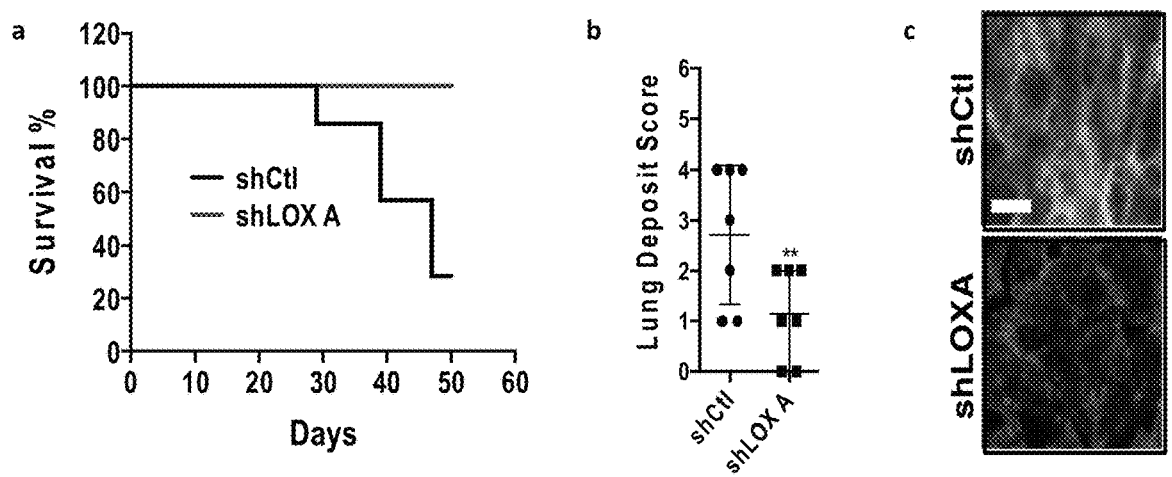
FIG. 9 shows the a) percentage survival, b) lung deposit score and plasma membrane of mice injected via tail vein with LOX-depleted (shLOX A) or control (shCtl) MDA-MB-231 cells.

LOX-depleted or control MDA-MB-231 cells were injected via tail vein in mice. After 50 days, animals that received LOX-depleted cells had all survived compared to only 2/7 of the control group and had a reduced lung tumour burden (FIG. 9a, b). In the LOX depleted tumours, EGFR localisation to the plasma membrane was disrupted (FIG. 9c).

Figure 10:
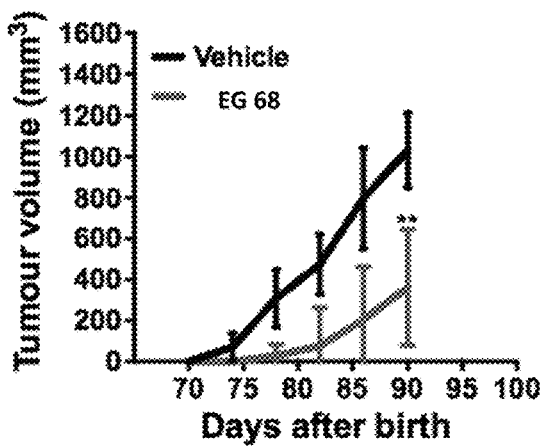
FIG. 10 shows the tumour volume over time in the transgenic mouse breast model driven by polyoma middle T (PyMT) for LOX inhibitor treated (Example 68) and control (vehicle).

LOX inhibitor of Example 68 also shows a significant tumour growth delay in the transgenic mouse breast model driven by polyoma middle T (PyMT)(FIG. 10). The tumour volume ratio of treated vs control is shown in Table 2 of the in vivo therapeutic efficacy section.

The compound of Example 68 described herein inhibits LOX at 0.89 µM. It is more selective than BAPN, because although neither inhibits the amine oxidases MAO-A or MAO-B, the compound of Example 68 also does not inhibit the plasma amine oxidase DAO or hERG. Further, it displays excellent stability in mouse liver microsomes. It is orally bioavailable, displays good pharmacokinetic properties and is well tolerated in mice at 150 mg/kg/day.

EGFR is overexpressed and drives tumour progression in a number of cancers, for example lung, glioma, colorectal, head & neck cancer, triple negative breast cancer. We have demonstrated that LOX drives tumour progression by increasing EGFR pathway signalling via EGFR trapping at the cell surface. We have also shown that LOX inhibition disrupts EGFR membrane localisation, reduces EGFR signalling, and suppresses tumour growth and metastasis. We expect that LOX inhibitors will be useful in the treatment of EGFR-driven cancers.

LOX Upregulates Matrilin2, which Traps EGFR on the Cell Surface

MATN2 is a secreted protein with 10 EGF-like repeats and we find that recombinant human MATN2 (rhMATN2) binds to the surface of cells, but that this binding is competed off by EGF and an EGFR neutralizing rhMATN2 increases the levels of EGFR at the cell surface. Moreover, depletion of endogenous MATN2 causes EGFR loss from the cell surface and this is rescued by rhMATN2 addition to the culture medium. Although rhMATN2 itself does not activate the EGFR, it strongly enhances EGF-induced EGFR.

LOX Depletion or Inhibition Downregulates MATN2

Figure 11:
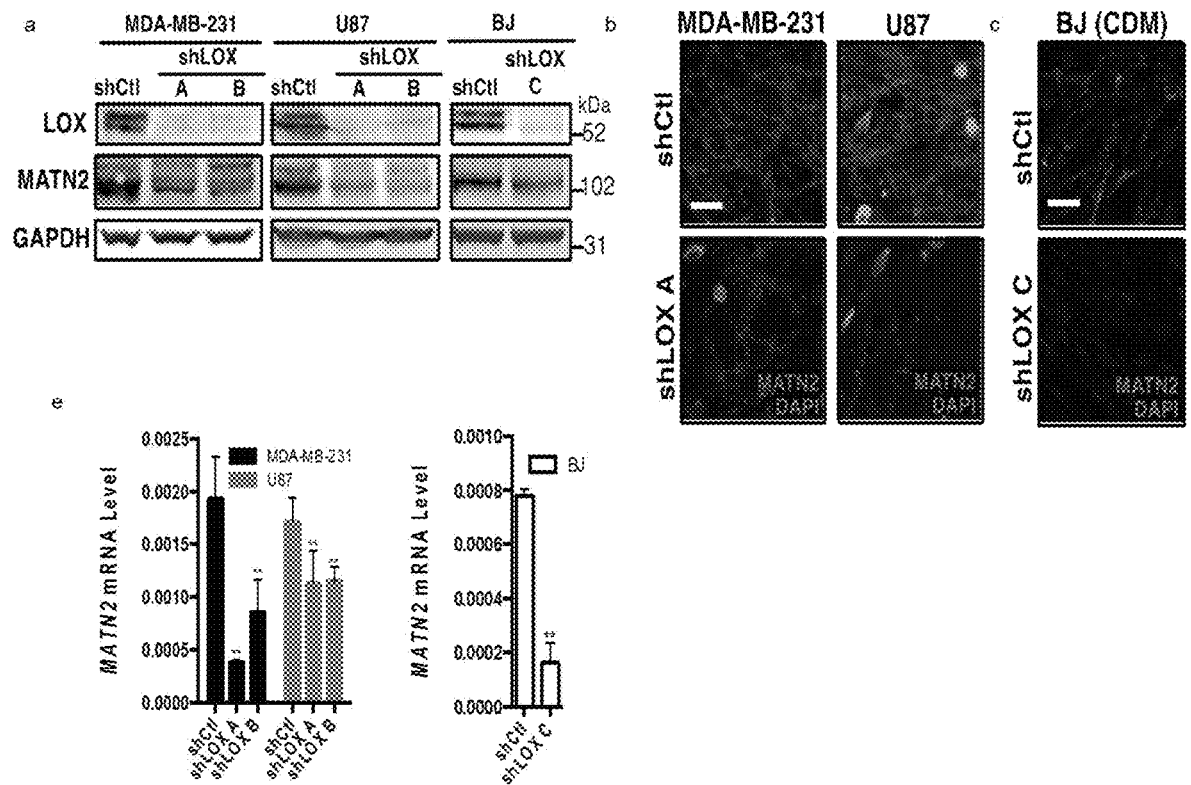
FIG. 11 shows a) expression of LOX, MATN2 and GADPH in control (shCtl) and LOX-depleted (shLOX A and shLOX B) MDA-MB-231, U87 and BJ cells; b) Photomicrographs of extracellular MATN2 in control (shCtl) or LOX-depleted (shLOX A) MDA-MB-231 and U87 cells; c) Photomicrographs of extracellular MATN2 in control (shCtl) or LOX-depleted (shLOX A) BJ cells and e) MATN2 mRNA level in control (shCtl) or LOX-depleted (shLOX A and shLOX B) MDA-MB-231, U87 and BJ cells.

We have discovered that LOX depletion also caused a substantial downregulation of MATN2 protein (FIG. 11a) and reduced accumulation of MATN2 in the extracellular space of cancer cells (MDA-MB-231 and U87 cells) grown on collagen gels (FIG. 11b). Similarly, LOX depletion in BJ dermal fibroblasts reduced extracellular MATN2 accumulation in the de novo synthesized extracellular matrix (FIG. 11a, c). Further investigation revealed that LOX depletion downregulated MATN2 mRNA (FIG. 11e).

Figure 12:
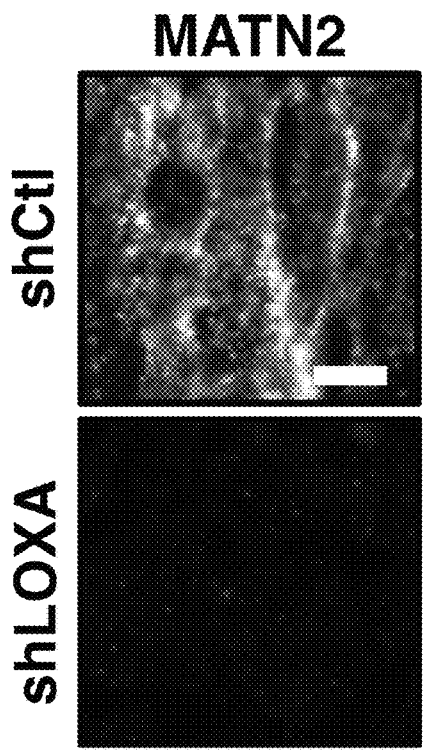
FIG. 12 shows photomicrographs of MATN2 in lung tumour samples of mice injected via tail vein with control (shCtl) and LOX-depleted (shLOX A) MDA-MB-231 cells.

A similar effect is seen in vivo: in lung tumour samples of mice injected via tail vein with LOX-depleted MDA-MB-231 cells MATN2 levels were significantly reduced compared to mice injected with control cells (FIG. 12).

Figure 13:
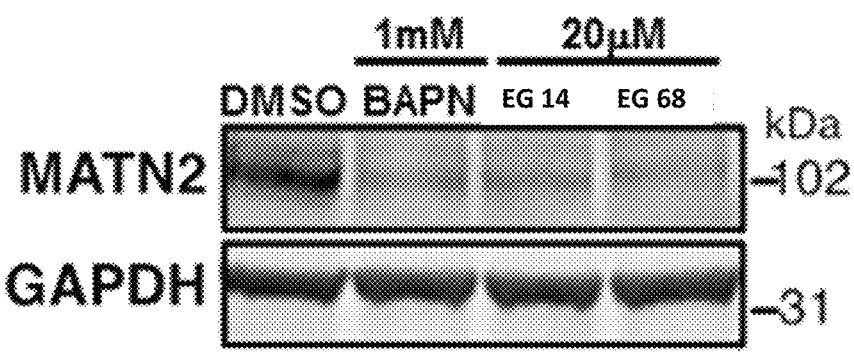
FIG. 13 shows MATN2 and GADPH in DMSO, BAPN (1 mM) and LOX inhibitor treated (Example 14 and Example 68 20 μM overnight).

LOX inhibitors show significant reduction of MATN2 in MDA-MB-231 cells treated at 20 µM overnight. The same effect was seen with the reported LOX inhibitor BAPN but at a much higher concentration (FIG. 13).

MATN2 Binds EGFR and Stabilises it on the Cell Surface

Figure 14:
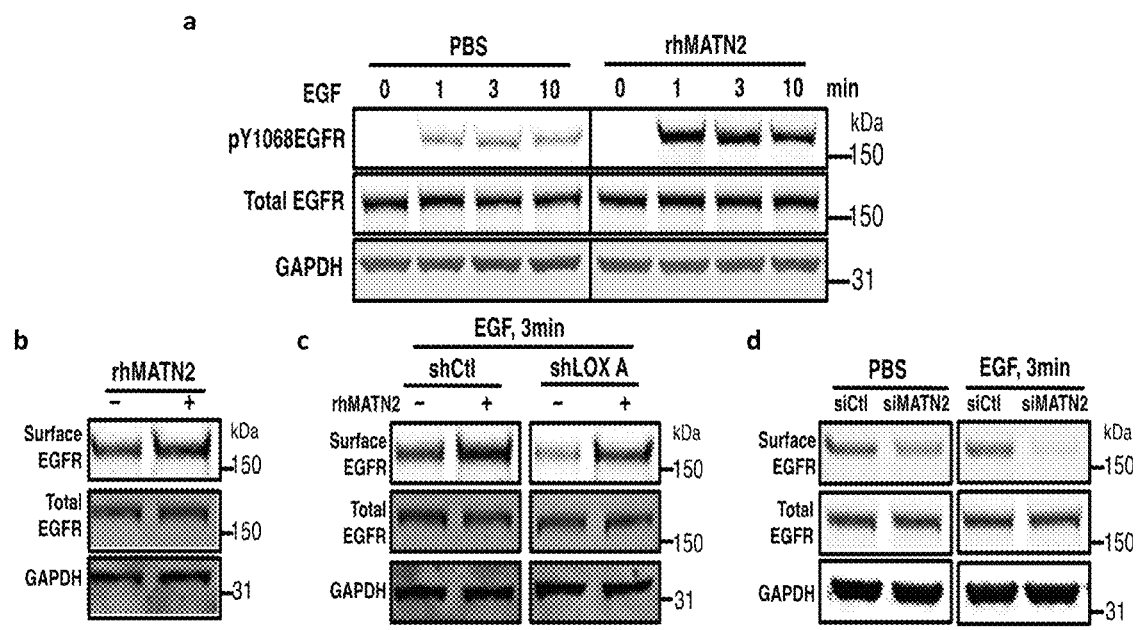
FIG. 14 shows a) phosphorylated (pY1068EGFR) and Total EGFR in PBS and human recombinant MATN2 (rhMATN2) treated and EGF stimulated MDA-MB-231 cells; b) rhMATN2 trapped EGFR on the surface of MDA-MB-231 cells; c) rhMATN2 restored EGFR retention at the surface of EGF stimulated LOX-depleted cells; d) MATN2 depletion by siRNA reduces EGFR levels at the cell surface.

Adding human recombinant MATN2 (rhMATN2) up to 1 µg/mL to MDA-MB-231 cells increases substantially the EGF-stimulated EGFR activation (FIG. 14a). Moreover, rhMATN2 trapped EGFR on the surface of MDA-MB-231 cells (FIG. 14b) and when LOX was depleted, rhMATN2 restored EGFR retention at the surface of EGF stimulated cells (FIG. 14c). We also show that MATN2 depletion by siRNA was sufficient to reduce EGFR levels at the cell surface (FIG. 14d).

We have shown significant reduction of MATN2 expression following inhibition of LOX by siRNA or small molecule inhibitors. MATN2 can be detected by immunohistochemistry from tumour samples and is therefore a new and potentially useful biomarker to assess the efficacy of LOX inhibition in vitro or in vivo including in a clinical setting.

LOX Upregulates TGFβ Signalling

Figure 15:
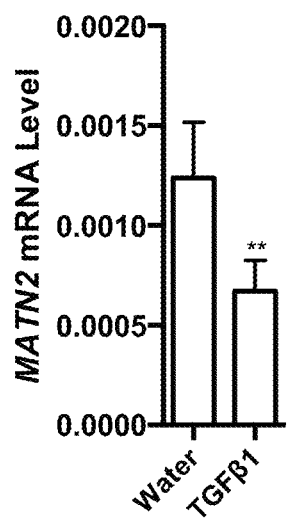
FIG. 15 shows a) MATN2 mRNA levels in MDA-MB-231 cells in absence or presence of TGFβ1. Error bars: s.d., n=3 independent experiments. **p<0.01; b) western blots pSMAD2, SMAD2/3 and GAPDH in DMSO, compound of Example 68 and BAPN treated MDA-MB-231 cells; and c) Western blots showing pSMAD2, SMAD2/3 and GAPDH in control (shCtl) or LOX-depleted (shLOX A) MDA-MB-231 and U87 cells.
Figure 15:
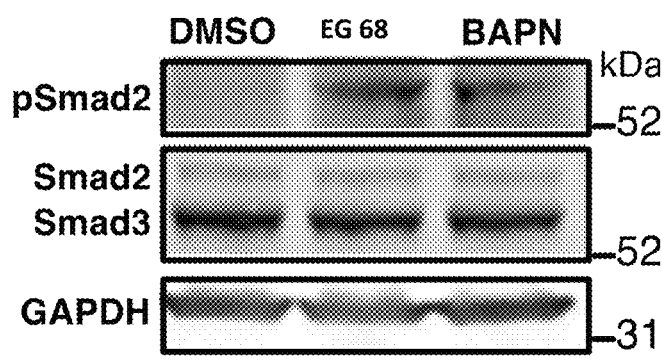
Figure 15:

MATN2 expression is negatively regulated by TGF beta signalling (FIG. 15a). Interestingly, LOX inhibition by the compound of Example 68 and BAPN increased TGF beta signalling as indicated by pSMAD2 leading to MATN2 reduction (FIG. 15b). This observation is consistent with increased SMAD2 phosphorylation when LOX expression is rediced in MDA-MB-231 and U87 cells (FIG. 15c). Therefore TGF beta signalling (i.e. phosphorylation of SMAD2, pSMAD2 levels) could also be used as biomarker for LOX inhibition.

LOX Depletion Reduces HTRA1 Levels and Suppresses SMAD2 Activation

Figure 16:
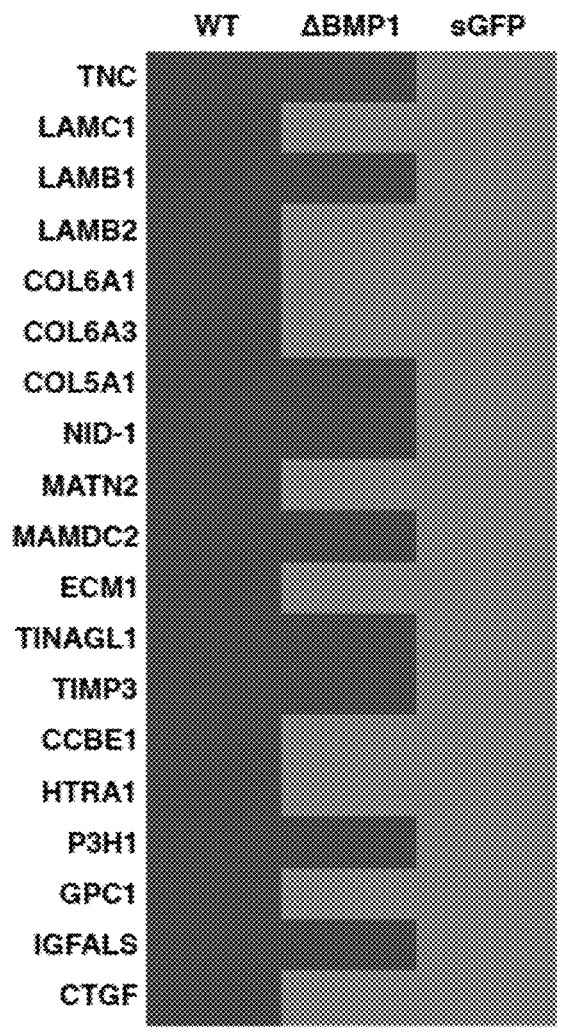
FIG. 16 shows binding of extracellular proteins to LOX-GFP (WT), LOXΔBMP-1-GFP (ABMP-1) or secreted GFP (sGFP) in MDA-MB-231 culture medium. Red: binding; Grey: no binding.
Figure 17:
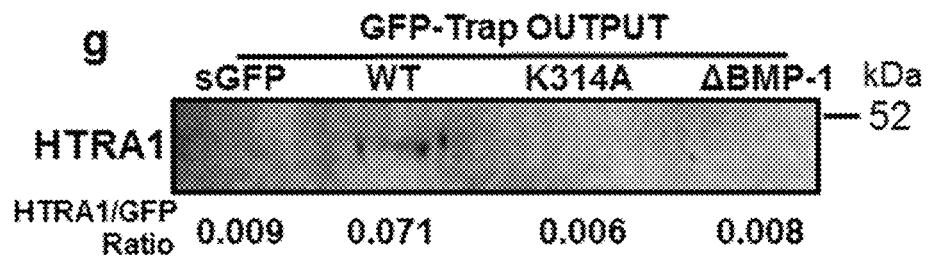
FIG. 17 shows a western blot depicting HTRA1 binding to LOX-GFP (WT). HTRA1/GFP ration indicates binding strength.
Figure 18:
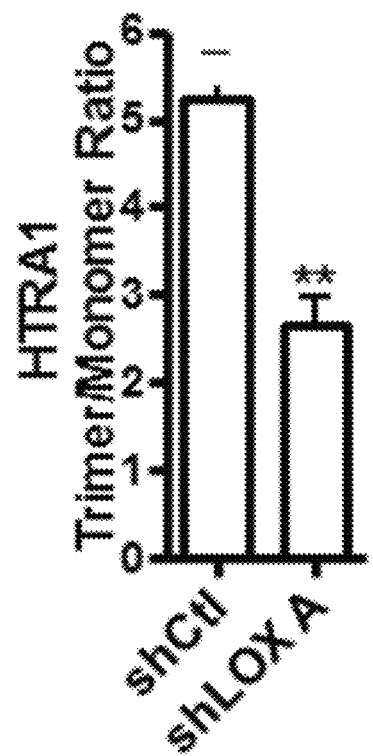
FIG. 18 shows HTRA1 trimer in control (shCtl) or LOX-depleted (shLOXA) MDA-MB-231 cell culture media. Error bars: s.d. n=4 independent experiments. **p<0.01.
Figure 19:
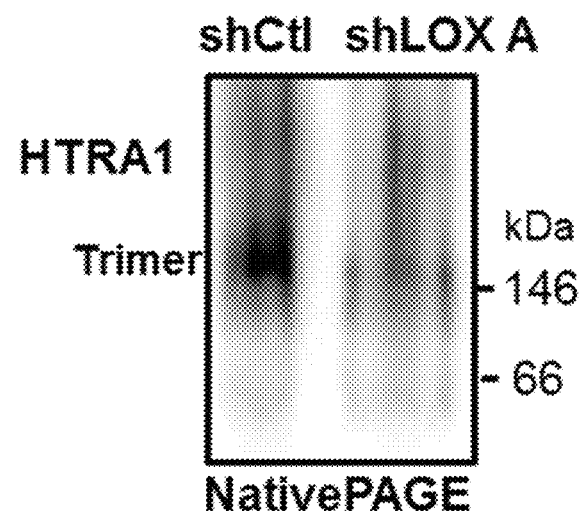
FIG. 19 is a NativePAGE showing extracellular HTRA1 trimer and monomer in MDA-MB-231 cell culture medium.
Figure 20:
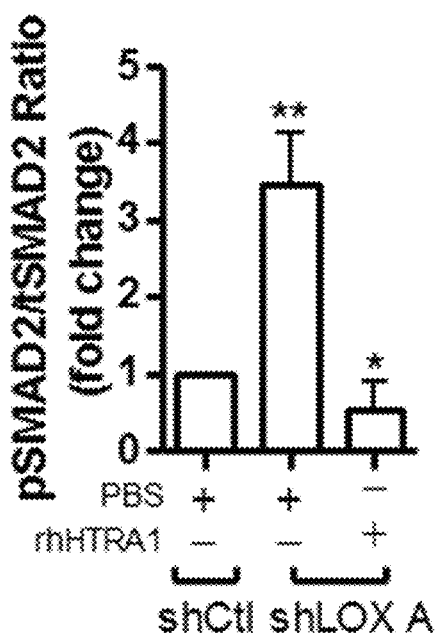
FIG. 20 shows SMAD2 activation in PBS or rhHTRA1 (10 ng/ml) treated control (shCtl) or LOX-depleted (shLOXA) MDA-MB-231 cells. Error bars: s.d. n=3 independent experiments. **p<0.01. *p=not-significant.
Figure 21:
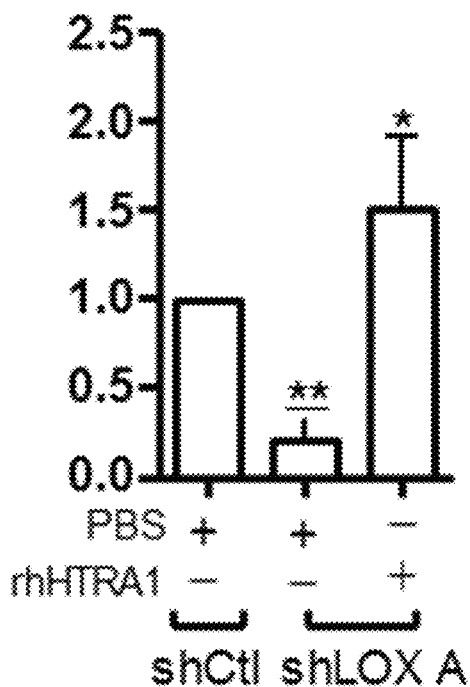
FIG. 21 shows MATN2 in PBS or rhHTRA1 (10 ng/ml) treated control (shCtl) or LOX-depleted (shLOXA) MDA-MB-231 cells. Error bars: s.d. n=3 independent experiments. **p<0.01. *p=not-significant.
Figure 22:
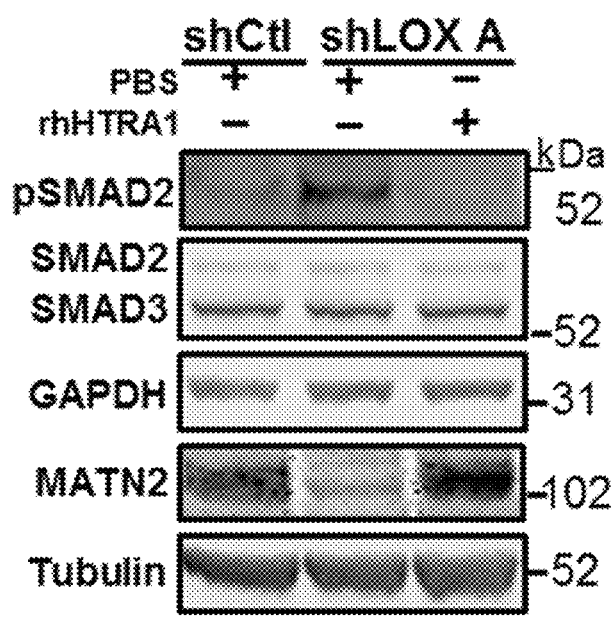
FIG. 22 is a western blot showing pSMAD2, SMAD2/3, GAPDH, MATN2 and Tubulin in PBS or rhHTRA1-treated control (shCtl) or LOX-depleted (shLOX A) MDA-MB-231 cells.

LOX binds to the secreted serine protease HTRA1 (FIGS. 16 and 17). LOX depletion reduces the levels of extracellular homotrimeric HTRA1, the active form of this enzyme (FIGS. 18 and 19). Moreover, recombinant human HTRA1 (rhHRA1) suppresses SMAD2 activation and rescues MATN2 expression in LOX depleted cells (FIGS. 20, 21 and 22).

Thus, we conclude that LOX regulates HTRA1 stability to suppress TGFβ1 signalling and induce MATN2 expression. Accordingly, HTRA1 expression could be used as a biomarker for LOX inhibition.

REFERENCES

Abourbih, D. A., et al. (2010). "Lysyl oxidase expression and inhibition in uveal melanoma." *Melanoma research* 20(2): 97-106.

Adam, O., et al. (2011). "Increased lysyl oxidase expression and collagen cross-linking during atrial fibrillation." *J. Mol. Cell. Cardiol.* 50(4): 678-685.

Akiri, G., et al. (2003). "Lysyl oxidase-related protein-1 promotes tumor fibrosis and tumor progression in vivo." *Cancer research* 63(7): 1657-1666.

Albinger-Hegyi, A., et al. (2010). "Lysyl oxidase expression is an independent marker of prognosis and a predictor of lymph node metastasis in oral and oropharyngeal squamous cell carcinoma (OSCC)." *International journal of cancer Journal international du cancer* 126(11): 2653-2662.

Alexandrescu, D. T. (2009). "Treatment of skin disorders with EGFR inhibitors". WO2009091889A1

Anderson, C., et al. (2007). "Chemical genetics suggests a critical role for lysyl oxidase in zebrafish notochord morphogenesis." *Mol Biosyst* 3(1): 51-59.

Aslam, T., et al. (2015). "Optical molecular imaging of lysyl oxidase activity—detection of active fibrogenesis in human lung tissue." *Chemical Science* 6(8): 4946-4953.

Baker, A.-M., et al. (2013). "Lysyl oxidase plays a critical role in endothelial cell stimulation to drive tumor angiogenesis." *Cancer research* 73(2): 583-594.

Baker, A.-M., et al. (2011). "The role of lysyl oxidase in SRC-dependent proliferation and metastasis of colorectal cancer." *Journal of the National Cancer Institute* 103(5): 407-424.

Barker, H. E., et al. (2013). "Tumor-Secreted LOXL2 Activates Fibroblasts through FAK Signaling." *Molecular Cancer Research* 11(11): 1425-1436.

Barker, H. E., et al. (2011). "LOXL2-mediated matrix remodeling in metastasis and mammary gland involution." *Cancer research* 71(5): 1561-1572.

Barker, H. E., et al. (2012). "The rationale for targeting the LOX family in cancer." *Nature reviews Cancer* 12(8): 540-552.

Barry-Hamilton, V., et al. (2010). "Allosteric inhibition of lysyl oxidase-like-2 impedes the development of a pathologic microenvironment." *Nat Med* 16(9): 1009-1017.

Beerlage, C., et al. (2013). "Hypoxia-inducible factor 1-regulated lysyl oxidase is involved in *Staphylococcus aureus* abscess formation." *Infect. Immun.* 81(7): 2562-2573.

Bianco, R., et al. (2007). "Rational bases for the development of EGFR inhibitors for cancer treatment." *The International Journal of Biochemistry & Cell Biology* 39 (7-8): 1416-1431.

Bondareva, A., et al. (2009). "The lysyl oxidase inhibitor, beta-aminopropionitrile, diminishes the metastatic colonization potential of circulating breast cancer cells." *PLoS One* 4(5): e5620.

Borad, M. J., et al. (2014). "Targeted chemotherapy of cancer using EGFR inhibitors". WO2014145751A2

Boufraqech, M., et al. (2015). "miR30a Inhibits LOX Expression and Anaplastic Thyroid Cancer Progression." *Cancer research* 75(2): 367-377.

Brasselet, C., et al. (2005). "Collagen and elastin cross-linking: A mechanism of constrictive remodeling after arterial injury." *Am. J. Physiol.* 289 (5, Pt. 2): H2228-H2233.

Burchardt, E. R. (2006). "Preparation of 2-phenyl-3-pyridazinones as lysyl oxidase inhibitors". DE102004056226A1

Burke A. A., et al (2017) Comparing hydrazine-derived reactive groups as inhibitors of quinone-dependent amine oxidases, *Journal of Enzyme Inhibition and Medicinal Chemistry*, 32:1, 496-503, Carrington, M. J., et al. (1984). "The inhibition of lysyl oxidase in vivo by isoniazid and its reversal by pyridoxal. Effect on collagen cross-linking in the chick embryo." *Biochem J* 221(3): 837-843.

Chang, J. et al (2017) Pre-clinical evaluation of small molecule LOXL2 inhibitors in breast cancer. Oncotarget, Advance Publication Chanoki, M., et al. (1995). "Increased expression of lysyl oxidase in skin with scleroderma." *Br J Dermatol* 133(5): 710-715.

Chen, W.-C., et al. (2015). "Matrix-Stiffness-Regulated Inverse Expression of Krüppel-Like Factor 5 and Krüppel-Like Factor 4 in the Pathogenesis of Renal Fibrosis." *The American Journal of Pathology* 185(9): 2468-2481.

Chien, J. W., et al. (2014). "Serum lysyl oxidase-like 2 levels and idiopathic pulmonary fibrosis disease progression." *European Respiratory Journal* 43(5): 1430-1438.

Cox, T. R., et al. (2013). "LOX-Mediated Collagen Cross-linking Is Responsible for Fibrosis-Enhanced Metastasis." *Cancer research* 73(6): 1721-1732.

Cox, T. R., et al. (2015). "The hypoxic cancer secretome induces pre-metastatic bone lesions through lysyl oxidase." *Nature* 522(7554): 106-110.

Crowley, V. et al. (2016). "Development of Glucose Regulated Protein 94-Selective Inhibitors Based on the Bnlm and Radamide Scaffold." *J Med. Chem.* 59, 3471-3488.

Curtis, M. et al. (2013). "Phenicol antibacterials." US2013/0237502A1. da Silva, R., et al. (2015). "LOX Expression and Functional Analysis in Astrocytomas and Impact of IDH1 Mutation." *PLoS One* 10(3): e0119781.

Decitre, M., et al. (1998). "Lysyl oxidase-like protein localizes to sites of de novo fibrinogenesis in fibrosis and in the early stromal reaction of ductal breast carcinomas." *Lab. Invest.* 78(2): 143-151.

Dentillo, D. B., et al. (2010). "Deregulation of LOXL1 and HTRA1 Gene Expression in Endometriosis." *Reproductive Sciences* 17(11): 1016-1023.

Di Donato, A., et al. (1997). "Lysyl oxidase expression and collagen cross-linking during chronic adriamycin nephropathy." *Nephron* 76(2): 192-200.

Dong, K.-f., et al. (2014). "Effects on apoptosis and chemosensitivity in human laryngeal cancer Hep-2 cells by silencing the lysyl oxidase gene expression." *Zhongguo Xiandai Yixue Zazhi* 24(29): 13-17.

Dong, K., et al. (2014). "Effects of lox gene expression on proliferation, invasion and radiosensitivity of laryngeal cancer hep-2 cells." *Tianjin Yiyao* 42(5): 417-420.

Erler, J. T., et al. (2009). "Hypoxia-induced lysyl oxidase is a critical mediator of bone marrow cell recruitment to form the premetastatic niche." *Cancer Cell* 15(1): 35-44.

Erler, J. T., et al. (2006). "Lysyl oxidase is essential for hypoxia-induced metastasis." *Nature* 440(7088): 1222-1226.

Fong, S. F., et al. (2007). "Lysyl oxidase-like 2 expression is increased in colon and esophageal tumors and associated with less differentiated colon tumors." *Genes Chromosomes Cancer* 46(7): 644-655.

Gao, Y., et al. (2010). "LKB1 inhibits lung cancer progression through lysyl oxidase and extracellular matrix remodeling." *Proceedings of the National Academy of Sciences* 107(44): 18892-18897.

Georges, P. C., et al. (2007). "Increased stiffness of the rat liver precedes matrix deposition: implications for fibrosis." *Am. J. Physiol.* 293 (6, Pt. 1): G1147-G1154.

Giboda, M., et al. (1992). "Experimental schistosomiasis mansoni: modulation of granulomas by inhibition of collagen cross-link formation. Preliminary report." *Ann Trop Med Parasitol* 86(6): 631-636.

Gilad, G. M. and V. H. Gilad (2001). "β-Aminopropionitrile treatment can accelerate recovery of mice after spinal cord injury." *Eur. J. Pharmacol.* 430(1): 69-72.

Gilad, G. M., et al. (2001). "Lysyl oxidase, the extracellular matrix-forming enzyme, in rat brain injury sites." *Neurosci. Lett.* 310(1): 45-48.

Gilad, G. M., et al. (2005). "Evidence for increased lysyl oxidase, the extracellular matrix-forming enzyme, in Alzheimer's disease brain." *Neurosci Lett* 376(3): 210-214.

Goeroegh, T., et al. (2007). "Selective upregulation and amplification of the lysyl oxidase like-4 (LOXL4) gene in head and neck squamous cell carcinoma." *J Pathol* 212 (1): 74-82.

Gonzalez, G. E., et al. (2014). "N-acetyl-seryl-aspartyl-lysyl-proline reduces cardiac collagen cross-linking and inflammation in angiotensin II-induced hypertensive rats." *Clin. Sci.* 126(1): 85-94.

Gopalan Balasubramanian. (1990) "Biphenyl-substituted guanidine derivatives useful as hypoglycaemic agents." U.S. Pat. No. 5,302,720.

Haase, V. H. (2009). "Pathophysiological Consequences of HIF Activation." *Annals of the New York Academy of Sciences* 1177(1): 57-65.

Halberg, N., et al. (2009). "Hypoxia-inducible factor 1a induces fibrosis and insulin resistance in white adipose tissue." *Mol. Cell. Biol.* 29(16): 4467-4483.

Hase, H., et al. (2014). "LOXL2 Status Correlates with Tumor Stage and Regulates Integrin Levels to Promote Tumor Progression in ccRCC." *Molecular Cancer Research* 12(12): 1807-1817.

He, Z. and V. Koprivica (2007). "EGFR inhibitors promote axon regeneration". WO2007008338A1

Herranz, N., et al. (2012). "Lysyl Oxidase-like 2 Deaminates Lysine 4 in Histone H3." *Molecular Cell* 46(3): 369-376.

Hornstra, I. K., et al. (2003). "Lysyl oxidase is required for vascular and diaphragmatic development in mice." *J Biol Chem* 278(16): 14387-14393.

Huang, C.-S., et al. (2013). "Long-term ethanol exposure-induced hepatocellular carcinoma cell migration and invasion through lysyl oxidase activation are attenuated by combined treatment with pterostilbene and curcumin analogues." *Journal of Agricultural and Food Chemistry* 61(18): 4326-4335.

Hynes, J. et al. (2009). "Imidazopyridine and imidazopyrazine compounds useful as kinase inhibitors." WO2009/155388A1.

Ingber, D. E. and A. Mammoto (2014). "Methods of altering vascular permeability by changing the mechanical properties of extracellular matrixes using agents such as lysyl oxidase (LOX)-modulating agents and uses for treatment of diseases". WO2014152122A2

Jiang, W.-P., et al. (2014). "Identification of the involvement of LOXL4 in generation of keratocystic odontogenic tumors by RNA-Seq analysis." *In J Oral Sci* 6(1): 31-38.

Jourdan-Le Saux, C., et al. (1994). "Lysyl oxidase cDNA of myofibroblast from mouse fibrotic liver." *Biochem Biophys Res Commun* 199(2): 587-592.

Jung, B. (2010). "Use of quinazoline derivatives for the treatment of viral diseases". WO2010026029A1

Kagan, H. M. (1994). "Lysyl oxidase: mechanism, regulation and relationship to liver fibrosis." *Pathol Res Pract* 190 (9-10): 910-919.

Kagan, H. M. and W. Li (2003). "Lysyl oxidase: properties, specificity, and biological roles inside and outside of the cell." *Journal of cellular biochemistry* 88(4): 660-672.

Kagan, H. M., et al. (1981). "Changes in aortic lysyl oxidase activity in diet-induced atherosclerosis in the rabbit." *Arteriosclerosis* 1(4): 287-291.

Karagiannis, G. S., et al. (2012). "Cancer-Associated Fibroblasts Drive the Progression of Metastasis through both Paracrine and Mechanical Pressure on Cancer Tissue." *Molecular Cancer Research* 10(11): 1403-1418.

Kasashima, H., et al. (2014). "Lysyl oxidase-like 2 (LOXL2) from stromal fibroblasts stimulates the progression of gastric cancer." *Cancer Letters* 354(2): 438-446.

Kasashima, H., et al. (2015). "Lysyl oxidase is associated with the epithelial-mesenchymal transition of gastric cancer cells in hypoxia." *Gastric Cancer:* 1-12.

Kim, Y.-M., et al. (2010). "The human lysyl oxidase-like 2 protein functions as an amine oxidase toward collagen and elastin." *Mol. Biol. Rep.* 38(1): 145-149.

Kim, Y., et al. (1999). "Coexpression of the lysyl oxidase-like gene (LOXL) and the gene encoding type Ill procollagen in induced liver fibrosis." *Journal of cellular biochemistry* 72(2): 181-188.

Kirschmann, D. A., et al. (2002). "A molecular role for lysyl oxidase in breast cancer invasion." *Cancer research* 62(15): 4478-4483.

Kumarasamy, A., et al. (2009). "Lysyl oxidase activity is dysregulated during impaired alveolarization of mouse and human lungs." *Am. J. Respir. Crit. Care Med.* 180 (12): 1239-1252.

Lee, G.-H., et al. (2011). "Lysyl oxidase-like-1 enhances lung metastasis when lactate accumulation and monocarboxylate transporter expression are involved." *Oncology Letters* 2(5): 831-838.

Levene, C. I., et al. (1992). "Inhibition of chick embryo lysyl oxidase by various lathyrogens and the antagonistic effect of pyridoxal." *Int J Exp Pathol* 73(5): 613-624.

Levental, K. R., et al. (2009). "Matrix crosslinking forces tumor progression by enhancing integrin signaling." *Cell* 139(5): 891-906.

Li, R.-k., et al. (2015). "Lysyl oxidase-like 4 (LOXL4) promotes proliferation and metastasis of gastric cancer via FAK/Src pathway." *Journal of Cancer Research and Clinical Oncology* 141(2): 269-281.

Li, W., et al. (2003). "Lysyl oxidase oxidizes basic fibroblast growth factor and inactivates its mitogenic potential." *Journal of cellular biochemistry* 88(1): 152-164.

Liu, G., et al. (1997). "Irreversible inhibition of lysyl oxidase by homocysteine thiolactone and its selenium and oxygen analogues. Implications for homocystinuria." *J Biol Chem* 272(51): 32370-32377.

Liu, J., et al. (2014). "Correlations of lysyl oxidase with MMP2/MMP9 expression and its prognostic value in non-small cell lung cancer." *Int J Clin Exp Pathol* 7(9): 6040-6047.

Lopez, B., et al. (2010). "Role of lysyl oxidase in myocardial fibrosis: from basic science to clinical aspects." *Am. J. Physiol.* 299 (1, Pt. 2): H1-H9.

Lopez, B., et al. (2013). "Osteopontin-mediated myocardial fibrosis in heart failure: a role for lysyl oxidase?" *Cardiovasc. Res.* 99(1): 111-120.

Lopez, B., et al. (2012). "Collagen Cross-Linking But Not Collagen Amount Associates With Elevated Filling Pressures in Hypertensive Patients With Stage C Heart Failure: Potential Role of Lysyl Oxidase." *Hypertension* 60(3): 677-683.

Lucero, H. A. and H. M. Kagan (2006). "Lysyl oxidase: an oxidative enzyme and effector of cell function." *Cellular and molecular life sciences: CMLS* 63 (19-20): 2304-2316.

Lucero, H. A., et al. (2008). "Lysyl oxidase oxidizes cell membrane proteins and enhances the chemotactic response of vascular smooth muscle cells." *J Biol Chem* 283(35): 24103-24117.

Ma, W. (2013). "Methods for treating alzheimer's disease by administering certain synthetic compounds". WO2013111013A2

Maki, J. M., et al. (2002). "Inactivation of the lysyl oxidase gene Lox leads to aortic aneurysms, cardiovascular dysfunction, and perinatal death in mice." *Circulation* 106(19): 2503-2509.

Mambetsariev, I., et al. (2014). "Stiffness-activated GEF-H1 expression exacerbates LPS-induced lung inflammation." *PLoS One* 9(4): e92670/92671-e92670/92612, 92612 pp.

Mammoto, A., et al. (2013). "Control of lung vascular permeability and endotoxin-induced pulmonary oedema by changes in extracellular matrix mechanics." *Nature communications* 4: 1759.

Mammoto, T., et al. (2013). "Role of Collagen Matrix in Tumor Angiogenesis and Glioblastoma Multiforme Progression." *The American Journal of Pathology* 183(4): 1293-1305.

Marshall, D. and V. Smith (2011). "In vivo screening assays for identifying inhibitors of LOXL2 activity". WO 2011022670

Marshall, D., et al. (2012). "Anti-LOXL2 antibody, siRNA, shRNA, ribozyme and triplex oligonucleotide to increase efficacy of antitumor agent and treat cancer". WO2012139045A1

Miana, M., et al. (2015). "The lysyl oxidase inhibitor β-aminopropionitrile reduces body weight gain and improves the metabolic profile in diet-induced obesity in rats." *Dis. Models Mech.* 8(6): 543-551.

Millanes-Romero, A., et al. (2013). "Regulation of Heterochromatin Transcription by Snail1/LOXL2 during Epithelial-to-Mesenchymal Transition." *Molecular Cell* 52(5): 746-757.

Miller, B. W., et al. (2015). "Targeting the LOX/hypoxia axis reverses many of the features that make pancreatic cancer deadly: inhibition of LOX abrogates metastasis and enhances drug efficacy." *EMBO Mol Med* 7(8): 1063-1076.

Moreno-Bueno, G., et al. (2011). "Lysyl oxidase-like 2 (LOXL2), a new regulator of cell polarity required for metastatic dissemination of basal-like breast carcinomas." *EMBO Mol Med* 3(9): 528-544.

Murawaki, Y., et al. (1991). "Serum lysyl oxidase activity in chronic liver disease in comparison with serum levels of prolyl hydroxylase and laminin." *Hepatology* 14(6): 1167-1173.

Nave, A. H., et al. (2014). "Lysyl Oxidases Play a Causal Role in Vascular Remodeling in Clinical and Experimental Pulmonary Arterial Hypertension." *Arterioscler., Thromb., Vasc. Biol.* 34(7): 1446-1458.

Neufeld, G. and V. Brekhman (2009). "Use of shRNA targeting LOXL2 gene in modulating angiogenesis and treating tumors, metastasis, fibrosis, and pulmonary alveolar proteinosis". WO2009010974A2

Nicholson, R. I., et al. (2001). "EGFR and cancer prognosis." *European Journal of Cancer* 37, Supplement 4: 9-15.

Nishikawa, R., et al. (2015). "Tumour-suppressive microRNA-29s directly regulate LOXL2 expression and inhibit cancer cell migration and invasion in renal cell carcinoma." *FEBS letters* 589(16): 2136-2145.

Nuthakki, V. K., et al. (2004). "Lysyl oxidase expression in a rat model of arterial balloon injury." *J Vasc Surg* 40(1): 123-129.

Offenberg, H., et al. (2008). "TIMP-1 expression in human colorectal cancer is associated with TGF-B1, LOXL2, INHBA1, TNF-AIP6 and TIMP-2 transcript profiles." *Mol Oncol* 2(3): 233-240.

Ohmura, H., et al. (2012). "Cardiomyocyte-specific transgenic expression of lysyl oxidase-like protein-1 induces cardiac hypertrophy in mice." *Hypertens. Res.* 35(11): 1063-1068.

Osawa, T., et al. (2013). "Lysyl oxidase secreted by tumour endothelial cells promotes angiogenesis and metastasis." *Br J Cancer* 109(8): 2237-2247.

Palfreyman, M. G., et al. (1989). "Preparation of allylamines, inhibitors of lysyl oxidase". EP330218A2

Papadantonakis, N., et al. (2012). "Megakaryocyte pathology and bone marrow fibrosis: the lysyl oxidase connection." *Blood* 120(9): 1774-1781.

Park, H.-Y. L., et al. (2014). "Lysyl oxidase-like 2 level and glaucoma surgical outcomes." *Invest. Ophthalmol. Visual Sci.* 55(5): 3337-3343.

Peinado, H., et al. (2005). "A molecular role for lysyl oxidase-like 2 enzyme in snail regulation and tumor progression." *EMBO J* 24(19): 3446-3458.

Peinado, H., et al. (2008). "Lysyl Oxidase-Like 2 as a New Poor Prognosis Marker of Squamous *Cell* Carcinomas." *Cancer research* 68(12): 4541-4550.

Peng, L., et al. (2009). "Secreted LOXL2 is a novel therapeutic target that promotes gastric cancer metastasis via the Src/FAK pathway." *Carcinogenesis* 30(10): 1660-1669.

Pickup, M. W., et al. (2013). "Stromally Derived Lysyl Oxidase Promotes Metastasis of Transforming Growth Factor-β-Deficient Mouse Mammary Carcinomas." *Cancer Res.* 73(17): 5336-5346.

Pinnell, S. R. and G. R. Martin (1968). "The cross-linking of collagen and elastin: enzymatic conversion of lysine in peptide linkage to alpha-aminoadipic-delta-semialdehyde (allysine) by an extract from bone." *Proceedings of the National Academy of Sciences* 61(2): 708-716.

Ree, A. H., et al. (2008). "Treatment and diagnosis of metastatic prostate cancer with inhibitors of epidermal growth factor receptor (EGFR)". WO2008125633A2

Reynault, O. et al. (1997). "A convenient synthesis of new halothienyl β-aminoacids as versatile building block." *Org. Prep. Proc. Int.* 29(4): 488-494.

Ricard-Blum, S., et al. (1996). "Mechanism of collagen network stabilization in human irreversible granulomatous liver fibrosis." *Gastroenterology* 111(1): 172-182.

Rimar, D., et al. (2014). "Brief report: lysyl oxidase is a potential biomarker of fibrosis in systemic sclerosis." *Arthritis Rheumatol* 66(3): 726-730.

Romero, F. et al. (2016). "4,5,6,7-Tetrahydro-1-H-pyrazolo[4,3-C]pyrimidine-3-amine compounds as CBP and/or EP300 inhibitors." WO2016/086200A1

Rosin, N. L., et al. (2015). "Disruption of Collagen Homeostasis Can Reverse Established Age-Related Myocardial Fibrosis." *Am. J. Pathol.* 185(3): 631-642.

Rowbottom, M. W. et al. (2016a). "Preparation of substituted pyridinylmethylamine compounds as lysyl oxidase-like 2 inhibitors". WO2016144702

Rowbottom, M. W. et al. (2016b). "Preparation of fluorinated pyridine derivatives as lysyl oxidase-like 2 inhibitors and uses thereof." WO2016144703

Rowbottom, M. W.; Hutchinson, J. H. (2017a). "Preparation of pyrimidine derivatives as Lysyl oxidase-like 2 inhibitors useful for the treatment of fibrosis." WO2017003862

Rowbottom, M. W.; Hutchinson, J. H. (2017b). "Lysyl oxidase-like 2 inhibitors and uses thereof." WO2017015221

Ruiz, L. A., et al. (2011). "Single-nucleotide polymorphisms in the lysyl oxidase-like protein 4 and complement component 3 genes are associated with increased risk for endometriosis and endometriosis-associated infertility." *Fertil Steril* 96(2): 512-515.

Sansom, O. (2012). Targeting the tumour microenvironment in pancreatic cancer. EACR-IACR Joint Conference: Tumour Microenvironment, Dublin, Ireland.

Sayre, L. M. (2007). "Amine compounds for amine oxidase inhibitors, and therapeutic use". WO2007005737A2

Schietke, R., et al. (2010). "The lysyl oxidases LOX and LOXL2 are necessary and sufficient to repress E-cadherin in hypoxia: insights into cellular transformation processes mediated by HIF-1." *J Biol Chem* 285(9): 6658-6669.

Schlotzer-Schrehardt, U., et al. (2008). "Genotype-correlated expression of lysyl oxidase-like 1 in ocular tissues of patients with pseudoexfoliation syndrome/glaucoma and normal patients." *American Journal of Pathology* 173(6): 1724-1735.

Schohe-Loop, R., et al. (2003). "Preparation of 2-phenyl-3 (2H)-pyridazinones as lysyl oxidase inhibitors for preventing and treating fibrosis". DE10216144A1

Schuetze, F., et al. (2015). "Inhibition of Lysyl Oxidases Improves Drug Diffusion and Increases Efficacy of Cytotoxic Treatment in 3D Tumor Models." *Sci. Rep.* 5: 17576.

Schweighauser, L., et al. (2015). "Attraction or Repulsion? London Dispersion Forces Control Azobenzene Switches." *Angew. Chem. Int ed* 54(45): 13436-13439.

Scola, N. and T. Gorogh (2010). "LOXL4 as a selective molecular marker in primary and metastatic head/neck carcinoma." *Anticancer Res* 30(11): 4567-4571.

Shen, C. J., et al. (2014). "Ionizing radiation induces tumor cell lysyl oxidase secretion." *BMC Cancer* 14: 532/531-532/510.

Siegel, R. C., et al. (1978). "Biochemical and immunochemical study of lysyl oxidase in experimental hepatic fibrosis in the rat." *Proceedings of the National Academy of Sciences* 75(6): 2945-2949.

Smith, V. and A. K. Holzer (2010). "Chemotherapeutic methods and compositions for treating cancer by inhibiting activity of lysyl oxidase-type enzyme". WO2010080769A2

Smith, V. and P. Van Vlasselaer (2011). "Tumor therapy by inhibiting the activity or expression of lysyl oxidase-like 2 with antibodies or inhibitory nucleic acids". WO2011022710A1

Stalmans, I., et al. (2010). "Use of lysyl oxidase related protein inhibitors for treatment of ocular neovascularization and fibrotic damage". WO2010091279A1

Stalmans, I., et al. (2011). "Methods of treatmenting ocular fibrosis by modulating the activity of lysyl oxidase-type enzymes". US20110076285A1

Stewart, G. D., et al. (2008). "Analysis of hypoxia-associated gene expression in prostate cancer: lysyl oxidase and glucose transporter-1 expression correlate with Gleason score." *Oncol Rep* 20(6): 1561-1567.

Tadmor, T., et al. (2013). "The expression of lysyl-oxidase gene family members in myeloproliferative neoplasms." *American Journal of Hematology* 88(5): 355-358.

Tang, S. S., et al. (1984). "Beta-substituted ethylamine derivatives as suicide inhibitors of lysyl oxidase." *J Biol Chem* 259(2): 975-979.

Threadgill, D. and C. J. Barrick (2007). "Use of EGFR inhibitors to prevent or treat obesity". WO2007011702A2

Toustrup, K., et al. (2011). "Development of a hypoxia gene expression classifier with predictive impact for hypoxic modification of radiotherapy in head and neck cancer." *Cancer research* 71(17): 5923-5931.

Tsang, A. W. and C. M. Furdui (2015). "Methods and compositions comprising epidermal growth factor receptor (EGFR) inhibitors for the treatment of Chlamydia infection and related diseases and disorders". WO2015038755A1

Uzel, M. I., et al. (2001). "Multiple bone morphogenetic protein 1-related mammalian metalloproteinases process pro-lysyl oxidase at the correct physiological site and control lysyl oxidase activation in mouse embryo fibroblast cultures." *J Biol Chem* 276(25): 22537-22543.

Vadasz, Z., et al. (2005). "Abnormal deposition of collagen around hepatocytes in Wilson's disease is associated with hepatocyte specific expression of lysyl oxidase and lysyl oxidase like protein-2." *J Hepatol* 43(3): 499-507.

Van Bergen, T., et al. (2013). "The role of LOX and LOXL2 in scar formation after glaucoma surgery." *Invest. Ophthalmol. Visual Sci.* 54(8): 5788-5796.

Van Bierbeek, A and Gingras, M. (1998) "Polysulfurated branched molecules containing functionalized m-phenylene sulfides." *Tetrahedron Lett.* 39(35): 6283-6286.

van Nimwegen, M. J. and B. van de Water (2007). "Focal adhesion kinase: a potential target in cancer therapy." *Biochem Pharmacol* 73(5): 597-609.

Weihua, Z., et al. (2008). "Survival of Cancer Cells Is Maintained by EGFR Independent of Its Kinase Activity." *Cancer Cell* 13(5): 385-393.

Wiel, C., et al. (2013). "Lysyl oxidase activity regulates oncogenic stress response and tumorigenesis." *Cell Death Dis* 4: e855.

Wilgus, M.-L., et al. (2011). "Lysyl oxidase: A lung adenocarcinoma biomarker of invasion and survival." *Cancer* 117(10): 2186-2191.

Wilhelmus, M. M. M., et al. (2013). "Extracellular matrix modulator lysyl oxidase colocalizes with amyloid-beta pathology in Alzheimer's disease and hereditary cerebral hemorrhage with amyloidosis-Dutch type." *Exp. Gerontol.* 48(2): 109-114.

Williamson, P. R. and H. M. Kagan (1987). "Electronegativity of aromatic amines as a basis for the development of ground state inhibitors of lysyl oxidase." *J Biol Chem* 262(30): 14520-14524.

Wong, C. C.-L., et al. (2011). "Hypoxia-inducible factor 1 is a master regulator of breast cancer metastatic niche formation." *Proceedings of the National Academy of Sciences* 108(39): 16369-16374.

Wong, C. C.-L., et al. (2014). "Lysyl oxidase-like 2 is critical to tumor microenvironment and metastatic niche formation in hepatocellular carcinoma." *Hepatology* (Hoboken, N.J., U. S.) 60(5): 1645-1658.

Xu, J., et al. (2014). "67 laminin receptor promotes the malignant potential of tumour cells up-regulating lysyl oxidase-like 2 expression in cholangiocarcinoma." *Digestive and Liver Disease* 46(8): 750-757.

Yang, X., et al. (2013). "Inactivation of lysyl oxidase by β-aminopropionitrile inhibits hypoxia-induced invasion and migration of cervical cancer cells." *Oncol Rep* 29(2): 542-548.

Yang, Z., et al. (2010). "Uric acid increases fibronectin synthesis through upregulation of lysyl oxidase expression in rat renal tubular epithelial cells." *Am. J. Physiol.* 299 (2, Pt. 2): F336-F346.

Zaffryar-Eilot, S., et al. (2013). "Lysyl oxidase-like-2 promotes tumour angiogenesis and is a potential therapeutic target in angiogenic tumours." *Carcinogenesis* 34(10): 2370-2379.

Zenkel, M., et al. (2011). "Regulation of lysyl oxidase-like 1 (LOXL1) and elastin-related genes by pathogenic factors associated with pseudoexfoliation syndrome." *Invest Ophthalmol Vis Sci* 52(11): 8488-8495.

Zhu, J., et al. (2015). "Lysyl Oxidase Is Predictive of Unfavorable Outcomes and Essential for Regulation of Vascular Endothelial Growth Factor in Hepatocellular Carcinoma." *Digestive Diseases and Sciences:* 1-13.

Zibadi, S., et al. (2010). "T lymphocyte regulation of lysyl oxidase in diet-induced cardiac fibrosis." *Cardiovasc Toxicol* 10(3): 190-198.

The invention claimed is:

1. A compound of Formula (I):

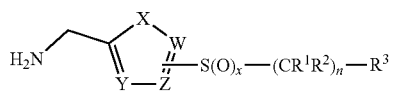

(I)

wherein:

X is selected from the group consisting of: S, $NR^N$ and O; wherein $R^N$ is selected from the group consisting of: H, $C_{1-4}$ alkyl, $C_{1-4}$ haloalkyl and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, =O, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

Y is selected from the group consisting of: N and CR; wherein R is selected from the group consisting of: H, halo, $C_{1-4}$ alkyl, $C_{1-4}$ haloalkyl, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{1-4}$ alkyl, $C_{1-4}$ haloalkyl and $C_{3-6}$ cycloalkyl groups are themselves optionally substituted with a substituent selected from the group consisting of: $R^{A1}$, halo, $-OR^{A1}$, =O, $-NR^{A1}R^{B1}$, $-SR^{A1}$, CN, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

Z is carbon and is bonded to the

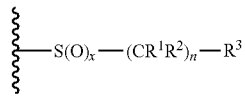

residue and W is selected from the group consisting of: N and CR; wherein R is selected from the group consisting of: H, halo, $-OR^{A1}$, $-NR^{A1}R^{B1}$, $-SR^{A1}$, $-CN$, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, wherein the $C_{3-6}$ cycloalkyl groups are themselves optionally substituted with a substituent selected from the group consisting of: $R^{A1}$, halo, $-OR^{A1}$, =O, $-NR^{A1}R^{B1}$, $-SR^{A1}$, CN, $-NO_2$, $-NR^{A1}C(O)R^{B1}$, $-C(O)NR^{A1}R^{B1}$, $-NR^{A1}C(O)OR^{B1}$, $-OC(O)NR^{A1}R^{B1}$, $-NR^{A1}C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl;

x is 1 or 2;

n is 0, 1, 2, 3, 4, 5 or 6;

$R^1$ and $R^2$ are independently selected at each occurrence from: H, halo, $C_{1-4}$ alkyl, $C_{1-4}$ haloalkyl, $-OR^{A1}$, $-NR^{A1}R^{B1}$, $-CN$, $-NO_2$, $-NR^{A1}C(O)R^{B1}$, $-C(O)NR^{A1}R^{B1}$, $-NR^{A1}SO_2R^{B1}$, $-SO_2NR^{A1}R^{B1}$, $-SO_2R^{A1}$, $-C(O)R^{A1}$, $-C(O)OR^{A1}$ and $C_{3-6}$ cycloalkyl, or together $R^1$ and $R^2$ are =O, wherein the $C_{1-4}$ alkyl, $C_{1-4}$ haloalkyl and $C_{3-6}$ cycloalkyl groups are themselves optionally substituted with $R^{A1}$, halo, —$OR^{A1}$, =O, —$NR^{A1}R^{B1}$, —$SR^{A1}$, —CN, —$NO_2$, —$NR^{A1}C(O)R^{B1}$, —$C(O)NR^{A1}R^{B1}$, —$NR^{A1}C(O)OR^{B1}$, —$OC(O)NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —$C(O)R^{A1}$, —$C(O)OR^{A1}$ and $C_{3-6}$ cycloalkyl;

when n is 0, $R^3$ is optionally substituted 3- to 15-membered ring system, including 0, 1, 2 or 3 heteroatoms selected from N, O or S, wherein the ring system is connected to the remainder of the compound of Formula (I) via a carbon atom, and when n is 1, 2, 3, 4, 5 or 6 $R^3$ is selected from the group consisting of optionally substituted 3- to 15-membered ring system, including 0, 1, 2 or 3 heteroatoms selected from N, O or S, halo, —$OR^{A1}$, —$NR^{A1}R^{B1}$, —$SR^{A1}$, —CN, —$NO_2$, —$NR^{A1}C(O)R^{B1}$, —$C(O)NR^{A1}R^{B1}$, —$NR^{A1}C(O)OR^{B1}$, —$OC(O)NR^{A1}R^{B1}$, —$NR^{A1}C(O)NR^{A1}R^{B1}$, —$NR^{A1}SO_2R^{B1}$, —$SO_2NR^{A1}R^{B1}$, —$SO_2R^{A1}$, —$C(O)R^{A1}$ and —$C(O)OR^{A1}$; and $R^{A1}$ and $R^{B1}$ are at each occurrence independently selected from the group consisting of: H, $C_{1-4}$ alkyl, $C_{1-4}$ haloalkyl and $C_{1-4}$ alkyl substituted with a substituent selected from the group consisting of: —$OR^{A5}$, —$NR^{A5}R^{B5}$, —CN, —$NO_2$, —$N_3$, —$NR^{A5}C(O)R^{B5}$, —$C(O)NR^{A5}R^{B5}$, —$NR^{A5}SO_2R^{B5}$, —$SO_2NR^{A5}R^{B5}$, —$SO_2R^{A5}$, —$C(O)R^{A5}$, —$C(O)OR^{A5}$ and $C_{3-6}$ cycloalkyl, wherein $R^{A5}$ and $R^{B5}$ are each independently selected from the group consisting of H and $C_{1-4}$ alkyl; wherein in the specific group —$NR^{A1}R^{B1}$, $R^{A1}$ and $R^{B1}$, together with the nitrogen atom to which they are bonded can form a 4- to 7-membered ring system; and wherein in the specific group —$NR^{A5}R^{B5}$, $R^{A5}$ and $R^{B5}$, together with the nitrogen atom to which they are bonded can form a 4- to 7-membered ring system;

or a pharmaceutically acceptable salt thereof.

2. The compound of claim 1, wherein X is S.
3. The compound of claim 2, wherein Y is N.
4. The compound of claim 1, wherein x is 2.
5. The compound of claim 1, wherein n is 0.
6. The compound of claim 1, having the structure according to Formula (VI):

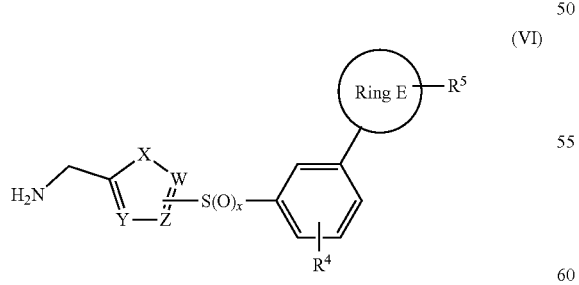

(VI)

wherein:
$R^4$ is selected from the group consisting of $C_{1-4}$ alkyl, $C_{1-4}$ haloalkyl, halo, —$OR^{A1}$, —$C(O)NR^{A2}R^{B2}$, —$SO_2R^{A2}$ and —$C(O)OR^{A2}$;
wherein $R^{A2}$ and $R^{B2}$ are at each occurrence independently selected from the group consisting of: H and $C_{1-4}$ alkyl, wherein the $C_{1-4}$ alkyl is optionally substituted with —OH; wherein in the specific group —$NR^{A2}R^{B2}$, $R^{A2}$ and $R^{B2}$, together with the nitrogen atom to which they are bonded can form a 4- to 7-membered ring system;

"Ring E" is selected from the group consisting of: phenyl, pyrrolidinyl, pyrazolyl and pyridinyl;
$R^5$ is selected from the group consisting of: H, $C_{1-4}$ alkyl and $C_{1-4}$ alkyl substituted with —O—$C_{1-4}$ alkyl.

7. The compound of claim 6, wherein $R^4$ is meta- to the —$S(O)_x$— group:

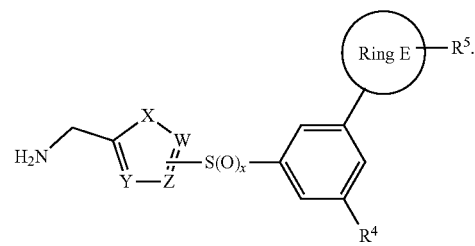

8. The compound of claim 6, wherein $R^4$ is selected from the group consisting of —$CH_2CH_3$, —$OCH_3$,

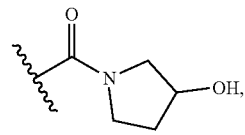

—$SO_2Me$, —$C(O)NMe_2$ and —$C(O)OH$.

9. The compound of claim 6, wherein Ring E is phenyl, optionally

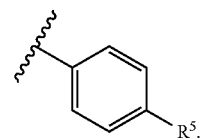

10. The compound of claim 6, wherein Ring E is

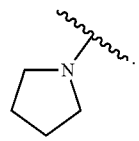 [SMILES: *N1CCCC1]

11. The compound of claim 6, wherein Ring E is

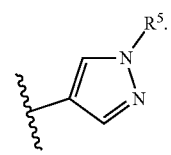

12. The compound of claim 6, wherein Ring E is

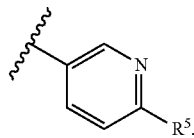

13. The compound of claim 6, wherein $R^5$ is selected from the group consisting of: H, —$CH_3$ and —$CH_2OCH_3$.

14. A pharmaceutical composition comprising a compound according to claim 1, or a pharmaceutically acceptable salt thereof, and a pharmaceutically acceptable excipient.

15. A method of treating a disease or medical condition mediated by LOX, in a subject in need thereof, comprising administering to the subject a therapeutically effective amount of a compound according to claim 1, or a pharmaceutically acceptable salt thereof, wherein treating refers to inhibiting, relieving or attenuating the disorder.

16. A method of treating a cancer in a subject in need thereof, comprising administering to the subject a therapeutically effective amount of a compound according to claim 1, or a pharmaceutically acceptable salt thereof,
wherein treating refers to inhibiting, relieving or attenuating the disorder; and
wherein the cancer is a carcinoma which is breast carcinoma, colon carcinoma, lung carcinoma, prostate carcinoma, ovarian carcinoma, esophageal carcinoma, basal-like breast carcinoma, basal cell carcinoma, head and neck carcinoma, stomach carcinoma, signet ring cell carcinoma, bladder carcinoma, bronchogenic carcinoma, colorectal carcinoma, anal carcinoma, gastric carcinoma, lung carcinoma, neuroendocrine tumor, adrenocortical carcinoma, thyroid carcinoma, pancreatic carcinoma, liver and bile duct carcinoma, brain tumour, germ cell tumor, sweat gland carcinoma, sebaceous gland carcinoma, papillary carcinoma, papillary adenocarcinoma, cystadenocarcinoma, kidney carcinoma, medullary carcinoma, ductal carcinoma in situ or bile duct carcinoma, choriocarcinoma, seminoma, embryonal carcinoma, cervical carcinoma, uterine carcinoma, testicular carcinoma, osteogenic carcinoma, epithelial carcinoma, sarcomatoid carcinoma, nasopharyngeal carcinoma, laryngeal carcinoma, or oral and oropharyngeal squamous carcinoma.

17. A method according to claim 16 wherein the cancer is a metastatic cancer.

18. A method of treating a fibrotic disorder in a subject in need thereof comprising administering to the subject a therapeutically effective amount of a compound according to claim 1, or a pharmaceutically acceptable salt thereof, wherein treating refers to inhibiting, relieving or attenuating the disorder.

19. A method according to claim 18 wherein the fibrotic disorder is
a fibrotic condition affecting the lungs,
a fibrotic condition affecting the liver,
a fibrotic condition affecting the kidneys,
a fibrotic condition affecting the heart or vascular system,
a fibrotic condition affecting the mediastinum,
a fibrotic condition affecting bone,
a fibrotic condition affecting the retroperitoneum,
a fibrotic condition affecting the skin,
a fibrotic condition affecting the GI tract,
a fibrotic condition affecting connective tissue,
a fibrotic condition affecting the eye.

20. A method according to claim 15, wherein the disease or medical condition is mediated by LOXL2.

21. A method according to claim 19 wherein the fibrotic disorder is a fibrotic condition affecting the lungs, which is pulmonary fibrosis secondary to cystic fibrosis, idiopathic pulmonary fibrosis, coal worker's progressive massive fibrosis, cryptogenic fibrosing alveolitis, chronic fibrosing interstitial pneumonia, interstitial lung disease (ILD), diffuse parenchymal lung disease (DPLD), emphysema, chronic obstructive pulmonary disease (COPD), or chronic asthma.

22. A method according to claim 19 wherein the fibrotic disorder is a fibrotic condition affecting the liver, which is cirrhosis, chronic viral hepatitis B, chronic viral hepatitis C, Wilson's disease, non-alcoholic fatty liver disease (NAFLD), alcoholic steatohepatitis (ASH), non-alcoholic steatohepatitis (NASH), primary biliary cirrhosis (PBC), biliary cirrhosis, or autoimmune hepatitis.

23. A method according to claim 19 wherein the fibrotic disorder is a fibrotic condition affecting the kidneys, which is diabetic nephropathy, vesicoureteral reflux, tubulointerstitial renal fibrosis, glomerulonephritis, glomerular nephritis, focal segmental glomerulosclerosis, membranous glomerulonephritis, or mesangiocapillary glomerular nephritis.

24. A method according to claim 19 wherein the fibrotic disorder is a fibrotic condition affecting the heart or vascular system, which is endomyocardial fibrosis, old myocardial infarction, atrial fibrosis, congestive heart failure, cardiomyopathy, hypertensive heart disease (HHD), hypertension, fibrosis associated with hypertension, atherosclerosis, restenosis, and heart disease associated with cardiac ischemic events.

25. A method according to claim 19 wherein the fibrotic disorder is a fibrotic condition affecting the heart or vascular system, which is pulmonary hypertension.

26. A method according to claim 19 wherein the fibrotic disorder is a fibrotic condition affecting the heart or vascular system, which is restenosis which is coronary, carotid, or cerebral lesions.

27. A method according to claim 19 wherein the fibrotic disorder is a fibrotic condition affecting the mediastinum, which is mediastinal fibrosis.

28. A method according to claim 19 wherein the fibrotic disorder is a fibrotic condition affecting bone, which is myelofibrosis, including primary myelofibrosis, post polycythemia vera or post essential thrombocythemia myelofibrosis.

29. A method according to claim 19 wherein the fibrotic disorder is a fibrotic condition affecting the retroperitoneum, which is retroperitoneal fibrosis skin.

30. A method according to claim 19 wherein the fibrotic disorder is a fibrotic condition affecting the skin, which is nephrogenic systemic fibrosis, keloid formation and scarring, systemic sclerosis, or scleroderma.

31. A method according to claim 19 wherein the fibrotic disorder is a fibrotic condition affecting the GI tract, which is fibrotic intestinal disorder, inflammatory bowel disease, ulcerative colitis or Crohn's disease.

32. A method according to claim 19 wherein the fibrotic disorder is a fibrotic condition affecting connective tissue, which is arthrofibrosis or capsulitis.

33. A method according to claim 19 wherein the fibrotic disorder is a fibrotic condition affecting the eye, which is ocular fibrosis following surgery or pseudoexfoliation syndrome glaucoma.

34. A method of treating a cancer in a subject in need thereof, the method comprising administering to the subject a therapeutically effective amount of a compound according to claim 1, wherein the cancer is selected from pancreatic, colorectal, breast and lung cancer, and wherein treating refers to inhibiting, relieving or attenuating the disorder.

* * * * *

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Forward primer used for cloning of LOX cDNA
      into pEGFP-N1/proGFP2-N1

<400> SEQUENCE: 1
gagagagcta gcatgcgttt cgcctggg                                        28

<210> SEQ ID NO 2
<211> LENGTH: 33
<212> TYPE: DNA
<213> ORGANISM: Artificial Sequence
<220> FEATURE:
<223> OTHER INFORMATION: Reverse primer used for cloning of LOX cDNA
      into pEGFP-N1/proGFP2-N1

<400> SEQUENCE: 2
tctctcctcg agatacggtg aaattgtgca gcc                                  33
```